(12) United States Patent
Falb et al.

(10) Patent No.: US 10,933,102 B2
(45) Date of Patent: *Mar. 2, 2021

(54) BACTERIA ENGINEERED TO TREAT A DISEASE OR DISORDER

(71) Applicant: Synlogic Operating Company, Inc., Cambridge, MA (US)

(72) Inventors: Dean Falb, Sherborn, MA (US); Paul F. Miller, Salem, CT (US); Jonathan W. Kotula, Berkeley, CA (US); Vincent M. Isabella, Medford, MA (US); Suman Machinani, Monroe, NY (US); Adam B. Fisher, Cambridge, MA (US); Yves Millet, Newton, MA (US)

(73) Assignee: Synlogic Operating Company, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/852,762

(22) Filed: Dec. 22, 2017

(65) Prior Publication Data

US 2018/0169154 A1 Jun. 21, 2018
US 2018/0280451 A9 Oct. 4, 2018

Related U.S. Application Data

(63) Continuation of application No. 15/319,564, filed as application No. PCT/US2016/032565 on May 13, 2016, now Pat. No. 9,889,164, which is a continuation-in-part of application No. 15/154,934, filed on May 13, 2016, now Pat. No. 10,610,546, and a continuation-in-part of application No. PCT/US2016/032562, filed on May 13, 2016, and a continuation-in-part of application No. PCT/US2016/020530, filed on Mar. 2, 2016, and a continuation-in-part of application No. 14/960,333, filed on Dec. 4, 2015, now Pat. No. 9,487,764, and a continuation-in-part of application No. PCT/US2015/064140, filed on Dec. 4, 2015.

(60) Provisional application No. 62/336,338, filed on May 13, 2016, provisional application No. 62/335,780, filed on May 13, 2016, provisional application No. 62/335,940, filed on May 13, 2016, provisional application No. 62/336,012, filed on May 13, 2016, provisional application No. 62/314,322, filed on Mar. 28, 2016, provisional application No. 62/313,691, filed on Mar. 25, 2016, provisional application No. 62/293,749, filed on Feb. 10, 2016, provisional application No. 62/277,654, filed on Jan. 12, 2016, provisional application No. 62/277,413, filed on Jan. 11, 2016, provisional application No. 62/277,346, filed on Jan. 11, 2016, provisional application No. 62/263,329, filed on Dec. 4, 2015, provisional application No. 62/256,041, filed on Nov. 16, 2015, provisional application No. 62/256,039, filed on Nov. 16, 2015, provisional application No. 62/256,052, filed on Nov. 16, 2015, provisional application No. 62/212,223, filed on Aug. 31, 2015, provisional application No. 62/199,445, filed on Jul. 31, 2015, provisional application No. 62/183,935, filed on Jun. 24, 2015, provisional application No. 62/173,761, (Continued)

(51) Int. Cl.
| | |
|---|---|
| A61K 35/74 | (2015.01) |
| A61K 39/02 | (2006.01) |
| C12N 9/88 | (2006.01) |
| C12N 9/06 | (2006.01) |
| C12N 15/70 | (2006.01) |
| C07K 14/245 | (2006.01) |
| A61K 35/741 | (2015.01) |
| C07K 14/195 | (2006.01) |
| A61K 38/00 | (2006.01) |
| A61K 35/00 | (2006.01) |

(52) U.S. Cl.
CPC ............ *A61K 35/74* (2013.01); *A61K 35/741* (2013.01); *A61K 39/02* (2013.01); *C07K 14/195* (2013.01); *C07K 14/245* (2013.01); *C12N 9/0014* (2013.01); *C12N 9/0022* (2013.01); *C12N 9/88* (2013.01); *C12N 15/70* (2013.01); *C12Y 104/03002* (2013.01); *C12Y 403/01024* (2013.01); *A61K 38/00* (2013.01); *A61K 2035/11* (2013.01); *Y02A 50/30* (2018.01)

(58) Field of Classification Search
None
See application file for complete search history.

(56) References Cited

U.S. PATENT DOCUMENTS

| | | |
|---|---|---|
| 9,487,764 B2 | 11/2016 | Falb et al. |
| 9,688,967 B2 | 6/2017 | Falb et al. |

(Continued)

FOREIGN PATENT DOCUMENTS

| | | |
|---|---|---|
| EP | 1666588 A1 | 6/2006 |
| EP | 2344626 B1 | 7/2011 |

(Continued)

OTHER PUBLICATIONS

Levanon, S. et al., Biotech. Biioeng., 2005, pp. 556-564.*

(Continued)

*Primary Examiner* — Michael D Burkhart
(74) *Attorney, Agent, or Firm* — Chang Hong, Esq.; Marcie B. Clarke

(57) ABSTRACT

Genetically programmed microorganisms, such as bacteria, pharmaceutical compositions thereof, and methods of modulating and treating a disease and/or disorder are disclosed.

22 Claims, 44 Drawing Sheets

Specification includes a Sequence Listing.

Related U.S. Application Data filed on Jun. 10, 2015, provisional application No. 62/173,706, filed on Jun. 10, 2015, provisional application No. 62/173,710, filed on Jun. 10, 2015, provisional application No. 62/161,137, filed on May 13, 2015.

(56) References Cited

U.S. PATENT DOCUMENTS

| 9,889,164 | B2 | 2/2018 | Falb et al. |
|---|---|---|---|
| 2015/0246083 | A1 | 9/2015 | Deming et al. |
| 2015/0246085 | A1 | 9/2015 | Al-Hafid et al. |
| 2017/0136073 | A1 | 5/2017 | Falb et al. |
| 2017/0216370 | A1 | 8/2017 | Falb et al. |
| 2017/0232043 | A1 | 8/2017 | Falb et al. |
| 2017/0253862 | A1 | 9/2017 | Falb et al. |

FOREIGN PATENT DOCUMENTS

| WO | 2008/073148 | A2 | 6/2008 |
|---|---|---|---|
| WO | 2012/078311 | A1 | 6/2012 |
| WO | 2013/134174 | A2 | 9/2013 |
| WO | WO 2014/066945 | * | 5/2014 |

OTHER PUBLICATIONS

Ashida et al., Nature Chem Biol., 2012, pp. 36-45.*
Reeves, A. et al., ACS Synth. Biol., 2015, pp. 644-654.*
Duan et al., Appl. Environ. Microbiol., 2008, pp. 7437-7438.*
Steidler et al., Nat. Biotech., 2003, pp. 785-789.*
Kadner et al., Methionine transport in *Escherichia coli*: physiological and genetic evidence for two uptake systems. J Bacteriol. Aug. 1974;119(2):401-9.
Kehres et al., SitABCD Is the Alkaline Mn2+ Transporter of *Salmonella enterica* Serovar Typhimurium. Journal of Bacteriology. Jun. 2002;184(12):3159-3166.
Koo et al., A reducing system of the superoxide sensor SoxR in *Escherichia coli*. EMBO J. Jun. 2, 2003;22 (11):2614-22.
Landick et al., The complete nucleotide sequences of the *Escherichia coli* LIV-BP and LS-BP genes. Implications for the mechanism of high-affinity branched-chain amino acid transport. J Biol Chem. Jul. 15, 1985;260(14):8257-61.
Lee et al., Systems metabolic engineering of microorganisms for natural and non-natural chemicals. Nat Chem Biol. May 17, 2012;8(6):536-46.
Li et al., Monomeric state and ligand binding of recombinant GABA transporter from *Escherichia coli*. FEBS Lett. Apr. 13, 2001;494(3):165-9.
Matano et al., Engineering of Corynebacterium glutamicum for growth and L-lysine and lycopene production from N-acetylglucosamine. Appl Microbiol Biotechnol. Jun. 2014;98(12):5633-43.
McAllister et al., Molecular analysis of the psa permease complex of *Streptococcus* pneumoniae. Mol Microbiol. Aug. 2004;53(3):889-901.
McEwen et al., Engineering Synechococcus elongatus PCC 7942 for continuous growth under diurnal conditions. Appl Environ Microbiol. Mar. 2013;79(5):1668-75.
Mengesha et al., Development of a flexible and potent hypoxia-inducible promoter for tumor-targeted gene expression in attenuated *Salmonella*. Cancer Biol Ther. Sep. 2006;5(9):1120-8.
Menzel et al., Purification of the putA gene product. A bifunctional membrane-bound protein from *Salmonella* typhimurium responsible for the two-step oxidation of proline to glutamate. J Biol Chem. Sep. 25, 1981;256(18):9755-61.
Merlin et al., The *Escherichia coli* metD locus encodes an ABC transporter which includes Abc (MetN), YaeE (MetI), and YaeC (MetQ). J Bacteriol. Oct. 2002;184(19):5513-7.
Mironov et al., Computer analysis of transcription regulatory patterns in completely sequenced bacterial genomes. Nucleic Acids Res. Jul. 15, 1999;27(14)1981-9.
Moore et al., Regulation of FNR dimerization by subunit charge repulsion. J Biol Chem. Nov. 3, 2006;281(44):33268-75.
Nazos et al., Cloning and characterization of livH, the structural gene encoding a component of the leucine transport system in *Escherichia coli*. J Bacteriol. May 1986;166(2):565-73.
Nazos et al., Identification of livG, a membrane-associated component of the branched-chain amino acid transport in *Escherichia coli*. J Bacteriol. Sep. 1985;163(3):1196-202.
Nji et al., Cloning, expression, purification, crystallization and preliminary X-ray diffraction of a lysine-specific permease from Pseudomonas aeruginosa. Acta Crystallogr F Struct Biol Commun. Oct. 2014;70(Pt 10):1362-7.
Norholm et al., Specificity and topology of the *Escherichia coli* xanthosine permease, a representative of the NHS subfamily of the major facilitator superfamily. J Bacterial. Aug. 2001;183(16):4900-4.
Ogawa et al., Cloning and expression of the gene for the Na+-coupled serine transporter from *Escherichia coli* and characteristics of the transporter. J Bacteriol. Dec. 1998;180(24):6749-52.
Ogawa et al., Isolation and characterization of an *Escherichia coli* mutant lacking the major serine transporter, and cloning of a serine transporter gene. J Biochem. Dec. 1997;122(6):1241-5.
Oh et al., Structural basis for multiple ligand specificity of the periplasmic lysine-, arginine-, ornithine-binding protein. J Biol Chem. Oct. 21, 1994;269(42):26323-30.
Ohnishi et al., Cloning and nucleotide sequence of the brnQ gene, the structural gene for a membrane-associated aomponent of the LIV-II transport system for branched-chain amino acids in *Salmonella typhimurium*. Jpn J Genet. Aug. 1988;63(4):343-57.
Ortuno-Olea et al., The L-asparagine operon of Rhizobium etli contains a gene encoding an atypical asparaginase. FEMS Microbial Lett. Aug. 15, 2000;189(2):177-82.
Ostrovsky De Spicer et al., PutA protein, a membrane-associated flavin dehydrogenase, acts as a redox-dependent transcriptional regulator. Proc Natl Acad Sci U S A. May 1, 1993;90(9):4295-8.
Oxender et al., Structural and functional analysis of cloned DNA containing genes responsible for branched-chain amino acid transport in *Escherichia coli*. Proc Natl Acad Sci U S A. Mar. 1980;77(3):1412-6.
Pi et al., Cloning and sequencing of the pheP gene, which encodes the phenylalanine-specific transport system of *Escherichia coli*. J Bacteriol. Jun. 1991;173(12):3622-9.
Pi et al., Functional consequences of changing proline residues in the phenylalanine-specific permease of *Escherichia coli*. J Bacteriol. Nov. 1998;180(21):5515-9.
Pi et al., Topology of the phenylalanine-specific permease of *Escherichia coli*. J Bacteriol. May 1996;178(9):2650-5.
Porcheron et al., Iron, copper, zinc, and manganese transport and regulation in pathogenic Enterobacteria: correlations between strains, site of infection and the relative importance of the different metal transport systems for virulence. Front Cell Infect Microbial. Dec. 5, 2013;3:90.
Quay et al., Role of transport systems in amino acid metabolism: leucine toxicity and the branched-chain amino acid transport systems. J Bacteriol. Mar. 1977;129(3):1257-65.
Que et al., Manganese homeostasis in Bacillus subtilis is regulated by MntR, a bifunctional regulator related to the diphtheria toxin repressor family of proteins. Mol Microbial. Mar. 2000;35(6):1454-68.
Rahmanian et al., Multiplicity of leucine transport systems in *Escherichia coli* K-12. J Bacterial. Dec. 1973;116(3):1258-66.
Ray et al., The effects of mutation of the arn gene on the aerobic respiratory chain of Pseudomonas aeruginosa. FEMS Microbial Lett. Nov. 15, 1997;156(2):227-32.
Rees et al., ABC transporters: The power to change. Nat Rev Mol Cell Biol. Mar. 2009:10(3)218-227.
Reister et al., Complete genome sequence of the gram-negative probiotic *Escherichia coli* strain Nissle 1917. J Biotechnol. Oct. 10, 2014;187:106-7.

(56) References Cited

OTHER PUBLICATIONS

Rembacken et al., Non-pathogenic *Escherichia coli* versus mesalazine for the treatment of ulcerative colitis: a randomised trial. Lancet. Aug. 21, 1999;354(9179):635-9.
Rodionov et al., Regulation of lysine biosynthesis and transport genes in bacteria: yet another RNA riboswitch? Nucleic Acids Res. Dec. 1, 2003;31(23):6748-57.
Rosen, Basic amino acid transport in *Escherichia coli*. J Biol Chem. Jun. 10, 1971;246(11):3653-62.
Ryan et al., Bacterial delivery of a novel cytolysin to hypoxic areas of solid tumors. Gene Ther. Mar. 2009;16(3):329-39.
Ryan et al., The uncoupled chloride conductance of a bacterial glutamate transporter homolog. Nat Struct Mol Biol. May 2007:14(5):365-71.
Salmon et al., Global gene expression profiling in *Escherichia coli* K12. The effects of oxygen availability and FNR. J Biol Chem. Aug. 8, 2003:278(32):29837-55.
Schultz, Clinical use of *E. coli* Nissle 1917 in inflammatory bowel disease. Inflamm Bowel Dis. Jul. 2008;14(7)1012-8.
Seep-Feldhaus et al., Molecular analysis of the Corynebacterium glutamicum lysI gene involved in lysine uptake. Mol Microbiol. Dec. 1991:5(12):2995-3005.
Shao et al., Sequencing and characterization of the sdaC gene and identification of the sdaCB operon in *Escherichia coli* K12. Eur J Biochem. Jun. 15, 1994;222(3):901-7.
Sheehan et al., Heterologous expression of BetL, a betaine uptake system, enhances the stress tolerance of Lactobacillus salivarius UCC118. Appl Environ Microbiol. Mar. 2006;72(3):2170-7.
Sleator et al., Rational design of improved pharmabiotics. J Biomed Biotechnol. 2009;2009:275287. 7 pages.
Slotboom et al., Structural features of the glutamate transporter family. Microbiol Mol Biol Rev. Jun. 1999;63(2):293-307.
Steffes et al., The lysP gene encodes the lysine-specific permease. J Bacteriol. May 1992;174(10):3242-9.
Steidler et al., Biological containment of genetically modified Lactococcus lactis for intestinal delivery of human interleukin 10. Nat Biotechnol. Jul. 2003;21(7):785-9.
Strauch et al., Oxygen regulation in *Salmonella typhimurium*. J Bacteriol. Feb. 1985;161(2):673-80.
Takahashi et al., Multiple Functions of Glutamate Uptake via Meningococcal GltT-GltM L-Glutamate ABC Transporter in Neisseria meningitidis Internalization into Human Brain Microvascular Endothelial Cells. Infect Immun. Sep. 2015;83(9):3555-67.
Tolner et al., Characterization and functional expression in *Escherichia coli* of the sodium/proton/glutamate symport proteins of Bacillus stearothermophilus and Bacillus caldotenax. Mol Microbial. Oct. 1992;6(19):2845-56.
Trip et al., Cloning, expression, and functional characterization of secondary amino acid transporters of Lactococcus lactis. J Bacteriol. Jan. 2013;195(2):340-50.
Trotschel et al., Characterization of methionine export in Corynebacterium glutamicum. J Bacteriol. Jun. 2005;187(11):3786-94.
Trunk et al., Anaerobic adaptation in Pseudomonas aeruginosa: definition of the Anr and Dnr regulons. Environ Microbiol. Jun. 2010;12(6):1719-33.
Ukena et al., Probiotic *Escherichia coli* Nissle 1917 inhibits leaky gut by enhancing mucosal integrity. PLoS One. Dec. 12, 2007;2(12):e1308. 9 pages.
Unden et al., Control of FNR function of *Escherichia coli* by O2 and reducing conditions. J Mol Microbial Biotechnol. May 2002;4(3):263-8.
Vaziri et al., Use of molecular modelling to probe the mechanism of the nucleoside transporter NupG. Mol Membr Biol. Mar. 2013;30(2):114-28.
Weisser et al., Functional expression of the glucose transporter of Zymomonas mobilis leads to restoration of glucose and fructose uptake in *Escherichia coli* mutants and provides evidence for its facilitator action. J Bacteriol. Jun. 1995;177(11):3351-4.

Willis et al., L-asparagine uptake in *Escherichia coli*. J Bacteriol. Sep. 1975;123(3):937-45.
Wissenbach et al., A third periplasmic transport system for L-arginine in *Escherichia coli*: molecular characterization of the artPIQMJ genes, arginine binding and transport. Mol Microbiol. Aug. 1995;17(4):675-86.
Wissenbach et al., Physical map location of the new artPIQMJ genes of *Escherichia coli*, encoding a periplasmic arginine transport system. J Bacterial. Jun. 1993;175(11)3687-8.
Wolken et al., The mechanism of the tyrosine transporter TyrP supports a proton motive tyrosine decarboxylation pathway in Lactobacillus brevis. J Bacterial. Mar. 2006;188(6):2198-206.
Wood, Leucine transport in *Escherichia coli*. The resolution of multiple transport systems and their coupling to metabolic energy. J Biol Chem. Jun. 25, 1975;250(12):4477-85.
Yamato et al., Genetic and biochemical studies of transport systems for branched-chain amino acids in *Escherichia coli* K-12: isolation and properties of mutants defective in leucine-repressible transport activities. J Bacterial. Oct. 1980;144(1):36-44.
Yamato et al., Genetic and biochemical studies of transport systems for branched-chain amino acids in *Escherichia coli*. J Bacteriol. Apr. 1979;138(1):24-32.
Yanofsky et al., Physiological studies of tryptophan transport and tryptophanase operon induction in *Escherichia coli*. J Bacterial. Oct. 1991;173(19):6009-17.
Zaprasis et al., Uptake of amino acids and their metabolic conversion into the compatible solute proline confers osmoprotection to Bacillus subtilis. Appl Environ Microbial. Jan. 2015;81(1):250-9.
Zhou et al., *Salmonella typhimurium* encodes a putative iron transport system within the centisome 63 pathogenicity island. Infect Immun. Apr. 1999;67(4):1974-81.
International Search Report and Written Opinion for Application No. PCT/US2016/032565, dated Aug. 5, 2016.
International Search Report for Application No. PCT/US2016/032562, dated Aug. 22, 2016.
Adams et al., Nucleotide sequence and genetic characterization reveal six essential genes for the LIV-I and LS transport systems of *Escherichia coli*. J Biol Chem. Jul. 15, 1990;265(20)11436-43.
Altenhoefer et al., The probiotic *Escherichia coli* strain Nissle 1917 interferes with invasion of human intestinal epithelial cells by different enteroinvasive bacterial pathogens. FEMS Immunol Med Microbiol. Apr. 9, 2004;40(3):223-9.
Anderson et al., *Escherichia coli* transport mutants lacking binding protein and other components of the branched-chain amino acid transport systems. J Bacteriol. Apr. 1977;130(1):384-92.
Anderson et al., Genetic separation of high- and low-affinity transport systems for branched-chain amino acids in *Escherichia coli* K-12. J Bacterial. Oct. 1978;136(1):168-74.
Arrach et al., *Salmonella* promoters preferentially activated inside tumors. Cancer Res. Jun. 15, 2008;68(12):4827-32.
Barel et al., The complex amino acid diet of Francisella in infected macrophages. Front Cell Infect Microbiol. Feb. 6, 2015;5:9. 5 pages.
Bearden et al., The Yfe system of Yersinia pestis transports iron and manganese and is required for full virulence of plague. Mol Microbial. Apr. 1999;32(2):403-14.
Becker et al., O2 as the regulatory signal for FNR-dependent gene regulation in *Escherichia coli*. J Bacteriol. Aug. 1996;178(15):4515-21.
Becker et al., Regulatory O2 tensions for the synthesis of fermentation products in *Escherichia coli* and relation to aerobic respiration. Arch Microbiol. Oct. 1997;168(4):290-6.
Boysen et al., Translational regulation of gene expression by an anaerobically induced small non-coding RNA in *Escherichia coli*. J Biol Chem. Apr. 2, 2010;285(14):10690-702.
Braat et al., A phase I trial with transgenic bacteria expressing interleukin-10 in Crohn's disease. Clin Gastroenterol Hepatol. Jun. 2006;4(6):754-9.
Bucarey et al., The *Salmonella enterica* serovar Typhi tsx gene, encoding a nucleoside-specific porin, is essential for prototrophic growth in the absence of nucleosides. Infect Immun. Oct. 2005;73(10):6210-9.

(56) References Cited

OTHER PUBLICATIONS

Cabrita et al., Molecular biology and regulation of nucleoside and nucleobase transporter proteins in eukaryotes and prokaryotes. Biochem Cell Biol. 2002;80(5):623-38.

Caldara et al., ArgR-dependent repression of arginine and histidine transport genes in *Escherichia coli* K-12. J Mol Biol. Oct. 19, 2007;373(2):251-67.

Callura et al., Tracking, tuning, and terminating microbial physiology using synthetic riboregulators. Proc Natl Acad Sci U S A. Sep. 7, 2010;107(36):15898-903.

Castiglione et al., The transcription factor DNR from Pseudomonas aeruginosa specifically requires nitric oxide and haem for the activation of a target promoter in *Escherichia coli*. Microbiology. Sep. 2009;155(Pt 9):2838-44.

Celis, Properties of an *Escherichia coli* K-12 mutant defective in the transport of arginine and ornithine. J Bacteriol. Jun. 1977;130(3):1234-43.

Cellier et al., Resistance to intracellular infections: comparative genomic analysis of Nramp. Trends Genet. Jun. 1996;12(6):201-4.

Chye et al., Transcription control of the aroP gene in *Escherichia coli* K-12: analysis of operator mutants. J Bacterial. Jan. 1987;169(1):386-93.

Den Hengst et al., Identification and functional characterization of the Lactococcus lactis CodY-regulated branched-chain amino acid permease BcaP (CtrA). J Bacteriol. May 2006;188(9):3280-9.

Duarte et al., PerR vs OhrR: selective peroxide sensing in Bacillus subtilis. Mol Biosyst. Feb. 2010;6(2):316-23.

Dubbs et al., Peroxide-sensing transcriptional regulators in bacteria. J Bacteriol. Oct. 2012;194(20):5495-503.

Dunn et al., The alternative oxidase (AOX) gene in Vibrio fischeri is controlled by NsrR and upregulated in response to nitric oxide. Mol Microbiol. Jul. 1, 2010;77(1):44-55.

Durand et al., Reprogramming of anaerobic metabolism by the FnrS small RNA. Mol Microbiol. Mar. 2010;75(5):1215-31.

Eiglmeier et al., Molecular genetic analysis of FNR-dependent promoters. Mol Microbiol. Jul. 1989;3(7):869-78.

Elkins et al., Genes encoding bile salt hydrolases and conjugated bile salt transporters in *Lactobacillus johnsonii* 100-100 and other *Lactobacillus* species. Microbiology. Dec. 2001;147(Pt 12):3403-12.

Forbes, Engineering the perfect (bacterial) cancer therapy. Nat Rev Cancer. Nov. 2010;10(11):785-94.

Galimand et al., Positive FNR-like control of anaerobic arginine degradation and nitrate respiration in Pseudomonas aeruginosa. J Bacteriol. Mar. 1991;173(5):1598-606.

Gouzy et al., *Mycobacterium tuberculosis* exploits asparagine to assimilate nitrogen and resist acid stress during infection. PLoS Pathog. Feb. 20, 2014;10(2):e1003928. 14 pages.

Grothe et al., roline transport and osmotic stress response in *Escherichia coli* K-12. J Bacteriol. Apr. 1986;166(1):253-9.

Guardiola et al., *Escherichia coli* K-12 mutants altered in the transport of branched-chain amino acids. J Bacteriol. Dec. 1971;108(3):1034-44.

Guardiola et al., Mutations affecting the different transport systems for isoleucine, leucine, and valine in *Escherichia coli* K-12. J Bacteriol. Feb. 1974;117(2):393-405.

Guarner et al., Gut flora in health and disease. Lancet. Feb. 8, 2003;361(9356):512-9.

Haney et al., Lrp, a leucine-responsive protein, regulates branched-chain amino acid transport genes in *Escherichia coli*. J Bacteriol. Jan. 1992;174(1):108-15.

Hasegawa et al., Activation of a consensus FNR-dependent promoter by DNR of Pseudomonas aeruginosa in response to nitrite. FEMS Microbiol Lett. Sep. 15, 1998;166(2):213-7.

Heatwole et al., The tryptophan-specific permease gene, mtr, is differentially regulated by the tryptophan and tyrosine repressors in *Escherichia coli* K-12. J Bacteriol. Jun. 1991;173(11):3601-4.

Higgins, ABC transporters: from microorganisms to man. Annu Rev Cell Biol. 1992;8:67-113.

Hoeren et al., Sequence and expression of the gene encoding the respiratory nitrous-oxide reductase from Paracoccus denitrificans. New and conserved structural and regulatory motifs. Eur J Biochem. Nov. 15, 1993;218(1):49-57.

Horsburgh et al., MntR modulates expression of the PerR regulon and superoxide resistance in *Staphylococcus aureus* through control of manganese uptake. Mol Microbiol. Jun. 2002;44(5):1269-86.

Horsburgh et al., PheP, a putative amino acid permease of *Staphylococcus aureus*, contributes to survival in vivo and during starvation. Infect Immun. May 2004;72(5):3073-6.

Hu et al., Membrane topology of the *Escherichia coli* gamma-aminobutyrate transporter: implications on the topography and mechanism of prokaryotic and eukaryotic transporters from the APC superfamily. Biochem J. Nov. 15; 1998;336 ( Pt 1):69-76.

Huibregtse et al., Genetically Modified Lactococcus lactis for Delivery of Human Interleukin-10 to Dendritic Cells. Gastroenterol Res Pract. 2012;2012:639291. 8 pages.

Isabella et al., Deep sequencing-based analysis of the anaerobic stimulon in Neisseria gonorrhoeae. BMC Genomics. Jan. 20, 2011;12:51. 24 pages.

Isabella et al., Functional analysis of NsrR, a nitric oxide-sensing Rrf2 repressor in Neisseria gonorrhoeae. Mol Microbiol. Jan. 2009;71(1):227-39.

Isabella et al., Identification of a conserved protein involved in anaerobic unsaturated fatty acid synthesis in Neiserria gonorrhoeae: implications for facultative and obligate anaerobes that lack FabA. Mol Microbiol. Oct. 2011;82(2):489-501.

Jack et al., The amino acid/polyamine/organocation (APC) superfamily of transporters specific for amino acids, polyamines and organocations. Microbiology. Aug. 2000;146 ( Pt 8):1797-814.

Jennings et al., Cloning and molecular analysis of the *Salmonella enterica* ansP gene, encoding an L-asparagine permease. Microbiology. Jan. 1995;141 ( Pt 1):141-6.

Jensen et al., Manganese Transport, Trafficking and Function in Invertebrates. Issues in Toxicology No. 22, Manganese in Health and Disease. Lucio G. Costa (Ed.). The Royal Society of Chemistry. Chapter 1, pp. 1-33 (2015).

Jolkver et al., Identification and characterization of a bacterial transport system for the uptake of pyruvate, propionate, and acetate in Corynebacterium glutamicum. J Bacteriol. Feb. 2009;191(3):940-8.

Kadaba et al., The high-affinity *E. coli* methionine ABC transporter: structure and allosteric regulation. Science. Jul. 11, 2008;321(5886):250-3.

Chen et al., High-level Expression of Phenylalanine Ammonia-lyase in Lactococcus lactis via Synthesized Sequence Based on Bias Codons. Chinese Journal of Biotechnology. 22(2):187-90.

Jia et al., A new strategeutics of gene therapy for hyperphenylalaninemia rats. National Medical Journal of China, 2000 Issue 06, English Abstract. Retrieved from: http://en.cnki.com.cn/Article_en/CJFDTOTAL-ZHYX200006029.htm. 3 pages. (2000).

Sarkissian et al., A different approach to treatment of phenylketonuria: Phenylalanine degradation with recombinant phenylalanine ammonia lyase. Proc Natl Acad Sci USA. Mar. 1999;96:2339-44.

U.S. Appl. No. 15/402,147, filed Jan. 9, 2017, 2017-0216370.

U.S. Appl. No. 14/960,333, filed Dec. 4, 2015, U.S. Pat. No. 9,487,764.

U.S. Appl. No. 15/164,828, filed May 25, 2016, U.S. Pat. No. 9,688,967.

U.S. Appl. No. 15/599,285, filed May 18, 2017, 2017-0253862.

\* cited by examiner

FIG. 4. Uptake of phenylalanine (□), tyrosine (◇), and tryptophan (○) (10 µM) by *E. coli* strain JP7910 carrying pMU4784 with *pheP* expressed from the *aroP* transcription and translation regions (a) and pMU2195 carrying *aroP* (b). DW, dry weight.

- Phe uptake activity similar between 2 transporters when expressed from same transcription/translation signals

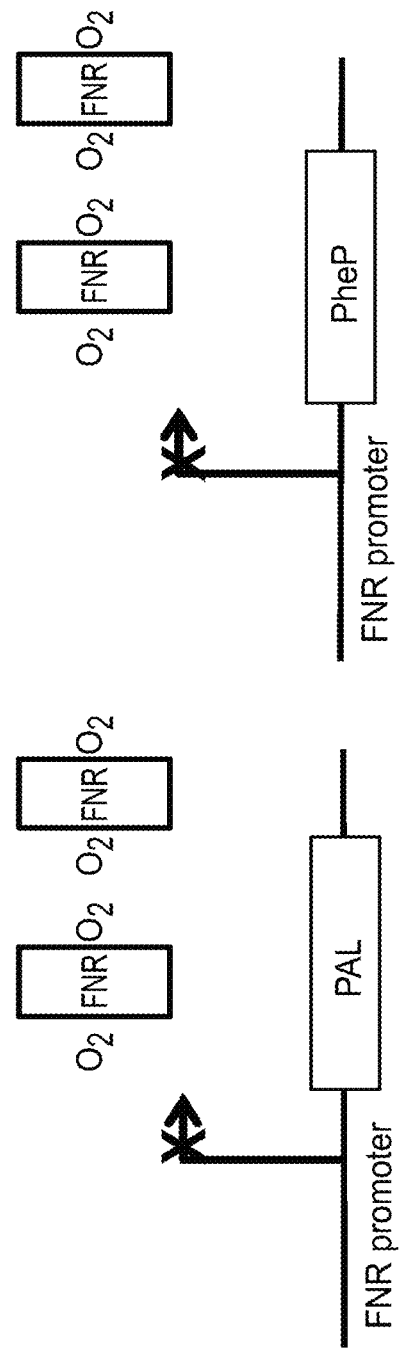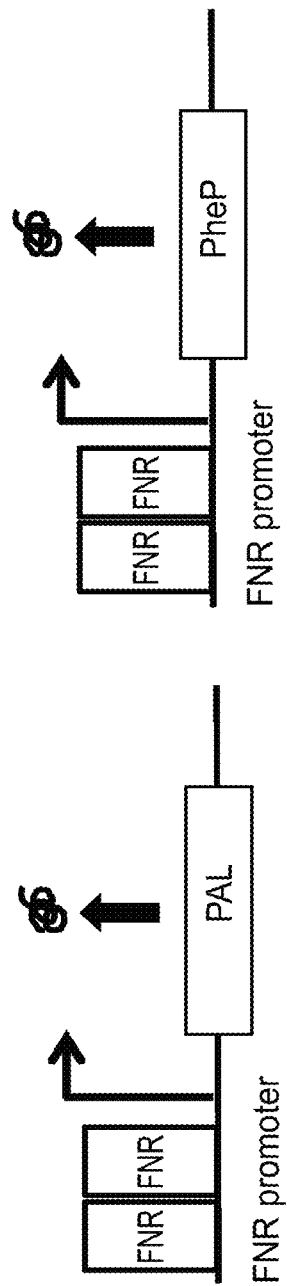
FIG. 9A
FIG. 9B

LC = low copy
HC = high copy

FIG. 13 Branched-Chain Amino Acids Metabolism

FIG. 17

Components of Exemplary BCAA Synthetic Probiotics

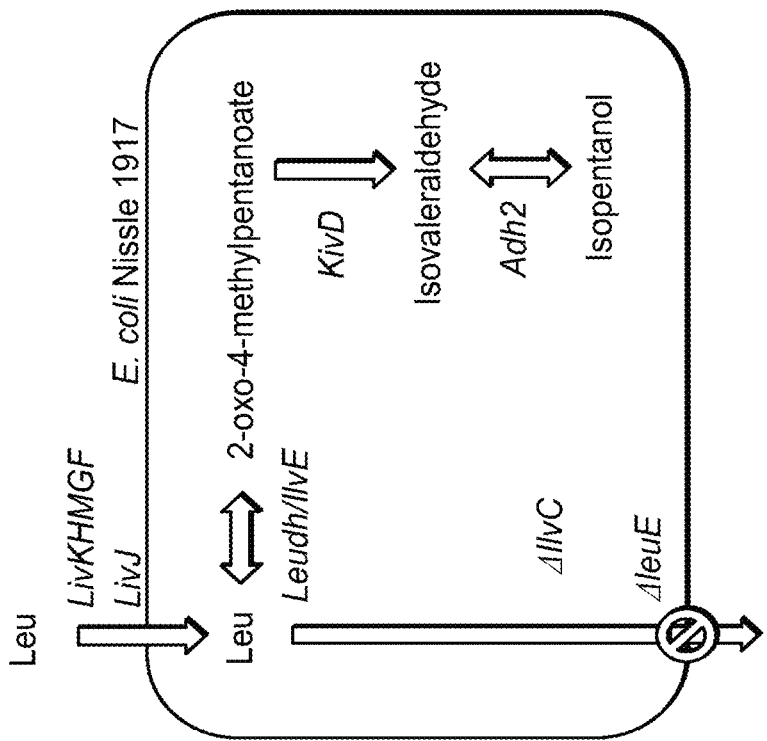

- livKHMGF: high-affinity leucine transporter
  – brings Leucine into the cell

- LivJ: Isoleucine/leucine/valine binding protein
  – Brings branched chain amino acids into the cell

- Leudh: leucine dehydrogenase
  – E.g., derived from *P. aeruginosa*
  – makes the α-ketoacid

- IlvE: branched chain amino acid aminotransferase
  – makes the α-ketoacid

- KivD: branched-chain α-ketoacid decarboxylase
  – E.g., Derived from *Lactococcus lactis* IFPL730

- Adh2: aldehyde dehydrogenase 2
  – E.g., Derived from *S. cerevisiae*

- LeuE: leucine exporter
  – Knockout keeps intracellular leucine concentration high

- IlvC: keto acid reductoisomerase
  – Required for branched chain amino acid synthesis
  – Knockout creates auxotroph and requires the cell to import leucine to survive

FIG. 18

Components of Exemplary BCAA Synthetic Probiotics

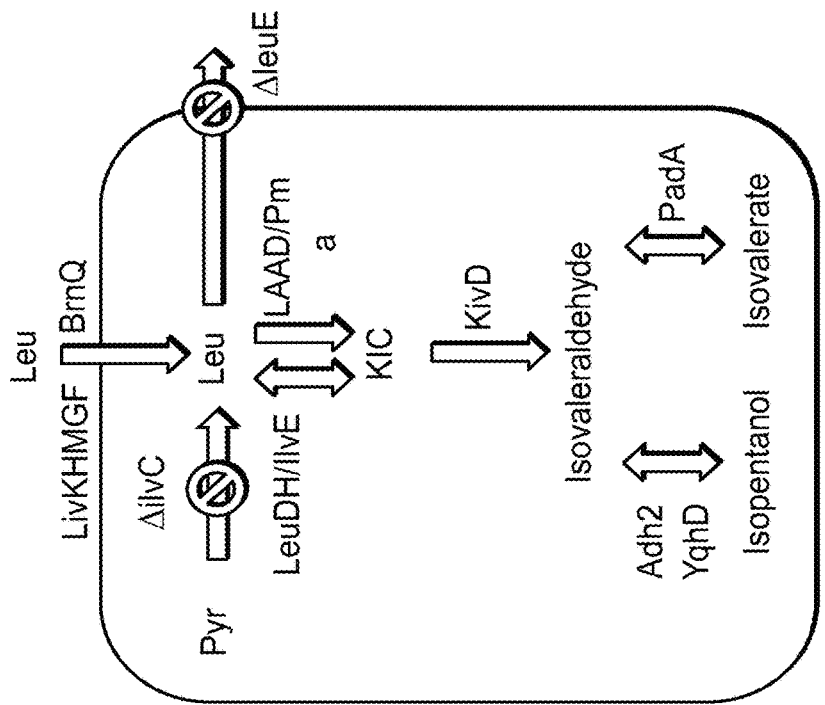

- livKHMGF: high-affinity leucine transporter
- BrnQ: low-affinity BCAA transporter
- LeuDH: leucinede hydrogenase
  - E.g., Derived from *Pseudomonas aeruginosa* PA01 or *Bacillus cereus*
- IlvE: BCAA aminotransferase
- LAAD: L-amino acid deaminase
  - E.g., Derived from *Proteus vulgaris* or *P. mirabilis*
- KivD: branched-chain α-ketoacid decarboxylase
  - E.g., Derived from *Lactococcus lactis*IFPL730
- Adh2, YqhD: alcohol dehydrogenase
  - Adh2: e.g., derived from *S. cerevisiae*
  - YqhD: e.g., from *E. coli*
- PadA: aldehyde dehydrogenase
  - E.g., derived from E. Coli K12, absent in E. Coli Nissle
- LeuE: leucine exporter
- IlvC: acetohydroxy acid isomeroreductase
  - Deletion leads to BCAA auxotrophy

FIG. 19

Example Components of an MSUD Synthetic Biotic

- Ldh (Leucine dehydrogenase)
  - Derived from *Pseudomonas aeruginosa* PA01
  - Active against leucine, isoleucine and valine
  - Octamer
  - Cofactor: NAD+
- KivD (Branched-chain α-ketoacid decarboxylase)
  - Derived from *Lactococcus lactis* IFPL730
  - Active against leucine, isoleucine and valine-derived α-ketoacids
  - Homotetramer
  - Cofactors: TPP, Mg$^{2+}$
- LivKHMGF (High-affinity leucine transporter)
  - ABC transporter
  - 5 subunits
    - LivK: periplasmic amino acid-binding protein
    - LivHM: membrane subunits
    - LivGF: ATP-binding subunits
- Adh: aldehyde dehydrogenase 2
  - Derived from *S. cerevisiae*
- *leuE* (encodes leucine exporter) also deleted from strain to maximize leucine accumulation

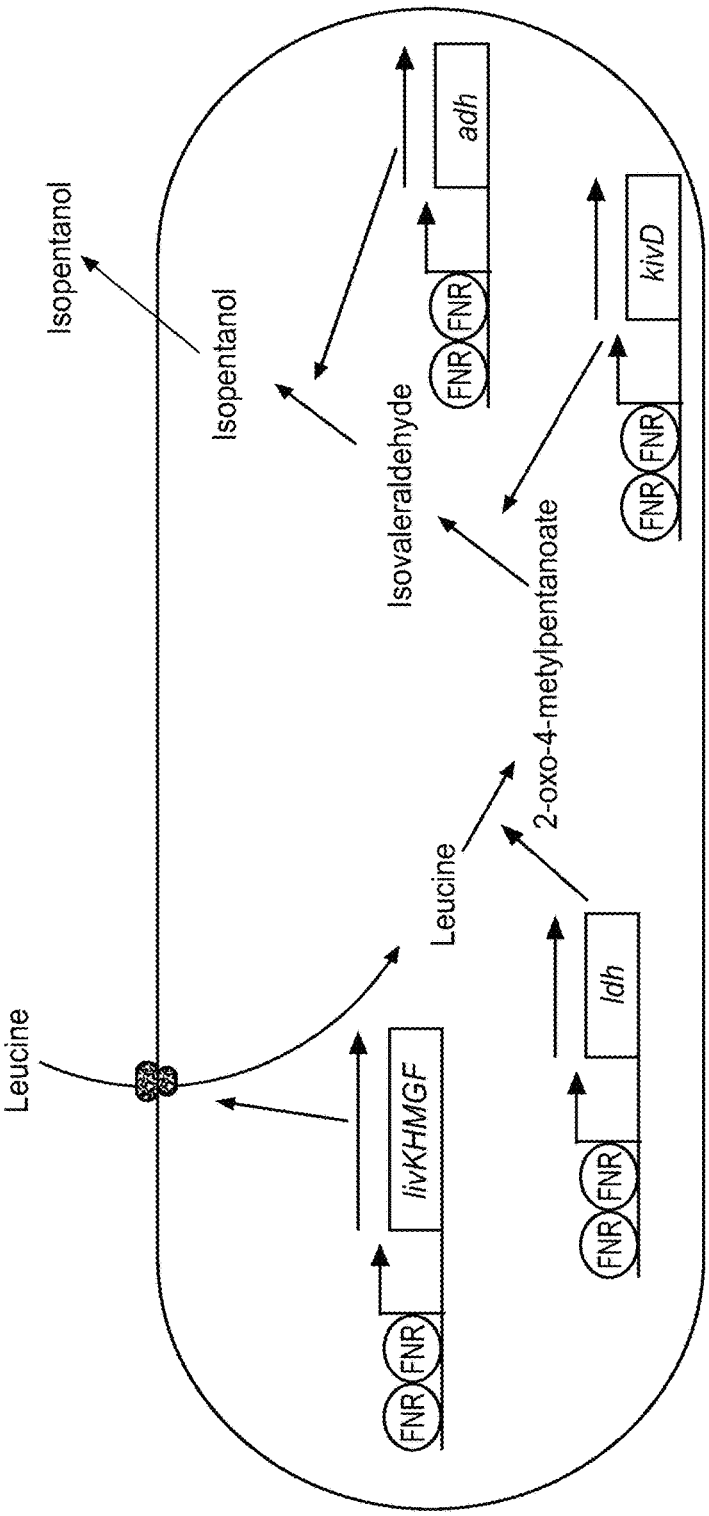

MSUD constructs for leucine degradation

Constructs expressed on a high-copy plasmid

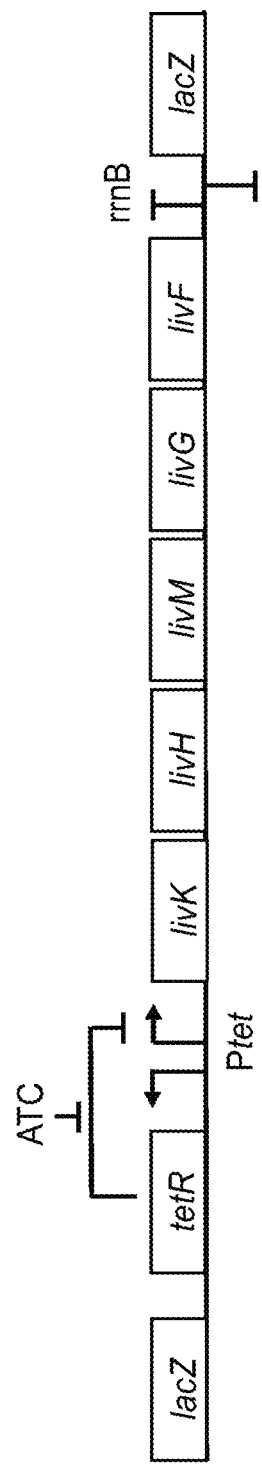
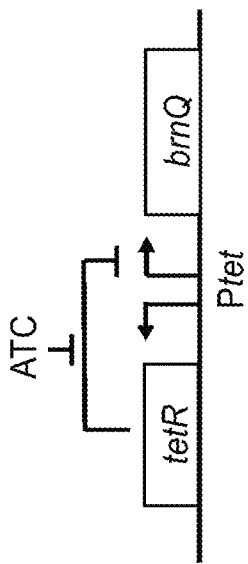
FIG. 22

FIG. 29  Components for *ldh*, *kivD* and *livKHMGF* Inducible Expression in *E. coli*

- Component #1: *kivD* cloned in a high-copy plasmid under the control of the Tet promoter

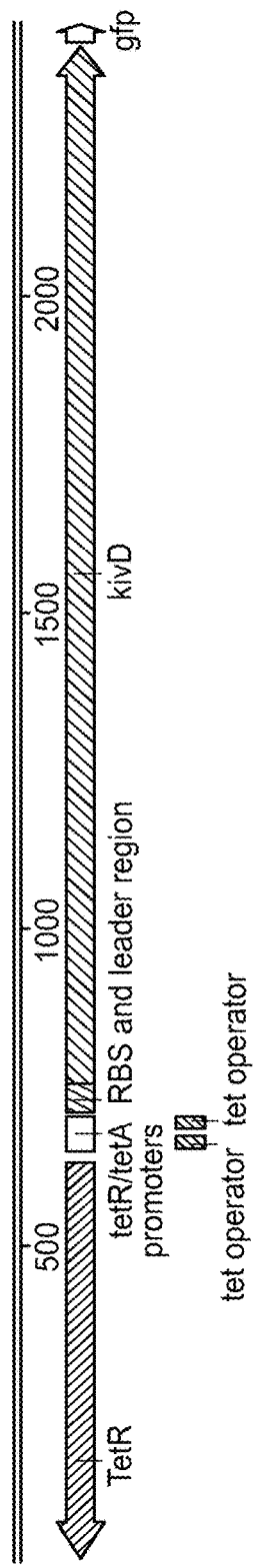

- Component #2: *kivD* and *ldh* cloned in a high-copy plasmid under the control of the Tet promoter

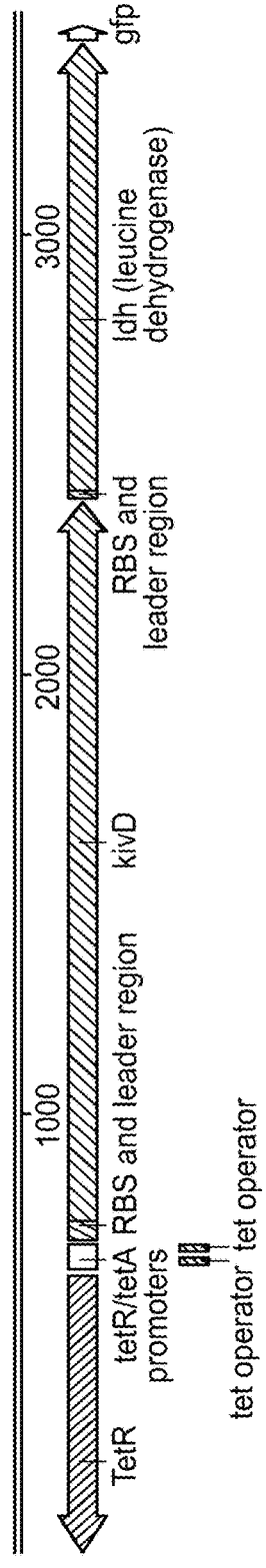

- Component #3: *livKHMGF* operon under the control of the Tet promoter, flanked by *lacZ* homologous region for chromosomal integration by lambda-red recombination

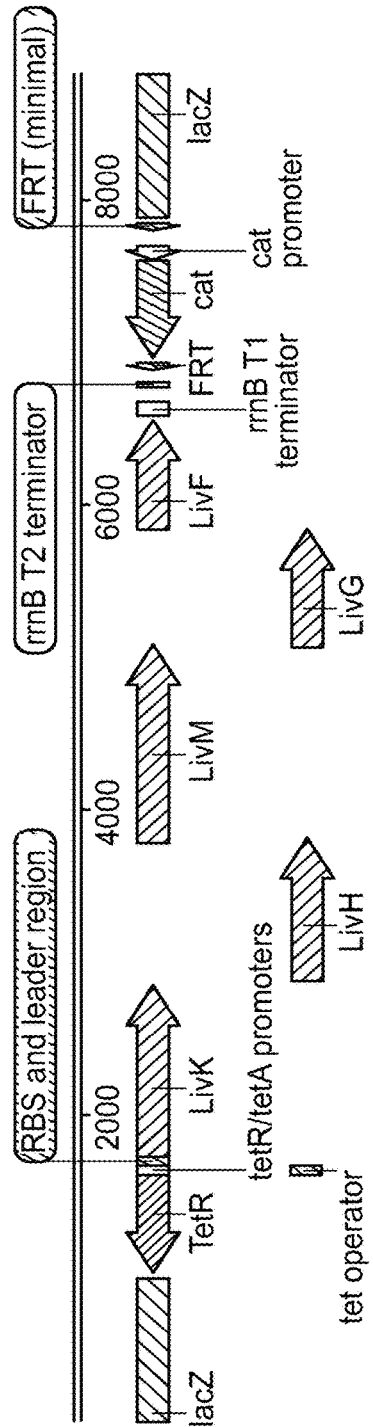

SEQUENCE LISTING

<160> NUMBER OF SEQ ID NOS: 172

<210> SEQ ID NO 1
<211> LENGTH: 290
<212> TYPE: DNA
<213> ORGANISM: Escherichia coli
<220> FEATURE:
<221> NAME/KEY: misc_feature
<222> LOCATION: (1)..(290)
<223> OTHER INFORMATION: FNR Responsive Promoter

<400> SEQUENCE: 1
gtcagcataa cacoctgacc tctcattaat tgttcatgcc gggcggcact atcgtcgtcc      60
ggccttttcc tctcttactc tgctacgtac atctatttct ataaatccgt tcaatttgtc     120
tgttttttgc acaaacatga aatatcgac aattccgtga cttaagaaaa tttatacaaa     180
tcagcaatat accccttaag gagtatataa aggtgaattt gatttacatc aataagcggg     240
gttgctgaat cgttaaggta ggcggtaata gaaaagaaat cgaggcaaaa                 290

<210> SEQ ID NO 2
<211> LENGTH: 173
<212> TYPE: DNA
<213> ORGANISM: Escherichia coli
<220> FEATURE:
<221> NAME/KEY: misc_feature
<222> LOCATION: (1)..(173)
<223> OTHER INFORMATION: FNR Responsive Promoter

<400> SEQUENCE: 2

```
atttcctctc atcccatccg gggtgagagt cttttccccc gacttatggc tcatgcatgc    60
atcaaaaaag atgtgagctt gatcaaaaac aaaaaatatt tcactcgaca ggagtattta   120
tattgcgccc gttacgtggg cttcgactgt aaatcagaaa ggagaaaaca cct          173
```

<210> SEQ ID NO 3
<211> LENGTH: 305
<212> TYPE: DNA
<213> ORGANISM: Escherichia coli
<220> FEATURE:
<221> NAME/KEY: misc_feature
<222> LOCATION: (1)..(305)
<223> OTHER INFORMATION: FNR Responsive Promoter

<400> SEQUENCE: 3

```
gtcagcataa caccctgacc tctcattaat tgttcatgcc gggcggcact atcgtcgtcc    60
ggccttttcc tctcttactc tgctacgtac atctatttct ataaatccgt tcaatttgtc   120
tgttttttgc acaaacatga aatatcagac aattccgtga cttaagaaaa tttatacaaa   180
tcagcaatat accccttaag gagtatataa aggtgaattt gatttacatc aataagcggg   240
gttgctgaat cgttaaggat ccctctagaa ataattttgt ttaactttaa gaaggagata   300
tacat                                                              305
```

<210> SEQ ID NO 4
<211> LENGTH: 180
<212> TYPE: DNA
<213> ORGANISM: Escherichia coli
<220> FEATURE:
<221> NAME/KEY: misc_feature
<222> LOCATION: (1)..(180)
<223> OTHER INFORMATION: FNR Responsive Promoter

<400> SEQUENCE: 4

```
catttcctct catcccatcc ggggtgagag tcttttcccc cgacttatgg ctcatgcatg    60
catcaaaaaa gatgtgagct tgatcaaaaa caaaaaatat ttcactcgac aggagtattt   120
atattgcgcc cggatccctc tagaaataat tttgtttaac tttaagaagg agatatacat   180
```

<210> SEQ ID NO 5
<211> LENGTH: 199
<212> TYPE: DNA
<213> ORGANISM: Escherichia coli
<220> FEATURE:
<221> NAME/KEY: misc_feature
<222> LOCATION: (1)..(199)
<223> OTHER INFORMATION: FNR Responsive Promoter

<400> SEQUENCE: 5

```
agttgttctt attggtggtg ttgctttatg gttgcatcgt agtaaatggt tgtaacaaaa    60 gcaattttc cggctgtctg tatacaaaaa cgccgtaaag tttgagcgaa gtcaataaac    120
tctctaccca ttcagggcaa tatctctctt ggatccctct agaaataatt ttgtttaact   180
ttaagaagga gatatacat                                                199
```

<210> SEQ ID NO 6
<211> LENGTH: 1647
<212> TYPE: DNA
<213> ORGANISM: Lactococcus lactis
<220> FEATURE:
<221> NAME/KEY: misc_feature
<222> LOCATION: (1)..(1647)
<223> OTHER INFORMATION: kivD (Lactococcus lactis IFPL730)

<400> SEQUENCE: 6

```
atgtatacag taggagatta cctattagac cgattacacg agttaggaat tgaagaaatt        60
tttggagtcc ctggagacta taacttacaa ttttttagatc aaattatttc ccacaaggat      120
atgaaatggg tcggaaatgc taatgaatta atgcttcat atatggctga tggctatgct        180
cgtactaaaa aagctgccgc atttcttaca acctttggag taggtgaatt gagtgcagtt      240
aatggattag caggaagtta cgccgaaaat ttaccagtag tagaaatagt gggatcacct      300
acatcaaaag ttcaaaatga aggaaaattt gttcatcata cgctggctga cggtgatttt      360
aaacactta tgaaaatgca cgaacctgtt acagcagctc gaactttact gacagcagaa        420
aatgcaaccg ttgaaattga ccgagtactt tctgcactat aaaagaaag aaaacctgtc        480
tatatcaact taccagttga tgttgctgct gcaaaagcag agaaaccctc actccctttg      540
aaaaaggaaa actcaacttc aaatacaagt gaccaagaaa ttttgaacaa aattcaagaa      600
agcttgaaaa atgccaaaaa accaatcgtg attacaggac atgaaataat tagttttggc      660
ttagaaaaaa cagtcactca atttatttca aagacaaaac tacctattac gacattaaac      720
tttggtaaaa gttcagttga tgaagccctc ccttcatttt taggaatcta taatggtaca      780
ctctcagagc taatcttaa agaattcgtg gaatcagccg acttcatctt gatgcttgga      840
gttaaactca cagactcttc aacaggagcc ttcactcatc atttaaatga aaataaaatg      900
atttcactga atatagatga aggaaaaata tttaacgaaa gaatccaaaa ttttgatttt      960
gaatccctca tctcctctct cttagaccta agcgaaatag aatacaaagg aaaatatatc     1020
gataaaaagc aagaagactt tgttccatca aatgcgcttt tatcacaaga ccgcctatgg     1080
caagcagttg aaaacctaac tcaaagcaat gaaacaatcg ttgctgaaca agggacatca     1140
ttctttggcg cttcatcaat tttcttaaaa tcaaagagtc atttattgg tcaacccta      1200
tggggatcaa ttggatatac attcccagca gcattaggaa gccaaattgc agataaagaa     1260
agcagacacc ttttatttat tggtgatggt tcacttcaac ttacagtgca agaattagga     1320
ttagcaatca gagaaaaaat taatccaatt tgctttatta tcaataatga tggttataca     1380
gtcgaaagag aaattcatgg accaaatcaa agctacaatg atattccaat gtggaattac     1440
tcaaaattac cagaatcgtt tggagcaaca gaagatcgag tagtctcaaa aatcgttaga     1500
actgaaaatg aatttgtgtc tgtcatgaaa gaagctcaag cagatccaaa tagaatgtac     1560
tggattgagt taattttggc aaaagaaggt gcaccaaaag tactgaaaaa atgggcaaa      1620
ctatttgctg aacaaaataa atcataa                                         1647
```

<210> SEQ ID NO 7
<211> LENGTH: 5739
<212> TYPE: DNA
<213> ORGANISM: Artificial Sequence
<220> FEATURE:
<223> OTHER INFORMATION: Synthetic: Tet-bkd construct sequence

<400> SEQUENCE: 7

```
gtaaaacgac ggccagtgaa ttcgttaaga cccacttca catttaagtt gtttttctaa        60
tccgcatatg atcaattcaa ggccgaataa gaaggctggc tctgcacctt ggtgatcaaa      120
taattcgata gcttgtcgta ataatggcgg catactatca gtagtaggtg tttcccttc      180
ttctttagcg acttgatgct cttgatcttc caatacgcaa cctaaagtaa aatgccccac      240
agcgctgagt gcatataatg cattctctag tgaaaaacct tgttggcata aaaaggctaa      300
```

```
ttgattttcg agagtttcat actgtttttc tgtaggccgt gtacctaaat gtacttttgc    360
tccatcgcga tgacttagta aagcacatct aaaacttttta gcgttattac gtaaaaaatc   420
ttgccagctt tccccttcta aagggcaaaa gtgagtatgg tgcctatcta acatctcaat    480
ggctaaggcg tcgagcaaag cccgcttatt ttttacatgc caatacaatg taggctgctc    540
tacacctagc ttctgggcga gtttacgggt tgttaaacct tcgattccga cctcattaag    600
cagctctaat gcgctgttaa tcactttact tttatctaat ctagacatca ttaattccta    660
atttttgttg acactctatc attgatagag ttattttacc actccctatc agtgatagag    720
aaaagtgaac tctagaaata attttgttta actttaagaa ggagatatac atatgagtga    780
ttacgagccg ttgcgtctgc atgtcccgga gcccaccggg cgtcctggct gcaagaccga    840
cttttcctat ctgcacctgt cccccgccgg cgaggtacgc aagccgccgg tggatgtcga    900
gcccgccgaa accagcgacc tggcctacag cctggtacgt gtgctcgacg acgacggcca    960
cgccgtcggt ccctggaatc cgcagctcag caacgaacaa ctgctgcgcg catgcgggc    1020
gatgctcaag acccgcctgt cgacgcgcg catgctcacc gcgcaacggc agaaaaagct   1080
ttccttctat atgcaatgcc tcggcgagga agccatcgcc accgcccaca ccctggccct   1140
gcgcgacggc gacatgtgct ttccgaccta tcgccagcaa ggcatcctga tcacccgcga   1200
atacccgctg gtggacatga tctgccagct tctctccaac gaggccgacc cgctcaaggg   1260
ccgccagctg ccgatcatgt actcgagcaa ggaggcaggt tcttctccaa tctccggcaa   1320
cctcgccacc cagttcatcc aggcggtcgg ctggggcatg gcctcggcga tcaagggcga   1380
cacgcgcatc gcctcggcct ggatcggcga cggcgccacc gccgagtcgg acttccacac   1440
cgccctcacc ttcgcccatg tctaccgcgc gccggtaatc ctcaacgtgg tcaacaacca   1500
gtgggcgatc tccaccttcc aggccatcgc cggcggcgaa ggcaccacct tcgccaaccg   1560
tggcgtgggc tgcgggatcg cctcgctgcg ggtcgacggc aatgacttcc tggcggtcta   1620
cgccgcctcc gagtgggccg ccgagcgcgc ccggcgcaac ctcgggccga gcctgatcga   1680
atgggtcacc taccgcgccg gcccgcactc gacttcggac gacccgtcca agtaccgccc   1740
cgccgacgac tggaccaact tcccgctggg cgacccgatc gcccgcctga gcggcacat    1800
gatcggcctc ggcatctggt cggaggaaca gcacgaagcc acccacaagg ccctcgaagc   1860
cgaagtactg gccgcgcaga acaggcgga gagccatggc accctgatcg acggccgggt   1920
gccgagcgcc gccagcatgt cgaggacgt ctatgcagaa ctgccggagc atctgcgccg   1980
gcaacgccag gagctcgggg tatgaatgcc atgaacccgc aacacgagaa cgcccagacg   2040
gtcaccagca tgaccatgat ccaggcgctg cgctcggcga tggacatcat gctcgagcgc   2100
gacgacgacg tggtggtatt cggccaggac gtcggctact tcggcggcgt gttccgctgc   2160
accgaaggcc tgcagaagaa atacggcacc tcgcgggtgt tcgatgcgcc gatctccgag   2220
agcggcatca tcggcgccgc ggtcggcatg ggtgcctacg gcctgcgccc ggtggtggag   2280
atccagttcg ccgactacgt ctacccggcc tccgaccagt tgatctccga ggcggcgcgc   2340
ctgcgctatc gctcggccgg cgacttcatc gtgccgatga ccgtacgcat gcctgtggc   2400
ggcggcatct acgcgggca aacgcacagc cagagcccgg aggcgatgtt cacccaggtc   2460
tgcggcctgc gcacggtgat gccgtccaac ccctacgacg ccaagggcct gctgatcgcc   2520
tgcatcgaga cgacgacccc ggtgatcttc ctcgagccca gcgcctcta caacggcccg   2580
ttcgatggcc accacgaccg cccggtgacg ccctggtcca agcatccggc cagccaggtg   2640
ccggacggct actacaaggt gccgctggac aaggcggcga tcgtccgccc cggcgcggcg   2700
```

```
ctgaccgtgc tgacctacgg caccatggtc tacgtggccc aggccgcggc cgacgaaacc   2760
ggcctggacg ccgagatcat cgacctgcgc agcctctggc cgctggacct ggaaaccatc   2820
gtcgcctcgg tgaagaagac cggccgctgc gtcatcgccc acgaggcgac ccgcacctgt   2880
gggttcggcg ccgagctgat gtcgctggtg caggagcact gcttccacca cctggaggcg   2940
ccgatcgagc gcgtcaccgg ttgggacacc ccctacccgc atgcccagga gtgggcgtat   3000
ttccccggcc ccgcgcgcgt cggcgcggca ttcaagcgtg tgatggaggt ctgaatgggt   3060
acccatgtga tcaagatgcc ggacatcggg aaggcatcg ccgaggtcga actggtggag    3120
tggcatgtcc aggtcggcga ctcggtcaat aagaccagg tcctcgccga ggtgatgacc    3180
gacaaggcca cggtggagat tccctcgccg gtggccggac gcatcctcgc cctcggcggc   3240
cagccgggcc aggtgatggc ggtgggcggc gaactgatcc gcctggaggt ggaaggcgcc   3300
ggcaacctcg ccgagagtcc ggccgcggcg acgccggccg cgcccgtcgc cgccaccccg   3360
gagaaaccga aggaagcccc ggtcgcggcg ccgaaagccg ccgccgaagc gccgcgcgcc   3420
ttgcgcgaca gcgaggcgcc acggcagcgg cgccagcccg cgaacgccc gctggcctcc    3480 cccgcggtgc gccagcgcgc ccgcgacctg ggcatcgagt tgcagttcgt gcagggcagc   3540
ggtcccgccg gacgcgtcct ccacgaggac ctcgatgcct acctgaccca ggatggcagc   3600
gtcgcgcgca gcgcggcgc cgcgcagggg tatgccgagc gacacgacga acaggcggtg    3660
ccggtgatcg gcctgcgtcg caagatcgcc cagaagatgc aggacgccaa gcgacgcatc   3720
ccgcatttca gctatgtcga ggaaatcgac gtcaccgatc tggaagccct gcgcgcccat   3780
ctcaaccaga aatggggtgg ccagcgcggc aagctgaccc tgctgccgtt cctggtccgc   3840
gccatggtcg tggcgctgcg cgacttcccg cagttgaacg cgcgctacga cgacgaggcc   3900
gaggtggtca cccgctacgg cgcggtgcac gtcggcatcg ccacccagag cgacaacggc   3960
ctgatggtgc cggtgctgcg ccacgccgaa tcgcgcgacc tctggggcaa cgccagcgaa   4020
gtggcgcgcc tggccgaagc cgcacgcagc ggcaaggcgc aacgccagga gctgtccggc   4080
tcgaccatca ccctgagcag cctcggcgtg ctcggcggga tcgtcagcac accggtgatc   4140
aaccatccgg aggtggccat cgtcggcgtc aaccgcatcg tcgagcgacc gatggtggtc   4200
ggcggcaaca tcgtcgtgcg caagatgatg aacctctcct cctccttcga ccaccgggtg   4260
gtcgacggga tggacgcggc ggccttcatc caggccgtgc gcggcctgct cgaacatccc   4320
gccaccctgt tcctggagta agcgatgagc cagatcctga agacttccct gctgatcgtc   4380
ggcggcggtc ccgcggccta cgtcgcgcg atccgtgccg gcaactggg cattcccacc    4440 gtactggtgg agggcgccgc cctcggcggc acctgtctga cgtcggctg catcccgtcg    4500 aaggcgctga tccacgccgc cgaggaatac ctcaaggccc gccactatgc cagccggtcg   4560
gcgctgggca tccaggtaca ggcgccgagc atcgacatcg cccgcaccgt ggaatggaag   4620
gacgccatcg tcgaccgcct caccagcggc gtcgccgcgc tgctgaagaa cacggggtc    4680 gatgtcgtcc agggctgggc gaggatcctc gacggcaaaa gcgtggcggt cgaactcgcc   4740
ggcggcggca gccagcgcat cgagtgcgag catctgctgc tggccgccgg ctcgcagagc   4800
gtcgagctac cgatcctgcc gctgggcggc aaggtgatct cctccaccga ggcgctggcg   4860
cccggcagcc tgcccaagcg cctggtggtg gtcggcggcg gctacatcgg cctggagctg   4920
ggtaccgcct accgcaagct cggcgtcgag gtggcggtgg tggaagcgca accacgcatc   4980
ctgccgggct acgacgaaga actgaccaag ccggtggccc aggccttgcg caggctgggc   5040
```

```
gtcgagctgt acctcgggca cagcctgctg ggcccgagcg agaacggcgt gcgggtccgc    5100
gacggcgccg gcgaggagcg cgagatcgcc gccgaccagg tactggtggc ggtcggccgc    5160
aagccgcgca gcgaaggctg gaacctggaa agcctgggcc tggacatgaa cggccgggcg    5220
gtgaaggtcg acgaccagtg ccgcacctcg atgcgcaatg tctgggccat aggcgatctc    5280
gccggcgagc cgatgctcgc gcaccgggcc atggcccagg gcgagatggt cgccgagctg    5340
atcgccggca gcgtcgcca gttcgccccg gtggcgatcc ccgcggtgtg cttcaccgat    5400
ccggaagtgg tggtcgccgg gttgtccccg gagcaggcga aggatgccgg cctggactgc    5460
ctggtggcga gcttcccgtt cgccgccaac ggtcgcgcca tgaccctgga ggccaacgaa    5520
ggcttcgtcc gcgtggtggc gcgtcgcgac aaccacctgg tcgtcggctg gcaggcggtg    5580
ggcaaggcgg tttcggaact gtccacggcc ttcgcccagt cgctggagat gggcgcccgc    5640
ctggaagaca tcgccggcac catccacgcc catccgaccc tcggcgaagc ggtccaggaa    5700
gccgccctgc gcgcgctggg acacgccctg cacatctga                         5739
```

<210> SEQ ID NO 8
<211> LENGTH: 6780
<212> TYPE: DNA
<213> ORGANISM: Artificial Sequence
<220> FEATURE:
<223> OTHER INFORMATION: Synthetic: Tet-ldh-bkd construct

<400> SEQUENCE: 8

```
gtaaaacgac ggccagtgaa ttcgttaaga cccactttca catttaagtt gttttttctaa      60 tccgcatatg atcaattcaa ggccgaataa gaaggctggc tctgcacctt ggtgatcaaa     120
taattcgata gcttgtcgta ataatggcgg catactatca gtagtaggtg tttcccttc     180 ttctttagcg acttgatgct cttgatcttc aatacgcaa cctaaagtaa aatgccccac     240
agcgctgagt gcatataatg cattctctag tgaaaaacct tgttggcata aaaaggctaa     300
ttgattttcg agagtttcat actgtttttc tgtaggccgt gtacctaaat gtactttgc     360 tccatcgcga tgacttagta aagcacatct aaaactttta gcgttattac gtaaaaaatc     420
ttgccagctt tccccttcta aagggcaaaa gtgagtatgg tgcctatcta acatctcaat     480
ggctaaggcg tcgagcaaag cccgcttatt ttttacatgc aatacaatg taggctgctc     540 tacacctagc ttctgggcga gtttacgggt tgttaaacct tcgattccga cctcattaag     600
cagctctaat gcgctgttaa tcactttact tttatctaat ctagacatca ttaattccta     660 attttttgttg acactctatc attgatagag ttattttacc actccctatc agtgatagag     720
aaaagtgaac tctagaaata attttgttta actttaagaa ggagatatac atatgttcga     780
catgatggac gcggcccggc tcgagggtct gcacctcgcc caagacccgg ccacgggact     840
caaggccatt atcgccatcc acagcacgcg actcggcccg gcgctgggtg gttgtcgcta     900
cctgccttac cccaacgacg aagccgccat cggcgacgcc atccgcctgg cccagggcat     960
gagctacaag gcgccctgg ccgggctgga gcagggcggc ggcaaggcgg tgatcatccg    1020
cccgccgcac ctggacaatc gcggcgcgct gttcgaggcc ttcgggcgct tcatcgaaag    1080
cctcggcgga cgctacatca ctgccggtgga cagcggtacc tccagcgccg acatggactg    1140
catcgcccag cagacccgcc acgtcaccag caccacccag gccggcgacc cctcgccgca    1200
taccgccctc ggcgtgttcg ccgggattcg cgccagcgca caggcgcgcc tcggcagcga    1260
cgacctggaa ggcctgcggg tcgcggtgca ggggctcggc cacgtcggct acgcattggc    1320
cgagcaactg gcggcggtcg gcgccgagct gctggtctgc gacctcgatc ccggccgggt    1380
```

```
gcaactggcc gtcgagcagc tcggtgccca tccgctggcg ccggaggcat tgctctccac   1440
cccttgcgac atcctcgcgc cctgcggcct gggcggcgtg ctcaccagcc agagcgtcag   1500
ccagttgcgc tgcgcggcgg tggccggggc ggcgaacaac cagttggagc ggccggaggt   1560
cgccgacgag ctggaggcgc gcggcatcct ctatgcgccg gactacgtga tcaactccgg   1620
cggcctgatc tacgtcgccc tcaagcaccg cggcgccgat ccgcacagca tcaccgcgca   1680 cctggcgcg attcccgcgc ggctcaccga gatctatgcc catgcccagg ccgaccacca   1740
gtcgccggcg cggatcgccg accgtctggc ggaacggatt ctctacggcc gcagtgaga   1800 aggagatata catatgagtg attacgagcc gttgcgtctg catgtcccgg agcccaccgg   1860
gcgtcctggc tgcaagaccg acttttccta tctgcacctg tccccgccg gcgaggtacg   1920 caagccgccg gtggatgtcg agccgccga accagcgac ctggcctaca gcctggtacg   1980
tgtgctcgac gacgacggcc acgccgtcgg tccctggaat ccgcagctca gcaacgaaca   2040
actgctgcgc ggcatgcggg cgatgctcaa gacccgcctg ttcgacgcgc gcatgctcac   2100
cgcgcaacgg cagaaaaagc tttccttcta tatgcaatgc ctcggcgagg aagccatcgc   2160
caccgcccac accctggccc tgcgcgacgg cgacatgtgc tttccgacct atcgccagca   2220
aggcatcctg atcacccgcg aatacccgct ggtggacatg atctgccagc ttctctccaa   2280
cgaggccgac ccgctcaagg gccgccagct gccgatcatg tactcgagca aggaggcagg   2340
tttcttctcc atctccggca acctcgccac ccagttcatc caggcggtcg gctgggcat   2400 ggcctcggcg atcaagggcg acacgcgcat cgcctcggcc tggatcggcg acggcgccac   2460
cgccgagtcg gacttccaca ccgccctcac cttcgcccat gtctaccgcg cgccggtaat   2520
cctcaacgtg gtcaacaacc agtgggcgat ctccaccttc caggccatcg ccggcggcga   2580
aggcaccacc ttcgccaacc gtggcgtggg ctgcgggatc gcctcgctgc gggtcgacgg   2640
caatgacttc ctggcggtct acgccgcctc cgagtgggcc gccgagcgcg cccggcgcaa   2700
cctcgggccg agcctgatcg aatgggtcac ctaccgcgcc ggcccgcact cgacttcgga   2760
cgacccgtcc aagtaccgcc ccgccgacga ctggaccaac ttcccgctgg gcgacccgat   2820
cgcccgcctg aagcggcaca tgatcggcct cggcatctgg tcggaggaac agcacgaagc   2880
cacccacaag gccctcgaag ccgaagtact ggccgcgcag aaacaggcgg agagccatgg   2940
caccctgatc gacggccggg tgccgagcgc cgccagcatg ttcgaggacg tctatgcaga   3000
actgccggag catctgcgcc ggcaacgcca ggagctcggg gtatgaatgc catgaacccg   3060
caacacgaga acgccagac ggtcaccagc atgaccatga tccaggcgct cgctcggcg   3120 atggacatca tgctcgagcg cgacgacgac gtggtggtat tcggccagga cgtcggctac   3180
ttcggcggcc tgttccgctg caccgaaggc ctgcagaaga aatacggcac ctcgcgggtg   3240
ttcgatgcgc cgatctccga gagcggcatc atcggcgccg cggtcggcat gggtgcctac   3300
ggcctgcgcc cggtggtgga gatccagttc gccgactacg tctacccggc ctccgaccag   3360
ttgatctccg aggcggcgcg cctgcgctat cgctcggccg gcgacttcat cgtgccgatg   3420
accgtacgca tgccctgtgg cggcggcatc tacggcgggc aaacgcacag ccagagcccg   3480
gaggcgatgt tcacccaggt ctgcggcctg cgcacggtga tgccgtccaa ccctacgac   3540 gccaagggcc tgctgatcgc ctgcatcgag aacgacgacc cggtgatctt cctcgagccc   3600
aagcgcctct acaacggccc gttcgatggc caccacgacc gcccggtgac gccctggtcc   3660
aagcatccgg ccagccaggt gccggacggc tactacaagg tgccgctgga caaggcggcg   3720
```

-continued

```
atcgtccgcc ccggcgcggc gctgaccgtg ctgacctacg gcaccatggt ctacgtggcc   3780
caggccgcgg ccgacgaaac cggcctggac gccgagatca tcgacctgcg cagcctctgg   3840
ccgctggacc tggaaaccat cgtcgcctcg gtgaagaaga ccggccgctg cgtcatcgcc   3900
cacgaggcga cccgcacctg tgggttcggc gccgagctga tgtcgctggt gcaggagcac   3960
tgcttccacc acctggaggc gccgatcgag cgcgtcaccg gttgggacac ccctacccg    4020
catgcccagg agtgggcgta ttccccggc cccgcgcgcg tcggcgcggc attcaagcgt    4080
gtgatggagg tctgaatggg tacccatgtg atcaagatgc cggacatcgg ggaaggcatc   4140
gccgaggtcg aactggtgga gtggcatgtc caggtcggcg actcggtcaa tgaagaccag   4200
gtcctcgccg aggtgatgac cgacaaggcc acggtggaga ttccctcgcc ggtggccgga   4260
cgcatcctcg ccctcggcgg ccagccgggc caggtgatgg cggtgggcgg cgaactgatc   4320
cgcctggagg tggaaggcgc cggcaacctc gccgagagtc cggccgcggc gacgccggcc   4380
gcgcccgtcg ccgccacccc ggagaaaccg aaggaagccc cggtcgcggc gccgaaagcc   4440
gccgccgaag cgccgcgcgc cttgcgcgac agcgaggcgc cacggcagcg cgccagccc    4500
ggcgaacgcc cgctggcctc ccccgcggtg cgccagcgcg cccgcgacct gggcatcgag   4560
ttgcagttcg tgcagggcag cggtcccgcc ggacgcgtcc tccacgagga cctcgatgcc   4620
tacctgaccc aggatggcag cgtcgcgcgc agcggcggcg ccgcgcaggg gtatgccgag   4680
cgacacgacg aacaggcggt gccggtgatc ggcctgcgtc gcaagatcgc ccagaagatg   4740
caggacgcca agcgacgcat cccgcatttc agctatgtcg aggaaatcga cgtcaccgat   4800
ctggaagccc tgcgcgccca tctcaaccag aaatggggtg ccagcgcgg  caagctgacc   4860
ctgctgccgt tcctggtccg cgccatggtc gtggcgctgc gcgacttccc gcagttgaac   4920
gcgcgctacg acgacgaggc cgaggtggtc acccgctacg gcgcggtgca cgtcggcatc   4980
gccacccaga gcgacaacgg cctgatggtg ccggtgctgc gccacgccga atcgcgcgac   5040
ctctggggca acgccagcga agtggcgcgc ctggccgaag ccgcacgcag cggcaaggcg   5100
caacgccagg agctgtccgg ctcgaccatc accctgagca gcctcggcgt gctcggcggg   5160
atcgtcagca caccggtgat caaccatccg gaggtggcca tcgtcggcgt caaccgcatc   5220
gtcgagcgac cgatggtggt cggcggcaac atcgtcgtgc gcaagatgat gaacctctcc   5280
tcctccttcg accaccgggt ggtcgacggg atggacgcgg cggccttcat ccaggccgtg   5340
cgcggcctgc tcgaacatcc cgccaccctg ttcctggagt aagcgatgag ccagatcctg   5400
aagacttccc tgctgatcgt cggcggcggt cccggcggct acgtcgcggc gatccgtgcc   5460
gggcaactgg gcattccac  cgtactggtg gagggcgccg cccctcggcgg cacctgtctg   5520
aacgtcggct gcatcccgtc gaaggcgctg atccacgccg ccgaggaata cctcaaggcc   5580
cgccactatg ccagccggtc ggcgctgggc atccaggtac aggcgccgag catcgacatc   5640
gcccgcaccg tggaatggaa ggacgccatc gtcgaccgcc tcaccagcgg cgtcgccgcg   5700
ctgctgaaga aacacggggt cgatgtcgtc cagggctggg cgaggatcct cgacggcaaa   5760
agcgtggcgg tcgaactcgc cggcggcggc agccagcgca tcgagtgcga gcatctgctg   5820
ctggccgccg gctcgcagag cgtcgagcta ccgatcctgc cgctgggcgg caaggtgatc   5880
tcctccaccg aggcgctggc gccggcagc  ctgcccaagc gcctggtggt ggtcggcggc   5940
ggctacatcg gcctggagct gggtaccgcc taccgcaagc tcggcgtcga ggtggcggtg   6000
gtggaagcgc aaccacgcat cctgccgggc tacgacgaag aactgaccaa gccggtggcc   6060
caggccttgc gcaggctggg cgtcgagctg tacctcgggc acagcctgct gggcccgagc   6120
```

```
gagaacggcg tgcgggtccg cgacggcgcc ggcgaggagc gcgagatcgc cgccgaccag    6180
gtactggtgg cggtcggccg caagccgcgc agcgaaggct ggaacctgga aagcctgggc    6240
ctggacatga acggccgggc ggtgaaggtc gacgaccagt gccgcacctc gatgcgcaat    6300
gtctgggcca taggcgatct cgccggcgag ccgatgctcg cgcaccgggc catggcccag    6360
ggcgagatgg tcgccgagct gatcgccggc aagcgtcgcc agttcgcccc ggtggcgatc    6420
cccgcggtgt gcttcaccga tccggaagtg gtggtcgccg ggttgtcccc ggagcaggcg    6480
aaggatgccg gcctggactg cctggtggcg agcttcccgt cgccgccaa cggtcgcgcc     6540 atgaccctgg aggccaacga aggcttcgtc cgcgtggtgg cgcgtcgcga caaccacctg    6600
gtcgtcggct ggcaggcggt gggcaaggcg gtttcggaac tgtccacggc cttcgcccag    6660
tcgctggaga tgggcgcccg cctggaagac atcgccggca ccatccacgc ccatccgacc    6720
ctcggcgaag cggtccagga agccgccctg cgcgcgctgg acacgcccct gcacatctga    6780
```

<210> SEQ ID NO 9
<211> LENGTH: 5597
<212> TYPE: DNA
<213> ORGANISM: Artificial Sequence
<220> FEATURE:
<223> OTHER INFORMATION: Synthetic: Tet-livKHMGF construct

<400> SEQUENCE: 9

```
ccagtgaatt cgttaagacc cactttcaca tttaagttgt ttttctaatc cgcatatgat     60
caattcaagg ccgaataaga aggctggctc tgcaccttgg tgatcaaata attcgatagc    120
ttgtcgtaat aatggcggca tactatcagt agtaggtgtt tcccttttctt ctttagcgac   180 ttgatgctct tgatcttcca atacgcaacc taaagtaaaa tgccccacag cgctgagtgc    240
atataatgca ttctctagtg aaaaaccttg ttggcataaa aaggctaatt gattttcgag    300
agtttcatac tgtttttctg taggccgtgt acctaaatgt acttttgctc catcgcgatg    360
acttagtaaa gcacatctaa aacttttagc gttattacgt aaaaaatctt gccagctttc    420
cccttctaaa gggcaaaagt gagtatggtg cctatctaac atctcaatgg ctaaggcgtc    480
gagcaaagcc cgcttatttt ttacatgcca atacaatgta ggctgctcta cacctagctt    540
ctgggcgagt ttacgggttg ttaaaccttc gattccgacc tcattaagca gctctaatgc    600
gctgttaatc actttacttt tatctaatct agacatcatt aattcctaat ttttgttgac    660
actctatcat tgatagagtt attttaccac tccctatcag tgatagagaa aagtgaactc    720
tagaaataat tttgtttaac tttaagaagg agatatacat atgaacgga atgcgaaaac    780 tatcatcgca gggatgattg cactggcaat tcacacacc gctatggctg acgatattaa     840
agtcgccgtt gtcggcgcga tgtccggcc gattgcccag tggggcgata tggaattaa      900 cggcgcgcgt caggcaatta aagacattaa tgccaaaggg ggaattaagg gcgataaact    960
ggttggcgtg gaatatgacg acgcatgcga cccgaaacaa gccgttgcgg tcgccaacaa   1020
aatcgttaat gacggcatta aatacgttat tggtcatctg tgttcttctt ctacccagcc   1080
tgcgtcagat atctatgaag acgaaggtat tctgatgatc tcgccgggag cgaccaaccc   1140
ggagctgacc caacgcggtt atcaacacat tatgcgtact gccgggctgg actcttccca   1200
ggggccaacg gcggcaaaat acattcttga cggtgaag cccagcgca tcgccatcat      1260 tcacgacaaa caacagtatg cgaagggct ggcgcgttcg gtgcaggacg gctgaaagc     1320 ggctaacgcc aacgtcgtct tcttcgacgg tattaccgcc ggggagaaag atttctccgc   1380
```

```
gctgatcgcc cgcctgaaaa aagaaaacat cgacttcgtt tactacggcg gttactaccc   1440
ggaaatgggg cagatgctgc gccaggcccg ttccgttggc ctgaaaaccc agtttatggg   1500
gccggaaggt gtgggtaatg cgtcgttgtc gaacattgcc ggtgatgccg ccgaaggcat   1560
gttggtcact atgccaaaac gctatgacca ggatccggca aaccagggca tcgttgatgc   1620
gctgaaagca gacaagaaag atccgtccgg gccttatgtc tggatcacct acgcggcggt   1680
gcaatctctg cgcgactgcc cttgagcgta ccggcagcga tgagccgctg gcgctggtga   1740
agatttaaaa gctaacggtg caaacaccgt gattgggccg ctgaactggg atgaaaaagg   1800
cgatcttaag ggatttgatt ttggtgtctt ccagtggcac gccgacggtt catccacggc   1860
agccaagtga tcatcccacc gcccgtaaaa tgcgggcggg tttagaaagg ttaccttatg   1920
tctgagcagt ttttgtattt cttgcagcag atgtttaacg gcgtcacgct gggcagtacc   1980
tacgcgctga tagccatcgg ctacaccatg gtttacggca ttatcggcat gatcaacttc   2040
gcccacggcg aggtttatat gattggcagc tacgtctcat ttatgatcat cgccgcgctg   2100
atgatgatgg gcattgatac cggctggctg ctggtagctg cgggattcgt cggcgcaatc   2160
gtcattgcca gcgcctacgg ctggagtatc gaacgggtgg cttaccgccc ggtgcgtaac   2220
tctaagcgcc tgattgcact catctctgca atcggtatgt ccatcttcct gcaaaactac   2280
gtcagcctga ccgaaggttc gcgcgacgtg gcgctgccga gcctgtttaa cggtcagtgg   2340
gtggtggggc atagcgaaaa cttctctgcc tctattacca ccatgcaggc ggtgatctgg   2400
attgttacct cctcgccat gctggcgctg acgattttca ttcgctattc ccgcatgggt   2460
cgcgcgtgtc gtgcctgcgc ggaagatctg aaaatggcga gtctgcttgg cattaacacc   2520
gaccgggtga ttgcgctgac ctttgtgatt ggcgcggcga tggcggcggt ggcgggtgtg   2580
ctgctcggtc agttctacgg cgtcattaac ccctacatcg gctttatggc cgggatgaaa   2640
gcctttaccg cggcggtgct cggtgggatt ggcagcattc cgggagcgat gattggcggc   2700
ctgattctgg ggattgcgga ggcgctctct tctgcctatc tgagtacgga atataaagat   2760
gtggtgtcat cgccctgct gattctggtg ctgctggtga tgccgaccgg tattctgggt   2820
cgcccggagg tagagaaagt atgaaaccga tgcatattgc aatggcgctg ctctctgccg   2880
cgatgttctt tgtgctggcg ggcgtcttta tgggcgtgca actggagctg atggcacca   2940 aactggtggt cgacacggct tcggatgtcc gttggcagtg ggtgtttatc ggcacgcgg   3000 tggtcttttt cttccagctt ttgcgaccgg cttttccagaa agggttgaaa agcgtttccg   3060
gaccgaagtt tattctgccc gccattgatg gctccacggt gaagcagaaa ctgttcctcg   3120
tggcgctgtt ggtgcttgcg gtggcgtggc cgtttatggt ttcacgcggg acggtggata   3180
ttgccaccct gaccatgatc tacattatcc tcggtctggg gctgaacgtg gttgttggtc   3240
tttctggtct gctggtgctg gggtacggcg gttttttacgc catcggcgct tacactttg   3300 cgctgctcaa tcactattac ggcttgggct tctggacctg cctgccgatt gctgattaa   3360 tggcagcggc ggcgggcttc ctgctcggtt ttccggtgct gcgtttgcgc ggtgactatc   3420
tggcgatcgt taccctcggt ttcggcgaaa ttgtgcgcat attgctgctc aataacaccg   3480
aaattaccgg cggcccgaac ggaatcagtc agatcccgaa accgacactc ttcggactcg   3540
agttcagccg taccgctcgt gaaggcggct gggacacgtt cagtaatttc tttggcctga   3600
aatacgatcc ctccgatcgt gtcatcttcc tctacctggt ggcgttgctg ctggtggtgc   3660
taagcctgtt tgtcattaac cgcctgctgc ggatgccgct ggggcgtgcg tgggaagcgt   3720
tgcgtgaaga tgaaatcgcc tgccgttcgc tgggcttaag cccgcgtcgt atcaagctga   3780
```

```
ctgcctttac cataagtgcc gcgtttgccg gttttgccgg aacgctgttt gcggcgcgtc    3840
agggctttgt cagcccggaa tccttcacct ttgccgaatc ggcgtttgtg ctggcgatag    3900
tggtgctcgg cggtatgggc tcgcaatttg cggtgattct ggcggcaatt ttgctggtgg    3960
tgtcgcgcga gttgatgcgt gatttcaacg aatacagcat gttaatgctc ggtggtttga    4020
tggtgctgat gatgatctgg cgtccgcagg gcttgctgcc catgacgcgc ccgcaactga    4080
agctgaaaaa cggcgcagcg aaaggagagc aggcatgagt cagccattat tatctgttaa    4140
cggcctgatg atgcgcttcg gcggcctgct ggcggtgaac aacgtcaatc ttgaactgta    4200
cccgcaggag atcgtctcgt taatcggccc taacggtgcc ggaaaaacca cggtttttaa    4260
ctgtctgacc ggattctaca acccaccgg cggcaccatt ttactgcgcg atcagcacct    4320
ggaaggttta ccggggcagc aaattgcccg catgggcgtg gtgcgcacct tccagcatgt    4380
gcgtctgttc cgtgaaatga cggtaattga aaacctgctg gtggcgcagc atcagcaact    4440
gaaaaccggg ctgttctctg gcctgttgaa acgccatcc ttccgtcgcg cccagagcga    4500
agcgctcgac cgcgccgcga cctggcttga gcgcattggt ttgctggaac acgccaaccg    4560
tcaggcgagt aacctggcct atggtgacca gcgccgtctt gagattgccc gctgcatggt    4620
gacgcagccg gagattttaa tgctcgacga acctgcggca ggtcttaacc cgaaagagac    4680
gaaagagctg gatgagctga ttgccgaact gcgcaatcat cacaacacca ctatcttgtt    4740
gattgaacac gatatgaagc tggtgatggg aatttcggac cgaatttacg tggtcaatca    4800
ggggacgccg ctggcaaacg gtacgccgga gcagatccgt aataacccgg acgtgatccg    4860
tgcctattta ggtgaggcat aagatggaaa aagtcatgtt gtcctttgac aaagtcagcg    4920
cccactacgg caaaatccag gcgctgcatg aggtgagcct gcatatcaat cagggcgaga    4980
ttgtcacgct gattggcgcg aacggggcgg ggaaaaccac cttgctcggc acgttatgcg    5040
gcgatccgcg tgccaccagc gggcgaattg tgtttgatga taaagacatt accgactggc    5100
agacagcgaa aatcatgcgc gaagcggtgg cgattgtccc ggaagggcgt cgcgtcttct    5160
cgcggatgac ggtggaagag aacctggcga tgggcggttt ttttgctgaa cgcgaccagt    5220
tccaggagcg cataaagtgg gtgtatgagc tgtttccacg tctgcatgag cgccgtattc    5280
agcgggcggg caccatgtcc ggcggtgaac agcagatgct ggcgattggt cgtgcgctga    5340
tgagcaaccc gcgtttgcta ctgcttgatg agccatcgct cggtcttgcg ccgattatca    5400
tccagcaaat tttcgacacc atcgagcagc tgcgcgagca ggggatgact atctttctcg    5460
tcgagcagaa cgccaaccag gcgctaaagc tggcggatcg cggctacgtg ctggaaaacg    5520
gccatgtagt gctttccgat actggtgatg cgctgctggc gaatgaagcg gtgagaagtg    5580
cgtatttagg cgggtaa                                                   5597
```

<210> SEQ ID NO 10  
<211> LENGTH: 1104  
<212> TYPE: DNA  
<213> ORGANISM: Escherichia coli  
<220> FEATURE:  
<221> NAME/KEY: misc_feature  
<222> LOCATION: (1)..(1104)  
<223> OTHER INFORMATION: livJ (Escherichia coli)

<400> SEQUENCE: 10

```
atgaacataa agggtaaagc gttactggca ggatgtatcg cgctggcatt cagcaatatg     60
gctctggcag aagatattaa agtcgcggtc gtgggcgcaa tgtccggtcc ggttgcgcag    120
```

```
tacggtgacc aggagtttac cggcgcagag caggcggttg cggatatcaa cgctaaaggc    180
ggcattaaag gcaacaaact gcaaatcgta aaatatgacg atgcctgtga cccgaaacag    240
gcggttgcgg tggcgaacaa agtcgttaac gacggcatta aatatgtgat tggtcacctc    300
tgttcttcat caacgcagcc tgcgtctgac atctacgaag acgaaggcat tttaatgatc    360
accccagcgg caaccgcgcc ggagctgacc gcccgtggct atcagctgat cctgcgcacc    420
accggcctgg actccgacca ggggccgacg gcggcgaaat atattcttga gaaagtgaaa    480
ccgcagcgta ttgctatcgt tcacgacaaa cagcaatacg gcgaaggtct ggcgcgagcg    540
gtgcaggacg gcctgaagaa aggcaatgca acgtggtgt tctttgatgg catcaccgcc     600
ggggaaaaag atttctcaac gctggtggcg cgtctgaaaa aagagaatat cgacttcgtt    660
tactacggcg ttatcacccc ggaaatgggg caaatcctgc gtcaggcacg cgcggcaggg    720
ctgaaaactc agtttatggg gccggaaggt gtggctaacg tttcgctgtc taacattgcg    780
ggcgaatcag cggaagggct gctggtgacc aagccgaaga actacgatca ggttccggcg    840
aacaaaccca ttgttgacgc gatcaaagcg aaaaaacagg acccaagtgg cgcattcgtt    900
tggaccacct acgccgcgct gcaatctttg caggcgggcc tgaatcagtc tgacgatccg    960
gctgaaatcg ccaaataccct gaaagcgaac tccgtggata ccgtaatggg accgctgacc   1020
tgggatgaga aggcgatct gaaaggcttt gagttcggcg tatttgactg gcacgccaac    1080
ggcacggcga ccgatgcgaa gtaa                                          1104

<210> SEQ ID NO 11
<211> LENGTH: 639
<212> TYPE: DNA
<213> ORGANISM: Escherichia coli
<220> FEATURE:
<221> NAME/KEY: misc_feature
<222> LOCATION: (1)..(639)
<223> OTHER INFORMATION: leucine exporter gene leuE (Escherichia coli
      Nissle 1917)

<400> SEQUENCE: 11
gtgttcgctg aatacggggt tctgaattac tggacctatc tggttgggc cattttatt      60 gtgttggtgc cagggccaaa taccctgttt gtactcaaaa atagcgtcag tagcggtatg    120
aaaggcggtt atcttgcggc ctgtggtgta tttattggcg atgcggtatt gatgtttctg    180
gcatgggctg gagtggcgac attaattaag accaccccga tattattcaa catcgtacgt    240
tatcttggtg cgttttattt gctctatctg gggagtaaaa ttctctacgc gaccctgaaa    300
ggtaaaaata gcgagaccaa atccgatgag ccccaatacg gtgccatttt taaacgcgcg    360
ttaattttga gcctgactaa tccgaaagcc attttgttct atgtgtcgtt tttcgtacag    420
tttatcgatg ttaatgcccc acatacggga atttcattct ttattctggc gacgacgctg    480
gaactggtga gtttctgcta tttgagcttc ctgattattt ctggggctt tgtcacgcag     540 tacatacgta ccaaaaagaa actggctaaa gtgggcaact cactgattgg tttgatgttc    600
gtgggtttcg ccgcccgact ggcgacgctg caatcctga                          639

<210> SEQ ID NO 12
<211> LENGTH: 2268
<212> TYPE: DNA
<213> ORGANISM: Escherichia coli
<220> FEATURE:
<221> NAME/KEY: misc_feature
<222> LOCATION: (1)..(2268)
<223> OTHER INFORMATION: Arginine decarboxylase (Escherichia coli)
```

```
<400> SEQUENCE: 12
atgatgaaag tgttaatcgt ggaatctgaa tttctgcacc aggatacgtg ggtcggtaac      60
gctgttgaac gtctggccga tgctttaagc cagcaaaatg tgacagttat caaatccacc     120
tcttttgacg atggctttgc cattctgtca agcaatgaag ccatcgattg tctgatgttc     180
tcgtaccaga tggaacaccc cgatgagcac caaaatgttc gtcagctgat cggcaaactt     240
cacgaacgtc aacagaacgt accggtcttt ctgttaggcg accgcgaaaa ggccttggcg     300
gctatggatc gcgatctgct ggagttggtc gacgagtttg cctggattct cgaggatacg     360
gcggatttta ttgccggtcg cgcagtcgcc gccatgacgc gctaccgcca acagctgctc     420
ccgccgctgt tttctgccct gatgaaatac tcggacattc acgaatacag ctgggcagct     480
cccgggcacc agggcggcgt tggcttcacg aaaaccccag ctggtcgctt ttatcatgac     540
tactacggcg agaatttatt tcgtaccgac atgggcattg aacgtaccag cctgggctcg     600
ctgctggacc acacgggcgc ttttggggaa tcagagaaat atgcagcacg cgtgttcggt     660
gcggaccgca gttggtccgt cgtggtgggc accagtggta gcaaccgcac cattatgcag     720
gcgtgcatga ccgataatga tgtggtagtg gtggatcgca attgtcataa gagcatcgaa     780
caaggcttga tgctgactgg cgctaaacca gtctatatgg tgccgtcccg taatcgctat     840
ggtattatcg gcccgattta tcctcaggag atgcagccgg aaaccctcca gaagaaaatc     900
tcagagtccc cgttaactaa agataaagct gggcaaaaac cgagttattg tgtagtaact     960
aattgtacgt atgatggtgt ttgctataac gctaaggagg cccaagatct tctggaaaaa    1020
acaagtgatc gtcttcattt tgatgaagct tggtacggtt atgcgcgttt caaccctatt    1080
tacgccgacc actatgcgat gcgtggtgaa cctggggatc ataatggccc tactgtgttt    1140
gccacccatt ctacgcataa actcctgaat gcgttgtcac aggcgagtta catccacgta    1200
cgcgaaggcc gtggcgctat taattttagc cgctttaacc aggcctatat gatgcacgcg    1260
acgacaagtc cgctgtatgc gatttgcgcg tccaacgatg ttgcggtcag catgatggac    1320
ggcaacagcg gtctgtcgtt aacccaggaa gtgattgatg aagcggtcga ctttcgccag    1380
gcgatggccc gtctgtacaa agaattcacc gccgatggct cgtggttctt caaaccctgg    1440
aataaagaag tcgtgactga cccgcagacg ggcaaaactt atgattttgc agatgccccg    1500
acgaagcttc ttactacggt ccaggattgc tgggtgatgc acccggggga gtcttggcat    1560
ggcttcaaag atatccctga taactggtct atgctcgacc caatcaaagt ttcaatttta    1620
gctccaggca tgggcgaaga tggcgaactg aagagacgg gggtaccagc tgcgttggtt    1680
accgcctggt taggccgcca tggtattgtt ccaacacgta ccactgattt tcagattatg    1740
tttctgttca gtatgggtgt gacgcgcggt aaatggggga cgctggtcaa cactctctgc    1800
tcctttaaac gccattatga tgcgaacacg cccctggcgc aagtcatgcc agagctggtg    1860
gaacaatacc ctgatactta tgcgaacatg ggtatccacg atctgggaga tactatgttc    1920
gcctggctta agaaaaataa cccgggggcc cgcctgaacg aagcatatag tggcctgccc    1980
atggcggaaa ttactccgcg tgaagcctat aatgccatcg ttgataataa cgtcgaatta    2040
gtatccatcg agaacctccc cggtcgtatt gcggcaaata gcgtaatccc gtacccgccg    2100
ggtattccca tgctgctcag cggcgaaaac ttcggtgata aaaattcccc gcaagtttct    2160
tatctgcgca gcctgcaatc gtgggaccat cactttcccg ggtttgagca tgaaactgaa    2220
gggacagaga tcatcgatgg catttatcat gtgatgtgcg tcaaggcg                 2268
```

<210> SEQ ID NO 13
<211> LENGTH: 780
<212> TYPE: DNA
<213> ORGANISM: Escherichia coli
<220> FEATURE:
<221> NAME/KEY: misc_feature
<222> LOCATION: (1)..(780)
<223> OTHER INFORMATION: ArgT (Escherichia coli)

<400> SEQUENCE: 13

| | | | | |
|---|---|---|---|---|
| atgaaaaaaa | gcatcctcgc | gctgtcactg | ttagtgggtc | tcagcgccgc | ggccagcagc | 60 |
| tatgctgctc | ttcctgaaac | ggtgcgcatc | gggacggata | ccacttatgc | accgtttagc | 120 |
| agcaaagatg | ctaaaggaga | cttcgtaggg | tttgatatcg | atttaggcaa | cgagatgtgc | 180 |
| aaacgtatgc | aagtgaaatg | tacctggtg | gcttcagact | tgatgcatt | aatcccgagt | 240 |
| ttgaaagcaa | aaaaaattga | cgcaattatt | tcgagcctga | gcattacaga | taagcgccaa | 300 |
| caagaaattg | ccttctcaga | taaattatat | gccgctgatt | cgcgtcttat | cgcggctaaa | 360 |
| ggctccccta | tccaaccaac | gttggacagc | ctgaagggga | acatgtagg | ggttctgcaa | 420 |
| gggtccacgc | aggaagctta | cgccaatgaa | acctggcgtt | cgaaaggggt | cgatgtggtg | 480 |
| gcgtacgcca | atcaggactt | ggtgtattcc | gatctggccg | caggtcgtct | ggacgcagct | 540 |
| ctgcaggacg | aagtggcggc | gagtgagggt | ttcctgaaac | agccagcagg | caaagatttt | 600 |
| gcgttcgccg | gctcgagtgt | aaaggataaa | aaatatttcg | gggatggcac | gggtgtcggt | 660 |
| ttacgcaaag | atgatgcaga | actgaccgcg | gcgtttaata | aagcccttgg | cgaactgcgc | 720 |
| caagacggca | catatgataa | aatggcgaaa | agtactttg | acttcaatgt | ttatggtgat | 780 |

<210> SEQ ID NO 14
<211> LENGTH: 726
<212> TYPE: DNA
<213> ORGANISM: Escherichia coli
<220> FEATURE:
<221> NAME/KEY: misc_feature
<222> LOCATION: (1)..(726)
<223> OTHER INFORMATION: artP (Escherichia coli)

<400> SEQUENCE: 14

| | | | | |
|---|---|---|---|---|
| atgtctattc | aattaaatgg | catcaactgt | ttctacggtg | cacatcaagc | cttatttgac | 60 |
| atcacgcttg | attgcccgca | aggggagaca | ctggtgctgc | tgggcccgag | tggagccggc | 120 |
| aaatcgtcgt | tgctgcgggt | gttgaacctg | ttggagatgc | cgcgctcagg | caccctgaat | 180 |
| atcgcgggca | accatttcga | ttttacgaaa | acaccgtccg | ataaagctat | tcgtgatctt | 240 |
| cgtcgcaacg | tcggcatggt | gtttcagcag | tataatttat | gtgctcatct | gacggttcag | 300 |
| caaaatctga | tcgaagcacc | gtgtcgtgtg | ttgggcctga | gcaaagacca | agccctggcc | 360 |
| agcgcagaaa | aattattaga | gcgcctgcgc | ttgaaaccat | attcggatcg | gtacccactt | 420 |
| cacttaagcg | ggggccagca | acagcgcgtt | gccatcgctc | gtgcgctgat | gatggagccg | 480 |
| caagttctcc | tttttgatga | acctaccgca | gcgcttgatc | cggagatcac | ggcgcagatc | 540 |
| gtcagcatca | ttcgtgaact | cgctgagacg | aatattacac | aagttattgt | gacacatgag | 600 |
| gtagaagtgg | ctcgcaagac | cgcgtctcgc | gtagtgtata | tggaaaacgg | tcatatcgtg | 660 |
| gagcaagggg | acgcctcatg | ttttacagag | ccgcagacag | aggcattcaa | aaattatctg | 720 |
| agccac | | | | | 726 |

<210> SEQ ID NO 15
<211> LENGTH: 732
<212> TYPE: DNA

<213> ORGANISM: Escherichia coli
<220> FEATURE:
<221> NAME/KEY: misc_feature
<222> LOCATION: (1)..(732)
<223> OTHER INFORMATION: artI (Escherichia coli)

<400> SEQUENCE: 15

```
atgaaaaaag tgcttattgc cgccctgatt gcgggcttct ctctgtctgc caccgcggcc    60
gaaaccatcc gttttgccac tgaagcgtca tatcccccctt tcgaaagcat tgacgccaac   120
aaccaaattg tcggtttcga cgttgacctc gcgcaggccc tgtgcaaaga aattgatgcc   180
acctgcacct tctctaacca agcgtttgac tcattgattc cttcgctgaa atttcgtcgc   240
gtggaagccg tcatgggcgg catggatatc accccccgagc gcgaaaaaca ggtcttgttt   300
actacaccgt actacgacaa ctcggctttg tttgtcggcc agcaaggcaa gtatacttct   360
gtcgaccagc tgaaaggtaa aaaagtccgt tcagtccaga acggcaccac tcaccagaaa   420
ttcatcatgg acaaacatcc tgagatcact accgtgccgt atgattctta ccagaacgcg   480
aagttagatc tggaaaatgg tcggattgat ggcgtctttg cgacaccgc tgtggtacat   540 gaatggctga agacaatcc taaattagtg gttgtgggag ataaggttac ggataaggat   600
tattttggca ccggtctcgg cattgcagtc cgccaaggta ataccgaatt gcaacagaaa   660
ttgaataccg cgctggaaaa agtgaaaaaa gacggtacat acgaaaccat ttacaacaaa   720
tggtttcaaa aa                                                        732
```

<210> SEQ ID NO 16
<211> LENGTH: 714
<212> TYPE: DNA
<213> ORGANISM: Escherichia coli
<220> FEATURE:
<221> NAME/KEY: misc_feature
<222> LOCATION: (1)..(714)
<223> OTHER INFORMATION: artQ (Escherichia coli)

<400> SEQUENCE: 16

```
atgaacgaat tcttccctct cgcgtctgcg gcaggtatga ccgtgggttt ggcggttgt     60 gcgctgattg tcggtctcgc tctggcaatg ttctttgccg tatgggagtc agcgaaatgg   120
cgtccggtcg cctgggcagg ttccgccctg gtaaccattc tgcgtggtct gccagagatc   180
ctggtagttc tgtttatcta ctttggctct tctcagttac tgttaacact gtctgacggg   240
tttacgatta acctgggttt tgtccagatt ccggtccaga tggatattga aaatttcgac   300 gtctccccctt ttctctgtgg cgtcatcgcg ctgagcttgc tctacgctgc atatgcatca   360
cagacccttc gtggtgcatt aaaagcggtg ccagtaggac agtgggaaag cggccaggcc   420
cttggcctga gcaagagcgc aattttttc cgccttgtta tgccggccga tgtccgccat   480
gcgttaccag gtctgggtaa tcaatggctg gtgttgttga agacaccgc ccttgtctcg   540 ctgattagcg tgaacgattt aatgctgcaa accaaatcga ttgcaacccg cactcaggaa   600
ccgtttacct ggtacatcgt ggcggcagca atctatctgg tgatcacact tctgagccag   660 tatatttaa aacgtattga cctgcgtgcc acccgctttg agcgccgccc tagc          714
```

<210> SEQ ID NO 17
<211> LENGTH: 666
<212> TYPE: DNA
<213> ORGANISM: Escherichia coli
<220> FEATURE:
<221> NAME/KEY: misc_feature
<222> LOCATION: (1)..(666)
<223> OTHER INFORMATION: artM (Escherichia coli)

<400> SEQUENCE: 17

```
atgtttgaat atctgccgga actgatgaaa ggtttgcata ctagtctgac gctgaccgtc      60
gcgagtctga tcgttgcgct tatcctggca ctgatcttca ccattattct gactctcaag     120
accccggtcc tggtgtggct ggtccgcggt tacattacct tattcaccgg gaccccgctc     180
ttggttcgca ttttcttat ttactatggt ccgggtcagt ttccgacctt gcaagaatat      240
cctgcgttat ggcacctgct gtctgaaccg tggctgtgcg ctctgattgc tctgagtgtt     300
aactcggcgg cctatacgac acagctgttc tacggtgcta ttcgtgcgat cccagaaggt     360
caatggcagt cttgtagcgc actgggcatg tcaaagaaag atactcttgc tattctgctg     420
ccgtacgctt ttaaacgctc tctgagctcg tacagcaatg aagttgtcct ggttttcaaa     480
agcactagct tagcgtatac gatcacgctg atggaagtca tgggttatag ccagttatta    540
tatggtcgca cgtacgacgt catggtgttt ggtgcagcgg gcattatcta tcttgtagtt     600
aatggattac tgacgttaat gatgcgcttg atcgaacgca aagccgtggc attcgagcgg     660
cgtaat                                                                666
```

<210> SEQ ID NO 18
<211> LENGTH: 729
<212> TYPE: DNA
<213> ORGANISM: Escherichia coli
<220> FEATURE:
<221> NAME/KEY: misc_feature
<222> LOCATION: (1)..(729)
<223> OTHER INFORMATION: artJ (Escherichia coli)

<400> SEQUENCE: 18

```
atgaaaaaat tggtgcttgc agcactgctg gccagtttca ctttcggcgc ttcggcggcc      60
gaaaagatta atttcggtgt cagcgcaact tacccaccgt tcgaaagcat cggtgcgaac     120
aatgagattg taggatttga tatcgatctg gccaaagcgt tatgcaaaca aatgcaagcg    180
gagtgcactt ttaccaatca tgcgtttgat agcctgatcc cgtcgctgaa gttccgtaaa    240
tacgacgccg tgatttcggg gatggacatc accctgagc gctcgaaaca ggtgagcttc     300
accactccat attatgaaaa ctcagcggtg gtgattgcga aaaagacac ctataaaaca     360
tttgccgacc tgaaagggaa atgtattggt atggagaacg gcaccaccca tcagaagtat    420
attcaagacc agcacccgga ggttaagacc gtaagctacg actcctacca gaatgctttc    480
attgatttaa aaatggtcg tattgatggt gtattcggag atacagccgt ggtgaatgag     540
tggctgaaaa ccaatccgca gttgggtgtt gcgaccgaaa aagtgacaga tccacaatac    600
tttgggactg gcctgggcat cgcggtgcgc ccggataaca aagccctgtt ggagaaactg    660
aacaacgcgt tagctgcgat taaagcggat gggacctatc agaagatttc agaccaatgg    720
ttcccgcaa                                                            729
```

<210> SEQ ID NO 19
<211> LENGTH: 633
<212> TYPE: DNA
<213> ORGANISM: Escherichia coli
<220> FEATURE:
<221> NAME/KEY: misc_feature
<222> LOCATION: (1)..(633)
<223> OTHER INFORMATION: ArgO (Escherichia coli)

<400> SEQUENCE: 19

```
atgttctcgt actatttcca aggcttagca ctgggtgcgg ccatgatctt accgctgggc      60
```

| | |
|---|---|
| ccacaaaacg cttttgttat gaaccaggga atccgccggc agtaccatat catgattgcg | 120 |
| ctgctgtgtg ccatctcgga tctggtcctg atttgcgccg gtattttgg cgggtcggcg | 180 |
| ttacttatgc aaagcccttg gctgctggcg ctggtaacgt ggggcggcgt agcatttctg | 240 |
| ctttggtatg gattcggcgc cttcaaaact gcgatgagtt cgaatatcga gcttgcgagt | 300 |
| gctgaggtaa tgaaacaggg ccgttggaaa attattgcga ccatgttagc cgtgacttgg | 360 |
| ttgaacccgc acgtgtacct ggatactttt gtggtgttgg gttcactcgg tgggcaatta | 420 |
| gatgtggaac cgaaacgctg gtttgccttg gcacaatct cggccagttt tttgtggttc | 480 |
| ttcgggctgg cgctgctggc cgcgtggctg caccacgtt tacgcaccgc caaggcccag | 540 |
| cgcatcatca acttagtcgt gggctgtgtg atgtggttca ttgctctgca actggcgcgc | 600 |
| gatggcattg cgcacgccca ggccctgttc tca | 633 |

<210> SEQ ID NO 20
<211> LENGTH: 1203
<212> TYPE: DNA
<213> ORGANISM: Flavobacterium limnosediminis JC2902
<220> FEATURE:
<221> NAME/KEY: misc_feature
<222> LOCATION: (1)..(1203)
<223> OTHER INFORMATION: monofunctional lysine-ketoglutarate reductase
      (Flavobacterium limnosediminis JC2902)

<400> SEQUENCE: 20

| | |
|---|---|
| atgatgcgct ttggcatcat taagaacgt aagaacccgc cagatcgtcg tgtagtgttt | 60 |
| acaccgtccg aactgatcaa actgaaagaa cagtttccgc tggccgaaat taaggtggaa | 120 |
| tcctcagata ttcgcatttt ttctgatgat gagtatcgta aacttggatt tgaagtaacc | 180 |
| gatgacctga gtgattgtga tgtcttgatt ggcgtgaaag aagtaccgat cgatgccctg | 240 |
| ctgcccggga aaagtatttt ttttttctct cacacaatta aaaaacagcc ttacaataaa | 300 |
| aaactgctga tcgcctgctt ggaaaaaaac atccgtctga ttgatcatga acgatcgtg | 360 |
| aatgaagata atcatcgttt gattgggttc ggccgttacg caggtatcgt gggggcctat | 420 |
| aacggtttcc gtgctttttgg tattaagtac gagctcttta acctgcccaa agcggaaacc | 480 |
| ttagcggaca aaacggcact tgtggaacgc ctgcgtcggc cgatgctgcc gccaatcaaa | 540 |
| attgtgttga ccggtcacgg caaagtaggt atgggtgcaa agagattct ggatgccatg | 600 |
| aaaatcaaac aagtttccgt ggaggactac ttaacaaaaa cctatgacaa gccggtgtat | 660 |
| acgcagatcg acgttctgga ctataacaag cggaaagatg gcaaaccggc ggaacgtgaa | 720 |
| cacttttatg ccaatccgca ggagtatgtc tcggacttcg aacgctttac caaggtgtcg | 780 |
| gatctgttca tcgcaggcca tttctatggc aacggtgcac cggtaattct gactcgcacc | 840 |
| atgcttaacg cttctgataa taaaattaaa gtagttgcgg atattagctg tgatgtcggt | 900 |
| ggccctatcg aatgtacgct gcgcagcagc accatcgcag agccgtttta tggttattat | 960 |
| ccttccgaag gtaaagaagt cgacgtcaac catccgggcg cggtggttgt gatgcggtg | 1020 |
| gacaatctgc cctgcgagct gcctaaagat gccagcgagg gtttcggaga atgtttctc | 1080 |
| aaacatgtga ttccagcctt ctacaacaac gataaggacg gcattcttga gcgggccaaa | 1140 |
| atcaccgaaa acggcaaatt aacaaaacgc ttctcctact tacaggacta tgtcgatggt | 1200 |
| gaa | 1203 |

<210> SEQ ID NO 21
<211> LENGTH: 1356
<212> TYPE: DNA

<213> ORGANISM: Flavobacteriumsp. EM1321
<220> FEATURE:
<221> NAME/KEY: misc_feature
<222> LOCATION: (1)..(1356)
<223> OTHER INFORMATION: saccharopine dehydrogenase (Flavobacteriumsp. EM1321)

<400> SEQUENCE: 21

```
atgcgtaata ttttgattat cggcgccggt cggtccgctt cctcgctgat tcagtactta    60
ttgaataagt cccaagaaga acagctgcat ttaaccattg ccgatttatc actcgaactg   120
gctcagaaga aaaccaataa ccatccgaac gctaccgcgc tggcgctgga tatttataat   180
aaggatgaac gtcgtgcggc catcgagaaa gcggccattg tgatcagcat gttgccagcg   240
catctgcata tcgaaatcgc ccgggattgc ctgtatttta aaagaaccct tgttacggcg   300
agctatatta gtgacgcgat gcaggagctt gatgcggaag ttaaagagaa caaactgatc   360
tttatgaatg aggtcggttt agacccgggt attgatcata tgagcgccat gaaagtcatc   420
gatgaaattc gggaacaagg cggcaaaatg cttctcttcg aaagttttg cggcggcctg    480
gtggcaccag aatcagataa caatttatgg aactataaat ttacctgggc cccacgtaac   540
gtagttctgg ctggccaggg tggtgtggca aaattcattc aagaaggcac ctataaatat   600
atcccgtatg acagcttatt tcgccggacc gagtttctgg aagtagaagg atacgggcgt   660
ttcgaagctt attcgaatcg cgattctctc aaatatcgga gtatttatgg gctcgatgac   720
gttctcaccc tgtttcgtgg tacaatccgt cgcgttggct tctccaaagc ttggaacatg   780
tttgtgcaac tggcatgac ggacgacagc tatgttatgg aagattctga gaatatgtcc    840
tatcgtcaat ttattaactc attcctgcct tatcacccaa ccgatagcgt tgaaattaag   900
acccgttttt tgttaaaaat cgatcaggat gatatcatgt gggacaaact gctggaactg   960
gatcttttca cgataaaaa aatggttggg ttgaaaaatg cgacgccggc acagatcctg   1020
gagaaaatcc tgaacgattc gtggaccctg caaccggaag ataaagatat gatcgtgatg  1080
tatcataaat ttggttacca gatcaacggc gaaaaagtgc agatggattc acagatggtg  1140
tgtatcggcc aggaccaaac gtataccgcg atgcaaaaa ccgtcggcct gcctgtggca   1200
atggcaactc tgctgattct gaacggtaaa atcaaaacaa cgggagttca gttgccaatc  1260
aataaagaag tttacctgcc ggtcctggag gaactggaga aatatggcgt tgtgttcaaa  1320
gaacagatgc tcccatatct tggatacaaa tatagt                            1356
```

<210> SEQ ID NO 22
<211> LENGTH: 1350
<212> TYPE: DNA
<213> ORGANISM: Bacillus methanolicus PB1
<220> FEATURE:
<221> NAME/KEY: misc_feature
<222> LOCATION: (1)..(1350)
<223> OTHER INFORMATION: Lysine aminotransferase (Bacillus methanolicus PB1)

<400> SEQUENCE: 22

```
atgaagaaaa atcattcctt gcagtcgctt aaaaaccaag atgagcgttt catttggcac    60
tcgatgaagc cgtataaccc cgacaagacg atcgttgtca ccaaggccga aggatcatgg   120
attacaacga gtgatggaaa gaagtatctt gacgcaatgg ccggtctttg gtgcgttaac   180
gtggggtatg gacgcaaaga gcttgccgat gccgcgtacg aacagatgat ggaaatggca   240
tactatccac tgactcagtc acatgtaccc gccattcagt agcggagaa gttgaacgat   300
ctgctggaag acgaatacgt aatcttttt agcaattcgg ggagtgaggc gaacgaggct   360
```

```
gcttttaaaa ttgctcgtca gtatcatcaa caaaaaggag accacaatcg ctataagatt     420
gttgcacgct accgtgcata tcatgggaac tcaattggag ccttggcagc gacagggcag     480
gcccagcgta aatataagta tgagcctctg cctttggat tcgtccatgt tgcccctcct      540
gactcctacc gtgatgaaac taacgtatcc gatccttcgc agttgtccgc agtcaaagaa     600
attgaccgtg taatgacgtg ggagctttcg gaaactatcg ccgcaatgat catggaaccg    660
attattactg gtggaggcat cttagtgccc cagaggggt atatgaaagc ggctaaggag     720
gtttgtgaaa agcacggggc tcttttgatt gtggacgagg tgatttgcgg gtttggtcgt   780
acgggtaagc cgttcggatt catgaactat ggagtcaagc cggacattat caccatggct   840
aaaggcatca ccagtgcgta tcttccgttg tcagcaactg cagtcaaaaa ggaaatctat    900
gatgccttta aggtgagga cgaatatgag ttcttccgtc atgtcaacac tttcggaggg    960
tcacccgccg catgtgcgct ggctatcaag aacattcaga ttttggagga ggaaaagctg   1020
tttgaccgct cgggcgacat gggcgaaaaa gttttaacag aacttcagaa cttgttacgc   1080
gatcacccct acgttggcga cgttcgtgga aagggtctgt taatcggaat tgaattggtt    1140
aaagacaagc agacgaaaga gcccttaaat acaagcaaag ttgacgaagt aatcgctctt   1200
tgtaaacagg aaggacttct gattggaaaa atggcatga ccgtggcagg ctataacaac    1260
gtccttacac tgtcccctcc gcttaatatc ccagagaccg acttagactt tttgatcaaa   1320
gtactgacgg cgtccttgga gaagattaag                                      1350

<210> SEQ ID NO 23
<211> LENGTH: 1098
<212> TYPE: DNA
<213> ORGANISM: Agrobacterium tumefaciens
<220> FEATURE:
<221> NAME/KEY: misc_feature
<222> LOCATION: (1)..(1098)
<223> OTHER INFORMATION: lysine dehydrogenase (Agrobacterium
      tumefaciens)

<400> SEQUENCE: 23
atgaaaaata tcgtagtgat cggggcaggg aatattggca gcgccattgc gtggatgttg     60
gcagctagcg gggattatcg cattactgta gcagaccgca gcgcggatca gttagctaat   120
gtaccggctc atgaacgtgt cgacattgtt gacattaccg accgccccgc gctggaagca   180
ctgttaaaag ggaaatttgc ggtacttagc gccgctccca ccgagtttca tttgactgcc    240
ggaattgcgg aagcggccgt cgcggtaggc acgcactact tagacttaac agaagatgtg   300
gagtctaccc gcaaggtaaa agcgctggct gagacggccg agacagcttt aatcccccaa   360
tgtgggctgg caccaggttt tatttcgatt gttgctgccg atttggctgt gaagtttgat   420
aaattagatt ctgttcgtat gcgcgtcggg gcgctgcctc agtatcccag taacgcattg   480
aattacaatt tgacttggag cacagatggc cttatcaacg agtacattga gccttgcgag   540
gggtttgtag aaggtcgctt gaccgcgtc ccggctttag aggaacgcga ggaatttagt    600
cttgatggga tcacctacga ggcattcaac acctcgggcg gacttgggac cttgtgcgcc   660
acccttgagg gtaaggtgcg cacaatgaac taccgtacca tccgctatcc gggtcatgta   720
gcaatcatga aggcacttct taatgacttg aacctgcgta atcgccgtga cgttttgaaa    780 gatcttttg aaaatgcact gcctggaacg atgcaagatg tcgtaattgt ttttgtaaca    840
gtgtgtggca ctcgcaacgg acgctttctg caagagactt atgccaataa agtgtacgcg   900
gggcctgtgt caggccgcat gatgtccgcg atccagatca caacagctgc tggaatttgc    960
```

```
acagtcctgg atttgttggc cgaaggcgcg cttccgcaga agggcttcgt tcgtcaagag    1020
gaggtcgcac tgcctaagtt tttggaaaat cgtttcggac gttattatgg ttctcacgaa    1080
ccgcttgctc gtgttggt                                                  1098
```

<210> SEQ ID NO 24
<211> LENGTH: 1179
<212> TYPE: DNA
<213> ORGANISM: Unknown
<220> FEATURE:
<223> OTHER INFORMATION: lysine racemase (uncultured bacterium)

<400> SEQUENCE: 24

```
atggcacata caggccgtat gtttaagatc gaagccgcgg agatcgtagt ggctcgcctg     60
ccgctgaaat tcgtttttga gacatctttc ggtgtccaga cacataaagt ggtgcccttta   120 ctgatcttac atggcgaagg tgttcaaggg gtcgcggagg ggacaatgga agctcgcccc   180
atgtaccgcg aagaaacgat tgccggagcc cttgatttgt tgcgtggaac tttttacct    240 gcgattctgg ccaaaacctt tgccaatcca gaagcggtaa gtgatgccct gggctcttac   300
cgcggcaatc gcatggcacg cgctatggtg gagatggcag cttgggactt gtgggcccgc   360
acccttggtg tgcctttggg cacactgttg ggtggtcaca aggaacaagt cgaggtgggt   420
gtatcgttgg gaatccaggc agatgagcaa gctacagtag acttagtgcg tcgtcatgtt   480
gaacaaggat atcgtcgcat taagttgaag attaagcctg ggtgggacgt tcaacctgta   540
cgtgcgaccc gtgaggcatt catgttaaac acgcttaatg tcggcgcctc tggttacgcg   600
ggcgcagaac tggttacata cgtgaaccgc cacccccata tgaacattac ggcgttgacc   660
gtatcagcac agtcaaacga tgcagggaag ttaatctccg atttgcatcc ccaattaaag   720
ggcatcgttg acttaccatt gcagccgatg tccgacatct ctgaattcag ccccggggta   780
gatgtagtgt tcctggctac agctcacgaa gtttcacacg acctggcccc gcaattttttg   840 gaggcgggtt gtgtggtctt tgatctgtcc ggcgcttttc gcgttaacga tgctacatttt  900 tacgagaagt attacggttt cacccaccaa tacccagagc tgctggaaca gcggcctac    960 gggcttgctg agtggtgtgg caacaaactt aaggaagcta atcttattgc agttcctgga   1020
tgttacccta ccgccgcaca gctggcgctg aagccgttaa ttgatgctga cctgctggac   1080
ctgaaccaat ggccggtgat caatgcgacc agtggcgtat ctggggcggg tcgtaaagcc   1140
gcaatttcaa actccttctg cgaggttagc ttacaaccg                          1179
```

<210> SEQ ID NO 25
<211> LENGTH: 1407
<212> TYPE: DNA
<213> ORGANISM: Bacillus subtilis
<220> FEATURE:
<221> NAME/KEY: misc_feature
<222> LOCATION: (1)..(1407)
<223> OTHER INFORMATION: Lysine transporter yvsh (Bacillus subtilis)

<400> SEQUENCE: 25

```
atggagcaga cgaagaaatg gggattttgg ttactgacgg ccttcgtcgt gggcaacatg     60
gtgggtagtg aatcttttc tcttccatcc tccctggcga gcatcgcgtc gcctttcgga    120
gctacgtccg cttggcttct gacaggtgcg ggggtgttaa tgatcgcctt agtattcgga   180
catttgtcca ttcgtaaacc cgaattgact gccgggcctc aatcatacgc ccgtgcattg   240
ttcagcgatc caaaaaaggg gaatgcggcc gggtttacta tggtttgggg ttactgggtc    300
```

```
gcgagctgga tcagtaacgt agcaatcatt acatctctgg cggggtatct gaccagcttc      360
ttccccatcc tggtagacaa acgcgaaatg ttttctattg ggggtcaaga ggtcaccctg      420
gggcagctgc tgacttttgc cgtttgcacc attctgttgt ggggcaccca tgcgattttg      480
gtcgcatcga tcaatggcgc aagcaagctg aattttgtga ccacattatc caaggtcttg      540
ggattcgtgt ttttcattgt ggcagggtta ttcgtcttcc agacgacgct ttttggtcat      600
ttctatttcc cggtccaagg cgagaatgga acgagcatcg gtattggggg acaggtgcat      660
aacgctgcga tttctacact ttgggctttc gtcggaatcg aaagcgccgt tatcttgtct      720
ggccgcgcgc gcagccagcg cgatgttaaa cgtgctacca ttaccggact tctgattgca      780
ctgtcgatct atattatcgt cacgttaatc acgatgggtg ttttacccca cgacaaatta      840
gtaggaagtg aaaagccatt tgtcgatgtt ttatatgcaa tcgtcgggaa cgctggttca      900
gtaatcatgg cactgctggc catcttgtgc ctttttggaa ccatgttggg gtggatttta      960
ctgggctcgg aggtgcccta ccaagcagcc aaagctggtg atttccccgc cttctttgcc     1020
aaaactaata agaaaggttc tccagtgatt gcgcttatca ttaccaatgt catgtcacag     1080
gttttcattt ttagcgtgat cagtcgtaca atttccgatg cttttacttt tttgactaca     1140
gcggccacgt tggcctatct gattccctac ttagtttcag cgatttatag tttgaaagtg     1200
gttattaaag gcgaaaccta tgaccagttg aaaggcagtc gtgtacgtga tggtcttatc     1260
gctatcttgg catgtgcata ctcagtcttc gtaatcgtga cgggtaccgc cgatttgacg     1320
acctttattt taggtattgg cttttttttt gtgggcctta tcgtgtaccc atttgtctcg     1380
aagaagtttc aaaaggagaa gcaggaa                                         1407

<210> SEQ ID NO 26
<211> LENGTH: 1404
<212> TYPE: DNA
<213> ORGANISM: Klebsiella sp.
<220> FEATURE:
<221> NAME/KEY: misc_feature
<222> LOCATION: (1)..(1404)
<223> OTHER INFORMATION: Lysine Transporter LysP (Klebsiella)

<400> SEQUENCE: 26
atgaccatga ttgctattgg cgggtcgatc ggcacagggc ttttcgttgc atccggagca       60
acgattagtc aagcaggtcc aggcggggct ctgctgtctt atattcttat cggcttaatg      120
gtgtattttc tgatgaccctc tcttggagag ctggccgctt ttatgccagt ctccggatcg      180
ttcgctacat atgggcaaaa ctacgtgagg gagggtttcg ggtttgcgct gggttggaat      240
tactggtata ttgggctgt gacgatcgca gttgacttgg tggcttcgca gcttgtgatg      300
agctattggt tccctgacac tccgggctgg atttggtctg cttttgtttttt ggcatcatg      360 ttcttgctta actggatctc cgttcgcggg ttcggtgaag ctgagtactg gttcagtctg      420
attaaagttg cgaccgttat tatcttcatc atcgttggcg tgatgatgat tgtcggcatt      480
ttcaaagggg cgcaaccggc tggatggtcc aactggggta tcgctgacgc cccatttgcg      540
gggggcttct cggcgatgat tggcgttgcc atgattgtcg ttttttcctt tcagggtaca      600
gagttaattg gaattgctgc tggtgaatcc gagaatcctg agaaaaatat tccacgtgcg      660
gtacgtcagg tattctggcg cattttactg ttttatgttt ttgcaatctt gattatctcg      720
ttgatcatcc cttatactga cccatcctta ttgcgtaacg atgtgaagga tatttccgtg      780 tctccccttca cgttggtatt tcagtatgct gggctgctta gtgccgctgc gatcatgaac      840
gcagtcattc ttacggctgt actgagcgct ggaaactcgg gaatgtacgc ttcaacacgc      900
```

```
atgttatata ccttggcatg tgacgggaaa gcaccgcgta tctttagcaa gctttcccgt    960
ggcggtgtgc cacgcaatgc tctgtatgca acaactgtaa ttgctgcctt atgctttctt   1020
accagcatgt tcggcaacca aacggtttat ctgtggttgc tgaacacttc gggaatgaca   1080
gggttcatcg cctggctggg tattgctatt tctcactatc gtttccgtcg cggctacgtg   1140
ctgcagggga atgatatcaa taatcttccg tatcgttcag gattttttcc tcttggaccc   1200
attttttgcat ttgtattgtg tttgattatt actcttggcc aaaattatga ggcgttctta   1260
aaagatacta tcgattgggg tggggtagcc gcaacctaca tcgggattcc cttgttcctt   1320
gttatttggt ttggatataa gttggctaag ggtacccgct ttgtccgtta ttccgaaatg   1380
accttcccag atcgttttaa acgc                                          1404
```

<210> SEQ ID NO 27
<211> LENGTH: 630
<212> TYPE: DNA
<213> ORGANISM: Pseudomonas sp.
<220> FEATURE:
<221> NAME/KEY: misc_feature
<222> LOCATION: (1)..(630)
<223> OTHER INFORMATION: Lysine Exporter (Pseudomonas)

<400> SEQUENCE: 27

```
atgagtatgg aagtctggct gggggttttttt gcagcgtgtt gggtgattag tttgtcaccg     60
ggagccggag ccatcgcctc tatgtcatcg ggtttacaat atggcttctg gcgtggctac    120
tggaatgcac ttggattgca gcttggttta attatgcaaa ttgcaattat cgctgcgggc    180
gtcggagccg tcttggcggc ctcggctacg gccttccagg taattaaatg gttcggagtt    240
gggtatcttg tgtatttagc atacaaacaa tggcgtgcac tgcccatgga tatgtcggat    300
gaaagcgggg tgcgtccaat cggcaaacca ttatcgctgg tatttcgtgg attttttggtg    360
aatatctcca acccaaaagc tttagtattc atgttggccg tttttacccca gttcctgaat    420
ccccacgccc ccttgttacc ccaatacgtg gctatcactg tgacaatggt tacagttgac    480
ttgttagtga tggccggata cacaggttta gcatctcatg tattacgtat gcttcgtacc    540
ccaaaacagc aaaaacgcct gaaccgcacc ttcgccggtt tattcatcgg agcggccaca    600
ttccttgcca ctttgcgccg cgcaccagta                                    630
```

<210> SEQ ID NO 28
<211> LENGTH: 1014
<212> TYPE: DNA
<213> ORGANISM: Escherichia coli
<220> FEATURE:
<221> NAME/KEY: misc_feature
<222> LOCATION: (1)..(1014)
<223> OTHER INFORMATION: Asparaginase (Escherichia coli)

<400> SEQUENCE: 28

```
atgcagaaga aatcgatcta cgtcgcgtac acgggcggca ccattgggat gcagcgttcg     60
gagcagggtt acatccccgt tccggtcac ttgcagcgcc agctggcctt gatgcccgag    120
ttccatcgcc ccgagatgcc agattttacc attcatgagt acactccact tatggattca    180
tcggacatga cgccggaaga ctggcaacac attgcagaag atatcaaggc tcactatgat    240
gattatgacg gctttgttat tttacacggt actgacacaa tggcatacac agcttctgca    300
ctttcctta tgcttgagaa ccttggtaag cccgtgatcg tgaccgggtc gcagatcccc    360
cttgccgaat tgcgcagtga cggggcagatc aatcttctta atgcgttata tgtggccgct    420
```

| | |
|---|---|
| aactatccga tcaatgaagt gactttattc ttcaataacc gcttgtaccg tggaaaccgc | 480 |
| actacgaaag cccatgctga tggctttgac gcctttgcat ccccaaatct gcctcccctt | 540 |
| ttggaagccg ggattcacat ccgtcgttta aatacacccc ccgccccaca tggagagggg | 600 |
| gagcttatcg tacatccaat taccccctcaa cctatcggag ttgtaacgat ttaccctggt | 660 |
| attagtgccg acgtagtccg caatttcctt cgccagcccg tgaaagcatt gatcttacgt | 720 |
| tcctacggtg tagggaacgc gccacagaat aaggcatttc tgcaagaatt acaagaggca | 780 |
| tcggatcgtg gtatcgtggt agtcaacctg acacagtgca tgtcaggtaa agttaatatg | 840 |
| ggtggatacg caaccgggaa tgcattagct catgcagggg taattggagg cgctgatatg | 900 |
| acggtcgaag ctaccctgac gaagcttcat tatctgttat cccaggagtt ggacaccgag | 960 |
| accattcgca aagctatgtc tcagaacctt cgcggtgagc ttactcccga tgac | 1014 |

<210> SEQ ID NO 29
<211> LENGTH: 1461
<212> TYPE: DNA
<213> ORGANISM: Mycobacterium bovis
<220> FEATURE:
<221> NAME/KEY: misc_feature
<222> LOCATION: (1)..(1461)
<223> OTHER INFORMATION: Asparagine transporter ansp2 (Mycobacterium
      bovis)

<400> SEQUENCE: 29

| | |
|---|---|
| atgccgcctc tggacatcac cgacgaacgc ttgactcgcg aagatacagg atatcacaaa | 60 |
| ggccttcact cccgtcagct tcagatgatc gctcttggag gtgctattgg gaccggactt | 120 |
| tttctggggg caggcggacg tctggcttct gccggaccgg gattattctt ggtttatggt | 180 |
| atctgtggca ttttgtctt tcttattctt cgtgccttgg gagaacttgt gcttcaccgc | 240 |
| cctagttcag gatcatttgt atcctacgcg ggggaatttt atggtgaaaa ggtcgcgttc | 300 |
| gtcgcggggt ggatgtattt tttgaattgg gcaatgactg ggattgtgga cactacagcc | 360 |
| atcgcccact attgccacta ttggcgcgct tttcaaccaa ttccacagtg gacgttggcc | 420 |
| cttattgcgt tgttagttgt attatccatg aatctgatct ccgtccgctt attcggggaa | 480 |
| cttgagtttt gggcctcgct tattaaagta attgcgcttg ttacgttcct gattgtaggg | 540 |
| actgtattcc tggcggggcg ttacaagatt gacgggcaag aaactggtgt atcattatgg | 600 |
| tcatctcatg gcggaatcgt tcctacgggg ttactgccca ttgtccttgt gacctctgga | 660 |
| gttgtgttcg catacgcagc catcgagctg gtaggaatcg cagccgggga gacggccgaa | 720 |
| ccagccaaaa tcatgccccg cgcaatcaat tcggtcgtcc ttcgtattgc gtgttttttat | 780 |
| gtgggatcta cggtgcttct ggcgttgctt ttaccataca cggcttataa ggagcacgta | 840 |
| agtcccttcg taacatttt cagcaaaatt ggaattgatg ccgcggggag tgtaatgaac | 900 |
| ttggtagtgc ttacggcagc gttatctagt ttgaacgctg gtttgtattc cacaggacgc | 960 |
| atcctgcgct caatggcgat caacggcagc ggaccacgct ttacggcacc catgagtaaa | 1020 |
| accggtgttc cttatggcgg tatcttgctt acagcaggta tcggtttatt gggaatcatt | 1080 |
| cttaatgcga tcaaaccctc gcaggcgttc gaaatcgttt tacacatcgc tgctaccggc | 1140 |
| gtaatcgcag cctgggctac gatcgtggct tgtcagttgc gcttacatcg catggccaac | 1200 |
| gctggccaac ttcagcgccc taagttccgt atgcccttgt caccttttag cgggtacctg | 1260 |
| actttggcgt ttctgcgggg cgtgctgatt ctgatgtatt cgatgagca gcacgggccc | 1320 |
| tggatgatcg ccgcgacagt aattgggggtt cctgcccttta ttgggggttg gtacttggtt | 1380 |

```
cgtaaccgtg tgactgccgt cgctcatcac gctattgacc acactaagag tgtagctgtg    1440
gttcattcgg cagatcccat t                                              1461

<210> SEQ ID NO 30
<211> LENGTH: 1344
<212> TYPE: DNA
<213> ORGANISM: Bacillus subtilis
<220> FEATURE:
<221> NAME/KEY: misc_feature
<222> LOCATION: (1)..(1344)
<223> OTHER INFORMATION: Serine ammonia lyase (Bacillus subtilis)

<400> SEQUENCE: 30
atgtccatta atcaggaggc gcttcacgta ctgttgaagg atccttttat tcatcgtctt      60
attgatgctg agccagtgtt ttgggcaaat ccaggtatga aggagggggct gcttttcac    120 gctgacgagt gggaaagtga gattgccgaa gcagagaaac gcttgcgtcg ttttgcgcct    180
tatatcgcgg aggttttccc agagaccaaa gatgcaaagg gcatgatcga gtctccactg    240
tttgagatgc aacatatgaa aagaaactg gaggcagcat accaacaacc tttccccgga    300
cgttggctgc ttaagtgtga ccatgaactt cccatttccg ggtcgattaa ggcccgcgga    360
ggtatctatg aagtcttgaa acatgccgaa aagctggctc ttcaggaggg gatgcttcaa    420
gagtcggacg attatcgtat gttgcaagaa gatcgtttcg cggccttctt cagccgctat    480
tctatcgcag tgggctccac gggcaattta ggtttaagta tcgggattat tggcgctgct    540
cttggtttcc gcgtaacagt tcacatgagt gctgacgcta agcaatggaa gaaagatctg    600
ttacgtcaga aaggggtaac cgtaatgaaa tatgagagcg attattcaga agcagttaaa    660
gaaggtcgtc gccaagcaga acaagaccca ttctgttact tcattgatga tgaacatagc    720
cgtcaattgt tcctgggcta cgcagttgcc gcgtcccgcc ttaagacaca actggattgc    780
atggaaatcc aacctggtcc cgaaacaccc ctgttcgtgt atcttccctg tggcgtaggt    840 gggggggccag gaggtgtcgc tttcgggttg aaactgctgt atggagatca cgtccatgta    900 ttttcggag aaccgacgca atccccgtgc atgcttttag gcttatattc tggcttacac    960
gagcagattt cagttcaaga cattggattg dacaaccgta ccgcggcgga tggcttggcg   1020
gtagggcgtc cctcaggatt cgtaggaaaa ttaatcgaac cactgctgtc gggctgctat   1080
actgtagaag acgatacact gtatgcttta ctgcacatgc tggcagcttc ggaatccaag   1140
tatcttgaac ctagcgcctt ggcggggatg ttcggcccga tccagctgtt cagcacagaa   1200
gaaggacgtc gctattctca gaaacataaa atggagcatg cggtgcacgt tatctggggg   1260
acggggggta gcatggtgcc aaaggaggag atggccgcat acaaccgcat cggggcggat   1320
ctgttaaaaa atgaaatgaa gaag                                         1344

<210> SEQ ID NO 31
<211> LENGTH: 1374
<212> TYPE: DNA
<213> ORGANISM: Pseudomonas fluorescens F113
<220> FEATURE:
<221> NAME/KEY: misc_feature
<222> LOCATION: (1)..(1374)
<223> OTHER INFORMATION: SdaA (Pseudomonas fluorescens F113)

<400> SEQUENCE: 31
atgtcccttt cagtgtttga tctttttaag atcggaattg gtccctcgtc ctctcatacc      60
gtaggaccta tgcgtgcggc cgctcgtttt gccgaaggtc tgcgccgcga cgacctgctg    120
aactgtacta ctagcgtgaa agtcgagctg tacggatctc tgggcgcgac tggtaagggg    180
```

```
cacggttcgg acaaagcagt gttactggga ttggagggag aacaccctga cactgtcgac      240
accgagacgg ttgacgctcg tttacaggcg atccgcagtt caggccgcct gaatttattg      300
ggggagcata gcattgagtt taatgaaaag ctgcacttgg caatgattcg caagccgtta      360
gctttccatc cgaatggcat gattttccgt gcgtttgatg ctgcgggctt acaggtacgt      420
tcccgtgagt attactccgt cggcggaggg ttcgttgtag acgaggacgc agcgggtgcc      480
gaccgtatcg tcgaggatgc aacacctttg acattcccct tcaagagcgc gaaggatctt      540
ttaggtcatt gttctactta tggtttaagc atcagccaag tcatgcttac aaacgagtct      600
gcgtggcgtc cggaagcgga gacccgcgca gggcttctta aaatttggca ggtgatgcaa      660
gactgcgttg ccgcggggtg tcgcaatgag ggcatccttc caggaggtct aaagtaaag       720 cgccgcgcg  ctgcgttgca tcgtcaattg tgtaagaacc ccgaggctgc cctgcgcgat      780
ccgttaagtg tattagattg ggtgaatttg tatgcgttag cggtaaatga agagaacgcc      840
tacggtggac gcgtggtcac ggcgcccact aatggagccg caggaatcat tcctgccgta      900
ttgcattact acatgcgctt tattccgggg gcatctgagg acggagtagt ccgcttcctt      960
cttacagcgg cggcaatcgg gatcttgtat aaagagaacg cctctattag tggggctgag     1020
gttggctgtc agggcgaagt aggagtggca tgctccatgg cagcggggc  gttgtgcgaa     1080 gtcttgggag gctcggtcca acaagtagaa acgcagcag  aaatcggaat ggagcataac     1140
cttggcttga catgtgatcc tatcggcggg ttagtacagg tcccgtgtat cgagcgtaac     1200
gcaatgggat ctgttaaagc cattaacgca gtacgcatgg ctatgcgcgg ggacggtcac     1260
catttcgtct cccttgacaa agtaattcgt accatgcgtc aaactggggc cgacatgaaa     1320
agcaagtaca aggaaaccgc gcgtggtgga cttgctgtca acatcatcga gtgt            1374

<210> SEQ ID NO 32
<211> LENGTH: 1365
<212> TYPE: DNA
<213> ORGANISM: Klebsiella pneumoniae
<220> FEATURE:
<221> NAME/KEY: misc_feature
<222> LOCATION: (1)..(1365)
<223> OTHER INFORMATION: sdaB(Klebsiella pneumoniae)

<400> SEQUENCE: 32
atgattagtg tgtttgacat ctttaaaatc ggtatcggtc cgtcttcttc ccatacggtt        60
ggtcccatga aagcagggaa gcagtttacc gacgacttaa ttgctcgtgg actgctggca      120
gaggtcagta aggtcgtggt tgatgtttat ggctcccttt cattgacggg caaaggtcac      180
catactgaca ttgctatcat tatgggtctg gcgggaaact tgccagacac cgttgacatc      240
gacgccatcc ccggcttcat ccaagatgtt aacactcacg acgtctgat  gttagcgaat      300 gggcagcatg aagttgattt cccggtagac cagtgtatga attttcacgc tgacaacctg      360
tccttgcacg agaatggaat gcgtattacg gctcttgcgg gagacaaagt gttgtactct      420
cagacttact actcaatcgg cggcggattc attgttgatg aggaacattt tggccaaaca      480
acggaggctc ctgtagccgt cccatatcca tacaaaaacg ccgctgattt gcagcgtcat      540
tgccgtgaaa ctggtttgag tttatctgga cttatgatgc aaaacgaact tgcattgcat      600
agcaaagaag ctctggaaca gcactttgct gcagtttggg aggttatgtc tgccggcatt      660
gagcgcggca ttcaactga  aggtgtgttg cctggcaaat acgtgtacc  ccgccgcgcc      720 gcggcactgc gtcgtatgtt agtctcgcaa gacacgacga actcggaccc tatggctgtt      780
```

| | |
|---|---|
| gtagattgga tcaatatgtt cgcgttggcc gtcaacgagg agaacgcggc gggcggtcgc | 840 |
| gttgttacag ccccccacaaa tggcgcgtgc ggaattgttc cggccgtgct ggcatattat | 900 |
| gacaaattta tccgcaaagt caactccaac agtctggcgc gttatatgct ggtggcaagt | 960 |
| gcaatcggct cactttataa gatgaatgcg agcatctccg gcgcagaagt tggctgccaa | 1020 |
| ggtgaagtgg gggtcgcctg ctctatggca gcggctggct tggcagagct gttgggcggg | 1080 |
| tcgccagggc aagtgtgcat tgcggctgaa attgcgatgg agcataactt gggccttacg | 1140 |
| tgcgatcccg tagctggcca agtgcaggta ccgtgtatcg aacgcaatgc aattgcagcc | 1200 |
| gtaaaagcag taaatgcggc tcgcatggcc ttacgtcgta cttccgagcc ccgtgtgtgc | 1260 |
| ttggataagg tgatcgaaac catgtatgag acaggtaagg acatgaatgc aaagtatcgt | 1320 |
| gaaacgtctc gtggaggcct ggccatgaag atcgtcgcgt gtgac | 1365 |

<210> SEQ ID NO 33
<211> LENGTH: 1362
<212> TYPE: DNA
<213> ORGANISM: Escherichia coli
<220> FEATURE:
<221> NAME/KEY: misc_feature
<222> LOCATION: (1)..(1362)
<223> OTHER INFORMATION: tdcG L-serine dehydratase (Escherichia coli
    O157:H7 str. SS17)

<400> SEQUENCE: 33

| | |
|---|---|
| atgattagtg cattcgatat tttcaagatt ggaatcggcc cctcgtcatc gcacacggtg | 60 |
| ggcccaatga cgcaggtaa gtccttcatt gatcgccttg agtcgagtgg cttattgaca | 120 |
| gcgacaagcc acattgtcgt ggacctgtac gggagtctgt cgttgacggg caaaggccat | 180 |
| gcgaccgatg ttgctattat catgggattg gccgggaatt caccgcagga cgtagtaatc | 240 |
| gatgaaatcc cggccttcat tgagctggta actcgttcgg gccgtctgcc agtcgcaagc | 300 |
| ggagctcata tcgttgactt cccagttgcc aagaacatta tttttcaccc tgaaatgtta | 360 |
| cctcgccatg agaacggaat gcgtatcaca gcatggaaag ctcaggaaga attattgagt | 420 |
| aagacgtatt actcggttgg tggcgggttc atcgtcgagg aagagcactt cggttttatct | 480 |
| catgacgtag aaacaccagt accatacgac ttccattcag caggtgagtt gttgaaaatg | 540 |
| tgcgattaca atggccttag tatttcggga cttatgatgc ataacgaatt agcgcttcgt | 600 |
| tcgaaggccg aaattgacgc cggcttcgca cgtatctggc aagttatgca tgatggcatc | 660 |
| gaacgtggta tgaacaccga aggtgtgtta ccaggaccct tgaatgttcc gcgtcgtgca | 720 |
| gtcgcactgc gtcgtcaact tgttagtagt gacaacattt ccaatgatcc aatgaacgtg | 780 |
| attgactgga tcaacatgta cgcgctggcg gtctcggagg aaaacgccgc tgggggtcgc | 840 |
| gtggtaacag cacctacgaa tggggcttgc gggatcatcc ctgcggtatt ggcctattac | 900 |
| gataagtttc gccgtccagt caatgagcgc tcaatcgctc gttacttcct ggcggcgggg | 960 |
| gctatcggcg ctttatacaa gatgaacgcc tctatttcag gggcggaggt cggttgtcaa | 1020 |
| ggagagattg gggtcgcgtg ctctatggca gctgcaggtt tgacagaatt attaggcggc | 1080 |
| agccagccc aagtttgcaa cgcggctgaa atcgcaatgg aacataatct tggtctgacc | 1140 |
| tgtgacccctg tcgcaggtca ggtacagatt ccttgcattg agcgtaatgc aatcaacgca | 1200 |
| gtaaaagctg ttaatgcggc gcgtatggct atgcgtcgca catcagcccc gcgtgtgagc | 1260 |
| ctggataagg taatcgagac catgtacgaa accggtaaag acatgaatga caaataccgc | 1320 |
| gaaacctctc gcgggggtct tgcaattaaa gtcgtgtgtg gc | 1362 |

<210> SEQ ID NO 34
<211> LENGTH: 1251
<212> TYPE: DNA
<213> ORGANISM: Escherichia coli
<220> FEATURE:
<221> NAME/KEY: misc_feature
<222> LOCATION: (1)..(1251)
<223> OTHER INFORMATION: glyA(Escherichia coliEPEC C342-62)

<400> SEQUENCE: 34

| | | | | | |
|---|---|---|---|---|---|
| atgttgaaac | gtgagatgaa | tattgccgac | tatgatgcag | aattatggca agctatggaa | 60 |
| caagagaaag | tccgccagga | agaacatatt | gaattaatcg | cctctgaaaa ttacactagt | 120 |
| ccccgcgtta | tgcaagccca | aggcagccaa | ttaactaaca | aatatgccga gggatatcct | 180 |
| gggaaacgct | actatggagg | ttgcgagtat | gtagatattg | tcgaacagtt agcaatcgac | 240 |
| cgcgcgaaag | agcttttcgg | cgcagactat | gcaaacgtgc | agccccattc gggtagccaa | 300 |
| gcgaattttg | cggtctatac | cgcactgctg | gaaccgggag | acacggtact gggtatgaat | 360 |
| ttagctcatg | gtggtcactt | aacgcacggg | tccccgtta | atttctctgg aaaactgtac | 420 |
| aacatcgtcc | cctatggaat | cgatgctacc | ggccacattg | attacgcgga tcttgagaag | 480 |
| caagctaagg | aacataaacc | aaagatgatc | attggcggtt | tttcagctta tagtggtgtc | 540 |
| gtcgactggg | ctaagatgcg | tgaaattgca | gactctattg | gcgcgtacct ttttgtcgac | 600 |
| atggcccacg | tggctggctt | ggtggcggca | ggggtctacc | cgaacccgt tccccatgcg | 660 |
| catgtcgtga | ccaccacgac | acataagaca | ctggctgggc | ctcgtggtgg cttaatcttg | 720 |
| gccaagggg | ggtctgagga | attatacaaa | aaacttaact | cagccgtttt tccaggcgga | 780 |
| cagggtggtc | cgttgatgca | cgtgattgct | ggaaaggcgg | tcgctcttaa ggaagccatg | 840 |
| gaacctgaat | tcaaaacgta | ccaacagcag | gttgcaaaaa | acgccaaagc gatggttgag | 900 |
| gttttcctgg | aacgtggtta | caaagtcgtt | agtgggggta | ccgataatca tcttttctta | 960 |
| gttgacctgt | agataaaaa | tttgaccgga | aaggaggcgg | acgctgcctt aggccgtgcg | 1020 |
| aatattaccg | tcaataaaaa | ctcggtgcca | aatgatccca | agtcgccttt cgtgacttca | 1080 |
| ggaatccgcg | taggaactcc | cgcaattaca | cgccgcgggt | tcaaggaagc tgaggcgaag | 1140 |
| gagttagcag | atggatgtg | tgatgttta | gactcgatta | acgatgaggc ggtgatcgaa | 1200 |
| cgtatcaaag | gtaaagtatt | agatatttgc | gcccgttatc | cagtttatgc c | 1251 |

<210> SEQ ID NO 35
<211> LENGTH: 1287
<212> TYPE: DNA
<213> ORGANISM: Escherichia coli
<220> FEATURE:
<221> NAME/KEY: misc_feature
<222> LOCATION: (1)..(1287)
<223> OTHER INFORMATION: SdaCserine STP transporter (Escherichia coliBL21(DE3)

<400> SEQUENCE: 35

| | | | | | |
|---|---|---|---|---|---|
| atggagacca | cgcagacttc | tacaattgcg | agcaaagata | gccgttctgc ttggcgcaaa | 60 |
| actgatacta | tgtggatgtt | gggcctgtat | ggaacagcta | ttggggccgg ggtactgttt | 120 |
| ttgccaatca | atgctggagt | gggggtatg | atcccgctga | tcattatggc gattcttgct | 180 |
| ttcccaatga | catttttgc | acatcgcggt | cttacacgct | tgtcctttc aggaaagaat | 240 |
| cctggggagg | acattacgga | ggttgtagaa | gaacattttg | gcattgggc tgggaaactt | 300 |
| atcacattgc | tgtattttt | tgcaatctat | cccattttgc | ttgtctatag cgtagcaatc | 360 |

```
acgaacaccg tagaatcatt catgtcgcac cagttaggca tgacacctcc gccacgtgcg    420
attctgtcat tgatcttgat cgtgggaatg atgacaattg ttcgtttcgg agagcaaatg    480
atcgtgaaag ccatgtcaat tttggtattt ccgttcgtgg gagtcttaat gttgctggca    540
ttgtatttaa ttccccagtg gaatggtgcc gctctggaga ccttgtcgtt ggatacggcg    600
tcagcgaccg gtaatggtct ttggatgacg ctttggttgg ccattccggt catggttttt    660
tcatttaacc actcaccgat cattagctcg ttcgctgtgg cgaaacgcga agaatacggt    720
gatatggctg aacaaaagtg ctcgaagatt ttggcattcg cccacatcat gatggtactt    780
acggtcatgt tcttcgtgtt ttcttgcgtc cttagtttaa ccccagcgga cctggcggct    840
gcaaaggaac aaaatatcag catcttaagc tatttggcga atcatttcaa cgcgcctgtt    900
atcgcatgga tggcacccat tatcgctatc attgcaatta ccaaatcttt cttagggcac    960
tacttgggtg cgcgcgaagg atttaacggg atggttatca agtcgcttcg tgggaaagga    1020
aagagtatcg agatcaataa acttaatcgc atcaccgcct tgttcatgtt agtaacaacg    1080
tggatcgtcg ctacacttaa tccctccatt ctggggatga ttgaaacgct tgggggtcca    1140
atcatcgcaa tgatcttgtt tctgatgccg atgtacgcta ccagaaggt  acccgcaatg    1200 cgtaaatact ctgggcatat ctccaacgtg tttgttgttg ttatgggatt aatcgctatt    1260
tctgctatct tctatagtct gttctcc                                        1287
```

<210> SEQ ID NO 36
<211> LENGTH: 438
<212> TYPE: DNA
<213> ORGANISM: Lactobacillus saniviri
<220> FEATURE:
<221> NAME/KEY: misc_feature
<222> LOCATION: (1)..(438)
<223> OTHER INFORMATION: threonine Serine Exporter (Lactobacillus
      saniviri JCM 17471 = DSM 24301)

<400> SEQUENCE: 36

```
atggcgtatt ctgtccagtt cctgatccaa ctgtccttct cgtaccttgc cactgtggct     60
tttgctatct gcatcaacgt tccacgtcgt gcgttaaatt tgccggatg ggccggtgcc    120 atcgggtgga tctgctactg gctgctgaac acacatggca cgggccgcat gttcgctaac    180
ctgattggcg ctgtcgcagt tgggggtatgt ggtatcatttt cgctcgcat caagaagatg    240 cccgtgatta ttttcaatat tccggggctg gtgccattag tgcctggagc aaccgcctac    300
caggcagttc gcgctcttgc gttgggaaat atggaccttg ctatccagct tggagttcgt    360
gttattatgg tcgcaggggc aatcgcggtg ggattcatgg ttagtcagct tctgtcagag    420
ttgacttacc gcttgcac                                                  438
```

<210> SEQ ID NO 37
<211> LENGTH: 930
<212> TYPE: DNA
<213> ORGANISM: Escherichia coli
<220> FEATURE:
<221> NAME/KEY: misc_feature
<222> LOCATION: (1)..(930)
<223> OTHER INFORMATION: glutaminase YbaS (Escherichia coli ST131)

<400> SEQUENCE: 37

```
atgctggatg ctaataagct gcagcaggct gtcgatcagg cttatactca atttcattct     60
ttgaatggtg ggcagaatgc cgattacatt cctttcttgg ctaatgtccc agggcaatta    120
gcagccgtag ctattgtaac atccgatggc aacgtgtatt ctgccgggga ctcggactac    180
```

```
cgcttcgcac ttgagtctat cagtaaagtc tgcactttgg cactggcgct ggaggacgtt    240
gggcctcagg ccgtgcagga caaggttggg gctgatccta cagggctgcc attcaactca    300
gtaattgctt tggaattaca cggtggaaaa ccactgtcac cgctggtgaa cgcggggca     360 atcgctacca cgtctttgat taatgcagaa aatacggaac agcgttggca acgtattttg    420
catattcagc agcagcttgc tggtgagcaa gtcgcacttt ctgatgaagt gaaccaaagt    480
gaacaaacta ctaattttca caaccgtgca attgcttggt tactgtacag tgctggctac    540
ttgtactgtg acgcaatgga agcctgtgat gtttatacac gtcagtgcag tactttgatc    600
aacacaatcg aattggcaac attgggagct acgttagccg ctgggggcgt gaatccgttg    660
acacataaac gcgttctgca agcggacaat gtgccctata ttttggctga aatgatgatg    720
gaagggcttt atggccgctc tggggactgg gcctaccgtg taggcttgcc aggaaagtcg    780
ggggtcggag gagggattct ggccgtggtg cccggcgtaa tgggaattgc cgcgttttcg    840
cctcccttag acgaagaagg taacagcgtg cgcggacaaa agatggttgc gagcgttgca    900
aagcagcttg ggtataacgt atttaaaggg                                     930
```

<210> SEQ ID NO 38
<211> LENGTH: 924
<212> TYPE: DNA
<213> ORGANISM: Escherichia coli
<220> FEATURE:
<221> NAME/KEY: misc_feature
<222> LOCATION: (1)..(924)
<223> OTHER INFORMATION: Glutaminase (Escherichia coli O145:H28 str. RM12581)

<400> SEQUENCE: 38

```
atggccgtcg caatggataa cgccatttta gagaatatcc tgcgccaagt gcgcccatta     60
atcggacaag gcaaggttgc ggattacatt ccggccttag ctacagtgga tgggagtcgc    120
ctgggaatcg ctatttgcac tgttgacggc caattgtttc aggcaggcga cgcacaagag    180
cgcttctcca tccagagcat ttctaaagtg ttgtcattgg ttgttgctat gcgtcactac    240
tctgaggagg aaatttggca gcgcgtgggg aaggacccgt ccggcagtcc atttaattcg    300
ttggtacagt tggagatgga acaaggaatc cctcgtaatc ccttcatcaa tgcaggtgct    360
cttgtagtct gcgacatgtt acaaggtcgt ttatctgccc ctcgccaacg catgttggaa    420
gttgtgcgtg gtttgtctgg agttagcgat atcagctacg acacggtcgt ggctcgcagt    480
gaatttgaac actcagcacg caatgcagcg attgcgtggt taatgaagtc gtttgggaat    540
tttcatcacg atgtgacgac agtccttcaa aattatttcc actactgcgc attgaagatg    600
tcgtgcgtag agcttgcccg tacgttcgtc tttcttgcga accagggcaa ggccatccat    660
atcgacgagc ccgtcgtaac cccgatgcag gcgcgtcaaa tcaatgcgct gatggcgaca    720
tcgggaatgt atcagaatgc ggggagttc gcctggcgtg tcggattacc agctaaatcc    780
ggtgtaggcg gtggaatcgt tgccattgtg ccccatgaaa tggctatcgc tgtgtggtcc    840
ccagaattag atgacgcagg aaattcgtta gcaggtattg cggttttaga acaacttacg    900
aaacaattag gacgctcggt gtat                                           924
```

<210> SEQ ID NO 39
<211> LENGTH: 927
<212> TYPE: DNA
<213> ORGANISM: Bacillus subtilis
<220> FEATURE:
<221> NAME/KEY: misc_feature
<222> LOCATION: (1)..(927)

<223> OTHER INFORMATION: ylaM (Bacillus subtilis subsp. subtilis str.
168)

<400> SEQUENCE: 39

| | | |
|---|---|---|
| atggtgtgtc agcataatga tgaattagag gctcttgtca agaaggcaaa aaaggttacg | 60 |
| gataaggggg aggtggctag ttacattcca gctctggcta aggcggacaa acacgactta | 120 |
| agtgtcgcaa tctactatag caataatgtg tgcctgtccg caggggacgt tgaaaagacg | 180 |
| ttcactctgc aatccatcag caaagttctg tcgttagctc tggtacttat ggagtatggg | 240 |
| aaggataagg tattcagtta tgttgggcag gaacctacag gtgatccctt aacagcatc | 300 |
| attaaactgg agacagtcaa ccccctctaag ccattaaatc cgatgatcaa tgcgggcgcg | 360 |
| ttagtagtga ccagtcttat ccgcggacgt acggtgaagg agcgtcttga ctatcttctt | 420 |
| agctttatcc gtcgtctgac taataatcaa gaaattacat actgccgcga ggtagcggaa | 480 |
| agcgaatatt ctacttcaat gattaaccgt gcgatgtgct attatatgaa acagtatgga | 540 |
| attttcgaag atgacgttga agcggttatg gacctttata caaagcaatg cgctattgaa | 600 |
| atgaactcac ttgatttggc taagatcggt tcggttttcg ccttgaacgg acgccatcct | 660 |
| gaaaccgggg agcaagtgat ttcgaaggat gtagcccgta tctgtaagac gtttatggtg | 720 |
| acgtgtggaa tgtataatgc ctctggtgaa tttgcgatca agttggtat ccctgcgaaa | 780 |
| tcgggagtgt caggtgggat tatgggtatc tccccttacg atttcggaat cgggatcttt | 840 |
| ggacccgcgc tggacgagaa ggggaatagt attgctggtg tgaagctttt agaaatcatg | 900 |
| agcgagatgt accgtcttag tatcttt | 927 |

<210> SEQ ID NO 40
<211> LENGTH: 981
<212> TYPE: DNA
<213> ORGANISM: Bacillus subtilis
<220> FEATURE:
<221> NAME/KEY: misc_feature
<222> LOCATION: (1)..(981)
<223> OTHER INFORMATION: ybgJ(Bacillus subtilis)

<400> SEQUENCE: 40

| | | |
|---|---|---|
| atgaaagagt tgattaaaga gcatcaaaag gatatcaatc ctgcattaca actgcatgac | 60 |
| tgggtagaat actaccgtcc atttgcggca aatggccaaa gtgcaaacta tatccccgct | 120 |
| ttagggaagg tgaacgacag ccagttaggg atctgcgtac tggaaccgga tggcaccatg | 180 |
| attcacgctg gggattggaa tgtgtccttt accatgcagt cgatttcaaa agtaattagc | 240 |
| ttcattgctg cctgcatgtc gcgtggaatc ccgtatgtct tggatcgtgt agacgtggaa | 300 |
| cccacaggag atgcttttaa tagtatcatc cgtttagaga tcaacaaacc aggaaagcct | 360 |
| ttcaatccta tgattaatgc cggagctttg actatcgcta gcattcttcc aggagagtcc | 420 |
| gcttacgaaa aacttgagtt tttgtatagc gtgatggaga ctttaatcgg taaacgcccc | 480 |
| cgtattcacg aagaagtatt ccgttctgaa tgggagaccg ctcatcgcaa tcgcgcctta | 540 |
| gcctactatc ttaaagaaac aaacttctta gaggccgagg tcgaagagac actggaagta | 600 |
| tatttgaaac aatgcgcgat ggaatcgacc acgaagaaca tcgccctgat cgggttgatc | 660 |
| ctggcccacg atgggtatca tcctatccgt catgagcagg tcattcccaa ggatgttgcc | 720 |
| aagttggcta aagcgttaat gttgacctgt ggcatgtata acgcttctgg aaagtatgcg | 780 |
| gctttcgttg gagtacccgc aaaatctgga gtttcgggtg gtattatggc cttggtgcct | 840 |
| ccaagtgcgc gtcgcgaaca gccgttccag agcgggtgcg gtatcgggat ttatggacct | 900 |

| | |
|---|---:|
| gcaattgatg agtacgggaa tagcctgacg ggcggcatgc ttttaaaaca catggcccaa | 960 |
| gagtgggaac tgagtatttt c | 981 |

<210> SEQ ID NO 41
<211> LENGTH: 3436
<212> TYPE: DNA
<213> ORGANISM: Escherichia coli
<220> FEATURE:
<221> NAME/KEY: misc_feature
<222> LOCATION: (1)..(3436)
<223> OTHER INFORMATION: Glutamine permease glnHPQ operon (Escherichia coli)

<400> SEQUENCE: 41

| | |
|---|---:|
| ccatggcaga acgtgcagtg cagctgggcg gtgtagctct ggggaccact caagttatca | 60 |
| acagcaaaac cccgctgaaa agttacccgc tggacatcca caacgttcag gatcacctga | 120 |
| aagaactggc tgaccgttac gcaatcgtcg ctaatgacgt acgcaaagcg attggcgaag | 180 |
| cgaaagatga cgacaccgca gatatcctga ccgccgcgtc tcgcgacctg gataaattcc | 240 |
| tgtggtttat cgagtctaac atcgaataaa tccatcgctg atggtgcaga actttagtac | 300 |
| ccgataaaag cggcttcctg acaggaggcc gttttgtttt gcagcccacc tcaacgcact | 360 |
| tatttagtgc atccatctgc tatctccagc tgattaagta aattttttgt atccacatca | 420 |
| tcacacaatc gttacataaa gattgttttt tcatcaggtt ttacgctaaa taatcactgt | 480 |
| gttgagtgca caattttagc gcaccagatt ggtgccccag aatggtgcat cttcagggta | 540 |
| ttgccctata aatcgtgcat cacgttttg ccgcatctcg aaaaatcaag gagttgcaaa | 600 |
| actggcacga ttttttcata tatgtgaatg tcacgcaggg gatcgtcccg tggatagaaa | 660 |
| aaaggaaatg ctatgaagtc tgtattaaaa gtttcactgg ctgcactgac cctggctttt | 720 |
| gcggtttctt ctcatgccgc ggataaaaaa ttagttgtcg gacggatac cgccttcgtt | 780 |
| ccgtttgaat ttaaacaggg cgataaatat gtgggctttg acgttgatct gtgggctgcc | 840 |
| atcgctaaag agctgaagct ggattacgaa ctgaagccga tggatttcag tgggatcatt | 900 |
| ccggcactgc aaaccaaaaa cgtcgatctg cgctggcgg gcattaccat caccgacgag | 960 |
| cgtaaaaaag cgatcgattt ctctgacggc tactacaaaa gcggcctgtt agtgatggtg | 1020 |
| aaagctaaca ataacgatgt gaaaagcgtg aaagatctcg acgggaaagt ggttgctgtg | 1080 |
| aagagcggta ctggctccgt tgattacgcg aaagcaaaca tcaaaactaa agatctgcgt | 1140 |
| cagttcccga acatcgataa cgcctatatg gaactgggca ccaaccgcgc agacgccgtt | 1200 |
| ctgcacgata cgccaaacat tctgtacttc atcaaaaccg ccggtaacgg tcagttcaaa | 1260 |
| gcggtaggtg actctctgga agcgcagcaa tacggtattg cgttcccgaa aggtagcgac | 1320 |
| gagctgcgta caaagtcaa cggcgcgttg aaaaccctgc gcgagaacgg aacttacaac | 1380 |
| gaaatctaca aaaaatggtt cggtactgaa ccgaaataat aacgctacac ctgtaaaacg | 1440 |
| cactggcagt tccctctccc ctatggggag aggattaggg tgaggggcgc aaacccgctc | 1500 |
| cggggccatt aattaccctg aatttgatta tttacaccac ggtaacagga acaacatatg | 1560 |
| cagtttgact ggagtgccat ctggcctgcc attccgcttc tgattgaagg tgccaaaatg | 1620 |
| accctgtgga tttcggtcct cggtctggca ggcggtctgg taatcggatt gctggcaggt | 1680 |
| tttgcacgca ccttcggagg ttggatagcc aaccgtcg cgctggtctt tattgaagtg | 1740 |
| atccgcggca cacctatcgt cgtccaggtg atgtttattt atttcgccct gccgatggcg | 1800 |
| tttaacgact tacgcatcga cccatttact gcggcggtgg tcaccatcat gatcaactcc | 1860 |

```
ggcgcgtata ttgcggaaat cacgcgtggt gcggtgctgt ctatccacaa aggttttcgt    1920
gaagcaggac tggcgctcgg tctttcacgt tgggaaacca ttcgctacgt cattttaccg    1980
ctggcactgc gtcgtatgct gccgccgctg ggtaaccagt ggatcatcag cattaaagac    2040
acctcgctgt ttattgtgat cggcgtggcg gaactgaccc gtcaggggca agaaattatt    2100
gccggtaact tccgcgccct tgagatctgg agcgccgtgg cggtgttcta tctgattatt    2160
accctggtgc tgagctttat tctgcgtcgt ctggaaagaa ggatgaaaat cctgtgattg    2220
aatttaaaaa cgtctccaag cactttggcc caacccaggt gctgcacaat atcgatttga    2280
acattgccca gggcgaagtc gtggtgatta tcgggccgtc cggttccggt aaatcgaccc    2340
tgctgcgctg catcaacaaa ctggaagaaa tcacctccgg cgatctgatt gtcgatggcc    2400
tgaaggttaa cgatccgaaa gttgacgagc gcctgattcg ccaggaagca ggtatggtgt    2460
tccagcagtt ttacctcttc ccgcatctga cagcgctgga aaacgtcatg tttggcccgc    2520
tacgcgtgcg tggcgcgaac aaagaagagg cggaaaaact ggcacgtgag ctgctggcga    2580
aagtcggtct ggcagaacgt gcacatcact acccttccga actttctggt ggtcaacagc    2640
agcgtgtggc gattgcccgc gcgctggcgg tgaagccgaa aatgatgctg tttgatgaac    2700
cgacttccgc tcttgacccg gaactgcgcc atgaagtgct gaaggttatg caggatctgg    2760
ctgaagaagg gatgacgatg gtgatcgtga cccacgaaat cggttttgcc gagaaagtag    2820
cttcgcggct gatctttatc gacaaaggcc ggattgcgga agatggcaat ccgcaggtgt    2880
tgatcaagaa cccgccgagc cagcgcttgc aggaattttt gcagcacgtc tcttaataag    2940
acacattgcc tgatcgtacg cttatcaggc ctacaggata tctggcaact tattaaaatt    3000
gcatgaactt gtaggacgga taaggcgttc acgcgcatcc ggcaaaaaag cccgcacgtt    3060
gtcagcaacc tgcttaatat cccttcctcc ctttcacccg aaagggaggc acaccagatt    3120
cctctcattt aaaatcgccc ctcctccagc atctatactt atctttttgc tctattttct    3180
cactggagga gtcatgcggt ggatcctgtt catcctcttc tgcctgctgg gcgcacctgc    3240
ccacgcggta tccatacccg gcgttacaac cacaacgaca acggactcaa cgactgaacc    3300
ggccccggaa ccggatatcg aacaaaaaaa agcggcctat gcgcactggc ggatgtgctg    3360
gataatgaca cctcgcgtaa agagttgatc gaccagttgc gcaccgttgc cgctacgccc    3420
ctgctgaacc ggtacc                                                   3436
```

<210> SEQ ID NO 42
<211> LENGTH: 744
<212> TYPE: DNA
<213> ORGANISM: Escherichia coli
<220> FEATURE:
<221> NAME/KEY: misc_feature
<222> LOCATION: (1)..(744)
<223> OTHER INFORMATION: Glutamine permease H glnH (Escherichia coliEPEC C342-62)

<400> SEQUENCE: 42

```
atgaaaagtg tacttaaagt gtcattggca gcactgacac ttgcatttgc agtctccagt      60
catgctgcgg acaaaaagtt agtcgtagcg actgacactg cgtttgttcc tttcgaattc     120
aagcaggggg acaagtacgt cggctttgac gtagaccttt gggccgccat tgcaaaagag     180
cttaagttgg attacgagtt aaagcctatg gacttcagtg gtatcattcc cgccctgcaa     240
acgaaaaacg tggatcttgc gcttgcaggc attactatta ccgacgaacg caagaaggcg     300
attgacttca gcgacggcta ttataagtcg ggtctttag ttatggtaaa agccaacaat     360
```

```
aatgatgtga aaagcgtgaa agatttggac gggaaagtag tggcagttaa atcaggtaca      420
gggagtgtgg attacgcgaa agctaatatc aaaaccaaag acttacgtca attcccgaat      480
atcgacaatg cgtatatgga actggggacg aaccgtgcgg atgcggtgct gcacgataca      540
cccaacatcc tttatttcat taaaacagct ggtaatggtc aatttaaagc tgtaggcgac      600
agcctggaag cccagcaata cgggatcgcg ttccctaagg gctctgatga gcttcgtgac      660
aaggtaaacg gggcgcttaa aacgctgcgt gaaaacggaa cgtacaatga aatctataag      720
aagtggttcg gaaccgagcc caaa                                             744

<210> SEQ ID NO 43
<211> LENGTH: 657
<212> TYPE: DNA
<213> ORGANISM: Escherichia coli
<220> FEATURE:
<221> NAME/KEY: misc_feature
<222> LOCATION: (1)..(657)
<223> OTHER INFORMATION: Glutamine permease P glnP (Escherichia
      coliB354)

<400> SEQUENCE: 43
atgcaattcg attggagtgc gatttggcct gccattcccc ttctgattga gggtgcaaaa       60
atgactctgt ggatttcagt gctggggtta gccggaggtc ttgttattgg gttattagca      120
gggtttgcac gcactttcgg gggatggatt gcaaatcatg ttgcgctggt cttcatcgaa      180
gtcattcgtg gcaccccccat cgtggtccaa gtgatgttta tttacttcgc gttgccaatg     240
gcatttaacg atcttcgtat tgatccattt actgcggcag tggtgactat catgattaat      300
agtggggcgt acattgcgga gattactcgc ggcgctgttc tttccattca caaaggtttt      360
cgtgaggccg gtttagctct tgggctttcc cgctgggaaa caattcgtta tgttatcttg      420
ccgcttgcct tgcgccgtat gttgccgccg ctgggtaacc aatggatcat ttctatcaaa      480
gatacttcgc ttttcattgt tattggagtg gctgaattaa cacgccaagg tcaagaaatc      540
atcgcgggga atttccgtgc attagagatc tggagtgctg tcgccgttt ctacttgatc       600 attacgctgg tgctgtcctt tattttgcgc cgcttggagc gtcgcatgaa gattctt         657

<210> SEQ ID NO 44
<211> LENGTH: 720
<212> TYPE: DNA
<213> ORGANISM: Escherichia coli
<220> FEATURE:
<221> NAME/KEY: misc_feature
<222> LOCATION: (1)..(720)
<223> OTHER INFORMATION: Glutamine Permease Q glnQ (Escherichia coliEPE
      C C342-62)

<400> SEQUENCE: 44
atgattgaat ttaagaatgt gtcgaagcat ttcggcccca cccaagtact tcacaacatt       60
gaccttaaca tcgcccaggg cgaggttgta gtaatcatcg gtccatctgg tagtggcaag      120
tccaccttgc tgcgttgtat caataaactt gaggaaatca ccagcggaga cttaattgtg      180
gacggtctta aagtcaacga tccaaaagtg gacgaacgct tgattcgtca ggaagcgggt     240 atggtttttcc agcagttcta cttgtttccg caccttacgg ctcttgagaa cgtcatgttc      300
ggaccgttac gcgtgcgcgg ggccaataag gaggaggcgg agaagttggc acgcgagctg      360
ttagcaaaag ttggcttggc tgaacgtgca catcattacc cttctgagct gtcaggtggg      420
caacagcaac gtgtcgccat cgcacgcgcg cttgctgtaa aaccaaagat gatgctgttc      480
gatgagccaa cgtcggcgct tgacccggag ttgcgccatg aggtccttaa ggttatgcaa      540
```

```
gacttagctg aagagggaat gacgatggta atcgtgacgc acgagattgg attcgcagag    600
aaggtagcat ctcgtttgat cttcatcgac aaaggtcgca ttgcagaaga cggcgaccca    660
caagttctga ttaagaaccc cccttcacag cgcctgcaag aatttctgca acatgtctcc    720
```

<210> SEQ ID NO 45
<211> LENGTH: 1437
<212> TYPE: DNA
<213> ORGANISM: Ustilago maydis 521
<220> FEATURE:
<221> NAME/KEY: misc_feature
<222> LOCATION: (1)..(1437)
<223> OTHER INFORMATION: tryptophanamino transferase (transaminase)
      (Ustilago maydis 521)

<400> SEQUENCE: 45

```
atgagttccg ccacaagtcc ggcactggat tatgcattgc tgttgtcttc ttctgctcgt     60
aaccgtatgc cttctgcaat ccgttccctg ttcccggcag aattaattcc aggcatggtc    120
tctcttttgt caggtaaacc gaattcgag accttccct ttcagcgcat cagtttggaa      180
cttaaaccct ccatccatct ggagggacag accgagacag tgagcatcga aggtagcgat    240
ttagacatcg ctcttcagta ttcagcaacg agtgggttgc caaagttggt agactggatc    300
attaaatttc aatctcgcgt tcacgctcgt aagcaggtcg atgagggcaa taagccgggt    360
gaagtatggc gctgtagctt tggcaacgga tctcaagacc tgctgaccaa gacatttgag    420
gctttagttg acgccggtga ttcagtagtc ctggaaagtc cggcttacag tggaattttg    480
ccgtcgttgg ttgcgcataa agccaacctt tcgaggcag aaactgacgc cgagggcgtt     540
gagcccacgg ctttagacac attgctgact aactggaaga ctgacagtgc aacacgtgac    600
tctcgttttc ccaagttttt atatactacc ccgactggtg caaatccgtc cgggacatca    660
gcctctgata atcgcaagcg tgcgatcctt gatattatcc gcaagcacaa tttacttctg    720
ctggaggatg atccttacta ttttttgtca ttccaagggt tggaaccggg ggctgacgcg    780
gtcaaacgca ctcgtgggaa gagctatttt cagttggaag ctcaggacga ctatggcgtc    840
ggccgtgttg ttcgctttga ttcatttagt aagatcttgt ctgccggatt acgcctgggt    900
ttcgttacag gacccaaaga gattctggac gccatcgacc tggacacttc ctcccgcaat    960
ttgcagacaa gtggcacttc ccaggcaatc gcctatgctt tgttgtctaa gtggggaatt   1020
gacggttttt tacatcatgc ggacaatgtc gcacgttttt accaaaatcg cttagaacgc   1080
tttgaagcca gtgcccaggc aatcttaacc ggaagcccta gcatcgcctc gtgggttcgt   1140
ccttcggcag ggatgttcct gtggatcaag ttaaagttgc ctccgtcgcc cgactcggcg   1200
gagggtgata gttttgacct gatctctaat aaagctaagg cagctggggt attggcttta   1260
cccggtgtgg ccttcaaacc accgagcagt tcaagtacgg gtggcaaacg taagacatcg   1320
gcatatgtcc gcacgtcatt ctcccaggtg cctctggacc aagtggatac cgcattcaca   1380
cgcctgcgtc aggtggtaga ggaggcctgg cgtgaggctg gacttcaaat ccccgcg     1437
```

<210> SEQ ID NO 46
<211> LENGTH: 1242
<212> TYPE: DNA
<213> ORGANISM: Escherichia coli
<220> FEATURE:
<221> NAME/KEY: misc_feature
<222> LOCATION: (1)..(1242)
<223> OTHER INFORMATION: Mtrtryptophan ArAAP transporter (Escherichia
      coliBL21(DE3))

<400> SEQUENCE: 46

```
atggctaccc ttactactac tcaaacttcc ccatcgcttc ttggaggagt cgttatcatc    60
ggtggaacta tcatcggagc agggatgttt tcactgccgg ttgtgatgtc gggagcatgg   120
ttctttggt caatggcggc tcttatcttc acgtggttct gtatgttgca tagtggcctg   180
atgatcctgg aagcaaatct gaactaccgt attgggtcct cttttgatac aattacaaag   240
gaccttctgg ggaaaggatg gaatgtagtt aatggaatta gtatcgcgtt cgtcctttac   300
atcttgacct acgcgtatat ctctgcctca gggagcatct tgcatcacac ttttgccgag   360
atgtcattga acgtgcccgc acgcgctgct ggctttggtt ttgcactgct tgtggcattc   420
gtagtctggt taagtacgaa ggctgtgagc cgtatgaccg ctatcgtcct tggggctaaa   480
gtaattacct tcttttaac attcggctcg ctgttaggac acgtgcagcc tgccactttg   540
ttcaatgtgg ctgaatcaaa cgcctcgtat gcccctatt tacttatgac tttgccgttt   600
tgtctggctt ccttcggtta tcacggaaac gtgccatcac tgatgaaata ttatggtaag   660
gatcctaaaa caattgtgaa gtgcttggta tacgggacct aatggcact tgcccttttac   720
acgatctggc ttcttgcaac gatgggcaat attcctcgcc ctgaatttat cgggatcgca   780
gaaaagggg ggaatattga cgtgctggtc caggctttat cgggtgtctt gaatagccgc   840
tctttggatc ttttgttagt tgtcttttcc aattttgccg tggcatcgag tttcttaggt   900
gtgacgctgg tcttttga ttacctggcc gatctgttcg gattcgacga cagcgcggtg   960
ggccgtctta aaactgcttt attaacattt gcgcccctg tagtgggagg tcttctgttt  1020
cctaacggat tcttatacgc catcggctac gccggattgg cggccacgat ttgggcagct  1080
atcgtcccgg ctttattggc acgtgcctca cgcaaacgct tcgggagtcc taaattccgt  1140
gtttggggcg ggaagcctat gattgccctt attttagtgt ttggagtcgg taatgcactt  1200
gtgcacatct tgtcatcgtt caatctgctt cccgtttatc aa                      1242
```

<210> SEQ ID NO 47
<211> LENGTH: 1245
<212> TYPE: DNA
<213> ORGANISM: Escherichia coli
<220> FEATURE:
<221> NAME/KEY: misc_feature
<222> LOCATION: (1)..(1245)
<223> OTHER INFORMATION: tryptophan permeaseTnaB (Escherichia colistr.
      K-12 substr. MC4100)

<400> SEQUENCE: 47

```
atgaccgacc aagctgaaaa gaagcattcg gcattctggg gagtaatggt cattgccggt    60
accgtgatcg gcggtgggat gtttgcttta cctgtggact tagcaggcgc gtggtttttt   120
tggggggcgt tcattctgat tattgcttgg ttttccatgc tgcatagtgg cttgctgctt   180
cttgaagcga atcttaacta tccggtgggg tcaagtttca ataccattac aaaggacctg   240
attggtaaca catggaatat catttcgggg atcacggtag catttgtatt gtatattctt   300
acatatgctt atatcagtgc gaatggcgca atcatttccg agacgatctc catgaacctg   360
gggtatcacg cgaatcccg tattgtcggc atctgcacag cgattttgt tgcgagcgta   420
ttatggctga gttcgttggc agcttcgcgt attacttccc ttttccttgg tttgaaaatc   480
atcagcttcg taattgtgtt tgggagttttt ttttccagg tcgactactc cattcttcgc   540
gatgcaacaa gtagcacagc aggcaccagt tacttcccat atatctttat ggccttaccg   600
gtttgtttag cgtcttttgg ttttcatggt aatatcccct cattaattat ttgctacggc   660
```

```
aagcgcaagg acaaattaat taagtctgtt gttttcggct ccttgttggc gcttgtaatc    720
tatttatttt ggctttattg tacgatgggg aacatccctc gcgaatcctt taaggctatt    780
atttcttcag gaggcaacgt agacagtttg gtaaaaagtt ttttgggtac gaagcagcat    840
ggtatcatcg agttttgttt acttgttttc agtaatcttg ccgttgcttc ctcattcttt    900
ggcgtgactc tggggctttt tgattatctg gcagatttat tcaagatcga caactcgcat    960
ggcgggcgct tcaaaacggt tctgcttaca tttcttcctc cagctttact ttacctgatc   1020
tttccgaatg gttttatcta tggtattggg ggggcaggcc tgtgcgccac tatctgggca   1080
gttatcattc ctgctgtatt ggctatcaag gcacgcaaaa agtttcccaa ccagatgttc   1140
accgtgtggg gcggcaattt gattccggca atcgtgatct tatttggtat cacggttatt   1200
ctttgctggt tcggcaatgt gtttaacgtc ctgcctaagt ttgga                   1245
```

```
<210> SEQ ID NO 48
<211> LENGTH: 1368
<212> TYPE: DNA
<213> ORGANISM: Escherichia coli
<220> FEATURE:
<221> NAME/KEY: misc_feature
<222> LOCATION: (1)..(1368)
<223> OTHER INFORMATION: aroP (Escherichia coliO104:H4 str. C227-11)

<400> SEQUENCE: 48
```

```
atggaagggc agcagcatgg cgaacagctt aagcgtggcc tgaagaatcg tcatatccag     60
cttatcgcat taggcggagc tattgggacc ggcttgttct taggctctgc ttcagtcatt    120
cagtctgcgg ggccaggcat tattttaggc tacgcgattg cgggcttcat cgccttttta    180
attatgcgcc agcttggcga gatggtggtg gaggaacccg tggcaggcag tttctctcac    240
tttgcataca gtattggggg aagttttgca ggctttgcga gcggttggaa ctactgggtt    300
ctgtacgttc tggtggccat ggcggaactg acagcagtcg gtaaatatat tcaattctgg    360
taccctgaaa ttcccacttg ggtctctgcc gctgtcttct ttgtcgtcat taatgcaatc    420
aacttgacca acgtcaaagt attcggcgag atggagtttt ggttcgctat tatcaaagtc    480
attgctgttg tggccatgat cattttcgga ggctggctgc ttttcagcgg caacggaggt    540
ccccaggcaa ctgtatcgaa tctttgggac cagggtggtt tcttgccaca tgggttcacg    600
gggttagtta tgatgatggc cattattatg ttctcgtttg gagggcttga attggtgggc    660
atcactgctg ctgaagctga taacccggag caaagcattc ctaaggccac aaatcaagtg    720
atctatcgca tccttatctt ttacattgga tcgttggcag tattgctgag tttgatgccc    780
tggacccgtg tcaccgctga tacaagccct tttgttttga ttttttcatga attaggggat    840 acttttgtgg caaatgcgtt aaacatcgtc gtattaactg ctgccttgtc agtatataac    900
tcctgcgtat actgtaatag ccgtatgctg ttcggcttgg ctcagcaggg gaacgctccg    960
aaagcactgg ccagtgtcga caagcgtgga gtacctgtga atacgatttt agtttctgct   1020
ctggtcactg cactttgtgt attgatcaac tacctggcgc tgagtcggc gtttggcctg   1080 ctgatggcgc tggtggttag cgcattggtc atcaattggg cgatgatctc cttggcacac   1140
atgaaattcc gccgtgctaa acaagaacag ggtgtggtta cacacttccc agcattatta   1200
taccctctgg gcaactggat tgcttacttt tttatggcag cggttctggt catcatgctg   1260
atgacgcctg gtatggctat ttctgtttat ctgattccgg tttggttaat cgtattaggg   1320
attggctatt tattcaagga aaaaactgca aaggctgtca aagcgcat                1368
```

<210> SEQ ID NO 49
<211> LENGTH: 879
<212> TYPE: DNA
<213> ORGANISM: Escherichia coli
<220> FEATURE:
<221> NAME/KEY: misc_feature
<222> LOCATION: (1)..(879)
<223> OTHER INFORMATION: Aromatic amino acid exporterYddG (Escherichia coliTW10598)

<400> SEQUENCE: 49

```
atgacccgcc agaaggcgac tctgatcggt ttgattgcta tcgtattatg gtccacaatg      60
gttggtttaa ttcgtggggt ttctgagggg cttggcccgg tgggcggagc agcagctatc     120
tactccctga gcggtctgtt attgatcttt acagttgggt ttccgcgtat ccgtcaaatc     180
cccaagggat acttattggc ggggagttta cttttgtga gctatgaaat ttgccttgcc      240
ttgtctctgg gctacgcagc gacacgccat caagcaattg aggtagggat ggttaattac     300
ctttggccgt cattgacgat tcttttcgca atcttattta acggtcagaa gactaattgg     360
ttgattgtac cgggtttatt attagcgttg gtgggagtat gctgggtgtt gggaggtgac     420
aatggtctgc attatgacga gattattaat aatatcacaa catcgcccct atcctacttt     480
ctggctttca ttggtgcctt tatctgggcc gcctattgca ccgtgacgaa taagtacgct     540
cgtggcttca acggaattac agtatttgtc ttgcttactg gtgcatcttt gtgggtatat     600
tatttcttga cccctcaacc agagatgatc ttctccaccc cggttatgat caaattaatt     660
tcagcagctt tcactttggg attcgcatac gcagcttgga atgtcggcat tcttcatggg     720
aatgtgacga ttatggcagt cggttcctac ttcacgcccg tacttagttc cgctttagca     780
gcggtactgc tgtcggcgcc tttgagtttt agtttctggc agggtgccct gatggtgtgt     840
gggggctccc ttttgtgctg gcttgctacc cgccgtggt                            879
```

<210> SEQ ID NO 50
<211> LENGTH: 1152
<212> TYPE: DNA
<213> ORGANISM: Escherichia coli
<220> FEATURE:
<221> NAME/KEY: misc_feature
<222> LOCATION: (1)..(1152)
<223> OTHER INFORMATION: S-adenosylmethioninesynthase Escherichia coli (strain K12)

<400> SEQUENCE: 50

```
atggcaaagc accttttcac gtcggaatct gtatctgaag gcatcccgga caaaattgca      60
gatcaaatct ccgacgcggt acttgatgct attctggaac aagatcccaa agcccgcgtc     120
gcttgcgaaa cttatgtcaa gacaggcatg gtgttagtcg gcggcgagat cactacctct     180
gcgtgggtgg atatcgagga aatcacgcgc aatacggtgc gtgagattgg ctatgtacac     240
tcggacatgg ggttcgacgc caacagttgt gcggttttaa gtgccattgg gaaacagtca     300
cctgatatta tcaggggggt ggatcgtgcg gaccctcttg aacaaggtgc tggtgaccaa     360
ggtctgatgt tcggttatgc tacgaacgaa accgatgtgt tgatgcccgc cccgatcaca     420
tacgcccacc gtctggtcca acgccaggcg gaggtccgta aaacggcac gcttccttgg      480
cttcgtccag atgctaagtc gcaggtcact ttccaatacg acgacgggaa gattgtcgga     540
atcgacgccg tggtcttgtc aactcagcat tcagaggaga tcgatcaaaa gagccttcag     600
gaagccgtca tggaagagat catcaagccg attctgcctg cagaatggtt aacttccgcg     660
accaagttct ttattaaccc caccgggcgt tttgtcattg gcggtcctat gggcgactgt     720
```

```
gggttgaccg gccgtaaaat tattgtcgac acttatggcg gaatggctcg tcatggcggt    780
ggggcattca gtggcaagga cccgtcaaag gtagatcgtt cagccgccta tgccgcccgt    840
tacgtagcca agaacattgt tgctgcagga cttgctgacc gctgtgaaat ccaagtgagc    900
tacgcgatcg gcgtagcaga acccacctcc attatggtgg aaactttggg caccgaaaaa    960
gtccccagtg agcaactgac cttattggtt cgtgagtttt ttgatttgcg cccttacgga    1020
cttatccaaa tgttagacct tttgcaccca atctacaaag aaactgcagc atacggtcac    1080
tttggacgcg agcattttcc ctgggagaag acagacaaag cacagctgtt acgtgacgcg    1140
gccggattga aa    1152
```

<210> SEQ ID NO 51
<211> LENGTH: 1275
<212> TYPE: DNA
<213> ORGANISM: Anabaena cylindrica PCC 7122
<220> FEATURE:
<221> NAME/KEY: misc_feature
<222> LOCATION: (1)..(1275)
<223> OTHER INFORMATION: adenosylhomocysteinase (Anabaena cylindrica PCC 7122)

<400> SEQUENCE: 51

```
atgacggcta cgacgccacg cctgaaacat gaagtgaagg accttgcgct tgcgccttta    60
ggtcgtcagc gtattgagtg ggcggggcgc gaaatgcctg tttttaaagca aatccgcgac    120 cgcttttgaaa aagaaaagcc cttcgcgggc ctgcgtatct cggcttgtgc gcatgttaca    180
acagagacgg ctcatttagc aattgccctg aaggccgggg gagctgatgc cgtattgatc    240
gcaagcaacc cactgtctac gcaggatgac gtagcagcct cgcttgtcgc tgatcatgag    300
atctctgtgt ttgcacaaaa gggcgaagac gccgcgacgt actcgcgtca cgtccaaatt    360
gcgttggacc accgccccaa tatcatcgtt gatgacggtt ccgacgtagt agctgaatta    420
gtacagcacc gtcagaatca gatcgcggat cttattggat ccactgaaga aactacaact    480
gggattgttc gccttcgcgc tatgttcaac gaggggggttt tgacgtttcc cgcgatgaat    540
gtcaacgacg cagacacaaa acattttttt gacaaccgct acggtacagg acaatctacc    600
ttggacggga tcattcgtgc aaccaacatc ttgcttgccg gcaaaactat cgtagttgta    660
ggctatggct ggtgcggaaa ggggaccgca ttacgcgccc gcgggatggg agctaatgtc    720
attgttaccg agatcgatca cattaaggca attgaggcgg tgatggatgg gtttcgcgtt    780
ctgcccatgg ctgaagccgc accgcatggt gatatcttta tcactgtaac gggtaataaa    840
cacgtagttc gtggtgaaca cttttgatgtc atgaaagacg cgccattgt ttgcaactca    900 ggtcacttcg atttggagtt ggattttaaaa tatttagcag caaatgccaa ggaaatcaaa    960
gatgtgcgcc cattcacaca agaatataaa ttaaccaacg gcaaaagcgt agtggtatta    1020
ggagaggggc gtttgattaa tcttgcagcg gcagaaggtc atccgtcggc agttatggac    1080 atgtcttcg ccaatcaagc cttagcagtc gagtatttag tgaaaaataa aggctccttg    1140
gcggctggat tacattcgat ccccgcgag gttgatgagg aaatcgctcg tttaaaattg    1200
caagcgatgg ggatttttat cgattccctg acagcagatc aaatcgatta tattaattct    1260
tggcagtcag ggacg    1275
```

<210> SEQ ID NO 52
<211> LENGTH: 1374
<212> TYPE: DNA
<213> ORGANISM: Klebsiella quasipneumoniae subsp. Quasipneumoniae
<220> FEATURE:

<221> NAME/KEY: misc_feature
<222> LOCATION: (1)..(1374)
<223> OTHER INFORMATION: Cystathionine-beta-synthase (Klebsiella
      quasipneumoniae subsp. Quasipneumoniae)

<400> SEQUENCE: 52

| atggtaatgt cgttattcca cagtgttagc gatttaatcg gtcacacacc tttattacaa | 60 |
| ttgcataagc ttgatacagg accctgtagt ttgttcttga aacttgagaa tcaaaaccca | 120 |
| ggagggtcaa ttaaagatcg tgtagcgctt agcatgatta acgaagcgga acgtcaggga | 180 |
| aaacttgcgc caggaggaac tatcatcgag gctacggcgg gaaatactgg gttggggctt | 240 |
| gctttgatcg cagcccagaa aaactaccgt cttatccttg tagttcccga caagatgtca | 300 |
| cgtgaaaaaa ttttccactt gcgtgcctta ggcgcaaccg tgcttttgac ccgttcagac | 360 |
| gtgaacaagg gcacccggc atattatcag gactatgctc gccgcttggc agatgagact | 420 |
| ccagggcgt tctacattga ccaattcaat aatgatgcca atcctttagc acatgcaaca | 480 |
| agcacggccc ctgagctgtt ccaacaatta gaaggggaca tcgatgccat tgtggttggt | 540 |
| gttgggtcgg gtgaacgtt gggcggcttg caggcctggt tcgcagaaca ctctcccaaa | 600 |
| acagagttca tcttggctga tccagctggg tcgattcttg ccgaccaggt agacacaggc | 660 |
| cgctacgggg aaacgggaag ctggcttgta gagggtattg gcgaggattt tatcccacca | 720 |
| cttgctcgcc tggaaggagt tcataccgca tatcgtgtat ctgatcgcga agcctttctt | 780 |
| acagcccgtc aactgcttca ggtagagggt gtattagcgg gctcgtcaac gggaacattg | 840 |
| ttatctgcgg ccttgcgcta ttgccgtgcc cagtctcgcc caaagcgtgt ggttaccttc | 900 |
| gcatgtgact ctggaaataa gtacttgagt aagatgttca atgacgactg gatgcgccaa | 960 |
| cagggactta ttgcgcgccc ggaacaggga gatctgagtg atttcatcgc cttacgtcac | 1020 |
| gacgaggggg ccacggtcac cgccgcgccc gacgacacac tggcggctgt atttactcgc | 1080 |
| atgcgcttgt acgatatctc ccagcttccg gtcttggaag acggtcgtgt cgttggcatt | 1140 |
| gtggacgaat gggatttaat tcgccatgta cgtggcgacc gtcaacgctt tccctgcca | 1200 |
| gtcagcgagg ctatgtcccg tcacgtagaa acgttagaca aacgcgcccc cgaatccgaa | 1260 |
| ttgcaagcta tcttagaccg tggactggta gcagtcattg cagacaatgc gcgctttctg | 1320 |
| ggactggtta cacgttcaga tgtcttaacg gcatggcgca atcgtgtggc gcaa | 1374 |

<210> SEQ ID NO 53
<211> LENGTH: 1146
<212> TYPE: DNA
<213> ORGANISM: Klebsiella pneumoniae subsp. pneumoniae HS11286
<220> FEATURE:
<221> NAME/KEY: misc_feature
<222> LOCATION: (1)..(1146)
<223> OTHER INFORMATION: cystathionine-gamma-lyase (Klebsiella
      pneumoniae subsp. pneumoniae HS11286)

<400> SEQUENCE: 53

| atgtcgtcta ttcacaccct gtctgttcat agtggcacct tcacggactc acatggcgcg | 60 |
| gtgatgcccc caatctatgc cacctccacg ttcgcgcaac ctgcgcccgg acagcacacc | 120 |
| ggatatgaat actcgcgcag tggaaatcct actcgtcatg ccttagagac tgcgatcgca | 180 |
| gacctggaga atggaacgcg cgggtacgca tttgcctcgg gcttggcagc gatctcgact | 240 |
| gtccttgaat tgttggataa ggacagccat ttagttgcag tggatgatgt ctatggtggg | 300 |
| acctaccgtt tacttgaaaa cgttcgtcgt cgttctgctg gctgcaagt gtcgtgggtc | 360 |
| aagccagacg atttagcggg gattgaggcg gctatccgtc ctgacacccg tatgatctgg | 420 |

```
gtcgaaacac ctactaatcc tttgctgaaa ttagccgatt tgagcgccat cgcagctatc    480
gcacgccgtc acaatcttat ttcagttgcg gataacacgt tcgcttcacc agccatccac    540
cgtcctcttg aacacggttt cgacattgtg gtgcattctg cgacaaaata cttaaatgga    600
cattccgatg tggttgcggg gttagctgtc gtcggagata actccggctt agccgagaaa    660
ttaggttatt tacaaaatgc agttggcggg gtattagacc ccttttcctc gttccttaca    720
ttgcgcggca tccgcactct ggcactgcgt atggaacgtc atagcgcgaa tgcactgcag    780
ttagccgaat ggttggaaca acagcccgaa gtagagcgtg tatggtttcc ttggctggcc    840
tcccatcctc atcatcaatt ggcacgtcag cagatggcat tacctggcgg gatgattagc    900
gtagtagtca aggagatga gggatatgct gagcgcatca tcagtaaact gcgttggttc    960
actcttgccg agtctttagg cggcgtcgag tcgttagttt cccagccgtt ctcaatgaca   1020
catgcttcga tcccacttga aaagcgtctt gcgaacggca ttacgcccca gcttattcgc   1080
cttagtgtgg ggatcgaaga cccacatgat cttatcgcgg attggcaaca agccctgcgt   1140
gccgaa                                                              1146

<210> SEQ ID NO 54
<211> LENGTH: 483
<212> TYPE: DNA
<213> ORGANISM: Bacillus subtilis
<220> FEATURE:
<221> NAME/KEY: misc_feature
<222> LOCATION: (1)..(483)
<223> OTHER INFORMATION: cysteinedioxygenase (Bacillus subtilissubsp.
      subtilis str. BAB-1)

<400> SEQUENCE: 54
atggagttat acgagtgcat ccaggacatc ttctcggggt tgaaaaaccc ttccgtgaaa     60
gatctggcaa catccctgaa acaaatcccg aatgcagcta aattatctca gccttacatt    120
aaagagcctg accagtatgc atacggtcgc aatgccatct accgtaacaa cgagttggag    180
attattgtta tcaacattcc tcccaacaaa gagacaaccg tacacgatca cggacaatcc    240
attggatgcg caatggttct ggaaggtaaa ttacttaata gcatttatcg ttctgctggt    300
gagcacgccg agctgtccaa ctcttacttt gttcacgagg gggaatgcct tatctcgact    360
aaaggcttga ttcacaaaat gagcaacccc acaagcgagc gcatggtatc gttgcatgtt    420
tattcgccac cgcttgagga catgacagta tttgaggaac agaaagaggt gttaaagaac    480
tct                                                                  483

<210> SEQ ID NO 55
<211> LENGTH: 891
<212> TYPE: DNA
<213> ORGANISM: Caenorhabditis elegans
<220> FEATURE:
<221> NAME/KEY: misc_feature
<222> LOCATION: (1)..(891)
<223> OTHER INFORMATION: Glutamate Oxaloacetate Transaminase
      (Caenorhabditis elegans)

<400> SEQUENCE: 55
atgagcgtta gtaaaaaact gttctctacg gctgtgcgtg gtaagagctg gtggtcacac     60
gtcgagatgg gccctcctga tgcgattttg ggggtgactg aagctttcaa agctgattct    120
aaccccaaga gatcaatttt gggcgtggga gcgtaccgtg atgaccaagg aaaaccgttc    180
gtacttccta gcgtcaagga agccgaacgt caagttattg cagcaaatct tgacaaggag    240
```

```
tacgccggga tcgttggcct gcctgaattc acgaaactta gtgctcagtt agcattaggg      300
gaaaacagtg acgtaatcaa aaacaagcgt attttttacga cgcaaagtat ttctgggact    360
ggtgcgctgc gtattggaag tgagttcctg agtaaatatg caaagactaa ggttatctat    420
caacccacgc ctacatgggg aaaccacgtg cctatcttca agttcgcggg cgtggatgtg    480
aaacagtatc gttattatga caagtctaca tgtggatttg atgagacggg ggcattggct    540
gatattgcgc aaatcccga aggtagcact attttgctgc acgcgtgcgc acataaccca    600 acggggtcg accctagtcg tgaccaatgg aaaaagattt cagatattgt taagaaacgc    660
aatttgttcg tgttttttga catggtgaat gagtcagtcc tgagtccgtt actgcctcgc    720
acgcttatgc gcctgcttgt gttgttactg aaatcccgca gtcttttcgc ccactcaaca   780
cccacccatc agtcgatgga attagctctt ttgccggcct cgtcgcgtat ccaactttct   840
acctccaatg ggtcagaaat gtccagctct tggcttatcg tcagcagccc t             891
```

<210> SEQ ID NO 56
<211> LENGTH: 1179
<212> TYPE: DNA
<213> ORGANISM: Bacillus halodurans C-125
<220> FEATURE:
<221> NAME/KEY: misc_feature
<222> LOCATION: (1)..(1179)
<223> OTHER INFORMATION: methionine gamma lyase (Bacillus halodurans C-125)

<400> SEQUENCE: 56

```
atgaaacgcg accaacattt tgaaacacgc gcgatccata ctggttacaa gccgaacgag       60
cattttgata gcttgactcc ccctatttac caaaccagca cgttcacatt tgcatcaatg     120
gagcaaggtg gcaaccgttt cgcaggcgag gaagcaggat atgtttattc acgcctgggg    180 aacccccaccg tgcaaatttt ggaacaacgc attgctgagt tggagggtgg ggaggcagct   240
cttgcctttg gatctggcat ggctgctgtc agtgcgattt tggtggggct tacgaaggcc   300
aacgaccaca tcttagtgag caatggagtg tatggttgta cgtttgggtt gttaacgatg   360
ttaaaggaaa aatacaacat cgacgccact ttcagtccga tggacagcgt agaggaaatc   420
ctggcaaaca tccaggataa taccacgtgc atttatgtgg aaacacctat caaccccacc   480
atgcagttaa tcgatttgga actggttgtg cgcgtagcga aggaaaaggg tattaaggta   540
atcgttgata acacgtttgc cacaccatac ttacaacaac cgattgctct gggatgtgac   600
ttcgttgtcc attcggccac gaaatacatc gggggtcatg ggacgtggt cgccggagtg   660 ctgattggag acaaggaaac aattcagttg atccgtaaga ccacccagaa ggatatgggg   720
ggcgtaattt ctccatttga tgcgtggctg ctgttgcgcg gattgaaaac acttgcagta   780
cgtatggatc gccattgcga gaatgctgaa aaattggccg agaaactgaa agagcatcca   840 aagtaagta cggttctgta cccgggagac tttgagcatc ccgatcactc catcgtcgcc   900
aaacagatga aaagggagg cggtttatta agctttgaga tcaaggggac tgaggcggac   960
atcgccaaag ttgtaaatca gttaaaactg attcgtattg ctgttagttt gggtgacgca  1020
gagaccttga ttcagcatcc tgcaaccatg acccatgcag tagtacccga aaagcgccgc  1080
actcaaatgg gtattagtaa aagttgtta cgcatgtcgg ccgggttaga ggcctggcaa  1140
gatgtctggg ctgacttaga gcaggcgtta aatcaactg                          1179
```

<210> SEQ ID NO 57
<211> LENGTH: 1269
<212> TYPE: DNA

<213> ORGANISM: Methylobacterium aquaticum
<220> FEATURE:
<221> NAME/KEY: misc_feature
<222> LOCATION: (1)..(1269)
<223> OTHER INFORMATION: Methionine aminotransferase (Methylobacterium aquaticum)

<400> SEQUENCE: 57

| | | |
|---|---|---|
| atgaccgcga ttccggcctt ggcagacctg caggctcgtt atgccgactt acaagggcgt | 60 |
| ggtctgaagt tagatatgac gcgcggtaaa ccggcgccag agcagttgga tttatcggac | 120 |
| gatcttttca ctttaccagg taaccgcgat caccgcacag agagcggaga agacgcgcgt | 180 |
| aattacggcg gagtacaggg cctggctgag gtccgtgcct tattcgcccc tgtgcttggt | 240 |
| gcgtcacccg atcgcattgc cgtaggtaat aactcatcgt tggcattgat gcatgactgc | 300 |
| attgcctatg cattgcttaa gggtgtaccc ggcggcgctc gtccttgggc aaaggaagag | 360 |
| gagattcgtt ttttatgccc agtcccaggg tacgaccgtc acttcgctct gtgcgagacc | 420 |
| tacgggattg gaatgattcc agtccctatg accgctgacg ggcctgatat ggaaatggtt | 480 |
| gaacgtgagg tacgcgatcc acgcgtcaaa ggtatgtggg cggtgccgca gtatagtaac | 540 |
| ccaggcggtg agacatactc cgacgcgact gttgagcgcc tggctcgtat ggaaaccggt | 600 |
| gcccctgact tccgtctttt ttgggacaac gcgtatgcac ttcaccattt gaccgaacgt | 660 |
| cgcccaaccc ttcgtaatgt gttagatgcc tgtgcggaag ccgggtcacc ggatcgtgct | 720 |
| attgtgtttg ctagtacgtc gaaagttaca ctggcggggg caggccttgc gatgcttgcg | 780 |
| tccagcgagg gcaatattcg ctggtattta gctaacgccg gcaaacgctc aattggtcca | 840 |
| gataagctta accagttgcg ccatgttcgc tttctgcgtg accagggcgg acttgatgca | 900 |
| ttaatggacg gccaccgccg tcttttagct cctaagttcc gcgctgtaac ggaaacccttt | 960 |
| gctcgtcatc tgggcgggac tggagtagcg cgctggagcg agccggaagg ggggtacttt | 1020 |
| atcctgctgg aagtccctga gggctgtgcg acacgcgtag ttaagcttgc tgctgcttgc | 1080 |
| ggactggctc tgacgcccgc aggggcgacg cacccatacg ggcgtgaccc tcaagataag | 1140 |
| ctgttacgtc ttgccccgtc atacccgaaa ccagcggagg tcgaggcagc cgctgaggta | 1200 |
| gtcgctgtgt gcgttttact tgcggcagct gaaagccgcg aagctggcgg ttcggggcag | 1260 |
| gttgctgca | 1269 |

<210> SEQ ID NO 58
<211> LENGTH: 1902
<212> TYPE: DNA
<213> ORGANISM: Saccharomyces cerevisiae YJM1615
<220> FEATURE:
<221> NAME/KEY: misc_feature
<222> LOCATION: (1)..(1902)
<223> OTHER INFORMATION: Aro10p decarboxylase (Saccharomyces cerevisiae YJM1615)

<400> SEQUENCE: 58

| | | |
|---|---|---|
| atggcacccg tcactattga gaaattcgtg aatcaagaag agcgtcattt agtgagcaat | 60 |
| cgttccgcca cgatcccttt tggagaatat attttcaagc gccttctttc cattgacacc | 120 |
| aaaagcgtct tcggggttcc cggcgacttc aatttatctt tattggaata tttatactcg | 180 |
| ccctccgtgg aatctgcggg tcttcgttgg gttggcacct gtaacgagtt aaatgcagcc | 240 |
| tacgctgcag atggatattc ccgctactct aataaaattg gatgcttaat caccacatac | 300 |
| ggcgtaggag aactgagtgc gcttaatgga atcgcgggtc cattcgctga aaatgtaaag | 360 |
| gttctgcata tcgtaggggt cgccaagtcc attgattccc gttcgtctaa cttctcggat | 420 |

```
cgtaacttac atcacttggt cccgcagtta catgattcga actttaaagg acccaaccat      480
aaggtctatc acgacatggt taaagatcgt gtcgcatgtt ccgtcgccta cctggaggat      540
attgagacgg cctgtgacca agttgataac gtgatccgtg acatttataa gtattcaaaa      600
cctggttaca ttttcgtccc agccgacttt gccgacatgt ccgtaacctg cgacaacttg      660
gtcaatgtac cgcgtatcag ccaacaagat tgtattgtct accccagcga gaaccaactg      720
tcagacatca ttaataaaat cactagctgg atctactcgt ctaagactcc agcaatcctt      780
ggagacgtct taactgatcg ttatggggta tcaaactttc tgaacaaact gatctgcaaa      840
accggtatct ggaacttctc caccgtgatg ggaaaatcag tcattgacga gagtaaccca      900
acttatatgg gtcaatacaa cggcaaagaa ggtcttaaac aggtctatga acatttcgag      960
ctgtgtgatt tggttttaca cttcggagta gatattaacg agatcaataa tggtcactac     1020
acgttcactt acaagccaaa tgcgaaaatt attcaattcc accctaatta tattcgttta     1080
gtagacactc gtcaggggaa tgaacaaatg ttcaaaggca tcaattttgc gccaatcttg     1140
aaagagttgt ataagcgtat cgacgtctct aaattatcgt tgcaatacga ttccaatgta     1200
acacaataca ccaatgagac tatgcgtctg gaggacccaa cgaatggtca atcgagcatc     1260
attacccaag tacacctgca aaagaccatg ccgaaatttt tgaatcccgg cgacgtcgtc     1320
gtgtgtgaga ctggtagttt ccaattcagt gtacgcgact tcgcattccc cagtcagttg     1380
aaatatatca gccagggttt cttttatcc attggtatgg ccttgcctgc cgcgttgggg     1440
gttgggatcg caatgcagga tcattccaac gcgcatatta acggagggaa cgtcaaagaa     1500
gactacaagc cccgcttaat tttgtttgaa ggtgacggcg ccgcgcagat gaccatccag     1560
gagcttagca cgatccttaa atgcaatatc cctttggagg tcattatctg gaataacaat     1620
ggatacacta tcgagcgtgc catcatgggt ccaacacgtt catataacga tgtgatgtcg     1680
tggaaatgga caaagttgtt cgaagccttt ggggatttcg atggtaagta tacgaattcg     1740
actttaattc agtgtcctag caaattagcg ttaaaacttg aagaattgaa gaattctaat     1800
aagcgttcgg ggatcgaact gttagaagtg aagctgggtg agcttgactt cccagagcaa     1860
ttgaagtgta tggtagaggc cgcagctctt aaacgtaata ag                        1902
```

<210> SEQ ID NO 59
<211> LENGTH: 666
<212> TYPE: DNA
<213> ORGANISM: Bacillus subtilis
<220> FEATURE:
<221> NAME/KEY: misc_feature
<222> LOCATION: (1)..(666)
<223> OTHER INFORMATION: Methionine import system permease proteinMetP
      (Bacillus subtilis)

<400> SEQUENCE: 59

```
atgtttgaga agtattttcc aaatgttgac ttgaccgagt tatggaatgc cacatatgaa       60
actctgtata tgacattgat ttccttactg tttgccttcg taatcggcgt catcctggga      120
ttgctgttat tcttaacatc taaggggtct cttttggcaaa ataaagcagt aaattccgtt      180
atcgcagccg ttgtcaacat cttttcgttca attcccttcc ttattttaat catcctgctt      240
cttggtttca ctaaattctt agtgggaaca attttgggac caaatgcggc tcttcccgcg      300
ttagtcatcg gtagtgctcc cttttatgct cgtctggtcg aaatcgcact tcgtgaagtg      360
gacaaaggag tgattgaggc ggcgaaatcg atggggcta agacgagcac tattattttt      420
aaggttctta tccccgagtc catgcccgcg ctgatttccg gaattacagt gactgcgatt      480
```

```
gcattgatcg ggtcaaccgc catcgcagga gctattggtt ctggtggatt gggaaactta    540
gcatacgttg aaggctatca atcgaataat gcggatgtga ccttcgtggc cacagttttc    600
atcctgatta ttgttttcat cattcagatc attggtgacc ttattaccaa catcatcgat    660
aaacgc                                                              666

<210> SEQ ID NO 60
<211> LENGTH: 1029
<212> TYPE: DNA
<213> ORGANISM: Escherichia coli
<220> FEATURE:
<221> NAME/KEY: misc_feature
<222> LOCATION: (1)..(1029)
<223> OTHER INFORMATION: DL-methionine transporter subunit MetN
      (Escherichia coli K-12])

<400> SEQUENCE: 60
atgattaaac tgagcaacat tactaaggtg ttccaccaag gtacacgtac gatccaggct     60
cttaataatg tgtcactgca cgttcctgct ggtcagattt atggggttat cggtgccagt    120
ggggctggga agagcactct gatccgctgc gtcaatctgt tagagcgccc tacagagggc    180
tcggtactgg tggacggtca agagttgact actctgtcgg agtccgagtt gacaaaagca    240
cgccgccaga ttggcatgat tttccaacat ttcaatttgt tatcgagccg tacagttttc    300
gggaacgtgg ccttaccact ggagttggac aatactccca agacgaagt caaacgtcgt    360 gtgaccgaat tattgtcctt ggtgggtctt ggtgacaaac acgacagtta tcccagtaat    420
ttgagtggcg gcaaaaaaca gcgtgttgcc atcgcacgcg cattagcttc gaatcccaag    480
gtgctgttat gtgatgaagc gaccagcgcc cttgacccag ccacaactcg tagcatcctg    540
gagcttttga aagatatcaa tcgtcgcctg ggtttgacca tcttattgat tacgcacgag    600
atggacgttg taaagcgtat ctgtgactgt gtagcggtga tctccaacgg tgaattaatc    660
gaacaggaca ccgtatcgga ggtcttctca catcctaaga cacccttgc acaaaaattc    720 atccaaagca cgctgcattt agatattcct gaagattatc aggaacgcct gcaggctgaa    780
ccgtttactg attgcgttcc aatgcttcgc ttagagttca cagggcaatc ggttgacgct    840
cccttattga gtgaaaccgc ccgccgtttc aatgttaata caacatcat tccgcgcaa    900 atggactacg cggggggtgt taaatttgga atcatgttaa ccgaaatgca cggcacacag    960
caggatacac aggcggcgat cgcatggctg caggaacatc atgttaaagt agaagtcctt   1020
gggtatgtg                                                          1029

<210> SEQ ID NO 61
<211> LENGTH: 654
<212> TYPE: DNA
<213> ORGANISM: Escherichia coli
<220> FEATURE:
<221> NAME/KEY: misc_feature
<222> LOCATION: (1)..(654)
<223> OTHER INFORMATION: metI  (Escherichia coli)

<400> SEQUENCE: 61
atgtctgagc cgatgatgtg gctgctggtt cgtggcgtat gggaaacgct ggcaatgacc     60
ttcgtatccg gtttttttgg ctttgtgatt ggtctgccgg ttggcgttct gctttatgtc    120
acgcgtccgg ggcaaattat tgctaacgcg aagctgtatc gtaccgtttc tgcgattgtg    180
aacatttttc cgttccatcc cgttcattat cttgcttgtat ggatgattcc gtttacccgc    240
gttattgtcg gtacatcgat tggtttgcag gcagcgattg ttccgttaac cgttggtgca    300
```

```
gcaccgttta ttgcccgtat ggtcgagaac gctctgctgg agatcccaac cgggttaatt      360
gaagcttccc gcgcaatggg tgccacgccg atgcagatcg tccgtaaggt gctgttaccg      420
gaagcgctgc cgggtctggt gaatgcggca actatcaccc tgattaccct ggtcggttat      480
tccgcgatgg gtggtgcagt cggtgccggt ggtttaggtc agattggcta tcagtatggc      540
tacatcggct ataacgcgac ggtgatgaat acggtactgg tattgctggt cattctggtt      600
tatttaattc agttcgcagg cgaccgcatc gtccgggctg tcactcgcaa gtaa            654
```

<210> SEQ ID NO 62
<211> LENGTH: 816
<212> TYPE: DNA
<213> ORGANISM: Escherichia coli
<220> FEATURE:
<221> NAME/KEY: misc_feature
<222> LOCATION: (1)..(816)
<223> OTHER INFORMATION: metQ (Escherichia coli)

<400> SEQUENCE: 62

```
atggcgttca aattcaaaac ctttgcggca gtgggagccc tgatcggatc actggcactg      60
gtaggctgcg gtcaggatga aaagatcca aaccacatta agtcggcgt gattgttggt       120 gccgaacagc aggttgcaga agtcgcgcag aaagttgcga agacaaata tggcctggac      180 gttgagctgg taaccttcaa cgactatgtt ctgccaaacg aagcattgag caaaggcgat      240
atcgacgcca acgccttcca gcataaaccg taccttgatc agcaactgaa agatcgtggc      300
tacaaactgg tcgcagtagg caacactttt gtttatccga ttgctggtta ctccaagaaa      360
atcaaatcac tggatgaact gcaggatggt tcgcaggttg ccgtgccaaa cgacccaact      420
aaccttggtc gttcactgct gctgctgcaa aaagtgggct tgatcaaact gaaagatggc      480
gttggcctgc tgccgaccgt tcttgatgtt gttgagaacc ccaaaaatct gaaaattgtt      540
gaactggaag caccgcaact gccgcgttct ctggacgacg cgcaaatcgc tctggcagtt      600
atcaatacca cctatgccag ccagattggc ctgactccgg cgaaagacgg tatctttgtt      660
gaagataaag agtccccgta cgtaaacctg atcgtgacgc gtgaagataa caaagacgcc      720
gagaacgtga agaaattcgt ccaggcttat cagtctgacg aagtttacga agcagcaaac      780
aaagtgttta acggcggagc tgttaaaggc tggtaa                                816
```

<210> SEQ ID NO 63
<211> LENGTH: 2286
<212> TYPE: DNA
<213> ORGANISM: Bacillus atrophaeus UCMB-5137
<220> FEATURE:
<221> NAME/KEY: misc_feature
<222> LOCATION: (1)..(2286)
<223> OTHER INFORMATION: MetE (Bacillus atrophaeus UCMB-5137)

<400> SEQUENCE: 63

```
atgacgacta tcaaaacatc aaatctgggc ttccctcgca ttggacttaa tcgcgaatgg      60
aaaaaatcac tggaagcgtt ttggaaaggt aacagcgaca agatacatt tcttaagcag      120 atggatgagt tatttcttac tgccgtaaaa acccagattg atcaaaaaat cgacatcgtg      180
cccgtgagcg acttcactca ctacgaccac gttcttgaca cagctatctc tttaattgg      240 attccagaac gctttaaaca cattacggat gcgactgata catatttcgc gctggcacgt      300
ggcattaagg atgctgttag ttcggaaatg actaagtggt ttaataccaa ttaccactat      360
atcgttccgg aatacaataa agacatcgaa ttccgtttaa cccgcaacaa gcagttagag      420
```

```
gactaccgcc gcgtcaaaca agcgtttggc gtcgaaacta aacccgtcat tgtcggtcct    480
tacacattcg tgacgcttgc caagggctac gaacaaagtg aggccaaaga aatccaaaag    540
cgtttagtcc cattgtatgt gcaattattg aaagaattgg aacaagaggg cgtgcagtgg    600
gtacaaatcg atgagccagc acttgtgaca gcctcatccg aggatgttag cgcggccaag    660
gagttatacc aggccattac gaatgagtta ccggcttga atgtcctttt gcagacttac    720
ttcgattctg ttgatgctta tgaggagtta atcagctacc cggtacaggg tatcggcttg    780
gattttgtac acgataaagg cgcaacttg gagcaattaa aagcgcatgg atttccgaag    840
gataaggtat tagcagctgg tgttattgat ggtcgtaaca tttggaagac ggatttagat    900
gagcgcttgg acgccatcct tgcgctgtta tcttcgacgg acattgacga attatggatt    960
caaccaagca attcgcttct tcatgtacca gtagcaaagc cccagacga gcacctggag    1020 aaggatctgt tgaatggctt gagttacgca aaagaaaagc tggcagaact gtccgcttta    1080
aaagagggtt tgttatcggg taaagcggca atctcggccg acattcagca ggccaaagcg    1140
gatttacagg ccctgaagca attcgccacc ggggctaaca gtgagcagaa agaggaatta    1200
aatcagttga ccgagaaaga ctttaagcgc ccgatcccct tcgaagagcg cctgaaaatc    1260
cagaatgaat ccttgggct tccctgctt cctactacga ctattggttc tttcctcaa    1320 agcgccgagg tgcgttcggc gcgccaaaag tggcgcaaaa gtgagtggag cgacgagcaa    1380
tatcaagaat ttatcaacgc ggaaacgaag cgctggatcg acattcagga agagcttgat    1440
cttgacgttt tagtacatgg agagttcgag cgcaccgaca tggtcgaata tttcggtgag    1500
aaactggctg gattcgcgtt tactaaatac gcatgggtcc agagctacgg atcccgctgt    1560
gtacgccctc ccgtcatcta tggggacgtg gagtttattg aacctatgac tgtcaaggac    1620
acagtgtacg ctcaatcttt aacgagtaag caggttaaag ggatgttgac tggcccggtc    1680
acaatcttga attggagctt cccgcgtaac gacattagcc gtaaggagat cgccttccaa    1740
atcgggttag ctcttcgcaa agaggtcaag gcgttggaag atgctggtat tcaaatcatc    1800
caagttgacg aaccggccct gcgtgaaggg ctgcctctga agaaaacga ttgggaagag    1860 tatttaacgt gggccgcgga ggcgttccgc ttaactactt cggctgtgaa aaacgacact    1920
cagattcata cacacatgtg ttattccaat tttgaggaca ttgtcgacac aattaatgac    1980
ttggatgcgg acgtcattac aatcgaacac tcccgcagtc acggtgggtt cttggactac    2040
ttgcgcgatc atccgtatct taaaggttta ggtcttggcg tgtacgatat tcacagccct    2100
cgtgtacccc cgacagagga aatttataag atcattgacg aagccctgac cgtatgtcct    2160
actgaccgct tctgggtaaa cccagactgc gggctgaaga cccgtcacca ggaggaaacg    2220
attgccgcgt tgaagaacat ggtcgaggct gctaaacagg ctcgtgccaa acagagtcaa    2280
cttgtc    2286
```

<210> SEQ ID NO 64
<211> LENGTH: 753
<212> TYPE: DNA
<213> ORGANISM: Corynebacterium glutamicum
<220> FEATURE:
<221> NAME/KEY: misc_feature
<222> LOCATION: (1)..(753)
<223> OTHER INFORMATION: BrnF (Corynebacterium glutamicum)

<400> SEQUENCE: 64

```
atgcagaaaa cacaggagat tcacagctcg ttagaggtta gccccagtaa agctgctctg     60
gagcccgacg ataaggggta tcgtcgttac gaaatcgcac aaggcctgaa gacctctctt    120
```

```
gctgcaggcc tgggaatgta tcctatcgga attgcattcg gcttactggt gattcaatat      180
ggttatgaat ggtgggccgc tccactgttc tccggcctga tttttgcggg gtctacggag      240
atgcttgtaa ttgcacttgt ggtcggcgct gctccgctgg gtgccattgc ccttacgacc      300
ttacttgtta atttccgtca tgttttctat gccttttcct ttcccttgca cgttgttaaa      360
aaccctattg cgcgcttcta ttctgtattc gctcttattg atgaagcata cgctgttaca      420
gccgctcgtc ccgccggttg gagtgcatgg cgtctgattt caatgcagat tgcgttccac      480
tcctactggg tatttggagg cttgaccggt gtagcaatcg cagagttaat tcctttcgag      540
atcaaaggcc tggagttcgc actttgttcg ttatttgtaa ctcttacttt agacagttgt      600
cgcactaaga aacaaattcc gagtttgtta ttggctggac tgagctttac tatcgcgtta      660
gtagtgatcc ccggccaagc tctgttcgct gcgttactta tctttctggg gcttctgaca      720
atccgttatt ttttcttagg gaaggcagcc aaa                                   753

<210> SEQ ID NO 65
<211> LENGTH: 324
<212> TYPE: DNA
<213> ORGANISM: Corynebacterium glutamicum
<220> FEATURE:
<221> NAME/KEY: misc_feature
<222> LOCATION: (1)..(324)
<223> OTHER INFORMATION: BrnE (Corynebacterium glutamicum)

<400> SEQUENCE: 65
atgacgactg atttctcctg catcctgttg gtggtcgcgg tatgtgcagt cattacattt       60
gcgcttcgtg ccgtaccttt tctgatcttg aaacccttgc gtgaatcgca atttgtggga      120
aaaatggcca tgtggatgcc tgcgggcatt ctggcaatcc tgacggcttc taccttccgt      180
tcaaacgcca tcgatttaaa gacgttgacg ttcggtctga ttgccgtggc aatcacagtc      240
gtagcccact tattaggagg ccgtcgcacc ttattatctg ttggcgctgg aacaattgtg      300
tttgtaggtc ttgttaattt gttt                                             324

<210> SEQ ID NO 66
<211> LENGTH: 1023
<212> TYPE: DNA
<213> ORGANISM: Salmonella enterica subsp. enterica serovar Typhistr.
       CT18
<220> FEATURE:
<221> NAME/KEY: misc_feature
<222> LOCATION: (1)..(1023)
<223> OTHER INFORMATION: threonine 3-dehydrogenase (Salmonella enterica
       subsp. enterica serovar Typhistr. CT18)

<400> SEQUENCE: 66
atgaaggccc tgagcaaatt gaaagccgag gaggggatct ggatgaccga tgttcctgaa       60
ccagaagtgg ggcacaacga cctttttaatc aaaattcgca agactgcaat ctgcgggaca     120
gacgtacata tctataactg ggacgagtgg agtcaaaaaa ctattcccgt ccctatggtg      180
gtcgggcacg agtatgtcgg agaggttgta ggaatcggac aagaagtcaa aggatttaaa      240
atcggggatc gtgtgagtgg ggagggtcac attacctgtg ggcattgccg caattgccgt      300
ggaggacgca cacatttgtg ccgtaacact acaggcgtag gcgtgaatcg tcccggatgt      360
ttcgcggaat accttgtcat tccagcgttt aacgccttta gatccctga caacatttca      420 gatgatttag catccatttt tgacccattc ggtaacgcgg tccatactgc gttgagcttc      480
gacttagttg gagaagatgt attagtttcc ggcgccggac cgattggcgt catggcagct      540
```

```
gccgttgcga agcacgtggg cgcacgtcat gtggtaatta cggacgtaaa tgagtatcgt      600
ctggagctgg cacgtaaaat gggggttaca cgtgccgtaa acgttgcgaa agagtcttta      660
aacgatgtca tggctgaact gggcatgacg aagggtttg atgtcggact ggaaatgtcc       720
ggtgccccgc cagccttccg taccatgttg acaccatga accatggggg ccgtatcgca       780
atgttgggaa ttccccgag cgacatgtct atcgactgga caaaggtaat ttttaaaggc       840
ctgttcatta aggggattta cggtcgtgag atgtttgaga cgtggtacaa gatggctgcc      900
ttgattcaat cggggttgga tctgagccct atcatcacac accgtttttc agtggatgac      960
tttcaaaaag ggtttgacgc catgtgcagc ggtcaatcag ggaaagtaat tctttcttgg     1020
gac                                                                   1023
```

<210> SEQ ID NO 67
<211> LENGTH: 999
<212> TYPE: DNA
<213> ORGANISM: Escherichia coli
<220> FEATURE:
<221> NAME/KEY: misc_feature
<222> LOCATION: (1)..(999)
<223> OTHER INFORMATION: threonine aldolase (Escherichia coliO26:H11 str. CVM10026)

<400> SEQUENCE: 67

```
atgattgacc ttcgttcgga caccgtaacc cgcccatctc acgcaatgtt ggaagctatg       60
atggccgcgc ctgtggggga tgacgtttat ggggatgacc cgaccgtcaa cgctttacaa     120
gattacgctg ctgaattgtc gggcaaagaa gcagcaatct tcttacctac aggtacacaa     180
gctaatcttg tcgccctgct tagtcactgt gagcgtggcg aagaatacat tgttggtcaa     240
gcagcgcata attacctgtt cgaagctgga ggggctgctg ttcttggtag cattcagccc     300
caacccattg atgctgctgc cgatggtact cttcctctgg ataaagtcgc tatgaaaatt     360
aagccagacg acattcactt cgcacgcaca aagctgctgt cgcttgagaa tacacacaat     420
ggaaaagtcc tgccccgtga gtacctgaaa gaggcttggg aatttacacg cgaacgcaac     480
ctggctctgc acgtagacgg tgctcgcatc ttcaacgccg ttgtcgccta cggttgcgaa     540
ttgaaagaga ttacgcaata ctgtgactcc ttcacgattt gcttgtccaa aggcttaggc     600
accccggtgg ttcattgtt ggtaggaaac cgtgactata ttaagcgcgc catccgctgg      660
cgtaaaatgg caggggtgg aatgcgtcaa tcagggattc ttgcggcagc tggcatgtac     720
gcgctgaaaa ataatgtggc tcgccttcaa gaggatcacg ataatgctgc gtggatggct     780
gagcaattac gtgaggcggg tgcagacgta atgcgccaag ataccaatat gctgttcgta     840
cgtgttgggg aagaaaacgc tgcggcctta ggagaataca tgaaggcgcg taacgtgttg     900
atcaacgcat ccctattgt tcgccttgta actcaccttg atgtttcacg tgaacaattg      960
gcggaagttg ccgcccactg gcgtgcctttt cttgctcgc                           999
```

<210> SEQ ID NO 68
<211> LENGTH: 1251
<212> TYPE: DNA
<213> ORGANISM: Escherichia coli
<220> FEATURE:
<221> NAME/KEY: misc_feature
<222> LOCATION: (1)..(1251)
<223> OTHER INFORMATION: serine hydroxymethyltransferase (Escherichia coli)

<400> SEQUENCE: 68

```
atgcttaaac gtgagatgaa tatcgccgac tacgacgccg aattatggca ggcgatggag       60
```

```
caggagaaag tccgccaaga ggaacacatt gagcttattg cgtcggagaa ctatacatcc      120
cctcgcgtta tgcaggcgca aggctcacag ttgacgaaca aatacgctga gggatatccg      180
ggaaagcgtt attatggcgg ttgcgagtac gttgacattg ttgaacagtt agcgattgat      240
cgtgctaagg agttatttgg agcggattat gccaatgttc aacctcactc gggcagccag      300
gctaactttg ctgtatacac cgcactttta gaacctggtg acacggtcct gggtatgaat      360
ttggcccatg gaggccactt aactcatgga agccctgtga attttagtgg gaagttgtat      420
aacatcgtgc cctacgggat cgacgccaca ggacacattg attacgcaga tttggagaaa      480
caagccaagg aacataagcc taaaatgatc atcggcggat tttcagcata tagcggagtg      540
gtagactggg ccaaaatgcg cgagattgct gattcgattg gtgcttacct gtttgtcgat      600
atggcgcatg tcgctggtct ggtcgctgcg ggagtttatc ctaacccgt gcctcacgct       660 cacgtcgtga cgactactac acataagact ttagcgggtc ctcgtggggg tttgattctt      720
gcgaaggggg gctcagagga actttataag aagcttaact ctgccgtatt tcccggcggt      780
caggggggcc ctcttatgca cgtcatcgca ggaaaggcgg tggctctgaa ggaagcgatg      840
gaacccgaat tcaagactta ccaacagcaa gtagccaaaa acgccaaagc catggtggag      900
gtattcctgg agcgcggcta caaggtagtt agcgggggga cggacaacca tttgttctta      960
gtcgatttag tggacaaaaa ccttactggt aaggaggctg atgctgctct tgggcgtgca     1020
aatatcacag tcaataagaa tagcgtgccc aatgacccaa agtcgccatt tgtgacttct     1080
ggcatccgcg ttgggactcc ggcaataccc cgtcgtggct ttaaggaggc agaggccaag     1140
gagctggcag ggtggatgtg tgacgtactg gactctatta atgatgaggc agttatcgaa     1200
cgtattaaag gcaaagtgct tgacatttgt gcgcgctacc ccgtgtatgc c               1251

<210> SEQ ID NO 69
<211> LENGTH: 1293
<212> TYPE: DNA
<213> ORGANISM: Escherichia coli
<220> FEATURE:
<221> NAME/KEY: misc_feature
<222> LOCATION: (1)..(1293)
<223> OTHER INFORMATION: tdcC(Escherichia coli)

<400> SEQUENCE: 69
atgtctactt cggactctat tgtttcatcg caaacaaaac agtcatcctg gcgtaaatca       60
gataccacct ggacttgggg tctgtttggt accgcgatcg gggctggtgt attgtttttc      120
ccgatccgcg ctggatttgg tggtttaatt cctatcctgc tgatgcttgt actggcatat      180
cctattgctt tttattgtca tcgcgcagcg cgcttgtgtt taagcggaag caacccctcg      240
ggtaatatca cagagacggt ggaggagcat ttcgggaaaa caggagggt cgtaatcaca       300 tttctgtact ttttttgctat ttgtcccctg ttgtggattt atggggttac gatcaccaat      360
acttttatga cgtttgggga gaatcaactg ggctttgcac cgcttaaccg cggattcgtg      420
gcgctgttcc ttttactgtt gatggcgttt gtcatctggt tcggtaaaga cttaatggtg      480
aaagtcatgt cttatttggt atggcctttc attgcttcac ttgtcttaat tagtctgtca      540 ttaatcccctt attggaactc ggcagtaatc gatcaagtag atctgggtag cctgtctttg      600
accggacatg atgggatctt aattaccgta tggctgggca tttctattat ggtctttagt      660
tttaactttt cacctatcgt gtcctccttt gtggtgtcca agcgcgagga atatgagaag      720
gattttggtc gtgattttac ggaacgtaag tgctcacaaa ttattagccg cgcgtctatg      780
```

```
cttatggtgg ctgtcgttat gttctttgct ttctcctgct tatttacctt gtcaccggcg    840
aacatggcgg aagcgaaggc gcaaaacatt ccagttttat catatcttgc taatcatttc    900
gcttctatga cagggaccaa aactactttt gccatcacat tggagtatgc ggcgtctatc    960
attgcattag tggccatttt taagtcgttc tttggccatt atttaggtac tttagaaggg    1020
ttgaatggct tagtcttgaa attcggatac aaggggggaca aaactaaagt ttccttgggt    1080
aagttgaaca caatctcgat gatctttatt atggggagta catgggtcgt tgcgtatgca    1140
aatccaaaca ttctggattt aattgaggcg atgggagcac cgattatcgc gtcattgttg    1200
tgccttttgc cgatgtacgc catccgtaag gcgccttcac tggccaaata tcgtgggcgc    1260
ttggataacg tgttcgtaac cgtcatcgtt tgc    1293
```

<210> SEQ ID NO 70
<211> LENGTH: 885
<212> TYPE: DNA
<213> ORGANISM: Escherichia coli
<220> FEATURE:
<221> NAME/KEY: misc_feature
<222> LOCATION: (1)..(885)
<223> OTHER INFORMATION: Threonine/ homoserine exporterRhtA, Escherichia coli (strain K12)

<400> SEQUENCE: 70

```
atgcctggtt ccttgcgtaa aatgccggtt tggttgccga ttgttattct tctggttgca     60
atggctagca tccaaggagg cgctagttta gcaaaaagtc tgtttccttt ggtgggggca    120
ccgggtgtga ccgcgctgcg tttggctttg ggcacttttaa ttttgattgc cttctttaag    180
ccctggcgcc ttcgttttgc taaagaacaa cgtttgccgc ttttgttcta cggcgtctca    240
cttggtggca tgaactatct tttttattta agcatccaaa ccgtacccct gggtattgcg    300
gtggctttgg agttcacggg tccattggca gttgcccttt tcagctcgcg tcgcccagtc    360
gatttcgtct gggtagtgct tgcggtactt ggactgtggt tcttactgcc cttaggccaa    420
gacgtgagtc acgtagacct taccgggtgt gcgctggctt tgggagccgg tgcttgttgg    480
gcaatttaca tcctgtcggg acagcgtgcg ggagcagagc acgggcctgc gacagtagcg    540
attgggtcgc tgatcgcagc cctgattttc gtccccattg gtgccttaca ggcaggagag    600
gcgttgtggc actggtcagt gattcccctta ggtttggcgg tagcaatcct gtctaccgca    660 cttcctttatt ctttagagat gattgcctta acccgtctgc cgacacgtac gtttggcacc    720
ttaatgtcga tggaaccggc attggctgcc gtttcaggta tgatcttcct gggagagacg    780
ttaactccca ttcagttgtt agctcttggg gcaatcatcg ctgcgagtat gggatcgacc    840
cttacggttc gtaaagagtc gaagattaaa gaattggaca tcaat    885
```

<210> SEQ ID NO 71
<211> LENGTH: 618
<212> TYPE: DNA
<213> ORGANISM: Escherichia coli
<220> FEATURE:
<221> NAME/KEY: misc_feature
<222> LOCATION: (1)..(618)
<223> OTHER INFORMATION: rhtB(Escherichia coliFVEC1302)

<400> SEQUENCE: 71

```
atgacgctgg agtggtggtt cgcatacttg ctgacatcca tcatcctgag tttaagcccc    60
ggatctggtg caatcaacac gatgactacg tctttgaatc acggctatcg tggtgctgtt    120
gcatccattg ccggcttgca gacgggatta gccatccata ttgttttagt gggtgtagga    180
```

```
cttggaacat tattcagtcg ctcggttatc gcctttgagg tcttaaagtg ggctggtgcc      240
gcttatttga tttggctggg aattcagcaa tggcgtgcag ccggtgcgat tgacttgaag      300
agccttgcgt ccacacagag ccgccgtcac ttgtttcaac gtgcagtatt cgtcaatttg      360 accaaccccca aaagtatcgt ctttctggcg gcactgtttc cccagttcat tatgcctcaa      420
cagccgcagt tgatgcagta catcgtcttg ggcgtcacca ccatcgtagt ggacattatt      480
gtaatgattg gatacgccac tctggcccaa cgtattgcgc tgtggatcaa gggcccgaaa      540
cagatgaagg cactgaacaa aattttttggt tctttgttta tgttggttgg ggcacttctt      600
gccagtgcac gtcacgcg                                                    618
```

```
<210> SEQ ID NO 72
<211> LENGTH: 618
<212> TYPE: DNA
<213> ORGANISM: Escherichia coli
<220> FEATURE:
<221> NAME/KEY: misc_feature
<222> LOCATION: (1)..(618)
<223> OTHER INFORMATION: RhtCthreonine Rht Transporter (Escherichia
      coliBL21(DE3))

<400> SEQUENCE: 72
atgctgatgc tttttttaac agtagcaatg gtgcatatcg tcgcattgat gtcaccggga      60
cctgactttt tttttgtttc acaaacagca gtatcacgct cacgtaagga ggcaatgatg     120
ggtgtcttag ggatcacttg cggcgtaatg gtatgggccg gtattgcact tctgggactg     180
catttaatta ttgagaagat ggcctggctt cacacattaa tcatggtagg cgtgggcttt     240
tatttatgtt ggatgggcta tcaaatgctg cgtggagctc ttaagaaaga agccgtgtcc     300
gcaccggctc cccaagtgga acttgcgaaa tcaggtcgct ccttcttgaa ggggttgttg     360
actaatcttg cgaaccctaa ggccatcatt tatttcggtt ctgtgtttag tttgttcgtt     420
ggggataatg tgggaaccac ggaacgctgg ggaatcttcg cattaatcat tatcgagacg     480
ttagcttggt tcaccgtcgt ggcctccctt tttgctctgc cgcaaatgcg ccgtggttac     540
caacgtttag caaagtggat cgacggtttt gctggagctt tatttgcggg tttcggcatt     600
catctgatta ttagccgt                                                   618
```

```
<210> SEQ ID NO 73
<211> LENGTH: 984
<212> TYPE: DNA
<213> ORGANISM: Escherichia coli
<220> FEATURE:
<221> NAME/KEY: misc_feature
<222> LOCATION: (1)..(984)
<223> OTHER INFORMATION: cysteine desulfhydrase (Escherichia coli)

<400> SEQUENCE: 73
atgcccctgc acaacttaac acgttttcca cgcctggaat tcattggtgc accgactccc      60
ttggaatatc tgcctcgctt ttcggactac ttaggccgcg agattttcat taagcgcgat     120
gatgttacac cgatggctat gggggtaac aaattgcgta aattggaatt tcttgcagcg     180
gatgcactgc gtgaaggcgc ggacacttta attaccgctg gtgcaattca gtcaaatcac     240
gtacgccaaa ctgcggcagt tgctgcgaag ttaggtcttc attgtgtcgc cttttggaa     300 aatccaattg gcacaacggc agaaaattac cttaccaacg ggaaccgttt gttgcttgac     360 cttttttaaca cacagatcga aatgtgcgac gctttaactg atcccaacgc tcaattggag     420
gagcttgcga ctcgcgtgga agctcaaggc ttccgtccgt atgttattcc ggtcggcggc     480
```

```
agcaatgctc ttggggcatt agggtatgta gagtccgctc tggagatcgc gcaacaatgt    540
gagggcgcgg ttaacatttc gagtgtagtt gtggcctctg gaagtgcggg cacccacgcc    600
gggctggctg tgggtcttga gcacttaatg cctgaatctg aactgatcgg ggtcacagtc    660
tcgcgttccg tcgcagatca gttacctaag gtagtaaact tacagcaagc cattgcgaaa    720
gaattagaat taaccgctag tgcagaaatc ttattatggg atgattactt tgcgcctggg    780
tacggtgtcc ccaatgatga aggtatggaa gcagtcaagc ttttagctcg tttggagggg    840
atcttgctgg accctgttta caccggcaaa gcaatggcag gcttaattga cggtatcagt    900
cagaaacgct tcaaagacga gggaccaatt ctgttcatcc ataccggcgg cgctcctgcc    960 cttttttgcct accaccctca cgtt                                           984

<210> SEQ ID NO 74
<211> LENGTH: 1413
<212> TYPE: DNA
<213> ORGANISM: Escherichia coli
<220> FEATURE:
<221> NAME/KEY: misc_feature
<222> LOCATION: (1)..(1413)
<223> OTHER INFORMATION: tnaA (Escherichia coliDH1)

<400> SEQUENCE: 74
atggagaatt tcaagcattt gcccgagccg ttccgcattc gtgtcattga gcctgtcaag     60
cgtactactc gcgcgtatcg cgaagaggcg attatcaaat cgggtatgaa tccattttta    120
cttgattcag aagatgtgtt catcgattta cttacagatt ctgggacagg cgcggtaacg    180
caatcgatgc aagcagcgat gatgcgcggt gacgaagcct attctggctc gcgctcctat    240
tatgctctgg ccgaatcagt caaaaacatt tttggttacc aatatacgat tcccacgcat    300
cagggacgcg gagcagagca aatctatatc ccagtcttaa tcaaaaagcg cgagcaagaa    360
aagggattgg accgctcgaa aatggtagcc ttctcaaatt acttcttcga cactactcag    420
gggcactcgc aaatcaacgg ctgcactgtt cgcaatgtgt atatcaagga agcctttgat    480
acaggcgtac gttacgattt caaggggaac tttgacctgg aaggtcttga acgtggcatt    540
gaagaagtag gacccaacaa cgtaccctat atcgtcgcca cgatcacatc taatagcgca    600
ggaggtcagc ctgtgtcttt ggcgaatctg aaagcgatgt attcgatcgc caaaaagtat    660
gatatccccg tcgtaatgga ttctgcacgt tttgcagaga cgcctacttc cattaaacag    720
cgtgaagcgg agtacaaaga ttggaccatc gaacagatca ctcgtgagac ttataaatat    780
gctgacatgc tggctatgtc ggctaagaag gacgctatgg tcccaatggg aggcctttta    840
tgcatgaagg acgatagttt tttttgacgtt tatacggaat gtcgcaccct tgtgtagtg    900 caggaaggat tccccactta tggcggcctt gaaggtggag cgatggaacg tttagctgtt    960
ggactgtatg atggtatgaa tctggattgg ctggcatatc gtattgcgca ggtgcagtac   1020
ctggtagacg ggttagagga gatcgggggtt gtgtgccagc aggccggggg ccatgcggcg   1080
ttcgtggacg caggaaaaact gcttccccac attcccgccg atcagttccc tgcgcaggca   1140
cttgcttgcg agttatacaa ggtggccggt atccgtgcgg tagagatcgg ctcgtttctt   1200
ttggggcgcg accctaaaac aggaaaaacaa ttgccctgcc ctgccgaact tcttcgcctt   1260
actatccctc gtgcgaccta cactcaaacc cacatggact ttattatcga ggccttcaaa   1320
catgtgaagg agaatgctgc taatatcaag ggcctgacct ttacctacga gccaaaggtt   1380
ttgcgccact ttacagcaaa acttaaagaa gtt                                1413
```

<210> SEQ ID NO 75
<211> LENGTH: 969
<212> TYPE: DNA
<213> ORGANISM: Escherichia coli
<220> FEATURE:
<221> NAME/KEY: misc_feature
<222> LOCATION: (1)..(969)
<223> OTHER INFORMATION: cysK (Escherichia coliO104:H4 str. C227-11)

<400> SEQUENCE: 75

```
atgtcaaaaa ttttcgagga taactcgtta acgatcggcc acactccctt ggttcgtctg      60
aatcgtatcg gtaacgggcg cattctggca aaggttgaat cacgcaatcc gtccttctca     120
gttaagtgcc gtattggagc gaatatgatt tgggatgctg agaagcgcgg agtcctgaag     180
cctggggtgg agttggtgga gccaacctct gggaatacag gtatcgcgct ggcttatgta     240
gctgcagcgc gtggctacaa attaacactt accatgcccg agaccatgtc aatcgaacgt     300
cgtaagttgt tgaaggcatt aggagcgaat ctggtactga ccgaaggagc taagggaatg     360
aagggcgcta ttcaaaaagc ggaagaaatt gtcgcaagta ccccgaaaaa gtatctttta     420
ctgcaacagt tttctaaccc tgcaaatcct gagatccacg aaaaaacaac aggtcccgaa     480
atctgggaag acaccgacgg tcaagttgac gtatttatcg ccggggtagg aactggagga     540
accttaacgg gggtcagtcg ttatattaag ggtacgaagg gaaagactga tttgattagc     600
gtagcagtgg agccaacgga tagtcctgtt attgccaag ccctggcggg ggaggaaatc     660
aaaccgggac ctcacaaaat ccaagggatt ggtgcgggtt ttatcccagc caatctggat     720
ctgaaacttg tcgacaaggt cattggaatt actaatgaag aggcgatctc cactgcgcgc     780
cgtttgatgg aggaagaagg gattttggca gggatttcaa gcggtgcggc ggtggcagca     840
gctttgaaat gcaagaaga cgagtcattc actaataaga atattgttgt tattttacca     900
agcagcggtg agcgctactt atcaaccgct ttgttcgctg atttatttac ggaaaaagag     960
ttacaacaa                                                             969
```

<210> SEQ ID NO 76
<211> LENGTH: 909
<212> TYPE: DNA
<213> ORGANISM: Escherichia coli
<220> FEATURE:
<221> NAME/KEY: misc_feature
<222> LOCATION: (1)..(909)
<223> OTHER INFORMATION: cysM (Escherichia coliFVEC1412)

<400> SEQUENCE: 76

```
atgtcaacat tagaacagac aattggtaat acccccctgg tcaaattgca gcgcatgggg      60
ccaaacaatg gaagcgaggt ttggctgaaa ttggaaggca caacccggc gggatctgtg     120
aaagaccgtg ccgcactgtc catgatcgta gaagctgaga acgtggcga gattaaacct     180
ggggatgttt taatcgaggc tacaagtggg aacactggaa tcgcccttgc catgattgcg     240
gctttaaagg gttatcgtat gaagttactt atgcccgata acatgagcca ggagcgccgt     300
gccgctatgc gtgcctatgg tgctgaactt atcttagtta ccaaggagca aggcatggaa     360
ggtgcgcgtg acttggcatt agaaatggcg aatcgtggcg aagggaagct gcttgaccaa     420
tttaataatc cagataaccc ttatgcacac tataccacga ccggcccgga atctggcaa     480
caaccggcg gcgcatcac ccactttgta tcatccatgg cacaactgg tacaattacg     540
ggcgtttctc gtttcatgcg cgagcagagt aaacctgtta caatcgtggg acttcaacct     600
gaggagggat cttcgatccc aggcattcgt cgttggcctg ctgagtactt acctggcatt     660
```

```
ttcaacgcat ccttagtgga tgaagttctt gacattcatc agcgcgaagc agagaatacc    720
atgcgcgagt ggcagtacg tgagggcatt ttctgcgggg tttcttctgg ggggccgtg    780 gcgggtgctt tacgtgtcgc caaagcaaac cccggagcag tagttgttgc cattatttgt    840
gatcgtggtg accgctactt atctacggga gtcttcggag aggaacactt ttcacaaggg    900
gccggaatt                                                            909
```

```
<210> SEQ ID NO 77
<211> LENGTH: 1170
<212> TYPE: DNA
<213> ORGANISM: Escherichia coli
<220> FEATURE:
<221> NAME/KEY: misc_feature
<222> LOCATION: (1)..(1170)
<223> OTHER INFORMATION: malY (Escherichia coli)

<400> SEQUENCE: 77
```

```
atgttcgatt tttcgaaagt cgtcgatcgt catgggacct ggtgcactca atgggactac     60
gtggcggacc gctttgggac agcagatttg ttaccgttca ctattagcga catggatttt    120
gccacagcac cttgcattat cgaggcactg aatcagcgct taatgcatgg ggttttcggt    180
tatagccgtt ggaagaacga tgagttcctt gcagcaattg cacattggtt cagtacccaa    240
cattataccg ctatcgattc ccagacggtt gtgtacggcc ccagcgttat ttacatggtg    300
agcgaattga tccgtcagtg gtctgaaaca ggagaaggtg tagtaatcca tactcccgcc    360
tatgacgcgt tctacaaagc cattgagggg aatcaacgta cagtaatgcc cgttgcctta    420
gaaaaacagg cagacggatg gttttgcgat atgggaaaat tagaggcggt acttgcaaaa    480
cccgagtgca aaatcatgct tttatgcagt ccgcaaaacc caacaggcaa ggtctggacc    540
tgtgatgaat tagagattat ggcggatttg tgcgagcgtc acggagtccg tgtcatctct    600
gacgagattc acatggacat ggtctggggg aacagccgc acattccttg gtctaatgtc    660
gcacgtggtg attgggccct tttgacatcg ggttcgaaaa gctttaacat tccagccctg    720
accggggcat atggaattat cgaaaactcg tcgagccgtg acgcgtattt atctgccctt    780
aagggacgtg atggactttc gagcccgtcg gttcttgcct tgacggcaca cattgctgct    840
taccaacagg gagcgccgtg gctggacgct cttcgcattt acctgaagga taaccttact    900
tacattgcgg ataagatgaa tgcggccttc ccagaactta actggcagat tccccagtca    960
acgtatttag cctggcttga ccttcgtccc ttaaacattg atgacaacgc actgcaaaag   1020
gcactgatcg aacaggaaaa ggtagccatc atgcctggct ataccctacgg cgaggagggc   1080 cgtgggttcg tccgcctgaa cgcaggatgt ccccgctcga aacttgaaaa agggtagct   1140 ggtcttatta atgctattcg cgctgtgcgc                                     1170
```

```
<210> SEQ ID NO 78
<211> LENGTH: 1185
<212> TYPE: DNA
<213> ORGANISM: Escherichia coli
<220> FEATURE:
<221> NAME/KEY: misc_feature
<222> LOCATION: (1)..(1185)
<223> OTHER INFORMATION: MetC (Escherichia coli)

<400> SEQUENCE: 78
```

```
atggccgaca agaagttgga tactcaactg gtgaacgccg gcgttccaa aaaatatacc      60 ttgggagctg ttaatagcgt tatccaacgt gcatcaagtt tagttttcga tagtgtcgaa   120
gcaaagaagc atgcgacacg caatcgcgca aatgggaat tattttatgg acgccgcggg   180
```

```
accttgaccc acttctcttt acagcaggcc atgtgtgagc tggaaggggg agccggttgt    240
gtattgttcc cctgcggagc cgcggcggtg gctaacagta tcctggcgtt cgtggagcag    300
ggtgatcacg tcctgatgac gaacaccgcg tacgaaccct cgcaagactt ctgcagtaaa    360
atcttatcca aattaggtgt gactacctcg tggtttgacc cgttgatcgg ggcggacatt    420
gtgaaacatc tgcagcccaa cacgaaaatt gttttttttgg agtctcccgg ttcgattact    480
atggaggtac acgacgtgcc agctatcgtt gcagcagttc gttccgtggc gcccgacgca    540
attatcatga tcgacaatac atgggccgca ggcgtccttt ttaaagcctt agattttggc    600
attgatgtaa gtatccaagc ggctaccaag tacttggtcg acattccga tgcgatgatt     660 ggtacagcag tatgcaatgc acgctgctgg gagcaattgc gtgaaaacgc ttacctgatg    720
gggcaaatgg tagacgcaga taccgcttat attaccagtc gtgggttgcg tacattagga    780
gtgcgtttgc gtcaacacca cgagtcatcc ctgaaagtgg ctgaatggct ggctgaacat    840
ccccaggttg ctcgcgtaaa ccaccccgca cttccgggat caagggcca tgaattttgg     900 aagcgcgact tcacgggctc cagtggattg ttttctttcg tacttaagaa aaagttgtct    960
aatgaagaat tggcgaatta ccttgataac tttagcttgt ttagtatggc atatagttgg    1020
gggggatatg aatcactgat tttggcaaat caaccagaac atattgctgc gattcgtcct   1080
caaggcgaaa ttgattttag cggaacgtta attcgtctgc acatcgggct tgaggatgtg    1140
gacgatttaa ttgcagattt ggatgcggga tttgcacgta ttgtg                    1185

<210> SEQ ID NO 79
<211> LENGTH: 1230
<212> TYPE: DNA
<213> ORGANISM: Trypanosoma grayi
<220> FEATURE:
<221> NAME/KEY: misc_feature
<222> LOCATION: (1)..(1230)
<223> OTHER INFORMATION: cystathione gamma lyase (Trypanosoma grayi)

<400> SEQUENCE: 79
atgtcaggtg cccagcactt gttcgcagat ttcagcgaag gatcaggatc gtggcaaccc     60
caggcccaag ggtttgagac gcttctggta catggtggcg taaagccaga tcccgtcacg    120
ggggcaatcc tgaccccgt ctaccagtct acgacgttcg tgcaagagag tatcgaacgt     180
tatcaagcaa agggctatag ctatacccgt tcagccaatc ctaccgtatc tgcattggaa    240
gagaaattgt gcgcaatcga gcacggcgaa tatgccactg tgtatagcac cggcatgtcc    300
gctacgacaa cggccatcag tagttttatg tctgctggcg accacgctat tgtgaccgaa    360
tgtagctatg gcggaaccaa tcgtgcctgc cgtgtcttct tcacgcgctt aggtatgtct    420
tttacattcg tagatatgcg cgacgttaaa aatgtagagg ctgccatcaa acccaatacc    480
aagctggtta tctcagaatc gccagcaaac cctacactga cgcttactga tattgacgca    540
cttagctcgc tttgcaaggc taagggtatt attcacatgt gtgacaacac tttcgcaacc    600
gctttcatta tgcgtccgct tgatcacgga gcagacgtga ccctgatctc cacgactaag    660
tttgttgatg ccacaatat gaccgtcgga ggggccttgg tcactaaatc caaggaatta    720
gacggaaagg tacgtttaac gcaaaatatc ttaggtaact gtatgagtcc atttgttgcg    780
ttccttcaat tacaaacggt gaagacgatg agccttcgca tttctcgtca atcagaaaac    840
gcccagaaag tagcggaatt tcttgagacc caccccgcag tggaacgcgt aatgtatcca    900
ggtcttaaat ctttcccaca gaaggcctta gcggatcgtc agcacgcaaa caatttacat    960
```

```
ggcggtatgt tatggtttga agtgcgcgga ggaacagcgg cagggcgtcg cttgatggac    1020
accgttcagc gcccgtggag cttatgcgag aatctgggtg cgacggaatc catcattact    1080
tgcccgagtg tcatgaccca cgcgaacatg actactgagg accgtatgaa ggtcggtatc    1140
accgacggat ttgtacgtgt cagctgcggg atcgaagatg cagccgatct tatctcagct    1200
ttgaaggccg cactggatgc cttgggcaag                                     1230

<210> SEQ ID NO 80
<211> LENGTH: 915
<212> TYPE: DNA
<213> ORGANISM: Helicobacter pylori 2017
<220> FEATURE:
<221> NAME/KEY: misc_feature
<222> LOCATION: (1)..(915)
<223> OTHER INFORMATION: Cystathione beta-synthase (Helicobacter pylori
      2017)

<400> SEQUENCE: 80
atgatcttaa cagcaatgca agatgcaatc gggcgtacac ctatcttcaa gtttacacgt      60
aaagattacc caattccatt gaagtcggca atttacgcga aattggaaca cttaaacccg     120
gggggatccg tgaaagatcg ccttgggcag tatcttatta aggaggcctt ccgtacacac     180
aagattacct ctactaccac tatcatcgaa cctactgctg ggaatactgg catcgccctt     240
gcccttgtag ctatcaaaca tcatcttaaa acgatctttg ttgttcccga aaaattttcg     300
gttgagaaac aacagatcat gcgtgctctt ggtgccttag taatcaatac gcctacctca     360
gagggtatct caggggccat taaaaaaagc aaagagttag ccgagtctat cccggacagc     420
tacttgcctc ttcaatttga aatcccgac aatccggctg cttattacca cactcttgct     480
cctgaaattg taaggaact ggggacgaat tttacctctt ttgtagcggg catcggttct     540
ggaggaactt tcgcaggcac cgccaagtac cttaaagaac gtatcccgaa catccgcttg     600
attggagttg aaccagaagg ttctatttta aatgggggtg aaccggggcc ccacgaaatc     660
gaaggaattg gagtagagtt catcccacca ttcttcgcta atttggatat tgatgggttt     720
gagacgattt cagacgaaga gggcttcagt tatacgcgca aattagccaa aaagaacgga     780
ttattagtgg gtagttcgtc cggagcagcg ttcgccgcgg ctcttaagga agtacaacgt     840
ctgcccgaag ggtcacaagt gttgacgatt tcccagata tggctgatcg ctaccttagt     900
aaaggcattt attcc                                                     915

<210> SEQ ID NO 81
<211> LENGTH: 1320
<212> TYPE: DNA
<213> ORGANISM: Helicobacter pylori 2017
<220> FEATURE:
<221> NAME/KEY: misc_feature
<222> LOCATION: (1)..(1320)
<223> OTHER INFORMATION: putativeamino transferase (Helicobacter pylori
      2017)

<400> SEQUENCE: 81
atgcaagctt tcttgaaccg ttcgttcgcg cccctttaa acccaaatga gaacctgctg      60
gatcaagtta agagttcgat tattttgaag aaaggtgtta gctactttga ctggggtgct    120
agtgggctgg ccagtgcatt ggtcgagaaa cgtgttaagt ccctgcttcc atattatgcc    180
aatgcccaca gcgtagcaag taaacatgcc atcttaatgg gcatgttact taagaatgc     240 caagagaagc tgaaacgctc gttaaacctt agtactaacc attgcgtgct tagcgccggg    300
tatggcgcga gctcagcgat caagaaattc caagagatcc tgggagtttg catcccctct    360
```

```
aaaaccaaaa agaatctgga accttattta aaagacatgg cgctgaaacg cgtaatcgta    420
ggtccttatg aacatcactc taacgaggtc tcttggcgcg agtctctttg tgaggtggtg    480
cgcattccac ttaacgaaca tggactgctg gatttggaga ttttagagca gatcttaaag    540 aaatcccca attctctggt ctccgtctcg gccgcaagta atgtaacggg gattctgaca    600
cccctgaaag aaattagctc actgtgcaag gagtatcgcg cgatcctggc gcttgatctg    660
gccaactttt ccgcacacgc gaacccgaaa gactgcgagt accagacggg gttctatgca    720
ccacacaagt tgttgggtgg tattgggga tgcgggcttc ttggaatctc caaagacttg    780
atcgatacac agatcccacc tagttttca gccggaggag tcattaagta cgcaaaccgc    840
acgcgtcacg aatttattga tgagctgccg ttgcgtgagg agttcggaac tccgggactg    900
ctgcaatttt atcgctcagt gttagcctac cagttacgtg acgaatgcgg tttgatttc    960 attcataaga aggagaataa tctgcttcgt gtgttaatgc atggcttgaa agatctgcca   1020
gctatcaaca tttacggcaa tttaaccgca agccgcgtag gagtagtcgc gtttaacatc   1080
ggaggcatta gtccatacga tcttgcccgt gtcctgagtt acgaatatgc tattgagact   1140
cgcgcagggt gctcttgtgc cggcccgtat ggacatgact tactgaattt gaatgcacaa   1200
aagtcttccg atttcaatgc aaaacctgga tggttgcgcg tctcacttca ttttacacac   1260
agtattaatg acattgacta tctgttggac tctctgaaga aagctgttaa gaaactgcgt   1320

<210> SEQ ID NO 82
<211> LENGTH: 918
<212> TYPE: DNA
<213> ORGANISM: Bacillus atrophaeus UCMB-5137
<220> FEATURE:
<221> NAME/KEY: misc_feature
<222> LOCATION: (1)..(918)
<223> OTHER INFORMATION: YdeD (Bacillus atrophaeus UCMB-5137)

<400> SEQUENCE: 82
atgaacggtg aacacgccgc gttggcccac tcccgcacaa aagggattgc tttggtttta     60
acgggcagta tcttatgggg cgtttcaggg acagttgcgc agtacttatt ccaacaacaa    120
cattttaacg tagagtggtt gaccgtcgtt cgcttgttgc tgtctggtat cttgctgctt    180
ggccttgcct atcgtaagga aaagcaacgc atctgggctg tctggaaaga caagacagat    240
ggtctgaatc tggttctgtt cgggattttg gggatgttgt ccgtccagta cacatacttt    300
gcggctatcc agcatggtaa tgcggcgacg gcaactgtac ttcagtatct ggccccggca    360
cttattacct gctacgtagc cattcgctct aagcgtcttc caaccgtcaa agagttgatc    420
gcagttttcc tggctattat tggaacgttt tttttagtca cccatgggga catccacagt    480
cttagtatct cagggtgggc tttattctgg ggattaagtt cggcgtttgc cctggcgttt    540
tacactttgc accctcataa acttctggcc aagtgggggg cggctatcgt tgttggctgg    600
ggtatgctta tcggagggct tggtctttcc ttaatccatc ctccatggaa atttgaggga    660
cagtggtcgg tctcggctta tgccgccgtt attttcattg tcctgtttgg gaccctgact    720
gccttctact gctacctgga atctttaaag tacttaactg ccagcgaaac ttcattaatc    780
gcctgcgcgg agcccttaag tgctgcgttc ttaagcgtga tttggttgca tgtgactttt    840
ggtatcagcg agtggcttgg tacttgttgt attttatcta cgattatgat cttatcgatt    900
aaggagaaga agctgaag                                                  918

<210> SEQ ID NO 83
```

```
<211> LENGTH: 585
<212> TYPE: DNA
<213> ORGANISM: Escherichia coli
<220> FEATURE:
<221> NAME/KEY: misc_feature
<222> LOCATION: (1)..(585)
<223> OTHER INFORMATION: proteinYfiK (Escherichia coli)

<400> SEQUENCE: 83
atgacaccca cgttgcttag cgccttctgg acgtacaccc ttattacagc catgacgcct      60
gggccaaata atatccttgc cttatcatcc gcaacgtcgc atgggttccg ccagtccacc     120
cgtgtgcttg caggtatgtc tcttggcttt ttaatcgtta tgctgttgtg cgcgggaatc     180
agtttctcct tggcggtaat cgaccccgcc gccgtacatt tattgtcttg ggctggtgcc     240
gcgtatattg tttggctggc ttggaaaatt gccacgtctc cgactaagga agatggttta     300
caagcaaaac ccatctcgtt tgggcttca tttgcacttc agttcgtgaa tgtcaagatt      360
attctttacg gggtaacagc cctgtccact ttcgttttac cccagacgca ggcgttgtca     420
tgggtagtcg gagtgtccgt cttattagcc atgatcggta cgtttgggaa tgtgtgctgg     480
gcgctggcgg gccacttgtt tcaacaatta ttccgtcagt acggtcgcca gttaaatatc     540
gttcttgctt tattactggt gtattgtgca gtccgcatct tctat                    585

<210> SEQ ID NO 84
<211> LENGTH: 1188
<212> TYPE: DNA
<213> ORGANISM: Escherichia coli
<220> FEATURE:
<221> NAME/KEY: misc_feature
<222> LOCATION: (1)..(1188)
<223> OTHER INFORMATION: multidrug efflux transporterBcr(Escherichia
      coli)

<400> SEQUENCE: 84
atgacgaccc gccagcatag ctcgttcgca atcgtattta ttcttggatt gcttgctatg      60
ttgatgccat tatcaatcga catgtactta ccagccctgc ctgttatttc ggcccaattt     120
ggagtacccg ctgggtcaac ccaaatgaca ttatcaacat acattctggg ttcgcttta      180
ggacagttga tttatggtcc aatggctgac tcgtttgggc gcaaaccagt ggtcttgggc     240
gggacactgg tctttgcggc cgcagccgtt gcgtgtgcct ggctaacac gatcgaccag      300
cttattgtaa tgcgtttctt ccatggctta gctgcggcgg ctgccagtgt agtgattaat     360
gcgcttatgc gtgacatcta tccgaaggag gaattcagcc gcatgatgag cttcgtaatg     420
ttggtaacga ccatcgctcc attaatggcc cctattgttg ggggttgggt cttagtctgg     480
cttttcatggc attacatttt ttggatcctt gccctggcgg ctattctggc ctcagcgatg     540
attttcttcc tgattaaaga aaccttcct ccggagcgcc gtcagccttt ccatattcgc      600
actactatcg gtaatttgc ggccttgttt cgccataaac gcgtgctgtc atacatgttg      660
gcaagcggct ttctttcgc gggtatgttc tcgttttta a gtgctggtcc cttcgtgtat     720
atcgaaatca atcacgtagc cccggagaac ttcggctatt acttcgcatt aaatatcgtg     780
tttcttttcg tcatgaccat cttcaactct cgcttcgtcc gtcgtatcgg tgccttaaat     840
atgtttcgtt cggggctgtg gatccaattt atcatggctg cgtggatggt gatctccgca     900
ctgttggggc ttgggttttg gtcgcttgtg gtgggcgtgg ctgcattcgt tggatgtgtc     960
agcatggtat cttctaacgc gatggctgta attttgatg agttcccaca tatgcagggg     1020
actgcttcct ctctggctgg cacatttcgc ttcggaattg gtgcaatcgt aggcgcgttg     1080
```

```
ctgagcttag cgacattcaa ttcggcgtgg cccatgattt ggtccattgc gttttgtgcg    1140
accagcagca tcctgttctg cctttatgct tcccgtccaa agaagcgt                 1188

<210> SEQ ID NO 85
<211> LENGTH: 1356
<212> TYPE: DNA
<213> ORGANISM: Pseudomonas fluorescens R124
<220> FEATURE:
<221> NAME/KEY: misc_feature
<222> LOCATION: (1)..(1356)
<223> OTHER INFORMATION: TolC (Pseudomonas fluorescens R124)

<400> SEQUENCE: 85
atgaacaaac ttagtatgct gggagctgcc ttcgcgttgt tggcagggaa ctcagcattg     60
gcagcaatgg ggccttttcga aatctacgaa caggctcttc gcaatgaccc agttttctta   120
ggggccatta aggagcgtga cgccggattg gaaaaccgca tcatcggccg cgcaggattg    180
ttaccacgct tggggtacaa ctacaatcgt ggccataaca cctctaaagc gacccagttg    240
acaaatcgtg gctctctgac tgaagaccgt aactataatt cgtatggttc aactcttaca    300
ttacagcaac ccttattaga ctatgaggcc tatgccgcct accgtaaggg agtagcgcaa    360
agcttgttcg ccgatgaagc cttccgcggt aagtcacagg aattattggt tcgcgtctta    420
gataattaca cgaaagcgtt gttcgcacaa gaccaaatcg atatcgcaca ggcgaaaaaa    480
aaagcttatg aacaacaatt tcagcagaac gaacatatgt caaacaaggc gaggggacg    540 cgcactgaca ttttggaagc tgaaagtcgt tatgaacttg ccacggcaga agaaatcgag    600
gcgcgtaacg aacaggatgc cgctcttcgc gagcttggtg cgcttgtcgg tgtcccaact    660
gtcgacattt ctgaacttgc acccttagac cagaattttc aaacgttcgc gctgatgcct    720
gctaactatg atacgtggca cgagttagca atttctaata atccgaacct ggcatcacag    780
cgtcaggccg tggaagtagc aaaaatacgaa gttgaacgta accgtgcagg acatttaccc    840
aaggtctcag catatgccag cattcgtcag actgagtctg acagtggtaa tacctacaat    900
caacgttatg atacgaacac cattggcttt gaggtaaacg tccctctgta tgcaggagga    960
ggagtctcag caagtacacg ccaagcatca cgcacgatgg agcaggcgga gtatgaatta   1020
gatggaaaga cgcgtgagac gttaattgaa ttacgtcgtc agttcagcgc gtgccttagt   1080
ggagttaata agttacgcgc ctatcagaaa gccctggcct cggccgaagc actggtggtc   1140
tcaaccaagc agagcattct tggcggcgaa cgcaccaact tggacgcgct taacgcggaa   1200
cagcagctgt tcaccacgcg tcgcgacctt gcacaggccc gctatgacta cttgatggcg   1260
tggacgaaac tgcattatta cgcaggaacc ctgaacgaac aagatttagc gcgtgtggac   1320
gaggcatttg gccaagggcc caaatcaaat cctcgc                             1356

<210> SEQ ID NO 86
<211> LENGTH: 1167
<212> TYPE: DNA
<213> ORGANISM: Sinorhizobium meliloti AK83
<220> FEATURE:
<221> NAME/KEY: misc_feature
<222> LOCATION: (1)..(1167)
<223> OTHER INFORMATION: Tyrosine transaminase (Sinorhizobium meliloti
      AK83)

<400> SEQUENCE: 86
atgttcgatg cgctggcgcg tcaagcggat gatccgcttt ggcgctgat cggactgttt     60 cgcaaagacg agcgccccgg taaagtggac ttaggtgtgg gagtttaccg cgacgaaact   120
```

```
ggccgcactc cgatctttcg cgcggttaaa gcagccgaaa aacgcttgct tgagactcag      180
gactcgaagg cctacatcgg cccggaagga gacctggttt tcttgaccg tttgtgggaa       240 cttgttgggg gggataccat tgaacgttct cacgtagctg gtgtacaaac acctggcggg      300
agcggcgcac ttcgtttggc ggcagattta atcgcccgca tgggcggtcg cgggatttgg      360
ttggggttgc catcctggcc gaatcacgct cccatttca aagcggctgg actggatatc       420
gcgacttacg atttctttga tatcccgagt caatccgtta tttttgataa cctggtgtct      480
gccctggaag gtgcagcatc tggcgatgcc gtcttattgc atgctagctg ccacaatcca      540 actgagggg tattatccga ggcacagtgg atggaaattg ccgcgctggt cgccgaacgc       600
ggactgttac cacttgttga tcttgcgtat caagggttcg gacgtgggct ggatcaagac      660
gtcgcgggct tacgccattt attaggtgta gttcccgaag cccttgtcgc cgttagctgc      720
tctaaatcgt tcggcttgta ccgcgaacgc gctggagcca tcttcgcccg tacatcatct     780
accgcttcag ccgaccgcgt ccgcagtaac ttagctggcc ttgctcgcac atcgtatagt      840
atgccccccg atcacggggc cgcggttgtc cgtacgatct tagacgaccc agagctgcgt     900
cgtgactgga ccgaggaatt agagacaatg cgcttgcgta tgacgggtct tcgccgctct     960
cttgcagagg gcttgcgcac ccgttggcag tctcttggcg ccgtagctga ccaagaaggg    1020
atgttctcga tgctgccgtt gtccgaagca gaggttatgc gccttcgcac tgagcatgga    1080
atttacatgc ccgcatcagg acgcattaac attgcggggt taaaaacggc ggaggctgcc   1140
gaaattgcag gtaaatttac gagtttg                                        1167

<210> SEQ ID NO 87
<211> LENGTH: 1209
<212> TYPE: DNA
<213> ORGANISM: Escherichia coli
<220> FEATURE:
<221> NAME/KEY: misc_feature
<222> LOCATION: (1)..(1209)
<223> OTHER INFORMATION: tyrosine transporterTyrP(Escherichia coliW)

<400> SEQUENCE: 87
atgaagaacc gcactcttgg atcagtattc attgttgcgg ggaccaccat cggtgcaggt      60
atgcttgcca tgcccctggc tgcagctggc gtcgggttca gcgttaccct gattttactg     120
attggtctgt gggctctgat gtgttacacg gcattgcttt gcttgaagt gtaccagcat      180 gtacccgcag acaccggtct tggcactctg gcgaaacgtt atttaggacg ttatggtcaa     240
tggctgaccg gttctccat gatgtttctg atgtatgcgc tgacggccgc atacattagt     300
ggtgcaggtg aactgctggc aagttcaatt tctgactgga cgggcatctc tatgagcgcg    360
actgctgggg ttttattgtt tacatttgtg gctggcggtg tagtgtgtgt agggacgtca    420
ttagttgatc tgtttaaccg cttccttttc agtgcaaaaa tcattttcct tgtagtaatg   480
cttgtcttat tattaccaca tattcataag gtaaatcttt tgacattacc attgcagcag   540
ggattggcgt tatcagccat ccctgtaatc ttcacatcct tcggattcca cgggtccgtc   600
ccatccatcg tgtcctacat ggacggcaat gtacgcaagt tacgttgggt ctttatcaca   660
gggagcgcca ttccccttgt agcgtatatt ttttggcaag ttgctactct ggggtcaatc   720
gactctacca ccttcatggg tttacttgcg aaccacgcgg ggttgaacgg actgttacag   780
gctttgcgtg aaatggttgc ctcgccacat gttgagttgg cggttcatct ttttgctgac   840
ttagccttag ctacctcttt ccttggggtt gcgctgggat tattcgacta tctggctgat   900 cttttttcaac gctccaacac cgtaggtgga cgtttacaga ctggagccat tactttcttg   960
```

```
ccccctttag cctttgcgct gttttatcca cgtgggtttg ttatggcctt ggggtatgct    1020
ggagtcgcct tagctgtact tgctcttatt attccatcgt tattaacgtg caatcgcgt     1080 aaacacaacc cccaagcagg gtaccgcgtg aagggaggac gccccgcgct ggtggttgtt    1140
tttctgtgcg ggattgccgt catcggcgtg caattttttga ttgcagcagg tttgttgccg   1200
gaggtgggg                                                            1209
```

<210> SEQ ID NO 88
<211> LENGTH: 1302
<212> TYPE: DNA
<213> ORGANISM: Variovorax paradoxus
<220> FEATURE:
<221> NAME/KEY: misc_feature
<222> LOCATION: (1)..(1302)
<223> OTHER INFORMATION: Beta-phenylalanine transaminase (Aromatic beta-amino acid aminotransferase;Beta-phenylalanineaminotransferase; VpAT)

<400> SEQUENCE: 88

```
atgactcatg ctgcaattga ccaggcgttg gcagacgcct atcgtcgttt tactgacgca    60
aaccctgcca gccagcgtca gtttgaagcg caagcccgct atatgcccgg ggctaactct   120
cgctctgttt tgttttatgc acccttttcca ttgacgatcg cacgtgggga aggcgccgct   180
ctttgggatg cggacggcca ccgttacgct gactttatcg cggaatacac agctggggtg   240
tatggacaca gtgccccaga gattcgtgac gcagtaatcg aagctatgca gggtgggatt   300
aatttgacgg gtcataattt gttggaaggc cgcttagccc gccttatttg tgagcgtttc   360
ccacagatcg aacagttgcg tttcacgaat agcggaacag aggccaatct gatggccctt   420
accgcggcgc ttcattttac tggtcgccgc aaaatcgtcg tatttagtgg aggttatcat   480 ggggggggttc ttgggttcgg tgcccgtcct agccctacca cagtaccatt tgacttcctt   540
gtgctgcctt acaacgatgc tcagacggct cgtgctcaga tcgagcgcca cggcccggag   600
atcgcggtcg tgttagtcga gcccatgcaa ggtgcttctg gctgcatccc aggtcagccc   660
gactttctgc aagccctgcg cgaatccgct actcaggtag gggcgctgtt agttttttgac   720 gaagtgatga ctagtcgctt agcgccacat ggtttagcta caaaattggg gatccgttcg    780
gatttgacaa ccctgggtaa gtacattggc ggcggtatgt catttggggc ctttggcggt    840
cgtgctgatg tcatggccct gttcgaccct cgcactggac ctttggctca ttccggtacg    900
tttaacaaca atgtgatgac gatggctgcc ggttatgctg gcttaacgaa attattcact    960
ccggaagcgg cagggggcatt ggcagagcgt ggagaagcgc ttcgcgcacg tcttaacgcc   1020
ctgtgtgcta acgaaggagt agcaatgcag ttcactggca tcggctcgct gatgaatgcc   1080
cacttcgtcc agggagacgt tcgtagctct gaggatctgg ccgcagttga tgggcgttta   1140
cgtcagttgt tgttctttca tttattgaat gaagatattt actcttcacc gcgtgggttt   1200
gttgtattat cgttgccatt gactgacgct gatattgacc gctacgttgc tgcgatcggt   1260
tcatttattg gcggtcatgg ggcgttgtta ccgcgcgcta ac                      1302
```

<210> SEQ ID NO 89
<211> LENGTH: 1401
<212> TYPE: DNA
<213> ORGANISM: Escherichia coli
<220> FEATURE:
<221> NAME/KEY: misc_feature
<222> LOCATION: (1)..(1401)
<223> OTHER INFORMATION: gadA glutamate decarboxylase (Escherichia coli)

<400> SEQUENCE: 89

```
atggaccaga agctgttaac ggatttccgc tcagaactac tcgattcacg ttttggcgca      60
aaggccattt ctactatcgc ggagtcaaaa cgatttccgc tgcacgaaat gcgcgatgat     120
gtcgcatttc agattatcaa tgatgaatta tatcttgatg caacgctcg tcagaacctg      180
gccactttct gccagacctg ggacgacgaa aacgtccata aattgatgga tttgtcgatc     240
aataaaaact ggatcgacaa agaagaatat ccgcaatccg cagccatcga cctgcgttgc     300
gtaaatatgg ttgccgatct gtggcatgcg cctgcgccga aaatggtca ggccgttggc     360
accaacacca ttggttcttc cgaggcctgt atgctcggcg gatggcgat gaaatggcgt     420
tggcgcaagc gtatggaagc tgcaggcaaa ccaacggata aaccaaacct ggtgtgcggt    480
ccggtacaaa tctgctggca taaattcgcc cgctactggg atgtggagct gcgtgagatc     540
cctatgcgcc ccggtcagtt gtttatggac ccgaaacgca tgattgaagc ctgtgacgaa    600
aacaccatcg cgctggtgcc gacttcggc gtgacctaca ccggtaacta tgagttccca     660
caaccgctgc acgatgcgct ggataaattc caggccgaca ccggtatcga catcgacatg     720
cacatcgacg ctgccagcgg tggcttcctg gcaccgttcg tcgccccgga tatcgtctgg     780
gacttccgcc tgccgcgtgt gaaatcgatc agtgcttcag gccataaatt cggtctggct     840
ccgctgggct gcggctgggt tatctggcgt gacgaagaag cgctgccgca ggaactggtg     900
ttcaacgttg actacctggg tggtcaaatt ggtacttttg ccatcaactt ctcccgcccg     960
gcgggtcagg taattgcaca gtactatgaa ttcctgcgcc tcggtcgtga aggctatacc    1020
aaagtacaga acgcctctta ccaggttgcc gcttatctgg cggatgaaat cgccaaactg    1080
gggccgtatg agttcatctg tacgggtcgc ccggacgaag gcatcccggc ggtttgcttc    1140
aaactgaaag atggtgaaga tccgggatac accctgtacg acctctctga acgtctgcgt    1200
ctgcgcggct ggcaggttcc ggccttcact ctcggcggtg aagccaccga catcgtggtg    1260
atgcgcatta tgtgtcgtcg cggcttcgaa atggactttg ctgaactgtt gctggaagac    1320
tacaaagcct ccctgaaata tctcagcgat cacccgaaac tgcagggtat tgcccagcag    1380
aacagcttta aacacacctg a                                              1401
```

<210> SEQ ID NO 90
<211> LENGTH: 1398
<212> TYPE: DNA
<213> ORGANISM: Escherichia coli
<220> FEATURE:
<221> NAME/KEY: misc_feature
<222> LOCATION: (1)..(1398)
<223> OTHER INFORMATION: glutamate decarboxylase (Escherichia coliKO11FL)

<400> SEQUENCE: 90

```
atggataaaa agcaagtgac ggacctgcgc tctgaacttc ttgacagtcg ttttggggca      60
aagagtatta gtaccattgc tgagtcaaag cgttttcctt tgcatgagat gcgcgatgac    120
gtcgcattcc agattatcaa cgacgagctg tatttggacg gcaatgcccg ccaaaacttg    180
gccacgtttt gtcagacttg ggatgacgag aatgttcata aacttatgga cctttcaatt    240
aacaaaaatt ggattgacaa agaagagtac ccccaatctg ccgcaattga tttacgttgt    300
gttaatatgg tggccgactt atggcatgca ccagccccta aaaacggcca agcggtggga    360
accaacacga tcgggtctag tgaggcatgt atgttaggcg gatgccat gaagtggcgt       420
tggcgtaaac gcatggaggc agcagggaaa ccaaccgata aacctaattt agtctgcgga    480
```

| | |
|---|---|
| ccggttcaga tctgttggca taaatttgcg cgctactggg atgtggaatt acgcgaaatt | 540 |
| ccgatgcgtc cgggccaact gttcatggat cccaaacgta tgatcgaagc atgtgacgaa | 600 |
| aacacgattg gggtggtacc cacctttggg gtcacatata caggtaacta cgagtttcca | 660 |
| caaccgttgc atgatgctct ggacaagttt caagctgaca ccgggatcga cattgatatg | 720 |
| cacattgacg ctgcctccgg cggattcttg gccccatttg tagcccctga cattgtctgg | 780 |
| gactttcgtc ttccccgtgt gaaatccatc agcgcatccg gtcacaagtt tgggcttgcc | 840 |
| ccattagggt gtggatgggt catctggcgt gatgaggaag cattacccca gaacttgtc | 900 |
| ttcaatgtag attaccttgg gggacagatt ggcacttttg ccatcaactt ttctcgccca | 960 |
| gcgggtcaag tgatcgccca gtattacgag tttctgcgcc tgggacgtga gggatataca | 1020 |
| aaagtgcaga acgcatcgta ccaggtagcg gcttaccttg cggacgaaat tgcaaagctg | 1080 |
| ggaccatacg agtttatctg taccgggcgt ccagatgaag gtattccggc tgtgtgtttt | 1140 |
| aagctgaaag acggggaaga tcccggatat acgctgtatg atctgtctga acgtttacgt | 1200 |
| ttgcgcggtt ggcaagttcc agccttcacg ttgggtggcg aagccactga tattgtagtc | 1260 |
| atgcgtatca tgtgtcgtcg cggctttgaa atggatttcg cagagttact tctggaagac | 1320 |
| tacaaagcga gcttaaaata tttgtctgac catcccaagt tgcaagggat cgcacagcaa | 1380 |
| aattcgttta aacacact | 1398 |

<210> SEQ ID NO 91
<211> LENGTH: 1287
<212> TYPE: DNA
<213> ORGANISM: Bacillus atrophaeus UCMB-5137
<220> FEATURE:
<221> NAME/KEY: misc_feature
<222> LOCATION: (1)..(1287)
<223> OTHER INFORMATION: GltT (Bacillus atrophaeus UCMB-5137)

<400> SEQUENCE: 91

| | |
|---|---|
| atgaagaaat tacgcttcgg actggcgact caaatctttg tggggctgat tcttggggta | 60 |
| gtagtgggcg ttatctggta cggtaatccg gcggtggtaa cttatttgca gccagttggg | 120 |
| gacctttttt tacgtttgat taaaatgatc gttattccta tcgtggtgtc ttctttgatc | 180 |
| attggcgtcg cgggagctgg gtccggaaaa caggtcggaa agctgggctt tcgtactatt | 240 |
| ctgtacttcg agatcatcac tacctttgcc atcattctgg gacttgctct ggcgaatctt | 300 |
| ttccagcctg gtacaggagt aaatatcgag agcgcgcaga aaagtgacat ttcccagtac | 360 |
| gtggagactg aaaaagagca atccaccaaa tccgtagctg agactttcct gcatatcgtg | 420 |
| cccaccaatt tctttcaatc acttgcggaa ggtgatcttc ttgctattat ctgctttacc | 480 |
| gtacttttcg cccttggcat ttcggctatc ggtgaacgtg gcaaaccggt gcttgctttc | 540 |
| tttgacggag tatcccacgc gatgtttcat gtagtgaacc ttgtgatgaa ggttgctccg | 600 |
| ttcggcgtat ttgctctgat tggagtaaca gtaagcaaat ttggactggg ttcttttactg | 660 |
| agcctgggta aacttgtggg gctggtatat gttgctctgg cattttttct tattgtaatc | 720 |
| tttggtattg ttggaaagct ggctggcgtg aatatcttca agttttttagc ttacatgaag | 780 |
| gatgaaatct tattagcgtt ctcgacctca tcgtccgaga ctgtgttgcc ccgcatcatg | 840 |
| gagaaaatgg agaagatcgg gtgtccaaag ggaattgtaa gctttgtagt ccccatcggt | 900 |
| tacacattca atcttgacgg ctcggtctta taccaatcta ttgctgcgct gttcttggca | 960 |
| caggtttacg gaatcgacct gactatttgg catcagatta ctctggtgtt agttctgatg | 1020 |
| gtcactagca aaggcatggc agccgttcct ggaactagct ttgtagtcct gctggcaacc | 1080 |

```
ttaggtacca ttggtgttcc agcggaaggg cttgcattca ttgcggggt tgaccgcatt      1140 atggacatgg ctcgcactgt ggtcaattta acaggcaatg ctcttgcgag tgtcgtaatg      1200
agcaagtggg agggtcagta cgacccggtg aaaggtgcag agattatgag ccgcagcaag      1260
acggaacagg acgctactat ctccgga                                          1287
```

<210> SEQ ID NO 92
<211> LENGTH: 858
<212> TYPE: DNA
<213> ORGANISM: Escherichia coli
<220> FEATURE:
<221> NAME/KEY: misc_feature
<222> LOCATION: (1)..(858)
<223> OTHER INFORMATION: mechanosensitive channelMscS(Escherichia coli)

<400> SEQUENCE: 92

```
atggaggact tgaacgtagt agatagcatt aatggagcgg ctcatggtt agtagccaac       60 caagccctgt tgttatcgta tgctgtaaat atcgtcgcag ccttagccat cattatcgtt      120
gggttaatca tcgcccgtat gatttctaat gcggtgaatc gcttaatgat ctcgcgcaag      180
atcgacgcca ctgtcgcgga tttcttgtcc gccctggtgc gttacggtat catcgcgttc      240
acattgattg cggcattagg gcgcgtagga gtccagacag cttctgtgat tgcggtatta      300
ggtgcagcag gattagctgt gggattggcg ttacaggggt ctctttccaa tctggcggcc      360
ggcgtacttc tggttatgtt tcgccccttt cgcgccggag agtatgtgga tttgggagga      420
gtggccggaa cagtgctgtc agtgcaaatc ttttctacca cgatgcgtac agcagatgga      480
aaaatcatcg tgatccccaa tggcaagatc atcgcgggta acattatcaa cttctcccgc      540
gaacctgttc gccgcaacga atttatcatc ggtgttgcct atgattcaga catcgatcag      600
gtcaaacaaa ttcttacgaa catcattcag tcagaggacc gtattctgaa agaccgcgaa      660
atgacggtgc gtttgaatga gttaggggct tcaagtatca acttcgtagt ccgcgtgtgg      720
agcaattccg gtgatttgca aaacgtgtat tgggacgtcc ttgagcgcat taagcgtgaa      780
ttcgatgctg ccgggatctc ctttccgtat cctcagatgg atgtgaattt caagcgtgta      840
aaggaagata aggctgcc                                                    858
```

<210> SEQ ID NO 93
<211> LENGTH: 1539
<212> TYPE: DNA
<213> ORGANISM: Bacillus amyloliquefaciens subsp. plantarum str. FZB42
<220> FEATURE:
<221> NAME/KEY: misc_feature
<222> LOCATION: (1)..(1539)
<223> OTHER INFORMATION: HutH (Bacillus amyloliquefaciens subsp.
       plantarum str. FZB42)

<400> SEQUENCE: 93

```
atgatggtca ccttggatgg gtcttcatta acgacggctg atgcacaacg tgtacttttc       60
gattttgaag aggtacaggc atcggctgaa tcgatggagc gcgtaaaaaa gagccgtgcc      120
gccgtggaac gcattgtaca agaagaaaaa actatctacg gaatcactac ggggtttggt      180
aagttttccg atgtgctgat ccaaaaagag gacgctgcgg atttacaatt gaatttgatc      240
ttgtcacatg catgtggagt cggcgatcct ttcccagagt cagtctcccg cgccatgctg      300
cttctgcgtg caaacgcatt gttaaaaggc ttctccggtg ttcgtacgga attaattgac      360 cagctttttag cgtacttaaa ccaccgtatc caccctgtta tccccaaca aggttcgctg      420 ggggcctccg gcgatttggc ccctcttagc caccttgcgt tggcactgat cggacaaggg      480
```

```
gaagtgttct acgaaggagc acgtatgccc actgctcatg cccttgaaca aaccaatctg    540
cagcccgcag tcctgacatc gaaggaaggg ctggcgttga tcaatgggac tcaggctatg    600
accgcaatgg gcttaatcgc ataccttgaa gccgaaaagt tggcatatca gagcgagcgc    660
atcgcttcat tgactatcga aggattgcaa ggtattattg acgcgtttga cgaagatatt    720
catgccgctc gtggatacca ggaacaaatg gatgtcgctg agcgcattcg ctattatctt    780
tcggattcga agctgacaac cgtacaaggc gagctgcgtg tgcaagatgc ttactccatt    840
cgctgcatcc ctcaagtcca cggagcttct tggcagaccc tggcgtatgt gaaggagaag    900
ttagaaattg agatgaacgc tgctactgat aacccttaa tttttgaaga cggggccaaa    960
attatctcgg gggggaactt tcacgggcaa ccgatcgcgt tgcaatggac cttcttgaaa   1020
gtagctgctg ctgagttggc taatatcagc gagcgccgta ttgagcgtct tgtcaatcca   1080
cagctgaatg accttcctcc ttttctttcg ccgcaaccgg gtttacagtc tggtgccatg   1140
attatgcagt acgccgctgc ctccttggtc tcggaaaaca aaacacttgc gcatcccgcc   1200
tcagtcgact caatcccctc ctcggctaac caggaggatc acgtctccat ggggacgatc   1260
gcttcacgtc atgcttacca gattattgca aacactcgtc gcgtattagc cgtcgaggcc   1320
atttgcgctt tacaagctgt agagtaccgt ggggaagagc actgcgctag ctacacgaaa   1380
caactttacc atgagatgcg taacatcgtg ccatcgattc aggaggaccg tgttttctcg   1440
tacgacatcg agcacttatc cgactggctt aaaaaggaat ccttcttacc taatgaacac   1500
caccaaaagt aatgactaa tgagggcggg ttaactcgc                            1539
```

```
<210> SEQ ID NO 94
<211> LENGTH: 780
<212> TYPE: DNA
<213> ORGANISM: Escherichia coli
<220> FEATURE:
<221> NAME/KEY: misc_feature
<222> LOCATION: (1)..(780)
<223> OTHER INFORMATION: Histidine ABC transporter, histidine-binding
      periplasmic protein precursorHisJ (Escherichia coliO145:H28 str.
      RM12581])

<400> SEQUENCE: 94
```

```
atgaagaaac ttgtccttc attgtctctg gtattagcgt tcagttcagc aactgcagca     60
ttcgctgcta ttccgcaaaa tatccgcatc gggacggatc ccacgtatgc gccattcgag   120
tcaaagaatt cacaaggtga attggtcggg ttcgatattg acctggcgaa agaattgtgt   180
aaacgtatca ataccaatg cacgttcgtg gaaaatccct tggatgcatt aattccgtct   240
ttgaaagcga aaaaatcga tgccatcatg tcatcccttt ctatcacaga aaagcgccag   300
caggagattg ccttcacaga caagttgtac gctgcagaca gccgctggt cgttgcaaag   360 aattctgaca ttcaacctac cgtggaatcg ctgaagggca agcgcgtagg ggtcttgcag   420
ggcactactc aggaaacatt tgggaacgaa cattgggcgc taagggaat tgagatcgtg   480 tcttatcagg gtcaggataa catctacagt gatctgacag ccggacgtat tgacgccgct   540
tttcaggacg aggtggcggc atctgaaggg ttcttaaagc agccagtcgg caaagactac   600
aaatttggtg ggccgagcgt gaaggacgag aaattgtttg gggtaggaac agggatgggc   660
ttgcgtaagg aggacaatga attacgtgaa gctcttaata aagcctttgc tgagatgcgt   720
gcggacggga cttacgaaaa acttgcaaaa aagtatttcg actttgacgt ctacggcggt   780
```

```
<210> SEQ ID NO 95
```

```
<211> LENGTH: 684
<212> TYPE: DNA
<213> ORGANISM: Escherichia coli
<220> FEATURE:
<221> NAME/KEY: misc_feature
<222> LOCATION: (1)..(684)
<223> OTHER INFORMATION: Histidine ABC transporter, permease proteinHisQ
      (Escherichia coliO145:H28 str. RM12581)

<400> SEQUENCE: 95
atgctgtatg gattcagtgg cgttatcttg caggggctc ttgtcacttt agagttagct    60
atctcgtccg ttgtgttagc tgtcattatt ggacttatcg gggctggtgg caaattgagt   120
cagaaccgtt tgagcggcct tatttttgaa gggtacacaa ccttaattcg cggagtccca   180
gacttagtgc tgatgttgct tattttctat ggtttacaga tcgctttgaa tacggttacc   240
gaggcaatgg gggtcggcca aatcgatatc gatcctatgg tggctggaat cattactttg   300
ggcttcattt acggggcata tttcacggag acgttccgcg gagctttcat ggccgtcccg   360
aagggccaca ttgaagcggc aacagctttt ggattcactc gtgggcaagt tttccgtcgc   420
atcatgtttc cagcgatgat gcgctatgcg cttcctggga tcgggaataa ctggcaggta   480
atcttaaaat cgacggcttt agtcagttta ttggggttgg aagatgtcgt aaaagcgacc   540
cagttggctg gaaatcgac ttgggagccc ttttacttcg ctattgtgtg tggcgttatt   600
tacttagttt tcactacagt atcaaacggt gtgttattgt ttttggaacg tcgctacagc   660
gtgggtgtaa agcgtgctga tttg                                         684

<210> SEQ ID NO 96
<211> LENGTH: 771
<212> TYPE: DNA
<213> ORGANISM: Escherichia coli
<220> FEATURE:
<221> NAME/KEY: misc_feature
<222> LOCATION: (1)..(771)
<223> OTHER INFORMATION: hisP (Escherichia coliEPEC C342-62)

<400> SEQUENCE: 96
atgtccgaga acaaattaaa tgttatcgat ttgcataagc gttatggaga gcatgaagtg    60
ttgaaaggag tgtctcttca agcaaacgcg ggggacgtaa tttctatcat cggatcgtct   120
ggttctggta agtcaacctt cctgcgttgt attaacttct tagagaagcc gtctgagggt   180
tctattgtag ttaatgggca gaccatcaat cttgtgcgcg ataaggacgg ccagttgaaa   240
gtggcagaca aaaaccaact tcgtttgctt cgcacccgtc ttaccatggt attccaacac   300
ttcaacctgt ggtcgcacat gacggtactt gagaacgtga tggaagcgcc aattcaggta   360
cttggattga gcaaacaaga agcccgcgaa cgtgcggtga atatttggc caaggtgggt   420 atcgacgagc gtgcgcaggg caaatacccc gttcacttgt ccggggtca acaacagcgt   480 gtcagtattg cccgcgctct ggctatggaa ccagaggtgc ttctgtttga cgagccgacg   540
tcagcttggg acccggaatt agtgggcgaa gtattgcgca tcatgcagca gttagcagaa   600
gaaggcaaga ccatggttgt tgtcacacac gaaatggggt tgcgcgtca tgtctcgact   660 catgtaatct tcttgcatca aggtaaaatc gaggaagaag gagcgccgga acagttattc   720
gggaatcctc aatcccccg tctgcagcag tttcttaaag ggtccttaaa g             771

<210> SEQ ID NO 97
<211> LENGTH: 660
<212> TYPE: DNA
<213> ORGANISM: Clostridium botulinum
<220> FEATURE:
```

<220> FEATURE:
<221> NAME/KEY: misc_feature
<222> LOCATION: (1)..(660)
<223> OTHER INFORMATION: proline reductase (Clostridium botulinum)

<400> SEQUENCE: 97

```
atgtcaatgt ccgctgagca cgctgaggaa ttaaaaaatg aacctgcggt cgtttgttgt      60
cgcactgagg aggggaccat cttgtcagcc gataatttgg aagacccaaa catttttcca     120
gatatggtgg atagcggttt actgaacatt cctggggact gcttaaaagt tggggaagta     180
atcggggcca aactgcttaa gacgattgac tctttgaccc ctcttgccaa ggacatcatt     240
gagggggcca aatccttaga cggagacgta cgcagtaaat cagagattca gatcgaatca     300
ccagaggaga aggcgatcct taaaaacaat ttgaaggcgg agatatattat caaggttgag     360
gacctggaga accctatgca cttcgccaag ttacaagatt cgcttcttat caagctggat     420
gagaaagtgc ttacgcgccg cgaagttgta gacgcgaaac ttacggaaga tgcaccggcg     480
atttcagggg tcactgcatc aatgttggaa ggcttcgagg aaaaggccct ggagattacc     540
caagatagca aggatgtgga cttcaattca gtaattccac tgaacggcaa tcgtgaattc     600
cttcgtttga aaatcgagga aggcacaggc atttatatcg aaattccctt tacccaagtc     660
```

<210> SEQ ID NO 98
<211> LENGTH: 1347
<212> TYPE: DNA
<213> ORGANISM: Escherichia coli
<220> FEATURE:
<221> NAME/KEY: misc_feature
<222> LOCATION: (1)..(1347)
<223> OTHER INFORMATION: ProlineporterII (Escherichia coli PMV-1)

<400> SEQUENCE: 98

```
atgtcagaaa aacttccggc acctcgcgag ggtttatccg gtaaagctat gcgtcgtgtt      60
gtcatgggta gctttgccgg tgcattaatg gaatggtatg atttcttcat ctttgggacg     120
gcggcgggtc ttgttttttgc accgctgttt tatcctgaca gtgatccgtt tattgggttg     180
atcgcgtcgt tcgctacatt tggagttggt tttttgaccc gcccgttagg aggtatcgtg     240
ttcggtcatt ttggtgacaa gatcgggcgt aagattacct taatctggac attggcgatt     300
gtggggtgtt ctacattctt aatcggtttc attccaacgt accaagaaat cggcatttgg     360
gccccttttgg tccttatggt tttgcgcctg attcagggtt ttggcttggg aggagaatac     420
ggagggggcgg cgttaatgac catcgaaagt gccccccgaaa gccgccgtgg tttttcttggg     480
tcattgccac agacggccgc cagcgtcggc atcatgcttg caacgggtat tttcgcgctt     540
tgtaatcatt tccttacttc tgaacagttc ttatcatggg gctggcgtat tcccttctgg     600
ttgtccgcgg ttatgttaat cgtcggactt tttatccgtc tgcatactga agagacgctt     660
gactttcaga agcaaaaaac gactaacaat aaagaaaagt cggttccccc ccttatcgag     720
cttttttaaga aacatccacg caatattttg ttggccttgg ggggccgcct tgcggagtca     780
gtaagcagca acatcattaa tgcattcggc atcgtctata tcagcagtca acttgcactg     840
agccgtgaca tcccccttgac tgggatgctg attgcaagcg ccatcggaat ttttagttgc     900
ccattggtag gctggctttc ggaccgtatc ggacagaaat cattatattt gtcaggcgct     960
ggattttgtg tcctgtttgc cttcccgttt tttctgctgt tggactcgaa gagtacactg    1020
attatctggt gctcaatgat ttgggctat aacttgggtc caactatgat gtttgctgta    1080
caaccaacat tgtttactcg tatgttcggc accaaggtcc gctacacagg cttatcattt    1140
gcttaccagt tctcggctat cttaggcggc ctgtccccac tgattgcatc ctcacttctt    1200
```

```
gcgttggggg cggcaaacc ctggtatgtc gccttgttcc ttttcgctgt gtccgtgtta    1260
tctttcgtct gtgtatggtt aatcgagccc acagacgaac aagagacggc ttcataccgc    1320
tacatccgcg aacaaagtca tgagaac                                        1347
```

<210> SEQ ID NO 99
<211> LENGTH: 1377
<212> TYPE: DNA
<213> ORGANISM: Escherichia coli
<220> FEATURE:
<221> NAME/KEY: misc_feature
<222> LOCATION: (1)..(1377)
<223> OTHER INFORMATION: Escherichia coli PheP

<400> SEQUENCE: 99

```
atgaaaaacg cgtcaaccgt atcggaagat actgcgtcga atcaagagcc gacgcttcat     60
cgcggattac ataaccgtca tattcaactg attgcgttgg gtggcgcaat ggtactggt    120 ctgtttcttg gcattggccc ggcgattcag atggcgggtc cggctgtatt gctgggctac    180
ggcgtcgccg ggatcatcgc tttcctgatt atgcgccagc ttggcgaaat ggtggttgag    240
gagccggtat ccggttcatt tgcccacttt gcctataaat actggggacc gtttgcgggc    300
ttcctctctg gctggaacta ctgggtaatg ttcgtgctgg tgggaatggc agagctgacc    360
gctgcgggca tctatatgca gtactggttc ccggatgttc caacgtggat ttgggctgcc    420
gccttcttta ttatcatcaa cgccgttaac ctggtgaacg tgcgcttata tggcgaaacc    480
gagttctggt ttgcgttgat taaagtgctg gcaatcatcg gtatgatcgg ctttggcctg    540
tggctgctgt tttctggtca cggcggcgag aaagccagta tcgacaacct ctggcgctac    600
ggtggtttct tcgccaccgg ctggaatggg ctgattttgt cgctggcggt aattatgttc    660
tccttcggcg gtctggagct gattgggatt actgccgctg aagcgcgcga tccggaaaaa    720
agcattccaa aagcggtaaa tcaggtggtg tatcgcatcc tgctgttta catcggttca    780 ctggtggttt tactggcgct ctatccgtgg gtggaagtga aatccaacag tagcccgttt    840
gtgatgattt tccataatct cgacagcaac gtggtagctt ctgcgctgaa cttcgtcatt    900
ctggtagcat cgctgtcagt gtataacagc ggggtttact ctaacagccg catgctgttt    960
ggcctttctg tgcagggtaa tgcgccgaag ttttgactc gcgtcagccg tcgcggtgtg   1020
ccgattaact cgctgatgct ttccggagcg atcacttcgc tggtggtgtt aatcaactat   1080
ctgctgccgc aaaaagcgtt tggtctgctg atggcgctgg tggtagcaac gctgctgttg   1140
aactggatta tgatctgtct ggcgcatctg cgttttcgtg cagcgatgcg acgtcagggg   1200
cgtgaaacac agtttaaggc gctgctctat ccgttcggca actatctctg cattgccttc   1260
ctcggcatga ttttgctgct gatgtgcacg atggatgata tgcgcttgtc agcgatcctg   1320
ctgccggtgt ggattgtatt cctgtttatg gcatttaaaa cgctgcgtcg gaaataa     1377
```

<210> SEQ ID NO 100
<211> LENGTH: 1704
<212> TYPE: DNA
<213> ORGANISM: Anabaena variabilis PAL1
<220> FEATURE:
<221> NAME/KEY: misc_feature
<222> LOCATION: (1)..(1704)
<223> OTHER INFORMATION: Anabaena variabilis PAL1

<400> SEQUENCE: 100

```
atgaaaacac tatcacaggc ccaatctaaa acttcttcac agcaattcag ctttaccggg    60
```

-continued

```
aactcgtctg cgaatgtaat tatcggcaat caaaagctga ccattaatga tgtagctcgc    120
gttgcccgga atggcacttt ggtgtcactg acgaacaata ccgacattct gcaaggtatt    180
caagctagct gcgattatat caataacgcc gttgaatctg gcgagccaat ctacggggta    240
acaagcggtt ttggtgggat ggcgaacgtt gccattagcc gtgaacaggc gagcgaactt    300
cagaccaacc tcgtttggtt cctaaagaca ggagctggta ataagttacc tctggctgac    360
gtaagagccg cgatgctgct tcgcgctaat agtcacatgc gcggcgccag tggtatccgt    420
cttgagctta tcaagaggat ggaaatcttc ctcaacgcgg gtgtcacacc atatgtttat    480
gagtttggta gtatcggagc cagtggtgat cttgttcccc tgagttatat tacgggttca    540
ttgattggtt tagacccgtc ctttaaagtg gattttaacg ggaaagaaat ggacgccccg    600
accgctttac gacagcttaa tctgagccca cttactttgc tccctaaaga aggtcttgcc    660
atgatgaatg gcacctctgt gatgactgga attgccgcga attgtgtgta tgacacgcag    720
atcctaacgg ccattgccat gggtgttcac gcgttggaca ttcaagccct gaatggtaca    780
aaccagtcgt ttcatccgtt tatccataat tcaaaacccc atccgggaca gctttgggct    840
gctgatcaga tgatctcact cctggccaat agtcaactgg ttcgggacga gctcgacggc    900
aaacatgatt atcgcgatca tgagctcatc caggaccggt attcacttcg ttgtctccca    960
caatacctgg ggcctatcgt tgatggtata tctcaaattg cgaagcaaat tgaaattgag   1020
atcaatagcg taaccgacaa cccgcttatc gatgttgata tcaggcctc ttatcacggt   1080 ggcaattttc tgggccagta tgttggtatg gggatggatc acctgcggta ctatattggg   1140
cttctggcta acatcttga tgtgcagatt gccttattag cttcaccaga atttcaaat    1200 ggactgccgc catcattgct cggtaacaga gaaaggaaag taaatatggg ccttaagggc   1260
cttcagatat gtggtaactc aatcatgccc ctcctgacct tttatgggaa ctcaattgct   1320
gatcgttttc cgacacatgc tgaacagttt aaccaaaaca ttaactcaca gggctataca   1380
tccgcgacgt tagcgcgtcg gtccgtggat atcttccaga attatgttgc tatcgctctg   1440
atgttcggcg tacaggccgt tgatttgcgc acttataaaa aaaccggtca ctacgatgct   1500
cgggcttgcc tgtcgcctgc caccgagcgg ctttatagcg ccgtacgtca tgttgtgggt   1560
cagaaaccga cgtcggaccg cccctatatt tggaatgata atgaacaagg gctggatgaa   1620
cacatcgccc ggatatctgc cgatattgcc gccggaggtg tcatcgtcca ggcggtacaa   1680
gacatacttc cttgcctgca ttaa                                          1704
```

<210> SEQ ID NO 101
<211> LENGTH: 1599
<212> TYPE: DNA
<213> ORGANISM: Photorhabdus luminescens PAL3
<220> FEATURE:
<221> NAME/KEY: misc_feature
<222> LOCATION: (1)..(1599)
<223> OTHER INFORMATION: Photorhabdus luminescens PAL3

<400> SEQUENCE: 101

```
atgaaagcta aagatgttca gccaaccatt attattaata aaaatggcct tatctctttg     60
gaagatatct atgacattgc gataaaacaa aaaaagtag aaatatcaac ggagatcact    120
gaacttttga cgcatggtcg tgaaaaatta gaggaaaaat taaattcagg agaggttata    180
tatggaatca atacaggatt tggagggaat gccaatttag ttgtgccatt tgagaaaatc    240
gcagagcatc agcaaaatct gttaactttt cttttctgctg gtactgggga ctatatgtcc    300
aaaccttgta ttaaagcgtc acaatttact atgttacttt ctgtttgcaa aggttggtct    360
```

-continued

```
gcaaccagac caattgtcgc tcaagcaatt gttgatcata ttaatcatga cattgttcct      420
ctggttcctc gctatggctc agtgggtgca agcggtgatt taattccttt atcttatatt      480
gcacgagcat tatgtggtat cggcaaagtt tattatatgg gcgcagaaat tgacgctgct      540
gaagcaatta aacgtgcagg gttgacacca ttatcgttaa aagccaaaga aggtcttgct      600
ctgattaacg gcacccgggt aatgtcagga atcagtgcaa tcaccgtcat taaactggaa      660
aaactattta aagcctcaat ttctgcgatt gcccttgctg ttgaagcatt acttgcatct      720
catgaacatt atgatgcccg gattcaacaa gtaaaaaatc atcctggtca aaacgcggtg      780
gcaagtgcat tgcgtaattt attggcaggt tcaacgcagg ttaatctatt atctggggtt      840
aaagaacaag ccaataaagc ttgtcgtcat caagaaatta cccaactaaa tgatacctta      900
caggaagttt attcaattcg ctgtgcacca caagtattag gtatagtgcc agaatcttta      960
gctaccgctc ggaaaatatt ggaacgggaa gttatctcag ctaatgataa tccattgata     1020
gatccagaaa atggcgatgt tctacacggt ggaaatttta tggggcaata tgtcgcccga     1080
acaatggatg cattaaaact ggatattgct ttaattgcca atcatcttca cgccattgtg     1140
gctcttatga tggataaccg tttctctcgt ggattaccta attcactgag tccgacaccc     1200
ggcatgtatc aaggtttaa aggcgtccaa ctttctcaaa ccgctttagt tgctgcaatt     1260
cgccatgatt gtgctgcatc aggtattcat accctcgcca cagaacaata caatcaagat     1320
attgtcagtt taggtctgca tgccgctcaa gatgttttag agatggagca gaaattacgc     1380
aatattgttt caatgacaat tctggtagtt tgtcaggcca ttcatcttcg cggcaatatt     1440
agtgaaattg cgcctgaaac tgctaaattt taccatgcag tacgcgaaat cagttctcct     1500
ttgatcactg atcgtgcgtt ggatgaagat ataatccgca ttgcggatgc aattattaat     1560
gatcaacttc ctctgccaga atcatgctg gaagaataa                             1599
```

<210> SEQ ID NO 102
<211> LENGTH: 819
<212> TYPE: DNA
<213> ORGANISM: Legionella pneumophila phhA
<220> FEATURE:
<221> NAME/KEY: misc_feature
<222> LOCATION: (1)..(819)
<223> OTHER INFORMATION: Legionella pneumophila phhA

<400> SEQUENCE: 102

```
atggagttta gtagccggta tgtcgcacat gtccctgatg ctcagggttt agtcgattat     60
tcggcacaag aaaatagaat ttggaatatt ttatttgaga ggcaactcaa gttattgcca    120
ggaagagctt gtgatgaatt tctgtctgga ttacagactt taggacttaa ctcctcgact    180
attccacaac ttccagaagt aagtgagcga ttaaaggcca aaacgggatg gcaagtagcg    240
ccagttgctg ctttaatttc agccagggaa ttttttgaat tattagcaga aaaatatttt    300
cctgcggcga cttttattcg aagtgaagaa gaattggatt atgttcaaga acctgatatt    360
tttcatgagc tttttggtca ttgtcctatg ttaaccgata gagtctatgc tgaatttgtc    420
catgattacg catgtaaggt attaactttt cctgaacagg attggccttt attgcaaaga    480
atgttttggt ttactgtaga gtttggattg attaaaacgc ctaaagggct tagagcatac    540
ggcgggggaa ttttatcttc tatcagtgaa acggtatatt gtgtggaaag tgatattcct    600
gtgcgaattt tatttgatcc agtggtggct tttcgaatgc cttatcggat tgaccagcta    660
caacctgttt atttcgttat tgacagctat caaaatttat atgatttcgt gctttctgac    720
```

| | |
|---|---|
| atgggtaaat tcatggatcg tgcgcgagag ttaggtgaat ttccaccgta ttttgatgtg | 780 |
| gatccggata atccaaatat tcatataagg gcttgttaa | 819 |

<210> SEQ ID NO 103
<211> LENGTH: 717
<212> TYPE: DNA
<213> ORGANISM: Escherichia coli hisM
<220> FEATURE:
<221> NAME/KEY: misc_feature
<222> LOCATION: (1)..(717)
<223> OTHER INFORMATION: Escherichia coli hisM

<400> SEQUENCE: 103

| | |
|---|---|
| gtgatcgaaa tcttacatga atactggaaa ccgctgctgt ggaccgacgg ttatcgcttt | 60 |
| actggtgtgg cgatcactct gtggctgctt attttgtcgg tagtgatagg cggagtcctg | 120 |
| gcgctgtttc tggcgattgg tcgtgtctcc agtaataaat acatccagtt tccaatctgg | 180 |
| ttatttacct atattttcg cggtacgccg ctgtatgttc agttgctggt gttctattcc | 240 |
| ggcatgtaca cgcttgagat tgttaaggga accgaattcc ttaacgcttt cttccgcagt | 300 |
| ggcctgaact gtaccgtgct ggcgctgacg cttaacacct gcgcttacac taccgagatt | 360 |
| tttgctgggg caatccgttc ggttccgcat ggggaaattg aagccgccag agcctatggc | 420 |
| ttctcgactt ttaaaatgta tcgctgcatt attttgcctt ctgcgctgcg tattgcgtta | 480 |
| ccggcataca gcaacgaagt gatcctgatg ctgcactcta ctgcgttggc atttactgcc | 540 |
| acggtgccgg atctgctgaa atagcccgc gatattaacg ccgccacgta tcaacctttt | 600 |
| accgccttcg gcattgccgc ggtgctctat ttaatcatct cttatgtcct gatcagcctc | 660 |
| tttcgcagag cggaaaaacg ctggttgcag catgtgaaac cttcttcaac gcactga | 717 |

<210> SEQ ID NO 104
<211> LENGTH: 967
<212> TYPE: DNA
<213> ORGANISM: Unknown
<220> FEATURE:
<223> OTHER INFORMATION: clbA (wild-type)

<400> SEQUENCE: 104

| | |
|---|---|
| caaatatcac ataatcttaa catatcaata aacacagtaa agtttcatgt gaaaaacatc | 60 |
| aaacataaaa tacaagctcg gaatacgaat cacgctatac acattgctaa caggaatgag | 120 |
| attatctaaa tgaggattga tatattaatt ggacatacta gttttttca tcaaaccagt | 180 |
| agagataact tccttcacta tctcaatgag gaagaaataa aacgctatga tcagtttcat | 240 |
| tttgtgagtg ataaagaact ctatatttta gccgtatcc tgctcaaaac agcactaaaa | 300 |
| agatatcaac ctgatgtctc attacaatca tggcaattta gtacgtgcaa atatggcaaa | 360 |
| ccatttatag tttttcctca gttggcaaaa aagatttttt ttaacctttc ccatactata | 420 |
| gatacagtag ccgttgctat tagttctcac tgcgagcttg gtgtcgatat tgaacaaata | 480 |
| agagatttag acaactctta tctgaatatc agtcagcatt tttttactcc acaggaagct | 540 |
| actaacatag tttcacttcc tcgttatgaa ggtcaattac tttttggaa aatgtggacg | 600 |
| ctcaaagaag cttacatcaa atatcgaggt aaaggcctat ctttaggact ggattgtatt | 660 |
| gaatttcatt taacaaataa aaaactaact tcaaaatata gaggttcacc tgtttatttc | 720 |
| tctcaatgga aaatatgtaa ctcatttctc gcattagcct ctccactcat cacccctaaa | 780 |
| ataactattg agctatttcc tatgcagtcc caacttatc accacgacta tcagctaatt | 840 |
| cattcgtcaa atgggcagaa ttgaatcgcc acggataatc tagacacttc tgagccgtcg | 900 |

```
ataatattga ttttcatatt ccgtcggtgg tgtaagtatc ccgcataatc gtgccattca    960
catttag                                                              967

<210> SEQ ID NO 105
<211> LENGTH: 424
<212> TYPE: DNA
<213> ORGANISM: Unknown
<220> FEATURE:
<223> OTHER INFORMATION: clbA knock-out

<400> SEQUENCE: 105 ggatggggggg aaacatggat aagttcaaag aaaaaaaccc gttatctctg cgtgaaagac    60
aagtattgcg catgctggca caaggtgatg agtactctca aatatcacat aatcttaaca   120
tatcaataaa cacagtaaag tttcatgtga aaaacatcaa acataaaata caagctcgga   180
atacgaatca cgctatacac attgctaaca ggaatgagat tatctaaatg aggattgatg   240
tgtaggctgg agctgcttcg aagttcctat actttctaga gaataggaac ttcggaatag   300
gaacttcgga ataggaacta aggaggatat tcatatgtcg tcaaatgggc agaattgaat   360
cgccacggat aatctagaca cttctgagcc gtcgataata ttgattttca tattccgtcg   420
gtgg                                                                 424

<210> SEQ ID NO 106
<211> LENGTH: 1921
<212> TYPE: DNA
<213> ORGANISM: Artificial Sequence
<220> FEATURE:
<223> OTHER INFORMATION: Synthetic: Prp promoter

<400> SEQUENCE: 106
ttacccgtct ggattttcag tacgcgcttt taaacgacgc cacagcgtgg tacggctgat    60
ccccaaataa cgtgcggcgg cgcgcttatc gccattaaag cgtgcgagca cctcctgcaa   120
tggaagcgct tctgctgacg agggcgtgat ttctgctgtg gtccccacca gttcaggtaa   180
taattgccgc ataaattgtc tgtccagtgt tggtgcggga tcgacgctta aaaaaagcgc   240
caggcgttcc atcatattcc gcagttcgcg aatattaccg ggccaatgat agttcagtag   300
aagcggctga cactgcgtca gcccatgacg caccgattcg gtaaaaggga tctccatcgc   360
ggccagcgat tgttttaaaa agttttccgc cagaggcaga atatcaggct gtcgctcgcg   420
caagggggga agcggcagac gcagaatgct caaacggtaa aacagatcgg tacgaaaacg   480
tccttgcgtt atctcccgat ccagatcgca atgcgtggcg ctgatcaccc ggacatctac   540
cgggatcggc tgatgcccgc aacgcgggt gacggctttt tcctccagta cgcgtagaag   600
gcgggtttgt aacggcagcg gcatttcgcc aatttcgtca agaaacagcg tgccgccgtg   660
ggcgacctca aacagccccg cacgtccacc tcgtcttgag ccggtaaacg ctccctcctc   720
atagccaaac agttcagcct ccagcaacga ctcggtaatc gcgccgcaat taacggcgac   780
aaagggcgga gaaggcttgt tctgacggtg gggctgacgg ttaaacaacg cctgatgaat   840
cgcttgcgcc gccagctctt tcccggtccc tgtttccccc tgaatcagca ctgccgcgcg   900
ggaacgggca tagagtgtaa tcgtatgcg aacctgctcc atttgtggtg aatcgccgag   960
gatatcgctc agcgcataac gggtctgtaa tcccttgctg gaggtatgct ggctatactg  1020
acgccgtgtc aggcgggtca tatccagcgc atcatggaaa gcctgacgta cggtggccgc  1080
tgaataaata aagatggcgg tcattcctgc ctcttccgcc aggtcggtaa ttagtcctgc  1140
```

```
cccaattaca gcctcaatgc cgttagcttt gagctcgtta atttgcccgc gagcatcctc    1200
ttcagtgata tagcttcgct gttcaagacg gaggtgaaac gttttctgaa aggcgaccag    1260
agccggaatg gtctcctgat aggtcacgat tcccattgag gaagtcagct ttcccgcttt    1320
tgccagagcc tgtaatacat cgaatccgct gggtttgatg aggatgacag gtaccgacag    1380
tcggcttttt aaataagcgc cgttggaacc tgccgcgata atcgcgtcgc agcgttcggt    1440
tgccagtttt ttgcgaatgt aggctactgc cttttcaaaa ccgagctgaa taggcgtgat    1500
cgtcgccaga tgatcaaact ccaggctgat atcccgaaat agttcgaaca ggcgcgttac    1560
cgagaccgtc cagatcaccg gtttatcgct attatcgcgc gaagcgctat gcacagtaac    1620
catcgtcgta gattcatgtt taaggaacga attcttgttt tatagatgtt tcgttaatgt    1680
tgcaatgaaa cacaggcctc cgtttcatga aacgttagct gactcgtttt tcttgtgact    1740
cgtctgtcag tattaaaaaa gattttcat ttaactgatt gttttaaat tgaatttat    1800 ttaatggttt ctcggttttt gggtctggca tatcccttgc tttaatgagt gcatcttaat    1860
taacaattca ataacaagag ggctgaatag taatttcaac aaaataacga gcattcgaat    1920
g                                                                   1921
```

<210> SEQ ID NO 107
<211> LENGTH: 864
<212> TYPE: DNA
<213> ORGANISM: Salmonella enterica subsp. enterica serovar Typhimurium LT2
<220> FEATURE:
<221> NAME/KEY: misc_feature
<222> LOCATION: (1)..(864)
<223> OTHER INFORMATION: Tsx - Salmonella enterica subsp. enterica serovar Typhimurium LT2 (STM0413)

<400> SEQUENCE: 107

```
atgaaaaaaa ctttactcgc agtcagcgca gcgctggcgc tcacctcatc ttttactgct     60
aacgcagcag aaaatgatca gccgcagtat ttgtccgact ggtggcacca gagcgtaaac    120
gtggtaggca gctaccatac ccgtttctcg ccgaaattga caacgacgt ctatctggaa     180 tatgaagcat ttgccaaaaa agactggttt gatttctacg gctatatcga tattcccaaa    240
acctttgatt ggggtaacgg caacgataaa ggtatctggt ccgacggttc tccgctgttc    300
atggaaatcg aaccgcgttt ctcaattgat aagctgaccg gcgcagacct gagcttcggc    360
ccgtttaaag agtggtattt cgccaacaac tacatctacg atatgggcga taacaaagcc    420
agccgccaga gcacgtggta tatgggtctg gggaccgata tcgacaccgg cctgccgatg    480
ggtctgtcgc tgaacgtgta tgcgaaatat cagtggcaaa actacggcgc gtccaatgaa    540
aacgaatggg acggctaccg tttcaaagtg aaatacttcg tccccatcac cgatctgtgg    600
ggcggtaaac tgagctatat cggctttacc aactttgact ggggatctga tttaggcgac    660
gatccgaacc gtaccagcaa ctccatcgct tccagccata tcctggcgct gaactacgat    720
cactggcact actcggtcgt tgcgcgttac ttcataacg gcgacagtg gcagaatggc    780 gcaaaactga actggggcga cggcgatttc agcgcgaaat ctaccggctg ggcggctac    840 ctggtcgtgg gttacaactt ctaa                                           864
```

<210> SEQ ID NO 108
<211> LENGTH: 885
<212> TYPE: DNA
<213> ORGANISM: Escherichia coli
<220> FEATURE:
<221> NAME/KEY: misc_feature

```
<222> LOCATION: (1)..(885)
<223> OTHER INFORMATION: Tsx - Escherichia coli K-12 MG1655 (b0411)

<400> SEQUENCE: 108
atgaaaaaaa cattactggc agccggtgcg gtactggcgc tctcttcgtc ttttactgtc      60
aacgcagctg aaaacgacaa accgcagtat ctttccgact ggtggcacca gagcgttaac     120
gttgtcggaa gctatcacac ccgtttcgga ccgcagatcc gcaacgatac ctaccttgag     180
tacgaagcat tcgctaaaaa agactggttc gacttctatg ttatgcgga tgcgccggta      240 ttcttcggcg gtaactccga tgctaaaggt atctggaacc acggttctcc gctgtttatg     300
gaaatcgaac cacgtttctc catcgacaag ctgaccaata ctgaccttag cttcggtccg     360
ttcaaagagt ggtacttcgc gaacaactac atttacgaca tgggtcgtaa taaagatggt     420
cgccagagca cctggtacat gggtctgggt accgatatcg acactggcct gccgatgagc     480
ctgtccatga acgtctatgc gaaataccag tggcagaact atggcgcagc gaacgaaaac     540
gagtgggacg gttaccgttt caaaattaaa tactttgtgc cgattaccga tctgtggggc     600
ggtcagctga gctacatcgg cttcaccaac ttcgactggg gttccgattt aggggatgac     660
agcggtaacg caatcaacgg tattaagacc cgtactaata actctatcgc ttccagccat     720
attctggctc tgaactacga tcactggcac tactctgtcg tagctcgtta ctggcacgac     780
ggtggtcagt ggaacgacga tgcagaactg aacttcggca acggcaactt caacgttcgc     840
tctaccggct ggggtggtta cctggtagta ggttacaact tctga                     885

<210> SEQ ID NO 109
<211> LENGTH: 1221
<212> TYPE: DNA
<213> ORGANISM: Bacillus halodurans
<220> FEATURE:
<221> NAME/KEY: misc_feature
<222> LOCATION: (1)..(1221)
<223> OTHER INFORMATION: BH1446 - Bacillus halodurans (BAB05165)

<400> SEQUENCE: 109
atgaatattt tgtggggttt attaggaatc gtcgttgttt ttctaatcgc ttttgcattt      60
tccacaaatc gtcgtgcaat aaaccacga acgatattag tggtctcgc gattcagcta      120 ttatttgcga ttattgtatt aaaaattcca gctggacaag cgttacttga gagcttaacc     180
aatgtagttt tgaacattat tagttatgcg aatgaaggga tcgacttcgt atttggtgga     240
tttttcgaag aaggttcagg cgtaggcttc gttttttgcaa ttaacgtttt gtctgtcgtc     300
attttcttct cagcactaat ctcgatcctt tattatttag ggatcatgca atttgtcatt     360
aaaattatcg gtggtgcgct gtcctggcta ctcggaacat caaaggcaga atcaatgtca     420
gcagcagcta acatttttcgt tgggcaaacg gaagcgccac tcgttgttaa gccatactta     480
ccaaaaatga cgcaatccga gctctttgcg gttatgaccg ggggacttgc ttctgttgct     540
ggttctgttt taatcggtta ttctcttttta ggagtaccgc tacaatatttt attagcggca    600 agctttatgg ctgctcctgc gggcttgatt atggcgaaaa tgatcatgcc tgaaacggag     660
aaaacaaccg atgcagaaga tgactttaag ctcgcaaagg atgaagagtc cacgaacttg     720
attgacgcgg ccgccaatgg ggcgagcact gggttaatgc tcgttctaaa tattgcggcg     780
atgttactag cgttcgttgc attgattgca ttaattaatg gaattcttgg atggatcgga     840
ggattgtttg gggcgtcgca attgtcttta gagttaatcc tcggatacgt gtttgctccg     900
cttgcgtttg tcatcggaat tccttgggct gaagcgcttc aagcgggaag ctacatcgga     960
```

| | |
|---|---|
| cagaaactcg tagtgaacga atttgttgcc tacttaagct ttgcaccaga aattgaaaac | 1020 |
| ctttcagata aagcggtgat ggtgattagt tttgcccttt gcggatttgc taacttctca | 1080 |
| tccctcggaa tccttttagg aggattgggt aagcttgctc cgagccgtcg ccctgatatt | 1140 |
| gcccgtctcg gattacgcgc gatccttgca ggtacgctag cttctttact cagcgcctcc | 1200 |
| attgcgggaa tgttattcta a | 1221 |

<210> SEQ ID NO 110
<211> LENGTH: 1182
<212> TYPE: DNA
<213> ORGANISM: Bacillus subtilis
<220> FEATURE:
<221> NAME/KEY: misc_feature
<222> LOCATION: (1)..(1182)
<223> OTHER INFORMATION: nupC Bacillus subtilis subsp. subtilis 168
      (BSU39410; CAA57663)

<400> SEQUENCE: 110

| | |
|---|---|
| atgaagtatt tgattgggat tatcggttta atcgtgtttt taggcctcgc gtggatcgcg | 60 |
| agcagcggca aaaaagaat taagatccgc ccaattgttg ttatgctcat tttgcaattt | 120 |
| attcttggct acattctcct caataccgga atagggaatt tcctcgtggg aggatttgca | 180 |
| aaaggattcg gttacctgct tgaatacgcg gcagagggaa ttaactttgt gtttggcggc | 240 |
| ttggtgaatg cggaccaaac gacattcttt atgaatgttc tcttgccaat cgtgtttatt | 300 |
| tccgctctga tcgggattct gcaaaagtgg aaagtcctcc cgtttatcat tagatatatc | 360 |
| ggccttgccc tcagcaaggt aaacggtatg ggaagattgg aatcgtataa cgcagtggct | 420 |
| tctgcgattt tagggcagtc agaagtattt atctccttga agaaagaact cggtcttta | 480 |
| aatcagcagc gcttgtacac gctttgcgca tctgcgatgt caactgtatc aatgtcgatt | 540 |
| gtcggtgcgt atatgacaat gctgaaaccg gaatatgttg taacagcgct tgttttgaac | 600 |
| ttatttggcg gtttcattat cgcttctatt atcaatccgt acgaggttgc aaaagaagag | 660 |
| gatatgcttc gtgttgagga agaagaaaaa caatccttct tcgaagtgct cggagaatac | 720 |
| attcttgacg gtttcaaagt agcggttgtc gtcgctgcga tgctgattgg atttgtcgcg | 780 |
| attattgcat tgatcaatgg catttttaat gcagtattcg gtatttcgtt ccaaggcatt | 840 |
| cttggatatg tgtttgctcc attcgctttt cttgtcggta tcccatggaa tgaagctgtt | 900 |
| aatgcgggaa gcattatggc aacaaaaatg gtatcgaatg aatttgtcgc catgacgtcg | 960 |
| cttacgcaaa acggtttcca tttcagcggc cgtacaacag cgatcgtatc ggtattcctt | 1020 |
| gtgtcatttg cgaacttctc ctcaatcgga atcattgccg gtgccgtaaa aggactgaat | 1080 |
| gaaaagcaag gaaatgtcgt cgctcgtttc ggcttgaaat tattatacgg tgctacgctt | 1140 |
| gtcagctttt tatcagcagc aattgtgggc ttgatttact ga | 1182 |

<210> SEQ ID NO 111
<211> LENGTH: 1215
<212> TYPE: DNA
<213> ORGANISM: Bacillus subtilis
<220> FEATURE:
<221> NAME/KEY: misc_feature
<222> LOCATION: (1)..(1215)
<223> OTHER INFORMATION: yutK - Bacillus subtilis subsp. subtilis 168:
      BSU32180

<400> SEQUENCE: 111

| | |
|---|---|
| atgaatgttc tgtgggggct gctgggcgca gttgcgatca ttgctatcgc gtttttattt | 60 |
| tcagaaaaga aaagcaatat taagataaga accgtcatcg ttggtttatg cacacaggtg | 120 |

-continued

```
gcgtttggat acatcgtgtt gaaatgggaa gcgggacgcg ctgttttttt atggttttca    180
agccgtgtac agcttctgat tgactatgcg aatgaaggca tcagttttat ttttggaccg    240
cttctaaagg tcggagacag tccggcattt gcattaagtg tactgcccgt tatcattttc    300
ttctcagcac tgattgcagt tttatatcat ttgaaaatca tgcagctcgt tttccgtgtc    360
attggcggcg gattgtcgaa gctccttgga acaagcaaaa cggaatctct ggcggctgct    420
gccaatattt ttgtaggaca atcagaatct ccgttagtga tcaaacccct gattgccggg    480
ctgacgcgct ctgagttgtt tacgattatg acgagcggtc tatcggcagt tgcgggatct    540
accttgtttg ggtacgcgct tctcggtatt ccgattgagt acttgctggc ggccagcttt    600
atggctgctc cagctggact agtctttggt aaattgatta tacccgaaac ggaaaaaacg    660
caaaccgtaa aaagcgattt caaaatggat gaaggcgaag cgcagccaa tgtcattgac    720 gcagctgcaa agggagcgtc aacaggactg caaattgcgt aaatgttgg ggcgatgctg    780 cttgcgtttg ttgcgttaat cgctgtagta acggtattc tcggcggggc tttcggcttg    840
ttcggtttaa aaggcgtaac attagaatcc attctcggct atgtgttttc tcctatcgcc    900
tttttgattg gcgtgccttg gcatgaagca ttgcaggcgg gaagctatat cggccagaaa    960
ttggtgctga atgagtttgt cgcttattct aacttcggtt cgcacatcgg cgagttttct   1020
aagaaaactg ctaccattat cagtttcgcg ttatgcggat tcgccaattt ttcatcaatt   1080
gcgattatgc ttggtacgct tggcggttta gcgcccagcc gccgttcaga tatcgcacgt   1140
ctcggcctga aggctgttct tgcaggaaca ttagccaatc tgctcagcgc agccattgcc   1200
ggcatgttta tataa                                                    1215
```

<210> SEQ ID NO 112
<211> LENGTH: 1194
<212> TYPE: DNA
<213> ORGANISM: Bacillus subtilis
<220> FEATURE:
<221> NAME/KEY: misc_feature
<222> LOCATION: (1)..(1194)
<223> OTHER INFORMATION: yxjA - Bacillus subtilis subsp. spizizenii W23
      (BSUW23_19355)

<400> SEQUENCE: 112

```
atgtactttt tattaaacct tgtcggtctc attgtgatta tggcagttgt gttcctatgc     60
tccccgcaga aaaagaaaat ccagtggcgt ccgatcatta cgttaattgt tctggaattg    120
ctgattactt ggtttatgct gggaacaaag gtcgggagct gggccatcgg taaaattggt    180
gatttcttca cttggctgat tgcttgcgcc agtgacggta tcgcgtttgc cttcccgtca    240
gtcatggcga atgaaacagt agactttttc tttagtgcac ttcttccaat tatctttatc    300
gtcacattct ttgatatttt aacatatttc ggcattttgc cttggctgat tgataaaatc    360
ggatgggtga tttcaaaggc ttcccgcttg ccgaaattag aaagcttttt ctctattcaa    420
atgatgttct tgggaaatac tgaagcactt gcggtcatcc gccagcagct tacgtatta    480 aataacaacc gcttgcttac atttggctta atgagcatga gcagcatcag cggctccatt    540
attggatctt acctgtcaat ggtgccggcg acatacgtgt ttacagcgat tccattgaac    600
tgcttaaacg cgctgattat tgcaaacctg ctgaaccctg ttcatgtgcc ggaggatgaa    660
gatatcatct atacaccgcc taagaagag aagaaagact ttttctctac gatttctaac    720
agtatgcttg tcggcatgaa catggttatc gttattttgg caatggtgat cggatatgta    780
gcattaacgt ctgcagtcaa tggcattctt ggtgtttcg tacacggcct gaccatccag    840
```

```
acaattttg cttatctctt cagtccgttc gcattcctgc ttggtctgcc agtacatgat    900
gcaatgtatg tcgctcagct aatgggaatg aaattggcaa cgaacgagtt tgttgcgatg    960
cttgacttga aaacaatct tacaacactt ccgcctcaca cagttgcggt ggcgacgaca   1020
ttcctgacgt catttgccaa cttcagtact gtcggcatga tttacggaac gtacaactcg   1080
atccttgacg gcgaaaagtc aacggtcatc gggaaaaacg tgtggaaatt gctcgtcagc   1140
ggcattgcgg tatctttact aagtgctgcg attgtcggcc tgtttgtgtg gtag         1194
```

<210> SEQ ID NO 113
<211> LENGTH: 1281
<212> TYPE: DNA
<213> ORGANISM: Caulobacter crescentus CB15
<220> FEATURE:
<221> NAME/KEY: misc_feature
<222> LOCATION: (1)..(1281)
<223> OTHER INFORMATION: ccCNT (CC2089) - Caulobacter crescentus CB15
      (AAK24060)

<400> SEQUENCE: 113

```
atgttccgtc ccgagaacgt tcaggccctc gcgggtctgg cgctcaccct gggcctgtgc     60
tggctcgttt ccgagaatcg caagcggttc ccctgggggcc tggccatcgg cgcggtcgtc    120
attcaggtcc tgctggtcct ggtcctgttc ggcctgccgc aagcccagca gatgctgcgc    180
ggcgtcaacg gcgcggtgga gggccttgcc gcctcgaccc aggccggcac cgccttcgtg    240
ttcggctttc tggccggcgg cgaccagccc tatccggtca gcaatccggg cgcgggcttc    300
atcttcgcct tccgcgtgct gccggtgatc ctggtggtct cgcccctgtc ggcgctgctg    360
tggcactgga agattctcaa gtggctggct cagggcttcg gctttgtgtt ccagaagacg    420
ctgggcctgc gcgccccgcc ggccctggcc accgccgcga ccatcttcat gggtcaggtc    480
gaggggccga tcttcatccg cgcctatctc gacaagctga gccgctcgga actcttcatg    540
ctgatcgcgg tcggcatggc ctgcgtgtcg ggctcgacca tggtcgccta cgccaccatc    600
ctggccgacg tcctgcccaa cgccgccgcc cacgtgctga ccgcctcgat catctcggct    660
ccggccggcg tgctgctggc ccggatcatt gtgccgtccg atccgatgga gaagagcgcc    720
gatcttgatc tgtcgaccga ggacaagacc tatggcagct cgatcgacgc cgtgatgaag    780
ggcaccaccg acggcctgca gatcgcgctg aacgtcggcg ccaccctgat cgtcttcgtg    840
gccctggcca ccatggtcga caaggtcctg ggcgccttcc cgccggtggg cggcgagccg    900
ctgagcatcg cgcgcggcct gggcgtggtc ttcgcgccgc tggcctggtc gatgggcatc    960
ccgtggaaag aagcgggcac ggccggcggt ctgctgggcg tgaagctgat cctgaccgag   1020
ttcaccgcct tcatccagct gtccaaggtg gcgaagccc tgctggacga acgcacccgg   1080
atgatcatga cctacgctct gtgcggtttc gccaatatcg gctcggtcgg catgaacgtc   1140
gccggcttct cggtgctggt gccccagcgc cggcaggaag tgctgggcct ggtctggaag   1200
gcgatgatgg ccggcttcct ggccacctgc ctgaccgcct cgctggtcgg cctgatgccg   1260
cgaagcctgt ttgggctgta a                                              1281
```

<210> SEQ ID NO 114
<211> LENGTH: 1251
<212> TYPE: DNA
<213> ORGANISM: Escherichia coli
<220> FEATURE:
<221> NAME/KEY: misc_feature
<222> LOCATION: (1)..(1251)
<223> OTHER INFORMATION: yeiJ - Escherichia coli K-12 W3110 (AAC75222;

```
                                          JW2148)

<400> SEQUENCE: 114
atggatgtca tgagaagtgt tctgggaatg gtggtattgc tgacgattgc gtttttactg      60
tcagtaaaca agaagaagat cagcctgcgt accgttggcg cggcgttagt gttacaggtc     120
gtgattggcg gcattatgct ttggttaccg ccagggcgtt gggtcgctga aaaagtcgct     180
tttggcgtgc ataaagtgat ggcgtacagc gacgcgggta gcgcatttat cttcggttct     240
ctggtcggac cgaaaatgga taccttattt gatggtgcag gatttatctt tggtttcagg     300
gtgttaccgg caattatctt cgtcaccgcg ctggtgagta ttctctacta catcggtgtg     360
atggggattt taattcgaat tctcggcggt atcttccaga aagcattaaa tatcagcaag     420
atcgagtcat tcgtcgcggt caccaccatt ttccctcggg caaaacgaaat tccggcaatc     480 gtcaaaccct ttatcgatcg tctgaatcgc aatgaattat ttacagcgat ttgtagtggc     540
atggcctcga ttgctggttc gacaatgatt ggttacgccg cactgggcgt gcctgtggaa     600
tatctgctgg cggcatcatt aatggcgatc cctggcggga tcttgtttgc ccgcctgtta     660
agcccggcaa cggaatcttc gcaggtttcc tttaataacc tctctttcac cgaaacaccg     720
ccaaaaagca ttattgaagc cgctgcgaca ggggcaatga ccgggctgaa aatcgccgca     780
ggtgtggcaa cagtggtgat ggcatttgtt gcaataattg cgttgattaa cggtattatc     840
ggcggcgttg gtggctggtt tggttttgaa catgcctcgc tggagtccat tttaggttac     900
ctgctggctc cactggcgtg ggtgatgggt gtggactgga gtgatgcgaa tcttgccggg     960
agtttgattg gacagaaact ggcaataaat gaatttgtcg cttatctcaa tttctcaccc    1020
tatctgcaaa cggctggcac tctcgatgct aaaactgtgg cgattatttc cttcgcgttg    1080
tgcggtttcg ctaactttgg ttctatcggg gtggtggtgg gggcgttttc tgcggttgcg    1140
ccacaccgtg cgccggaaat cgcccagctt ggtttacggg cgctggcggc ggcgacgctt    1200
tccaacttga tgagtgcgac cattgccggg ttctttattg gtttagcttg a              1251

<210> SEQ ID NO 115
<211> LENGTH: 1251
<212> TYPE: DNA
<213> ORGANISM: Escherichia coli
<220> FEATURE:
<221> NAME/KEY: misc_feature
<222> LOCATION: (1)..(1251)
<223> OTHER INFORMATION: yeiM - Escherichia coli K-12 W3110 (AAC75225;
      JW2151)

<400> SEQUENCE: 115
atggatataa tgagaagtgt tgtggggatg gtggtgttac tggcaatagc atttctgttg      60
tcagtgaata aaaagagcat cagtttgcgc acggttggag ccgcactgct gctgcaaatc     120
gctattggtg gcatcatgct ctacttccca ccgggaaaat gggcagtaga acaggcggca     180
ttaggcgttc ataaagtgat gtcttacagt gatgccggta gcgccttcat ttttggttcg     240
ctggttgggc cgaaaatgga tgtcctgttt gacggtgcgg gttttatctt cgcctttcgc     300
gtacttccgg cgattatttt cgttactgcg ctcatcagtc tgctgtacta cattggcgtg     360
atggggctgc tgattcgcat ccttggcagc attttccaga aagccctcaa catcagcaaa     420
atcgaatctt ttgttgcggt tactactatt ttcctcgggc aaaatgagat cccggcgatc     480
gttaaaccgt ttatcgatcg catgaatcgc aacgagttgt ttaccgcaat tgtagcgggg     540
atggcgtcca ttgctggttc gatgatgatt ggttatgccg gaatgggcgt accaattgac     600
```

```
tacctgttag cggcatcgct gatggcgatc cctggcggga ttttgtttgc acgtattctt      660
agcccggcaa ccgagccttc gcaggtcaca tttgaaaatc tgtcgttcag cgaaacgccg      720
ccaaaaagct ttatcgaagc ggcggcgagc ggtgcgatga ccgggctaaa aatcgccgct      780
ggtgtggcga cggtggtaat ggcgtttgtc gcaattattg cgctgatcaa cggcattatc      840
ggcggaattg gcggctggtt tggtttcgcc aatgcctctc tggaaagtat ttttggctat      900
gtgctggcac cgctggcgtg gatcatgggt gtggactgga gtgatgccaa tcttgcgggt      960
agcctgattg ggcagaaact ggcgattaac gaattcgtcg cttacctgag tttctcccca     1020
tacctgcaaa cgggcggcac gctggaagtg aaaaccattg cgattatctc ctttgcgctt     1080
tgtggttttg ctaactttgg ttctatcggt gttgtcgttg gcgcattttc ggctatttcg     1140
ccaaaacgcg cgccggaaat cgcccagctt ggtttacggg cgctggcagc agcaacgctt     1200
tccaacctga tgagtgcgac tattgccggg ttctttattg gtctggcgta a              1251
```

<210> SEQ ID NO 116
<211> LENGTH: 1254
<212> TYPE: DNA
<213> ORGANISM: Haemophilus influenzae
<220> FEATURE:
<221> NAME/KEY: misc_feature
<222> LOCATION: (1)..(1254)
<223> OTHER INFORMATION: HI0519 - Haemophilus influenzae Rd KW20
      serotype d(AAC22177)

<400> SEQUENCE: 116

```
atgagtgtgt taagcagcat tttgggaatg gtcgtattaa tcgctattgc cgtgttactt       60
tctaataatc gtaaagcgat tagtattcga accgtagtag gggcgttagc aatccaagta      120
ggatttgccg cccttatttt atatgtgcca gcaggtaaac aagcgttggg tgccgctgcg      180
gatatggtat ccaatgttat tgcctatggt aatgacggga ttaatttcgt tttcggcgga      240
ttggcagatc caagtaaacc atccggtttc attttttgcag tgaaagtatt accgattatc      300
gtgttcttct ctggcttaat ttctgtgctt tactatctcg gcattatgca agtcgtgatt      360
aaagtattag gtggcgcatt acaaaaagca ttgggtacgt caaaagcgga atcaatgtca      420
gcggcggcga atatcttcgt cggtcaaact gaagcaccat tagttgttcg cccttacatt      480
aaaaatatga cccaatctga attatttgcc attatggtgg gtggtacagc gtctatcgcg      540
ggttcagtaa tggcaggtta tgctggaatg ggcgtgccat tgacatactt aatcgctgcg      600
tcatttatgg cggcaccagc aggtttatta tttgcgaaat taatgttccc acaaaccgaa      660
caattcacag ataaacaacc agaagacaat gattcagaaa aaccaactaa cgtacttgaa      720
gcaatggcgg gcggtgcgag tgcaggtatg caacttgcgt taaacgtagg tgcaatgtta      780
atcgcattcg ttggtttaat tgcattaatt aatggtattt taagtggcgt aggcggatgg      840
ttcggctatg gcgacttaac cttacaatct atctttggtt aattttttaa accattagca      900
tacttaatcg gtgtaactga tggtgctgaa gcaggtattg caggacaaat gatcgggatg      960
aaattagcgg ttaatgaatt tgtgggttat cttgaatttg caaaatattt acaaccagat     1020
tctgcaattg tattaactga aaaaaccaaa gcgattatta cttttcgcact ttgtggtttt     1080 gctaacttca gctcaattgc aatcttaatt ggtggtttag gtggtatggc accagccgt      1140 cgtagtgatg ttgctcgttt aggtatcaaa gccgttatcg ctggtactct cgctaactta     1200
atgagtgcaa ctattgctgg tttatttatc ggcttaggtg ctgcagcact ttaa           1254
```

<210> SEQ ID NO 117

<211> LENGTH: 1257
<212> TYPE: DNA
<213> ORGANISM: Helicobacter pylori 26695
<220> FEATURE:
<221> NAME/KEY: misc_feature
<222> LOCATION: (1)..(1257)
<223> OTHER INFORMATION: nupC (HP1180) - Helicobacter pylori 26695 (AAD08224)

<400> SEQUENCE: 117

```
atgattttta gctctctttt tagtgttgta gggatggcgg tgcttttttct tattgcttgg      60
gtgttttcta gcaataaaag ggctattaat tatcgcacga ttgtcagtgc ctttgtgatt     120
caagtggctt tagggggcgtt ggctttatat gtgcctttgg gtagggaaat gctgcaaggc     180
ttagccagcg gcatacaaag cgtgattttct tacggctatg aggggtgcg ttttttattt     240
ggcaatctcg ctccaaacgc taagggcgat caagggatag gggggtttgt ctttgcgatc     300
aatgttttag cgatcattat ctttttttgct agcttgattt cacttctata ttatttaaaa     360
atcatgcctt tatttatcaa tctcatcggt ggggcgttgc aaaaatgctt aggcacttct     420
agagcagaaa gcatgagtgc agcggctaat attttttgtag cgcacaccga agcgccctta     480
gtcattaaac cttatttgaa aagcatgagc gattcagaga ttttttgcggt catgtgcgtg     540
ggcatggcta gcgttgcggg gcctgtgtta gccgggtatg cgagcatggg cattcctttg     600
ccttatttga tcgccgcttc gtttatgtcc gctcctgggg ggttgttgtt cgctaaaatc     660
atttacccac aaaacgaaac catttctagc catgcagatg tttctataga aaagcatgtc     720
aatgccatag aagctatcgc taatggggca agcacagggc taaatttagc cttgcatgtg     780
ggagcgatgc ttttagcctt tgtggggatg ctcgcgctca ttaacgggct tttaggggtt     840
gtaggggggtt ttttaggcat ggagcatttg tctttagggt tgattttagg cacgctctta     900
aaacccttag cctttatgtt aggcattcct tggagccagg ccgggattgc cggagaaatc     960
ataggcatta aaatcgcgct caatgaattt gtgggctata tgcagttatt gccttatttg    1020
ggcgataacc ctcctttaat cttgagcgag aaaactaaag cgatcatcac ttttgcgttg    1080
tgcgggtttg ctaatttaag ctcagtcgct atgctcattg gagggcttgg cagtttagtg    1140
cctaaaaaga aggatctcat tgtaaggctt gctttaaaag cggtgcttgt aggcacgctt    1200
tctaatttca tgagcgcgac tatcgccggg ttattcatag ggctaaacgc tcattaa      1257
```

<210> SEQ ID NO 118
<211> LENGTH: 1230
<212> TYPE: DNA
<213> ORGANISM: Staphylococcus aureus
<220> FEATURE:
<221> NAME/KEY: misc_feature
<222> LOCATION: (1)..(1230)
<223> OTHER INFORMATION: nupC (SA0600) - Staphylococcus aureus subsp. aureus N315 (BAB41833)

<400> SEQUENCE: 118

```
atgtttttat taatcaacat tattggtcta attgtatttc ttggtattgc ggtattattt      60
tcaagagatc gcaaaaatat ccaatggcaa tcaattggga tcttagttgt tttaaacctg     120
tttttagcat ggttctttat ttatttttgat tggggtcaaa aagcagtaag aggagcagcc     180
aatggtatcg cttgggtagt tcagtcagcg catgctggta caggttttgc atttgcaagt     240
ttgacaaatg ttaaaatgat ggatatggct gttgcagcct tattcccaat attattaata     300
gtgccattat ttgatatctt aatgtacttt aatattttac cgaaaattat tggaggtatt     360
ggttggttac tagctaaagt aacaagacaa cctaaattcg agtcattctt tgggatagaa     420
```

```
atgatgttct taggaaatac tgaagcatta gccgtatcaa gtgagcaact aaaacgtatg    480
aatgaaatgc gtgtattaac aatcgcaatg atgtcaatga gctctgtatc cggagctatt    540
gtaggtgcgt atgtacaaat ggtaccagga gaactggtac taacggcaat tccactaaat    600
atcgttaacg cgattattgt gtcatgcttg ttgaatccag taagtgttga agagaaagaa    660
gatattattt acagtcttaa aaacaatgaa gttgaacgtc aaccattctt ctcattcctt    720
ggagattctg tattagcagc aggtaaatta gtattaatca tcatcgcatt tgttattagt    780
tttgtagcgt tagctgatct atttgatcgt tttatcaatt tgattacagg attgatagca    840
ggatggatag gcataaaagg tagtttcggt ttaaaccaaa ttttaggtgt gtttatgtat    900
ccatttgcgc tattactcgg tttaccttat gatgaagcgt ggttggtagc acaacaaatg    960
gctaagaaaa ttgttacaaa tgaatttgtt gttatgggtg aaatttctaa agatattgca   1020
tcttatacac cacaccatcg tgcggttatt acaacattct taatttcatt tgcaaacttc   1080
tcaacgattg gtatgattat cggtacattg aaaggcattg ttgataaaaa gacatcagac   1140
tttgtatcta aatatgtacc tatgatgcta ttatcaggta tcctagtttc attattaaca   1200
gcagctttcg ttggtttatt tgcatggtaa                                    1230
```

<210> SEQ ID NO 119  
<211> LENGTH: 1230  
<212> TYPE: DNA  
<213> ORGANISM: Staphylococcus aureus  
<220> FEATURE:  
<221> NAME/KEY: misc_feature  
<222> LOCATION: (1)..(1230)  
<223> OTHER INFORMATION: nupC (SAV0645) -Staphylococcus aureus subsp.  
      aureus Mu50 (BAB56807)

<400> SEQUENCE: 119

```
atgtttttat taatcaacat tattggtcta attgtatttc ttggtattgc ggtattattt     60
tcaagagatc gcaaaaatat ccaatggcaa tcaattggga tcttagttgt tttaaacctg    120
tttttagcat ggttctttat ttatttttgat tggggtcaaa aagcagtaag aggagcagcc    180
aatggtatcg cttgggtagt tcagtcagcg catgctggta caggttttgc atttgcaagt    240
ttgacaaatg ttaaaatgat ggatatggct gttgcagcct tattcccaat attattaata    300
gtgccattat ttgatatctt aatgtacttt aatattttac cgaaaattat tggaggtatt    360
ggttggttac tagctaaagt aacaagacaa cctaaattcg agtcattctt tgggatagaa    420
atgatgttct taggaaatac tgaagcatta gccgtatcaa gtgagcaact aaaacgtatg    480
aatgaaatgc gtgtattaac aatcgcaatg atgtcaatga gctctgtatc cggagctatt    540
gtaggtgcgt atgtacaaat ggtaccagga gaactggtac taacggcaat tccactaaat    600
atcgttaacg cgattattgt gtcatgcttg ttgaatccag taagtgttga agagaaagaa    660
gatattattt acagtcttaa aaacaatgaa gttgaacgtc aaccattctt ctcattcctt    720
ggagattctg tattagcagc aggtaaatta gtattaatca tcatcgcatt tgttattagt    780
tttgtagcgt tagctgatct atttgatcgt tttatcaatt tgattacagg attgatagca    840
ggatggatag gcataaaagg tagtttcggt ttaaaccaaa ttttaggtgt gtttatgtat    900
ccatttgcgc tattactcgg tttaccttat gatgaagcgt ggttggtagc acaacaaatg    960
gctaagaaaa ttgttacaaa tgaatttgtt gttatgggtg aaatttctaa agatattgca   1020
tcttatacac cacaccatcg tgcggttatt acaacattct taatttcatt tgcaaacttc   1080
tcaacgattg gtatgattat cggtacattg aaaggcattg ttgataaaaa gacatcagac   1140
```

```
tttgtatcta aatatgtacc tatgatgcta ttatcaggta tcctagtttc attattaaca    1200
gcagctttcg ttggtttatt tgcatggtaa                                     1230

<210> SEQ ID NO 120
<211> LENGTH: 1203
<212> TYPE: DNA
<213> ORGANISM: Streptococcus pyogenes
<220> FEATURE:
<221> NAME/KEY: misc_feature
<222> LOCATION: (1)..(1203)
<223> OTHER INFORMATION: nupC (SpNupC) - Streptococcus pyogenes SF370
      serotype M1 (AAK34582)

<400> SEQUENCE: 120
atgcaattta tttatagtat tattggtatt ttattggtat taggaattgt gtatgcaatt     60
tctttcaatc gtaagagtgt ttctctaagt ttaattggaa aagctcttat cgttcaattc    120
attattgcgc taatcttagt acgtatccca ctaggccaac aaattgttag tgttgtttca    180
actggagtta ctagcgtaat caactgtggt caagctggtt taaattttgt gtttgggtca    240
ttagcagata gtggcgcaaa aactggtttt attttcgcta ttcaaacgct tggtaatatt    300
gttttcttat ctgccctagt tagtctactt tattatgtag gaatccttgg atttgtagta    360
aaatggatag gtaagggcgt tggtaaaatt atgaaatcct cagaggttga gagttttgtt    420
gctgtagcta atatgtttct tggtcaaaca gacagtccaa tcttggttag caaataccta    480
ggtcgtatga ctgatagtga gataatggtt gtgttggtat caggtatggg aagtatgtca    540
gtttctattc ttggtggcta tattgcatta ggcattccaa tggaatatct cttgattgct    600
tcaacaatgg ttcctattgg cagtattctc attgctaaaa tcttattgcc tcaaacagaa    660
cctgttcaaa aaattgatga cattaagatg gataataaag gtaataacgc caatgtgatt    720
gatgcaatcg ctgagggtgc aagcacaggt gcacaaatgg ctttctcaat tggtgctagt    780
ttgattgcct tgttggtttt agtttctttg attaatatga tgttaagtgg attgggaatc    840
cgcttagaac aaatcttttc atatgttttt gctccatttg gttttcttat gggatttgac    900
cacaaaaaca ttcttctaga aggaaacctt cttggaagta agttgatttt aaatgagttt    960
gtttcgttcc aacaattggg tcacctaatc aaatctttag attatcgtac agcattggta   1020
gcaactattt cactctgtgg ttttgctaat ttatcaagtt taggtatttg tgtttcaggt   1080
attgctgttc tttgcccgga gaacgtagc accctagctc gacttgtttt ccgtgcaatg   1140
attggtggta ttgctgtaag tatgcttagc gcctttatcg tcggtattgt aactctattc   1200
taa                                                                 1203

<210> SEQ ID NO 121
<211> LENGTH: 1257
<212> TYPE: DNA
<213> ORGANISM: Vibrio cholerae O1 biovar El Tor N16961
<220> FEATURE:
<221> NAME/KEY: misc_feature
<222> LOCATION: (1)..(1257)
<223> OTHER INFORMATION: nupC (VC2352) - Vibrio cholerae O1 biovar El
      Tor N16961 (AAF95495)

<400> SEQUENCE: 121
atgagcctgt ttatgagcct catcggcatg gcagttctgc taggaatcgc agttctactg     60
tcaagtaacc gtaaagctat caatctaaga actgtgggtg gcgcttttgc tatccaattt    120
tcactgggtg catttattct gtatgtgcct tggggccaag agctacttcg tggcttttcg    180
```

| | |
|---|---|
| gatgccgtat cgaatgttat taactacggt aacgatggta cttcattcct cttcggtgga | 240 |
| ctggtatcag gcaaaatgtt tgaagtgttt ggcggcggcg gtttcatttt cgcattccgc | 300 |
| gtactaccaa cactgatctt cttctcagca ctgatttctg tactgtacta cttgggtgtt | 360 |
| atgcaatggg ttatccgcat tcttggcggt ggtctgcaaa aagcactggg tacatcacgc | 420 |
| gcggaatcta tgtctgcggc tgcaaacatt ttcgtgggtc aaactgaagc accattagtt | 480 |
| gttcgtccat tcgttccaaa aatgactcaa tctgagctgt tgcggtaat gtgtggtggc | 540 |
| ttggcttcta tcgcaggtgg tgtacttgcg ggttacgctt caatgggcgt taagatcgaa | 600 |
| tacttggtag cggcgtcatt catggcggca ccgggtggtc tgctgttcgc aaaactgatg | 660 |
| atgcctgaaa ctgaaaaacc acaagacaat gaagacatta ctcttgatgg tggtgacgac | 720 |
| aaaccggcta acgttatcga tgcggctgct ggcggtgctt ctgctggtct gcaacttgct | 780 |
| ctgaacgttg gtgcaatgtt gattgccttt atcggtttga ttgctctgat caacggtatg | 840 |
| ttgggtggca tcggtggttg gttcggtatg cctgaactga aactggaaat gctactgggc | 900 |
| tggttgtttg cgcctctggc tttcctgatc ggtgttcctt ggaacgaagc aactgttgcg | 960 |
| ggtgagttca tcggtctaaa aaccgttgct aacgaattcg ttgcttactc tcagtttgcg | 1020 |
| ccttacctga ctgaagcggc accagtggtt ctgtctgaga aaaccaaagc gatcatctct | 1080 |
| ttcgctctgt gtggttttgc gaaccttttct tctatcgcaa ttctgcttgg tggtttgggt | 1140 |
| agcttggcac ctaagcgtcg tggcgacatc gctcgtatgg gggtcaaagc ggttatcgca | 1200 |
| ggtactctat ctaacctgat ggcagcgacc atcgctggct tcttcctctc tttctaa | 1257 |

<210> SEQ ID NO 122
<211> LENGTH: 1218
<212> TYPE: DNA
<213> ORGANISM: Vibrio cholerae O1 biovar El Tor N16961
<220> FEATURE:
<221> NAME/KEY: misc_feature
<222> LOCATION: (1)..(1218)
<223> OTHER INFORMATION: nupC (VC1953) - Vibrio cholerae O1 biovar El
      Tor N16961 (AAF95101)

<400> SEQUENCE: 122

| | |
|---|---|
| ttgggcggcg ttatgtcatc actcctcggt atgggcgcaa ttttgctggt tgcgtggcta | 60 |
| ttttctacca atagaaaaaa tatcaacttg cgtacagttt ctttagcgtt actgctgcaa | 120 |
| atcttcttcg ccttactggt gctgtatgta cctgcgggta aagaggcact caatcgtgtg | 180 |
| acgggcgcgg tgtcacaact gatcaactat gggcaagatg gtatcggttt tgtgtttggt | 240 |
| ggcctcgcca atggcagcgt aggttttgtg tttgcgatta atgtccttgg catcatcatt | 300 |
| ttcttctctg cactgatttc tggccttttac catttaggca tcatgccgaa agtgattaac | 360 |
| ctcatcggtg gtgggtttaca gaaattgctt ggcacaggcc gtgcagaatc cctttctgct | 420 |
| accgcaaaca ttttcgtggg tatgattgaa gcgccgctgg tggtgaaacc ttatcttcat | 480 |
| aaaatgaccg attcgcaatt ctttgcagtg atgacgggcg gcttagcgtc ggttgctggc | 540 |
| ggtactttgg ttggttatgc ctctttaggt gtggaattga actatctgat cgcggcggct | 600 |
| ttcatgtctg cccctgcggg tcttttgatg gcaaaaatca tgttgccaga aaccgaacac | 660 |
| gtcgatgccg cgattgcgca agatgagttg gatctgccga atccactaa cgtcgtcgaa | 720 |
| gcgattgcgg atggcgcgat gtcgggtgtg aaaattgctg ttgcggtagg ggcgactttg | 780 |
| ctcgctttcg tgagtgtgat tgctctgtta aacggcttgc tcggttggtt tggtggctgg | 840 |
| tttggcatcg agctaagctt tgaactgatc atggggtatg ttttcgctcc ggtagcttgg | 900 |

```
ctgattggta ttccatggca tgaggcgatc acggcaggct cgctgattgg taacaaagtg      960
gtggtgaacg agtttgtcgc tttcattcaa ctgattgaag tgaaagagca attgagtgcg     1020
cattcacaag cgatcgtgac tttcgcgctg tgcggttttg cgaatatttc taccatggcg     1080
attttgattg gtggtttggg tagccttgta cctgaacgtc gctctttat  ctcccaatac     1140 ggcttccgtg cgattggcgc aggcgtatta gctaacctaa tgagtgcatc gatcgctgga     1200
gtgattttgt ctttgtga                                                   1218
```

<210> SEQ ID NO 123
<211> LENGTH: 1209
<212> TYPE: DNA
<213> ORGANISM: Vibrio cholerae O1 biovar El Tor N16961
<220> FEATURE:
<221> NAME/KEY: misc_feature
<222> LOCATION: (1)..(1209)
<223> OTHER INFORMATION: nupC (VCA0179) - Vibrio cholerae O1 biovar El Tor N16961 (AAF96092)

<400> SEQUENCE: 123

```
atggcgattt tgtttggaat catcggtgtt acggtactga tcttatgcgc gtatctgctc       60
tctgaaagcc gcagtgcgat taattggaaa accatttccc gagccttgtt gttgcaaatt      120
ggttttgcgg ctcttgtgct ttatttccca ttggggcaaa ccgcgctaag cagcttgagt      180
aatggggttt ctggtttgct tggttttgcc gatgtcggca ttcgcttcct gtttggtgat      240
cttgccgata cgggctttat ttttgctgtt cgtgtattac ctatcatcat cttcttcagt      300
gcgctgattt ctgccccttta ttaccttggt gtgatgcaaa aagtgatcgc cctgatcggc      360
ggtggcattc aacgcttctt aggcaccagt aaggcggaat cactggtcgc gacaggcaat      420
attttcctat cacaaggcga atcgccactt ttggtgcgcc ccttccttgc caatatgaca      480
cgctctgaac tgtttgcggt catggcgggc ggtatggcat cggtagcagg ctctgtgctg      540
ggtggttacg caggttttagg ggttgagctg aaatacctga ttgcagcgag tttcatggcg      600
gcgccgggca gtttaatgat ggcgaaaatc atcgttcctg agcgtggtgt gccaatcgat      660
caaagccaag tcgagttaga taaagcgcaa gacagcaact tgattgatgc tctcgctagc      720
ggtgcgatga atggtatgaa agtcgccgtt gcagtgggca ctatgttgat tgcgttcgtc      780
agcgtgatcg ctatggtcaa cactggcctt gaaaatctgg cgatctggt  tgggtttagc      840 ggcattacct acaagccat  gttcggttat ctgtttgctc ctctggcatg ggtgattggc      900
attccaagtc acgaagtgct ggcggcaggt tcctacatcg tcagaaagt  ggtgatgaac      960 gaatttgtgg ctttcattga ctttgttgag cataaagcgc tgctttctga gcatagccaa     1020
gtcatcatca cgtttgcatt gtgtggcttt gccaacattg ctctatcgc  gatccaatta     1080 ggctccattg gcgtgatagc ccctgagcgc cgctcggaag tggcgaacct aggcataaaa     1140
gcggtcattg ctggcacttt agccaaccta atgagcgctt gcttagcggg gattttcatc     1200
tcgctataa                                                             1209
```

<210> SEQ ID NO 124
<211> LENGTH: 1278
<212> TYPE: DNA
<213> ORGANISM: Escherichia coli
<220> FEATURE:
<221> NAME/KEY: misc_feature
<222> LOCATION: (1)..(1278)
<223> OTHER INFORMATION: yegT - Escherichia coli K-12 W3110 (P76417; JW2085)

<400> SEQUENCE: 124

```
atgaaaacaa cagcaaagct gtcgttcatg atgtttgttg aatggttat  ctggggcgcg    60
tggtttgtgc cattgtggtt gtggttaagt aaaagcggtt ttagtgccgg agaaattggc   120
tggtcgtatg cctgtaccgc cattgcggcg atcctgtcgc caattctggt tggctccatc   180
actgaccgct ttttctcggc gcaaaaagtg ctggcggtat tgatgttcgc aggcgcgctg   240
ctgatgtatt tcgctgcgca acagaccact tttgccgggt tcttcccgtt actgctggcc   300
tactcgctaa cctatatgcc gaccattgcg ctgactaaca gcatcgcttt tgccaacgtg   360
ccggatgttg agcgtgattt cccgcgcatt cgtgtgatgg cactatcgg  ctggattgcc   420
tccggtctgg catgtggttt cttgccgcaa atactgggg  atgccgatat ctcaccgact   480
aacatcccgc tgctgattac cgccggaagt tctgctctgc tcggtgtgtt tgcgttttc   540
ctgcccgaca cgccaccaaa aagcaccggc aaaatggata ttaaagtcat gctcggcctg   600
gatgcgctga tcctgctgcg cgataaaaac ttcctcgtct ttttcttctg ttcattcctg   660
tttgcgatgc cactagcgtt ctattacatc tttgccaacg gttatctgac cgaagttggc   720
atgaaaaacg ccaccggctg gatgacgctc ggccagttct ctgaaatctt ctttatgctg   780
gcattgccgt ttttcactaa cgctttggt  atcaaaaagg tattattgct tggtctggtc   840
accgctgcga tccgctatgg cttctttatt tacggtagtg cggatgaata tttcacctac   900
gcgttactgt tcctcggtat tttgcttcac ggcgtaagtt acgatttta  ctacgttacc   960
gcttacatct atgtcgataa aaaagccccc gtgcatatgc gtaccgctgc gcaggggctg  1020
atcacgctct gctgccaggg cttcggcagt ttgctcggct atcgtcttgg cggtgtgatg  1080
atggaaaaga tgttcgctta tcaggaaccg gtaaacggac tgactttcaa ctggtccggg  1140
atgtggactt tcggcgcggt gatgattgcc attatcgccg tgctgttcat gattttttc   1200
cgcgaatccg acaacgaaat tacggctatc aaggtcgatg atcgcgatat tgcgttgaca  1260
caagggggaag ttaaatga                                              1278
```

<210> SEQ ID NO 125
<211> LENGTH: 1257
<212> TYPE: DNA
<213> ORGANISM: Escherichia coli
<220> FEATURE:
<221> NAME/KEY: misc_feature
<222> LOCATION: (1)..(1257)
<223> OTHER INFORMATION: nupG - Escherichia coli K-12 W3110 (P09452; JW2932)

<400> SEQUENCE: 125

```
atgaatctta agctgcagct gaaaatcctc tcttttctgc agttctgtct gtggggaagt    60
tggctgacga ccctcggctc ctatatgttt gttaccctga agtttgacgg tgcttctatt   120
ggcgcagttt atagctcact gggtatcgca gcggtcttta tgcctgcgct gctggggatt   180
gtggccgaca aatggttaag tgcgaaatgg gtatatgcca tttgccacac cattggcgct   240
atcacgctgt tcatggcggc acaggtcacg acaccggaag cgatgttcct tgtgatattg   300
attaactcgt ttgcttatat gccaacgctt gggttaatca acaccatctc ttactatcgc   360
ctgcaaaatg ccgggatgga tatcgttact gacttcccgc caatccgtat ctggggcacc   420
atcggcttta tcatggcaat gtgggtggtg agcctgtctg gcttcgaatt aagccacatg   480
cagctgtata ttggcgcagc actttccgcc attctggttc tgtttaccct gactctgccg   540
catattccgg ttgctaaaca gcaagcgaat cagagctgga caaccctgct gggcctcgat   600
gcattcgcgc tgtttaaaaa caagcgtatg gcaatcttct ttatcttctc aatgctgctg   660
```

```
ggcgcggaac tgcagattac caacatgttc ggtaatacct tcctgcacag cttcgacaaa    720
gatccgatgt ttgccagcag ctttattgtg cagcatgcgt caatcatcat gtcgatttcg    780
cagatctctg aaaccctgtt cattctgacc atcccgttct tcttaagccg ctacggtatt    840
aagaacgtaa tgatgatcag tattgtggcg tggatcctgc gttttgcgct gtttgcttac    900
ggcgacccga ctccgttcgg tactgtactg ctggtactgt cgatgatcgt ttacggttgc    960
gcattcgact tcttcaacat ctctggttcg gtgtttgtcg aaaagaagt tagcccggca    1020 attcgcgcca gtgcacaagg gatgttcctg atgatgacta acggcttcgg ctgtatcctc    1080
ggcggcatcg tgagcggtaa agttgttgag atgtacaccc aaaacggcat taccgactgg    1140
cagaccgtat ggttgatttt cgctggttac tccgtggttc tggccttcgc gttcatggcg    1200
atgttcaaat ataaacacgt tcgtgtcccg acaggcacac agacggttag ccactaa    1257
```

<210> SEQ ID NO 126
<211> LENGTH: 1257
<212> TYPE: DNA
<213> ORGANISM: Escherichia coli
<220> FEATURE:
<221> NAME/KEY: misc_feature
<222> LOCATION: (1)..(1257)
<223> OTHER INFORMATION: xapB - Escherichia coli K-12 W3110 (P45562; JW2397)

<400> SEQUENCE: 126

```
atgagcatcg cgatgcgctt aaaggtaatg tccttttgc aatatttat ctgggggagc      60 tggctggtta ccctcggctc ttacatgatt aatactcttc atttcaccgg cgctaatgtt    120
ggcatggttt acagttccaa agggatcgcc gcgattatta tgcctggtat aatggggatc    180
atcgcagaca aatggctgcg cgcagaacgt gcatacatgc tgtgtcacct ggtgtgtgcg    240
ggcgtacttt tttatgcggc atccgtaact gatccggata tgatgttttg ggtgatgtta    300
gtcaatgcga tggcgtttat gccgactatt gcgttatcga cagcgtctc ttattcctgt    360 cttgcccagg cagggcttga cccggtgacc gctttcccgc ccattcgcgt ttttggtacg    420
gtggggttca ttgtcgcgat gtgggcagta agcctgctgc atctggaatt gagtagtctg    480
cagctgtata tcgcgtccgg tgcgtcattg ctgctgtcgg cttatgcgct gactttgccg    540
aagattccgg ttgcggagaa aaaagcgacc acatcgcttg ccagcaagct gggtctggat    600
gccttcgtgc tgtttaaaaa tccacgcatg gccatctttt tcctctttgc catgatgctg    660
ggtgcggtac tgcaaattac caacgttttt ggtaatccgt tcctacatga tttcgcccgt    720
aacccggagt ttgctgacag ttttgtggtg aaatatccct ccattttact gtcagtttca    780
cagatggcag aagtgggctt tatactgact atcccattct tttaaagcg atttggcatt    840 aaaaccgtca tgctgatgag tatggtggcc tggacgctgc gctttggctt cttcgcctat    900
ggcgatccgt caacaaccgg atttattttg ctgctgctgt cgatgattgt ttatggctgt    960
gcattcgatt tcttcaatat ttctggttcg gtatttgtcg aacaggaagt tgattccagc    1020
attcgtgcca gcgcgcaggg gctctttatg accatggtaa atggtgtcgg cgcatgggtt    1080
ggctcgattc tgagtggcat ggcagtagat tacttttcgg tggatggcgt aaaagactgg    1140
caaactatct ggctggtgtt tgcaggatat gctctttttc tcgcagtgat attttctttt    1200
gggtttaaat ataatcatga ccctgaaaag ataaagcatc gagcggtgac tcattaa      1257
```

<210> SEQ ID NO 127
<211> LENGTH: 1242

<212> TYPE: DNA
<213> ORGANISM: Caulobacter crescentus CB15
<220> FEATURE:
<221> NAME/KEY: misc_feature
<222> LOCATION: (1)..(1242)
<223> OTHER INFORMATION: CC1628 - Caulobacter crescentus CB15 (AAK23606)

<400> SEQUENCE: 127

```
atggggacga gtttccgtct gttcgtgatg atggtgctgc agctggcgat ctggggcgcc    60
tgggcgccca agatcttccc ctacatgggc atgctgggct cgcgccctg gcagcagtcg    120
ctggtcggca gcgcctgggg cgtggcggcg ctggtgggca tcttcttctc gaatcagttc    180
gccgaccgga acttctcggc cgagcggttc ctggcggtca gccacctgat cggcggcgtg    240
gcgctgctgg gcacggcctt ctcgacggag ttctggccgt tctttgcctg ttacctcgtt    300
ttcagcctgt tctatgtgcc gacgctgtcg gtcaccaact cgatcgcctt cgccaatctg    360
cgcgatccgg cggccggctt cggcggggtg cggatgggcg gaaccgtcgg ctgggtgctg    420
gtcagctggc ccttcgtgtt cctgctgggc gcccaagcga cggtggagca ggtccgctgg    480
atcttcctgg tggcggcgat cgtctccttc gttttcgccg gttacgctct gaccctgccg    540
cacacgccgc cgcgcaaggc cgatgacgct gtcgacaagc tggcctggcg acgggcgttc    600
aagctactgg gcgcgcccct cgtgtttgtc ctctttgtcg tgaccttcat cgattccgtg    660
atccacaacg gctacttcgt gatggccgac gccttcctga ccaaccgggt cgggatcgcg    720
ggcaatctca gcatggtcgt gctgagcctg gccaggtgg ccgaaatcat caccatgctg    780
ctgttgggcc gcgtgctggc caagctgggc tggaaggtca ccatgatcgt cggcgtgctg    840
ggccacgccg cgcgctttgc ggtcttcgcc tacttcgccg acagcgtgcc ggtcatcgtg    900
gcggtgcagc tgctgcacgg cgtctgctac gccttcttct cgccacggt ttacatcttc    960
gtcgacgccg tcttcccgaa agatgtccgc tccagcgcgc agggtctgtt caacttgctg   1020
atcctgggcg tcggcaatgt ggccgccagc ttcatcttcc ccgcgctgat cggtcgcctg   1080
accaccgatg ggtccgtcga ctacacgacg ctgttcctcg tgccgaccgc catggctttg   1140
gcggcggtct gcctgctggc gctgttcttc cggccgccca cgcggggacc tgtttcggag   1200
gcggattccg cttcatccgc cgccagttcg gcccaagcct ag                      1242
```

<210> SEQ ID NO 128
<211> LENGTH: 1260
<212> TYPE: DNA
<213> ORGANISM: Escherichia coli
<220> FEATURE:
<221> NAME/KEY: misc_feature
<222> LOCATION: (1)..(1260)
<223> OTHER INFORMATION: codB - Escherichia coli K-12 W3110 (P25525; JW0327)

<400> SEQUENCE: 128

```
gtgtcgcaag ataacaactt tagccagggg ccagtcccgc agtcggcgcg gaaagggta     60
ttggcattga cgttcgtcat gctgggatta accttctttt ccgccagtat gtggaccggc   120
ggcactctcg gaaccggtct tagctatcat gatttcttcc tcgcagttct catcggtaat   180
cttctcctcg gtatttacac ttcatttctc ggttacattg gcgcaaaaac cggcctgacc   240
actcatcttc ttgctcgctt ctcgtttggt gttaaaggct catggctgcc ttcactgcta   300
ctgggcggaa ctcaggttgg ctggtttggc gtcggtgtgg cgatgtttgc cattccggtg   360
ggtaaggcaa ccgggctgga tattaatttg ctgattgccg tttccggttt actgatgacc   420
gtcaccgtct tttttggcat ttcggcgctg acggttcttt cggtgattgc ggttccggct   480
```

```
atcgcctgcc tgggcggtta ttccgtgtgg ctggctgtta acggcatggg cggcctggac    540
gcattaaaag cggtcgttcc cgcacaaccg ttagatttca atgtcgcgct ggcgctggtt    600
gtggggtcat ttatcagtgc gggtacgctc accgctgact tgtccggtt tggtcgcaat     660 gccaaactgg cggtgctggt ggcgatggtg gccttttcc tcggcaactc gttgatgttt     720
attttcggtg cagcgggcgc tgcggcactg gcatggcgg atatctctga tgtgatgatt     780
gctcagggcc tgctgctgcc tgcgattgtg gtgctggggc tgaatatctg gaccaccaac    840
gataacgcac tctatgcgtc gggtttaggt ttcgccaaca ttaccgggat gtcgagcaaa    900
accctttcgg taatcaacgg tattatcggt acggtctgcg cattatggct gtataacaat    960
tttgtcggct ggttgacctt ccttcggca gctattcctc cagtgggtgg cgtgatcatc    1020
gccgactatc tgatgaaccg tcgccgctat gagcactttg cgaccacgcg tatgatgagt    1080
gtcaattggg tggcgattct ggcggtcgcc ttggggattg ctgcaggcca ctggttaccg    1140
ggaattgttc cggtcaacgc ggtattaggt ggcgcgctga gctatctgat ccttaacccg    1200
attttgaatc gtaaaacgac agcagcaatg acgcatgtgg aggctaacag tgtcgaataa    1260
```

<210> SEQ ID NO 129
<211> LENGTH: 1656
<212> TYPE: DNA
<213> ORGANISM: Corynebacterium sp.
<220> FEATURE:
<221> NAME/KEY: misc_feature
<222> LOCATION: (1)..(1656)
<223> OTHER INFORMATION: mctC Corynebacterium

<400> SEQUENCE: 129

```
atgaattcca ctattctcct tgcacaagac gctgtttctg agggcgtcgg taatccgatt     60
cttaacatca gtgtcttcgt cgtcttcatt attgtgacga tgaccgtggt gcttcgcgtg    120
ggcaagagca ccagcgaatc caccgacttc tacaccggtg gtgcttcctt ctccggaacc    180
cagaacggtc tggctatcgc aggtgactac ctgtctgcag cgtccttcct cggaatcgtt    240
ggtgcaattt cactcaacgg ttacgacgga ttccttact ccatcggctt cttcgtcgca     300
tggcttgttg cactgctgct cgtggcagag ccacttcgta acgtgggccg cttcaccatg    360
gctgacgtgc tgtccttccg actgcgtcag aaaccagtcc gcgtcgctgc ggcctgcggt    420
accctcgcgg ttaccctctt ttacttgatc gctcagatgg ctggtgcagg ttcgcttgtg    480
tccgttctgc tggacatcca cgagttcaag tggcaggcag ttgttgtcgg tatcgttggc    540
attgtcatga tcgcctacgt tcttcttggc ggtatgaagg gcaccacata cgttcagatg    600
attaaggcag ttctgctggt cggtggcgtt gccattatga ccgttctgac cttcgtcaag    660
gtgtctggtg gcctgaccac cctttaaat gacgctgttg agaagcacgc cgcttcgat     720 tacgctgcca ccaaggggta cgatccaacc cagatcctgg agcctggtct gcagtacggt    780
gcaactctga ccactcagct ggacttcatt tccttggctc tcgctctgtg tcttggaacc    840
gctggtctgc cacacgttct gatgcgcttc tacaccgttc ctaccgccaa ggaagcacgt    900
aagtctgtga cctgggctat cgtcctcatt ggtgcgttct acctgatgac cctggtcctt    960
ggttacggcg ctgcggcact ggtcggtcca gaccgcgtca ttgccgcacc aggtgctgct   1020
aatgctgctg ctcctctgct ggccttcgag cttggtggtt ccatcttcat ggcgctgatt   1080
tccgcagttg cgttcgctac cgttctcgcc gtggtcgcag gtcttgcaat taccgcatcc   1140
gctgctgttg gtcacgacat ctacaacgct gttatccgca acggtcagtc caccgaagcg   1200
```

| | |
|---|---|
| gagcaggtcc gagtatcccg catcaccgtt gtcgtcattg gcctgatttc cattgtcctg | 1260 |
| ggaattcttg caatgaccca gaacgttgcg ttcctcgtgg ccctggcctt cgcagttgca | 1320 |
| gcatccgcta acctgccaac catcctgtac tccctgtact ggaagaagtt caacaccacc | 1380 |
| ggcgctgtgg ccgctatcta caccggtctc atctccgcgc tgctgctgat cttcctgtcc | 1440 |
| ccagcagtct ccggtaatga cagcgcaatg gttccaggtg cagactgggc aatcttccca | 1500 |
| ctgaagaacc caggcctcgt ctccatccca ctggcattca tcgctggttg gatcggcact | 1560 |
| ttggttggca agccagacaa catggatgat cttgctgccg aaatggaagt tcgttccctc | 1620 |
| accggtgtcg gtgttgaaaa ggctgttgat cactaa | 1656 |

<210> SEQ ID NO 130
<211> LENGTH: 1521
<212> TYPE: DNA
<213> ORGANISM: Virgibacillus sp.
<220> FEATURE:
<221> NAME/KEY: misc_feature
<222> LOCATION: (1)..(1521)
<223> OTHER INFORMATION: putP_6 - Virgibacillus sp.

<400> SEQUENCE: 130

| | |
|---|---|
| atggatctta cgacattaat aactttata gtatatctac tagggatgtt ggcgattggc | 60 |
| ctcatcatgt attatcgaac caataattta tcagattatg ttcttggtgg acgtgatctt | 120 |
| ggtccaggcg tagctgcatt gagtgctggt gcatcggata tgagtggttg gctgttatta | 180 |
| ggtttgcctg gagcgattta tgcatctggt atgtctgaag cttggatggg gatcgggtta | 240 |
| gctgtaggtg cttatttaaa ttggcaattt gtagctaagc gattacgcgt ttataccgag | 300 |
| gtatcaaata attccattac gatcccagat tattttgaaa atcggtttaa agataactca | 360 |
| catattcttc gtgttatatc tgctatcgta attttgttat tcttcacttt ttatacatct | 420 |
| tcaggaatgg ttgcaggagc aaaattattt gaggcttcat tcggtctcca atacgaaact | 480 |
| gctctgtgga ttggtgcggt tgtagttgta tcttatacgt tacttggagg atttctagcg | 540 |
| gttgcatgga cagactttat tcaaggtatt cttatgttcc ttgcactaat tgttgttcca | 600 |
| atcgtcgcat tagatcaaat gggtggctgg aatcaagcgg tacaagctgt tggtgaaatt | 660 |
| aatccttccc acctcaatat ggttgaaggt gttggaataa tggcaattat ttcatcactt | 720 |
| gcttggggct taggttattt tggacagcca catattattg ttcgttttat ggcattacgt | 780 |
| tcggcgaaag atgttccgaa agcgaaattt attggaacag cttggatgat tttaggactt | 840 |
| tatggagcaa tctttactgg ttttgtagga ctagcattta tcagtacaca agaagtaccg | 900 |
| attctgtctg aattcgggat tcaagtagtt aatgagaatg gtttacaaat gttagccgat | 960 |
| cctgaaaaga tatttattgc tttctcccaa atactattcc atccagtagt tgccggtatc | 1020 |
| ttactagcgg caatcttgtc tgcaattatg agtaccgttg attcacagtt acttgtatca | 1080 |
| tcttcagcgg ttgcagaaga tttctataaa gctattttcc gtaaaaaagc tactggtaaa | 1140 |
| gagcttgttt gggttggacg tattgctaca gtgataattg cgattgttgc tttaattatt | 1200 |
| gcaatgaacc cagatagctc tgtattggat ctagttagtt atgcatgggc tggatttggt | 1260 |
| gcagcatttg gaccaattat catccttgtca ttattctgga agagaatcac aagaaatggt | 1320 |
| gcactagcgg gtatcattgt aggtgccatt acggtaattg tatggggaga ctttctatct | 1380 |
| ggaggtatct ttgacctcta cgaaattgtt ccaggcttta tcttaaatat gattgtcacc | 1440 |
| gttattgtga gtcttatcga taaaccgaat ccagatttag aagctgactt tgatgaaacc | 1500 |
| gtagaaaaaa tgaaagaata a | 1521 |

<210> SEQ ID NO 131
<211> LENGTH: 1323
<212> TYPE: DNA
<213> ORGANISM: Lactobacillus johnsonii
<220> FEATURE:
<221> NAME/KEY: misc_feature
<222> LOCATION: (1)..(1323)
<223> OTHER INFORMATION: cbsT1 - Lactobacillus johnsonii

<400> SEQUENCE: 131

```
atgtcgacca caccgacaca gccatcatca cgaaaacagg ctgtttaccc gtacttgatc      60
gtgctgtcgg gcatcgtctt cacggccatc ccggtatcgc tggtctgcag ttgcgcaggt     120
atcttcttca cgcctgtcag cagctacttc catgttccca aggccgcatt caccggatat     180
ttcagcatat tcagcatcac catggtcgcc ttcctgccgg tggccggatg gctgatgcac     240
cgctacgatc tgcgcatcgt actgaccgca agcaccgtcc tggctggact gggctgcctg     300
ggtatgtccc gatcatccgc catgtggcag ttctatctat gcggagtggt tctgggaatc     360
ggcatgccgg ccgtcctcta tctgtcagtg ccaacactca tcaacgcctg gttccgcaag     420
cgggtcgggt tcttcatcgg cctgtgcatg gccttcaccg gcataggcgg cgtgatcttc     480
aaccagatag gcaccatgat catcagatcc gcccctgatg gatggaggcg gggatatctg     540
gttttcgcta ttctcatcct ggtgatcacc ctgcccttca ccattttcgt cattcgcagc     600
acacccgaac agatgggtct gcatccctac ggcgccgacc aggagcctga tgcagctgag     660
acggccacca atagtgcagg caccgggagc aaagaccaaa agagtcctga gcctgcagcg     720
tcaaccgtag gcatgactgc ctcccaggcc ttgcgctccc ctgccttctg ggcgctggcg     780
ctcttctgcg gtctgatcac catgaatcag accatttacc agttcctgcc ctcctacgcg     840
gcatccctgc catccatggc agcctacacg ggactgatcg cctcctcctg catggccggc     900
caggccatcg gcaagatcat cctgggcatg gtcaacgacg gcagcatcgt aggcggtctc     960
tgtctgggca tcggcggcgg cattctcggc gtctgcctca tggtcgcctt ccccggattg    1020
cccgtgctcc tcctgctggg agcctttgcc ttcggccttg tctacgcctg cactactgtg    1080
cagacaccaa tcctggttac agcggtcttc ggctcgcgcg actacaccaa catctatgca    1140
cgtatccaga tggttgggtc cctagcctcg gccttcgcag ctctcttctg gggcgccatc    1200
gctgaccagc ccacggcta catcatcatg ttcggtctga gcatcctgat catggttgtg    1260
gccttgttcc taggcattat ccctctgaaa ggtacgcgca agttgaccga tcagatcgcc    1320
tga                                                                  1323
```

<210> SEQ ID NO 132
<211> LENGTH: 1356
<212> TYPE: DNA
<213> ORGANISM: Lactobacillus johnsonii
<220> FEATURE:
<221> NAME/KEY: misc_feature
<222> LOCATION: (1)..(1356)
<223> OTHER INFORMATION: cbsT2 - Lactobacillus johnsonii

<400> SEQUENCE: 132

```
atgtctactg atgccgctac taaagataaa gtagtaagca agggctataa atacttcatg      60
gttttccttt gtatgttaac ccaagctatt ccttatggaa ttgctcaaaa cattcagcct     120
ttgtttatcc acccttttagt taatactttc cactttaccct tagcatcgta cacattaatt     180
tttacgtttg gtgcggtttt tgcttcagtt gcttctccat ttattggtaa ggcattagaa     240
```

```
aaagttaact tccgactaat gtatttaatt ggtattggtc tttctgctat tgcctacgta    300 attttggaa ttagtacaaa actacccggt ttctatattg ccgctatcat ttgtatggtt    360
ggttcaacct tttactccgg ccaaggtgtt ccctgggtta ttaaccactg gttcccagca    420
aagggacgtg gggctgcctt aggaattgcc ttctgcggtg ttctattgg taatatcttt    480 ttacaaccag caacccaagc tattttaaaa cactacatga caggtaatac taagaccggt    540
catttaacct ctatggcacc attctttatc tttgccgtag ctttattagt aatcggtgta    600
attatcgcct gcttcattag aaccctaag aaagacgaaa ttgttgtttc tgatgcagaa     660
ctagctgaaa gcaagaaagc tgaagccgca gccaaagcta aagagtttaa aggctggact    720
agtaaacaag tgttacaaat gaaatggttc tggattttca gccttggttt cttaatcatt    780
ggtttaggct tagcttcttt aaatgaagac tatgccgcct tccttgatac taagctttct    840
ttaaccgatg ttggtttagt tgggtcaatg tacggtgttg gttgtttaat cggaaatatt    900
tctggtggtt tcttatttga taaatttggt acagcaaaat caatgaccta tgctggttgt    960
atgtatattt tatctattct gatgatgatc tttattagct tccagccata tggttcatct   1020
attagtaagg ctgctggcat tggctatgct atcttttgcg gcttagctgt atttagttac   1080
atgtcaggcc cagccttcat ggcaaaagac ctctttggtt caagagatca aggtgtcatg   1140
cttggatacg ttggtttagc ttatgcaatt ggctatgcca tggtgctcc actatttggg    1200 attattaagg gagcggcaag ctttacagtt gcttggtact ttatgattgc ctttgttgca    1260
attggtttta tcattttagt atttgccgtt atccaaatta agagatacca aaagaaatac   1320
attgcagagc aagcagcaaa agctaatgct aaataa                              1356
```

<210> SEQ ID NO 133
<211> LENGTH: 1287
<212> TYPE: DNA
<213> ORGANISM: Escherichia coli
<220> FEATURE:
<221> NAME/KEY: misc_feature
<222> LOCATION: (1)..(1287)
<223> OTHER INFORMATION: amtB - Escherichia coli K-12 MG1655 (B0451; 945084)

<400> SEQUENCE: 133

```
atgaagatag cgacgataaa aactgggctt gcttcactgg cgatgcttcc gggactggta    60
atggctgcac ctgcggtggc cgataaagcc gacaatgcgt ttatgatgat tgtactgcg   120 ctggtgctgt ttatgactat tccggggatt gccctgtttt acggtgggtt gattcgcggc   180
aaaaacgtgc tgtcgatgct gacgcaggtg acggtgacat ttgcactggt ctgtattctc   240
tgggtggttt acggttactc gctggcgttt ggtgagggca caacttctt cggcaacatt   300 aactggttga tgctgaaaaa catcgaactg acggcggtga tgggcagcat ttatcagtat   360
atccacgtgg cgtttcaggg atcgtttgcc tgcattaccg tcggcttgat agttggggcg    420
ctggcggaac gaatccgctt ctcagctgtg ttgattttcg tggtggtatg gctgacgctc    480
tcttacattc cgattgcgca tatggtgtgg ggcggtggtt tgctggcttc tcacggtgcg   540
ctggatttcg cgggtggcac cgtggtgcac attaacgccg caatcgccgg tctggtgggc   600
gcgtatctga taggaaaacg cgtgggcttc ggtaaagagg cgtttaaacc gcacaacctg   660
ccgatggtct tcaccgggac tgccattctc tatatcggtt ggtttggctt aacgccggg    720 tcagcgggca cggcgaatga aatcgcgca ctggcatttg tgaatactgt ggtcgcaacg    780
gcggcggcaa ttcttggctg gatcttcggt gaatgggcgc tgcgtggtaa gccttcactg    840
```

```
ctgggggcgt gttctggcgc gattgccggt ctggtcggcg tgacgccagc ctgcggctac      900
attggggttg gcggcgcgtt gattatcggc gtggtagctg gtctggcggg cttgtggggc      960
gttaccatgc tcaaacgctt gctgcgggtg gatgatccct gcgatgtctt cggtgtgcac     1020
ggcgtttgtg gcattgtcgg ctgtatcatg accgggattt tgccgccag ctcgctgggc     1080 ggcgtgggct cgctgaagg tgtgacgatg gccatcagt tgctggtaca gctggaaagc     1140
atcgccatta cgatcgtctg gtccggtgtt gtggcattta tcggctacaa attggcggat     1200
ctgacggttg gtctgcgtgt accggaagag caggagcgag aagggctgga tgtcaacagc     1260
cacggcgaga atgcctataa cgcgtaa                                          1287

<210> SEQ ID NO 134
<211> LENGTH: 1401
<212> TYPE: DNA
<213> ORGANISM: Escherichia coli
<220> FEATURE:
<221> NAME/KEY: misc_feature
<222> LOCATION: (1)..(1401)
<223> OTHER INFORMATION: GABA permease GabP  Escherichia coli

<400> SEQUENCE: 134
atggggcaat catcgcaacc acatgagtta ggcggcgggc tgaagtcacg ccacgtcacc       60
atgttgtcta ttgccggtgt tatcggcgca agtctgtttg tcggttccag cgtcgccatc      120
gccgaagcgg gccggcggt attactggcc tatctgttcg ccggattact ggtggttatg      180
attatgcgga tgttggcgga aatggcagtt gccacgcccg ataccggttc gttttccacc      240
tatgccgata aagccattgg ccgctgggcg ggttatacca tcggctggct gtactggtgg      300
ttttgggtac tggttatccc gctggaagcc aacatcgccg ctatgatcct gcactcgtgg      360
gttccaggca ttcccatctg gttattttcc ctcgtcatta ccctcgcctt aactggcagt      420
aatttattaa gcgttaaaaa ctacggcgaa tttgagttct ggctggcgct gtgcaaagtc      480
atcgctatcc tggcctttat tttccttggt gcagtcgcaa ttagcggttt ttacccttat      540
gccgaagtga gcgggatctc aagattgtgg gatagcggcg ctttatgcc caacggtttc      600 ggtgcggtat taagcgcgat gttgatcacc atgttctcgt ttatgggcgc agaaattgtc      660
accattgccg ccgcggaatc cgacacgccg gaaaaacata ttgtccgcgc cactaactcg      720
gttatctggc gtatttctat cttctatttg tgctctattt ttgtcgtagt ggcgttaata      780
ccgtggaata tgccggggct gaaagccgtt ggttcttatc gctcggttct ggaattgctc      840
aatattcccc atgcgaaatt aatcatggac tgcgtgatat actttccgt aaccagctgt      900 ctgaactcgg cgctgtatac cgcgtcaagg atgctctact ccttaagccg tcgcggtgat      960
gcgcccgcgg taatgggcaa atcaaccgc agtaaaaccc cgtatgtggc ggtgttactc     1020
tccaccggag cggcattttt aacggtggtg gtgaactatt acgcacctgc gaaagtgttt     1080
aaattcctga tagacagctc cggtgctatc gccctgctgg tttatttagt catcgccgtt     1140
tcacagttgc ggatgcgtaa aattctgcga gcagaaggaa gcgaaattcg cttgcgcatg     1200
tggctttacc cgtggctcac ctggctggta ataggcttta ttaccttttgt gttggtagtg     1260 atgctattcc gcccggcgca acagttagaa gtgatctcta ccggcttatt agcgataggg     1320
attatctgta ccgtgccgat tatggcgcgc tggaaaaagc tggtattgtg gcaaaaaaca     1380
cccgttcata atacgcgctg a                                                1401

<210> SEQ ID NO 135
<211> LENGTH: 1239
```

```
<212> TYPE: DNA
<213> ORGANISM: Escherichia coli
<220> FEATURE:
<221> NAME/KEY: misc_feature
<222> LOCATION: (1)..(1239)
<223> OTHER INFORMATION: mtnH  Escherichia coli

<400> SEQUENCE: 135
atgacgaact atcgcgttga gagtagcagc ggacgggcgg cgcgcaagat gaggctcgca      60
ttaatgggac ctgcgttcat tgcggcgatt ggttatatcg atcccggtaa ctttgcgacc     120
aatattcagg cgggtgccag cttcggctat cagctactgt gggttgtcgt ttgggccaac     180
ctgatggcga tgctgattca gatcctctct gccaaactag ggattgccac cggtaaaaat     240
ctggcggagc agattcgcga tcactatccg cgtcccgtag tgtggttcta ttgggttcag     300
gcagaaatta ttgcgatggc aaccgacctg gcggaattta ttggtgcggc gatcggtttt     360
aaactcattc ttggtgtctc gttgttgcag ggcgcggtgc tgacggggat cgcgactttc     420
ctgattttaa tgctgcaacg tcgcgggcaa aaaccgctgg agaaagtgat tggcgggtta     480
ctgttgtttg ttgccgcggc ttacattgtc gagttgattt tctcccagcc taacctggcg     540
cagctgggta aggaatggt gatcccgagt ttacctactt cggaggcggt cttcctggca     600
gcaggcgtgt taggggcgac gattatgccg catgtgattt atttgcactc ctcgctcact     660
cagcatttac atggcggttc gcgtcaacaa cgttattccg ccaccaaatg ggatgtggct     720
atcgccatga cgattgccgg ttttgtcaat ctggcgatga tggctacagc tgcggcggcg     780
ttccactttt ctggtcatac tggtgttgcc gatcttgatg aggcttatct gacgctgcaa     840
ccgctgttaa gccatgctgc ggcaacggtc tttgggttaa gtctggttgc tgccggactg     900
tcctcaacgg tggtgggac actgcggggg caggtggtga tgcagggatt cattcgcttc     960
catatcccgc tgtgggtgcg tcgtacagtc accatgttgc cgtcatttat tgtcattctg    1020
atgggattag atccgacacg gattctggtt atgagtcagg tgctgttaag ttttggtatc    1080
gccctggcgc tggttccact gctgattttc accagtgaca gcaagttgat gggcgatctg    1140
gtgaacagca aacgcgtaaa acagacaggc tgggtgattg tagtgctggt cgtggcgctg    1200
aatatctggt tgttggtggg gacggcgctg ggattgtag                           1239

<210> SEQ ID NO 136
<211> LENGTH: 287
<212> TYPE: PRT
<213> ORGANISM: Salmonella enterica
<220> FEATURE:
<221> NAME/KEY: misc_feature
<222> LOCATION: (1)..(287)
<223> OTHER INFORMATION: Tsx - Salmonella enterica subsp. enterica
      serovar Typhimurium LT2 (STM0413)

<400> SEQUENCE: 136

Met Lys Lys Thr Leu Leu Ala Val Ser Ala Ala Leu Ala Leu Thr Ser
1               5                   10                  15

Ser Phe Thr Ala Asn Ala Ala Glu Asn Asp Gln Pro Gln Tyr Leu Ser
                20                  25                  30

Asp Trp Trp His Gln Ser Val Asn Val Val Gly Ser Tyr His Thr Arg
            35                  40                  45

Phe Ser Pro Lys Leu Asn Asn Asp Val Tyr Leu Glu Tyr Glu Ala Phe
        50                  55                  60

Ala Lys Lys Asp Trp Phe Asp Phe Tyr Gly Tyr Ile Asp Ile Pro Lys
65                  70                  75                  80
```

```
Thr Phe Asp Trp Gly Asn Gly Asn Asp Lys Gly Ile Trp Ser Asp Gly
                85                  90                  95

Ser Pro Leu Phe Met Glu Ile Glu Pro Arg Phe Ser Ile Asp Lys Leu
            100                 105                 110

Thr Gly Ala Asp Leu Ser Phe Gly Pro Phe Lys Glu Trp Tyr Phe Ala
            115                 120                 125

Asn Asn Tyr Ile Tyr Asp Met Gly Asp Asn Lys Ala Ser Arg Gln Ser
        130                 135                 140

Thr Trp Tyr Met Gly Leu Gly Thr Asp Ile Thr Gly Leu Pro Met
145                 150                 155                 160

Gly Leu Ser Leu Asn Val Tyr Ala Lys Tyr Gln Trp Gln Asn Tyr Gly
                165                 170                 175

Ala Ser Asn Glu Asn Glu Trp Asp Gly Tyr Arg Phe Lys Val Lys Tyr
            180                 185                 190

Phe Val Pro Ile Thr Asp Leu Trp Gly Gly Lys Leu Ser Tyr Ile Gly
            195                 200                 205

Phe Thr Asn Phe Asp Trp Gly Ser Asp Leu Gly Asp Asp Pro Asn Arg
        210                 215                 220

Thr Ser Asn Ser Ile Ala Ser Ser His Ile Leu Ala Leu Asn Tyr Asp
225                 230                 235                 240

His Trp His Tyr Ser Val Val Ala Arg Tyr Phe His Asn Gly Gly Gln
                245                 250                 255

Trp Gln Asn Gly Ala Lys Leu Asn Trp Gly Asp Gly Asp Phe Ser Ala
            260                 265                 270

Lys Ser Thr Gly Trp Gly Gly Tyr Leu Val Val Gly Tyr Asn Phe
            275                 280                 285

<210> SEQ ID NO 137
<211> LENGTH: 406
<212> TYPE: PRT
<213> ORGANISM: Bacillus halodurans
<220> FEATURE:
<221> NAME/KEY: misc_feature
<222> LOCATION: (1)..(406)
<223> OTHER INFORMATION: BH1446 - Bacillus halodurans (BAB05165)

<400> SEQUENCE: 137

Met Asn Ile Leu Trp Gly Leu Gly Ile Val Val Phe Leu Ile
1               5                   10                  15

Ala Phe Ala Phe Ser Thr Asn Arg Arg Ala Ile Lys Pro Arg Thr Ile
            20                  25                  30

Leu Gly Gly Leu Ala Ile Gln Leu Leu Phe Ala Ile Ile Val Leu Lys
        35                  40                  45

Ile Pro Ala Gly Gln Ala Leu Leu Glu Ser Leu Thr Asn Val Val Leu
    50                  55                  60

Asn Ile Ile Ser Tyr Ala Asn Glu Gly Ile Asp Phe Val Phe Gly Gly
65                  70                  75                  80

Phe Phe Glu Glu Gly Ser Gly Val Gly Phe Val Phe Ala Ile Asn Val
                85                  90                  95

Leu Ser Val Val Ile Phe Phe Ser Ala Leu Ile Ser Ile Leu Tyr Tyr
            100                 105                 110

Leu Gly Ile Met Gln Phe Val Ile Lys Ile Ile Gly Gly Ala Leu Ser
            115                 120                 125

Trp Leu Leu Gly Thr Ser Lys Ala Glu Ser Met Ser Ala Ala Ala Asn
        130                 135                 140

Ile Phe Val Gly Gln Thr Glu Ala Pro Leu Val Val Lys Pro Tyr Leu
```

```
                145                 150                 155                 160
Pro Lys Met Thr Gln Ser Glu Leu Phe Ala Val Met Thr Gly Gly Leu
                165                 170                 175
Ala Ser Val Ala Gly Ser Val Leu Ile Gly Tyr Ser Leu Leu Gly Val
                180                 185                 190
Pro Leu Gln Tyr Leu Leu Ala Ala Ser Phe Met Ala Ala Pro Ala Gly
                195                 200                 205
Leu Ile Met Ala Lys Met Ile Met Pro Glu Thr Glu Lys Thr Thr Asp
            210                 215                 220
Ala Glu Asp Asp Phe Lys Leu Ala Lys Asp Glu Glu Ser Thr Asn Leu
225                 230                 235                 240
Ile Asp Ala Ala Ala Asn Gly Ala Ser Thr Gly Leu Met Leu Val Leu
                245                 250                 255
Asn Ile Ala Ala Met Leu Leu Ala Phe Val Ala Leu Ile Ala Leu Ile
                260                 265                 270
Asn Gly Ile Leu Gly Trp Ile Gly Gly Leu Phe Gly Ala Ser Gln Leu
                275                 280                 285
Ser Leu Glu Leu Ile Leu Gly Tyr Val Phe Ala Pro Leu Ala Phe Val
                290                 295                 300
Ile Gly Ile Pro Trp Ala Glu Ala Leu Gln Ala Gly Ser Tyr Ile Gly
305                 310                 315                 320
Gln Lys Leu Val Val Asn Glu Phe Val Ala Tyr Leu Ser Phe Ala Pro
                325                 330                 335
Glu Ile Glu Asn Leu Ser Asp Lys Ala Val Met Val Ile Ser Phe Ala
                340                 345                 350
Leu Cys Gly Phe Ala Asn Phe Ser Ser Leu Gly Ile Leu Leu Gly Gly
                355                 360                 365
Leu Gly Lys Leu Ala Pro Ser Arg Arg Pro Asp Ile Ala Arg Leu Gly
                370                 375                 380
Leu Arg Ala Ile Leu Ala Gly Thr Leu Ala Ser Leu Leu Ser Ala Ser
385                 390                 395                 400
Ile Ala Gly Met Leu Phe
                405

<210> SEQ ID NO 138
<211> LENGTH: 393
<212> TYPE: PRT
<213> ORGANISM: Bacillus subtilis
<220> FEATURE:
<221> NAME/KEY: misc_feature
<222> LOCATION: (1)..(393)
<223> OTHER INFORMATION: nupC Bacillus subtilis subsp. subtilis 168
      (BSU39410; CAA57663)

<400> SEQUENCE: 138

Met Lys Tyr Leu Ile Gly Ile Ile Gly Leu Ile Val Phe Leu Gly Leu
1               5                   10                  15
Ala Trp Ile Ala Ser Ser Gly Lys Lys Arg Ile Lys Ile Arg Pro Ile
                20                  25                  30
Val Val Met Leu Ile Leu Gln Phe Ile Leu Gly Tyr Ile Leu Leu Asn
                35                  40                  45
Thr Gly Ile Gly Asn Phe Leu Val Gly Phe Ala Lys Gly Phe Gly
                50                  55                  60
Tyr Leu Leu Glu Tyr Ala Ala Glu Gly Ile Asn Phe Val Phe Gly Gly
65                  70                  75                  80
Leu Val Asn Ala Asp Gln Thr Thr Phe Phe Met Asn Val Leu Leu Pro
```

```
                    85                  90                  95

Ile Val Phe Ile Ser Ala Leu Ile Gly Ile Leu Gln Lys Trp Lys Val
                100                 105                 110

Leu Pro Phe Ile Ile Arg Tyr Ile Gly Leu Ala Leu Ser Lys Val Asn
                115                 120                 125

Gly Met Gly Arg Leu Glu Ser Tyr Asn Ala Val Ala Ser Ala Ile Leu
            130                 135                 140

Gly Gln Ser Glu Val Phe Ile Ser Leu Lys Lys Glu Leu Gly Leu Leu
145                 150                 155                 160

Asn Gln Gln Arg Leu Tyr Thr Leu Cys Ala Ser Ala Met Ser Thr Val
                165                 170                 175

Ser Met Ser Ile Val Gly Ala Tyr Met Thr Met Leu Lys Pro Glu Tyr
                180                 185                 190

Val Val Thr Ala Leu Val Leu Asn Leu Phe Gly Gly Phe Ile Ile Ala
                195                 200                 205

Ser Ile Ile Asn Pro Tyr Glu Val Ala Lys Glu Glu Asp Met Leu Arg
            210                 215                 220

Val Glu Glu Glu Lys Gln Ser Phe Phe Glu Val Leu Gly Glu Tyr
225                 230                 235                 240

Ile Leu Asp Gly Phe Lys Val Ala Val Val Ala Ala Met Leu Ile
                245                 250                 255

Gly Phe Val Ala Ile Ala Leu Ile Asn Gly Ile Phe Asn Ala Val
                260                 265                 270

Phe Gly Ile Ser Phe Gln Gly Ile Leu Gly Tyr Val Phe Ala Pro Phe
                275                 280                 285

Ala Phe Leu Val Gly Ile Pro Trp Asn Glu Ala Val Asn Ala Gly Ser
            290                 295                 300

Ile Met Ala Thr Lys Met Val Ser Asn Glu Phe Val Ala Met Thr Ser
305                 310                 315                 320

Leu Thr Gln Asn Gly Phe His Phe Ser Gly Arg Thr Thr Ala Ile Val
                325                 330                 335

Ser Val Phe Leu Val Ser Phe Ala Asn Phe Ser Ser Ile Gly Ile Ile
                340                 345                 350

Ala Gly Ala Val Lys Gly Leu Asn Glu Lys Gln Gly Asn Val Val Ala
            355                 360                 365

Arg Phe Gly Leu Lys Leu Leu Tyr Gly Ala Thr Leu Val Ser Phe Leu
            370                 375                 380

Ser Ala Ala Ile Val Gly Leu Ile Tyr
385                 390

<210> SEQ ID NO 139
<211> LENGTH: 404
<212> TYPE: PRT
<213> ORGANISM: Bacillus subtilis
<220> FEATURE:
<221> NAME/KEY: misc_feature
<222> LOCATION: (1)..(404)
<223> OTHER INFORMATION: yutK - Bacillus subtilis subsp. subtilis 168:
      BSU32180

<400> SEQUENCE: 139

Met Asn Val Leu Trp Gly Leu Leu Gly Ala Val Ala Ile Ile Ala Ile
1               5                   10                  15

Ala Phe Leu Phe Ser Glu Lys Lys Ser Asn Ile Lys Ile Arg Thr Val
                20                  25                  30

Ile Val Gly Leu Cys Thr Gln Val Ala Phe Gly Tyr Ile Val Leu Lys
```

```
                35                  40                  45
Trp Glu Ala Gly Arg Ala Val Phe Leu Trp Phe Ser Ser Arg Val Gln
 50                  55                  60

Leu Leu Ile Asp Tyr Ala Asn Glu Gly Ile Ser Phe Ile Phe Gly Pro
 65                  70                  75                  80

Leu Leu Lys Val Gly Asp Ser Pro Ala Phe Ala Leu Ser Val Leu Pro
                 85                  90                  95

Val Ile Ile Phe Phe Ser Ala Leu Ile Ala Val Leu Tyr His Leu Lys
                100                 105                 110

Ile Met Gln Leu Val Phe Arg Val Ile Gly Gly Leu Ser Lys Leu
            115                 120                 125

Leu Gly Thr Ser Lys Thr Glu Ser Leu Ala Ala Ala Asn Ile Phe
130                 135                 140

Val Gly Gln Ser Glu Ser Pro Leu Val Ile Lys Pro Leu Ile Ala Gly
145                 150                 155                 160

Leu Thr Arg Ser Glu Leu Phe Thr Ile Met Thr Ser Gly Leu Ser Ala
                165                 170                 175

Val Ala Gly Ser Thr Leu Phe Gly Tyr Ala Leu Leu Gly Ile Pro Ile
                180                 185                 190

Glu Tyr Leu Leu Ala Ala Ser Phe Met Ala Ala Pro Ala Gly Leu Val
            195                 200                 205

Phe Gly Lys Leu Ile Ile Pro Glu Thr Glu Lys Thr Gln Thr Val Lys
210                 215                 220

Ser Asp Phe Lys Met Asp Glu Gly Glu Gly Ala Ala Asn Val Ile Asp
225                 230                 235                 240

Ala Ala Ala Lys Gly Ala Ser Thr Gly Leu Gln Ile Ala Leu Asn Val
                245                 250                 255

Gly Ala Met Leu Leu Ala Phe Val Ala Leu Ile Ala Val Val Asn Gly
                260                 265                 270

Ile Leu Gly Gly Ala Phe Gly Leu Phe Gly Leu Lys Gly Val Thr Leu
            275                 280                 285

Glu Ser Ile Leu Gly Tyr Val Phe Ser Pro Ile Ala Phe Leu Ile Gly
290                 295                 300

Val Pro Trp His Glu Ala Leu Gln Ala Gly Ser Tyr Ile Gly Gln Lys
305                 310                 315                 320

Leu Val Leu Asn Glu Phe Val Ala Tyr Ser Asn Phe Gly Ser His Ile
                325                 330                 335

Gly Glu Phe Ser Lys Lys Thr Ala Thr Ile Ile Ser Phe Ala Leu Cys
            340                 345                 350

Gly Phe Ala Asn Phe Ser Ser Ile Ala Ile Met Leu Gly Thr Leu Gly
        355                 360                 365

Gly Leu Ala Pro Ser Arg Arg Ser Asp Ile Ala Arg Leu Gly Leu Lys
370                 375                 380

Ala Val Leu Ala Gly Thr Leu Ala Asn Leu Leu Ser Ala Ala Ile Ala
385                 390                 395                 400

Gly Met Phe Ile

<210> SEQ ID NO 140
<211> LENGTH: 397
<212> TYPE: PRT
<213> ORGANISM: Bacillus subtilis
<220> FEATURE:
<221> NAME/KEY: misc_feature
<222> LOCATION: (1)..(397)
<223> OTHER INFORMATION: yxjA - Bacillus subtilis subsp. spizizenii W23
```

(BSUW23_19355)

<400> SEQUENCE: 140

```
Met Tyr Phe Leu Leu Asn Leu Val Gly Leu Ile Val Ile Met Ala Val
1               5                   10                  15

Val Phe Leu Cys Ser Pro Gln Lys Lys Lys Ile Gln Trp Arg Pro Ile
            20                  25                  30

Ile Thr Leu Ile Val Leu Glu Leu Leu Ile Thr Trp Phe Met Leu Gly
        35                  40                  45

Thr Lys Val Gly Ser Trp Ala Ile Gly Lys Ile Gly Asp Phe Phe Thr
    50                  55                  60

Trp Leu Ile Ala Cys Ala Ser Asp Gly Ile Ala Phe Ala Phe Pro Ser
65                  70                  75                  80

Val Met Ala Asn Glu Thr Val Asp Phe Phe Ser Ala Leu Leu Pro
                85                  90                  95

Ile Ile Phe Ile Val Thr Phe Phe Asp Ile Leu Thr Tyr Phe Gly Ile
                100                 105                 110

Leu Pro Trp Leu Ile Asp Lys Ile Gly Trp Val Ile Ser Lys Ala Ser
            115                 120                 125

Arg Leu Pro Lys Leu Glu Ser Phe Phe Ser Ile Gln Met Met Phe Leu
    130                 135                 140

Gly Asn Thr Glu Ala Leu Ala Val Ile Arg Gln Gln Leu Thr Val Leu
145                 150                 155                 160

Asn Asn Asn Arg Leu Leu Thr Phe Gly Leu Met Ser Met Ser Ser Ile
                165                 170                 175

Ser Gly Ser Ile Ile Gly Ser Tyr Leu Ser Met Val Pro Ala Thr Tyr
                180                 185                 190

Val Phe Thr Ala Ile Pro Leu Asn Cys Leu Asn Ala Leu Ile Ile Ala
            195                 200                 205

Asn Leu Leu Asn Pro Val His Val Pro Glu Asp Glu Asp Ile Ile Tyr
                210                 215                 220

Thr Pro Pro Lys Glu Glu Lys Lys Asp Phe Phe Ser Thr Ile Ser Asn
225                 230                 235                 240

Ser Met Leu Val Gly Met Asn Met Val Ile Val Ile Leu Ala Met Val
                245                 250                 255

Ile Gly Tyr Val Ala Leu Thr Ser Ala Val Asn Gly Ile Leu Gly Val
                260                 265                 270

Phe Val His Gly Leu Thr Ile Gln Thr Ile Phe Ala Tyr Leu Phe Ser
            275                 280                 285

Pro Phe Ala Phe Leu Leu Gly Leu Pro Val His Asp Ala Met Tyr Val
    290                 295                 300

Ala Gln Leu Met Gly Met Lys Leu Ala Thr Asn Glu Phe Val Ala Met
305                 310                 315                 320

Leu Asp Leu Lys Asn Asn Leu Thr Thr Leu Pro Pro His Thr Val Ala
                325                 330                 335

Val Ala Thr Thr Phe Leu Thr Ser Phe Ala Asn Phe Ser Thr Val Gly
            340                 345                 350

Met Ile Tyr Gly Thr Tyr Asn Ser Ile Leu Asp Gly Glu Lys Ser Thr
            355                 360                 365

Val Ile Gly Lys Asn Val Trp Lys Leu Leu Val Ser Gly Ile Ala Val
        370                 375                 380

Ser Leu Leu Ser Ala Ala Ile Val Gly Leu Phe Val Trp
385                 390                 395
```

<210> SEQ ID NO 141
<211> LENGTH: 426
<212> TYPE: PRT
<213> ORGANISM: Caulobacter crescentus CB15
<220> FEATURE:
<221> NAME/KEY: misc_feature
<222> LOCATION: (1)..(426)
<223> OTHER INFORMATION: ccCNT (CC2089) - Caulobacter crescentus CB15
     (AAK24060)

<400> SEQUENCE: 141

```
Met Phe Arg Pro Glu Asn Val Gln Ala Leu Ala Gly Leu Ala Leu Thr
1               5                   10                  15

Leu Gly Leu Cys Trp Leu Val Ser Glu Asn Arg Lys Arg Phe Pro Trp
            20                  25                  30

Gly Leu Ala Ile Gly Ala Val Val Ile Gln Val Leu Leu Val Leu Val
        35                  40                  45

Leu Phe Gly Leu Pro Gln Ala Gln Gln Met Leu Arg Gly Val Asn Gly
    50                  55                  60

Ala Val Glu Gly Leu Ala Ala Ser Thr Gln Ala Gly Thr Ala Phe Val
65                  70                  75                  80

Phe Gly Phe Leu Ala Gly Asp Gln Pro Tyr Pro Val Ser Asn Pro
                85                  90                  95

Gly Ala Gly Phe Ile Phe Ala Phe Arg Val Leu Pro Val Ile Leu Val
            100                 105                 110

Val Cys Ala Leu Ser Ala Leu Leu Trp His Trp Lys Ile Leu Lys Trp
        115                 120                 125

Leu Ala Gln Gly Phe Gly Phe Val Phe Gln Lys Thr Leu Gly Leu Arg
    130                 135                 140

Gly Pro Pro Ala Leu Ala Thr Ala Ala Thr Ile Phe Met Gly Gln Val
145                 150                 155                 160

Glu Gly Pro Ile Phe Ile Arg Ala Tyr Leu Asp Lys Leu Ser Arg Ser
                165                 170                 175

Glu Leu Phe Met Leu Ile Ala Val Gly Met Ala Cys Val Ser Gly Ser
            180                 185                 190

Thr Met Val Ala Tyr Ala Thr Ile Leu Ala Asp Val Leu Pro Asn Ala
        195                 200                 205

Ala Ala His Val Leu Thr Ala Ser Ile Ser Ala Pro Ala Gly Val
    210                 215                 220

Leu Leu Ala Arg Ile Ile Val Pro Ser Asp Pro Met Glu Lys Ser Ala
225                 230                 235                 240

Asp Leu Asp Leu Ser Thr Glu Asp Lys Thr Tyr Gly Ser Ser Ile Asp
                245                 250                 255

Ala Val Met Lys Gly Thr Thr Asp Gly Leu Gln Ile Ala Leu Asn Val
            260                 265                 270

Gly Ala Thr Leu Ile Val Phe Val Ala Leu Ala Thr Met Val Asp Lys
        275                 280                 285

Val Leu Gly Ala Phe Pro Pro Val Gly Gly Glu Pro Leu Ser Ile Ala
    290                 295                 300

Arg Gly Leu Gly Val Val Phe Ala Pro Leu Ala Trp Ser Met Gly Ile
305                 310                 315                 320

Pro Trp Lys Glu Ala Gly Thr Ala Gly Gly Leu Leu Gly Val Lys Leu
                325                 330                 335

Ile Leu Thr Glu Phe Thr Ala Phe Pro Ile Gln Leu Ser Lys Val Gly Glu
            340                 345                 350
```

```
Ala Leu Leu Asp Glu Arg Thr Arg Met Ile Met Thr Tyr Ala Leu Cys
            355                 360                 365

Gly Phe Ala Asn Ile Gly Ser Val Gly Met Asn Val Ala Gly Phe Ser
    370                 375                 380

Val Leu Val Pro Gln Arg Arg Gln Glu Val Leu Gly Leu Val Trp Lys
385                 390                 395                 400

Ala Met Met Ala Gly Phe Leu Ala Thr Cys Leu Thr Ala Ser Leu Val
                405                 410                 415

Gly Leu Met Pro Arg Ser Leu Phe Gly Leu
            420                 425

<210> SEQ ID NO 142
<211> LENGTH: 416
<212> TYPE: PRT
<213> ORGANISM: Escherichia coli
<220> FEATURE:
<221> NAME/KEY: misc_feature
<222> LOCATION: (1)..(416)
<223> OTHER INFORMATION: yeiJ - Escherichia coli K-12 W3110 (AAC75222;
      JW2148)

<400> SEQUENCE: 142

Met Asp Val Met Arg Ser Val Leu Gly Met Val Val Leu Leu Thr Ile
1               5                   10                  15

Ala Phe Leu Leu Ser Val Asn Lys Lys Lys Ile Ser Leu Arg Thr Val
            20                  25                  30

Gly Ala Ala Leu Val Leu Gln Val Val Ile Gly Gly Ile Met Leu Trp
        35                  40                  45

Leu Pro Pro Gly Arg Trp Val Ala Glu Lys Val Ala Phe Gly Val His
50                  55                  60

Lys Val Met Ala Tyr Ser Asp Ala Gly Ser Ala Phe Ile Phe Gly Ser
65                  70                  75                  80

Leu Val Gly Pro Lys Met Asp Thr Leu Phe Asp Gly Ala Gly Phe Ile
                85                  90                  95

Phe Gly Phe Arg Val Leu Pro Ala Ile Ile Phe Val Thr Ala Leu Val
            100                 105                 110

Ser Ile Leu Tyr Tyr Ile Gly Val Met Gly Ile Leu Ile Arg Ile Leu
        115                 120                 125

Gly Gly Ile Phe Gln Lys Ala Leu Asn Ile Ser Lys Ile Glu Ser Phe
    130                 135                 140

Val Ala Val Thr Thr Ile Phe Leu Gly Gln Asn Glu Ile Pro Ala Ile
145                 150                 155                 160

Val Lys Pro Phe Ile Asp Arg Leu Asn Arg Asn Glu Leu Phe Thr Ala
                165                 170                 175

Ile Cys Ser Gly Met Ala Ser Ile Ala Gly Ser Thr Met Ile Gly Tyr
            180                 185                 190

Ala Ala Leu Gly Val Pro Val Glu Tyr Leu Leu Ala Ala Ser Leu Met
        195                 200                 205

Ala Ile Pro Gly Gly Ile Leu Phe Ala Arg Leu Leu Ser Pro Ala Thr
    210                 215                 220

Glu Ser Ser Gln Val Ser Phe Asn Asn Leu Ser Phe Thr Glu Thr Pro
225                 230                 235                 240

Pro Lys Ser Ile Ile Glu Ala Ala Thr Gly Ala Met Thr Gly Leu
                245                 250                 255

Lys Ile Ala Ala Gly Val Ala Thr Val Val Met Ala Phe Val Ala Ile
            260                 265                 270
```

```
Ile Ala Leu Ile Asn Gly Ile Gly Gly Val Gly Gly Trp Phe Gly
            275                 280                 285

Phe Glu His Ala Ser Leu Glu Ser Ile Leu Gly Tyr Leu Leu Ala Pro
290                 295                 300

Leu Ala Trp Val Met Gly Val Asp Trp Ser Asp Ala Asn Leu Ala Gly
305                 310                 315                 320

Ser Leu Ile Gly Gln Lys Leu Ala Ile Asn Glu Phe Val Ala Tyr Leu
                325                 330                 335

Asn Phe Ser Pro Tyr Leu Gln Thr Ala Gly Thr Leu Asp Ala Lys Thr
                340                 345                 350

Val Ala Ile Ile Ser Phe Ala Leu Cys Gly Phe Ala Asn Phe Gly Ser
                355                 360                 365

Ile Gly Val Val Val Gly Ala Phe Ser Ala Val Ala Pro His Arg Ala
            370                 375                 380

Pro Glu Ile Ala Gln Leu Gly Leu Arg Ala Leu Ala Ala Thr Leu
385                 390                 395                 400

Ser Asn Leu Met Ser Ala Thr Ile Ala Gly Phe Phe Ile Gly Leu Ala
                405                 410                 415

<210> SEQ ID NO 143
<211> LENGTH: 416
<212> TYPE: PRT
<213> ORGANISM: Escherichia coli
<220> FEATURE:
<221> NAME/KEY: misc_feature
<222> LOCATION: (1)..(416)
<223> OTHER INFORMATION: yeiM - Escherichia coli K-12 W3110 (AAC75225;
      JW2151)

<400> SEQUENCE: 143

Met Asp Ile Met Arg Ser Val Val Gly Met Val Val Leu Leu Ala Ile
1               5                   10                  15

Ala Phe Leu Leu Ser Val Asn Lys Lys Ser Ile Ser Leu Arg Thr Val
                20                  25                  30

Gly Ala Ala Leu Leu Leu Gln Ile Ala Ile Gly Gly Ile Met Leu Tyr
            35                  40                  45

Phe Pro Pro Gly Lys Trp Ala Val Glu Gln Ala Ala Leu Gly Val His
50                  55                  60

Lys Val Met Ser Tyr Ser Asp Ala Gly Ser Ala Phe Ile Phe Gly Ser
65                  70                  75                  80

Leu Val Gly Pro Lys Met Asp Val Leu Phe Asp Gly Ala Gly Phe Ile
                85                  90                  95

Phe Ala Phe Arg Val Leu Pro Ala Ile Ile Phe Val Thr Ala Leu Ile
                100                 105                 110

Ser Leu Leu Tyr Tyr Ile Gly Val Met Gly Leu Leu Ile Arg Ile Leu
            115                 120                 125

Gly Ser Ile Phe Gln Lys Ala Leu Asn Ile Ser Lys Ile Glu Ser Phe
130                 135                 140

Val Ala Val Thr Thr Ile Phe Leu Gly Gln Asn Glu Ile Pro Ala Ile
145                 150                 155                 160

Val Lys Pro Phe Ile Asp Arg Met Asn Arg Asn Glu Leu Phe Thr Ala
                165                 170                 175

Ile Cys Ser Gly Met Ala Ser Ile Ala Gly Ser Met Met Ile Gly Tyr
                180                 185                 190

Ala Gly Met Gly Val Pro Ile Asp Tyr Leu Leu Ala Ala Ser Leu Met
            195                 200                 205
```

Ala Ile Pro Gly Gly Ile Leu Phe Ala Arg Ile Leu Ser Pro Ala Thr
            210                 215                 220

Glu Pro Ser Gln Val Thr Phe Glu Asn Leu Ser Phe Ser Glu Thr Pro
225                 230                 235                 240

Pro Lys Ser Phe Ile Glu Ala Ala Ser Gly Ala Met Thr Gly Leu
                245                 250                 255

Lys Ile Ala Ala Gly Val Ala Thr Val Val Met Ala Phe Val Ala Ile
            260                 265                 270

Ile Ala Leu Ile Asn Gly Ile Gly Gly Ile Gly Trp Phe Gly
                275                 280                 285

Phe Ala Asn Ala Ser Leu Glu Ser Ile Phe Gly Tyr Val Leu Ala Pro
            290                 295                 300

Leu Ala Trp Ile Met Gly Val Asp Trp Ser Asp Ala Asn Leu Ala Gly
305                 310                 315                 320

Ser Leu Ile Gly Gln Lys Leu Ala Ile Asn Glu Phe Val Ala Tyr Leu
                325                 330                 335

Ser Phe Ser Pro Tyr Leu Gln Thr Gly Gly Thr Leu Glu Val Lys Thr
                340                 345                 350

Ile Ala Ile Ile Ser Phe Ala Leu Cys Gly Phe Ala Asn Phe Gly Ser
                355                 360                 365

Ile Gly Val Val Val Gly Ala Phe Ser Ala Ile Ser Pro Lys Arg Ala
370                 375                 380

Pro Glu Ile Ala Gln Leu Gly Leu Arg Ala Leu Ala Ala Thr Leu
385                 390                 395                 400

Ser Asn Leu Met Ser Ala Thr Ile Ala Gly Phe Phe Ile Gly Leu Ala
                405                 410                 415

<210> SEQ ID NO 144
<211> LENGTH: 417
<212> TYPE: PRT
<213> ORGANISM: Haemophilus influenzae
<220> FEATURE:
<221> NAME/KEY: misc_feature
<222> LOCATION: (1)..(417)
<223> OTHER INFORMATION: HI0519 - Haemophilus influenzae Rd KW20
      serotype d(AAC22177)

<400> SEQUENCE: 144

Met Ser Val Leu Ser Ser Ile Leu Gly Met Val Val Leu Ile Ala Ile
1               5                   10                  15

Ala Val Leu Leu Ser Asn Asn Arg Lys Ala Ile Ser Ile Arg Thr Val
            20                  25                  30

Val Gly Ala Leu Ala Ile Gln Val Gly Phe Ala Ala Leu Ile Leu Tyr
        35                  40                  45

Val Pro Ala Gly Lys Gln Ala Leu Gly Ala Ala Ala Asp Met Val Ser
    50                  55                  60

Asn Val Ile Ala Tyr Gly Asn Asp Gly Ile Asn Phe Val Phe Gly Gly
65                  70                  75                  80

Leu Ala Asp Pro Ser Lys Pro Ser Gly Phe Ile Phe Ala Val Lys Val
                85                  90                  95

Leu Pro Ile Ile Val Phe Phe Ser Gly Leu Ile Ser Val Leu Tyr Tyr
            100                 105                 110

Leu Gly Ile Met Gln Val Val Ile Lys Val Leu Gly Gly Ala Leu Gln
        115                 120                 125

Lys Ala Leu Gly Thr Ser Lys Ala Glu Ser Met Ser Ala Ala Ala Asn
    130                 135                 140

```
Ile Phe Val Gly Gln Thr Glu Ala Pro Leu Val Arg Pro Tyr Ile
145                 150                 155                 160

Lys Asn Met Thr Gln Ser Glu Leu Phe Ala Ile Met Val Gly Gly Thr
                165                 170                 175

Ala Ser Ile Ala Gly Ser Val Met Ala Gly Tyr Ala Gly Met Gly Val
            180                 185                 190

Pro Leu Thr Tyr Leu Ile Ala Ala Ser Phe Met Ala Pro Ala Gly
        195                 200                 205

Leu Leu Phe Ala Lys Leu Met Phe Pro Gln Thr Glu Gln Phe Thr Asp
    210                 215                 220

Lys Gln Pro Glu Asp Asn Asp Ser Glu Lys Pro Thr Asn Val Leu Glu
225                 230                 235                 240

Ala Met Ala Gly Gly Ala Ser Ala Gly Met Gln Leu Ala Leu Asn Val
                245                 250                 255

Gly Ala Met Leu Ile Ala Phe Val Gly Leu Ile Ala Leu Ile Asn Gly
            260                 265                 270

Ile Leu Ser Gly Val Gly Gly Trp Phe Gly Tyr Gly Asp Leu Thr Leu
        275                 280                 285

Gln Ser Ile Phe Gly Leu Ile Phe Lys Pro Leu Ala Tyr Leu Ile Gly
    290                 295                 300

Val Thr Asp Gly Ala Glu Ala Gly Ile Ala Gly Gln Met Ile Gly Met
305                 310                 315                 320

Lys Leu Ala Val Asn Glu Phe Val Gly Tyr Leu Glu Phe Ala Lys Tyr
                325                 330                 335

Leu Gln Pro Asp Ser Ala Ile Val Leu Thr Glu Lys Thr Lys Ala Ile
            340                 345                 350

Ile Thr Phe Ala Leu Cys Gly Phe Ala Asn Phe Ser Ser Ile Ala Ile
        355                 360                 365

Leu Ile Gly Gly Leu Gly Gly Met Ala Pro Ser Arg Arg Ser Asp Val
    370                 375                 380

Ala Arg Leu Gly Ile Lys Ala Val Ile Ala Gly Thr Leu Ala Asn Leu
385                 390                 395                 400

Met Ser Ala Thr Ile Ala Gly Leu Phe Ile Gly Leu Gly Ala Ala Ala
                405                 410                 415

Leu
```

<210> SEQ ID NO 145
<211> LENGTH: 418
<212> TYPE: PRT
<213> ORGANISM: Helicobacter pylori 26695
<220> FEATURE:
<221> NAME/KEY: misc_feature
<222> LOCATION: (1)..(418)
<223> OTHER INFORMATION: nupC (HP1180) - Helicobacter pylori 26695
      (AAD08224)

<400> SEQUENCE: 145

```
Met Ile Phe Ser Ser Leu Phe Ser Val Val Gly Met Ala Val Leu Phe
1               5                   10                  15

Leu Ile Ala Trp Val Phe Ser Ser Asn Lys Arg Ala Ile Asn Tyr Arg
            20                  25                  30

Thr Ile Val Ser Ala Phe Val Ile Gln Val Ala Leu Gly Ala Leu Ala
        35                  40                  45

Leu Tyr Val Pro Leu Gly Arg Glu Met Leu Gln Gly Leu Ala Ser Gly
    50                  55                  60

Ile Gln Ser Val Ile Ser Tyr Gly Tyr Glu Gly Val Arg Phe Leu Phe
```

```
                65                  70                  75                  80
Gly Asn Leu Ala Pro Asn Ala Lys Gly Asp Gln Gly Ile Gly Phe
                    85                  90                  95
Val Phe Ala Ile Asn Val Leu Ala Ile Ile Phe Ala Ser Leu
                100                 105                 110
Ile Ser Leu Leu Tyr Tyr Leu Lys Ile Met Pro Leu Phe Ile Asn Leu
                115                 120                 125
Ile Gly Gly Ala Leu Gln Lys Cys Leu Gly Thr Ser Arg Ala Glu Ser
            130                 135                 140
Met Ser Ala Ala Ala Asn Ile Phe Val Ala His Thr Glu Ala Pro Leu
145                 150                 155                 160
Val Ile Lys Pro Tyr Leu Lys Ser Met Ser Asp Ser Glu Ile Phe Ala
                165                 170                 175
Val Met Cys Val Gly Met Ala Ser Val Ala Gly Pro Val Leu Ala Gly
                180                 185                 190
Tyr Ala Ser Met Gly Ile Pro Leu Pro Tyr Leu Ile Ala Ala Ser Phe
                195                 200                 205
Met Ser Ala Pro Gly Gly Leu Leu Phe Ala Lys Ile Ile Tyr Pro Gln
            210                 215                 220
Asn Glu Thr Ile Ser Ser His Ala Asp Val Ser Ile Glu Lys His Val
225                 230                 235                 240
Asn Ala Ile Glu Ala Ile Ala Asn Gly Ala Ser Thr Gly Leu Asn Leu
                245                 250                 255
Ala Leu His Val Gly Ala Met Leu Leu Ala Phe Val Gly Met Leu Ala
                260                 265                 270
Leu Ile Asn Gly Leu Leu Gly Val Val Gly Phe Leu Gly Met Glu
                275                 280                 285
His Leu Ser Leu Gly Leu Ile Leu Gly Thr Leu Leu Lys Pro Leu Ala
            290                 295                 300
Phe Met Leu Gly Ile Pro Trp Ser Gln Ala Gly Ile Ala Gly Glu Ile
305                 310                 315                 320
Ile Gly Ile Lys Ile Ala Leu Asn Glu Phe Val Gly Tyr Met Gln Leu
                325                 330                 335
Leu Pro Tyr Leu Gly Asp Asn Pro Pro Leu Ile Leu Ser Glu Lys Thr
                340                 345                 350
Lys Ala Ile Ile Thr Phe Ala Leu Cys Gly Phe Ala Asn Leu Ser Ser
                355                 360                 365
Val Ala Met Leu Ile Gly Gly Leu Gly Ser Leu Val Pro Lys Lys Lys
                370                 375                 380
Asp Leu Ile Val Arg Leu Ala Leu Lys Ala Val Leu Val Gly Thr Leu
385                 390                 395                 400
Ser Asn Phe Met Ser Ala Thr Ile Ala Gly Leu Phe Ile Gly Leu Asn
                405                 410                 415
Ala His
```

<210> SEQ ID NO 146
<211> LENGTH: 409
<212> TYPE: PRT
<213> ORGANISM: Staphylococcus aureus
<220> FEATURE:
<221> NAME/KEY: misc_feature
<222> LOCATION: (1)..(409)
<223> OTHER INFORMATION: nupC (SA0600) - Staphylococcus aureus subsp.
      aureus N315 (BAB41833)

<400> SEQUENCE: 146

```
Met Phe Leu Leu Ile Asn Ile Ile Gly Leu Ile Val Phe Leu Gly Ile
1               5                   10                  15

Ala Val Leu Phe Ser Arg Asp Arg Lys Asn Ile Gln Trp Gln Ser Ile
            20                  25                  30

Gly Ile Leu Val Val Leu Asn Leu Phe Leu Ala Trp Phe Phe Ile Tyr
            35                  40                  45

Phe Asp Trp Gly Gln Lys Ala Val Arg Gly Ala Ala Asn Gly Ile Ala
    50                  55                  60

Trp Val Val Gln Ser Ala His Ala Gly Thr Gly Phe Ala Phe Ala Ser
65                  70                  75                  80

Leu Thr Asn Val Lys Met Met Asp Met Ala Val Ala Ala Leu Phe Pro
                85                  90                  95

Ile Leu Leu Ile Val Pro Leu Phe Asp Ile Leu Met Tyr Phe Asn Ile
                100                 105                 110

Leu Pro Lys Ile Ile Gly Gly Ile Gly Trp Leu Leu Ala Lys Val Thr
        115                 120                 125

Arg Gln Pro Lys Phe Glu Ser Phe Phe Gly Ile Glu Met Met Phe Leu
130                 135                 140

Gly Asn Thr Glu Ala Leu Ala Val Ser Ser Glu Gln Leu Lys Arg Met
145                 150                 155                 160

Asn Glu Met Arg Val Leu Thr Ile Ala Met Met Ser Met Ser Ser Val
                165                 170                 175

Ser Gly Ala Ile Val Gly Ala Tyr Val Gln Met Val Pro Gly Glu Leu
                180                 185                 190

Val Leu Thr Ala Ile Pro Leu Asn Ile Val Asn Ala Ile Ile Val Ser
            195                 200                 205

Cys Leu Leu Asn Pro Val Ser Val Glu Glu Lys Glu Asp Ile Ile Tyr
210                 215                 220

Ser Leu Lys Asn Asn Glu Val Glu Arg Gln Pro Phe Phe Ser Phe Leu
225                 230                 235                 240

Gly Asp Ser Val Leu Ala Ala Gly Lys Leu Val Leu Ile Ile Ile Ala
                245                 250                 255

Phe Val Ile Ser Phe Val Ala Leu Ala Asp Leu Phe Asp Arg Phe Ile
                260                 265                 270

Asn Leu Ile Thr Gly Leu Ile Ala Gly Trp Ile Gly Ile Lys Gly Ser
            275                 280                 285

Phe Gly Leu Asn Gln Ile Leu Gly Val Phe Met Tyr Pro Phe Ala Leu
    290                 295                 300

Leu Leu Gly Leu Pro Tyr Asp Glu Ala Trp Leu Val Ala Gln Gln Met
305                 310                 315                 320

Ala Lys Lys Ile Val Thr Asn Glu Phe Val Val Met Gly Glu Ile Ser
                325                 330                 335

Lys Asp Ile Ala Ser Tyr Thr Pro His His Arg Ala Val Ile Thr Thr
            340                 345                 350

Phe Leu Ile Ser Phe Ala Asn Phe Ser Thr Ile Gly Met Ile Ile Gly
        355                 360                 365

Thr Leu Lys Gly Ile Val Asp Lys Lys Thr Ser Asp Phe Val Ser Lys
370                 375                 380

Tyr Val Pro Met Met Leu Leu Ser Gly Ile Leu Val Ser Leu Leu Thr
385                 390                 395                 400

Ala Ala Phe Val Gly Leu Phe Ala Trp
                405
```

<210> SEQ ID NO 147
<211> LENGTH: 409
<212> TYPE: PRT
<213> ORGANISM: Staphylococcus aureus
<220> FEATURE:
<221> NAME/KEY: misc_feature
<222> LOCATION: (1)..(409)
<223> OTHER INFORMATION: nupC (SAV0645) -Staphylococcus aureus subsp.
      aureus Mu50 (BAB56807)

<400> SEQUENCE: 147

```
Met Phe Leu Leu Ile Asn Ile Ile Gly Leu Ile Val Phe Leu Gly Ile
1               5                   10                  15

Ala Val Leu Phe Ser Arg Asp Arg Lys Asn Ile Gln Trp Gln Ser Ile
            20                  25                  30

Gly Ile Leu Val Val Leu Asn Leu Phe Leu Ala Trp Phe Phe Ile Tyr
        35                  40                  45

Phe Asp Trp Gly Gln Lys Ala Val Arg Gly Ala Ala Asn Gly Ile Ala
    50                  55                  60

Trp Val Val Gln Ser Ala His Ala Gly Thr Gly Phe Ala Phe Ala Ser
65                  70                  75                  80

Leu Thr Asn Val Lys Met Met Asp Met Ala Val Ala Ala Leu Phe Pro
                85                  90                  95

Ile Leu Leu Ile Val Pro Leu Phe Asp Ile Leu Met Tyr Phe Asn Ile
            100                 105                 110

Leu Pro Lys Ile Ile Gly Gly Ile Gly Trp Leu Leu Ala Lys Val Thr
        115                 120                 125

Arg Gln Pro Lys Phe Glu Ser Phe Phe Gly Ile Glu Met Met Phe Leu
    130                 135                 140

Gly Asn Thr Glu Ala Leu Ala Val Ser Ser Glu Gln Leu Lys Arg Met
145                 150                 155                 160

Asn Glu Met Arg Val Leu Thr Ile Ala Met Met Ser Met Ser Ser Val
                165                 170                 175

Ser Gly Ala Ile Val Gly Ala Tyr Val Gln Met Val Pro Gly Glu Leu
            180                 185                 190

Val Leu Thr Ala Ile Pro Leu Asn Ile Val Asn Ala Ile Ile Val Ser
        195                 200                 205

Cys Leu Leu Asn Pro Val Ser Val Glu Glu Lys Glu Asp Ile Ile Tyr
    210                 215                 220

Ser Leu Lys Asn Asn Glu Val Glu Arg Gln Pro Phe Phe Ser Phe Leu
225                 230                 235                 240

Gly Asp Ser Val Leu Ala Ala Gly Lys Leu Val Leu Ile Ile Ile Ala
                245                 250                 255

Phe Val Ile Ser Phe Val Ala Leu Ala Asp Leu Phe Asp Arg Phe Ile
            260                 265                 270

Asn Leu Ile Thr Gly Leu Ile Ala Gly Trp Ile Gly Ile Lys Gly Ser
        275                 280                 285

Phe Gly Leu Asn Gln Ile Leu Gly Val Phe Met Tyr Pro Phe Ala Leu
    290                 295                 300

Leu Leu Gly Leu Pro Tyr Asp Glu Ala Trp Leu Val Ala Gln Gln Met
305                 310                 315                 320

Ala Lys Lys Ile Val Thr Asn Glu Phe Val Val Met Gly Glu Ile Ser
                325                 330                 335

Lys Asp Ile Ala Ser Tyr Thr Pro His His Arg Ala Val Ile Thr Thr
            340                 345                 350
```

```
Phe Leu Ile Ser Phe Ala Asn Phe Ser Thr Ile Gly Met Ile Ile Gly
            355                 360                 365

Thr Leu Lys Gly Ile Val Asp Lys Thr Ser Asp Phe Val Ser Lys
    370                 375                 380

Tyr Val Pro Met Met Leu Leu Ser Gly Ile Leu Val Ser Leu Leu Thr
385                 390                 395                 400

Ala Ala Phe Val Gly Leu Phe Ala Trp
                405

<210> SEQ ID NO 148
<211> LENGTH: 400
<212> TYPE: PRT
<213> ORGANISM: Streptococcus pyogenes SF370
<220> FEATURE:
<221> NAME/KEY: misc_feature
<222> LOCATION: (1)..(400)
<223> OTHER INFORMATION: nupC (SpNupC) - Streptococcus pyogenes SF370
      serotype M1 (AAK34582)

<400> SEQUENCE: 148

Met Gln Phe Ile Tyr Ser Ile Ile Gly Ile Leu Leu Val Leu Gly Ile
1               5                   10                  15

Val Tyr Ala Ile Ser Phe Asn Arg Lys Ser Val Ser Leu Ser Leu Ile
            20                  25                  30

Gly Lys Ala Leu Ile Val Gln Phe Ile Ala Leu Ile Leu Val Arg
        35                  40                  45

Ile Pro Leu Gly Gln Gln Ile Val Ser Val Ser Thr Gly Val Thr
    50                  55                  60

Ser Val Ile Asn Cys Gly Gln Ala Gly Leu Asn Phe Val Phe Gly Ser
65                  70                  75                  80

Leu Ala Asp Ser Gly Ala Lys Thr Gly Phe Ile Phe Ala Ile Gln Thr
                85                  90                  95

Leu Gly Asn Ile Val Phe Leu Ser Ala Leu Val Ser Leu Leu Tyr Tyr
            100                 105                 110

Val Gly Ile Leu Gly Phe Val Val Lys Trp Ile Gly Lys Gly Val Gly
        115                 120                 125

Lys Ile Met Lys Ser Ser Glu Val Glu Ser Phe Val Ala Val Ala Asn
    130                 135                 140

Met Phe Leu Gly Gln Thr Asp Ser Pro Ile Leu Val Ser Lys Tyr Leu
145                 150                 155                 160

Gly Arg Met Thr Asp Ser Glu Ile Met Val Val Leu Val Ser Gly Met
                165                 170                 175

Gly Ser Met Ser Val Ser Ile Leu Gly Gly Tyr Ile Ala Leu Gly Ile
            180                 185                 190

Pro Met Glu Tyr Leu Leu Ile Ala Ser Thr Met Val Pro Ile Gly Ser
        195                 200                 205

Ile Leu Ile Ala Lys Ile Leu Leu Pro Gln Thr Glu Pro Val Gln Lys
    210                 215                 220

Ile Asp Asp Ile Lys Met Asp Asn Lys Gly Asn Asn Ala Asn Val Ile
225                 230                 235                 240

Asp Ala Ile Ala Glu Gly Ala Ser Thr Gly Ala Gln Met Ala Phe Ser
                245                 250                 255

Ile Gly Ala Ser Leu Ile Ala Phe Val Gly Leu Val Ser Leu Ile Asn
            260                 265                 270

Met Met Leu Ser Gly Leu Gly Ile Arg Leu Glu Gln Ile Phe Ser Tyr
        275                 280                 285
```

```
Val Phe Ala Pro Phe Gly Phe Leu Met Gly Phe Asp His Lys Asn Ile
            290                 295                 300

Leu Leu Glu Gly Asn Leu Leu Gly Ser Lys Leu Ile Leu Asn Glu Phe
305                 310                 315                 320

Val Ser Phe Gln Gln Leu Gly His Leu Ile Lys Ser Leu Asp Tyr Arg
                325                 330                 335

Thr Ala Leu Val Ala Thr Ile Ser Leu Cys Gly Phe Ala Asn Leu Ser
                340                 345                 350

Ser Leu Gly Ile Cys Val Ser Gly Ile Ala Val Leu Cys Pro Glu Lys
                355                 360                 365

Arg Ser Thr Leu Ala Arg Leu Val Phe Arg Ala Met Ile Gly Gly Ile
370                 375                 380

Ala Val Ser Met Leu Ser Ala Phe Ile Val Gly Ile Val Thr Leu Phe
385                 390                 395                 400

<210> SEQ ID NO 149
<211> LENGTH: 418
<212> TYPE: PRT
<213> ORGANISM: Vibrio cholerae O1 biovar El Tor N16961
<220> FEATURE:
<221> NAME/KEY: misc_feature
<222> LOCATION: (1)..(418)
<223> OTHER INFORMATION: nupC (VC2352) - Vibrio cholerae O1 biovar El
      Tor N16961 (AAF95495)

<400> SEQUENCE: 149

Met Ser Leu Phe Met Ser Leu Ile Gly Met Ala Val Leu Leu Gly Ile
1               5                   10                  15

Ala Val Leu Leu Ser Ser Asn Arg Lys Ala Ile Asn Leu Arg Thr Val
                20                  25                  30

Gly Gly Ala Phe Ala Ile Gln Phe Ser Leu Gly Ala Phe Ile Leu Tyr
            35                  40                  45

Val Pro Trp Gly Gln Glu Leu Leu Arg Gly Phe Ser Asp Ala Val Ser
50                  55                  60

Asn Val Ile Asn Tyr Gly Asn Asp Gly Thr Ser Phe Leu Phe Gly Gly
65                  70                  75                  80

Leu Val Ser Gly Lys Met Phe Glu Val Phe Gly Gly Gly Phe Ile
                85                  90                  95

Phe Ala Phe Arg Val Leu Pro Thr Leu Ile Phe Phe Ser Ala Leu Ile
                100                 105                 110

Ser Val Leu Tyr Tyr Leu Gly Val Met Gln Trp Val Ile Arg Ile Leu
                115                 120                 125

Gly Gly Gly Leu Gln Lys Ala Leu Gly Thr Ser Arg Ala Glu Ser Met
130                 135                 140

Ser Ala Ala Asn Ile Phe Val Gly Gln Thr Glu Ala Pro Leu Val
145                 150                 155                 160

Val Arg Pro Phe Val Pro Lys Met Thr Gln Ser Glu Leu Phe Ala Val
                165                 170                 175

Met Cys Gly Gly Leu Ala Ser Ile Ala Gly Gly Val Leu Ala Gly Tyr
                180                 185                 190

Ala Ser Met Gly Val Lys Ile Glu Tyr Leu Val Ala Ala Ser Phe Met
                195                 200                 205

Ala Ala Pro Gly Gly Leu Leu Phe Ala Lys Leu Met Met Pro Glu Thr
                210                 215                 220

Glu Lys Pro Gln Asp Asn Glu Asp Ile Thr Leu Asp Gly Gly Asp Asp
225                 230                 235                 240
```

```
Lys Pro Ala Asn Val Ile Asp Ala Ala Ala Gly Gly Ala Ser Ala Gly
                245                 250                 255

Leu Gln Leu Ala Leu Asn Val Gly Ala Met Leu Ile Ala Phe Ile Gly
            260                 265                 270

Leu Ile Ala Leu Ile Asn Gly Met Leu Gly Gly Ile Gly Gly Trp Phe
        275                 280                 285

Gly Met Pro Glu Leu Lys Leu Glu Met Leu Leu Gly Trp Leu Phe Ala
    290                 295                 300

Pro Leu Ala Phe Leu Ile Gly Val Pro Trp Asn Glu Ala Thr Val Ala
305                 310                 315                 320

Gly Glu Phe Ile Gly Leu Lys Thr Val Ala Asn Glu Phe Val Ala Tyr
                325                 330                 335

Ser Gln Phe Ala Pro Tyr Leu Thr Glu Ala Ala Pro Val Val Leu Ser
            340                 345                 350

Glu Lys Thr Lys Ala Ile Ile Ser Phe Ala Leu Cys Gly Phe Ala Asn
        355                 360                 365

Leu Ser Ser Ile Ala Ile Leu Leu Gly Leu Gly Ser Leu Ala Pro
    370                 375                 380

Lys Arg Arg Gly Asp Ile Ala Arg Met Gly Val Lys Ala Val Ile Ala
385                 390                 395                 400

Gly Thr Leu Ser Asn Leu Met Ala Ala Thr Ile Ala Gly Phe Phe Leu
                405                 410                 415

Ser Phe

<210> SEQ ID NO 150
<211> LENGTH: 405
<212> TYPE: PRT
<213> ORGANISM: Vibrio cholerae O1 biovar El Tor N16961
<220> FEATURE:
<221> NAME/KEY: misc_feature
<222> LOCATION: (1)..(405)
<223> OTHER INFORMATION: nupC (VC1953) - Vibrio cholerae O1 biovar El
      Tor N16961 (AAF95101)

<400> SEQUENCE: 150

Met Gly Gly Val Met Ser Ser Leu Leu Gly Met Gly Ala Ile Leu Leu
1               5                   10                  15

Val Ala Trp Leu Phe Ser Thr Asn Arg Lys Asn Ile Asn Leu Arg Thr
            20                  25                  30

Val Ser Leu Ala Leu Leu Leu Gln Ile Phe Phe Ala Leu Leu Val Leu
        35                  40                  45

Tyr Val Pro Ala Gly Lys Glu Ala Leu Asn Arg Val Thr Gly Ala Val
    50                  55                  60

Ser Gln Leu Ile Asn Tyr Gly Gln Asp Gly Ile Gly Phe Val Phe Gly
65                  70                  75                  80

Gly Leu Ala Asn Gly Ser Val Gly Phe Val Phe Ala Ile Asn Val Leu
                85                  90                  95

Gly Ile Ile Ile Phe Phe Ser Ala Leu Ile Ser Gly Leu Tyr His Leu
            100                 105                 110

Gly Ile Met Pro Lys Val Ile Asn Leu Ile Gly Gly Gly Leu Gln Lys
        115                 120                 125

Leu Leu Gly Thr Gly Arg Ala Glu Ser Leu Ser Ala Thr Ala Asn Ile
    130                 135                 140

Phe Val Gly Met Ile Glu Ala Pro Leu Val Val Lys Pro Tyr Leu His
145                 150                 155                 160

Lys Met Thr Asp Ser Gln Phe Phe Ala Val Met Thr Gly Gly Leu Ala
```

```
                165                 170                 175
Ser Val Ala Gly Gly Thr Leu Val Gly Tyr Ala Ser Leu Gly Val Glu
            180                 185                 190

Leu Asn Tyr Leu Ile Ala Ala Phe Met Ser Ala Pro Ala Gly Leu
            195                 200                 205

Leu Met Ala Lys Ile Met Leu Pro Glu Thr Glu His Val Asp Ala Ala
            210                 215                 220

Ile Ala Gln Asp Glu Leu Asp Leu Pro Lys Ser Thr Asn Val Val Glu
225                 230                 235                 240

Ala Ile Ala Asp Gly Ala Met Ser Gly Val Lys Ile Ala Val Ala Val
                245                 250                 255

Gly Ala Thr Leu Leu Ala Phe Val Ser Val Ile Ala Leu Leu Asn Gly
            260                 265                 270

Leu Leu Gly Trp Phe Gly Gly Trp Phe Gly Ile Glu Leu Ser Phe Glu
            275                 280                 285

Leu Ile Met Gly Tyr Val Phe Ala Pro Val Ala Trp Leu Ile Gly Ile
            290                 295                 300

Pro Trp His Glu Ala Ile Thr Ala Gly Ser Leu Ile Gly Asn Lys Val
305                 310                 315                 320

Val Val Asn Glu Phe Val Ala Phe Ile Gln Leu Ile Glu Val Lys Glu
                325                 330                 335

Gln Leu Ser Ala His Ser Gln Ala Ile Val Thr Phe Ala Leu Cys Gly
            340                 345                 350

Phe Ala Asn Ile Ser Thr Met Ala Ile Leu Ile Gly Gly Leu Gly Ser
            355                 360                 365

Leu Val Pro Glu Arg Arg Ser Phe Ile Ser Gln Tyr Gly Phe Arg Ala
            370                 375                 380

Ile Gly Ala Gly Val Leu Ala Asn Leu Met Ser Ala Ser Ile Ala Gly
385                 390                 395                 400

Val Ile Leu Ser Leu
                405

<210> SEQ ID NO 151
<211> LENGTH: 425
<212> TYPE: PRT
<213> ORGANISM: Escherichia coli
<220> FEATURE:
<221> NAME/KEY: misc_feature
<222> LOCATION: (1)..(425)
<223> OTHER INFORMATION: yegT - Escherichia coli K-12 W3110 (P76417;
      JW2085)

<400> SEQUENCE: 151

Met Lys Thr Thr Ala Lys Leu Ser Phe Met Met Phe Val Glu Trp Phe
1               5                   10                  15

Ile Trp Gly Ala Trp Phe Val Pro Leu Trp Leu Trp Leu Ser Lys Ser
            20                  25                  30

Gly Phe Ser Ala Gly Glu Ile Gly Trp Ser Tyr Ala Cys Thr Ala Ile
        35                  40                  45

Ala Ala Ile Leu Ser Pro Ile Leu Val Gly Ser Ile Thr Asp Arg Phe
    50                  55                  60

Phe Ser Ala Gln Lys Val Leu Ala Val Leu Met Phe Ala Gly Ala Leu
65                  70                  75                  80

Leu Met Tyr Phe Ala Ala Gln Gln Thr Thr Phe Ala Gly Phe Phe Pro
                85                  90                  95

Leu Leu Leu Ala Tyr Ser Leu Thr Tyr Met Pro Thr Ile Ala Leu Thr
```

|     |     |     |     | 100 |     |     |     | 105 |     |     |     | 110 |     |     |
| --- | --- | --- | --- | --- | --- | --- | --- | --- | --- | --- | --- | --- | --- | --- |

Asn Ser Ile Ala Phe Ala Asn Val Pro Asp Val Glu Arg Asp Phe Pro
              115                 120                 125

Arg Ile Arg Val Met Gly Thr Ile Gly Trp Ile Ala Ser Gly Leu Ala
    130                 135                 140

Cys Gly Phe Leu Pro Gln Ile Leu Gly Tyr Ala Asp Ile Ser Pro Thr
145                 150                 155                 160

Asn Ile Pro Leu Leu Ile Thr Ala Gly Ser Ser Ala Leu Leu Gly Val
                165                 170                 175

Phe Ala Phe Phe Leu Pro Asp Thr Pro Pro Lys Ser Thr Gly Lys Met
            180                 185                 190

Asp Ile Lys Val Met Leu Gly Leu Asp Ala Leu Ile Leu Leu Arg Asp
        195                 200                 205

Lys Asn Phe Leu Val Phe Phe Cys Ser Phe Leu Phe Ala Met Pro
    210                 215                 220

Leu Ala Phe Tyr Tyr Ile Phe Ala Asn Gly Tyr Leu Thr Glu Val Gly
225                 230                 235                 240

Met Lys Asn Ala Thr Gly Trp Met Thr Leu Gly Gln Phe Ser Glu Ile
                245                 250                 255

Phe Phe Met Leu Ala Leu Pro Phe Phe Thr Lys Arg Phe Gly Ile Lys
            260                 265                 270

Lys Val Leu Leu Leu Gly Leu Val Thr Ala Ala Ile Arg Tyr Gly Phe
        275                 280                 285

Phe Ile Tyr Gly Ser Ala Asp Glu Tyr Phe Thr Tyr Ala Leu Leu Phe
    290                 295                 300

Leu Gly Ile Leu Leu His Gly Val Ser Tyr Asp Phe Tyr Val Thr
305                 310                 315                 320

Ala Tyr Ile Tyr Val Asp Lys Lys Ala Pro Val His Met Arg Thr Ala
                325                 330                 335

Ala Gln Gly Leu Ile Thr Leu Cys Cys Gln Gly Phe Gly Ser Leu Leu
            340                 345                 350

Gly Tyr Arg Leu Gly Gly Val Met Met Glu Lys Met Phe Ala Tyr Gln
        355                 360                 365

Glu Pro Val Asn Gly Leu Thr Phe Asn Trp Ser Gly Met Trp Thr Phe
    370                 375                 380

Gly Ala Val Met Ile Ala Ile Ala Val Leu Phe Met Ile Phe Phe
385                 390                 395                 400

Arg Glu Ser Asp Asn Glu Ile Thr Ala Ile Lys Val Asp Asp Arg Asp
                405                 410                 415

Ile Ala Leu Thr Gln Gly Glu Val Lys
            420                 425

<210> SEQ ID NO 152
<211> LENGTH: 418
<212> TYPE: PRT
<213> ORGANISM: Escherichia coli
<220> FEATURE:
<221> NAME/KEY: misc_feature
<222> LOCATION: (1)..(418)
<223> OTHER INFORMATION: nupG - Escherichia coli K-12 W3110 (P09452;
      JW2932

<400> SEQUENCE: 152

Met Asn Leu Lys Leu Gln Leu Lys Ile Leu Ser Phe Leu Gln Phe Cys
1               5                   10                  15

Leu Trp Gly Ser Trp Leu Thr Thr Leu Gly Ser Tyr Met Phe Val Thr

```
                  20                  25                  30
Leu Lys Phe Asp Gly Ala Ser Ile Gly Ala Val Tyr Ser Ser Leu Gly
            35                  40                  45
Ile Ala Ala Val Phe Met Pro Ala Leu Leu Gly Ile Val Ala Asp Lys
        50                  55                  60
Trp Leu Ser Ala Lys Trp Val Tyr Ala Ile Cys His Thr Ile Gly Ala
65                  70                  75                  80
Ile Thr Leu Phe Met Ala Ala Gln Val Thr Thr Pro Glu Ala Met Phe
                85                  90                  95
Leu Val Ile Leu Ile Asn Ser Phe Ala Tyr Met Pro Thr Leu Gly Leu
            100                 105                 110
Ile Asn Thr Ile Ser Tyr Tyr Arg Leu Gln Asn Ala Gly Met Asp Ile
        115                 120                 125
Val Thr Asp Phe Pro Pro Ile Arg Ile Trp Gly Thr Ile Gly Phe Ile
    130                 135                 140
Met Ala Met Trp Val Val Ser Leu Ser Gly Phe Glu Leu Ser His Met
145                 150                 155                 160
Gln Leu Tyr Ile Gly Ala Ala Leu Ser Ala Ile Leu Val Leu Phe Thr
                165                 170                 175
Leu Thr Leu Pro His Ile Pro Val Ala Lys Gln Ala Asn Gln Ser
            180                 185                 190
Trp Thr Thr Leu Leu Gly Leu Asp Ala Phe Ala Leu Phe Lys Asn Lys
        195                 200                 205
Arg Met Ala Ile Phe Phe Ile Phe Ser Met Leu Leu Gly Ala Glu Leu
    210                 215                 220
Gln Ile Thr Asn Met Phe Gly Asn Thr Phe Leu His Ser Phe Asp Lys
225                 230                 235                 240
Asp Pro Met Phe Ala Ser Ser Phe Ile Val Gln His Ala Ser Ile Ile
                245                 250                 255
Met Ser Ile Ser Gln Ile Ser Glu Thr Leu Phe Ile Leu Thr Ile Pro
            260                 265                 270
Phe Phe Leu Ser Arg Tyr Gly Ile Lys Asn Val Met Met Ile Ser Ile
        275                 280                 285
Val Ala Trp Ile Leu Arg Phe Ala Leu Phe Ala Tyr Gly Asp Pro Thr
    290                 295                 300
Pro Phe Gly Thr Val Leu Leu Val Leu Ser Met Ile Val Tyr Gly Cys
305                 310                 315                 320
Ala Phe Asp Phe Phe Asn Ile Ser Gly Ser Val Phe Val Glu Lys Glu
                325                 330                 335
Val Ser Pro Ala Ile Arg Ala Ser Ala Gln Gly Met Phe Leu Met Met
            340                 345                 350
Thr Asn Gly Phe Gly Cys Ile Leu Gly Gly Ile Val Ser Gly Lys Val
        355                 360                 365
Val Glu Met Tyr Thr Gln Asn Gly Ile Thr Asp Trp Gln Thr Val Trp
    370                 375                 380
Leu Ile Phe Ala Gly Tyr Ser Val Val Leu Ala Phe Ala Phe Met Ala
385                 390                 395                 400
Met Phe Lys Tyr Lys His Val Arg Val Pro Thr Gly Thr Gln Thr Val
                405                 410                 415
Ser His

<210> SEQ ID NO 153
<211> LENGTH: 418
```

```
<212> TYPE: PRT
<213> ORGANISM: Escherichia coli
<220> FEATURE:
<221> NAME/KEY: misc_feature
<222> LOCATION: (1)..(418)
<223> OTHER INFORMATION: xapB - Escherichia coli K-12 W3110 (P45562;
      JW2397)

<400> SEQUENCE: 153
```

Met Ser Ile Ala Met Arg Leu Lys Val Met Ser Phe Leu Gln Tyr Phe
1               5                   10                  15

Ile Trp Gly Ser Trp Leu Val Thr Leu Gly Ser Tyr Met Ile Asn Thr
            20                  25                  30

Leu His Phe Thr Gly Ala Asn Val Gly Met Val Tyr Ser Ser Lys Gly
        35                  40                  45

Ile Ala Ala Ile Ile Met Pro Gly Ile Met Gly Ile Ile Ala Asp Lys
    50                  55                  60

Trp Leu Arg Ala Glu Arg Ala Tyr Met Leu Cys His Leu Val Cys Ala
65                  70                  75                  80

Gly Val Leu Phe Tyr Ala Ala Ser Val Thr Asp Pro Asp Met Met Phe
                85                  90                  95

Trp Val Met Leu Val Asn Ala Met Ala Phe Met Pro Thr Ile Ala Leu
            100                 105                 110

Ser Asn Ser Val Ser Tyr Ser Cys Leu Ala Gln Ala Gly Leu Asp Pro
        115                 120                 125

Val Thr Ala Phe Pro Pro Ile Arg Val Phe Gly Thr Val Gly Phe Ile
    130                 135                 140

Val Ala Met Trp Ala Val Ser Leu Leu His Leu Glu Leu Ser Ser Leu
145                 150                 155                 160

Gln Leu Tyr Ile Ala Ser Gly Ala Ser Leu Leu Leu Ser Ala Tyr Ala
                165                 170                 175

Leu Thr Leu Pro Lys Ile Pro Val Ala Glu Lys Lys Ala Thr Thr Ser
            180                 185                 190

Leu Ala Ser Lys Leu Gly Leu Asp Ala Phe Val Leu Phe Lys Asn Pro
        195                 200                 205

Arg Met Ala Ile Phe Phe Leu Phe Ala Met Met Leu Gly Ala Val Leu
    210                 215                 220

Gln Ile Thr Asn Val Phe Gly Asn Pro Phe Leu His Asp Phe Ala Arg
225                 230                 235                 240

Asn Pro Glu Phe Ala Asp Ser Phe Val Val Lys Tyr Pro Ser Ile Leu
                245                 250                 255

Leu Ser Val Ser Gln Met Ala Glu Val Gly Phe Ile Leu Thr Ile Pro
            260                 265                 270

Phe Phe Leu Lys Arg Phe Gly Ile Lys Thr Val Met Leu Met Ser Met
        275                 280                 285

Val Ala Trp Thr Leu Arg Phe Gly Phe Phe Ala Tyr Gly Asp Pro Ser
    290                 295                 300

Thr Thr Gly Phe Ile Leu Leu Leu Leu Ser Met Ile Val Tyr Gly Cys
305                 310                 315                 320

Ala Phe Asp Phe Phe Asn Ile Ser Gly Ser Val Phe Val Glu Gln Glu
                325                 330                 335

Val Asp Ser Ser Ile Arg Ala Ser Ala Gln Gly Leu Phe Met Thr Met
            340                 345                 350

Val Asn Gly Val Gly Ala Trp Val Gly Ser Ile Leu Ser Gly Met Ala
        355                 360                 365

```
Val Asp Tyr Phe Ser Val Asp Gly Val Lys Asp Trp Gln Thr Ile Trp
    370                 375                 380

Leu Val Phe Ala Gly Tyr Ala Leu Phe Leu Ala Val Ile Phe Phe
385                 390                 395                 400

Gly Phe Lys Tyr Asn His Asp Pro Glu Lys Ile Lys His Arg Ala Val
                405                 410                 415

Thr His

<210> SEQ ID NO 154
<211> LENGTH: 413
<212> TYPE: PRT
<213> ORGANISM: Escherichia coli
<220> FEATURE:
<221> NAME/KEY: misc_feature
<222> LOCATION: (1)..(413)
<223> OTHER INFORMATION: CC1628 - Caulobacter crescentus CB15 (AAK23606)

<400> SEQUENCE: 154

Met Gly Thr Ser Phe Arg Leu Phe Val Met Met Val Leu Gln Leu Ala
1               5                   10                  15

Ile Trp Gly Ala Trp Ala Pro Lys Ile Phe Pro Tyr Met Gly Met Leu
                20                  25                  30

Gly Phe Ala Pro Trp Gln Gln Ser Leu Val Gly Ser Ala Trp Gly Val
            35                  40                  45

Ala Ala Leu Val Gly Ile Phe Phe Ser Asn Gln Phe Ala Asp Arg Asn
50                  55                  60

Phe Ser Ala Glu Arg Phe Leu Ala Val Ser His Leu Ile Gly Gly Val
65                  70                  75                  80

Ala Leu Leu Gly Thr Ala Phe Ser Thr Glu Phe Trp Pro Phe Phe Ala
                85                  90                  95

Cys Tyr Leu Val Phe Ser Leu Val Tyr Val Pro Thr Leu Ser Val Thr
                100                 105                 110

Asn Ser Ile Ala Phe Ala Asn Leu Arg Asp Pro Ala Ala Gly Phe Gly
            115                 120                 125

Gly Val Arg Met Gly Gly Thr Val Gly Trp Val Leu Val Ser Trp Pro
130                 135                 140

Phe Val Phe Leu Leu Gly Ala Gln Ala Thr Val Glu Gln Val Arg Trp
145                 150                 155                 160

Ile Phe Leu Val Ala Ala Ile Val Ser Phe Val Phe Ala Gly Tyr Ala
                165                 170                 175

Leu Thr Leu Pro His Thr Pro Pro Arg Lys Ala Asp Asp Ala Val Asp
            180                 185                 190

Lys Leu Ala Trp Arg Arg Ala Phe Lys Leu Leu Gly Ala Pro Phe Val
        195                 200                 205

Phe Val Leu Phe Val Val Thr Phe Ile Asp Ser Val Ile His Asn Gly
    210                 215                 220

Tyr Phe Val Met Ala Asp Ala Phe Leu Thr Asn Arg Val Gly Ile Ala
225                 230                 235                 240

Gly Asn Leu Ser Met Val Val Leu Ser Leu Gly Gln Val Ala Glu Ile
                245                 250                 255

Ile Thr Met Leu Leu Leu Gly Arg Val Leu Ala Lys Leu Gly Trp Lys
            260                 265                 270

Val Thr Met Ile Val Gly Val Leu Gly His Ala Ala Arg Phe Ala Val
        275                 280                 285

Phe Ala Tyr Phe Ala Asp Ser Val Pro Val Ile Val Ala Val Gln Leu
    290                 295                 300
```

```
Leu His Gly Val Cys Tyr Ala Phe Phe Ala Thr Val Tyr Ile Phe
305                 310                 315                 320

Val Asp Ala Val Phe Pro Lys Asp Val Arg Ser Ser Ala Gln Gly Leu
                325                 330                 335

Phe Asn Leu Leu Ile Leu Gly Val Gly Asn Val Ala Ala Ser Phe Ile
                340                 345                 350

Phe Pro Ala Leu Ile Gly Arg Leu Thr Thr Asp Gly Ser Val Asp Tyr
                355                 360                 365

Thr Thr Leu Phe Leu Val Pro Thr Ala Met Ala Leu Ala Ala Val Cys
            370                 375                 380

Leu Leu Ala Leu Phe Phe Arg Pro Pro Thr Arg Gly Pro Val Ser Glu
385                 390                 395                 400

Ala Asp Ser Ala Ser Ser Ala Ala Ser Ser Ala Gln Ala
                405                 410

<210> SEQ ID NO 155
<211> LENGTH: 419
<212> TYPE: PRT
<213> ORGANISM: Escherichia coli
<220> FEATURE:
<221> NAME/KEY: misc_feature
<222> LOCATION: (1)..(419)
<223> OTHER INFORMATION: codB - Escherichia coli K-12 W3110 (P25525;
      JW0327)

<400> SEQUENCE: 155

Met Ser Gln Asp Asn Asn Phe Ser Gln Gly Pro Val Pro Gln Ser Ala
1               5                   10                  15

Arg Lys Gly Val Leu Ala Leu Thr Phe Val Met Leu Gly Leu Thr Phe
                20                  25                  30

Phe Ser Ala Ser Met Trp Thr Gly Gly Thr Leu Gly Thr Gly Leu Ser
                35                  40                  45

Tyr His Asp Phe Phe Leu Ala Val Leu Ile Gly Asn Leu Leu Leu Gly
            50                  55                  60

Ile Tyr Thr Ser Phe Leu Gly Tyr Ile Gly Ala Lys Thr Gly Leu Thr
65                  70                  75                  80

Thr His Leu Leu Ala Arg Phe Ser Phe Gly Val Lys Gly Ser Trp Leu
                85                  90                  95

Pro Ser Leu Leu Leu Gly Gly Thr Gln Val Gly Trp Phe Gly Val Gly
                100                 105                 110

Val Ala Met Phe Ala Ile Pro Val Gly Lys Ala Thr Gly Leu Asp Ile
                115                 120                 125

Asn Leu Leu Ile Ala Val Ser Gly Leu Leu Met Thr Val Thr Val Phe
                130                 135                 140

Phe Gly Ile Ser Ala Leu Thr Val Leu Ser Val Ile Ala Val Pro Ala
145                 150                 155                 160

Ile Ala Cys Leu Gly Gly Tyr Ser Val Trp Leu Ala Val Asn Gly Met
                165                 170                 175

Gly Gly Leu Asp Ala Leu Lys Ala Val Val Pro Ala Gln Pro Leu Asp
                180                 185                 190

Phe Asn Val Ala Leu Ala Leu Val Val Gly Ser Phe Ile Ser Ala Gly
                195                 200                 205

Thr Leu Thr Ala Asp Phe Val Arg Phe Gly Arg Asn Ala Lys Leu Ala
            210                 215                 220

Val Leu Val Ala Met Val Ala Phe Phe Leu Gly Asn Ser Leu Met Phe
225                 230                 235                 240
```

-continued

```
Ile Phe Gly Ala Ala Gly Ala Ala Leu Gly Met Ala Asp Ile Ser
                245                 250                 255

Asp Val Met Ile Ala Gln Gly Leu Leu Leu Pro Ala Ile Val Val Leu
        260                 265                 270

Gly Leu Asn Ile Trp Thr Thr Asn Asp Asn Ala Leu Tyr Ala Ser Gly
            275                 280                 285

Leu Gly Phe Ala Asn Ile Thr Gly Met Ser Ser Lys Thr Leu Ser Val
    290                 295                 300

Ile Asn Gly Ile Ile Gly Thr Val Cys Ala Leu Trp Leu Tyr Asn Asn
305                 310                 315                 320

Phe Val Gly Trp Leu Thr Phe Leu Ser Ala Ala Ile Pro Pro Val Gly
                325                 330                 335

Gly Val Ile Ile Ala Asp Tyr Leu Met Asn Arg Arg Arg Tyr Glu His
                340                 345                 350

Phe Ala Thr Thr Arg Met Met Ser Val Asn Trp Val Ala Ile Leu Ala
            355                 360                 365

Val Ala Leu Gly Ile Ala Ala Gly His Trp Leu Pro Gly Ile Val Pro
    370                 375                 380

Val Asn Ala Val Leu Gly Gly Ala Leu Ser Tyr Leu Ile Leu Asn Pro
385                 390                 395                 400

Ile Leu Asn Arg Lys Thr Thr Ala Ala Met Thr His Val Glu Ala Asn
                405                 410                 415

Ser Val Glu

<210> SEQ ID NO 156
<211> LENGTH: 428
<212> TYPE: PRT
<213> ORGANISM: Escherichia coli
<220> FEATURE:
<221> NAME/KEY: misc_feature
<222> LOCATION: (1)..(428)
<223> OTHER INFORMATION: amtB - Escherichia coli K-12 MG1655 (B0451;
      945084)

<400> SEQUENCE: 156

Met Lys Ile Ala Thr Ile Lys Thr Gly Leu Ala Ser Leu Ala Met Leu
1               5                   10                  15

Pro Gly Leu Val Met Ala Ala Pro Ala Val Ala Asp Lys Ala Asp Asn
            20                  25                  30

Ala Phe Met Met Ile Cys Thr Ala Leu Val Leu Phe Met Thr Ile Pro
        35                  40                  45

Gly Ile Ala Leu Phe Tyr Gly Gly Leu Ile Arg Gly Lys Asn Val Leu
    50                  55                  60

Ser Met Leu Thr Gln Val Thr Val Thr Phe Ala Leu Val Cys Ile Leu
65                  70                  75                  80

Trp Val Val Tyr Gly Tyr Ser Leu Ala Phe Gly Glu Gly Asn Asn Phe
                85                  90                  95

Phe Gly Asn Ile Asn Trp Leu Met Leu Lys Asn Ile Glu Leu Thr Ala
            100                 105                 110

Val Met Gly Ser Ile Tyr Gln Tyr Ile His Val Ala Phe Gln Gly Ser
        115                 120                 125

Phe Ala Cys Ile Thr Val Gly Leu Ile Val Gly Ala Leu Ala Glu Arg
    130                 135                 140

Ile Arg Phe Ser Ala Val Leu Ile Phe Val Val Val Trp Leu Thr Leu
145                 150                 155                 160
```

```
Ser Tyr Ile Pro Ile Ala His Met Val Trp Gly Gly Leu Leu Ala
            165                 170                 175

Ser His Gly Ala Leu Asp Phe Ala Gly Gly Thr Val His Ile Asn
            180                 185                 190

Ala Ala Ile Ala Gly Leu Val Gly Ala Tyr Leu Ile Gly Lys Arg Val
            195                 200                 205

Gly Phe Gly Lys Glu Ala Phe Lys Pro His Asn Leu Pro Met Val Phe
            210                 215                 220

Thr Gly Thr Ala Ile Leu Tyr Ile Gly Trp Phe Gly Phe Asn Ala Gly
225                 230                 235                 240

Ser Ala Gly Thr Ala Asn Glu Ile Ala Ala Leu Ala Phe Val Asn Thr
            245                 250                 255

Val Val Ala Thr Ala Ala Ile Leu Gly Trp Ile Phe Gly Glu Trp
            260                 265                 270

Ala Leu Arg Gly Lys Pro Ser Leu Leu Gly Ala Cys Ser Gly Ala Ile
            275                 280                 285

Ala Gly Leu Val Gly Val Thr Pro Ala Cys Gly Tyr Ile Gly Val Gly
            290                 295                 300

Gly Ala Leu Ile Ile Gly Val Val Ala Gly Leu Ala Gly Leu Trp Gly
305                 310                 315                 320

Val Thr Met Leu Lys Arg Leu Leu Arg Val Asp Asp Pro Cys Asp Val
            325                 330                 335

Phe Gly Val His Gly Val Cys Gly Ile Val Gly Cys Ile Met Thr Gly
            340                 345                 350

Ile Phe Ala Ala Ser Ser Leu Gly Gly Val Gly Phe Ala Glu Gly Val
            355                 360                 365

Thr Met Gly His Gln Leu Leu Val Gln Leu Glu Ser Ile Ala Ile Thr
            370                 375                 380

Ile Val Trp Ser Gly Val Val Ala Phe Ile Gly Tyr Lys Leu Ala Asp
385                 390                 395                 400

Leu Thr Val Gly Leu Arg Val Pro Glu Glu Gln Glu Arg Glu Gly Leu
            405                 410                 415

Asp Val Asn Ser His Gly Glu Asn Ala Tyr Asn Ala
            420                 425

<210> SEQ ID NO 157
<211> LENGTH: 466
<212> TYPE: PRT
<213> ORGANISM: Escherichia coli
<220> FEATURE:
<221> NAME/KEY: misc_feature
<222> LOCATION: (1)..(466)
<223> OTHER INFORMATION: GABA permease GabP Escherichia coli

<400> SEQUENCE: 157

Met Gly Gln Ser Ser Gln Pro His Glu Leu Gly Gly Gly Leu Lys Ser
1               5                   10                  15

Arg His Val Thr Met Leu Ser Ile Ala Gly Val Ile Gly Ala Ser Leu
            20                  25                  30

Phe Val Gly Ser Ser Val Ala Ile Ala Glu Ala Gly Pro Ala Val Leu
        35                  40                  45

Leu Ala Tyr Leu Phe Ala Gly Leu Leu Val Val Met Ile Met Arg Met
    50                  55                  60

Leu Ala Glu Met Ala Val Ala Thr Pro Asp Thr Gly Ser Phe Ser Thr
65                  70                  75                  80

Tyr Ala Asp Lys Ala Ile Gly Arg Trp Ala Gly Tyr Thr Ile Gly Trp
```

```
                    85                  90                  95
Leu Tyr Trp Trp Phe Trp Val Leu Val Ile Pro Leu Glu Ala Asn Ile
                100                 105                 110
Ala Ala Met Ile Leu His Ser Trp Val Pro Gly Ile Pro Ile Trp Leu
                115                 120                 125
Phe Ser Leu Val Ile Thr Leu Ala Leu Thr Gly Ser Asn Leu Leu Ser
130                 135                 140
Val Lys Asn Tyr Gly Glu Phe Glu Phe Trp Leu Ala Leu Cys Lys Val
145                 150                 155                 160
Ile Ala Ile Leu Ala Phe Ile Phe Leu Gly Ala Val Ala Ile Ser Gly
                165                 170                 175
Phe Tyr Pro Tyr Ala Glu Val Ser Gly Ile Ser Arg Leu Trp Asp Ser
                180                 185                 190
Gly Gly Phe Met Pro Asn Gly Phe Gly Ala Val Leu Ser Ala Met Leu
                195                 200                 205
Ile Thr Met Phe Ser Phe Met Gly Ala Glu Ile Val Thr Ile Ala Ala
                210                 215                 220
Ala Glu Ser Asp Thr Pro Glu Lys His Ile Val Arg Ala Thr Asn Ser
225                 230                 235                 240
Val Ile Trp Arg Ile Ser Ile Phe Tyr Leu Cys Ser Ile Phe Val Val
                245                 250                 255
Val Ala Leu Ile Pro Trp Asn Met Pro Gly Leu Lys Ala Val Gly Ser
                260                 265                 270
Tyr Arg Ser Val Leu Glu Leu Leu Asn Ile Pro His Ala Lys Leu Ile
                275                 280                 285
Met Asp Cys Val Ile Leu Leu Ser Val Thr Ser Cys Leu Asn Ser Ala
                290                 295                 300
Leu Tyr Thr Ala Ser Arg Met Leu Tyr Ser Leu Ser Arg Arg Gly Asp
305                 310                 315                 320
Ala Pro Ala Val Met Gly Lys Ile Asn Arg Ser Lys Thr Pro Tyr Val
                325                 330                 335
Ala Val Leu Leu Ser Thr Gly Ala Ala Phe Leu Thr Val Val Val Asn
                340                 345                 350
Tyr Tyr Ala Pro Ala Lys Val Phe Lys Phe Leu Ile Asp Ser Ser Gly
                355                 360                 365
Ala Ile Ala Leu Leu Val Tyr Leu Val Ile Ala Val Ser Gln Leu Arg
                370                 375                 380
Met Arg Lys Ile Leu Arg Ala Glu Gly Ser Glu Ile Arg Leu Arg Met
385                 390                 395                 400
Trp Leu Tyr Pro Trp Leu Thr Trp Leu Val Ile Gly Phe Ile Thr Phe
                405                 410                 415
Val Leu Val Val Met Leu Phe Arg Pro Ala Gln Gln Leu Glu Val Ile
                420                 425                 430
Ser Thr Gly Leu Leu Ala Ile Gly Ile Ile Cys Thr Val Pro Ile Met
                435                 440                 445
Ala Arg Trp Lys Lys Leu Val Leu Trp Gln Lys Thr Pro Val His Asn
                450                 455                 460
Thr Arg
465

<210> SEQ ID NO 158
<211> LENGTH: 412
<212> TYPE: PRT
<213> ORGANISM: Escherichia coli
```

<220> FEATURE:
<221> NAME/KEY: misc_feature
<222> LOCATION: (1)..(412)
<223> OTHER INFORMATION: mtnH Escherichia coli

<400> SEQUENCE: 158

```
Met Thr Asn Tyr Arg Val Glu Ser Ser Ser Gly Arg Ala Ala Arg Lys
1               5                   10                  15

Met Arg Leu Ala Leu Met Gly Pro Ala Phe Ile Ala Ala Ile Gly Tyr
            20                  25                  30

Ile Asp Pro Gly Asn Phe Ala Thr Asn Ile Gln Ala Gly Ala Ser Phe
            35                  40                  45

Gly Tyr Gln Leu Leu Trp Val Val Val Trp Ala Asn Leu Met Ala Met
 50                  55                  60

Leu Ile Gln Ile Leu Ser Ala Lys Leu Gly Ile Ala Thr Gly Lys Asn
 65                  70                  75                  80

Leu Ala Glu Gln Ile Arg Asp His Tyr Pro Arg Pro Val Val Trp Phe
                 85                  90                  95

Tyr Trp Val Gln Ala Glu Ile Ile Ala Met Ala Thr Asp Leu Ala Glu
            100                 105                 110

Phe Ile Gly Ala Ala Ile Gly Phe Lys Leu Ile Leu Gly Val Ser Leu
            115                 120                 125

Leu Gln Gly Ala Val Leu Thr Gly Ile Ala Thr Phe Leu Ile Leu Met
130                 135                 140

Leu Gln Arg Arg Gly Gln Lys Pro Leu Glu Lys Val Ile Gly Gly Leu
145                 150                 155                 160

Leu Leu Phe Val Ala Ala Ala Tyr Ile Val Glu Leu Ile Phe Ser Gln
                165                 170                 175

Pro Asn Leu Ala Gln Leu Gly Lys Gly Met Val Ile Pro Ser Leu Pro
            180                 185                 190

Thr Ser Glu Ala Val Phe Leu Ala Ala Gly Val Leu Gly Ala Thr Ile
            195                 200                 205

Met Pro His Val Ile Tyr Leu His Ser Ser Leu Thr Gln His Leu His
210                 215                 220

Gly Gly Ser Arg Gln Gln Arg Tyr Ser Ala Thr Lys Trp Asp Val Ala
225                 230                 235                 240

Ile Ala Met Thr Ile Ala Gly Phe Val Asn Leu Ala Met Met Ala Thr
                245                 250                 255

Ala Ala Ala Ala Phe His Phe Ser Gly His Thr Gly Val Ala Asp Leu
            260                 265                 270

Asp Glu Ala Tyr Leu Thr Leu Gln Pro Leu Leu Ser His Ala Ala Ala
            275                 280                 285

Thr Val Phe Gly Leu Ser Leu Val Ala Ala Gly Leu Ser Ser Thr Val
290                 295                 300

Val Gly Thr Leu Ala Gly Gln Val Val Met Gln Gly Phe Ile Arg Phe
305                 310                 315                 320

His Ile Pro Leu Trp Val Arg Arg Thr Val Thr Met Leu Pro Ser Phe
                325                 330                 335

Ile Val Ile Leu Met Gly Leu Asp Pro Thr Arg Ile Leu Val Met Ser
            340                 345                 350

Gln Val Leu Leu Ser Phe Gly Ile Ala Leu Ala Leu Val Pro Leu Leu
            355                 360                 365

Ile Phe Thr Ser Asp Ser Lys Leu Met Gly Asp Leu Val Asn Ser Lys
370                 375                 380
```

Arg Val Lys Gln Thr Gly Trp Val Ile Val Val Leu Val Val Ala Leu
385                 390                 395                 400

Asn Ile Trp Leu Leu Val Gly Thr Ala Leu Gly Leu
            405                 410

<210> SEQ ID NO 159
<211> LENGTH: 1320
<212> TYPE: DNA
<213> ORGANISM: Escherichia coli
<220> FEATURE:
<221> NAME/KEY: misc_feature
<222> LOCATION: (1)..(1320)
<223> OTHER INFORMATION: Nucleotide sequence: BCAA transporter BrnQ from
      E. coli

<400> SEQUENCE: 159
atgacccatc aattaagatc gcgcgatatc atcgctctgg gctttatgac atttgcgttg     60
ttcgtcggcg caggtaacat tatttttcct ccaatggtcg gcttgcaggc aggcgaacac    120
gtctggactg cggcattcgg cttcctcatt actgccgttg gcctaccggt attaacggta    180
gtggcgctgg caaaagttgg cggcggtgtt gacagtctca gcacgccaat ggtaaagtc     240 gctggcgtac tgctggcaac agtttgttac ctggcggtgg ggccgctttt tgctacgccg    300
cgtacagcta ccgtttcttt tgaagtgggc attgcgccgc tgacgggtga ttccgcgctg    360
ccgctgttta tttacagcct ggtctatttc gctatcgtta ttctggtttc gctctatccg    420
ggcaagctgc tggataccgt gggcaacttc cttgcgccgc tgaaaattat cgcgctggtc    480
atcctgtctg ttgccgcaat tatctggccg gcgggttcta tcagtacggc gactgaggct    540
tatcaaaacg ctgcgttttc taacggcttc gtcaacggct atctgaccat ggatacgctg    600
ggcgcaatgg tgtttggtat cgttattgtt aacgcggcgc gttctcgtgg cgttaccgaa    660
gcgcgtctgc tgacccgtta taccgtctgg gctggcctga tggcgggtgt tggtctgact    720
ctgctgtacc tggcgctgtt ccgtctgggt tcagacagcg cgtcgctggt cgatcagtct    780
gcaaacggtg cggcgatcct gcatgcttac gttcagcata cctttggcgg cggcggtagc    840
ttcctgctgg cggcgttaat cttcatcgcc tgcctggtca cggcggttgg cctgacctgt    900
gcttgtgcag aattcttcgc ccagtacgta ccgctctctt atcgtacgct ggtgtttatc    960
ctcggcggct tctcgatggt ggtgtctaac ctcggcttga ccagctgat tcagatctct   1020 gtaccggtgc tgaccgccat ttatccgccg tgtatcgcac tggttgtatt aagttttaca   1080
cgctcatggt ggcataattc gtcccgcgtg attgctccgc gatgtttat cagcctgctt    1140 tttggtattc tcgacgggat caaggcatct gcattcagcg atatcttacc gtcctgggcg   1200
cagcgtttac cgctggccga acaaggtctg gcgtggttaa tgccaacagt ggtgatggtg   1260
gttctggcca ttatctggga tcgtgcggca ggtcgtcagg tgacctccag cgctcactaa   1320

<210> SEQ ID NO 160
<211> LENGTH: 439
<212> TYPE: PRT
<213> ORGANISM: Escherichia coli
<220> FEATURE:
<221> NAME/KEY: misc_feature
<222> LOCATION: (1)..(439)
<223> OTHER INFORMATION: AA sequence: BCAA transporter BrnQ from E. coli

<400> SEQUENCE: 160

Met Thr His Gln Leu Arg Ser Arg Asp Ile Ile Ala Leu Gly Phe Met
1               5                   10                  15

Thr Phe Ala Leu Phe Val Gly Ala Gly Asn Ile Ile Phe Pro Pro Met

-continued

```
                    20                  25                  30
Val Gly Leu Gln Ala Gly Glu His Val Trp Thr Ala Ala Phe Gly Phe
                35                  40                  45
Leu Ile Thr Ala Val Gly Leu Pro Val Leu Thr Val Val Ala Leu Ala
            50                  55                  60
Lys Val Gly Gly Gly Val Asp Ser Leu Ser Thr Pro Ile Gly Lys Val
65                  70                  75                  80
Ala Gly Val Leu Leu Ala Thr Val Cys Tyr Leu Ala Val Gly Pro Leu
                85                  90                  95
Phe Ala Thr Pro Arg Thr Ala Thr Val Ser Phe Glu Val Gly Ile Ala
            100                 105                 110
Pro Leu Thr Gly Asp Ser Ala Leu Pro Leu Phe Ile Tyr Ser Leu Val
            115                 120                 125
Tyr Phe Ala Ile Val Ile Leu Val Ser Leu Tyr Pro Gly Lys Leu Leu
            130                 135                 140
Asp Thr Val Gly Asn Phe Leu Ala Pro Leu Lys Ile Ile Ala Leu Val
145                 150                 155                 160
Ile Leu Ser Val Ala Ala Ile Ile Trp Pro Ala Gly Ser Ile Ser Thr
                165                 170                 175
Ala Thr Glu Ala Tyr Gln Asn Ala Ala Phe Ser Asn Gly Phe Val Asn
            180                 185                 190
Gly Tyr Leu Thr Met Asp Thr Leu Gly Ala Met Val Phe Gly Ile Val
            195                 200                 205
Ile Val Asn Ala Ala Arg Ser Arg Gly Val Thr Glu Ala Arg Leu Leu
            210                 215                 220
Thr Arg Tyr Thr Val Trp Ala Gly Leu Met Ala Gly Val Gly Leu Thr
225                 230                 235                 240
Leu Leu Tyr Leu Ala Leu Phe Arg Leu Gly Ser Asp Ser Ala Ser Leu
                245                 250                 255
Val Asp Gln Ser Ala Asn Gly Ala Ala Ile Leu His Ala Tyr Val Gln
            260                 265                 270
His Thr Phe Gly Gly Gly Gly Ser Phe Leu Leu Ala Ala Leu Ile Phe
            275                 280                 285
Ile Ala Cys Leu Val Thr Ala Val Gly Leu Thr Cys Ala Cys Ala Glu
            290                 295                 300
Phe Phe Ala Gln Tyr Val Pro Leu Ser Tyr Arg Thr Leu Val Phe Ile
305                 310                 315                 320
Leu Gly Gly Phe Ser Met Val Val Ser Asn Leu Gly Leu Ser Gln Leu
                325                 330                 335
Ile Gln Ile Ser Val Pro Val Leu Thr Ala Ile Tyr Pro Pro Cys Ile
            340                 345                 350
Ala Leu Val Val Leu Ser Phe Thr Arg Ser Trp His Asn Ser Ser
            355                 360                 365
Arg Val Ile Ala Pro Pro Met Phe Ile Ser Leu Leu Phe Gly Ile Leu
            370                 375                 380
Asp Gly Ile Lys Ala Ser Ala Phe Ser Asp Ile Leu Pro Ser Trp Ala
385                 390                 395                 400
Gln Arg Leu Pro Leu Ala Glu Gln Gly Leu Ala Trp Leu Met Pro Thr
                405                 410                 415
Val Val Met Val Val Leu Ala Ile Ile Trp Asp Arg Ala Ala Gly Arg
            420                 425                 430
Gln Val Thr Ser Ser Ala His
            435
```

<210> SEQ ID NO 161
<211> LENGTH: 18
<212> TYPE: DNA
<213> ORGANISM: Artificial Sequence
<220> FEATURE:
<223> OTHER INFORMATION: Synthetic: consensus sequence

<400> SEQUENCE: 161
ttgttgayry rtcaacwa                                                   18

<210> SEQ ID NO 162
<211> LENGTH: 15
<212> TYPE: DNA
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (8)..(8)
<223> OTHER INFORMATION: n is a, c, g, or t

<400> SEQUENCE: 162
ttataatnat tataa                                                      15

<210> SEQ ID NO 163
<211> LENGTH: 355
<212> TYPE: DNA
<213> ORGANISM: Artificial Sequence
<220> FEATURE:
<223> OTHER INFORMATION: Synthetic: katG Regulatory sequence

<400> SEQUENCE: 163
tgtggctttt atgaaaatca cacagtgatc acaaatttta aacagagcac aaaatgctgc     60
ctcgaaatga gggcgggaaa ataaggttat cagccttgtt ttctccctca ttacttgaag    120
gatatgaagc taaaacccctt ttttataaag catttgtccg aattcggaca taatcaaaaa   180
agcttaatta agatcaattt gatctacatc tctttaacca acaatatgta agatctcaac    240
tatcgcatcc gtggattaat tcaattataa cttctctcta acgctgtgta tcgtaacggt    300
aacactgtag aggggagcac attgatgcga attcattaaa gaggagaaag gtacc         355

<210> SEQ ID NO 164
<211> LENGTH: 228
<212> TYPE: DNA
<213> ORGANISM: Artificial Sequence
<220> FEATURE:
<223> OTHER INFORMATION: Synthetic: dps Regulatory sequence

<400> SEQUENCE: 164
ttccgaaaat tcctggcgag cagataaata agaattgttc ttatcaatat atctaactca     60
ttgaatcttt attagttttg tttttcacgc ttgttaccac tattagtgtg ataggaacag    120
ccagaatagc ggaacacata gccggtgcta tacttaatct cgttaattac tgggacataa    180
catcaagagg atatgaaatt cgaattcatt aaagaggaga aggtacc                  228

<210> SEQ ID NO 165
<211> LENGTH: 334
<212> TYPE: DNA
<213> ORGANISM: Artificial Sequence
<220> FEATURE:
<223> OTHER INFORMATION: Synthetic: ahpC Regulatory sequence

<400> SEQUENCE: 165

```
gcttagatca ggtgattgcc ctttgtttat gagggtgttg taatccatgt cgttgttgca      60
tttgtaaggg caacacctca gcctgcaggc aggcactgaa gataccaaag ggtagttcag     120
attacacggt cacctggaaa gggggccatt ttacttttta tcgccgctgg cggtgcaaag     180
ttcacaaagt tgtcttacga aggttgtaag gtaaaactta tcgatttgat aatggaaacg     240
cattagccga atcggcaaaa attggttacc ttacatctca tcgaaaacac ggaggaagta     300
tagatgcgaa ttcattaaag aggagaaagg tacc                                 334
```

<210> SEQ ID NO 166
<211> LENGTH: 134
<212> TYPE: DNA
<213> ORGANISM: Artificial Sequence
<220> FEATURE:
<223> OTHER INFORMATION: Synthetic: oxyS Regulatory sequence

<400> SEQUENCE: 166

```
ctcgagttca ttatccatcc tccatcgcca cgatagttca tggcgatagg tagaatagca      60
atgaacgatt atccctatca agcattctga ctgataattg ctcacacgaa ttcattaaag     120
aggagaaagg tacc                                                       134
```

<210> SEQ ID NO 167
<211> LENGTH: 416
<212> TYPE: PRT
<213> ORGANISM: Pseudomonas sp.
<220> FEATURE:
<221> NAME/KEY: misc_feature
<222> LOCATION: (1)..(416)
<223> OTHER INFORMATION: Pseudomonas kynureninase

<400> SEQUENCE: 167

```
Met Thr Thr Arg Asn Asp Cys Leu Ala Leu Asp Ala Gln Asp Ser Leu
1               5                   10                  15

Ala Pro Leu Arg Gln Gln Phe Ala Leu Pro Glu Gly Val Ile Tyr Leu
            20                  25                  30

Asp Gly Asn Ser Leu Gly Ala Arg Pro Val Ala Ala Leu Ala Arg Ala
        35                  40                  45

Gln Ala Val Ile Ala Glu Glu Trp Gly Asn Gly Leu Ile Arg Ser Trp
    50                  55                  60

Asn Ser Ala Gly Trp Arg Asp Leu Ser Glu Arg Leu Gly Asn Arg Leu
65                  70                  75                  80

Ala Thr Leu Ile Gly Ala Arg Asp Gly Glu Val Val Val Thr Asp Thr
                85                  90                  95

Thr Ser Ile Asn Leu Phe Lys Val Leu Ser Ala Ala Leu Arg Val Gln
            100                 105                 110

Ala Thr Arg Ser Pro Glu Arg Arg Val Ile Val Thr Glu Thr Ser Asn
        115                 120                 125

Phe Pro Thr Asp Leu Tyr Ile Ala Glu Gly Leu Ala Asp Met Leu Gln
    130                 135                 140

Gln Gly Tyr Thr Leu Arg Leu Val Asp Ser Pro Glu Glu Leu Pro Gln
145                 150                 155                 160

Ala Ile Asp Gln Asp Thr Ala Val Val Met Leu Thr His Val Asn Tyr
                165                 170                 175

Lys Thr Gly Tyr Met His Asp Met Gln Ala Leu Thr Ala Leu Ser His
            180                 185                 190

Glu Cys Gly Ala Leu Ala Ile Trp Asp Leu Ala His Ser Ala Gly Ala
        195                 200                 205
```

```
Val Pro Val Asp Leu His Gln Ala Gly Ala Asp Tyr Ala Ile Gly Cys
    210                 215                 220

Thr Tyr Lys Tyr Leu Asn Gly Gly Pro Gly Ser Gln Ala Phe Val Trp
225                 230                 235                 240

Val Ser Pro Gln Leu Cys Asp Leu Val Pro Gln Pro Leu Ser Gly Trp
            245                 250                 255

Phe Gly His Ser Arg Gln Phe Ala Met Glu Pro Arg Tyr Glu Pro Ser
            260                 265                 270

Asn Gly Ile Ala Arg Tyr Leu Cys Gly Thr Gln Pro Ile Thr Ser Leu
            275                 280                 285

Ala Met Val Glu Cys Gly Leu Asp Val Phe Ala Gln Thr Asp Met Ala
290                 295                 300

Ser Leu Arg Arg Lys Ser Leu Ala Leu Thr Asp Leu Phe Ile Glu Leu
305                 310                 315                 320

Val Glu Gln Arg Cys Ala Ala His Glu Leu Thr Leu Val Thr Pro Arg
                325                 330                 335

Glu His Ala Lys Arg Gly Ser His Val Ser Phe Glu His Pro Glu Gly
            340                 345                 350

Tyr Ala Val Ile Gln Ala Leu Ile Asp Arg Gly Val Ile Gly Asp Tyr
            355                 360                 365

Arg Glu Pro Arg Ile Met Arg Phe Gly Phe Thr Pro Leu Tyr Thr Thr
370                 375                 380

Phe Thr Glu Val Trp Asp Ala Val Gln Ile Leu Gly Glu Ile Leu Asp
385                 390                 395                 400

Arg Lys Thr Trp Ala Gln Ala Gln Phe Gln Val Arg His Ser Val Thr
                405                 410                 415

<210> SEQ ID NO 168
<211> LENGTH: 465
<212> TYPE: PRT
<213> ORGANISM: Homo sapiens
<220> FEATURE:
<221> NAME/KEY: misc_feature
<222> LOCATION: (1)..(465)
<223> OTHER INFORMATION: Human kynureninase

<400> SEQUENCE: 168

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
                20                  25                  30

Leu Asp Glu Glu Asp Lys Leu Arg His Phe Arg Glu Cys Phe Tyr Ile
            35                  40                  45

Pro Lys Ile Gln Asp Leu Pro Pro Val Asp Leu Ser Leu Val Asn Lys
        50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Leu Asp Lys Trp Ala Lys
                85                  90                  95

Ile Ala Ala Tyr Gly His Glu Val Gly Lys Arg Pro Trp Ile Thr Gly
                100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
130                 135                 140

Met Leu Ser Phe Phe Lys Pro Thr Pro Lys Arg Tyr Lys Ile Leu Leu
```

```
                145                 150                 155                 160
Glu Ala Lys Ala Phe Pro Ser Asp His Tyr Ala Ile Glu Ser Gln Leu
                165                 170                 175
Gln Leu His Gly Leu Asn Ile Glu Glu Ser Met Arg Met Ile Lys Pro
                180                 185                 190
Arg Glu Gly Glu Thr Leu Arg Ile Glu Asp Ile Leu Glu Val Ile
                195                 200                 205
Glu Lys Glu Gly Asp Ser Ile Ala Val Ile Leu Phe Ser Gly Val His
                210                 215                 220
Phe Tyr Thr Gly Gln His Phe Asn Ile Pro Ala Ile Thr Lys Ala Gly
225                 230                 235                 240
Gln Ala Lys Gly Cys Tyr Val Gly Phe Asp Leu Ala His Ala Val Gly
                245                 250                 255
Asn Val Glu Leu Tyr Leu His Asp Trp Gly Val Asp Phe Ala Cys Trp
                260                 265                 270
Cys Ser Tyr Lys Tyr Leu Asn Ala Gly Ala Gly Ile Ala Gly Ala
                275                 280                 285
Phe Ile His Glu Lys His Ala His Thr Ile Lys Pro Ala Leu Val Gly
                290                 295                 300
Trp Phe Gly His Glu Leu Ser Thr Arg Phe Lys Met Asp Asn Lys Leu
305                 310                 315                 320
Gln Leu Ile Pro Gly Val Cys Gly Phe Arg Ile Ser Asn Pro Pro Ile
                325                 330                 335
Leu Leu Val Cys Ser Leu His Ala Ser Leu Glu Ile Phe Lys Gln Ala
                340                 345                 350
Thr Met Lys Ala Leu Arg Lys Lys Ser Val Leu Leu Thr Gly Tyr Leu
                355                 360                 365
Glu Tyr Leu Ile Lys His Asn Tyr Gly Lys Asp Lys Ala Ala Thr Lys
                370                 375                 380
Lys Pro Val Val Asn Ile Ile Thr Pro Ser His Val Glu Glu Arg Gly
385                 390                 395                 400
Cys Gln Leu Thr Ile Thr Phe Ser Val Pro Asn Lys Asp Val Phe Gln
                405                 410                 415
Glu Leu Glu Lys Arg Gly Val Val Cys Asp Lys Arg Asn Pro Asn Gly
                420                 425                 430
Ile Arg Val Ala Pro Val Pro Leu Tyr Asn Ser Phe His Asp Val Tyr
                435                 440                 445
Lys Phe Thr Asn Leu Leu Thr Ser Ile Leu Asp Ser Ala Glu Thr Lys
450                 455                 460
Asn
465

<210> SEQ ID NO 169
<211> LENGTH: 378
<212> TYPE: PRT
<213> ORGANISM: Shewanella sp.
<220> FEATURE:
<221> NAME/KEY: misc_feature
<222> LOCATION: (1)..(378)
<223> OTHER INFORMATION: Shewanella kynureninase

<400> SEQUENCE: 169

Met Leu Leu Asn Val Lys Gln Asp Phe Cys Leu Ala Gly Pro Gly Tyr
1               5                   10                  15
Leu Leu Asn His Ser Val Gly Arg Pro Leu Lys Ser Thr Glu Gln Ala
                20                  25                  30
```

Leu Lys Gln Ala Phe Phe Ala Pro Trp Gln Glu Ser Gly Arg Glu Pro
 35                  40                  45

Trp Gly Gln Trp Leu Gly Val Ile Asp Asn Phe Thr Ala Ala Leu Ala
 50                  55                  60

Ser Leu Phe Asn Gly Gln Pro Gln Asp Phe Cys Pro Gln Val Asn Leu
65                  70                  75                  80

Ser Ser Ala Leu Thr Lys Ile Val Met Ser Leu Asp Arg Leu Thr Arg
                 85                  90                  95

Asp Leu Thr Arg Asn Gly Gly Ala Val Val Leu Met Ser Glu Ile Asp
            100                 105                 110

Phe Pro Ser Met Gly Phe Ala Leu Lys Lys Ala Leu Pro Ala Ser Cys
        115                 120                 125

Glu Leu Arg Phe Ile Pro Lys Ser Leu Asp Val Thr Asp Pro Asn Val
130                 135                 140

Trp Asp Ala His Ile Cys Asp Asp Val Asp Leu Val Phe Val Ser His
145                 150                 155                 160

Ala Tyr Ser Asn Thr Gly Gln Gln Ala Pro Leu Ala Gln Ile Ile Ser
                165                 170                 175

Leu Ala Arg Glu Arg Gly Cys Leu Ser Leu Val Asp Val Ala Gln Ser
            180                 185                 190

Ala Gly Ile Leu Pro Leu Asp Leu Ala Lys Leu Gln Pro Asp Phe Met
        195                 200                 205

Ile Gly Ser Ser Val Lys Trp Leu Cys Ser Gly Pro Gly Ala Ala Tyr
210                 215                 220

Leu Trp Val Asn Pro Ala Ile Leu Pro Glu Cys Gln Pro Gln Asp Val
225                 230                 235                 240

Gly Trp Phe Ser His Glu Asn Pro Phe Glu Phe Asp Ile His Asp Phe
                245                 250                 255

Arg Tyr His Pro Thr Ala Leu Arg Phe Trp Gly Gly Thr Pro Ser Ile
            260                 265                 270

Ala Pro Tyr Ala Ile Ala Ala His Ser Ile Glu Tyr Phe Ala Asn Ile
        275                 280                 285

Gly Ser Gln Val Met Arg Glu His Asn Leu Gln Leu Met Glu Pro Val
290                 295                 300

Val Gln Ala Leu Asp Asn Glu Leu Val Ser Pro Gln Glu Val Asp Lys
305                 310                 315                 320

Arg Ser Gly Thr Ile Ile Leu Gln Phe Gly Glu Arg Gln Pro Gln Ile
                325                 330                 335

Leu Ala Ala Leu Ala Ala Ala Asn Ile Ser Val Asp Thr Arg Ser Leu
            340                 345                 350

Gly Ile Arg Val Ser Pro His Ile Tyr Asn Asp Glu Ala Asp Ile Ala
        355                 360                 365

Arg Leu Leu Gly Val Ile Lys Ala Asn Arg
370                 375

<210> SEQ ID NO 170
<211> LENGTH: 1424
<212> TYPE: DNA
<213> ORGANISM: Pseudomonas sp.
<220> FEATURE:
<221> NAME/KEY: misc_feature
<222> LOCATION: (1)..(1424)
<223> OTHER INFORMATION: Ptet-kynU(Pseudomonas)

<400> SEQUENCE: 170

```
atctaatcta gacatcatta attcctaatt tttgttgaca ctctatcatt gatagagtta      60
ttttaccact ccctatcagt gatagagaaa agtgaattat ataaaagtgg gaggtgcccg     120
aatgacgacc cgaaatgatt gcctagcgtt ggatgcacag gacagtctgg ctccgctgcg    180
ccaacaattt gcgctgccgg agggtgtgat atacctggat ggcaattcgc tgggcgcacg    240
tccggtagct gcgctggctc gcgcgcaggc tgtgatcgca gaagaatggg gcaacgggtt    300
gatccgttca tggaactctg cgggctggcg tgatctgtct gaacgcctgg gtaatcgcct    360
ggctaccctg attggtgcgc gcgatgggga agtagttgtt actgatacca cctcgattaa    420 tctgttttaaa gtgctgtcag cggcgctgcg cgtgcaagct acccgtagcc cggagcgccg    480
tgttatcgtg actgagacct cgaatttccc gaccgacctg tatattgcgg aagggttggc    540
ggatatgctg caacaaggtt acactctgcg tttggtggat tcaccggaag agctgccaca    600
ggctatagat caggacaccg cggtggtgat gctgacgcac gtaaattata aaaccggtta    660
tatgcacgac atgcaggctc tgaccgcgtt gagccacgag tgtggggctc tggcgatttg    720
ggatctggcg cactctgctg gcgctgtgcc ggtggacctg caccaagcgg gcgcggacta    780
tgcgattggc tgcacgtaca aatacctgaa tggcggcccg ggttcgcaag cgtttgtttg    840
ggtttcgccg caactgtgcg acctggtacc gcagccgctc tctggttggt tcggccatag    900
tcgccaattc gcgatggagc cgcgctacga accttctaac ggcattgctc gctatctgtg    960
cggcactcag cctattacta gcttggctat ggtggagtgc ggcctggatg tgtttgcgca   1020
gacggatatg gcttcgctgc gccgtaaaag tctggcgctg actgatctgt tcatcgagct   1080
ggttgaacaa cgctgcgctg cacacgaact gaccctggtt actccacgtg aacacgcgaa   1140
acgcggctct cacgtgtctt ttgaacaccc cgagggttac gctgttattc aagctctgat   1200
tgatcgtggc gtgatcggcg attaccgtga gccacgtatt atgcgtttcg gtttcactcc   1260
tctgtatact acttttacgg aagtttggga tgcagtacaa atcctgggcg aaatcctgga   1320
tcgtaagact tgggcgcagg ctcagtttca ggtgcgccac tctgttactt aaaaataaaa   1380
cgaaaggctc agtcgaaaga ctgggccttt cgttttatct gttg                    1424
```

<210> SEQ ID NO 171
<211> LENGTH: 1571
<212> TYPE: DNA
<213> ORGANISM: Homo sapiens
<220> FEATURE:
<221> NAME/KEY: misc_feature
<222> LOCATION: (1)..(1571)
<223> OTHER INFORMATION: Ptet-kynU(Human)

<400> SEQUENCE: 171

```
atctaatcta gacatcatta attcctaatt tttgttgaca ctctatcatt gatagagtta     60
ttttaccact ccctatcagt gatagagaaa agtgaatatc aagacacgag gaggtaagat    120
tatggagcct tcatctttag aactgccagc ggacacggtg cagcgcatcg cggcggaact    180
gaagtgccat ccgactgatg agcgtgtggc gctgcatctg gacgaagaag ataaactgcg    240
ccactttcgt gaatgttttt atattcctaa aattcaagac ttgccgccgg tagatttgag    300
tctcgttaac aaagatgaaa acgcgatcta ctttctgggc aactctctgg gtctgcaacc    360
aaaaatggtt aaaacgtacc tggaggaaga actggataaa tgggcaaaaa tcgcggctta    420
tggtcacgaa gtgggcaagc gtccttggat tactggcgac gagtctattg tgggtttgat    480
gaaagatatt gtgggcgcga atgaaaagga aattgcactg atgaatgctc tgaccgttaa    540
tctgcacctg ctgatgctgt cttttttttaa accgaccccg aaacgctaca aaatactgct    600
```

```
ggaagcgaaa gcgtttccgt cggatcacta tgctatagaa agtcaactgc agttgcatgg    660
tctgaatatc gaggaatcta tgcgcatgat taaaccgcgt gagggtgaag aaacgctgcg    720
tattgaagac attctggaag ttattgaaaa agaaggtgat tctatcgcag ttatactgtt    780
ttctggcgtg cactttata caggtcagca cttcaatatc ccggcaatca ctaaagcggg    840
gcaggcaaaa ggctgctatg ttggttttga cctggcgcat gcagtgggga atgttgaact    900
gtatctgcac gattggggcg ttgatttcgc gtgttggtgt agctacaaat atctgaacgc    960
tggcgcgggt ggcattgctg cgcttttat tcacgaaaaa cacgcgcaca ccattaaacc   1020
ggctctggtt ggctggttcg gtcatgagct gagtactcgc tttaaaatgg ataacaaact   1080
gcaattgatt ccgggtgttt gcggcttccg tatcagcaat ccgccgattc tgctggtttg   1140
cagcctgcac gctagtctgg aaatctttaa gcaggcgact atgaaagcgc tgcgcaaaaa   1200
atctgtgctg ctgaccggct atctggagta tctgatcaaa cacaattatg caaagataa    1260 agctgcaact aaaaaaccgg tagtgaacat tatcacccc tcacacgtgg aggagcgcgg    1320
ttgtcagctg actattactt tcagtgtacc taataaagat gtgttccagg aactggaaaa   1380
acgcggcgtt gtttgtgata aacgtaaccc gaatggtatt cgcgtggctc ctgtgccgct   1440
gtacaattca ttccacgatg tttataaatt caccaacctg ctgacttcta ttctcgacag   1500
tgctgagact aaaaattaaa aataaaacga aaggctcagt cgaaagactg gcctttcgt    1560 tttatctgtt g                                                        1571

<210> SEQ ID NO 172
<211> LENGTH: 1310
<212> TYPE: DNA
<213> ORGANISM: Shewanella sp.
<220> FEATURE:
<221> NAME/KEY: misc_feature
<222> LOCATION: (1)..(1310)
<223> OTHER INFORMATION: ptet-kynU(Shewanella)

<400> SEQUENCE: 172
atctaatcta gacatcatta attcctaatt tttgttgaca ctctatcatt gatagagtta     60
ttttaccact ccctatcagt gatagagaaa agtgaatggt tcaccaccac aaggagggat    120
tatgctgctg aatgtaaaac aggacttttg cctggcaggc ccgggctacc tgctgaatca    180
ctcggttggc cgtccgctga atcaactga gcaagcgctg aaacaagcat ttttgctcc     240 gtggcaagag agcggtcgtg aaccgtgggg ccagtggctg ggtgttattg ataatttcac    300
tgctgcgctg gcatctctgt ttaatggtca accgcaggat ttttgtccgc aggttaacct    360
gagcagcgcg ctgactaaaa ttgtgatgtc actggatcgt ctgactcgcg atctgacccg    420
caatggcggt gctgttgtgc tgatgtctga atcgatttc ccatctatgg gcttcgcgtt    480
gaaaaaagcg ctgccagcga gctgcgaact gcgtttatc ccgaaaagtc tggacgtgac    540
tgatccgaac gtatgggatg cacacatctg tgatgatgta gacctggttt ttgtgtctca    600
cgcctatagt aatacgggcc aacaggctcc gctggcgcaa atcatctctc tggcgcgtga    660
acgtggctgc ctgtcactgg tggatgtagc gcaatcagcg gggattttgc cgctggatct    720
ggcgaaactg caaccggact tcatgatcgg cagttcggtt aaatggctgt gctcgggccc    780
tggtgcggca tatctgtggg ttaatccggc gattctgccg gaatgtcagc cgcaggatgt    840
gggctggttt tcacatgaga atcccttga attcgacatc cacgatttcc gctaccaccc    900
gactgcactg cgcttttggg gtggtacgcc gtcgatcgcg ccttatgcga tcgcggcgca    960
```

```
ctcgatcgaa tattttgcca atatcggctc gcaagtgatg cgtgaacaca acctgcaact   1020
gatggaaccg gtggttcagg cgctggacaa tgaactggtg agcccgcagg aagtggataa   1080
acgctcaggc actattattc tgcaattcgg tgaacgtcaa ccgcaaattc tggcggctct   1140
ggctgcggcg aacatttcgg tggacactcg ttctttgggg attcgtgtta gtccgcacat   1200
ttataatgat gaggcggaca ttgcgcgcct gctgggtgtg atcaaagcaa atcgctaaaa   1260
ataaaacgaa aggctcagtc gaaagactgg gcctttcgtt ttatctgttg               1310
```

BACTERIA ENGINEERED TO TREAT A DISEASE OR DISORDER

RELATED APPLICATIONS

This application is a continuation of U.S. application Ser. No. 15/319,564, filed on Dec. 16, 2016, now issued as U.S. Pat. No. 9,889,164 on Feb. 13, 2018, which is a 35 U.S.C. § 371 national stage filing of International Application No. PCT/US2016/032565, filed on May 13, 2016. PCT/US2016/032565, filed on May 13, 2016, in turn claims priority to U.S. Provisional Patent Application No. 62/335,780, filed on May 13, 2016; U.S. Provisional Patent Application No. 62/336,338, filed on May 13, 2016; U.S. Provisional Patent Application No. 62/336,012, filed on May 13, 2016; and U.S. Provisional Patent Application No. 62/335,940, filed on May 13, 2016. PCT/US2016/032565, filed on May 13, 2016, is further a continuation-in-part of U.S. patent application Ser. No. 15/154,934, filed on May 13, 2016; and a continuation-in-part of International Application No. PCT/US2016/032562, filed on May 13, 2016. PCT/US2016/032565, filed on May 13, 2016, further claims priority to U.S. Provisional Patent Application No. 62/277,654, filed on Jan. 12, 2016; U.S. Provisional Patent Application No. 62/277,413, filed on Jan. 11, 2016; and U.S. Provisional Patent Application No. 62/293,749, filed on Feb. 10, 2016. PCT/US2016/032565, filed on May 13, 2016, is further a continuation-in-part of International Application No. PCT/US2016/020530, filed on Mar. 2, 2016. PCT/US2016/032565, filed on May 13, 2016, further claims priority to U.S. Provisional Patent Application No. 62/173,761, filed on Jun. 10, 2015; U.S. Provisional Patent Application No. 62/173,706, filed on Jun. 10, 2015; U.S. Provisional Patent Application No. 62/173,710, filed on Jun. 10, 2015; U.S. Provisional Patent Application No. 62/277,346, filed on Jan. 11, 2016; U.S. Provisional Patent Application No. 62/199,445, filed on Jul. 31, 2015; U.S. Provisional Patent Application No. 62/314,322, filed on Mar. 28, 2016; and U.S. Provisional Patent Application No. 62/313,691, filed on Mar. 25, 2016. PCT/US2016/032565, filed on May 13, 2016, is further a continuation-in-part of U.S. patent application Ser. No. 14/960,333, filed on Dec. 4, 2015, now issued as U.S. Pat. No. 9,487,764 on Nov. 8, 2016; and a continuation-in-part of International Application No. PCT/US2015/064140, filed on Dec. 4, 2015. PCT/US2016/032565, filed on May 13, 2016, further claims priority to U.S. Provisional Patent Application No. 62/263,329, filed on Dec. 4, 2015; U.S. Provisional Patent Application No. 62/256,041, filed on Nov. 16, 2015; U.S. Provisional Patent Application No. 62/256,039, filed on Nov. 16, 2015; U.S. Provisional Patent Application No. 62/212,223, filed on Aug. 31, 2015; U.S. Provisional Patent Application No. 62/183,935, filed on Jun. 24, 2015; U.S. Provisional Patent Application No. 62/256,052, filed on Nov. 16, 2015; and U.S. Provisional Patent Application No. 62/161,137, filed on May 13, 2015. The entire contents of each of the foregoing applications are expressly incorporated herein by reference.

SEQUENCE LISTING

The instant application contains a Sequence Listing which has been submitted electronically in ASCII format and is hereby incorporated by reference in its entirety. Said ASCII copy, created on Dec. 22, 2017, is named 126046-01403_Sequence_Listing.txt and is 355,163 bytes in size.

BACKGROUND OF THE INVENTION

It has recently been discovered that the microbiome in mammals plays a large role in health and disease (see Cho and Blaser, *Nature Rev. Genet.*, 13:260-270, 2012 and Owyang and Wu, *Gastroenterol.*, 146(6):1433-1436, 2014). Indeed, bacteria-free animals have abnormal gut epithelial and immune function, suggesting that the microbiome in the gut plays a critical role in the mammalian immune system. Specifically, the gut microbiome has been shown to be involved in diseases, including, for example, immune diseases (such as Inflammatory Bowel Disease), autism, liver disease, cancer, food allergy, metabolic diseases (such as urea cycle disorder, phenylketonuria, and maple syrup urine disease), obesity, and infection, among many others.

Fecal transplantation of native microbial strains has recently garnered much attention for its potential to treat certain microbial infections and immune diseases in the gut (Owyang and Wu, 2014). There have also been recent efforts to engineer microbes to produce, e.g., secrete, therapeutic molecules and administer them to a subject in order to deliver the therapeutic molecule(s) directly to the site where therapy is needed, such as various sites in the gut. However, such efforts have been frustrated for several reasons, mostly relating to the constitutive production of the bacteria and its gene product(s). For example, the viability and stability of the engineered microbes have been compromised due, in part, to the constitutive production of large amounts of foreign protein(s). Unfortunately, genetically engineered microbes which have been engineered to express intracellular therapeutic enzymes which degrade target molecules associated with disease states or disorders, e.g., diseases or disorders associated with the overexpression of a molecule which is harmful to a subject, have also been shown to have low efficacy and enzyme activity levels in vitro and in vivo. Accordingly, a need exists for improved genetically engineered microbes which are useful for therapeutic purposes.

SUMMARY

The instant invention surprisingly provides genetically engineered microbes which express a heterologous transporter in order to regulate, e.g., increase, the transport of target molecules associated with disease into the genetically engineered microbes in order to increase the therapeutic efficacy of the microbe.

In one aspect, the invention provides a genetically-engineered non-pathogenic microorganism comprising at least one heterologous gene encoding a substrate transporter, wherein the gene encoding the substrate transporter is operably linked to an inducible promoter.

In one embodiment, the bacterium is a Gram-positive bacterium. In one embodiment, the bacterium is a Gram-negative bacterium. In one embodiment, the bacterium is an obligate anaerobic bacterium. In one embodiment, the bacterium is a facultative anaerobic bacterium.

In one embodiment, the bacterium is an aerobic bacterium. In one embodiment, the bacterium is selected from *Clostridium novyi* NT, *Clostridium butyricum*, *E. coli* Nissle, and *E. Coli* K-12.

In one embodiment, the inducible promoter is induced by low-oxygen or anaerobic conditions. In one embodiment, the inducible promoter is selected from a FNR-inducible promoter, an ANR-inducible promoter, and a DNR-inducible promoter. In one embodiment, the inducible promoter is P-fnrs promoter.

In one embodiment, the substrate transporter is capable of importing into the bacterium a substrate selected from the group consisting of an amino acid, a nucleoside, kynurenine, prostaglandin E2, lactic acid, propionate, bile salt, γ-aminobutyric acid (GABA), manganese, a toxin, and a peptide.

In one embodiment, the substrate transporter is an amino acid transporter capable of importing into the bacterium an amino acid selected from the group consisting of leucine, isoleucine, valine, arginine, lysine, asparagine, serine, glycine, glutamine, tryptophan, methionine, threonine, cysteine, tyrosine, phenylalanine, glutamic acid, aspartic acid, alanine, histidine, and proline.

In one embodiment, the heterologous gene encoding the amino acid transporter is from Agrobacterium tumefaciens, Anabaena cylindrical, Anabaena variabilis, Bacillus amyiquefaciens, Bacillus atrophaeus, Bacillus halodurans, Bacillus methanolicus, Bacillus subtilis, Caenorhabditis elegans, Clostridium botulinum, Corynebacterium glutamicum, Escherichia coli, Flavobacterium limosediminis, Helicobacter pylori, Klebsiella pneumonia, Lactococcus lactis, Lactobacillus saniviri, Legionella pneumophila Methylobacterium aquaticum, Mycobacterium bovis, Photorhabdus luminescens, Pseudomonas aeruginosa, Pseudomonas fluorescens, Saccharomyces cerevisiae, Salmonella enterica, Sinorhizobium meliloti, or Ustilago maydis. In one embodiment, the heterologous gene encoding the amino acid transporter has a sequence with at least 90% identity to any one of SEQ ID NOs:9, 10, 13-18, 25, 26, 29, 35, 41-44, 46-48, 59-62, 69, 87, 91, 94-96, 98, or 103. In one embodiment, the heterologous gene encoding the amino acid transporter has a sequence comprising any one of SEQ ID NOs:9, 10, 13-18, 25, 26, 29, 35, 41-44, 46-48, 59-62, 69, 87, 91, 94-96, 98, or 103. In one embodiment, the heterologous gene encoding the amino acid transporter has a sequence consisting of any one of SEQ ID NOs:9, 10, 13-18, 25, 26, 29, 35, 41-44, 46-48, 59-62, 69, 87, 91, 94-96, 98, or 103.

In one embodiment, the substrate transporter is a nucleoside transporter capable of importing into the bacterium a nucleoside selected from the group consisting of adenosine, guanosine, uridine, inosine, xanthosine, thymidine and cytidine. In one embodiment, the heterologous gene encoding the nucleoside transporter is from Bacillus halodurans, Bacillus subtilis, Caulobacter crescentus, Escherichia coli, Haemophilus influenzae, Helicobacter pylori, Pseudomonas, Bacillus subtilis, Escherichia coli, Prevotella intermedia, Porphytomonas gingivalis, Salmonella typhimurium, Salmonella enterica, or Vibrio cholera.

In one embodiment, the heterologous gene encoding the nucleoside transporter has a sequence with at least 90% identity to any one of SEQ ID NOs:108-128. In one embodiment, the heterologous gene encoding the amino acid transporter has a sequence comprising any one of SEQ ID NOs:108-128. In one embodiment, the heterologous gene encoding the amino acid transporter has a sequence consisting of any one of SEQ ID NOs:108-128.

In one embodiment, the substrate transporter is a kynurenine transporter capable of importing kynurenine into the bacterium. In one embodiment, the heterologous gene encoding the kynurenine transporter is from Escherichia coli, Saccharomyces cerevisiae or Corynebacterium glutamicum. In one embodiment, the heterologous gene encoding the kynurenine transporter has a sequence with at least 90% identity to any one of SEQ ID NOs:46-48. In one embodiment, the heterologous gene encoding the kynurenine transporter has a sequence comprising any one of SEQ ID NOs:46-48. In one embodiment, the heterologous gene encoding the amino acid transporter has a sequence consisting of any one of SEQ ID NOs:46-48.

In one embodiment, the substrate transporter is a prostaglandin E2 transporter capable of importing prostaglandin E2 into the bacterium. In one embodiment, the heterologous gene encoding the prostaglandin E2 (PGE2) transporter is from Escherichia coli, Saccharomyces cerevisiae or Corynebacterium glutamicum.

In one embodiment, the substrate transporter is a lactic acid transporter capable of importing lactic acid into the bacterium. In one embodiment, the heterologous gene encoding the lactic acid transporter is from Escherichia coli, Saccharomyces cerevisiae and Corynebacterium glutamicum.

In one embodiment, the substrate transporter is a propionate transporter capable of importing propionate into the bacterium. In one embodiment, the heterologous gene encoding the propionate transporter is from Bacillus subtilis, Campylobacter jejuni, Clostridium perfringens, Escherichia coli, Lactobacillus delbrueckii, Mycobacterium smegmatis, Nocardia farcinica, Pseudomonas aeruginosa, Salmonella typhimurium, Virgibacillus, or Staphylococcus aureus. In one embodiment, the heterologous gene encoding the propionate transporter has a sequence with at least 90% identity to any one of SEQ ID NOs:129-130. In one embodiment, the heterologous gene encoding the propionate transporter has a sequence comprising any one of SEQ ID NOs:129-130. In one embodiment, the heterologous gene encoding the propionate transporter has a sequence consisting of any one of SEQ ID NOs:129-130.

In one embodiment, the substrate transporter is a bile salt transporter capable of importing bile salt into the bacterium. In one embodiment, the heterologous gene encoding the bile salt transporter is from Lactobacillus johnsonni. In one embodiment, the heterologous gene encoding the bile acid transporter has a sequence with at least 90% identity to any one of SEQ ID NOs:131-132. In one embodiment, the heterologous gene encoding the bile salt transporter has a sequence comprising any one of SEQ ID NOs:131-132. In one embodiment, the heterologous gene encoding the bile salt transporter has a sequence consisting of any one of SEQ ID NOs:131-132.

In one embodiment, the substrate transporter is a bile salt transporter capable of importing ammonia into the bacterium. In one embodiment, the heterologous gene encoding the ammonia transporter is from Corynebacterium glutamicum, Escherichia coli, Streptomyces coelicolor or Ruminococcus albus. In one embodiment, the heterologous gene encoding the ammonia transporter has a sequence with at least 90% identity to SEQ ID NO:133. In one embodiment, the heterologous gene encoding the ammonia transporter has a sequence comprising SEQ ID NO:133. In one embodiment, the heterologous gene encoding the ammonia transporter has a sequence consisting of SEQ ID NO:133.

In one embodiment, the substrate transporter is a γ-aminobutyric acid (GABA) transporter capable of importing GABA into the bacterium. In one embodiment, the heterologous gene encoding the GABA transporter is from Escherichia coli or Bacillus subtilis. In one embodiment, the heterologous gene encoding the GABA transporter has a sequence with at least 90% identity to SEQ ID NO:134. In one embodiment, the heterologous gene encoding the GABA transporter has a sequence comprising SEQ ID NO:134. In one embodiment, the heterologous gene encoding the GABA transporter has a sequence consisting of SEQ ID NO:134.

In one embodiment, the substrate transporter is a manganese transporter capable of importing manganese into the bacterium. In one embodiment, the heterologous gene encoding the manganese transporter is from Bacillus subtilis, Staphylococcus aureus, Salmonella typhimurium, Shigella flexneri, Yersinia pestis, or Escherichia coli. In one embodiment, the heterologous gene encoding the manganese transporter has a sequence with at least 90% identity to SEQ ID NO:135. In one embodiment, the heterologous gene encoding the manganese transporter has a sequence comprising SEQ ID NO:135. In one embodiment, the heterologous gene encoding the manganese transporter has a sequence consisting of SEQ ID NO:135.

In one embodiment, the substrate transporter is a toxin transporter capable of importing a toxin into the bacterium. In one embodiment, the substrate transporter is a peptide transporter capable of importing a peptide into the bacterium.

In one embodiment, the heterologous gene encoding the substrate transporter and operatively linked promoter are present on a chromosome in the bacterium. In one embodiment, the heterologous gene encoding the substrate transporter and operatively linked promoter are present on a plasmid in the bacterium.

In one embodiment, the bacterium is an auxotroph comprising a deletion or mutation in a gene required for cell survival and/or growth. In one embodiment, the gene required for cell survival and/or growth is selected from thyA, dapD, and dapA.

In one embodiment, the bacterium comprises a kill switch.

In one aspect, the present disclosure provides a pharmaceutical composition comprising a recombinant bacterium disclosed herein and a pharmaceutically acceptable carrier.

In another aspect, the present invention provides a method of treating a disease in a subject in need thereof comprising the step of administering to the subject a pharmaceutical composition comprising a recombinant bacterium disclosed herein and a pharmaceutically acceptable carrier.

BRIEF DESCRIPTION OF THE FIGURES

FIG. 6B depicts an additional copy of the endogenous E. coli high affinity phenylalanine transporter, pheP, driven by the PfnrS promoter and inserted into the lacZ locus on the Nissle chromosome.

FIG. 7A depicts phenylalanine degradation components integrated into the E. coli Nissle chromosome. In some embodiments, engineered plasmid-free bacterial strains are used to prevent plasmid conjugation in vivo. In some embodiments, multiple insertions of the PAL gene result in increased copy number and/or increased phenylalanine degradation activity. In some embodiments, a copy of the endogenous E. coli high affinity phenylalanine transporter, pheP, is driven by the PfnrS promoter and is inserted into the lacZ locus. FIG. 7B depicts a schematic diagram of one non-limiting embodiment of the disclosure, wherein the E. coli Nissle chromosome is engineered to contain four copies of PfnrS-PAL inserted at four different insertion sites across the genome (malE/K, yicS/nepI, agaI/rsmI, and cea), and one copy of a phenylalanine transporter gene inserted at a different insertion site (lacZ). In this embodiment, the PAL gene is PAL3 derived from P. luminescens, and the phenylalanine transporter gene is pheP derived from E. coli. In one embodiment, the strain is SYN-PKU511. FIG. 7C depicts a schematic diagram of one preferred embodiment of the disclosure, wherein the E. coli Nissle chromosome is engineered to contain five copies of PAL under the control of an oxygen level-dependent promoter (e.g., PfnrS-PAL3) inserted at different integration sites on the chromosome (malE/K, yicS/nepI, malP/T, agaI/rsmI, and cea), and one copy of a phenylalanine transporter gene under the control of an oxygen level-dependent promoter (e.g., PfnrS-pheP) inserted at a different integration site on the chromosome (lacZ). The genome is further engineered to include a thyA auxotrophy, in which the thyA gene is deleted and/or replaced with an unrelated gene, as well as a kanamycin resistance gene.

FIGS. 9A and 9B depict the state of one non-limiting embodiment of the PAL construct under non-inducing (FIG. 9A) and inducing (FIG. 9B) conditions. FIG. 9A depicts relatively low PAL and PheP production under aerobic conditions due to oxygen ($O_2$) preventing FNR from dimerizing and activating PAL and/or pheP gene expression. FIG. 9B depicts up-regulated PAL and PheP production under anaerobic conditions due to FNR dimerizing and inducing FNR promoter-mediated expression of PAL and pheP (squiggle above "PAL" and "pheP"). Arrows adjacent to a single rectangle, or a cluster of rectangles, depict the promoter responsible for driving transcription (in the direction of the arrow) of such gene(s). Arrows above each rectangle depict the expression product of each gene.

FIG. 17 depicts possible components of a branched chain amino acid synthetic biotic disclosed herein FIG. 18 depicts possible components of a branched chain amino acid synthetic biotic disclosed herein.

FIG. 19 depicts possible components of a branched chain amino acid synthetic biotic disclosed herein

FIG. 22 depicts exemplary components of a branched chain amino acid synthetic biotic disclosed herein for leucine import.

FIG. 29 depicts examples of circuit components for ldh, kivD and livKHMGF inducible expression in *E. coli*.

DETAILED DESCRIPTION

Figure 1:
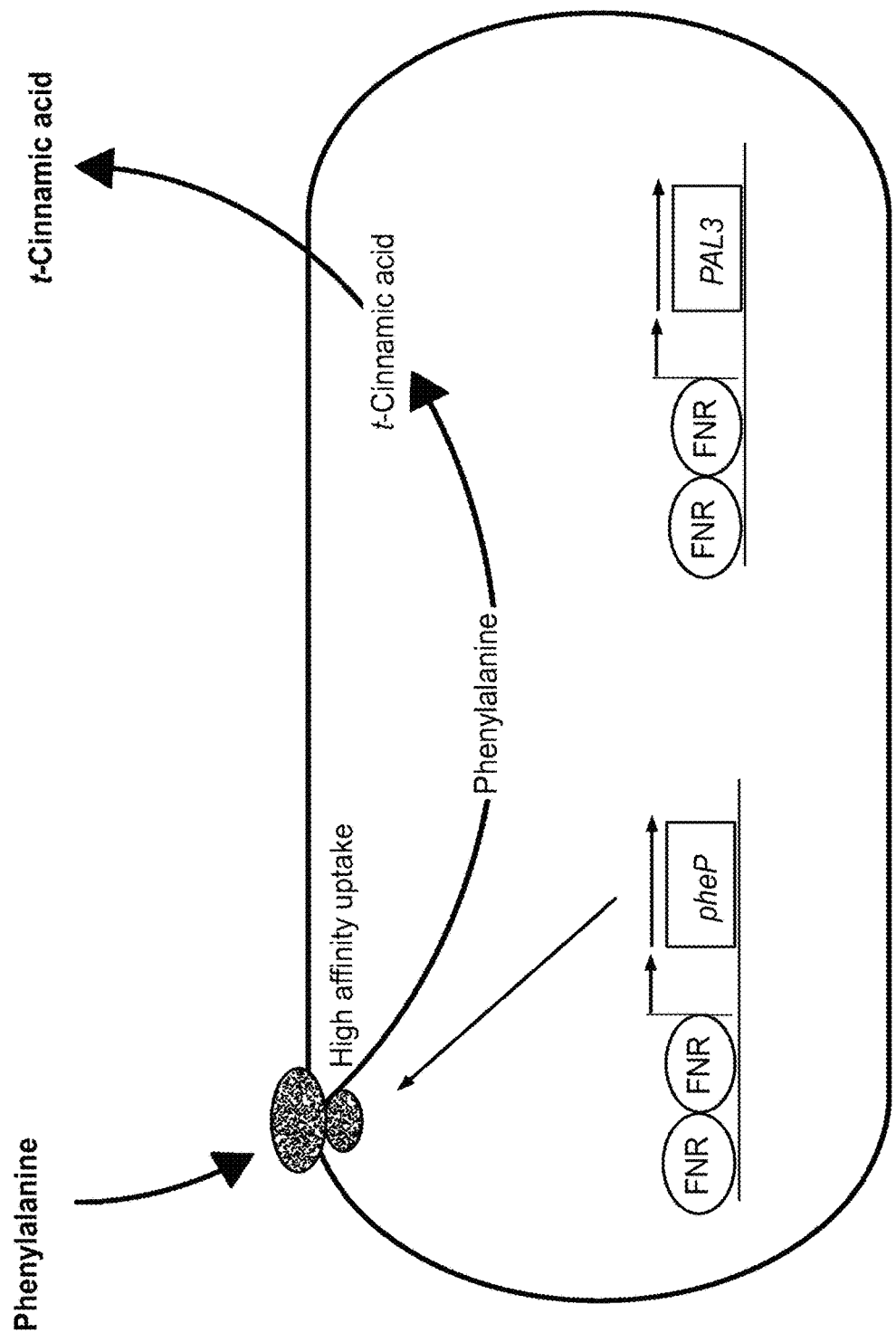
FIG. 1 depicts a synthetic biotic for treating phenylketonuria (PKU) and disorders characterized by hyperphenylalaninemia.
Figure 2:
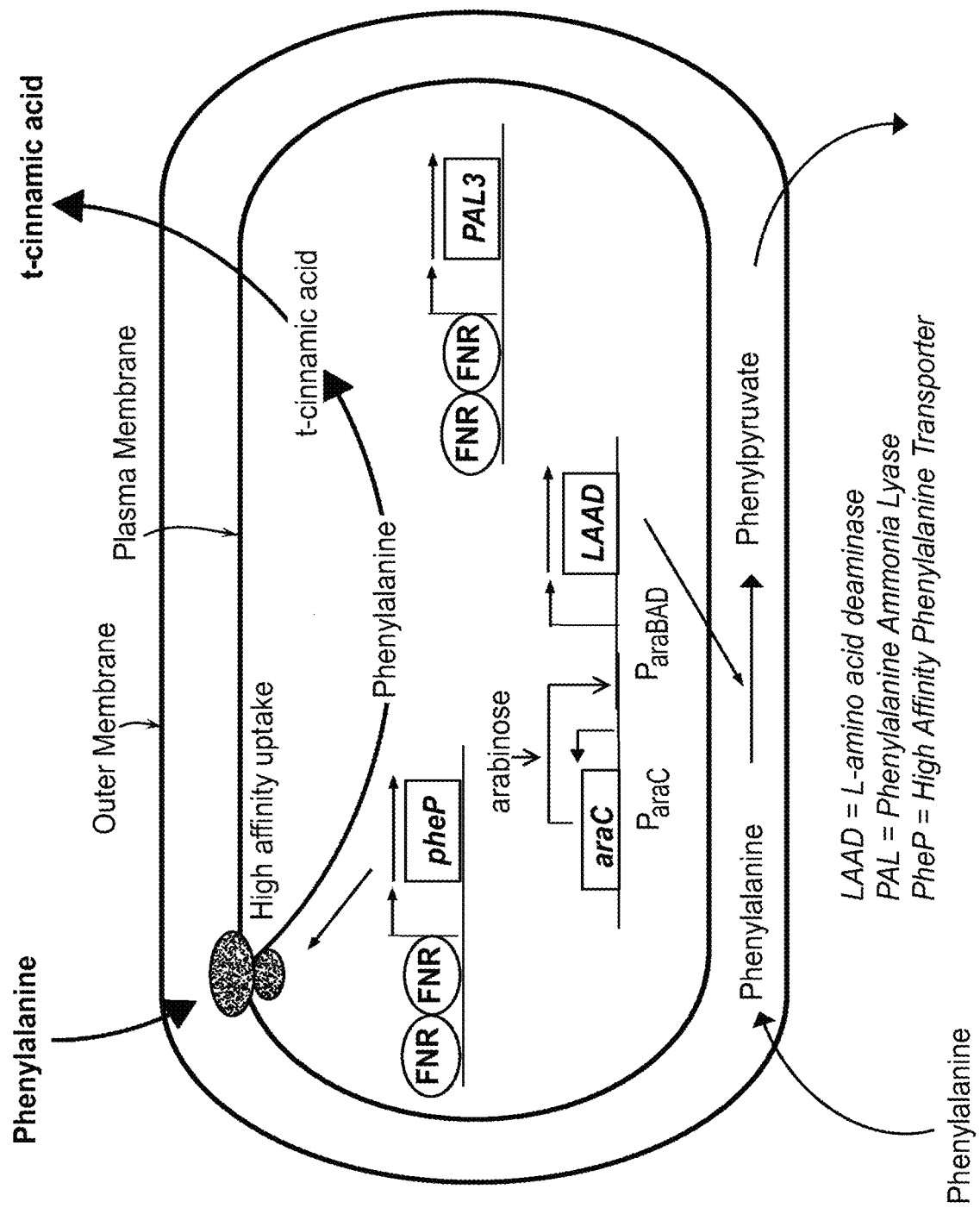
FIG. 2 depicts a synthetic biotic for treating phenylketonuria (PKU) and disorders characterized by hyperphenylalaninemia.
Figure 3:
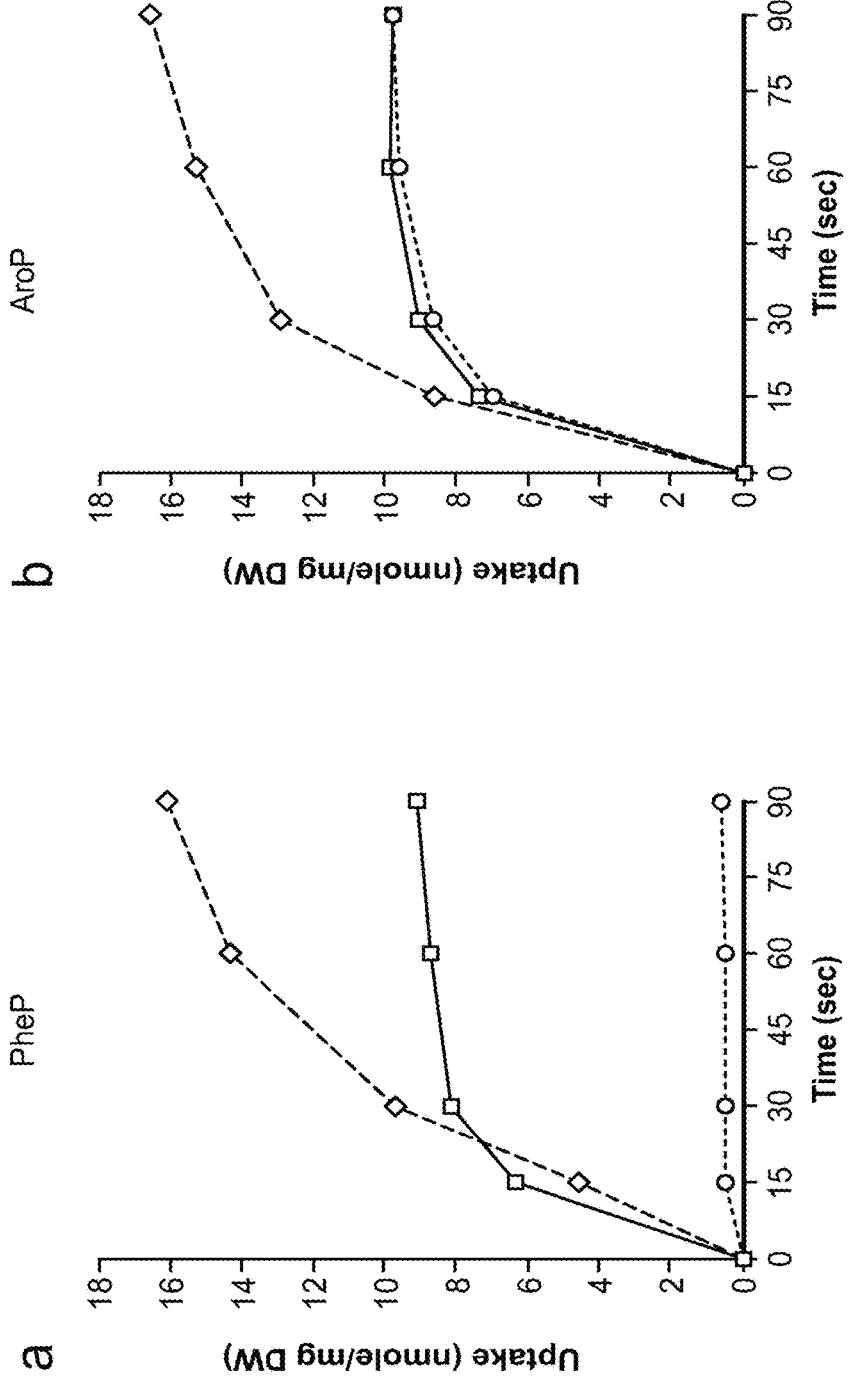
FIG. 3 is a graph showing that PheP and AroP Transport Phe at the same rate.

The invention includes genetically engineered microorganisms, e.g., genetically engineered bacteria, pharmaceutical compositions thereof, and methods of modulating or treating a disease.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

As used herein, the term "amino acid" refers to a class of organic compounds that contain at least one amino group and one carboxyl group Amino acids include leucine, isoleucine, valine, arginine, lysine, asparagine, serine, glycine, glutamine, tryptophan, methionine, threonine, cysteine, tyrosine, phenylalanine, glutamic acid, aspartic acid, alanine, histidine, and proline.

As used herein, the term "auxotroph" or "auxotrophic" refers to an organism that requires a specific factor, e.g., an amino acid, a sugar, or other nutrient, to support its growth. An "auxotrophic modification" is a genetic modification that causes the organism to die in the absence of an exogenously added nutrient essential for survival or growth because it is unable to produce said nutrient. As used herein, the term "essential gene" refers to a gene which is necessary to for cell growth and/or survival. Essential genes are described in more detail infra and include, but are not limited to, DNA synthesis genes (such as thyA), cell wall synthesis genes (such as dapA), and amino acid genes (such as serA and metA).

"Cancer" or "cancerous" is used to refer to a physiological condition that is characterized by unregulated cell growth. In some embodiments, cancer refers to a tumor. "Tumor" is used to refer to any neoplastic cell growth or proliferation or any pre-cancerous or cancerous cell or tissue. A tumor may be malignant or benign. Types of cancer include, but are not limited to, adrenal cancer, adrenocortical carcinoma, anal cancer, appendix cancer, bile duct cancer, bladder cancer, bone cancer (e.g., Ewing sarcoma tumors, osteosarcoma, malignant fibrous histiocytoma), brain cancer (e.g., astrocytomas, brain stem glioma, craniopharyngioma, ependymoma), bronchial tumors, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, gestational trophoblastic disease, heart cancer, Kaposi sarcoma, kidney cancer, largyngeal cancer, hypopharyngeal cancer, leukemia (e.g., acute lymphoblastic leukemia, acute myeloid leukemia, chronic lymphocytic leukemia, chronic myelogenous leukemia), liver cancer, lung cancer, lymphoma (e.g., AIDS-related lymphoma, Burkitt lymphoma, cutaneous T cell lymphoma, Hodgkin lymphoma, Non-Hodgkin lymphoma, primary central nervous system lymphoma), malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer (e.g., basal cell carcinoma, melanoma), small intestine cancer, stomach cancer, teratoid tumor, testicular cancer, throat cancer, thymus cancer, thyroid cancer, unusual childhood cancers, urethral cancer, uterine cancer, uterine sarcoma, vaginal cancer, vulvar cancer, Waldenström macroglobulinemia, and Wilms tumor. Side effects of cancer treatment may include, but are not limited to, opportunistic autoimmune disorder(s), systemic toxicity, anemia, loss of appetite, irritation of bladder lining, bleeding and bruising (thrombocytopenia), changes in taste or smell, constipation, diarrhea, dry mouth, dysphagia, edema, fatigue, hair loss (alopecia), infection, infertility, lymphedema, mouth sores, nausea, pain, peripheral neuropathy, tooth decay, urinary tract infections, and/or problems with memory and concentration (National Cancer Institute).

As used herein, the term "coding region" refers to a nucleotide sequence that codes for a specific amino acid sequence. The term "regulatory sequence" refers to a nucleotide sequence located upstream (5' non-coding sequences), within, or downstream (3' non-coding sequences) of a coding sequence, and which influences the transcription, RNA processing, RNA stability, or translation of the associated coding sequence. Examples of regulatory sequences include, but are not limited to, promoters, translation leader sequences, effector binding sites, and stem-loop structures. In one embodiment, the regulatory sequence comprises a promoter, e.g., an FNR responsive promoter.

As used herein the term "codon-optimized" refers to the modification of codons in a gene or a coding region of a nucleic acid molecule to improve translation in a host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. Such optimization includes replacing at least one, or more than one, or a significant number, of codons with one or more codons that are more frequently used in the genes of the host organism.

Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^S$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive *Bacillus subtilis* $\sigma^B$ promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_I712074; BBa_I719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), and a bacteriophage SP6 promoter (e.g., SP6 promoter (BBa_J64998)).

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

"Exogenous environmental condition(s)" refer to setting(s) or circumstance(s) under which the promoter described herein is induced. The phrase "exogenous environmental conditions" is meant to refer to the environmental conditions external to the intact (unlysed) recombinant micororganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are low-oxygen, microaerobic, or anaerobic conditions, such as hypoxic and/or necrotic tissues. In some embodiments, the exogenous environmental condition is a low-pH environment. In some embodiments, the recombinant bacterial cell of the disclosure comprise a pH-dependent promoter. In some embodiments, the recombinant bacterial cell of the disclosure comprise an oxygen level-dependent promoter. In some aspects, bacteria have evolved transcription factors that are capable of sensing oxygen levels (i.e., oxygen-level dependent transcription factors). Different signaling pathways may be triggered by different oxygen levels and occur with different kinetics. An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR (fumarate and nitrate reductase)-responsive promoters, ANR (anaerobic nitrate respiration)-responsive promoters, and DNR (dissimilatory nitrate respiration regulator)-responsive promoters. Multiple FNR-responsive promoters, ANR-responsive promoters, and DNR-responsive promoters which can be used in the present invention are known in the art (see, e.g., Castiglione et al. (2009) Microbiology 155(Pt. 9): 2838-44; Eiglmeier et al. (1989) *Mol. Microbiol.* 3(7): 869-78; Galimand et al. (1991) *J. Bacteriol.* 173(5): 1598-1606; Hasegawa et al. (1998) *FEMS Microbiol. Lett.* 166(2): 213-217; Hoeren et al. (1993) Eur. J. Biochem. 218(1): 49-57; Salmon et al. (2003) *J. Biol. Chem.* 278(32): 29837-55), and non-limiting examples are shown in Table 1.

TABLE 1

Examples of transcription factors and responsive genes and regulatory regions

| Transcription Factor | Examples of responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

In a non-limiting example, a promoter (PfnrS) from the *E. coli* Nissle fumarate and nitrate reductase gene S (fnrS) that is known to be highly expressed under conditions of low or no environmental oxygen can be used in the present invention (Durand and Storz, 2010; Boysen et al, 2010). The PfnrS promoter is activated under anaerobic conditions by the global transcriptional regulator FNR that is naturally found in *E. coli* Nissle. Under anaerobic conditions, FNR forms a dimer and binds to specific sequences in the promoters of genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as "FNRS", "fnrs", "FNR", "P-FNRS" promoter and other such related designations to indicate the promoter PfnrS.

As used herein, the term "expression" refers to the transcription and stable accumulation of sense (mRNA) or anti-sense RNA derived from a nucleic acid, and/or to translation of an mRNA into a polypeptide.

As used herein, the term "gene" refers to a nucleic acid fragment that encodes a protein or a fragment thereof, optionally including regulatory sequences preceding (5' non-coding sequences) and following (3' non-coding sequences) the coding sequence. In one embodiment, a "gene" does not include regulatory sequences preceding and following the coding sequence. A "native gene" refers to a gene as found in nature, optionally with its own regulatory sequences preceding and following the coding sequence. A "chimeric gene" refers to any gene that is not a native gene, optionally comprising regulatory sequences preceding and following the coding sequence, wherein the coding sequence and/or the regulatory sequence, in whole or in part, are not found together in nature. Thus, a chimeric gene may comprise a regulatory sequence and a coding sequence, each derived from different sources, or a regulatory and a coding sequence each derived from the same source, but arranged differently than they are found in nature.

The term "genetic modification," as used herein, refers to any genetic change. Exemplary genetic modifications include those that increase, decrease, or abolish the expression of a gene, including, for example, modifications of native chromosomal or extrachromosomal genetic material. Exemplary genetic modifications also include the introduction of at least one plasmid, modification, mutation, base deletion, base addition, and/or codon modification of chromosomal or extrachromosomal genetic sequence(s), gene over-expression, gene amplification, gene suppression, promoter modification or substitution, gene addition (either single or multi-copy), antisense expression or suppression, or any other change to the genetic elements of a host cell, whether the change produces a change in phenotype or not. Genetic modification can include the introduction of a plasmid, e.g., a plasmid comprising at least one substrate transporter operably linked to a promoter, into a bacterial cell. Genetic modification can also involve a targeted replacement in the chromosome, e.g., to replace a native gene promoter with an inducible promoter, regulated promoter, strong promoter, weak promoter, or constitutive promoter. Genetic modification can also involve gene amplification, e.g., introduction of at least one additional copy of a native gene into the chromosome of the cell. Alternatively, chromosomal genetic modification can involve a genetic mutation.

As used herein, the term "genetic mutation" refers to a change or multiple changes in a nucleotide sequence of a gene or related regulatory region that alters the nucleotide sequence as compared to its native or wild-type sequence. Mutations include, for example, substitutions, insertions, and deletions, in whole or in part, within the wild-type sequence. Such substitutions, insertions, or deletions can be single nucleotide changes (e.g., one or more point mutations), or can be two or more nucleotide changes, which may result in substantial changes to the sequence. Mutations can occur within the coding region of the gene as well as within the non-coding and regulatory sequence of the gene. The term "genetic mutation" is intended to include silent and conservative mutations within a coding region as well as changes which alter the amino acid sequence of the polypeptide encoded by the gene. A genetic mutation in a gene coding sequence may, for example, increase, decrease, or otherwise alter the activity (e.g., import activity) of the polypeptide product encoded by the gene. A genetic mutation in a regulatory sequence may increase, decrease, or otherwise alter the expression of sequences operably linked to the altered regulatory sequence.

It is routine for one of ordinary skill in the art to make mutations in a gene of interest. Mutations include substitutions, insertions, deletions, and/or truncations of one or more specific amino acid residues or of one or more specific nucleotides or codons in the polypeptide or polynucleotide of interest. Mutagenesis and directed evolution methods are well known in the art for creating variants. See, e.g., U.S. Pat. No. 7,783,428; 6,586,182; 6,117,679; and Ling, et al., 1999, "Approaches to DNA mutagenesis: an overview," *Anal. Biochem.*, 254(2):157-78; Smith, 1985, "In vitro mutagenesis," *Ann. Rev. Genet.*, 19:423-462; Carter, 1986, "Site-directed mutagenesis," *Biochem. J.*, 237:1-7; and Minshull, et al., 1999, "Protein evolution by molecular breeding," *Current Opinion in Chemical Biology*, 3:284-290. For example, the lambda red system can be used to knock-out genes in *E. coli* (see, e.g., Datta et al., *Gene*, 379:109-115 (2006)).

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

As used herein, "heterologous" as used in the context of a nucleic acid or polypeptide sequence, "heterologous gene", or "heterologous sequence", refers to a nucleotide or polypeptide sequence that is not normally found in a given cell in nature. As used herein, a heterologous sequence encompasses a nucleic acid sequence that is exogenously introduced into a given cell. "Heterologous gene" includes a native gene, or fragment thereof, that has been introduced into the host cell in a form that is different from the corresponding native gene. For example, a heterologous gene may include a native coding sequence that is a portion of a chimeric gene to include a native coding sequence that is a portion of a chimeric gene to include non-native regulatory regions that is reintroduced into the host cell. A heterologous gene may also include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature. As used herein, the term "endogenous gene" refers to a native gene in its natural location in the genome of an organism. As used herein, the term "transgene" refers to a gene that has been introduced into the host organism, e.g., host bacterial cell, genome.

The term "inactivated" as applied to a gene refers to any genetic modification that decreases or eliminates the expression of the gene and/or the functional activity of the corresponding gene product (mRNA and/or protein). The term "inactivated" encompasses complete or partial inactivation, suppression, deletion, interruption, blockage, promoter alterations, antisense RNA, dsRNA, or down-regulation of a gene. This can be accomplished, for example, by gene "knockout," inactivation, mutation (e.g., insertion, deletion, point, or frameshift mutations that disrupt the expression or activity of the gene product), or by use of inhibitory RNAs (e.g., sense, antisense, or RNAi technology). A deletion may encompass all or part of a gene's coding sequence. The term "knockout" refers to the deletion of most (at least about 95%, at least about 96%, at least about 97%, at least about 98%, or at least about 99%) or all (100%) of the coding sequence of a gene. In some embodiments, any number of nucleotides can be deleted, from a single base to an entire piece of a chromosome.

An "inducible promoter" refers to a regulatory nucleic acid region that is operably linked to one or more genes, wherein transcription of the gene(s) is increased in response to a stimulus (e.g., an inducer) or an exogenous environmental condition. A "directly inducible promoter" refers to a regulatory region, wherein the regulatory region is operably linked to a gene encoding a protein or polypeptide, where, in the presence of an inducer of said regulatory region, the protein or polypeptide is expressed. An "indirectly inducible promoter" refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by "inducible promoter." Examples of inducible promoters include, but are not limited to, an FNR promoter, a $P_{araC}$ promoter, a $P_{araBAD}$ promoter, a propionate promoter, and a $P_{TctR}$ promoter, each of which are described in more detail herein. Examples of other inducible promoters are provided herein below.

An "isolated" polypeptide, or a fragment, variant, or derivative thereof, refers to a polypeptide that is not in its natural milieu. No particular level of purification is required. Recombinantly-produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

As used herein the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 2014/0079701, the contents of which are herein incorporated by reference in its entirety.

As used herein, the terms "modulate" and "treat" and their cognates refer to an amelioration of a disease or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease or condition, either physically (e.g., stabilization of a discernible symptom), physiologically (e.g., stabilization of a physical parameter), or both. In another embodiment, "modulate" and "treat" refer to slowing the progression or reversing the progression of a disease or condition. As used herein, "prevent" and its cognates refer to delaying the onset or reducing the risk of acquiring a given disease or condition.

As used herein, a "non-native" nucleic acid sequence refers to a nucleic acid sequence not normally present in a microorganism, e.g., an extra copy of an endogenous sequence, or a heterologous sequence such as a sequence from a different organism (e.g., an organism from a different species, strain, or substrain of a prokaryote or eukaryote), or a sequence that is modified and/or mutated as compared to the unmodified native or wild-type sequence. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes (e.g., genes in a gene cassette or operon). In some embodiments, "non-native" refers to two or more nucleic acid sequences that are not found in the same relationship to each other in nature. The non-native nucleic acid sequence may be present on a plasmid or chromosome. In some embodiments, the genetically engineered bacteria of the disclosure comprise a gene that is operably linked to a directly or indirectly inducible promoter that is not associated with said gene in nature, e.g., an FNR-responsive promoter (or other promoter described herein) operably linked to a gene encoding a substrate transporter.

"Microorganism" refers to an organism or microbe of microscopic, submicroscopic, or ultramicroscopic size that typically consists of a single cell. Examples of microrganisms include bacteria, viruses, parasites, fungi, certain algae, and protozoa. In some aspects, the microorganism is engineered ("engineered microorganism") to produce one or more anti-cancer molecules. In certain embodiments, the engineered microorganism is an engineered bacteria. In certain embodiments, the engineered microorganism is an engineered oncolytic virus.

"Non-pathogenic bacteria" refer to bacteria that are not capable of causing disease or harmful responses in a host. In some embodiments, non-pathogenic bacteria are commensal bacteria. Examples of non-pathogenic bacteria include, but are not limited to *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus*, and *Lactococcus lactis* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Operably linked" refers to the association of nucleic acid sequences on a single nucleic acid fragment so that the function of one is affected by the other. A regulatory element is operably linked with a coding sequence when it is capable of affecting the expression of the gene coding sequence, regardless of the distance between the regulatory element and the coding sequence. More specifically, operably linked refers to a nucleic acid sequence that is joined to a regulatory sequence in a manner which allows expression of the nucleic acid sequence. In other words, the regulatory sequence acts in cis. In one embodiment, a gene may be "directly linked" to a regulatory sequence in a manner which allows expression of the gene. In another embodiment, a gene may be "indirectly linked" to a regulatory sequence in a manner which allows expression of the gene. In one embodiment, two or more genes may be directly or indirectly linked to a regulatory sequence in a manner which allows expression of the two or more genes.

As used herein, "payload" refers to one or more molecules of interest to be produced by a genetically engineered microorganism, such as a bacteria. In some embodiments, the payload is a therapeutic payload. In some embodiments, the payload is a regulatory molecule, e.g., a transcriptional regulator such as FNR. In some embodiments, the payload comprises a regulatory element, such as a promoter or a repressor. In some embodiments, the payload comprises an inducible promoter, such as from FNRS. In some embodiments the payload comprises a repressor element, such as a kill switch. In some embodiments, the payload is encoded by a gene or multiple genes or an operon. In alternate embodiments, the payload is produced by a biosynthetic or biochemical pathway, wherein the biosynthetic or biochemical pathway may optionally be endogenous to the microorganism. In some embodiments, the genetically engineered microorganism comprises two or more payloads.

As used herein a "pharmaceutical composition" refers to a preparation of bacterial cells disclosed herein with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

As used herein, the term "plasmid" or "vector" refers to an extrachromosomal nucleic acid, e.g., DNA, construct that is not integrated into a bacterial cell's genome. Plasmids are usually circular and capable of autonomous replication. Plasmids may be low-copy, medium-copy, or high-copy, as is well known in the art. Plasmids may optionally comprise a selectable marker, such as an antibiotic resistance gene, which helps select for bacterial cells containing the plasmid and which ensures that the plasmid is retained in the bacterial cell. A plasmid disclosed herein may comprise a nucleic acid sequence encoding a heterologous gene, e.g., a gene encoding at least one substrate transporter.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with, any of these terms. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered bacteria of the current invention. In some embodiments, a polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids.

Polypeptides may have a defined three-dimensional structure, although they must not necessarily have such structure. Polypeptides with a defined three-dimensional structure are referred to as folded, and polypeptides, which do not possess a defined three-dimensional structure, but rather can adopt a large number of different conformations, are referred to herein as unfolded.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins. Typically, fusion proteins result from well known in vitro recombination techniques. Fusion proteins may have a similar structural function (but not necessarily to the same extent), and/or similar regulatory function (but not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids. "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, lie, Leu, Met, Ala, Phe; -Lys, Arg, His; -Phe, Tyr, Trp, His; and -Asp, Glu.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic bacteria. Examples of probiotic bacteria include, but are not limited to, *Bifidobacteria, Escherichia coli*, and *Lactobacillus*, e.g., *Bifidobacterium bifidum, Enterococcus faecium, Escherichia coli* strain Nissle, *Lactobacillus acidophilus, Lactobacillus bulgaricus, Lactobacillus paracasei*, and *Lactobacillus plantarum* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

A "promoter" as used herein, refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Prokaryotic promoters are typically classified into two classes: inducible and constitutive.

As used herein, the term "recombinant bacterial cell", "recombinant bacteria" or "genetically modified bacteria" refers to a bacterial cell or bacteria that have been genetically modified from their native state. For instance, a recombinant bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Recombinant bacterial cells of the disclosure may comprise exogenous nucleotide sequences on plasmids. Alternatively, recombinant bacterial cells may comprise exogenous nucleotide sequences stably incorporated into their chromosome.

As used herein, "stably maintained" or "stable" bacterium is used to refer to a bacterial host cell carrying non-native genetic material, e.g., an amino acid catabolism enzyme, that is incorporated into the host genome or propagated on a self-replicating extrachromosomal plasmid, such that the non-native genetic material is retained, expressed, and propagated. The stable bacterium is capable of survival and/or growth in vitro, e.g., in medium, and/or in vivo, e.g., in the gut. For example, the stable bacterium may be a genetically engineered bacterium comprising an substrate transporter gene, in which the plasmid or chromosome carrying the substrate transporter gene is stably maintained in the bacterium, such that the substrate transporter can be expressed in the bacterium, and the bacterium is capable of survival and/or growth in vitro and/or in vivo. In some embodiments, copy number affects the stability of expression of the non-native genetic material. In some embodiments, copy number affects the level of expression of the non-native genetic material.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 9:2%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

The terms "therapeutically effective dose" and "therapeutically effective amount" are used to refer to an amount of a compound that results in prevention, delay of onset of symptoms, or amelioration of symptoms of a condition or disease. A therapeutically effective amount, as well as a therapeutically effective frequency of administration, can be determined by methods known in the art and discussed below.

As used herein, the term "transform" or "transformation" refers to the transfer of a nucleic acid fragment into a host bacterial cell, resulting in genetically-stable inheritance. Host bacterial cells comprising the transformed nucleic acid fragment are referred to as "recombinant" or "transgenic" or "transformed" organisms.

As used herein, the term "toxin" refers to a protein, enzyme, or polypeptide fragment thereof, or other molecule which is capable of arresting, retarding, or inhibiting the growth, division, multiplication or replication of the recombinant bacterial cell of the disclosure, or which is capable of killing the recombinant bacterial cell of the disclosure. The term "toxin" is intended to include bacteriostatic proteins and bactericidal proteins. The term "toxin" is intended to include, but not limited to, lytic proteins, bacteriocins (e.g., microcins and colicins), gyrase inhibitors, polymerase inhibitors, transcription inhibitors, translation inhibitors, DNases, and RNases. The term "anti-toxin" or "antitoxin," as used herein, refers to a protein or enzyme which is capable of inhibiting the activity of a toxin. The term anti-toxin is intended to include, but not limited to, immunity modulators, and inhibitors of toxin expression. Examples of toxins and antitoxins are known in the art and described in more detail infra.

As used herein, the term "treat" and its cognates refer to an amelioration of a disease, or at least one discernible symptom thereof. In another embodiment, "treat" refers to an amelioration of at least one measurable physical parameter, not necessarily discernible by the patient. In another embodiment, "treat" refers to inhibiting the progression of a disease, either physically (e.g., stabilization of a discernible symptom), physiologically (e.g., stabilization of a physical parameter), or both. In another embodiment, "treat" refers to slowing the progression or reversing the progression of a disease. As used herein, "prevent" and its cognates refer to delaying the onset or reducing the risk of acquiring a given disease.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease. Disorders associated with or involved with amino acid metabolism, e.g., cancer, may be caused by inborn genetic mutations for which there are no known cures. Diseases can also be secondary to other conditions, e.g., an intestinal disorder or a bacterial infection. Treating diseases associated with amino acid metabolism may encompass reducing normal levels of one or more substrates, e.g., an amino acid, reducing excess levels of one or more substrates, e.g., an amino acid, or eliminating one or more substrates, e.g., an amino acid, and does not necessarily encompass the elimination of the underlying disease.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Bacterial Strains

The disclosure provides a bacterial cell that comprises a heterologous gene encoding a substrate transporter. In some embodiments, the bacterial cell is a non-pathogenic bacterial cell. In some embodiments, the bacterial cell is a commensal bacterial cell. In some embodiments, the bacterial cell is a probiotic bacterial cell.

In certain embodiments, the bacterial cell is selected from the group consisting of a *Bacteroides fragilis, Bacteroides thetaiotaomicron, Bacteroides subtilis, Bifidobacterium animalis, Bifidobacterium bifidum, Bifidobacterium infantis, Bifidobacterium lactis, Clostridium butyricum, Clostridium scindens, Escherichia coli, Lactobacillus acidophilus, Lactobacillus plantarum, Lactobacillus reuteri, Lactococcus lactis,* and *Oxalobacter formigenes* bacterial cell. In one embodiment, the bacterial cell is a *Bacteroides fragilis* bacterial cell. In one embodiment, the bacterial cell is a *Bacteroides thetaiotaomicron* bacterial cell. In one embodiment, the bacterial cell is a *Bacteroides subtilis* bacterial cell. In one embodiment, the bacterial cell is a *Bifidobacterium animalis* bacterial cell. In one embodiment, the bacterial cell is a *Bifidobacterium bifidum* bacterial cell. In one embodiment, the bacterial cell is a *Bifidobacterium infantis* bacterial cell. In one embodiment, the bacterial cell is a *Bifidobacterium lactis* bacterial cell. In one embodiment, the bacterial cell is a *Clostridium butyricum* bacterial cell. In one embodiment, the bacterial cell is a *Clostridium scindens* bacterial cell. In one embodiment, the bacterial cell is an *Escherichia coli* bacterial cell. In one embodiment, the bacterial cell is a *Lactobacillus acidophilus* bacterial cell. In one embodiment, the bacterial cell is a *Lactobacillus plantarum* bacterial cell. In one embodiment, the bacterial cell is a *Lactobacillus reuteri* bacterial cell. In one embodiment, the bacterial cell is a *Lactococcus lactis* bacterial cell. In one embodiment, the bacterial cell is a *Oxalobacter formigenes* bacterial cell. In another embodiment, the bacterial cell does not include *Oxalobacter formigenes*.

In one embodiment, the bacterial cell is a Gram positive bacterial cell. In another embodiment, the bacterial cell is a Gram negative bacterial cell.

In some embodiments, the bacterial cell is *Escherichia coli* strain Nissle 1917 (*E. coli* Nissle), a Gram-negative bacterium of the Enterobacteriaceae family that "has evolved into one of the best characterized probiotics" (Ukena et al., 2007). The strain is characterized by its "complete harmlessness" (Schultz, 2008), and "has GRAS (generally recognized as safe) status" (Reister et al., 2014, emphasis added). Genomic sequencing confirmed that *E. coli* Nissle "lacks prominent virulence factors (e.g., *E. coli* α-hemolysin, P-fimbrial adhesins)" (Schultz, 2008), and *E. coli* Nissle "does not carry pathogenic adhesion factors and does not produce any enterotoxins or cytotoxins, it is not invasive, not uropathogenic" (Sonnenborn et al., 2009). As early as in 1917, *E. coli* Nissle was packaged into medicinal capsules, called Mutaflor, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella, Yersinia,* and *Shigella* in vitro (Altenhoefer et al., 2004). It is commonly accepted that *E. coli* Nissle's "therapeutic efficacy and safety have convincingly been proven" (Ukena et al., 2007).

In one embodiment, the recombinant bacterial cell of the disclosure does not colonize the subject to whom the cell is administered.

One of ordinary skill in the art would appreciate that the genetic modifications disclosed herein may be adapted for other species, strains, and subtypes of bacteria. Furthermore, genes from one or more different species can be introduced into one another.

In some embodiments, the bacterial cell is a genetically engineered bacterial cell. In another embodiment, the bacterial cell is a recombinant bacterial cell. In some embodiments, the disclosure comprises a colony of recombinant bacterial cells.

In another aspect, the disclosure provides a recombinant bacterial culture which comprises bacterial cells disclosed herein. In one aspect, the disclosure provides a recombinant bacterial culture which reduces levels of a substrate, e.g., an amino acid or a peptide, in the media of the culture. In one embodiment, the levels of substrate is reduced by about 50%, by about 60%, by about 70%, by about 75%, by about 80%, by about 90%, by about 95%, or about 100% in the media of the cell culture. In another embodiment, the levels of a substrate is reduced by about two-fold, three-fold, four-fold, five-fold, six-fold, seven-fold, eight-fold, nine-fold, ten-fold, fifteen-fold, twenty-fold, thirty-fold, forty-fold, or fifty-fold, in the media of the cell culture. In one embodiment, the levels of a substrate are reduced below the limit of detection in the media of the cell culture.

In some embodiments of the above described recombinant bacterial cells, the gene encoding a substrate transporter is present on a plasmid in the bacterium and operatively linked on the plasmid to the promoter that is induced under low-oxygen or anaerobic conditions. In other embodiments, the gene encoding a substrate transporter is present in the bacterial chromosome and is operatively linked in the chromosome to the promoter that is induced under low-oxygen or anaerobic conditions.

In some embodiments, the recombinant bacterial cell comprising a heterologous substrate transporter is an auxotroph. In one embodiment, the recombinant bacterial cell is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thiI auxotroph. In some embodiments, the recombinant bacterial cell has more than one auxotrophy, for example, they may be a ΔthyA and ΔdapA auxotroph.

In some embodiments, the recombinant bacterial cell comprising a heterologous substrate transporter further comprises a kill-switch circuit, such as any of the kill-switch circuits provided herein. For example, in some embodiments, the recombinant bacterial cells may further comprise one or more genes encoding one or more recombinase(s) under the control of an inducible promoter, and an inverted toxin sequence. In some embodiments, the recombinant bacterial cell further comprises one or more genes encoding an antitoxin. In some embodiments, the recombinant bacterial cell further comprise one or more genes encoding one or more recombinase(s) under the control of an inducible promoter and one or more inverted excision genes, wherein the excision gene(s) encode an enzyme that deletes an essential gene. In some embodiments, the recombinant bacterial cell further comprise one or more genes encoding an antitoxin. In some embodiments, the recombinant bacterial cell further comprises one or more genes encoding a toxin under the control of an promoter having a TetR repressor binding site and a gene encoding the TetR under the control of an inducible promoter that is induced by arabinose, such as $P_{araBAD}$. In some embodiments, the recombinant bacterial cell further comprises one or more genes encoding an antitoxin.

In some embodiments, the recombinant bacterial cell is an auxotroph comprising a heterologous substrate transporter gene and further comprises a kill-switch circuit, such as any of the kill-switch circuits described herein.

In some embodiments of the above described recombinant bacterial cell, the heterologous gene encoding a substrate transporter is present on a plasmid in the bacterium and operatively linked on the plasmid to the promoter that is induced under low-oxygen or anaerobic conditions. In other embodiments, the gene encoding a substrate transporter is present in the bacterial chromosome and is operatively linked in the chromosome to the promoter that is induced under low-oxygen or anaerobic conditions.

A. Amino Acid Transporters

In one embodiment, the recombinant bacterial cell of the invention comprises a heterologous gene encoding a substrate transporter, wherein the substrate transporter is an amino acid transporter. In one embodiment, the amino acid transporter transports at least one amino acid selected from the group consisting of leucine, isoleucine, valine, arginine, lysine, asparagine, serine, glycine, glutamine, tryptophan, methionine, threonine, cysteine, tyrosine, phenylalanine, glutamic acid, aspartic acid, alanine, histidine, and proline, into the cell.

The uptake of amino acids into bacterial cells is mediated by proteins well known to those of skill in the art Amino acid transporters may be expressed or modified in the bacteria in order to enhance amino acid transport into the cell. Specifically, when the amino acid transporter is expressed in the recombinant bacterial cells, the bacterial cells import more amino acid(s) into the cell when the transporter is expressed than unmodified bacteria of the same bacterial subtype under the same conditions. In one embodiment, the bacterial cell comprises a heterologous gene encoding an amino acid transporter. In one embodiment, the bacterial cell comprises a heterologous gene encoding an amino acid transporter and a genetic modification that reduces export of an amino acid, e.g., a genetic mutation in an exporter gene or promoter.

In one embodiment, the bacterial cell comprises at least one gene encoding an amino acid transporter from a different organism, e.g., a different species of bacteria. In one embodiment, the bacterial cell comprises at least one native gene encoding an amino acid transporter. In some embodiments, the at least one native gene encoding an amino acid transporter is not modified. In another embodiment, the bacterial cell comprises more than one copy of at least one native gene encoding an amino acid transporter. In yet another embodiment, the bacterial cell comprises a copy of at least one gene encoding a native amino acid transporter, as well as at least one copy of at least one heterologous gene encoding anamino acid transporter from a different bacterial species. In one embodiment, the bacterial cell comprises at least one, two, three, four, five, or six copies of the at least one heterologous gene encoding an amino acid transporter. In one embodiment, the bacterial cell comprises multiple copies of the at least one heterologous gene encoding an amino acid transporter.

In one embodiment, the recombinant bacterial cell comprises a heterologous gene encoding an amino acid transporter, wherein said amino acid transporter comprises an amino acid sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of a polypeptide encoded by an amino acid transporter gene disclosed herein.

In some embodiments, the amino acid transporter is encoded by an amino acid transporter gene derived from a bacterial genus or species, including but not limited to, *Bacillus, Campylobacter, Clostridium, Escherichia, Lacto-* bacillus, *Pseudomonas, Salmonella, Staphylococcus, Bacillus subtilis, Campylobacter jejuni, Clostridium perfringens, Escherichia coli, Lactobacillus delbrueckii, Pseudomonas aeruginosa, Salmonella typhimurium*, or *Staphylococcus aureus*. In some embodiments, the bacterial species is *Escherichia coli*. In some embodiments, the bacterial species is *Escherichia coli* strain Nissle.

The present disclosure further comprises genes encoding functional fragments of an amino acid transporter or functional variants of an amino acid transporter. As used herein, the term "functional fragment thereof" or "functional variant thereof" of an amino acid transporter relates to an element having qualitative biological activity in common with the wild-type amino acid transporter from which the fragment or variant was derived. For example, a functional fragment or a functional variant of a mutated amino acid transporter is one which retains essentially the same ability to import an amino acid into the bacterial cell as does the amino acid transporter protein from which the functional fragment or functional variant was derived. In one embodiment, the recombinant bacterial cell comprises at least one heterologous gene encoding a functional fragment of an amino acid transporter. In another embodiment, the recombinant bacterial cell comprises a heterologous gene encoding a functional variant of an amino acid transporter.

Assays for testing the activity of an amino acid transporter, a functional variant of an amino acid transporter, or a functional fragment of an amino acid transporter are well known to one of ordinary skill in the art. For example, import of an amino acid may be determined using the methods as described in Haney et al., *J. Bact.*, 174(1):108-15, 1992; Rahmanian et al., *J. Bact.*, 116(3):1258-66, 1973; and Ribardo and Hendrixson, *J. Bact.*, 173(22):6233-43, 2011, the entire contents of each of which are expressly incorporated by reference herein.

In one embodiment, the genes encoding the amino acid transporter have been codon-optimized for use in the host organism, e.g., a bacterial cell disclosed herein. In one embodiment, the genes encoding the amino acid transporter have been codon-optimized for use in *Escherichia coli*.

The present disclosure also encompasses genes encoding an amino acid transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding an amino acid transporter is mutagenized; mutants exhibiting increased amino acid import are selected; and the mutagenized at least one gene encoding an amino acid transporter is isolated and inserted into the bacterial cell. In some embodiments, the at least one gene encoding an amino acid transporter is mutagenized; mutants exhibiting decreased amino acid import are selected; and the mutagenized at least one gene encoding an amino acid transporter is isolated and inserted into the bacterial cell. The transporter modifications described herein may be present on a plasmid or chromosome.

In some embodiments, the bacterial cell comprises a heterologous gene encoding an amino acid transporter operably linked to a promoter. In one embodiment, the at least one gene encoding an amino acid transporter is directly operably linked to the promoter. In another embodiment, the at least one gene encoding an amino acid transporter is indirectly operably linked to the promoter.

In one embodiment, the promoter is not operably linked with the at least one gene encoding an amino acid transporter in nature. In some embodiments, the at least one gene encoding the amino acid transporter is controlled by its native promoter. In some embodiments, the at least one gene encoding the amino acid transporter is controlled by an inducible promoter. In some embodiments, the at least one gene encoding the amino acid transporter is controlled by a promoter that is stronger than its native promoter. In some embodiments, the at least one gene encoding the amino acid transporter is controlled by a constitutive promoter.

In another embodiment, the promoter is an inducible promoter. Inducible promoters are described in more detail infra.

In one embodiment, the at least one gene encoding an amino acid transporter is located on a plasmid in the bacterial cell. In some embodiments, the plasmid is a high copy number plasmid. In some embodiments, the plasmid is a low copy number plasmid. In another embodiment, the at least one gene encoding an amino acid transporter is located in the chromosome of the bacterial cell. In yet another embodiment, a native copy of the at least one gene encoding an amino acid transporter is located in the chromosome of the bacterial cell, and a copy of at least one gene encoding an amino acid transporter from a different species of bacteria is located on a plasmid in the bacterial cell. In yet another embodiment, a native copy of the at least one gene encoding an amino acid transporter is located on a plasmid in the bacterial cell, and a copy of at least one gene encoding an amino acid transporter from a different species of bacteria is located on a plasmid in the bacterial cell. In yet another embodiment, a native copy of the at least one gene encoding an amino acid transporter is located in the chromosome of the bacterial cell, and a copy of the at least one gene encoding an amino acid transporter from a different species of bacteria is located in the chromosome of the bacterial cell.

In some embodiments, the at least one native gene encoding the amino acid transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the amino acid transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the amino acid transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the amino acid transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the amino acid transporter is expressed in the recombinant bacterial cells, the bacterial cells import 10% more amino acids into the bacterial cell when the transporter is expressed than unmodified bacteria of the same bacterial subtype under the same conditions. In another embodiment, when the amino acid transporter is expressed in the recombinant bacterial cells, the bacterial cells import 20%, 30%, 40%, 50%, 60%, 70%, 80%, 90% or 100% more amino acids, into the bacterial cell when the transporter is expressed than unmodified bacteria of the same bacterial subtype under the same conditions. In yet another embodiment, when the amino acid transporter is expressed in the recombinant bacterial cells, the bacterial cells import two-fold more amino acids into the cell when the transporter is expressed than unmodified bacteria of the same bacterial subtype under the same conditions. In yet another embodiment, when the amino acid transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more amino acid into the cell when the transporter is expressed than unmodified bacteria of the same bacterial subtype under the same conditions.

In one embodiment, the recombinant bacterial cells described herein comprise a first heterologous amino acid transporter and a second heterologous amino acid transporter. In one embodiment, said first amino acid transporter is derived from a different organism than said second amino acid transporter. In some embodiments, said first amino acid transporter is derived from the same organism as said second amino acid transporter. In some embodiments, said first amino acid transporter imports the same amino acid as said second amino acid transporter. In other embodiment, said first amino acid transporter imports a different amino acid from said second amino acid transporter. In some embodiments, said first amino acid transporter is a wild-type amino acid transporter and said second amino acid transporter is a mutagenized version of said first amino acid transporter. In some embodiments, the recombinant bacterial cells described herein comprise at least a third heterologous amino acid transporter. In some embodiments, the recombinant bacterial cells described herein comprise at least four heterologous amino acid transporters. In some embodiments, the recombinant bacterial cells described herein comprise at least five heterologous amino acid transporters or more.

In one embodiment, the amino acid transporter imports one amino acid into the bacterial cell. In another embodiment, the amino acid transporter imports two amino acids into the bacterial cell. In yet another embodiment, the amino acid transporter imports three amino acids into the bacterial cell. In another embodiment, the amino acid transporter imports four or more amino acids into the cell. In one embodiment, the amino acid transporter is an arginine transporter. In another embodiment, the amino acid transporter is an asparagine transporter. In another embodiment, the amino acid transporter is a serine transporter. In another embodiment, the amino acid transporter is an transporter of glycine. In another embodiment, the amino acid transporter is a tryptophan transporter. In another embodiment, the amino acid transporter is a methionine transporter. In another embodiment, the amino acid transporter is a threonine transporter. In another embodiment, the amino acid transporter is a cysteine transporter. In another embodiment, the amino acid transporter is a tyrosine transporter. In another embodiment, the amino acid transporter is a phenylalanine transporter. In another embodiment, the amino acid transporter is a glutamic acid transporter. In another embodiment, the amino acid transporter is a histidine transporter. In another embodiment, the amino acid transporter is a proline transporter. In another embodiment, the amino acid transporter is an transporter of leucine. In another embodiment, the amino acid transporter is an transporter of isoleucine. In another embodiment, the amino acid transporter is an transporter of valine. In another embodiment, the amino acid transporter is a lysine transporter. In another embodiment, the amino acid transporter is a glutamine transporter. In another embodiment, the amino acid transporter is an transporter of aspartic acid. In another embodiment, the amino acid transporter is an transporter of alanine. In another embodiment, the amino acid transporter is an transporter of branched chain amino acids.

In some embodiment, the recombinant bacterial cell comprising a heterologous gene encoding an amino acid transporter may be used to treat a disease, condition, and/or symptom associated with amino acid metabolism. In some embodiments, disclosed herein are methods for reducing, ameliorating, or eliminating one or more symptom(s) associated with these diseases or disorders.

As used herein the terms "disease associated with amino acid metabolism" or a "disorder associated with amino acid metabolism" is a disease or disorder involving the abnormal, e.g., increased, levels of one or more amino acids in a subject. In one embodiment, a disease or disorder associated with amino acid metabolism is a cancer, e.g., a cancer described herein. In another embodiment, a disease or disorder associated with amino acid metabolism is a metabolic disease. In one embodiment, the cancer is glioma. In another embodiment, the cancer is breast cancer. In another embodiment, the cancer is melanoma. In another embodiment, the cancer is hepatocarcinoma. In another embodiment, the cancer is acute lymphoblastic leukemia (ALL). In another embodiment, the cancer is ovarian cancer. In another embodiment, the cancer is prostate cancer. In another embodiment, the cancer is lymphoblastic leukemia. In another embodiment, the cancer is non-small cell lung cancer.

Multiple distinct transporters of amino acids are well known in the art and are described in the subsections, below.

1. Branched Chain Amino Acid Transporters

In one embodiment, the amino acid transporter is a branched chain amino acid transporter. The term "branched chain amino acid" or "BCAA," as used herein, refers to an amino acid which comprises a branched side chain. Leucine, isoleucine, and valine are naturally occurring amino acids comprising a branched side chain. However, non-naturally occurring, usual, and/or modified amino acids comprising a branched side chain are also encompassed by the term branched chain amino acid.

Branched chain amino acid transporters may be expressed or modified in the recombinant bacteria described herein in order to enhance branched chain amino acid transport into the cell. Specifically, when the transporter of branched chain amino acids is expressed in the recombinant bacterial cells described herein, the bacterial cells import more branched chain amino acids into the cell when the transporter is expressed than unmodified bacteria of the same bacterial subtype under the same conditions. Thus, the genetically engineered bacteria comprising a heterologous gene encoding an transporter of branched chain amino acids may be used to import one or more branched chain amino acids into the bacteria.

The uptake of branched chain amino acids into bacterial cells is mediated by proteins well known to those of skill in the art. For example, two well characterized BCAA transport systems have been characterized in several bacteria, including *Escherichia coli*. BCAAs are transported by two systems into bacterial cells (i.e., imported), the osmotic-shock-sensitive systems designated LIV-I and LS (leucine-specific), and by an osmotic-shock resistant system, BrnQ, formerly known as LIV-II (see Adams et al., *J. Biol. Chem.* 265: 11436-43 (1990); Anderson and Oxender, *J. Bacteriol.* 130: 384-92 (1977); Anderson and Oxender, *J. Bacteriol.* 136: 168-74 (1978); Haney et al., *J. Bacteriol.* 174:108-15 (1992); Landick and Oxender, *J. Biol. Chem.* 260:8257-61 (1985); Nazos et al., *J. Bacteriol.* 166:565-73 (1986); Nazos et al., *J. Bacteriol.* 163:1196-202 (1985); Oxender et al., *Proc. Natl. Acad. Sci. USA* 77:1412-16 (1980); Quay et al., *J. Bacteriol.* 129:1257-65 (1977); Rahmanian et al., *J. Bacteriol.* 116:1258-66 (1973); Wood, *J. Biol. Chem.* 250: 4477-85 (1975); Guardiola et al., *J. Bacteriol.* 117:393-405 (1974); Guardiola and Iaccarino, *J. Bacteriol.* 108:1034-44 (1971); Ohnishi et al., *Jpn. J. Genet.* 63:343-57)(1988); Yamato and Anraku, *J. Bacteriol.* 144:36-44 (1980); and Yamato et al., *J. Bacteriol.* 138:24-32 (1979)). Transport by the BrnQ system is mediated by a single membrane protein. Transport mediated by the LIV-I system is dependent on the substrate binding protein LivJ (also known as LIV-BP), while transport mediated by LS system is mediated by the substrate binding protein LivK (also known as LS-BP). LivJ is encoded by the livJ gene, and binds isoleucine, leucine and valine with $K_d$ values of ~$10^{-6}$ and ~$10^{-7}$ M, while LivK is encoded by the livK gene, and binds leucine with a $K_d$ value of ~$10^{-6}$ M (See Landick and Oxender, *J. Biol. Chem.* 260:8257-61 (1985)). Both LivJ and LivK interact with the inner membrane components LivHMGF to enable ATP-hydrolysis-coupled transport of their substrates into the cell, forming the LIV-I and LS transport systems, respectively. The LIV-I system transports leucine, isoleucine and valine, and to a lesser extent serine, threonine and alanine, whereas the LS system only transports leucine. The six genes encoding the *E. coli* LIV-I and LS systems are organized into two transcriptional units, with livKHMGF transcribed as a single operon, and livJ transcribed separately. The *Escherichia coli* liv genes can be grouped according to protein function, with the livJ and livK genes encoding periplasmic binding proteins with the binding affinities described above, the livH and livM genes encoding inner membrane permeases, and the livG and livF genes encoding cytoplasmic ATPases.

In one embodiment, the at least one gene encoding an branched chain amino acid transporter is the brnQ gene. An exemplary sequence for brnQ is provided below.

BCAA transporter BrnQ from *E. coli*:
Nucleotide sequence:
atgacccatcaattaagatcgcgcgatatcatcgctctgggctttatgac atttgcgttgttcgtcggcgcaggtaacattattttccctccaatggtcg gcttgcaggcaggcgaacacgtctggactgcggcattcggcttcctcatt actgccgttggcctaccggtattaacggtagtggcgctggcaaaagttgg cggcggtgttgacagtctcagcacgccaattggtaaagtcgctggcgtac tgctggcaacagtttgttacctggcggtggggccgcttttttgctacgccg cgtacagctaccgtttcttttgaagtgggcattgcgccgctgacgggtga ttccgcgctgccgctgtttatttacagcctggtctatttcgctatcgtta ttctggtttcgctctatccgggcaagctgctggataccgtgggcaacttc cttgcgccgctgaaaattatcgcgctggtcatcctgtctgttgccgcaat tatctggccggcgggttctatcagtacggcgactgaggcttatcaaaacg ctgcgttttctaacggcttcgtcaacggctatctgaccatggatacgctg ggcgcaatggtgtttggtatcgttattgttaacgcggcgcgttctcgtgg cgttaccgaagcgcgtctgctgacccgttataccgtctgggctggcctga tggcgggtgttggtctgactctgctgtacctggcgctgttccgtctgggt tcagacagcgcgtcgctggtcgatcagtctgcaaacggtgcggcgatcct gcatgcttacgttcagcataccttggcggcggcggtagcttcctgctgg cggcgttaatcttcatcgcctgcctggtcacggcggttggcctgacctgt gcttgtgcagaattcttcgcccagtacgtaccgctctcttatcgtacgct ggtgtttatcctcggcggcttctcgatggtggtgtctaacctcggcttga gccagctgattcagatctctgtaccggtgctgaccgccatttatccgccg tgtatcgcactggttgtattaagttttacacgctcatggtggcataattc gtcccgcgtgattgctccgccgatgtttatcagcctgcttttggtattc tcgacgggatcaaggcatctgcattcagcgatatcttaccgtcctgggcg cagcgtttaccgctggccgaacaaggtctggcgtggttaatgccaacagt ggtgatggtggttctggccattatctgggatcgtgcggcaggtcgtcagg tgacctccagcgctcactaa AA sequence:
MTHQLRSRDIIALGFMTFALFVGAGNIIFPPMVGLQAGEHVWTAAFGFLI

TAVGLPVLTVVALAKVGGGVDSLSTPIGKVAGVLLATVCYLAVGPLFATP

RTATVSFEVGIAPLTGDSALPLFIYSLVYFAIVILVSLYPGKLLDTVGNF

LAPLKIIALVILSVAAIIWPAGSISTATEAYQNAAFSNGFVNGYLTMDTL

GAMVFGIVIVNAARSRGVTEARLLTRYTVWAGLMAGVGLTLLYLALFRLG

SDSASLVDQSANGAAILHAYVQHTFGGGGSFLLAALIFIACLVTAVGLTC

ACAEFFAQYVPLSYRTLVFILGGFSMVVSNLGLSQLIQISVPVLTAIYPP

CIALVVLSFTRSWWHNSSRVIAPPMFISLLFGILDGIKASAFSDILPSWA

QRLPLAEQGLAWLMPTVVMVVLAIIWDRAAGRQVTSSAH

In one embodiment, the at least one gene encoding an branched chain amino acid transporter is the livJ gene. In one embodiment, the at least one gene encoding an branched chain amino acid transporter is the livH gene. In one embodiment, the at least one gene encoding an branched chain amino acid transporter is the livM gene. In one embodiment, the at least one gene encoding an branched chain amino acid transporter is the livG gene. In one embodiment, the at least one gene encoding an branched chain amino acid transporter is the livF gene. In one embodiment, the at least one gene encoding an branched chain amino acid transporter is the livKHMGF operon. In one embodiment, the at least one gene encoding an branched chain amino acid transporter is the livK gene. In another embodiment, the livKHMGF operon is an *Escherichia coli* livKHMGF operon. In another embodiment, the at least one gene encoding an branched chain amino acid transporter comprises the livKHMGF operon and the livJ gene. In one embodiment, the bacterial cell of the invention has been genetically engineered to comprise at least one heterologous gene encoding a LIV-I system. In one embodiment, the bacterial cell of the invention has been genetically engineered to comprise at least one heterologous gene encoding a LS system. In one embodiment, the bacterial cell of the invention has been genetically engineered to comprise at least one heterologous gene encoding a LIV-I system. In one embodiment, the bacterial cell of the invention has been genetically engineered to comprise at least one heterologous livJ gene, and at least one heterologous gene selected from the group consisting of livH, livM, livG, and livF. In one embodiment, the bacterial cell of the invention has been genetically engineered to comprise at least one heterologous livK gene, and at least one heterologous gene selected from the group consisting of livH, livM, livG, and livF.

In one embodiment, the branched chain amino acid transporter gene has at least about 80% identity with the uppercase sequence of SEQ ID NO:9. Accordingly, in one embodiment, the branched chain amino acid transporter gene has at least about 90% identity with the uppercase sequence of SEQ ID NO:9. Accordingly, in one embodiment, the branched chain amino acid transporter gene has at least about 95% identity with the uppercase sequence of SEQ ID NO:9. Accordingly, in one embodiment, the branched chain amino acid transporter gene has at least about 70%, 75%, 80%, 85%, 86%, 87%, 88%, 89%, 90%, 91%, 92%, 93%, 94%, 95%, 96%, 97%, 98%, or 99% identity with the uppercase sequence of SEQ ID NO:9. In another embodiment, the branched chain amino acid transporter gene comprises the uppercase sequence of SEQ ID NO:9. In yet another embodiment the branched chain amino acid transporter gene consists of the uppercase sequence of SEQ ID NO:9.

In one embodiment, the branched chain amino acid transporter gene has at least about 80% identity with the sequence of SEQ ID NO:10. Accordingly, in one embodiment, the branched chain amino acid transporter gene has at least about 90% identity with the sequence of SEQ ID NO:10. Accordingly, in one embodiment, the branched chain amino acid transporter gene has at least about 95% identity with the sequence of SEQ ID NO:10. Accordingly, in one embodiment, the branched chain amino acid transporter gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:10. In another embodiment, the branched chain amino acid transporter gene comprises the sequence of SEQ ID NO:10. In yet another embodiment the branched chain amino acid transporter gene consists of the sequence of SEQ ID NO:10.

In some embodiments, the branched chain amino acid transporter is encoded by an branched chain amino acid transporter gene derived from a bacterial genus or species, including but not limited to, *Escherichia coli*. In some embodiments, the bacterial species is *Escherichia coli*. In some embodiments, the bacterial species is *Escherichia coli* strain Nissle.

Assays for testing the activity of a branched chain amino acid transporter, a functional variant of a branched chain amino acid transporter, or a functional fragment of a branched chain amino acid transporter are well known to one of ordinary skill in the art. For example, import of an amino acid may be determined using the methods as described in Haney et al., *J. Bact.*, 174(1):108-15, 1992; Rahmanian et al., *J. Bact.*, 116(3):1258-66, 1973; and Ribardo and Hendrixson, *J. Bact.*, 173(22):6233-43, 2011, the entire contents of each of which are expressly incorporated by reference herein.

In one embodiment, when the branched chain amino acid transporter is expressed in the recombinant bacterial cells described herein, the bacterial cells import 10% more branched chain amino acid into the bacterial cell when the transporter is expressed than unmodified bacteria of the same bacterial subtype under the same conditions. In another embodiment, when the transporter of branched chain amino acids is expressed in the recombinant bacterial cells described herein, the bacterial cells import 20%, 30%, 40%, 50%, 60%, 70%, 80%, 90% or 100% more branched chain amino acids into the bacterial cell when the transporter is expressed than unmodified bacteria of the same bacterial subtype under the same conditions. In yet another embodiment, when the branched chain amino acid transporter is expressed in the recombinant bacterial cells described herein, the bacterial cell imports two-fold more branched chain amino acids into the cell when the transporter is expressed than unmodified bacteria of the same bacterial subtype under the same conditions. In yet another embodiment, when the branched chain amino acid transporter is expressed in the recombinant bacterial cell described herein, the bacterial cell import three-fold, four-fold, five-fold, six-fold, seven-fold, eight-fold, nine-fold, or ten-fold, fifteen-fold, twenty-fold, thirty-fold, forty-fold, or fifty-fold, more branched chain amino acid into the cell when the transporter is expressed than unmodified bacteria of the same bacterial subtype under the same conditions.

In some embodiment, the recombinant bacterial cell comprising a heterologous gene encoding a branched chain amino acid transporter may be used to treat a disease, condition, and/or symptom associated with the catabolism of a branched chain amino acid. In some embodiments, disclosed herein are methods for reducing, ameliorating, or eliminating one or more symptom(s) associated with these diseases or disorders. In one embodiment, the disorder involving the catabolism of a branched chain amino acid is a metabolic disorder involving the abnormal catabolism of a branched chain amino acid. Metabolic diseases associated with abnormal catabolism of a branched chain amino acid include maple syrup urine disease (MSUD), isovaleric acidemia, propionic acidemia, methylmalonic acidemia, and diabetes ketoacidosis. In one embodiment, the disease associated with abnormal catabolism of a branched chain amino acid is isovaleric acidemia. In one embodiment, the disease associated with abnormal catabolism of a branched chain amino acid is propionic acidemia. In one embodiment, the disease associated with abnormal catabolism of a branched chain amino acid is methylmalonic acidemia. In another embodiment, the disease associated with abnormal catabolism of a branched chain amino acid is diabetes.

2. Arginine Transporters

In one embodiment, the amino acid transporter is an arginine transporter. Arginine transporters may be expressed or modified in the recombinant bacteria described herein in order to enhance arginine transport into the cell. Specifically, when the arginine transporter is expressed in the recombinant bacterial cells described herein, the bacterial cells import more arginine into the cell when the arginine transporter is expressed than unmodified bacteria of the same bacterial subtype under the same conditions. Thus, the genetically engineered bacteria comprising a heterologous gene encoding an arginine transporter which may be used to import arginine into the bacteria.

The uptake of arginine into bacterial cells is mediated by proteins well known to those of skill in the art. For example, three different arginine transport systems have been characterized in several bacteria: the arginine-specific system encoded by the artPIQM operon and the artJ gene (see, e.g., Wissenbach et al. (1993) *J. Bacteriol.* 175(11): 3687-8); the basic amino acid uptake system, known as LAO (lysine, arginine, ornithine) (see, e.g., Rosin et al. (1971) *J. Biol. Chem.* 246: 3653-62); and the AO (arginine, ornithine) system (see, e.g., Celis (1977) *J. Bacteriol.* 130: 1234-43). Transport by the arginine-specific system is mediated by several proteins encoded by the two transcriptional units, the artPIQM operon and the artJ gene. In this system, ArtP (encoded by artP) is an ATPase, ArtQ and ArtM (encoded by artQ and artM, respectively) are transmembrane proteins, and ArtI and ArtJ (encoded by artI and artJ, respectively) are arginine-binding periplasmic proteins. This system has been well characterized in *Escherichia coli* (see, e.g., Wissenbach U. (1995) Mol. Microbiol. 17(4): 675-86; Wissenbach et al. (1993) *J. Bacteriol.* 175(11): 3687-88). In addition, bacterial systems that are homologous and orthologous of the *E. coli* arginine-specific system have been characterized in other bacterial species, including, for example, *Haemophilus influenzae* (see, e.g., Mironov et al. (1999) Nucleic Acids Res. 27(14): 2981-9). The second arginine transport system, the basic amino acid LAO system, consists of the periplasmic LAO protein (also referred to herein as ArgT; encoded by argT), which binds lysine, arginine and ornithine, and the membranous and membrane-associated proteins of the histidine permease (Q M P complex), encoded by the hisJQMP operon, resulting in the uptake of arginine (see, e.g., Oh et al. (1994) *J. Biol. Chem.* 269(42): 26323-30). Members of the basic amino acid LAO system have been well characterized in *Escherichia coli* and *Salmonella enterica*. Finally, the third arginine transport system, the AO system, consists of the binding protein AbpS (encoded by abpS) and the ATP hydrolase ArgK (encoded by argK) which mediate the ATP-dependent uptake of arginine (see, e.g., Celis et al. (1998) *J. Bacteriol.* 180(18): 4828-33).

In one embodiment, the at least one gene encoding an arginine transporter is the artJ gene. In one embodiment, the at least one gene encoding an arginine transporter is the artPIQM operon. In one embodiment, the at least one gene encoding an arginine transporter is the artP gene. In one embodiment, the at least one gene encoding an arginine transporter is the artI gene. In one embodiment, the at least one gene encoding an arginine transporter is the artQ gene. In one embodiment, the at least one gene encoding an arginine transporter is the artM gene. In one embodiment, the at least one gene encoding an arginine transporter is the argT gene. In one embodiment, the at least one gene encoding an arginine transporter is the hisJQMP operon. In one embodiment, the at least one gene encoding an arginine transporter is the hisJ gene. In one embodiment, the at least one gene encoding an arginine transporter is the hisQ gene. In one embodiment, the at least one gene encoding an arginine transporter is the hisM gene. In one embodiment, the at least one gene encoding an arginine transporter is the hisP gene. In one embodiment, the at least one gene encoding an arginine transporter is the abpS gene. In one embodiment, the at least one gene encoding an arginine transporter is the argK gene. In another embodiment, the at least one gene encoding an arginine transporter comprises the artPIQM operon and the artJ gene. In another embodiment, the at least one gene encoding an arginine transporter comprises the hisJQMP operon and the argT gene. In yet another embodiment, the at least one gene encoding an arginine transporter comprises the abpS gene and the argK gene.

In one embodiment, the argT gene has at least about 80% identity with the sequence of SEQ ID NO:13. Accordingly, in one embodiment, the argT gene has at least about 90% identity with the sequence of SEQ ID NO:13. Accordingly, in one embodiment, the argT gene has at least about 95% identity with the sequence of SEQ ID NO:13. Accordingly, in one embodiment, the argT gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:13. In another embodiment, the argT gene comprises the sequence of SEQ ID NO:13. In yet another embodiment the argT gene consists of the sequence of SEQ ID NO:13.

In one embodiment, the artP gene has at least about 80% identity with the sequence of SEQ ID NO:14. Accordingly, in one embodiment, the artP gene has at least about 90% identity with the sequence of SEQ ID NO:14. Accordingly, in one embodiment, the artP gene has at least about 95% identity with the sequence of SEQ ID NO:14. Accordingly, in one embodiment, the artP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:14. In another embodiment, the artP gene comprises the sequence of SEQ ID NO:14. In yet another embodiment the artP gene consists of the sequence of SEQ ID NO:14.

In one embodiment, the artI gene has at least about 80% identity with the sequence of SEQ ID NO:15. Accordingly, in one embodiment, the artI gene has at least about 90% identity with the sequence of SEQ ID NO:15. Accordingly, in one embodiment, the artI gene has at least about 95% identity with the sequence of SEQ ID NO:15. Accordingly, in one embodiment, the artI gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:15. In another embodiment, the artI gene comprises the sequence of SEQ ID NO:15. In yet another embodiment the artI gene consists of the sequence of SEQ ID NO:15.

In one embodiment, the artQ gene has at least about 80% identity with the sequence of SEQ ID NO:16. Accordingly, in one embodiment, the artQ gene has at least about 90% identity with the sequence of SEQ ID NO:16. Accordingly, in one embodiment, the artQ gene has at least about 95% identity with the sequence of SEQ ID NO:16. Accordingly, in one embodiment, the artQ gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:16. In another embodiment, the artQ gene comprises the sequence of SEQ ID NO:16. In yet another embodiment the artQ gene consists of the sequence of SEQ ID NO:16.

In one embodiment, the artM gene has at least about 80% identity with the sequence of SEQ ID NO:17. Accordingly, in one embodiment, the artM gene has at least about 90% identity with the sequence of SEQ ID NO:17. Accordingly, in one embodiment, the artM gene has at least about 95% identity with the sequence of SEQ ID NO:17. Accordingly, in one embodiment, the artM gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:17. In another embodiment, the artM gene comprises the sequence of SEQ ID NO:17. In yet another embodiment the artM gene consists of the sequence of SEQ ID NO:17.

In one embodiment, the artJ gene has at least about 80% identity with the sequence of SEQ ID NO:18. Accordingly, in one embodiment, the artJ gene has at least about 90% identity with the sequence of SEQ ID NO:18. Accordingly, in one embodiment, the artJ gene has at least about 95% identity with the sequence of SEQ ID NO:18. Accordingly, in one embodiment, the artJ gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:18. In another embodiment, the artJ gene comprises the sequence of SEQ ID NO:18. In yet another embodiment the artJ gene consists of the sequence of SEQ ID NO:18.

In some embodiments, the arginine transporter is encoded by an arginine transporter gene derived from a bacterial genus or species, including but not limited to, *Escherichia, Haemophilus, Salmonella, Escherichia coli, Haemophilus influenza, Salmonella enterica*, or *Salmonella typhimurium*. In some embodiments, the bacterial species is *Escherichia coli*. In some embodiments, the bacterial species is *Escherichia coli* strain Nissle.

Assays for testing the activity of an arginine transporter, a functional variant of an arginine transporter, or a functional fragment of arginine transporter are well known to one of ordinary skill in the art. For example, import of arginine may be determined using the methods as described in Sakanaka et al (2015) *J. Biol. Chem.* 290(35): 21185-98, the entire contents of each of which are expressly incorporated by reference herein.

In one embodiment, when the arginine transporter is expressed in the recombinant bacterial cells described herein, the bacterial cells import 10% more arginine into the bacterial cell when the arginine transporter is expressed than unmodified bacteria of the same bacterial subtype under the same conditions. In another embodiment, when the arginine transporter is expressed in the recombinant bacterial cells described herein, the bacterial cells import 20%, 30%, 40%, 50%, 60%, 70%, 80%, 90% or 100% more arginine into the bacterial cell when the arginine transporter is expressed than unmodified bacteria of the same bacterial subtype under the same conditions. In yet another embodiment, when the arginine transporter is expressed in the recombinant bacterial cells described herein, the bacterial cells import two-fold more arginine into the cell when the transporter is expressed than unmodified bacteria of the same bacterial subtype under the same conditions. In yet another embodiment, when the arginine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more arginine into the cell when the transporter is expressed than unmodified bacteria of the same bacterial subtype under the same conditions.

3. Lysine Transporters

In one embodiment, the amino acid transporter is a lysine transporter. Lysine transporters may be expressed or modified in the recombinant bacteria described herein in order to enhance lysine transport into the cell. Specifically, when the transporter of lysine is expressed in the recombinant bacterial cells described herein, the bacterial cells import more lysine into the cell when the lysine transporter is expressed than unmodified bacteria of the same bacterial subtype under the same conditions. Thus, the genetically engineered bacteria comprising a heterologous gene encoding a lysine transporter which may be used to import lysine into the bacteria.

The uptake of lysine into bacterial cells is mediated by proteins well known to those of skill in the art. For example, LysP is a lysine-specific permease originally identified in *E. coli*, that has now been further characterized in other bacterial species (Steffes et al. (1992) *J. Bacteriol.* 174: 3242-9; Trip et al. (2013) *J. Bacteriol.* 195(2): 340-50; Nji et al. (2014) *Acta Crystallogr. F Struct. Biol. Commun.* 70(Pt 10): 1362-7). Another lysine transporter, YsvH, has been described in *Bacillus*, having similarities to the lysine permease LysI of *Corynebacterium glutamicum* (Rodionov et al. (2003) *Nucleic Acids Res.* 31(23): 6748-57).

In one embodiment, the at least one gene encoding a lysine transporter is the lysP gene. In one embodiment, the bacterial cell described herein has been genetically engineered to comprise at least one heterologous lysP gene. In one embodiment, the at least one gene encoding a lysine transporter is the *Escherichia coli* lysP gene. In one embodiment, the at least one gene encoding a lysine transporter is the *Lactococcus lactis* lysP gene. In one embodiment, the at least one gene encoding a lysine transporter is the *Pseudomonas aeruginosa* lysP gene. In one embodiment, the at least one gene encoding a lysine transporter is the *Klebsiella pneumoniae* lysP gene.

In one embodiment, the lysP gene has at least about 80% identity with the sequence of SEQ ID NO:26. Accordingly, in one embodiment, the lysP gene has at least about 90% identity with the sequence of SEQ ID NO:26. Accordingly, in one embodiment, the lysP gene has at least about 95% identity with the sequence of SEQ ID NO:26. Accordingly, in one embodiment, the lysP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:26. In another embodiment, the lysP gene comprises the sequence of SEQ ID NO:26. In yet another embodiment the lysP gene consists of the sequence of SEQ ID NO:26.

In one embodiment, the at least one gene encoding a lysine transporter is the ysvH gene. In one embodiment, the bacterial cell described herein has been genetically engineered to comprise at least one heterologous ysvH gene. In one embodiment, the at least one gene encoding a lysine transporter is the *Bacillus subtilis* ysvH gene. In one embodiment, the at least one gene encoding a lysine transporter is the *Bacillus cereus* ysvH gene. In one embodiment, the at least one gene encoding a lysine transporter is the *Bacillus stearothermophilus* ysvH gene.

In one embodiment, the at least one gene encoding a lysine transporter is the *Corynebacterium glutamicum* (see, e.g., Seep-Feldhaus et al. (1991) *Mol. Microbiol.* 5(12): 2995-3005, the entire contents of which are incorporated herein by reference).

In one embodiment, the ysvH gene has at least about 80% identity with the sequence of SEQ ID NO:25. Accordingly, in one embodiment, the ysvH gene has at least about 90% identity with the sequence of SEQ ID NO:25. Accordingly, in one embodiment, the ysvH gene has at least about 95% identity with the sequence of SEQ ID NO:25. Accordingly, in one embodiment, the ysvH gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:25. In another embodiment, the ysvH gene comprises the sequence of SEQ ID NO:25. In yet another embodiment the ysvH gene consists of the sequence of SEQ ID NO:25.

In some embodiments, the transporter of lysine is encoded by a lysine transporter gene derived from a bacterial genus or species, including but not limited to, *Bacillus subtilis, Bacillus cereus, Bacillus stearothermophilus, Corynebacterium glutamicum, Escherichia coli, Lactococcus lactis, Pseudomonas aeruginosa,* and *Klebsiella pneumoniae*. In some embodiments, the bacterial species is *Escherichia coli*. In some embodiments, the bacterial species is *Escherichia coli* strain Nissle.

Assays for testing the activity of a lysine transporter, a functional variant of a lysine transporter, or a functional fragment of a lysine transporter are well known to one of ordinary skill in the art. For example, import of lysine may be determined using the methods as described in Steffes et al. (1992) *J. Bacteriol.* 174: 3242-9, the entire contents of each of which are expressly incorporated by reference herein.

In one embodiment, when the lysine transporter is expressed in the recombinant bacterial cells described herein, the bacterial cells import 10% more lysine into the bacterial cell when the lysine transporter is expressed than unmodified bacteria of the same bacterial subtype under the same conditions. In another embodiment, when the lysine transporter is expressed in the recombinant bacterial cells described herein, the bacterial cells import 20%, 30%, 40%, 50%, 60%, 70%, 80%, 90% or 100% more lysine into the bacterial cell when the transporter is expressed than unmodified bacteria of the same bacterial subtype under the same conditions. In yet another embodiment, when the lysine transporter is expressed in the recombinant bacterial cells described herein, the bacterial cells import two-fold more lysine into the cell when the transporter is expressed than unmodified bacteria of the same bacterial subtype under the same conditions. In yet another embodiment, when the transporter of lysine is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more lysine into the cell when the transporter is expressed than unmodified bacteria of the same bacterial subtype under the same conditions.

4. Asparagine Transporters

In one embodiment, the amino acid transporter is an asparagine transporter. Asparagine transporters may be expressed or modified in the recombinant bacteria described herein in order to enhance asparagine transport into the cell. Specifically, when the asparagine transporter is expressed in the recombinant bacterial cells described herein, the bacterial cells import more asparagine into the cell when the asparagine transporter is expressed than unmodified bacteria of the same bacterial subtype under the same conditions. Thus, the genetically engineered bacteria comprising a heterologous gene encoding an asparagine transporter which may be used to import asparagine into the bacteria.

The uptake of asparagine into bacterial cells is mediated by proteins well known to those of skill in the art. For example, two distinct systems for asparagine uptake, distinguishable on the basis of their specificity for asparagine have been identified in *E. coli* (see, e.g., Willis and Woolfolk (1975) *J. Bacteriol.* 123: 937-945). The bacterial gene ansP encodes an asparagine permease responsible for asparagine uptake in many bacteria (see, e.g., Jennings et al. (1995) *Microbiology* 141: 141-6; Ortuño-Olea and Durán-Vargas (2000) FEMS *Microbiol. Lett.* 189(2): 177-82; Barel et al. (2015) *Front. Cell. Infect. Microbiol.* 5: 9; and Gouzy et al. (2014) *PLoS Pathog.* 10(2): e1003928).

In one embodiment, the at least one gene encoding an asparagine transporter is the ansP gene. In one embodiment, the bacterial cell described herein has been genetically engineered to comprise at least one heterologous ansP gene. In one embodiment, the at least one gene encoding an asparagine transporter is the *Escherichia coli* ansP gene. In one embodiment, the at least one gene encoding an asparagine transporter is the *Francisella tularensis* ansP gene. In one embodiment, the at least one gene encoding an asparagine transporter is the *Mycobacterium bovis* ansP2 gene. In one embodiment, the at least one gene encoding an asparagine transporter is the *Salmonella enterica* ansP gene. In one embodiment, the at least one gene encoding an asparagine transporter is the *Yersinia pestis* ansP gene.

In one embodiment, the ansP2 gene has at least about 80% identity with the sequence of SEQ ID NO:29. Accordingly, in one embodiment, the ansP2 gene has at least about 90% identity with the sequence of SEQ ID NO:29. Accordingly, in one embodiment, the ansP2 gene has at least about 95% identity with the sequence of SEQ ID NO:29. Accordingly, in one embodiment, the ansP2 gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:29. In another embodiment, the ansP2 gene comprises the sequence of SEQ ID NO:29. In yet another embodiment the ansP2 gene consists of the sequence of SEQ ID NO:29.

In some embodiments, the asparagine transporter is encoded by an asparagine transporter gene derived from a bacterial genus or species, including but not limited to, *Escherichia, Francisella, Mycobacterium, Salmonella, Yersinia, Escherichia coli, Francisella tularensis, Mycobacterium tuberculosis, Salmonella enterica*, or *Yersinia pestis*. In some embodiments, the bacterial species is *Escherichia coli*. In some embodiments, the bacterial species is *Escherichia coli* strain Nissle.

Assays for testing the activity of an asparagine transporter, a functional variant of an asparagine transporter, or a functional fragment of asparagine transporter are well known to one of ordinary skill in the art. For example, import of asparagine may be determined using the methods as described in Jennings et al. (1995) *Microbiology* 141: 141-6, the entire contents of each of which are expressly incorporated by reference herein.

In one embodiment, when the transporter of an asparagine is expressed in the recombinant bacterial cells described herein, the bacterial cells import 10% more asparagine into the bacterial cell when the transporter is expressed than unmodified bacteria of the same bacterial subtype under the same conditions. In another embodiment, when the asparagine transporter is expressed in the recombinant bacterial cells described herein, the bacterial cells import 20%, 30%, 40%, 50%, 60%, 70%, 80%, 90% or 100% more asparagine into the bacterial cell when the transporter is expressed than unmodified bacteria of the same bacterial subtype under the same conditions. In yet another embodiment, when the asparagine transporter is expressed in the recombinant bacterial cells described herein, the bacterial cells import two-fold more asparagine into the cell when the transporter is expressed than unmodified bacteria of the same bacterial subtype under the same conditions. In yet another embodiment, when the asparagine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more asparagine into the cell when the transporter is expressed than unmodified bacteria of the same bacterial subtype under the same conditions.

5. Serine Transporters

In one embodiment, the amino acid transporter is a serine transporter. Serine transporters may be expressed or modified in the recombinant bacteria described herein in order to enhance serine transport into the cell. Specifically, when the serine transporter is expressed in the recombinant bacterial cells described herein, the bacterial cells import more serine into the cell when the transporter is expressed than unmodified bacteria of the same bacterial subtype under the same conditions. Thus, the genetically engineered bacteria comprising a heterologous gene encoding a serine transporter which may be used to import serine into the bacteria.

The uptake of serine into bacterial cells is mediated by proteins well known to those of skill in the art. For example, SdaC (encoded by the sdaC gene; also known as DcrA) is an inner membrane threonine-insensitive serine transporter that was originally identified in *Escherichia coli* (Shao et al. (1994) *Eur. J. Biochem.* 222: 901-7). Additional serine transporters that have been identified include the Na+/serine symporter, SstT (encoded by the sstT gene), the leucine-isoleucine-valine transporter LIV-1, which transports serine slowly, and the H+/serine-threonine symporter TdcC (encoded by the tdcC gene) (see, e.g., Ogawa et al. (1998) *J. Bacteria* 180: 6749-52; Ogawa et al. (1997) *J. Biochem.* 122(6): 1241-5).

In one embodiment, the at least one gene encoding a serine transporter is the sdaC gene. In one embodiment, the bacterial cell described herein has been genetically engineered to comprise at least one heterologous sdaC gene. In one embodiment, the at least one gene encoding a serine transporter is the *Escherichia coli* sdaC gene. In one embodiment, the at least one gene encoding a serine transporter is the *Campylobacter jejuni* sdaC gene.

In one embodiment, the sdaC gene has at least about 80% identity with the sequence of SEQ ID NO:35. Accordingly, in one embodiment, the sdaC gene has at least about 90% identity with the sequence of SEQ ID NO:35. Accordingly, in one embodiment, the sdaC gene has at least about 95% identity with the sequence of SEQ ID NO:35. Accordingly, in one embodiment, the sdaC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:35. In another embodiment, the sdaC gene comprises the sequence of SEQ ID NO:35. In yet another embodiment the sdaC gene consists of the sequence of SEQ ID NO:35.

In one embodiment, the at least one gene encoding a serine transporter is the sstT gene. In one embodiment, the bacterial cell described herein has been genetically engineered to comprise at least one heterologous sstT gene. In one embodiment, the at least one gene encoding a serine transporter is the *Escherichia coli* sstT gene.

In one embodiment, the at least one gene encoding a serine transporter is the tdcC gene. In one embodiment, the bacterial cell described herein has been genetically engineered to comprise at least one heterologous tdcC gene. In one embodiment, the at least one gene encoding a serine transporter is the *Escherichia coli* tdcC gene.

In some embodiments, the serine transporter is encoded by a serine transporter gene derived from a bacterial genus or species, including but not limited to, *Campylobacter, Campylobacter jejuni, Escherichia*, and *Escherichia coli* In some embodiments, the bacterial species is *Escherichia coli*. In some embodiments, the bacterial species is *Escherichia coli* strain Nissle.

Assays for testing the activity of a serine transporter, a functional variant of a serine transporter, or a functional fragment of transporter of serine are well known to one of ordinary skill in the art. For example, import of serine may be determined using the methods as described in Hama et al. (1987) *Biochim. Biophys. Acta* 905: 231-9, the entire contents of each of which are expressly incorporated by reference herein.

In one embodiment, when the transporter of a serine is expressed in the recombinant bacterial cells described herein, the bacterial cells import 10% more serine into the bacterial cell when the transporter is expressed than unmodified bacteria of the same bacterial subtype under the same conditions. In another embodiment, when the serine transporter is expressed in the recombinant bacterial cells described herein, the bacterial cells import 20%, 30%, 40%, 50%, 60%, 70%, 80%, 90% or 100% more serine into the bacterial cell when the transporter is expressed than unmodified bacteria of the same bacterial subtype under the same conditions. In yet another embodiment, when the serine transporter is expressed in the recombinant bacterial cells described herein, the bacterial cells import two-fold more serine into the cell when the transporter is expressed than unmodified bacteria of the same bacterial subtype under the same conditions. In yet another embodiment, when the serine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more serine into the cell when the transporter is expressed than unmodified bacteria of the same bacterial subtype under the same conditions.

6. Glutamine Transporters

In one embodiment, the amino acid transporter is a glutamine transporter. Glutamine transporters may be expressed or modified in the recombinant bacteria described herein in order to enhance glutamine transport into the cell. Specifically, when the glutamine transporter is expressed in the recombinant bacterial cells described herein, the bacterial cells import more glutamine into the cell when the transporter is expressed than unmodified bacteria of the same bacterial subtype under the same conditions. Thus, the genetically engineered bacteria comprising a heterologous gene encoding a glutamine transporter which may be used to import glutamine into the bacteria.

The uptake of glutamine into bacterial cells is mediated by proteins well known to those of skill in the art. For example, a glutamine permease glnHPQ operon has been identified in *Escherichia coli* (Nohno et al., *Mol. Gen. Genet.* 205(2):260-269, 1986).

In one embodiment, the at least one gene encoding a glutamine transporter is the glnHPQ operon. In one embodiment, the bacterial cell described herein has been genetically engineered to comprise at least one heterologous gene from the glnHPQ operon. In one embodiment, the bacterial cell described herein has been genetically engineered to comprise at least one heterologous glnH gene. In one embodiment, the bacterial cell described herein has been genetically engineered to comprise at least one heterologous glnP gene. In one embodiment, the bacterial cell described herein has been genetically engineered to comprise at least one heterologous glnQ gene.

In one embodiment, the glnHPQ operon has at least about 80% identity with the sequence of SEQ ID NO:41. Accordingly, in one embodiment, the glnHPQ operon has at least about 90% identity with the sequence of SEQ ID NO:41. Accordingly, in one embodiment, the glnHPQ operon has at least about 95% identity with the sequence of SEQ ID NO:41. Accordingly, in one embodiment, the glnHPQ operon has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:41. In another embodiment, the glnHPQ operon comprises the sequence of SEQ ID NO:41. In yet another embodiment the glnHPQ operon consists of the sequence of SEQ ID NO:41.

In one embodiment, the glnH gene has at least about 80% identity with the sequence of SEQ ID NO:42. Accordingly, in one embodiment, the glnH gene has at least about 90% identity with the sequence of SEQ ID NO:42. Accordingly, in one embodiment, the glnH gene has at least about 95% identity with the sequence of SEQ ID NO:42. Accordingly, in one embodiment, the glnH gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:42. In another embodiment, the glnH gene comprises the sequence of SEQ ID NO:42. In yet another embodiment the glnH gene consists of the sequence of SEQ ID NO:42.

In one embodiment, the glnP gene has at least about 80% identity with the sequence of SEQ ID NO:43. Accordingly, in one embodiment, the glnP gene has at least about 90% identity with the sequence of SEQ ID NO:43. Accordingly, in one embodiment, the glnP gene has at least about 95% identity with the sequence of SEQ ID NO:43. Accordingly, in one embodiment, the glnP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:43. In another embodiment, the glnP gene comprises the sequence of SEQ ID NO:43. In yet another embodiment the glnP gene consists of the sequence of SEQ ID NO:43.

In one embodiment, the glnQ gene has at least about 80% identity with the sequence of SEQ ID NO:44. Accordingly, in one embodiment, the glnQ gene has at least about 90% identity with the sequence of SEQ ID NO:44. Accordingly, in one embodiment, the glnQ gene has at least about 95% identity with the sequence of SEQ ID NO:44. Accordingly, in one embodiment, the glnQ gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:44. In another embodiment, the glnQ gene comprises the sequence of SEQ ID NO:44. In yet another embodiment the glnQ gene consists of the sequence of SEQ ID NO:44.

In some embodiments, the glutamine transporter is encoded by a glutamine transporter gene derived from a bacterial genus or species, including but not limited to, *Escherichia coli*. In some embodiments, the bacterial species is *Escherichia coli* strain Nissle.

Assays for testing the activity of a glutamine transporter, a functional variant of a glutamine transporter, or a functional fragment of transporter of glutamine are well known to one of ordinary skill in the art. For example, import of glutamine may be determined using the methods as described in Nohno et al., *Mol. Gen. Genet.*, 205(2):260-269, 1986, the entire contents of which are expressly incorporated by reference herein.

In one embodiment, when the glutamine transporter is expressed in the recombinant bacterial cells described herein, the bacterial cells import 10% more glutamine into the bacterial cell when the transporter is expressed than unmodified bacteria of the same bacterial subtype under the same conditions. In another embodiment, when the glutamine transporter is expressed in the recombinant bacterial cells described herein, the bacterial cells import 20%, 30%, 40%, 50%, 60%, 70%, 80%, 90% or 100% more glutamine into the bacterial cell when the transporter is expressed than unmodified bacteria of the same bacterial subtype under the same conditions. In yet another embodiment, when the glutamine transporter is expressed in the recombinant bacterial cells described herein, the bacterial cells import two-fold more glutamine into the cell when the transporter is expressed than unmodified bacteria of the same bacterial subtype under the same conditions. In yet another embodiment, when the glutamine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more glutamine into the cell when the transporter is expressed than unmodified bacteria of the same bacterial subtype under the same conditions.

7. Tryptophan Transporters

In one embodiment, the amino acid transporter is a tryptophan transporter. Tryptophan transporters may be expressed or modified in the recombinant bacteria described herein in order to enhance tryptophan transport into the cell. Specifically, when the tryptophan transporter is expressed in the recombinant bacterial cells described herein, the bacterial cells import more tryptophan into the cell when the transporter is expressed than unmodified bacteria of the same bacterial subtype under the same conditions. Thus, the genetically engineered bacteria comprising a heterologous gene encoding a tryptophan transporter which may be used to import tryptophan into the bacteria.

The uptake of tryptophan into bacterial cells is mediated by proteins well known to those of skill in the art. For example, three different tryptophan transporters, distinguishable on the basis of their affinity for tryptophan have been identified in *E. coli* (see, e.g., Yanofsky et al. (1991) *J. Bacteriol.* 173: 6009-17). The bacterial genes mtr, aroP, and tnaB encode tryptophan permeases responsible for tryptophan uptake in bacteria. High affinity permease, Mtr, is negatively regulated by the trp repressor and positively regulated by the TyR product (see, e.g., Yanofsky et al. (1991) *J. Bacteria* 173: 6009-17 and Heatwole et al. (1991) *J. Bacteriol.* 173: 3601-04), while AroP is negatively regulated by the tyR product (Chye et al. (1987) *J. Bacteria* 169:386-93).

In one embodiment, the at least one gene encoding a tryptophan transporter is a gene selected from the group consisting of mtr, aroP and tnaB. In one embodiment, the bacterial cell described herein has been genetically engineered to comprise at least one heterologous gene selected from the group consisting of mtr, aroP and tnaB. In one embodiment, the at least one gene encoding a tryptophan transporter is the *Escherichia coli* mtr gene. In one embodiment, the at least one gene encoding a tryptophan transporter is the *Escherichia coli* aroP gene. In one embodiment, the at least one gene encoding a tryptophan transporter is the *Escherichia coli* tnaB gene.

In one embodiment, the mtr gene has at least about 80% identity with the sequence of SEQ ID NO:46. Accordingly, in one embodiment, the mtr gene has at least about 90% identity with the sequence of SEQ ID NO:46. Accordingly, in one embodiment, the mtr gene has at least about 95% identity with the sequence of SEQ ID NO:46. Accordingly, in one embodiment, the mtr gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:46. In another embodiment, the mtr gene comprises the sequence of SEQ ID NO:46. In yet another embodiment the mtr gene consists of the sequence of SEQ ID NO:46.

In one embodiment, the tnaB gene has at least about 80% identity with the sequence of SEQ ID NO:47. Accordingly, in one embodiment, the tnaB gene has at least about 90% identity with the sequence of SEQ ID NO:47. Accordingly, in one embodiment, the tnaB gene has at least about 95% identity with the sequence of SEQ ID NO:47. Accordingly, in one embodiment, the tnaB gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:47. In another embodiment, the tnaB gene comprises the sequence of SEQ ID NO:47. In yet another embodiment the tnaB gene consists of the sequence of SEQ ID NO:47.

In one embodiment, the aroP gene has at least about 80% identity with the sequence of SEQ ID NO:48. Accordingly, in one embodiment, the aroP gene has at least about 90% identity with the sequence of SEQ ID NO:48. Accordingly, in one embodiment, the aroP gene has at least about 95% identity with the sequence of SEQ ID NO:48. Accordingly, in one embodiment, the aroP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:48. In another embodiment, the aroP gene comprises the sequence of SEQ ID NO:48. In yet another embodiment the aroP gene consists of the sequence of SEQ ID NO:48.

In some embodiments, the tryptophan transporter is encoded by a tryptophan transporter gene derived from a bacterial genus or species, including but not limited to, *Escherichia, Corynebacterium, Escherichia coli, Saccharomyces cerevisiae* or *Corynebacterium glutamicum*. In some embodiments, the bacterial species is *Escherichia coli*. In some embodiments, the bacterial species is *Escherichia coli* strain Nissle.

Assays for testing the activity of a tryptophan transporter, a functional variant of a tryptophan transporter, or a functional fragment of transporter of tryptophan are well known to one of ordinary skill in the art. For example, import of tryptophan may be determined using the methods as described in Shang et al. (2013) *J. Bacteriol.* 195:5334-42, the entire contents of each of which are expressly incorporated by reference herein.

In one embodiment, when the tryptophan transporter is expressed in the recombinant bacterial cells described herein, the bacterial cells import 10% more tryptophan into the bacterial cell when the transporter is expressed than unmodified bacteria of the same bacterial subtype under the same conditions. In another embodiment, when the tryptophan transporter is expressed in the recombinant bacterial cells described herein, the bacterial cells import 20%, 30%, 40%, 50%, 60%, 70%, 80%, 90% or 100% more tryptophan into the bacterial cell when the transporter is expressed than unmodified bacteria of the same bacterial subtype under the same conditions. In yet another embodiment, when the tryptophan transporter is expressed in the recombinant bacterial cells described herein, the bacterial cells import two-fold more tryptophan into the cell when the transporter is expressed than unmodified bacteria of the same bacterial subtype under the same conditions. In yet another embodiment, when the tryptophan transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more tryptophan into the cell when the transporter is expressed than unmodified bacteria of the same bacterial subtype under the same conditions.

8. Methionine Transporters

In one embodiment, the amino acid transporter is a methionine transporter. Methionine transporters may be expressed or modified in the recombinant bacteria described herein in order to enhance methionine transport into the cell. Specifically, when the methionine transporter is expressed in the recombinant bacterial cells described herein, the bacterial cells import more methionine into the cell when the transporter is expressed than unmodified bacteria of the same bacterial subtype under the same conditions. Thus, the genetically engineered bacteria comprising a heterologous gene encoding a methionine transporter which may be used to import methionine into the bacteria.

The uptake of methionine into bacterial cells is mediated by proteins well known to those of skill in the art. For example, a methionine transporter operon has been identified in *Corynebacterium glutamicum* (Trotschel et al., *J. Bacteriology*, 187(11):3786-3794, 2005). In addition, the high affinity MetD ABC transporter system has been characterized in *Escherichia coli* (Kadaba et al. (2008) Science 5886: 250-253; Kadner and Watson (1974) *J. Bacteriol.* 119: 401-9). The MetD transporter system is capable of mediating the translocation of several substrates across the bacterial membrane, including methionine. The metD system of *Escherichia coli* consists of MetN (encoded by metN), which comprises the ATPase domain, MetI (encoded by metI), which comprises the transmembrane domain, and MetQ (encoded by metQ), the cognate binding protein which is located in the periplasm. Orthologues of the genes encoding the *E. coli* metD transporter system have been identified in multiple organisms including, e.g., *Yersinia pestis, Vibrio cholerae, Pasteurella multocida, Haemophilus influenza, Agrobacterium tumefaciens, Sinorhizobium meliloti, Brucella meliloti*, and *Mesorhizobium loti* (Merlin et al. (2002) *J. Bacteriol.* 184: 5513-7).

In one embodiment, the at least one gene encoding a methionine transporter is a metP gene, a metN gene, a metI gene, or a metQ gene from *Corynebacterium glutamicum, Escherichia coli*, and *Bacillus subtilis* (Trotschel et al., *J. Bacteriology*, 187(11):3786-3794, 2005).

In one embodiment, the metP gene has at least about 80% identity with the sequence of SEQ ID NO:59. Accordingly, in one embodiment, the metP gene has at least about 90% identity with the sequence of SEQ ID NO:59. Accordingly, in one embodiment, the metP gene has at least about 95% identity with the sequence of SEQ ID NO:59. Accordingly, in one embodiment, the metP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:59. In another embodiment, the metP gene comprises the sequence of SEQ ID NO:59. In yet another embodiment the metP gene consists of the sequence of SEQ ID NO:59.

In one embodiment, the metN gene has at least about 80% identity with the sequence of SEQ ID NO:60. Accordingly, in one embodiment, the metN gene has at least about 90% identity with the sequence of SEQ ID NO:60. Accordingly, in one embodiment, the metN gene has at least about 95% identity with the sequence of SEQ ID NO:60. Accordingly, in one embodiment, the metN gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:60. In another embodiment, the metN gene comprises the sequence of SEQ ID NO:60. In yet another embodiment the metN gene consists of the sequence of SEQ ID NO:60.

In one embodiment, the metI gene has at least about 80% identity with the sequence of SEQ ID NO:61. Accordingly, in one embodiment, the metI gene has at least about 90% identity with the sequence of SEQ ID NO:61. Accordingly, in one embodiment, the metI gene has at least about 95% identity with the sequence of SEQ ID NO:61. Accordingly, in one embodiment, the metI gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:61. In another embodiment, the metI gene comprises the sequence of SEQ ID NO:61. In yet another embodiment the metI gene consists of the sequence of SEQ ID NO:61.

In one embodiment, the metQ gene has at least about 80% identity with the sequence of SEQ ID NO:62. Accordingly, in one embodiment, the metQ gene has at least about 90% identity with the sequence of SEQ ID NO:62. Accordingly, in one embodiment, the metQ gene has at least about 95% identity with the sequence of SEQ ID NO:62. Accordingly, in one embodiment, the metQ gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:62. In another embodiment, the metQ gene comprises the sequence of SEQ ID NO:62. In yet another embodiment the metQ gene consists of the sequence of SEQ ID NO:62.

In some embodiments, the methionine transporter is encoded by a methionine transporter gene derived from a bacterial genus or species, including but not limited to, *Corynebacterium glutamicum, Escherichia coli*, and *Bacillus subtilis*. In some embodiments, the bacterial species is *Escherichia coli* strain Nissle.

Assays for testing the activity of a methionine transporter, a functional variant of a methionine transporter, or a functional fragment of a methionine transporter are well known to one of ordinary skill in the art. For example, import of methionine may be determined using the methods as described in Trotschel et al., *J. Bacteriology*, 187(11):3786-3794, 2005, the entire contents of which are expressly incorporated by reference herein.

In one embodiment, when the methionine transporter is expressed in the recombinant bacterial cells described herein, the bacterial cells import 10% more methionine into the bacterial cell when the transporter is expressed than unmodified bacteria of the same bacterial subtype under the same conditions. In another embodiment, when the methionine transporter is expressed in the recombinant bacterial cells described herein, the bacterial cells import 20%, 30%, 40%, 50%, 60%, 70%, 80%, 90% or 100% more methionine into the bacterial cell when the transporter is expressed than unmodified bacteria of the same bacterial subtype under the same conditions. In yet another embodiment, when the methionine transporter is expressed in the recombinant bacterial cells described herein, the bacterial cells import two-fold more methionine into the cell when the transporter is expressed than unmodified bacteria of the same bacterial subtype under the same conditions. In yet another embodiment, when the methionine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more methionine into the cell when the transporter is expressed than unmodified bacteria of the same bacterial subtype under the same conditions.

9. Threonine Transporters

In one embodiment, the amino acid transporter is a threonine transporter. Threonine transporters may be expressed or modified in the recombinant bacteria described herein in order to enhance threonine transport into the cell. Specifically, when the threonine transporter is expressed in the recombinant bacterial cells described herein, the bacterial cells import more threonine into the cell when the transporter is expressed than unmodified bacteria of the same bacterial subtype under the same conditions. Thus, the genetically engineered bacteria comprising a heterologous gene encoding a threonine transporter which may be used to import threonine into the bacteria.

The uptake of threonine into bacterial cells is mediated by proteins well known to those of skill in the art. For example, the threonine transporter TdcC has been identified (Wook Lee et al., *Nature Chemical Biology*, 8:536-546, 2012). Additional serine/threonine transporters have been identified and are disclosed in the serine section herein.

In one embodiment, the at least one gene encoding a threonine transporter is the tdcC gene. In one embodiment, the bacterial cell described herein has been genetically engineered to comprise at least one heterologous tdcC gene. In one embodiment, the at least one gene encoding a threonine transporter is the *Escherichia coli* tdcC gene. In one embodiment, the at least one gene encoding a threonine transporter is the *Salmonella typhimurium* tdcC gene.

In one embodiment, the tdcC gene has at least about 80% identity with the sequence of SEQ ID NO:69. Accordingly, in one embodiment, the tdcC gene has at least about 90% identity with the sequence of SEQ ID NO:69. Accordingly, in one embodiment, the tdcC gene has at least about 95% identity with the sequence of SEQ ID NO:69. Accordingly, in one embodiment, the tdcC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:69. In another embodiment, the tdcC gene comprises the sequence of SEQ ID NO:69. In yet another embodiment the tdcC gene consists of the sequence of SEQ ID NO:69.

In some embodiments, the threonine transporter is encoded by a threonine transporter gene derived from a bacterial genus or species, including but not limited to, *Escherichia coli* or *Salmonella typhimurium*. In some embodiments, the bacterial species is *Escherichia coli*. In some embodiments, the bacterial species is *Escherichia coli* strain Nissle.

Assays for testing the activity of a threonine transporter, a functional variant of a threonine transporter, or a functional fragment of transporter of threonine are well known to one of ordinary skill in the art. For example, import of threonine may be determined using the methods as described in Wook Lee et al. (2012) *Nature Chemical Biology*, 8:536-546, the entire contents of which are expressly incorporated by reference herein.

In one embodiment, when the threonine transporter is expressed in the recombinant bacterial cells described herein, the bacterial cells import 10% more threonine into the bacterial cell when the transporter is expressed than unmodified bacteria of the same bacterial subtype under the same conditions. In another embodiment, when the threonine transporter is expressed in the recombinant bacterial cells described herein, the bacterial cells import 20%, 30%, 40%, 50%, 60%, 70%, 80%, 90% or 100% more threonine into the bacterial cell when the transporter is expressed than unmodified bacteria of the same bacterial subtype under the same conditions. In yet another embodiment, when the threonine transporter is expressed in the recombinant bacterial cells described herein, the bacterial cells import two-fold more threonine into the cell when the transporter is expressed than unmodified bacteria of the same bacterial subtype under the same conditions. In yet another embodiment, when the threonine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more threonine into the cell when the transporter is expressed than unmodified bacteria of the same bacterial subtype under the same conditions.

10. Cysteine Transporters

In one embodiment, the amino acid transporter is a cysteine transporter. Cysteine transporters may be expressed or modified in the recombinant bacteria described herein in order to enhance cysteine transport into the cell. Specifically, when the cysteine transporter is expressed in the recombinant bacterial cells described herein, the bacterial cells import more cysteine into the cell when the transporter is expressed than unmodified bacteria of the same bacterial subtype under the same conditions. Thus, the genetically engineered bacteria comprising a heterologous gene encoding a cysteine transporter which may be used to import cysteine into the bacteria so that any gene encoding a cysteine catabolism enzyme expressed in the organism can catabolize the cysteine to treat a disease associated with cysteine, such as cancer.

The uptake of cysteine into bacterial cells is mediated by proteins well known to those of skill in the art.

In some embodiments, the cysteine transporter is encoded by a cysteine transporter gene derived from a bacterial genus or species, including but not limited to, *Escherichia coli*. In some embodiments, the bacterial species is *Escherichia coli*. In some embodiments, the bacterial species is *Escherichia coli* strain Nissle.

Assays for testing the activity of a cysteine transporter, a functional variant of a cysteine transporter, or a functional fragment of transporter of cysteine are well known to one of ordinary skill in the art.

In one embodiment, when the transporter of a cysteine is expressed in the recombinant bacterial cells described herein, the bacterial cells import 10% more cysteine into the bacterial cell when the transporter is expressed than unmodified bacteria of the same bacterial subtype under the same conditions. In another embodiment, when the cysteine transporter is expressed in the recombinant bacterial cells described herein, the bacterial cells import 20%, 30%, 40%, 50%, 60%, 70%, 80%, 90% or 100% more cysteine into the bacterial cell when the transporter is expressed than unmodified bacteria of the same bacterial subtype under the same conditions. In yet another embodiment, when the cysteine transporter is expressed in the recombinant bacterial cells described herein, the bacterial cells import two-fold more cysteine into the cell when the transporter is expressed than unmodified bacteria of the same bacterial subtype under the same conditions. In yet another embodiment, when the cysteine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more cysteine into the cell when the transporter is expressed than unmodified bacteria of the same bacterial subtype under the same conditions.

11. Tyrosine Transporters

In one embodiment, the amino acid transporter is a tyrosine transporter. Tyrosine transporters may be expressed or modified in the recombinant bacteria described herein in order to enhance tyrosine transport into the cell. Specifically, when the tyrosine transporter is expressed in the recombinant bacterial cells described herein, the bacterial cells import more tyrosine into the cell when the transporter is expressed than unmodified bacteria of the same bacterial subtype under the same conditions. Thus, the genetically engineered bacteria comprising a heterologous gene encoding a tyrosine transporter which may be used to import tyrosine into the bacteria.

The uptake of tyrosine into bacterial cells is mediated by proteins well known to those of skill in the art. For example, a tyrosine transporter TyrP has been identified in *Lactobacillus brevis* (Wolken et al., *J. Bacteriol.*, 188(6): 2198-2206, 2006) and *Escherichia coli*.

In one embodiment, the at least one gene encoding a tyrosine transporter is the tyrP gene. In one embodiment, the bacterial cell described herein has been genetically engineered to comprise at least one heterologous tyrP gene. In one embodiment, the at least one gene encoding a tyrosine transporter is the *Escherichia coli* tyrP gene. In one embodiment, the at least one gene encoding a tyrosine transporter is the *Lactobacillus brevi* tyrP gene.

In one embodiment, the tyrP gene has at least about 80% identity with the sequence of SEQ ID NO:87. Accordingly, in one embodiment, the tyrP gene has at least about 90% identity with the sequence of SEQ ID NO:87. Accordingly, in one embodiment, the tyrP gene has at least about 95% identity with the sequence of SEQ ID NO:87. Accordingly, in one embodiment, the tyrP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:87. In another embodiment, the tyrP gene comprises the sequence of SEQ ID NO:87. In yet another embodiment the tyrP gene consists of the sequence of SEQ ID NO:87.

In some embodiments, the tyrosine transporter is encoded by a tyrosine transporter gene derived from a bacterial genus or species, including but not limited to, *Escherichia coli* or *Lactobacillus brevis*. In some embodiments, the bacterial species is *Escherichia coli*. In some embodiments, the bacterial species is *Escherichia coli* strain Nissle.

Assays for testing the activity of a tyrosine transporter, a functional variant of a tyrosine transporter, or a functional fragment of a tyrosine transporter are well known to one of ordinary skill in the art. For example, import of tyrosine may be determined using the methods as described in Wolken et al., *J. Bacteriol.*, 188(6):2198-2206, 2006, the entire contents of which are expressly incorporated by reference herein. In one embodiment, when the tyrosine transporter is expressed in the recombinant bacterial cells described herein, the bacterial cells import 10% more tyrosine into the bacterial cell when the transporter is expressed than unmodified bacteria of the same bacterial subtype under the same conditions. In another embodiment, when the tyrosine transporter is expressed in the recombinant bacterial cells described herein, the bacterial cells import 20%, 30%, 40%, 50%, 60%, 70%, 80%, 90% or 100% more tyrosine into the bacterial cell when the transporter is expressed than unmodified bacteria of the same bacterial subtype under the same conditions. In yet another embodiment, when the tyrosine transporter is expressed in the recombinant bacterial cells described herein, the bacterial cells import two-fold more tyrosine into the cell when the transporter is expressed than unmodified bacteria of the same bacterial subtype under the same conditions. In yet another embodiment, when the tyrosine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more tyrosine into the cell when the transporter is expressed than unmodified bacteria of the same bacterial subtype under the same conditions.

12. Phenylalanine Transporters

In one embodiment, the amino acid transporter is a phenylalanine transporter. Phenylalanine transporters may be expressed or modified in the recombinant bacteria described herein in order to enhance phenylalanine transport into the cell. Specifically, when the phenylalanine transporter is expressed in the recombinant bacterial cells described herein, the bacterial cells import more phenylalanine into the cell when the transporter is expressed than unmodified bacteria of the same bacterial subtype under the same conditions. Thus, the genetically engineered bacteria comprising a heterologous gene encoding a phenylalanine transporter which may be used to import phenylalanine into the bacteria.

The uptake of phenylalanine into bacterial cells is mediated by proteins well known to those of skill in the art. For example, a phenylalanine transporter PheP has been identified (Pi et al. (1991) *J. Bacteriol.* 173(12): 3622-9; Pi et al. (1996) *J. Bacteriol.* 178(9): 2650-5; Pi et al. (1998) *J. Bacteriol.* 180(21): 5515-9; and Horsburgh et al. (2004) *Infect. Immun.* 72(5): 3073-3076). Additional phenylalanine transporters have been identified and are known in the art.

In one embodiment, the at least one gene encoding a phenylalanine transporter is the pheP gene. In one embodiment, the bacterial cell described herein has been genetically engineered to comprise at least one heterologous pheP gene. In one embodiment, the at least one gene encoding a phenylalanine transporter is the *Escherichia coli* pheP gene. In one embodiment, the at least one gene encoding a phenylalanine transporter is the *Staphylococcus aureus* pheP gene. "Phenylalanine transporter" is used to refer to a membrane transport protein that is capable of transporting phenylalanine into bacterial cells (see, e.g., Pi et al., 1991). In *Escherichia coli*, the pheP gene encodes a high affinity phenylalanine-specific permease responsible for phenylalanine transport (Pi et al., 1998). In some embodiments, the phenylalanine transporter is encoded by a pheP gene derived from a bacterial species, including but not limited to, *Acinetobacter calcoaceticus, Salmonella enterica*, and *Escherichia coli*. Other phenylalanine transporters include Aageneral amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by a aroP gene derived from a bacterial species. In some embodiments, the phenylalanine transporter is encoded by LIV-binding protein and LS-binding protein and LivHMGF genes derived from a bacterial species. In some embodiments, the genetically engineered bacteria comprise more than one type of phenylalanine transporter, selected from pheP, aroP, and the LIV-I/LS system.

In one embodiment, the pheP gene has at least about 80% identity with the sequence of SEQ ID NO:98. Accordingly, in one embodiment, the pheP gene has at least about 90% identity with the sequence of SEQ ID NO:98. Accordingly, in one embodiment, the pheP gene has at least about 95% identity with the sequence of SEQ ID NO:98. Accordingly, in one embodiment, the pheP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:98. In another embodiment, the pheP gene comprises the sequence of SEQ ID NO:98. In yet another embodiment the pheP gene consists of the sequence of SEQ ID NO:98.

In some embodiments, the phenylalanine transporter is encoded by a phenylalanine transporter gene derived from a bacterial genus or species, including but not limited to, *Escherichia coli* or *Staphylococcus aureus*. In some embodiments, the bacterial species is *Escherichia coli*. In some embodiments, the bacterial species is *Escherichia coli* strain Nissle.

Assays for testing the activity of a phenylalanine transporter, a functional variant of a phenylalanine transporter, or a functional fragment of a phenylalanine transporter are well known to one of ordinary skill in the art. For example, import of phenylalanine may be determined using the methods as described in Pi et al. (1998) *J. Bacteriol.* 180(21): 5515-9, the entire contents of which are expressly incorporated by reference herein.

In one embodiment, when the phenylalanine transporter is expressed in the recombinant bacterial cells described herein, the bacterial cells import 10% more phenylalanine into the bacterial cell when the transporter is expressed than unmodified bacteria of the same bacterial subtype under the same conditions. In another embodiment, when the phenylalanine transporter is expressed in the recombinant bacterial cells described herein, the bacterial cells import 20%, 30%, 40%, 50%, 60%, 70%, 80%, 90% or 100% more phenylalanine into the bacterial cell when the transporter is expressed than unmodified bacteria of the same bacterial subtype under the same conditions. In yet another embodiment, when the phenylalanine transporter is expressed in the recombinant bacterial cells described herein, the bacterial cells import two-fold more phenylalanine into the cell when the transporter is expressed than unmodified bacteria of the same bacterial subtype under the same conditions. In yet another embodiment, when the phenylalanine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more phenylalanine into the cell when the transporter is expressed than unmodified bacteria of the same bacterial subtype under the same conditions.

In some embodiment, the recombinant bacterial cell comprising a heterologous gene encoding a phenylalanie transporter may be used to treat a disease, condition, and/or symptom associated with cancer, e.g., a cancer described herein. In some embodiments, the recombinant bacterial cells described herein may be used to reduce, ameliorate, or eliminate one or more symptom(s) associated with a cancer.

In some embodiment, the recombinant bacterial cell comprising a heterologous gene encoding a phenylalanine transporter may be used to treat a disease, condition, and/or symptom associated with hyperphenylalaninemia. In some embodiments, the recombinant bacterial cells described herein may be used to reduce, ameliorate, or eliminate one or more symptom(s) associated with hyperphenylalaninemia. In some embodiments, the disease is selected from the group consisting of: phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. In some embodiments, hyperphenylalaninemia is secondary to other conditions, e.g., liver diseases. In some embodiments, the invention provides methods for reducing, ameliorating, or eliminating one or more symptom(s) associated with these diseases, including but not limited to neurological deficits, mental retardation, encephalopathy, epilepsy, eczema, reduced growth, microcephaly, tremor, limb spasticity, and/or hypopigmentation. In some embodiments, the subject to be treated is a human patient.

It was discovered that PAL1 and PAL3 expressed on a high-copy plasmid and a low-copy plasmid in genetically engineered E. coli Nissle metabolized and reduced phenylalanine to similar levels, and the rate-limiting step of phenylalanine metabolism was phenylalanine availability. Thus, in some embodiments for the treatment of PKU, it is advantageous to increase phenylalanine transport into the cell, thereby enhancing phenylalanine metabolism. Unexpectedly, even low-copy PAL plasmids are capable of almost completely eliminating Phe from a test sample when expressed in conjunction with pheP. Furthermore, there may be additional advantages to using a low-copy PAL-expressing plasmid in conjunction with pheP in order to enhance the stability of PAL expression while maintaining high phenylalanine metabolism, and to reduce negative selection pressure on the transformed bacterium. In alternate embodiments, the phenylalanine transporter is used in conjunction with the high-copy plasmid.

The genetically engineered bacteria further comprise a gene encoding a phenylalanine transporter. Phenylalanine transporters may be expressed or modified in the genetically engineered bacteria of the invention in order to enhance phenylalanine transport into the cell.

PheP is a membrane transport protein that is capable of transporting phenylalanine into bacterial cells (see, e.g., Pi et al., 1991). In some embodiments, the native pheP gene in the genetically modified bacteria of the invention is not modified. In some embodiments, the genetically engineered bacteria of the invention comprise multiple copies of the native pheP gene. In some embodiments, the genetically engineered bacteria of the invention comprise multiple copies of a non-native pheP gene. In some embodiments, the genetically engineered bacteria of the invention comprise a pheP gene that is controlled by its native promoter, an inducible promoter, a promoter that is stronger than the native promoter, e.g., the GlnRS promoter or the P(Bla) promoter, or a constitutive promoter. In some embodiments, expression of the pheP gene is controlled by a different promoter than the promoter that controls expression of the gene encoding the phenylalanine-metabolizing enzyme and/or the transcriptional regulator. In some embodiments, expression of the pheP gene is controlled by the same promoter that controls expression of the phenylalanine-metabolizing enzyme and/or the transcriptional regulator. In some embodiments, the pheP gene and the phenylalanine-metabolizing enzyme and/or the transcriptional regulator are divergently transcribed from a promoter region. In some embodiments, expression of each of the genes encoding PheP, the phenylalanine-metabolizing enzyme, and the transcriptional regulator is controlled by a different promoter. In some embodiments, expression of the genes encoding PheP, the phenylalanine-metabolizing enzyme, and the transcriptional regulator is controlled by the same promoter.

In some embodiments, the native pheP gene in the genetically modified bacteria is not modified, and one or more additional copies of the native pheP gene are inserted into the genome under the control of the same inducible promoter that controls expression of PAL, e.g., the FNR promoter, or a different inducible promoter than the one that controls expression of PAL, or a constitutive promoter. In alternate embodiments, the native pheP gene is not modified, and a copy of a non-native pheP gene from a different bacterial species is inserted into the genome under the control of the same inducible promoter that controls expression of PAL, e.g., the FNR promoter, or a different inducible promoter than the one that controls expression of PAL, or a constitutive promoter.

In some embodiments, the native pheP gene in the genetically modified bacteria is not modified, and one or more additional copies of the native pheP gene are present in the bacteria on a plasmid and under the control of the same inducible promoter that controls expression of PAL, e.g., the FNR promoter, or a different inducible promoter than the one that controls expression of the PME, or a constitutive promoter. In alternate embodiments, the native pheP gene is not modified, and a copy of a non-native pheP gene from a different bacterial species is present in the bacteria on a plasmid and under the control of the same inducible promoter that controls expression of PAL, e.g., the FNR promoter, or a different inducible promoter than the one that controls expression of PAL, or a constitutive promoter.

In some embodiments, the native pheP gene is mutagenized, mutants exhibiting increased phenylalanine transport are selected, and the mutagenized pheP gene is isolated and inserted into the genetically engineered bacteria (see, e.g., Pi et al., 1996; Pi et al., 1998). The phenylalanine transporter modifications described herein may be present on a plasmid or chromosome.

In some embodiments, the genetically engineered bacterium is E. coli Nissle, and the native pheP gene in E. coli Nissle is not modified; one or more additional copies the native E. coli Nissle pheP genes are inserted into the E. coli Nissle genome under the control of the same inducible promoter that controls expression of PAL, e.g., the FNR promoter, or a different inducible promoter than the one that controls expression of PAL, or a constitutive promoter. In an alternate embodiment, the native pheP gene in E. coli Nissle is not modified, and a copy of a non-native pheP gene from a different bacterium is inserted into the E. coli Nissle genome under the control of the same inducible promoter that controls expression of PAL, e.g., the FNR promoter, or a different inducible promoter than the one that controls expression of PAL, or a constitutive promoter. In some embodiments, the genetically engineered bacterium is E. coli Nissle, and the native pheP gene in E. coli Nissle is not modified; one or more additional copies the native E. coli Nissle pheP genes are present in the bacterium on a plasmid and under the control of the same inducible promoter that controls expression of PAL, e.g., the FNR promoter, or a different inducible promoter than the one that controls expression of PAL, or a constitutive promoter. In an alternate embodiment, the native pheP gene in E. coli Nissle is not modified, and a copy of a non-native pheP gene from a different bacterium, are present in the bacterium on a plasmid and under the control of the same inducible promoter that controls expression of PAL, e.g., the FNR promoter, or a different inducible promoter than the one that controls expression of PAL, or a constitutive promoter.

It has been reported that *Escherichia coli* has five distinct transport systems (AroP, Mtr, PheP, TnaB, and TyrP) for the accumulation of aromatic amino acids. A general amino acid permease, encoded by the aroP gene, transports three aromatic amino acids, including phenylalanine, with high affinity, and is thought, together with PheP, responsible for the lion share of phenylalanine import. Additionally, a low level of accumulation of phenylalanine was observed in an aromatic amino acid transporter-deficient *E. coli* strain (ΔaroP ΔpheP Δmtr Δtna ΔtyrP), and was traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF (Koyanagi et al., and references therein; Identification of the LIV-I/LS System as the Third Phenylalanine Transporter in *Escherichia coli* K-12).

In some embodiments, the genetically engineered bacteria comprise an aroP gene. In some embodiments, the genetically engineered bacterium is *E. coli* Nissle, and the native aroP gene in *E. coli* Nissle is not modified; one or more additional copies the native *E. coli* Nissle aroP genes are present in the bacterium on a plasmid and under the control of the same inducible promoter that controls expression of the PME, e.g., the FNR promoter, or the araBAD promoter, a different inducible promoter than the one that controls expression of the PME, or a constitutive promoter. In an alternate embodiment, the native aroP gene in *E. coli* Nissle is not modified, and a copy of a non-native aroP gene from a different bacterium, are present in the bacterium on a plasmid and under the control of the same inducible promoter that controls expression of the PME, e.g., the FNR promoter or the AraBAD promoter, or a different inducible promoter than the one that controls expression of the PME, or a constitutive promoter.

In other embodiments, the genetically engineered bacteria comprise AroP and PheP, under the control of the same or different inducible or constitutive promoters.

In some embodiments, the pheP gene is expressed on a chromosome. In some embodiments, expression from the chromosome may be useful for increasing stability of expression of pheP. In some embodiments, the pheP gene is integrated into the bacterial chromosome at one or more integration sites in the genetically engineered bacteria. In some embodiments, the pheP gene is inserted into the bacterial genome at one or more of the following insertion sites in *E. coli* Nissle: malE/K, araC/BAD, lacZ, agaI/rsmI, thyA, and malP/T. Any suitable insertion site may be used (see, e.g., The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacterium comprises multiple mechanisms of action and/or one or more auxotrophies. In certain embodiments, the bacteria are genetically engineered to comprise five copies of PAL under the control of an oxygen level-dependent promoter (e.g., $P_{fnrS}$-PAL3) inserted at different integration sites on the chromosome (e.g., malE/K, yicS/nepI, malP/T, agaI/rsmI, and cea), and one copy of a phenylalanine transporter gene under the control of an oxygen level-dependent promoter (e.g., $P_{fnrS}$-pheP) inserted at a different integration site on the chromosome (e.g., lacZ). In a more specific aspect, the bacteria are genetically engineered to further include a kanamycin resistance gene, and a thyA auxotrophy, in which the thyA gene is deleted and/or replaced with an unrelated gene.

13. Glutamic Acid Transporters

In one embodiment, the amino acid transporter is a glutamic transporter. Glutamic acid transporters may be expressed or modified in the recombinant bacteria described herein in order to enhance glutamic acid transport into the cell. Specifically, when the glutamic acid transporter is expressed in the recombinant bacterial cells described herein, the bacterial cells import more glutamic acid into the cell when the transporter is expressed than unmodified bacteria of the same bacterial subtype under the same conditions. Thus, the genetically engineered bacteria comprising a heterologous gene encoding a glutamic acid transporter which may be used to import glutamic acid into the bacteria.

The uptake of glutamic acid into bacterial cells is mediated by proteins well known to those of skill in the art. For example, a Na+coupled symporter GltT for glutamic acid uptake has been identified in *Bacillus subtilis* (see, e.g., Zaprasis et al. (2015) *App. Env. Microbiol.* 81:250-9). The bacterial gene gltT encodes a glutamic acid transporter responsible for glutamic acid uptake in many bacteria (see, e.g., Jan Slotboom et al. (1999) *Microb. Mol. Biol. Rev.* 63:293-307; Takahashi et al. (2015) *Inf. Imm.* 83:3555-67; Ryan et al. (2007) *Nat. Struct. Mol. Biol.* 14:365-71; and Tolner et al. (1992) *Mol. Microbiol.* 6:2845-56).

In one embodiment, the at least one gene encoding a glutamic acid transporter is the gltT gene. In one embodiment, the bacterial cell described herein has been genetically engineered to comprise at least one heterologous gltT gene. In one embodiment, the at least one gene encoding a glutamic acid transporter is the *Escherichia coli* gltP gene. In one embodiment, the at least one gene encoding a glutamic acid transporter is the *Bacillus subtilis* gltT gene. In one embodiment, the at least one gene encoding a glutamic acid transporter is the *Mycobacterium tuberculosis* dctA gene. In one embodiment, the at least one gene encoding a glutamic acid transporter is the *Salmonella typhimurium* dctA gene. In one embodiment, the at least one gene encoding a glutamic acid transporter is the *Caenorhabditis elegans* gltT gene.

In one embodiment, the gltT gene has at least about 80% identity with the sequence of SEQ ID NO:91. Accordingly, in one embodiment, the gltT gene has at least about 90% identity with the sequence of SEQ ID NO:91. Accordingly, in one embodiment, the gltT gene has at least about 95% identity with the sequence of SEQ ID NO:91. Accordingly, in one embodiment, the gltT gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:91. In another embodiment, the gltT gene comprises the sequence of SEQ ID NO:91. In yet another embodiment the gltT gene consists of the sequence of SEQ ID NO:91.

In some embodiments, the glutamic acid transporter is encoded by a glutamic acid transporter gene derived from a bacterial genus or species, including but not limited to, *Escherichia*, *Bacillus*, *Chlamydia*, *Mycobacterium*, *Salmonella*, *Escherichia coli*, *Mycobacterium tuberculosis*, *Salmonella typhimurium*, or *Caenorhabditis elegans* (see, e.g., Jan Slotboom et al. (1999) *Microbiol. Mol. Biol. Rev.* 63:293-307) In some embodiments, the bacterial species is

*Escherichia coli*. In some embodiments, the bacterial species is *Escherichia coli* strain Nissle.

Assays for testing the activity of a glutamic acid transporter, a functional variant of a glutamic acid transporter, or a functional fragment of transporter of glutamic acid are well known to one of ordinary skill in the art. For example, import of glutamic acid may be determined using the methods as described in Zaprasis et al. (2015) *App. Env. Microbiol.* 81:250-9, the entire contents of each of which are expressly incorporated by reference herein.

In one embodiment, when the glutamic acid transporter is expressed in the recombinant bacterial cells described herein, the bacterial cells import 10% more glutamic acid into the bacterial cell when the transporter is expressed than unmodified bacteria of the same bacterial subtype under the same conditions. In another embodiment, when the glutamic acid transporter is expressed in the recombinant bacterial cells described herein, the bacterial cells import 20%, 30%, 40%, 50%, 60%, 70%, 80%, 90% or 100% more glutamic acid into the bacterial cell when the transporter is expressed than unmodified bacteria of the same bacterial subtype under the same conditions. In yet another embodiment, when the glutamic acid transporter is expressed in the recombinant bacterial cells described herein, the bacterial cells import two-fold more glutamic acid into the cell when the transporter is expressed than unmodified bacteria of the same bacterial subtype under the same conditions. In yet another embodiment, when the glutamic acid transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more glutamic acid into the cell when the transporter is expressed than unmodified bacteria of the same bacterial subtype under the same conditions.

14. Histidine Transporters

In one embodiment, the amino acid transporter is a histidine transporter. Histidine transporters may be expressed or modified in the recombinant bacteria described herein in order to enhance histidine transport into the cell. Specifically, when the histidine transporter is expressed in the recombinant bacterial cells described herein, the bacterial cells import more histidine into the cell when the transporter is expressed than unmodified bacteria of the same bacterial subtype under the same conditions. Thus, the genetically engineered bacteria comprising a heterologous gene encoding a histidine transporter which may be used to import histidine into the bacteria.

The uptake of histidine into bacterial cells is mediated by proteins well known to those of skill in the art. For example, a histidine transport system is encoded by the hisJQMP operon and the artJ gene (see, e.g., Caldara et al. (2007) *J. Mol. Biol.* 373(2): 251-67). Transport by the histidine transport system is mediated by several proteins regulated by the ArgR-L-arginine DNA-binding transcriptional dual regulator. ArgR complexed with L-arginine represses the transcription of several genes involved in transport of histidine. In this system, HisJ (encoded by hisJ) is a histidine ABC transporter-periplasmic binding protein, HisQ and HisM (encoded by hisQ and hisM respectively) are the lysine/arginine/ornithine ABC transporter/histidine ABC transporter-membrane subunits, HisP (encoded by hisP) is a lysine/arginine/ornithine ABC transporter/histidine ABC transporter-ATP binding subunit. This system has been well characterized in *Escherichia coli*. In addition, bacterial systems that are homologous and orthologous to the *E. coli* histidine-specific system have been characterized in other bacterial species, including, for example, *Pseudomonas fluorescens* (see, e.g., Bender (2012) *Microbiol. Mol. Biol. Reviews* 76: 565-584). The membranous and membrane-associated proteins of the histidine permease (Q M P complex), encoded by the hisJQMP operon mediate the uptake of histidine (see, e.g., Oh et al. (1994) *J. Biol. Chem.* 269(42): 26323-30).

In one embodiment, the at least one gene encoding a histidine transporter comprises the hisJQMP operon. In one embodiment, the at least one gene encoding a histidine transporter comprises the hisJ gene. In one embodiment, the at least one gene encoding a histidine transporter comprises the hisQ gene. In one embodiment, the at least one gene encoding a histidine transporter comprises the hisM gene. In one embodiment, the at least one gene encoding a histidine transporter comprises the hisP gene.

In one embodiment, the hisJ gene has at least about 80% identity with the sequence of SEQ ID NO:94. Accordingly, in one embodiment, the hisJ gene has at least about 90% identity with the sequence of SEQ ID NO:94. Accordingly, in one embodiment, the hisJ gene has at least about 95% identity with the sequence of SEQ ID NO:94. Accordingly, in one embodiment, the hisJ gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:94. In another embodiment, the hisJ gene comprises the sequence of SEQ ID NO:94. In yet another embodiment, the hisJ gene consists of the sequence of SEQ ID NO:94.

In one embodiment, the hisQ gene has at least about 80% identity with the sequence of SEQ ID NO:95. Accordingly, in one embodiment, the hisQ gene has at least about 90% identity with the sequence of SEQ ID NO:95. Accordingly, in one embodiment, the hisQ gene has at least about 95% identity with the sequence of SEQ ID NO:95. Accordingly, in one embodiment, the hisQ gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:95. In another embodiment, the hisQ gene comprises the sequence of SEQ ID NO:95. In yet another embodiment, the hisQ gene consists of the sequence of SEQ ID NO:95.

In one embodiment, the hisM gene has at least about 80% identity with the sequence of SEQ ID NO:103. Accordingly, in one embodiment, the hisM gene has at least about 90% identity with the sequence of SEQ ID NO:103. Accordingly, in one embodiment, the hisM gene has at least about 95% identity with the sequence of SEQ ID NO:103. Accordingly, in one embodiment, the hisM gene nhas at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:103. In another embodiment, the hisM gene comprises the sequence of SEQ ID NO:103. In yet another embodiment, the hisM gene consists of the sequence of SEQ ID NO:103.

In one embodiment, the hisP gene has at least about 80% identity with the sequence of SEQ ID NO:96. Accordingly, in one embodiment, the hisP gene has at least about 90% identity with the sequence of SEQ ID NO:96. Accordingly, in one embodiment, the hisP gene has at least about 95% identity with the sequence of SEQ ID NO:96. Accordingly, in one embodiment, the hisP gene nhas at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:96. In another embodiment, the hisP gene comprises the sequence of SEQ ID NO:96. In yet another embodiment, the hisP gene consists of the sequence of SEQ ID NO:96.

In some embodiments, the histidine transporter is encoded by a histidine transporter gene derived from a bacterial genus or species, including but not limited to, *Escherichia* and *Pseudomonas* In some embodiments, the bacterial species is *Escherichia coli*. In some embodiments, the bacterial species is *Escherichia coli* strain Nissle.

Assays for testing the activity of a histidine transporter, a functional variant of a histidine transporter, or a functional fragment of a histidine transporter are well known to one of ordinary skill in the art. For example, import of histidine may be determined using the methods described in Liu et al. (1997) *J. Biol. Chem.* 272: 859-866 and Shang et al. (2013) *J. Bacteriology.* 195(23): 5334-5342, the entire contents of each of which are expressly incorporated by reference herein.

In one embodiment, when the histidine transporter is expressed in the recombinant bacterial cells described herein, the bacterial cells import 10% more histidine into the bacterial cell when the transporter is expressed than unmodified bacteria of the same bacterial subtype under the same conditions. In another embodiment, when the histidine transporter is expressed in the recombinant bacterial cells described herein, the bacterial cells import 20%, 30%, 40%, 50%, 60%, 70%, 80%, 90% or 100% more histidine into the bacterial cell when the transporter is expressed than unmodified bacteria of the same bacterial subtype under the same conditions. In yet another embodiment, when the histidine transporter is expressed in the recombinant bacterial cells described herein, the bacterial cells import two-fold more histidine into the cell when the transporter is expressed than unmodified bacteria of the same bacterial subtype under the same conditions. In yet another embodiment, when the histidine transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more histidine into the cell when the transporter is expressed than unmodified bacteria of the same bacterial subtype under the same conditions.

15. Proline Transporters

In one embodiment, the amino acid transporter is a proline transporter. Proline transporters may be expressed or modified in the recombinant bacteria described herein in order to enhance proline transport into the cell. Specifically, when the proline transporter is expressed in the recombinant bacterial cells described herein, the bacterial cells import more proline into the cell when the transporter is expressed than unmodified bacteria of the same bacterial subtype under the same conditions. Thus, the genetically engineered bacteria comprising a heterologous gene encoding a proline transporter which may be used to import proline into the bacteria.

The uptake of proline into bacterial cells is mediated by proteins well known to those of skill in the art. The proline utilization operon (put) allows bacterial cells to transport and use proline. The put operon consists of two genes putA and putP. In bacteria, there are two distinct systems for proline uptake, proline porter I (PPI) and proline porter II (PPII) (see, e.g., Grothe (1986) *J. Bacteriol.* 166: 253-259). The bacterial gene putP encodes a proline transporter responsible for proline uptake in many bacteria (see, e.g., Ostrovsky et al. (1993) *Proc. Natl. Acad. Sci.* 90: 429-8; Grothe (1986) *J. Bacteriol.* 166: 253-259). The putA gene expresses a polypeptide that has proline dehydrogenase (EC 1.5.99.8) activity and pyrroline-5-carboxylate (P5C) (EC 1.5.1.12) activity (see, e.g., Menzel and Roth (1981) *J. Biol. Chem.* 256:9755-61). In the absence of proline, putA remains in the cytoplasm and represses put gene expression. In the presence of proline, putA binds to the membrane relieving put repression allowing put gene expression (see, e.g., Ostrovsky et al. (1993) *Proc. Natl. Acad. Sci.* 90: 429-8).

In one embodiment, the at least one gene encoding a proline transporter is the putP gene. In one embodiment, the bacterial cell described herein has been genetically engineered to comprise at least one heterologous putP gene. In one embodiment, the at least one gene encoding a proline transporter is the *Escherichia coli* putP gene. In one embodiment, the at least one gene encoding a proline transporter is the *Salmonella typhimurium* putP gene. In one embodiment, the at least one gene encoding a proline transporter is the *Escherichia coli* putP gene.

In one embodiment, the putP gene has at least about 80% identity with the sequence of SEQ ID NO:98. Accordingly, in one embodiment, the putP gene has at least about 90% identity with the sequence of SEQ ID NO:98. Accordingly, in one embodiment, the putP gene has at least about 95% identity with the sequence of SEQ ID NO:98. Accordingly, in one embodiment, the putP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:98. In another embodiment, the putP gene comprises the sequence of SEQ ID NO:98. In yet another embodiment the putP gene consists of the sequence of SEQ ID NO:98.

In some embodiments, the proline transporter is encoded by a proline transporter gene derived from a bacterial genus or species, including but not limited to, *Escherichia, Salmonella, Escherichia coli* or *Salmonella typhimurium*. In some embodiments, the bacterial species is *Escherichia coli*. In some embodiments, the bacterial species is *Escherichia coli* strain Nissle.

Assays for testing the activity of a proline transporter, a functional variant of a proline transporter, or a functional fragment of a proline transporter are well known to one of ordinary skill in the art. For example, import of proline may be determined using the methods as described in Moses et al. (2012) *Journal of Bacteriology* 194: 745-58 and Hoffman et al. (2012) *App. and Enviro. Microbiol.* 78: 5753-62), the entire contents of each of which are expressly incorporated by reference herein.

In one embodiment, when the proline transporter is expressed in the recombinant bacterial cells described herein, the bacterial cells import 10% more proline into the bacterial cell when the transporter is expressed than unmodified bacteria of the same bacterial subtype under the same conditions. In another embodiment, when the proline transporter is expressed in the recombinant bacterial cells described herein, the bacterial cells import 20%, 30%, 40%, 50%, 60%, 70%, 80%, 90% or 100% more proline into the bacterial cell when the transporter is expressed than unmodified bacteria of the same bacterial subtype under the same conditions. In yet another embodiment, when the proline transporter is expressed in the recombinant bacterial cells described herein, the bacterial cells import two-fold more proline into the cell when the transporter is expressed than unmodified bacteria of the same bacterial subtype under the same conditions. In yet another embodiment, when the proline transporter is expressed in the recombinant bacterial cells described herein, the bacterial cells import three-fold, four-fold, five-fold, six-fold, seven-fold, eight-fold, nine-fold, ten-fold, fifteen-fold, twenty-fold, thirty-fold, forty-fold, or fifty-fold, more proline into the cell when the transporter is expressed than unmodified bacteria of the same bacterial subtype under the same conditions.

B. Nucleoside Transporters

In one embodiment, the recombinant bacterial cell of the invention comprises a heterologous gene encoding a substrate transporter, wherein the substrate transporter is a nucleoside transporter. In one embodiment, the nucleoside transporter is a purine nucleoside transporter. In one embodiment, the nucleoside transporter is a pyrimidine nucleoside transporter. In one embodiment, the nucleoside transporter transports at least one nucleoside selected from the group consisting of adenosine, guanosine, uridine, inosine, xanthosine, thymidine and cytidine, into the cell.

The uptake of nucleosides into bacterial cells is mediated by proteins well known to those of skill in the art. For example, many bacteria scavenge nucleosides from the environment for the synthesis of nucleotides and deoxynucleotides. In some bacterial species, e.g., *Escherichia coli*, nucleosides can be used as the sole source of nitrogen and carbon for growth (see, e.g., Neuhard and Nygaard "Biosynthesis and conversion of nucleotides, purines and pyrimidines," in: Neidhardt F C, Ingraham J L, Low K B, Magasanik B, Schaechter M, Umbarger H E, editors. *Escherichia coli* and *Salmonella typhimurium*: Cellular and Molecular Biology. Washington D.C.: ASM Press; 1987. pp. 445-473). Two evolutionarily unrelated cation-linked transporter families have been identified: the concentrative nucleoside transporter (CNT) family and the nucleoside:$H^+$ Symporter (NHS) family, both of which are responsible for nucleoside uptake (see, e.g., Cabrita et al. (2002) *Biochem. Cell Biol.* 80(5): 623-38, the contents of which is herein incorporated by reference in its entirety).

Passive transport of nucleosides across the outer membrane of some Gram-negative bacteria, e.g., *Salmonella enterica*, and into the periplasm can be mediated by the Tsx porin, encoded by the tsx gene (see, e.g., Bucarey et al. (20005) *Infect. Immun.* 73(10): 6210-9).

Active transport of nucleosides across the inner membrance is mediated by the nucleoside permeases NupC and NupG, encoded by the nupC and nupG genes, respectively. NupG can facilitate the uptake of all tested purine and pyrimidine nucleosides while NupC has specificity towards the pyrimidine nucleosides and their deoxyderivatives. Both permeases are powered by proton motive force. *E. coli* mutants defective in both the nupC and nupG genes cannot grow with nucleosides as their single carbon source. Both permeases are proton-linked but they differ in their selectivity. NupG is capable of transporting a wide range of nucleosides and deoxynucleosides; in contrast, NupC does not transport guanosine or deoxyguanosine. Homologs of NupG from *E. coli* are found in a wide range of bacteria, including human gut pathogens such as *Salmonella typhimurium*, organisms associated with periodontal disease such as *Porphyromonas gingivalis* and *Prevotella intermedia*, and plant pathogens of the genus *Erwinia* (see, e.g., Vaziri et al. (2013) *Mol. Membr. Biol.* 30(1-2): 114-128, the contents of which is herein incorporated by reference in its entirety).

An additional nucleoside transporter, the xanthosine permease, XapB, having 58% identity to NupG was identified in *Escherichia coli* Norholm and Dandanell (2001) *J. Bacteriol.* 183(16): 4900-4. XapB exhibits similar specificity to NupG, since it appears to be able to transport all nucleosides except guanosine. Putative bacterial transporters from the CNT superfamily and transporters from the NupG/XapB family include those listed in the tables 2 and 3 below. In addition, codB (GenBank P25525, *Escherichia coli*) was identified based on homology to a yeast transporter family termed the uracil/allantoin transporter family (Cabrita et al. (2002)).

TABLE 2

Putative CNT family transporters

| Name | GenBank Accession No. | Organism |
|---|---|---|
| BH1446 | BAB05165 | *Bacillus halodurans* |
| BsNupC | CAA57663 | *Bacillus subtilis* |
| BsyutK | CAB15208 | *B. subtilis* |
| BsyxjA | CAB15938 | *B. subtilis* |
| CcCNT (CC2089) | AAK24060 | *Caulobacter crescentus* |
| yeiJ | AAC75222 | *E. coli* |
| yeiM | AAC75225 | *E. coli* |
| HI0519 | AAC22177 | *Haemophilus influenzae* |
| HP1180 (NupC) | AAD08224 | *Helicobacter pylori* |
| SA0600 (NupC) | BAB41833 | *Staphylococcus aureus* |
| SAV0645 (NupC) | BAB56807 | *S. aureus* |
| SpNupC | AAK34582 | *Streptococcus pyogenes* |
| VC2352 (NupC) | AAF95495 | *Vibrio cholerae* |
| VC1953 (NupC) | AAF95101 | *V. cholera* |
| VCA0179 | AAF96092 | *V. cholera* |

TABLE 3

Bacterial transporters from the NupG/XapB family

| Protein (gene name) | GenBank Accession No. | Organism |
|---|---|---|
| yegT | P76417 | *Escherichia coli* |
| NupG | P09452 | *E. coli* |
| XapB | P45562 | *E. coli* |
| CC1628 | AAK23606 | *Caulobacter crescentus* |

In one embodiment, the nucleoside transporter is a nucleoside permease (e.g., NupC or NupG). In one embodiment, the nucleoside transporter is a adenosine permease. In one embodiment, the nucleoside transporter is a guanosine permease. In one embodiment, the nucleoside transporter is a uridine permease. In one embodiment, the nucleoside transporter is a inosine permease. In one embodiment, the nucleoside transporter is a xanthosine permease. In one embodiment, the nucleoside transporter is a thymidine permease. In one embodiment, the nucleoside transporter is a cytidine permease.

In one embodiment, the nucleoside transporter is a nucleoside porin (e.g., Tsx). In one embodiment, the nucleoside transporter is a sodium-dependent nucleoside transporter. In one embodiment, the nucleoside transporter is a xanthosine transporter (e.g., XapB).

Nucleoside transporters may be expressed or modified in the bacteria in order to enhance nucleoside transport into the cell. Specifically, when the nucleoside transporter is expressed in the recombinant bacterial cells, the bacterial cells import more nucleoside(s) into the cell when the transporter is expressed than unmodified bacteria of the same bacterial subtype under the same conditions. In one embodiment, the bacterial cell comprises a heterologous gene encoding a nucleoside transporter. In one embodiment, the bacterial cell comprises a heterologous gene encoding a nucleoside transporter and a genetic modification that reduces export of a nucleoside, e.g., a genetic mutation in an exporter gene or promoter.

In one embodiment, the bacterial cell comprises at least one gene encoding a nucleoside transporter from a different organism, e.g., a different species of bacteria. In one embodiment, the bacterial cell comprises at least one native gene encoding a nucleoside transporter. In some embodiments, the at least one native gene encoding a nucleoside transporter is not modified. In another embodiment, the bacterial cell comprises more than one copy of at least one native gene encoding a nucleoside transporter. In yet another embodiment, the bacterial cell comprises a copy of at least one gene encoding a native nucleoside transporter, as well as at least one copy of at least one heterologous gene encoding annucleoside transporter from a different bacterial species. In one embodiment, the bacterial cell comprises at least one, two, three, four, five, or six copies of the at least one heterologous gene encoding a nucleoside transporter. In one embodiment, the bacterial cell comprises multiple copies of the at least one heterologous gene encoding a nucleoside transporter.

In one embodiment, the recombinant bacterial cell comprises a heterologous gene encoding a nucleoside transporter, wherein said nucleoside transporter comprises a nucleoside sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the nucleoside sequence of a polypeptide encoded by a nucleoside transporter gene disclosed herein.

In some embodiments, the nucleoside transporter is encoded by a nucleoside transporter gene derived from a bacterial genus or species, including but not limited to, *Bacillus halodurans, Bacillus subtilis, Caulobacter crescentus, Escherichia coli, Haemoophilus influenzae, Helicobacter pylori, Pseudomonas, Bacillus subtilis, Escherichia coli, Prevotella intermedia, Porphytomonas gingivalis, Salmonella typhimurium, Salmonella enterica,* or *Vibrio cholera*. In some embodiments, the bacterial species is *Escherichia coli*. In some embodiments, the bacterial species is *Escherichia coli* strain Nissle.

The present disclosure further comprises genes encoding functional fragments of a nucleoside transporter or functional variants of a nucleoside transporter. As used herein, the term "functional fragment thereof" or "functional variant thereof" of a nucleoside transporter relates to an element having qualitative biological activity in common with the wild-type nucleoside transporter from which the fragment or variant was derived. For example, a functional fragment or a functional variant of a mutated nucleoside transporter is one which retains essentially the same ability to import a nucleoside into the bacterial cell as does the nucleoside transporter protein from which the functional fragment or functional variant was derived. In one embodiment, the recombinant bacterial cell comprises at least one heterologous gene encoding a functional fragment of a nucleoside transporter. In another embodiment, the recombinant bacterial cell comprises a heterologous gene encoding a functional variant of a nucleoside transporter.

Assays for testing the activity of a nucleoside transporter, a functional variant of a nucleoside transporter, or a functional fragment of a nucleoside transporter are well known to one of ordinary skill in the art. For example, import of a nucleoside may be determined using, e.g., a $^{14}$C-labeled nucleoside uptake assay as described in Norholm and Dandanell (2001) *J. Bacteriol.* 183(16): 4900-4, the entire contents of each of which are expressly incorporated by reference herein.

In one embodiment, the genes encoding the nucleoside transporter have been codon-optimized for use in the host organism, e.g., a bacterial cell disclosed herein. In one embodiment, the genes encoding the nucleoside transporter have been codon-optimized for use in *Escherichia coli*.

The present disclosure also encompasses genes encoding a nucleoside transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a nucleoside transporter is mutagenized; mutants exhibiting increased nucleoside import are selected; and the mutagenized at least one gene encoding a nucleoside transporter is isolated and inserted into the bacterial cell. In some embodiments, the at least one gene encoding a nucleoside transporter is mutagenized; mutants exhibiting decreased nucleoside import are selected; and the mutagenized at least one gene encoding a nucleoside transporter is isolated and inserted into the bacterial cell. The transporter modifications described herein may be present on a plasmid or chromosome.

In some embodiments, the bacterial cell comprises a heterologous gene encoding a nucleoside transporter operably linked to a promoter. In one embodiment, the at least one gene encoding a nucleoside transporter is directly operably linked to the promoter. In another embodiment, the at least one gene encoding a nucleoside transporter is indirectly operably linked to the promoter.

In one embodiment, the promoter is not operably linked with the at least one gene encoding a nucleoside transporter in nature. In some embodiments, the at least one gene encoding the nucleoside transporter is controlled by its native promoter. In some embodiments, the at least one gene encoding the nucleoside transporter is controlled by an inducible promoter. In some embodiments, the at least one gene encoding the nucleoside transporter is controlled by a promoter that is stronger than its native promoter. In some embodiments, the at least one gene encoding the nucleoside transporter is controlled by a constitutive promoter.

In another embodiment, the promoter is an inducible promoter. Inducible promoters are described in more detail infra.

In one embodiment, the at least one gene encoding a nucleoside transporter is located on a plasmid in the bacterial cell. In some embodiments, the plasmid is a high copy number plasmid. In some embodiments, the plasmid is a low copy number plasmid. In another embodiment, the at least one gene encoding a nucleoside transporter is located in the chromosome of the bacterial cell. In yet another embodiment, a native copy of the at least one gene encoding a nucleoside transporter is located in the chromosome of the bacterial cell, and a copy of at least one gene encoding a nucleoside transporter from a different species of bacteria is located on a plasmid in the bacterial cell. In yet another embodiment, a native copy of the at least one gene encoding a nucleoside transporter is located on a plasmid in the bacterial cell, and a copy of at least one gene encoding a nucleoside transporter from a different species of bacteria is located on a plasmid in the bacterial cell. In yet another embodiment, a native copy of the at least one gene encoding a nucleoside transporter is located in the chromosome of the bacterial cell, and a copy of the at least one gene encoding a nucleoside transporter from a different species of bacteria is located in the chromosome of the bacterial cell.

In some embodiments, the at least one native gene encoding the nucleoside transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the nucleoside transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the nucleoside transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the nucleoside transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In one embodiment, the nucleoside transporter is encoded by a tsx gene, e.g., a tsx gene disclosed herein. In one embodiment, the tsx gene has at least about 80% identity with the sequence of SEQ ID NO:107. Accordingly, in one embodiment, the tsx gene has at least about 90% identity with the sequence of SEQ ID NO:107. Accordingly, in one embodiment, the tsx gene has at least about 95% identity with the sequence of SEQ ID NO:107. Accordingly, in one embodiment, the tsx gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:107. In another embodiment, the tsx gene comprises the sequence of SEQ ID NO:107. In yet another embodiment the tsx gene consists of the sequence of SEQ ID NO:107.

In one embodiment, the tsx gene has at least about 80% identity with the sequence of SEQ ID NO:108. Accordingly, in one embodiment, the tsx gene has at least about 90% identity with the sequence of SEQ ID NO:108. Accordingly, in one embodiment, the tsx gene has at least about 95% identity with the sequence of SEQ ID NO:108. Accordingly, in one embodiment, the tsx gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:108. In another embodiment, the tsx gene comprises the sequence of SEQ ID NO:108. In yet another embodiment the tsx gene consists of the sequence of SEQ ID NO:108.

In one embodiment, the nucleoside transporter is encoded by a BH1446 gene, e.g., a BH1446 gene disclosed herein. In one embodiment, the BH1446 gene has at least about 80% identity with the sequence of SEQ ID NO:109. Accordingly, in one embodiment, the BH1446 gene has at least about 90% identity with the sequence of SEQ ID NO:109. Accordingly, in one embodiment, the BH1446 gene has at least about 95% identity with the sequence of SEQ ID NO:109. Accordingly, in one embodiment, the BH1446 gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:109. In another embodiment, the BH1446 gene comprises the sequence of SEQ ID NO:109. In yet another embodiment the BH1446 gene consists of the sequence of SEQ ID NO:109.

In one embodiment, the nucleoside transporter is encoded by a nupC gene, e.g., a nupC gene disclosed herein. In one embodiment, the nupC gene is a nupC gene from *Bacillus subtilis*. In one embodiment, the nupC gene has at least about 80% identity with the sequence of SEQ ID NO:110. Accordingly, in one embodiment, the nupC gene has at least about 90% identity with the sequence of SEQ ID NO:110. Accordingly, in one embodiment, the nupC gene has at least about 95% identity with the sequence of SEQ ID NO:110. Accordingly, in one embodiment, the nupC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:110. In another embodiment, the nupC gene comprises the sequence of SEQ ID NO:110. In yet another embodiment the nupC gene consists of the sequence of SEQ ID NO:110.

In one embodiment, the nupC gene is a nupC gene from *Helicobacter pylori*. In one embodiment, the nupC gene has at least about 80% identity with the sequence of SEQ ID NO:117. Accordingly, in one embodiment, the nupC gene has at least about 90% identity with the sequence of SEQ ID NO:117. Accordingly, in one embodiment, the nupC gene has at least about 95% identity with the sequence of SEQ ID NO:117. Accordingly, in one embodiment, the nupC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:117. In another embodiment, the nupC gene comprises the sequence of SEQ ID NO:117. In yet another embodiment the nupC gene consists of the sequence of SEQ ID NO:117.

In one embodiment, the nupC (also referred to herein as SA0600) gene is a nupC gene from *Staphylococcus aureus*. In one embodiment, the nupC gene has at least about 80% identity with the sequence of SEQ ID NO:118. Accordingly, in one embodiment, the nupC gene has at least about 90% identity with the sequence of SEQ ID NO:118. Accordingly, in one embodiment, the nupC gene has at least about 95% identity with the sequence of SEQ ID NO:118. Accordingly, in one embodiment, the nupC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:118. In another embodiment, the nupC gene comprises the sequence of SEQ ID NO:118. In yet another embodiment the nupC gene consists of the sequence of SEQ ID NO:118.

In one embodiment, the nupC (also referred to herein as SAV0645) gene is a nupC gene from *Staphylococcus aureus*. In one embodiment, the nupC gene has at least about 80% identity with the sequence of SEQ ID NO:119. Accordingly, in one embodiment, the nupC gene has at least about 90% identity with the sequence of SEQ ID NO:119. Accordingly, in one embodiment, the nupC gene has at least about 95% identity with the sequence of SEQ ID NO:119. Accordingly, in one embodiment, the nupC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:119. In another embodiment, the nupC gene comprises the sequence of SEQ ID NO:119. In yet another embodiment the nupC gene consists of the sequence of SEQ ID NO:119.

In one embodiment, the nupC (also referred to herein as spNupC) gene is a nupC gene from *Streptococcus pyogenes*. In one embodiment, the nupC gene has at least about 80% identity with the sequence of SEQ ID NO:120. Accordingly, in one embodiment, the nupC gene has at least about 90% identity with the sequence of SEQ ID NO:120. Accordingly, in one embodiment, the nupC gene has at least about 95% identity with the sequence of SEQ ID NO:120. Accordingly, in one embodiment, the nupC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:120. In another embodiment, the nupC gene comprises the sequence of SEQ ID NO:120. In yet another embodiment the nupC gene consists of the sequence of SEQ ID NO:120.

In one embodiment, the nupC (also referred to herein as VC2352) gene is a nupC gene from *Vibrio cholerae*. In one embodiment, the nupC gene has at least about 80% identity with the sequence of SEQ ID NO:121. Accordingly, in one embodiment, the nupC gene has at least about 90% identity with the sequence of SEQ ID NO:121. Accordingly, in one embodiment, the nupC gene has at least about 95% identity with the sequence of SEQ ID NO:121. Accordingly, in one embodiment, the nupC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:121. In another embodiment, the nupC gene comprises the sequence of SEQ ID NO:121. In yet another embodiment the nupC gene consists of the sequence of SEQ ID NO:121.

In one embodiment, the nupC (also referred to herein as VC1953) gene is a nupC gene from *Vibrio cholerae*. In one embodiment, the nupC gene has at least about 80% identity with the sequence of SEQ ID NO:122. Accordingly, in one embodiment, the nupC gene has at least about 90% identity with the sequence of SEQ ID NO:122. Accordingly, in one embodiment, the nupC gene has at least about 95% identity with the sequence of SEQ ID NO:122. Accordingly, in one embodiment, the nupC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:122. In another embodiment, the nupC gene comprises the sequence of SEQ ID NO:122. In yet another embodiment the nupC gene consists of the sequence of SEQ ID NO:122.

In one embodiment, the nupC (also referred to herein as VCA0179) gene is a nupC gene from *Vibrio cholerae*. In one embodiment, the nupC gene has at least about 80% identity with the sequence of SEQ ID NO:123. Accordingly, in one embodiment, the nupC gene has at least about 90% identity with the sequence of SEQ ID NO:123. Accordingly, in one embodiment, the nupC gene has at least about 95% identity with the sequence of SEQ ID NO:123. Accordingly, in one embodiment, the nupC gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:123. In another embodiment, the nupC gene comprises the sequence of SEQ ID NO:123. In yet another embodiment the nupC gene consists of the sequence of SEQ ID NO:123.

In one embodiment, the nucleoside transporter is encoded by a yutK gene, e.g., a yutK gene disclosed herein. In one embodiment, the yutK gene is a yutK gene from *Bacillus subtilis*. In one embodiment, the yutK gene has at least about 80% identity with the sequence of SEQ ID NO:111. Accordingly, in one embodiment, the yutK gene has at least about 90% identity with the sequence of SEQ ID NO:111. Accordingly, in one embodiment, the yutK gene has at least about 95% identity with the sequence of SEQ ID NO:111. Accordingly, in one embodiment, the yutK gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:111. In another embodiment, the yutK gene comprises the sequence of SEQ ID NO:111. In yet another embodiment the yutK gene consists of the sequence of SEQ ID NO:111.

In one embodiment, the nucleoside transporter is encoded by a yxjA gene, e.g., a yxjA gene disclosed herein. In one embodiment, the yxjA gene is a yxjA gene from *Bacillus subtilis*. In one embodiment, the yxjA gene has at least about 80% identity with the sequence of SEQ ID NO:112. Accordingly, in one embodiment, the yxjA gene has at least about 90% identity with the sequence of SEQ ID NO:112. Accordingly, in one embodiment, the yxjA gene has at least about 95% identity with the sequence of SEQ ID NO:112. Accordingly, in one embodiment, the yxjA gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:112. In another embodiment, the yxjA gene comprises the sequence of SEQ ID NO:112. In yet another embodiment the yxjA gene consists of the sequence of SEQ ID NO:112.

In one embodiment, the nucleoside transporter is encoded by a sodium-dependent nucleoside transporter gene, e.g., a sodium-dependent nucleoside transporter gene disclosed herein. In one embodiment, the sodium-dependent nucleoside transporter gene is a CC2089 (also referred to herein as CcCNT) gene. In one embodiment, the sodium-dependent nucleoside transporter gene is a CC2089 gene from *Caulobacter crescentus*. In one embodiment, the sodium-dependent nucleoside transporter gene has at least about 80% identity with the sequence of SEQ ID NO:113. Accordingly, in one embodiment, the sodium-dependent nucleoside transporter gene has at least about 90% identity with the sequence of SEQ ID NO:113. Accordingly, in one embodiment, the sodium-dependent nucleoside transporter gene has at least about 95% identity with the sequence of SEQ ID NO:113. Accordingly, in one embodiment, the sodium-dependent nucleoside transporter gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:113. In another embodiment, the sodium-dependent nucleoside transporter gene comprises the sequence of SEQ ID NO:113. In yet another embodiment the sodium-dependent nucleoside transporter gene consists of the sequence of SEQ ID NO:113.

In one embodiment, the nucleoside transporter is encoded by a yeiJ gene, e.g., a yeiJ gene disclosed herein. In one embodiment, the yeiJ gene is a yeiJ gene from *Escherichia coli*. In one embodiment, the yeiJ gene has at least about 80% identity with the sequence of SEQ ID NO:114. Accordingly, in one embodiment, the yeiJ gene has at least about 90% identity with the sequence of SEQ ID NO:114. Accordingly, in one embodiment, the yeiJ gene has at least about 95% identity with the sequence of SEQ ID NO:114. Accordingly, in one embodiment, the yeiJ gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:114. In another embodiment, the yeiJ gene comprises the sequence of SEQ ID NO:114. In yet another embodiment the yeiJ gene consists of the sequence of SEQ ID NO:114.

In one embodiment, the nucleoside transporter is encoded by a yeiM gene, e.g., a yeiM gene disclosed herein. In one embodiment, the yeiM gene is a yeiM gene from *Escherichia coli*. In one embodiment, the yeiM gene has at least about 80% identity with the sequence of SEQ ID NO:115.

Accordingly, in one embodiment, the yeiM gene has at least about 90% identity with the sequence of SEQ ID NO:115. Accordingly, in one embodiment, the yeiM gene has at least about 95% identity with the sequence of SEQ ID NO:115. Accordingly, in one embodiment, the yeiM gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:115. In another embodiment, the yeiM gene comprises the sequence of SEQ ID NO:115. In yet another embodiment the yeiM gene consists of the sequence of SEQ ID NO:115.

In one embodiment, the nucleoside transporter is encoded by a HI0519 gene, e.g., a HI0519 gene disclosed herein. In one embodiment, the HI0519 gene is a HI0519 gene from *Haemophilus influenzae*. In one embodiment, the HI0519 gene has at least about 80% identity with the sequence of SEQ ID NO:116. Accordingly, in one embodiment, the HI0519 gene has at least about 90% identity with the sequence of SEQ ID NO:116. Accordingly, in one embodiment, the HI0519 gene has at least about 95% identity with the sequence of SEQ ID NO:116. Accordingly, in one embodiment, the HI0519 gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:116. In another embodiment, the HI0519 gene comprises the sequence of SEQ ID NO:116. In yet another embodiment the HI0519 gene consists of the sequence of SEQ ID NO:116.

In one embodiment, the nucleoside transporter is encoded by a yegT gene, e.g., a yegT gene disclosed herein. In one embodiment, the yegT gene is a yegT gene from *Escherichia coli*. In one embodiment, the yegT gene has at least about 80% identity with the sequence of SEQ ID NO:124. Accordingly, in one embodiment, the yegT gene has at least about 90% identity with the sequence of SEQ ID NO:124. Accordingly, in one embodiment, the yegT gene has at least about 95% identity with the sequence of SEQ ID NO:124. Accordingly, in one embodiment, the yegT gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:124. In another embodiment, the yegT gene comprises the sequence of SEQ ID NO:124. In yet another embodiment the yegT gene consists of the sequence of SEQ ID NO:124.

In one embodiment, the nucleoside transporter is encoded by a nupG gene, e.g., a nupG gene disclosed herein. In one embodiment, the nupG gene is a nupG gene from *Escherichia coli*. In one embodiment, the nupG gene has at least about 80% identity with the sequence of SEQ ID NO:125. Accordingly, in one embodiment, the nupG gene has at least about 90% identity with the sequence of SEQ ID NO:125. Accordingly, in one embodiment, the nupG gene has at least about 95% identity with the sequence of SEQ ID NO:125. Accordingly, in one embodiment, the nupG gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:125. In another embodiment, the nupG gene comprises the sequence of SEQ ID NO:125. In yet another embodiment the nupG gene consists of the sequence of SEQ ID NO:125.

In one embodiment, the nucleoside transporter is encoded by a xapB gene, e.g., a xapB gene disclosed herein. In one embodiment, the xapB gene is a xapB gene from *Escherichia coli*. In one embodiment, the xapB gene has at least about 80% identity with the sequence of SEQ ID NO:126. Accordingly, in one embodiment, the xapB gene has at least about 90% identity with the sequence of SEQ ID NO:126. Accordingly, in one embodiment, the xapB gene has at least about 95% identity with the sequence of SEQ ID NO:126. Accordingly, in one embodiment, the xapB gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:126. In another embodiment, the xapB gene comprises the sequence of SEQ ID NO:126. In yet another embodiment the xapB gene consists of the sequence of SEQ ID NO:126.

In one embodiment, the nucleoside transporter is encoded by a CC1628 gene, e.g., a CC1628 gene disclosed herein. In one embodiment, the CC1628 gene is a CC1628 gene from *Caulobacter crescentus*. In one embodiment, the CC1628 gene has at least about 80% identity with the sequence of SEQ ID NO:127. Accordingly, in one embodiment, the CC1628 gene has at least about 90% identity with the sequence of SEQ ID NO:127. Accordingly, in one embodiment, the CC1628 gene has at least about 95% identity with the sequence of SEQ ID NO:127. Accordingly, in one embodiment, the CC1628 gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:127. In another embodiment, the CC1628 gene comprises the sequence of SEQ ID NO:127. In yet another embodiment the CC1628 gene consists of the sequence of SEQ ID NO:127.

In one embodiment, the nucleoside transporter is a cytosine permease, e.g., CodB. In one embodiment, the nucleoside transporter is encoded by a codB gene, e.g., a codB gene disclosed herein. In one embodiment, the codB gene is a codB gene from *Escherichia coli*. In one embodiment, the codB gene has at least about 80% identity with the sequence of SEQ ID NO:128. Accordingly, in one embodiment, the codB gene has at least about 90% identity with the sequence of SEQ ID NO:128. Accordingly, in one embodiment, the codB gene has at least about 95% identity with the sequence of SEQ ID NO:128. Accordingly, in one embodiment, the codB gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:128. In another embodiment, the codB gene comprises the sequence of SEQ ID NO:128. In yet another embodiment the codB gene consists of the sequence of SEQ ID NO:128.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the nucleoside transporter is expressed in the recombinant bacterial cells, the bacterial cells import 10% more nucleosides into the bacterial cell when the transporter is expressed than unmodified bacteria of the same bacterial subtype under the same conditions. In another embodiment, when the nucleoside transporter is expressed in the recombinant bacterial cells, the bacterial cells import 20%, 30%, 40%, 50%, 60%, 70%, 80%, 90% or 100% more nucleosides, into the bacterial cell when the transporter is expressed than unmodified bacteria of the same bacterial subtype under the same conditions. In yet another embodiment, when the nucleoside transporter is expressed in the recombinant bacterial cells, the bacterial cells import two-fold more nucleosides into the cell when the transporter is expressed than unmodified bacteria of the same bacterial subtype under the same conditions. In yet another embodiment, when the nucleoside transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more nucleoside into the cell when the transporter is expressed than unmodified bacteria of the same bacterial subtype under the same conditions.

In one embodiment, the recombinant bacterial cells described herein comprise a first heterologous nucleoside transporter and a second heterologous nucleoside transporter. For, example, in one embodiment, the recombinant bacterial cell comprises at least one outer membrane nucleoside transporter, e.g., tsx, and at least one inner membrane nucleoside transporter, e.g., nupC and/or nupG. In one embodiment, said first nucleoside transporter is derived from a different organism than said second nucleoside transporter. In some embodiments, said first nucleoside transporter is derived from the same organism as said second nucleoside transporter. In some embodiments, said first nucleoside transporter imports the same nucleoside as said second nucleoside transporter. In other embodiment, said first nucleoside transporter imports a different nucleoside from said second nucleoside transporter. In some embodiments, said first nucleoside transporter is a wild-type nucleoside transporter and said second nucleoside transporter is a mutagenized version of said first nucleoside transporter. In some embodiments, the recombinant bacterial cells described herein comprise at least a third heterologous nucleoside transporter. In some embodiments, the recombinant bacterial cells described herein comprise at least four heterologous nucleoside transporters. In some embodiments, the recombinant bacterial cells described herein comprise at least five heterologous nucleoside transporters or more.

In one embodiment, the nucleoside transporter imports one nucleoside into the bacterial cell. In another embodiment, the nucleoside transporter imports two nucleosides into the bacterial cell. In yet another embodiment, the nucleoside transporter imports three nucleosides into the bacterial cell. In another embodiment, the nucleoside transporter imports four or more nucleosides into the cell. In one embodiment, the nucleoside transporter is an outer membrane nucleoside transporter. In one embodiment, the nucleoside transporter is an inner membrane nucleoside transporter. In one embodiment, the nucleoside transporter is an adenosine transporter. In another embodiment, the nucleoside transporter is an guanosine transporter. In another embodiment, the nucleoside transporter is an uridine transporter. In another embodiment, the amino acid transporter is a inosine transporter. In another embodiment, the amino acid transporter is a xanthosine transporter. In another embodiment, the amino acid transporter is a thymidine transporter. In one embodiment, the nucleoside transporter is an cytidine transporter.

In some embodiment, the recombinant bacterial cell comprising a heterologous gene encoding a nucleoside transporter, e.g., an adenosine transporter, may be used to treat a disease, condition, and/or symptom associated with cancer, e.g., a cancer described herein. In some embodiments, the recombinant bacterial cells described herein may be used to reduce, ameliorate, or eliminate one or more symptom(s) associated with a cancer.

For example, an important barrier to successful cancer immunotherapy is that tumors employ a number of mechanisms to facilitate immune escape, including the production of anti-inflammatory cytokines, the recruitment of regulatory immune subsets, and the production of immunosuppressive metabolites. One such immunosuppressive pathway is the production of extracellular adenosine, a potent immunosuppressive molecule, by CD73. The purinergic system regulates and refines immune cell functions, such as cell-to-cell interactions, cytokine and chemokine secretion, surface antigen shedding, intracellular pathogen removal, and generating reactive oxygen species. Extracellular ATP, released by damaged or dying cells and bacteria, promotes the recruitment of immune phagocytes and activates P2X7R, a coactivator of the NLRP3 inflammasome, which then triggers the production of proinflammatory cytokines, such as IL-1β and IL-18. The catabolism of extracellular ATP into ADP, AMP and adenosine is controlled by glycosylphosphatidylinositol (GPI-) anchored ectonucleotidases and membrane-bound kinases. CD39 (ecto-nucleoside triphosphate diphosphohydrolase 1, E-NTPDase1) hydrolyzes ATP into AMP, which is then dephosphorylated into adenosine by CD73 (ecto-5'-nucleotidase, Ecto5'NTase). Thus, CD39 and CD73 act in concert to convert proinflammatory ATP into immunosuppressive adenosine. Notably, the activity of CD39 is reversible by the actions of NDP kinase and adenylate kinase, whereas the activity of CD73 is virtually irreversible. Thus, CD73 represents a crucial checkpoint in the conversion of an ATP-driven proinflammatory environment to an anti-inflammatory milieu induced by adenosine. Stated another way, CD73 negatively regulates the proinflammatory effects of extracellular adenosine triphosphate (ATP).

In the tumor setting, CD39 and CD73 generate increased adenosine levels characteristic of the tumor microenvironment. High expression and activity of CD39 and CD73 has been observed in several blood or solid tumors. In addition, CD39- and CD73-expressing cancer exosomes can also raise adenosine levels within the tumor microenvironment. The CD39/CD73 complex participates in the process of tumor immunoescape, by inhibiting the activation, clonal expansion, and homing of tumor-specific T cells (in particular, T helper and cytotoxic T cells), impairing tumor cell killing by cytolytic effector T lymphocytes, and inducing the suppressive capabilities of Treg and Th17 cells, and enhancing the conversion of type 1 macrophages into tumor-promoting type 2 macrophages (reviewed in Antonioli et al., Trends Mol Med. 2013 June; 19(6): 355-367. CD39 and CD73 in immunity and inflammation). Myeloid-derived suppressor cells (MDSCs), also appear to promote tumor growth by a CD39-mediated mechanism.

Beside its immunoregulatory roles, the ectonucleotidase pathway contributes directly to the modulation of cancer cell growth, differentiation, invasion, migration, metastasis, and tumor angiogenesis. Agents targeting these enzymes show anti-tumor efficacy and a favorable tolerability profile in several murine models of malignancy (Anonioli et al., 2013). In some embodiments, the genetically engineered bacteria comprise a means for removing excess adenosine from the tumor microenvironment. Many bacteria scavenge low concentrations of nucleosides from the environment for synthesis of nucleotides and deoxynucleotides by salvage pathways of synthesis. Additionally, in *Escherichia coli*, nucleosides can be used as the sole source of nitrogen and carbon for growth (Neuhard J, Nygaard P. Biosynthesis and conversion of nucleotides, purines and pyrimidines. In: Neidhardt F C, Ingraham J L, Low K B, Magasanik B, Schaechter M, Umbarger H E, editors. *Escherichia coli* and *Salmonella typhimurium*: Cellular and molecular biology. Washington D.C.: ASM Press; 1987. pp. 445-473). Two evolutionarily unrelated cation-linked transporter families, the Concentrative Nucleoside Transporter (CNT) family and the Nucleoside:H+ Symporter (NHS) family, are responsible for nucleoside uptake (see e.g., Cabrita et al., Biochem. Cell Biol. Vol. 80, 2002. Molecular biology and regulation of nucleoside and nucleobase transporter proteins in eukaryotes and prokaryotes), the contents of which is herein incorporated by reference in its entirety. NupC and NupG, are the transporter family members in *E. coli*. Mutants defective in both the nupC and nupG genes cannot grow with nucleosides as a single carbon source. Both of these transporters are proton-linked but they differ in their selectivity. NupG is capable of transporting a wide range of nucleosides and deoxynucleosides; in contrast, NupC does not transport guanosine or deoxyguanosine. Homologs of NupG from *E. coli* are found in a wide range of eubacteria, including human gut pathogens such as *Salmonella typhimurium*, organisms associated with periodontal disease such as *Porphyromonas gingivalis* and *Prevotella intermedia*, and plant pathogens in the genus *Erwinia* (As described in Vaziri et al., Mol Membr Biol. 2013 March; 30(1-2): 114-128. Use of molecular modelling to probe the mechanism of the nucleoside transporter NupG, the contents of which is herein incorporated by reference in its entirety). Putative bacterial transporters from the CNT superfamily and transporters from the NupG/XapB family include those listed herein. In addition, codB (GenBank P25525, *Escherichia coli*) was identified based on homology to a yeast transporter family termed the uracil/allantoin transportor family (Cabrita et al., supra).

Figure 34:
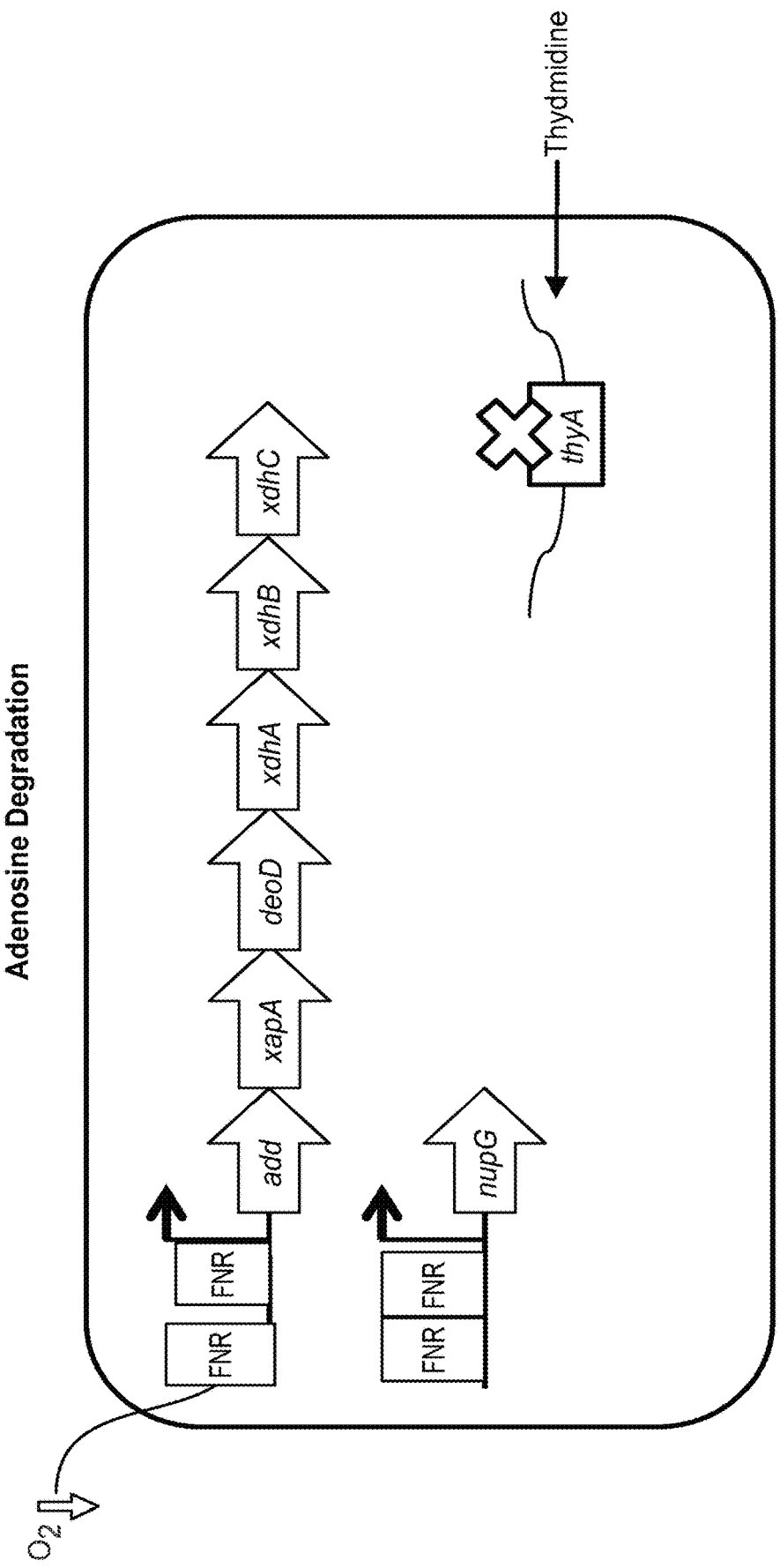
FIG. 34 is schematic depicting an exemplary Adenosine Degradation Circuit. Adenosine is imported into the cell through expression of the *E. coli* Nucleoside Permease nupG transporter. Adenosine is converted to Inosine through expression of Adenine Deaminase add. Inosine is converted to hypoxyxanthine through expression of Inosine Phosphorylase, xapA, and deoD. Hypoxanthine is converted to Xanthine and Urate through expression of Hypoxanthine Hydroxylase, xdhA, xdhB, xdhC. All of these genes are optionally expressed from an inducible promoter, e.g., a FNR-inducible promoter. The bacteria may also include an auxotrophy, e.g., deletion of thyA (ΔthyA; thymindine dependence). Non-limiting example of a bacterial strain is listed.
Figure 35:
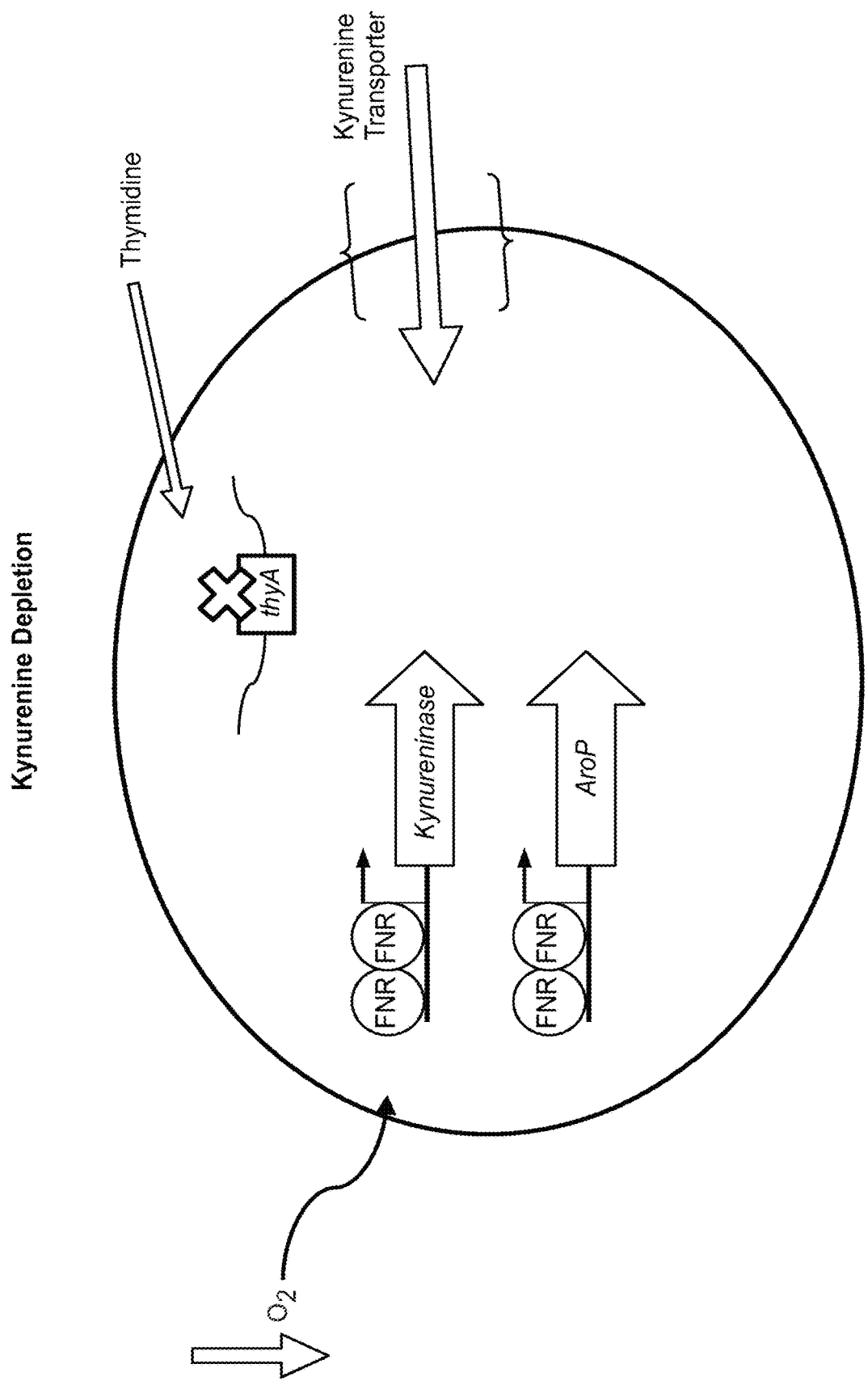
FIG. 35. is a schematic depicting an exemplary circuit for depleting kynurenine.

Thus, the genetically engineered bacteria comprise a means for metabolizing or degrading adenosine. In some embodiments, the genetically engineered bacteria comprise one or more gene sequences encoding one or more enzymes that are capable of converting adenosine to urate. In some embodiments, the genetically engineered bacteria comprise sequence(s) encoding add, xapA, deoD, xdhA, xdhB, and xdhC genes from *E. Coli*. In some embodiments, the genetically engineered bacteria or genetically engineered oncolytic virus further comprise a means for importing adenosine into the engineered bacteria from the tumor microenvironment. In some embodiments, the genetically engineered bacteria comprise sequence for encoding a nucleoside transporter. In some embodiments, the genetically engineered bacteria for encoding an adenosine transporter. In certain embodiments, genetically engineered bacteria for encoding *E. coli* Nucleoside Permease nupG or nupC. In some embodiments, the genetically engineered bacteria comprise sequence(s) encoding add, xapA, deoD, xdhA, xdhB, and xdhC genes from *E. Coli* and comprise sequence encoding a nucleoside or adenosine transporter. In some embodiments, the genetically engineered bacteria comprise sequence(s) encoding add, xapA, deoD, xdhA, xdhB, and xdhC genes from *E. Coli* and comprise sequence encoding nupG or nupC. An exemplary engineered bacteria is shown in FIG. 34.

C. Kynurenine Transporters

The catabolism of the essential amino acid tryptophan is a central pathway maintaining the immunosuppressive microenvironment in many types of cancers. Tumor cells or myeloid cells in the tumor microenvironment express high levels of indoleamine-2,3-dioxygenase 1 (IDO1), which is the first and rate-limiting enzyme in the degradation of tryptophan. This enzymatic activity results in the depletion of tryptophan in the local microenvironment and subsequent inhibition of T cell responses, which results in immunosuppression (as T cells are particularly sensitive to low tryptophan levels). More recent preclinical studies suggest an alternative route of tryptophan degradation in tumors via the enzyme TRP-2,3-dioxygenase 2 (TDO). Thus, tumor cells may express and catabolize tryptophan via TDO instead of or in addition to IDO1.

In addition, several studies have proposed that immunosuppression by tryptophan degradation is not solely a consequence of lowering local tryptophan levels but also of accumulating high levels of tryptophan metabolites. Preclinical studies and analyses of human tumor tissue have demonstrated that T cell responses are inhibited by tryptophan metabolites, primarily by binding to the aryl hydrocarbon receptor (AHR), a cytoplasmic transcription factor. These studies show that binding of the tryptophan metabolite kynurenine to the aryl hydrocarbon receptor results in reprogramming the differentiation of naïve CD4+T-helper (Th) cells favoring a regulatory T cells phenotype (Treg) while suppressing the differentiation into interleukin-17 (IL-17)-producing Th (Th17) cells. Activation of the aryl hydrogen receptor also results in promoting a tolerogenic phenotype on dendritic cells. As discussed above, studies have shown that the binding of kynurenine to the aryl hydrocarbon receptor results in the production of regulatory T cells (Tregs). Thus, in some embodiments, the engineered microbe has a mechanism for importing (transporting) Kynurenine from the local environment into the cell. Thus, in some embodiments, the genetically engineered bacteria comprise gene sequence(s) encoding a kynureninase transporter. In some embodiments, the genetically engineered bacteria comprise one or more copies of aroP, tnaB or mtr gene.

In one embodiment, the recombinant bacterial cell of the invention comprises a heterologous gene encoding a substrate transporter, wherein the substrate transporter is a kynurenine transporter. In one embodiment, the kynurenine transporter transports kynurenine into the cell.

The uptake of kynurenine into bacterial cells is mediated by proteins well known to those of skill in the art. In one embodiment, the at least one gene encoding a transporter is a gene selected from the group consisting of mtr, aroP and tnaB. In one embodiment, the bacterial cell described herein has been genetically engineered to comprise at least one heterologous gene selected from the group consisting of mtr, aroP and tnaB. In one embodiment, the at least one gene encoding a kynurenine transporter is the *Escherichia coli* mtr gene. In one embodiment, the at least one gene encoding a kynurenine transporter is the *Escherichia coli* aroP gene. In one embodiment, the at least one gene encoding a kynurenine transporter is the *Escherichia coli* tnaB gene.

In some embodiments, the kynurenine transporter is encoded by a kynurenine transporter gene derived from a bacterial genus or species, including but not limited to, *Escherichia, Corynebacterium, Sacharomyces, Escherichia coli, Saccharomyces cerevisiae* or *Corynebacterium glutamicum*. In some embodiments, the bacterial species is *Escherichia coli*. In some embodiments, the bacterial species is *Escherichia coli* strain Nissle.

Assays for testing the activity of a kynurenine transporter, a functional variant of a kynurenine transporter, or a functional fragment of transporter of kynurenine are well known to one of ordinary skill in the art.

Kynurenine transporters may be expressed or modified in the bacteria in order to enhance kynurenine transport into the cell. Specifically, when the kynurenine transporter is expressed in the recombinant bacterial cells, the bacterial cells import more kynurenine(s) into the cell when the transporter is expressed than unmodified bacteria of the same bacterial subtype under the same conditions. In one embodiment, the bacterial cell comprises a heterologous gene encoding a kynurenine transporter. In one embodiment, the bacterial cell comprises a heterologous gene encoding a kynurenine transporter and a genetic modification that reduces export of a kynurenine, e.g., a genetic mutation in an exporter gene or promoter.

In one embodiment, the bacterial cell comprises at least one gene encoding a kynurenine transporter from a different organism, e.g., a different species of bacteria. In one embodiment, the bacterial cell comprises at least one native gene encoding a kynurenine transporter. In some embodiments, the at least one native gene encoding a kynurenine transporter is not modified. In another embodiment, the bacterial cell comprises more than one copy of at least one native gene encoding a kynurenine transporter. In yet another embodiment, the bacterial cell comprises a copy of at least one gene encoding a native kynurenine transporter, as well as at least one copy of at least one heterologous gene encoding a kynurenine transporter from a different bacterial species. In one embodiment, the bacterial cell comprises at least one, two, three, four, five, or six copies of the at least one heterologous gene encoding a kynurenine transporter. In one embodiment, the bacterial cell comprises multiple copies of the at least one heterologous gene encoding a kynurenine transporter.

In one embodiment, the recombinant bacterial cell comprises a heterologous gene encoding a kynurenine transporter, wherein said kynurenine transporter comprises a kynurenine sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the kynurenine sequence of a polypeptide encoded by a kynurenine transporter gene disclosed herein.

The present disclosure further comprises genes encoding functional fragments of a kynurenine transporter or functional variants of a kynurenine transporter. As used herein, the term "functional fragment thereof" or "functional variant thereof" of a kynurenine transporter relates to an element having qualitative biological activity in common with the wild-type kynurenine transporter from which the fragment or variant was derived. For example, a functional fragment or a functional variant of a mutated kynurenine transporter is one which retains essentially the same ability to import a kynurenine into the bacterial cell as does the kynurenine transporter protein from which the functional fragment or functional variant was derived. In one embodiment, the recombinant bacterial cell comprises at least one heterologous gene encoding a functional fragment of a kynurenine transporter. In another embodiment, the recombinant bacterial cell comprises a heterologous gene encoding a functional variant of a kynurenine transporter.

In one embodiment, the genes encoding the kynurenine transporter have been codon-optimized for use in the host organism, e.g., a bacterial cell disclosed herein. In one embodiment, the genes encoding the kynurenine transporter have been codon-optimized for use in *Escherichia coli.*

The present disclosure also encompasses genes encoding a kynurenine transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a kynurenine transporter is mutagenized; mutants exhibiting increased kynurenine import are selected; and the mutagenized at least one gene encoding a kynurenine transporter is isolated and inserted into the bacterial cell. In some embodiments, the at least one gene encoding a kynurenine transporter is mutagenized; mutants exhibiting decreased kynurenine import are selected; and the mutagenized at least one gene encoding a kynurenine transporter is isolated and inserted into the bacterial cell. The transporter modifications described herein may be present on a plasmid or chromosome.

In some embodiments, the bacterial cell comprises a heterologous gene encoding a kynurenine transporter operably linked to a promoter. In one embodiment, the at least one gene encoding a kynurenine transporter is directly operably linked to the promoter. In another embodiment, the at least one gene encoding a kynurenine transporter is indirectly operably linked to the promoter.

In one embodiment, the promoter is not operably linked with the at least one gene encoding a kynurenine transporter in nature. In some embodiments, the at least one gene encoding the kynurenine transporter is controlled by its native promoter. In some embodiments, the at least one gene encoding the kynurenine transporter is controlled by an inducible promoter. In some embodiments, the at least one gene encoding the kynurenine transporter is controlled by a promoter that is stronger than its native promoter. In some embodiments, the at least one gene encoding the kynurenine transporter is controlled by a constitutive promoter.

In another embodiment, the promoter is an inducible promoter. Inducible promoters are described in more detail infra.

In one embodiment, the at least one gene encoding a kynurenine transporter is located on a plasmid in the bacterial cell. In some embodiments, the plasmid is a high copy number plasmid. In some embodiments, the plasmid is a low copy number plasmid. In another embodiment, the at least one gene encoding a kynurenine transporter is located in the chromosome of the bacterial cell. In yet another embodiment, a native copy of the at least one gene encoding a kynurenine transporter is located in the chromosome of the bacterial cell, and a copy of at least one gene encoding a kynurenine transporter from a different species of bacteria is located on a plasmid in the bacterial cell. In yet another embodiment, a native copy of the at least one gene encoding a kynurenine transporter is located on a plasmid in the bacterial cell, and a copy of at least one gene encoding a kynurenine transporter from a different species of bacteria is located on a plasmid in the bacterial cell. In yet another embodiment, a native copy of the at least one gene encoding a kynurenine transporter is located in the chromosome of the bacterial cell, and a copy of the at least one gene encoding a kynurenine transporter from a different species of bacteria is located in the chromosome of the bacterial cell.

In some embodiments, the at least one native gene encoding the kynurenine transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the kynurenine transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the kynurenine transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the kynurenine transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In one embodiment, the mtr gene has at least about 80% identity with the sequence of SEQ ID NO:46. Accordingly, in one embodiment, the mtr gene has at least about 90% identity with the sequence of SEQ ID NO:46. Accordingly, in one embodiment, the mtr gene has at least about 95% identity with the sequence of SEQ ID NO:46. Accordingly, in one embodiment, the mtr gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:46. In another embodiment, the mtr gene comprises the sequence of SEQ ID NO:46. In yet another embodiment the mtr gene consists of the sequence of SEQ ID NO:46.

In one embodiment, the tnaB gene has at least about 80% identity with the sequence of SEQ ID NO:47. Accordingly, in one embodiment, the tnaB gene has at least about 90% identity with the sequence of SEQ ID NO:47. Accordingly, in one embodiment, the tnaB gene has at least about 95% identity with the sequence of SEQ ID NO:47. Accordingly, in one embodiment, the tnaB gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:47. In another embodiment, the tnaB gene comprises the sequence of SEQ ID NO:47. In yet another embodiment the tnaB gene consists of the sequence of SEQ ID NO:47.

In one embodiment, the aroP gene has at least about 80% identity with the sequence of SEQ ID NO:48. Accordingly, in one embodiment, the aroP gene has at least about 90% identity with the sequence of SEQ ID NO:48. Accordingly, in one embodiment, the aroP gene has at least about 95% identity with the sequence of SEQ ID NO:48. Accordingly, in one embodiment, the aroP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:48. In another embodiment, the aroP gene comprises the sequence of SEQ ID NO:48. In yet another embodiment the aroP gene consists of the sequence of SEQ ID NO:48.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the kynurenine transporter is expressed in the recombinant bacterial cells, the bacterial cells import 10% more kynurenine into the bacterial cell when the transporter is expressed than unmodified bacteria of the same bacterial subtype under the same conditions. In another embodiment, when the kynurenine transporter is expressed in the recombinant bacterial cells, the bacterial cells import 20%, 30%, 40%, 50%, 60%, 70%, 80%, 90% or 100% more kynurenine, into the bacterial cell when the transporter is expressed than unmodified bacteria of the same bacterial subtype under the same conditions. In yet another embodiment, when the kynurenine transporter is expressed in the recombinant bacterial cells, the bacterial cells import two-fold more kynurenine into the cell when the transporter is expressed than unmodified bacteria of the same bacterial subtype under the same conditions. In yet another embodiment, when the kynurenine transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more kynurenine into the cell when the transporter is expressed than unmodified bacteria of the same bacterial subtype under the same conditions.

In one embodiment, the recombinant bacterial cells described herein comprise a first heterologous kynurenine transporter and a second heterologous kynurenine transporter. In one embodiment, said first kynurenine transporter is derived from a different organism than said second kynurenine transporter. In some embodiments, said first kynurenine transporter is derived from the same organism as said second kynurenine transporter. In some embodiments, said first kynurenine transporter imports the same kynurenine as said second kynurenine transporter. In other embodiment, said first kynurenine transporter imports a different kynurenine from said second kynurenine transporter. In some embodiments, said first kynurenine transporter is a wild-type kynurenine transporter and said second kynurenine transporter is a mutagenized version of said first kynurenine transporter. In some embodiments, the recombinant bacterial cells described herein comprise at least a third heterologous kynurenine transporter. In some embodiments, the recombinant bacterial cells described herein comprise at least four heterologous kynurenine transporters. In some embodiments, the recombinant bacterial cells described herein comprise at least five heterologous kynurenine transporters or more.

In some embodiment, the recombinant bacterial cell comprising a heterologous gene encoding a kynurenine transporter may be used to treat a disease, condition, and/or symptom associated with cancer, e.g., a cancer described herein. In some embodiments, the recombinant bacterial cells described herein may be used to reduce, ameliorate, or eliminate one or more symptom(s) associated with a cancer.

Means for optimizing kynurenine uptake are provided in the Example section.

D. Prostaglandin E2 Transporters

Prostaglandin E2 (PGE2) is overproduced in many tumors, where it aids in cancer progression. PGE2 is a pleiotropic molecule involved in numerous biological processes, including angiogenesis, apoptosis, inflammation, and immune suppression. PGE2 is synthesized from arachidonic acid by cyclooxygenase 2 (COX-2). COX-2, converts arachidonic acid (AA) to prostaglandin endoperoxide H2 (PGH2). PHG2 is then converted to PHE2 by prostaglandin E synthase (PGES), of which there are three forms. PGE2 can be catabolized into biologically inactive 15-keto-PGs by 15-PGDH and carbonyl reductase or secreted by the transporter MRP4.

MDSCs are thought to play a key role in the PGE2 production in the tumor environment. Tumor derived factors induce COX2, PGES1, and MRP4 and downregulate the expression of 15-PGDH in MDSCs, and is associated with MDSC suppressive activity. Inhibition of PGE2 through COX-2 inhibitors show promise as cancer treatments, but systemic administration is associated with serious side effects, and in the case of the COX-2 inhibitor celecoxib, resistance to tumor prevention has been observed.

In addition to inhibition of PGE production, the degradation of PGE2 by 15-hydroxyprostaglandin dehydrogenase (15-PGDH) is another way to reduce PGE2 levels in tumors. A lack of prostaglandin dehydrogenase prevents catabolism of prostaglandin E2, which helps cancer cells both to evade the immune system and circumvent drug treatment. Recent studies have demonstrated that 15-PGDH delivered locally to the tumor microenvironment can effect an antitumor immune response. For example, injection of an adenovirus encoding 15-PGDH into mouse tumors comprising non-lymphocyte white blood cells expressing CD11b (which have increased PGE2 levels, higher COX-2 expression and significantly reduced expression of 15-PGDH as compared with cells from outside the tumor), resulted in significantly slowed tumor growth. These studies further showed that 15-PGDH expression was highest in tumor cells but also significant in tumor-associated CD11b cells, where it produced a four-fold reduction in PGE2 secretion. This was associated with reduced secretion of immunosuppressive cytokines by the CD11b cells which resulted in a switch in their fate, promoting their differentiation into dendritic cells. These studies show that overproduction of PGE2 in tumors contributes to immune evasion by preventing maturation of antigen-presenting cells, and that evasion can be overcome by enforced expression of 15-PGDH. (Eruslanov et al., Volume 88, November 2010 Journal of Leukocyte Biology; Tumor-mediated induction of myeloid-derived suppressor cells and M2-polarized macrophages by altering intracellular PGE2 catabolism in myeloid cells).

Other studies confirm the benefit of local PGE2 catabolism in cancer treatment. Celecoxib, a non-steroidal anti-inflammatory COX-2 inhibitor used to treat pain and inflammation, reduces the recurrence of colon adenomas but does not work in some patients who have low levels of 15-PGDH. These results correspond with studies which show that in mice, gene knockout of 15-PGDH confers near-complete resistance to the ability of celecoxib to prevent colon tumors. These and other studies highlight the potential importance of reducing PGE2 levels in cancer, either through inhibition of synthesis or promotion of catalysis or both.

In one embodiment, the recombinant bacterial cell of the invention comprises a heterologous gene encoding a substrate transporter, wherein the substrate transporter is a prostaglandin E2 (PGE2) transporter. In one embodiment, the PGE2 transporter transports PGE2 into the cell.

The uptake of PGE2 into bacterial cells is mediated by proteins well known to those of skill in the art.

In some embodiments, the PGE2 transporter is encoded by a PGE2 transporter gene derived from a bacterial genus or species, including but not limited to, *Escherichia, Corynebacterium, Escherichia coli, Saccharomyces cerevisiae* or *Corynebacterium glutamicum*. In some embodiments, the bacterial species is *Escherichia coli*. In some embodiments, the bacterial species is *Escherichia coli* strain Nissle.

Assays for testing the activity of a PGE2 transporter, a functional variant of a PGE2 transporter, or a functional fragment of transporter of PGE2 are well known to one of ordinary skill in the art. For example, import of PGE2 may be determined using the methods as described in, the entire contents of each of which are expressly incorporated by reference herein.

PGE2 transporters may be expressed or modified in the bacteria in order to enhance PGE2 transport into the cell. Specifically, when the PGE2 transporter is expressed in the recombinant bacterial cells, the bacterial cells import more PGE2 into the cell when the transporter is expressed than unmodified bacteria of the same bacterial subtype under the same conditions. In one embodiment, the bacterial cell comprises a heterologous gene encoding a PGE2 transporter. In one embodiment, the bacterial cell comprises a heterologous gene encoding a PGE2 transporter and a genetic modification that reduces export of a PGE2, e.g., a genetic mutation in an exporter gene or promoter.

In one embodiment, the bacterial cell comprises at least one gene encoding a PGE2 transporter from a different organism, e.g., a different species of bacteria. In one embodiment, the bacterial cell comprises at least one native gene encoding a PGE2 transporter. In some embodiments, the at least one native gene encoding a PGE2 transporter is not modified. In another embodiment, the bacterial cell comprises more than one copy of at least one native gene encoding a PGE2 transporter. In yet another embodiment, the bacterial cell comprises a copy of at least one gene encoding a native PGE2 transporter, as well as at least one copy of at least one heterologous gene encoding a PGE2 transporter from a different bacterial species. In one embodiment, the bacterial cell comprises at least one, two, three, four, five, or six copies of the at least one heterologous gene encoding a PGE2 transporter. In one embodiment, the bacterial cell comprises multiple copies of the at least one heterologous gene encoding a PGE2 transporter.

In one embodiment, the recombinant bacterial cell comprises a heterologous gene encoding a PGE2 transporter, wherein said PGE2 transporter comprises a PGE2 sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the PGE2 sequence of a polypeptide encoded by a PGE2 transporter gene disclosed herein.

The present disclosure further comprises genes encoding functional fragments of a PGE2 transporter or functional variants of a PGE2 transporter. As used herein, the term "functional fragment thereof" or "functional variant thereof" of a PGE2 transporter relates to an element having qualitative biological activity in common with the wild-type PGE2 transporter from which the fragment or variant was derived. For example, a functional fragment or a functional variant of a mutated PGE2 transporter is one which retains essentially the same ability to import PGE2 into the bacterial cell as does the PGE2 transporter protein from which the functional fragment or functional variant was derived. In one embodiment, the recombinant bacterial cell comprises at least one heterologous gene encoding a functional fragment of a PGE2 transporter. In another embodiment, the recombinant bacterial cell comprises a heterologous gene encoding a functional variant of a PGE2 transporter.

In one embodiment, the genes encoding the PGE2 transporter have been codon-optimized for use in the host organism, e.g., a bacterial cell disclosed herein. In one embodiment, the genes encoding the PGE2 transporter have been codon-optimized for use in *Escherichia coli*.

The present disclosure also encompasses genes encoding a PGE2 transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a PGE2 transporter is mutagenized; mutants exhibiting increased PGE2 import are selected; and the mutagenized at least one gene encoding a PGE2 transporter is isolated and inserted into the bacterial cell. In some embodiments, the at least one gene encoding a PGE2 transporter is mutagenized; mutants exhibiting decreased PGE2 import are selected; and the mutagenized at least one gene encoding a PGE2 transporter is isolated and inserted into the bacterial cell. The transporter modifications described herein may be present on a plasmid or chromosome.

In some embodiments, the bacterial cell comprises a heterologous gene encoding a PGE2 transporter operably linked to a promoter. In one embodiment, the at least one gene encoding a PGE2 transporter is directly operably linked to the promoter. In another embodiment, the at least one gene encoding a PGE2 transporter is indirectly operably linked to the promoter.

In one embodiment, the promoter is not operably linked with the at least one gene encoding a PGE2 transporter in nature. In some embodiments, the at least one gene encoding the PGE2 transporter is controlled by its native promoter. In some embodiments, the at least one gene encoding the PGE2 transporter is controlled by an inducible promoter. In some embodiments, the at least one gene encoding the PGE2 transporter is controlled by a promoter that is stronger than its native promoter. In some embodiments, the at least one gene encoding the PGE2 transporter is controlled by a constitutive promoter.

In another embodiment, the promoter is an inducible promoter. Inducible promoters are described in more detail infra.

In one embodiment, the at least one gene encoding a PGE2 transporter is located on a plasmid in the bacterial cell. In some embodiments, the plasmid is a high copy number plasmid. In some embodiments, the plasmid is a low copy number plasmid. In another embodiment, the at least one gene encoding a PGE2 transporter is located in the chromosome of the bacterial cell. In yet another embodiment, a native copy of the at least one gene encoding a PGE2 transporter is located in the chromosome of the bacterial cell, and a copy of at least one gene encoding a PGE2 transporter from a different species of bacteria is located on a plasmid in the bacterial cell. In yet another embodiment, a native copy of the at least one gene encoding a PGE2 transporter is located on a plasmid in the bacterial cell, and a copy of at least one gene encoding a PGE2 transporter from a different species of bacteria is located on a plasmid in the bacterial cell. In yet another embodiment, a native copy of the at least one gene encoding a PGE2 transporter is located in the chromosome of the bacterial cell, and a copy of the at least one gene encoding a PGE2 transporter from a different species of bacteria is located in the chromosome of the bacterial cell.

In some embodiments, the at least one native gene encoding the PGE2 transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the PGE2 transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the PGE2 transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the PGE2 transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the PGE2 transporter is expressed in the recombinant bacterial cells, the bacterial cells import 10% more PGE2 into the bacterial cell when the transporter is expressed than unmodified bacteria of the same bacterial subtype under the same conditions. In another embodiment, when the PGE2 transporter is expressed in the recombinant bacterial cells, the bacterial cells import 20%, 30%, 40%, 50%, 60%, 70%, 80%, 90% or 100% more PGE2, into the bacterial cell when the transporter is expressed than unmodified bacteria of the same bacterial subtype under the same conditions. In yet another embodiment, when the PGE2 transporter is expressed in the recombinant bacterial cells, the bacterial cells import two-fold more PGE2 into the cell when the transporter is expressed than unmodified bacteria of the same bacterial subtype under the same conditions. In yet another embodiment, when the PGE2 transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more PGE2 into the cell when the transporter is expressed than unmodified bacteria of the same bacterial subtype under the same conditions.

In one embodiment, the recombinant bacterial cells described herein comprise a first heterologous PGE2 transporter and a second heterologous PGE2 transporter. In one embodiment, said first PGE2 transporter is derived from a different organism than said second PGE2 transporter. In some embodiments, said first PGE2 transporter is derived from the same organism as said second PGE2 transporter. In some embodiments, said first PGE2 transporter is a wild-type PGE2 transporter and said second PGE2 transporter is a mutagenized version of said first PGE2 transporter. In some embodiments, the recombinant bacterial cells described herein comprise at least a third heterologous PGE2 transporter. In some embodiments, the recombinant bacterial cells described herein comprise at least four heterologous PGE2 transporters. In some embodiments, the recombinant bacterial cells described herein comprise at least five heterologous PGE2 transporters or more.

In some embodiment, the recombinant bacterial cell comprising a heterologous gene encoding a PGE2 transporter may be used to treat a disease, condition, and/or symptom associated with cancer, e.g., a cancer described herein. In some embodiments, the recombinant bacterial cells described herein may be used to reduce, ameliorate, or eliminate one or more symptom(s) associated with a cancer.

E. Lactic Acid Transporters

The anti-cancer immune response is influenced by the environmental pH; an acidic pH has been shown to inhibit the function of immune cells. Lowering the environmental pH to 6.0-6.5, as can be found in tumour masses, has been reported to lead to loss of T-cell function of human and murine tumour-infiltrating lymphocytes (eg impairment of cytolytic activity and cytokine secretion); the T-cell function could be completely restored by buffering the pH at physiological values. The primary cause responsible for the acidic pH and pH-dependent T-cell function-suppressive effect in a tumour micro-environment has been identified as lactic acid (as reviewed in Chio et al., *J Pathol.* 2013 August; 230(4): 350-355. Cancer-generated lactic acid: a regulatory, immunosuppressive metabolite?), the contents of which is herein incorporated by reference in its entirety. It has also been demonstrated that cancer-generated lactic acid and the resultant acidification of the micro-environment increase the expression of ARG1 in tumour-associated macrophages, characteristic of the M2 helper phenotype.

In some embodiments, the genetically engineered bacterium are able to import lactic acid from the tumor microenvironment. In one embodiment, the recombinant bacterial cell of the invention comprises a heterologous gene encoding a substrate transporter, wherein the substrate transporter is a lactic acid transporter. In one embodiment, the lactic acid transporter transports lactic acid into the cell.

The uptake of lactic acid into bacterial cells is mediated by proteins well known to those of skill in the art.

In some embodiments, the lactic acid transporter is encoded by a lactic acid transporter gene derived from a bacterial genus or species, including but not limited to, *Escherichia, Corynebacterium, Escherichia coli, Saccharomyces cerevisiae* or *Corynebacterium glutamicum.* In some embodiments, the bacterial species is *Escherichia coli.* In some embodiments, the bacterial species is *Escherichia coli* strain Nissle.

Assays for testing the activity of a lactic acid transporter, a functional variant of a lactic acid transporter, or a functional fragment of transporter of lactic acid are well known to one of ordinary skill in the art.

lactic acid transporters may be expressed or modified in the bacteria in order to enhance lactic acid transport into the cell. Specifically, when the lactic acid transporter is expressed in the recombinant bacterial cells, the bacterial cells import more lactic acid into the cell when the transporter is expressed than unmodified bacteria of the same bacterial subtype under the same conditions. In one embodiment, the bacterial cell comprises a heterologous gene encoding a lactic acid transporter. In one embodiment, the bacterial cell comprises a heterologous gene encoding a lactic acid transporter and a genetic modification that reduces export of a lactic acid, e.g., a genetic mutation in an exporter gene or promoter.

In one embodiment, the bacterial cell comprises at least one gene encoding a lactic acid transporter from a different organism, e.g., a different species of bacteria. In one embodiment, the bacterial cell comprises at least one native gene encoding a lactic acid transporter. In some embodiments, the at least one native gene encoding a lactic acid transporter is not modified. In another embodiment, the bacterial cell comprises more than one copy of at least one native gene encoding a lactic acid transporter. In yet another embodiment, the bacterial cell comprises a copy of at least one gene encoding a native lactic acid transporter, as well as at least one copy of at least one heterologous gene encoding a lactic acid transporter from a different bacterial species. In one embodiment, the bacterial cell comprises at least one, two, three, four, five, or six copies of the at least one heterologous gene encoding a lactic acid transporter. In one embodiment, the bacterial cell comprises multiple copies of the at least one heterologous gene encoding a lactic acid transporter.

In one embodiment, the recombinant bacterial cell comprises a heterologous gene encoding a lactic acid transporter, wherein said lactic acid transporter comprises a lactic acid sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the lactic acid sequence of a polypeptide encoded by a lactic acid transporter gene disclosed herein.

The present disclosure further comprises genes encoding functional fragments of a lactic acid transporter or functional variants of a lactic acid transporter. As used herein, the term "functional fragment thereof" or "functional variant thereof" of a lactic acid transporter relates to an element having qualitative biological activity in common with the wild-type lactic acid transporter from which the fragment or variant was derived. For example, a functional fragment or a functional variant of a mutated lactic acid transporter is one which retains essentially the same ability to import lactic acid into the bacterial cell as does the lactic acid transporter protein from which the functional fragment or functional variant was derived. In one embodiment, the recombinant bacterial cell comprises at least one heterologous gene encoding a functional fragment of a lactic acid transporter. In another embodiment, the recombinant bacterial cell comprises a heterologous gene encoding a functional variant of a lactic acid transporter.

In one embodiment, the genes encoding the lactic acid transporter have been codon-optimized for use in the host organism, e.g., a bacterial cell disclosed herein. In one embodiment, the genes encoding the lactic acid transporter have been codon-optimized for use in *Escherichia coli.*

The present disclosure also encompasses genes encoding a lactic acid transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a lactic acid transporter is mutagenized; mutants exhibiting increased lactic acid import are selected; and the mutagenized at least one gene encoding a lactic acid transporter is isolated and inserted into the bacterial cell. In some embodiments, the at least one gene encoding a lactic acid transporter is mutagenized; mutants exhibiting decreased lactic acid import are selected; and the mutagenized at least one gene encoding a lactic acid transporter is isolated and inserted into the bacterial cell. The transporter modifications described herein may be present on a plasmid or chromosome.

In some embodiments, the bacterial cell comprises a heterologous gene encoding a lactic acid transporter operably linked to a promoter. In one embodiment, the at least one gene encoding a lactic acid transporter is directly operably linked to the promoter. In another embodiment, the at least one gene encoding a lactic acid transporter is indirectly operably linked to the promoter.

In one embodiment, the promoter is not operably linked with the at least one gene encoding a lactic acid transporter in nature. In some embodiments, the at least one gene encoding the lactic acid transporter is controlled by its native promoter. In some embodiments, the at least one gene encoding the lactic acid transporter is controlled by an inducible promoter. In some embodiments, the at least one gene encoding the lactic acid transporter is controlled by a promoter that is stronger than its native promoter. In some embodiments, the at least one gene encoding the lactic acid transporter is controlled by a constitutive promoter.

In another embodiment, the promoter is an inducible promoter. Inducible promoters are described in more detail infra.

In one embodiment, the at least one gene encoding a lactic acid transporter is located on a plasmid in the bacterial cell. In some embodiments, the plasmid is a high copy number plasmid. In some embodiments, the plasmid is a low copy number plasmid. In another embodiment, the at least one gene encoding a lactic acid transporter is located in the chromosome of the bacterial cell. In yet another embodiment, a native copy of the at least one gene encoding a lactic acid transporter is located in the chromosome of the bacterial cell, and a copy of at least one gene encoding a lactic acid transporter from a different species of bacteria is located on a plasmid in the bacterial cell. In yet another embodiment, a native copy of the at least one gene encoding a lactic acid transporter is located on a plasmid in the bacterial cell, and a copy of at least one gene encoding a lactic acid transporter from a different species of bacteria is located on a plasmid in the bacterial cell. In yet another embodiment, a native copy of the at least one gene encoding a lactic acid transporter is located in the chromosome of the bacterial cell, and a copy of the at least one gene encoding a lactic acid transporter from a different species of bacteria is located in the chromosome of the bacterial cell.

In some embodiments, the at least one native gene encoding the lactic acid transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the lactic acid transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the lactic acid transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the lactic acid transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the lactic acid transporter is expressed in the recombinant bacterial cells, the bacterial cells import 10% more lactic acid into the bacterial cell when the transporter is expressed than unmodified bacteria of the same bacterial subtype under the same conditions. In another embodiment, when the lactic acid transporter is expressed in the recombinant bacterial cells, the bacterial cells import 20%, 30%, 40%, 50%, 60%, 70%, 80%, 90% or 100% more lactic acid, into the bacterial cell when the transporter is expressed than unmodified bacteria of the same bacterial subtype under the same conditions. In yet another embodiment, when the lactic acid transporter is expressed in the recombinant bacterial cells, the bacterial cells import two-fold more lactic acid into the cell when the transporter is expressed than unmodified bacteria of the same bacterial subtype under the same conditions. In yet another embodiment, when the lactic acid transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more lactic acid into the cell when the transporter is expressed than unmodified bacteria of the same bacterial subtype under the same conditions.

In one embodiment, the recombinant bacterial cells described herein comprise a first heterologous lactic acid transporter and a second heterologous lactic acid transporter. In one embodiment, said first lactic acid transporter is derived from a different organism than said second lactic acid transporter. In some embodiments, said first lactic acid transporter is derived from the same organism as said second lactic acid transporter. In some embodiments, said first lactic acid transporter is a wild-type lactic acid transporter and said second lactic acid transporter is a mutagenized version of said first lactic acid transporter. In some embodiments, the recombinant bacterial cells described herein comprise at least a third heterologous lactic acid transporter. In some embodiments, the recombinant bacterial cells described herein comprise at least four heterologous lactic acid transporters. In some embodiments, the recombinant bacterial cells described herein comprise at least five heterologous lactic acid transporters or more.

In some embodiment, the recombinant bacterial cell comprising a heterologous gene encoding a lactic acid transporter may be used to treat a disease, condition, and/or symptom associated with cancer, e.g., a cancer described herein. In some embodiments, the recombinant bacterial cells described herein may be used to reduce, ameliorate, or eliminate one or more symptom(s) associated with a cancer.

E. Propionate Transporters

In one embodiment, the recombinant bacterial cell of the invention comprises a heterologous gene encoding a substrate transporter, wherein the substrate transporter is a propionate transporter. In one embodiment, the propionate transporter transports propionate into the cell.

The uptake of propionate into bacterial cells typically occurs via passive diffusion (see, for example, Kell et al., 1981, *Biochem. Biophys. Res. Commun.*, 9981-8). However, the active import of propionate is also mediated by proteins well known to those of skill in the art. For example, a bacterial transport system for the update of propionate in *Corynebacterium glutamicum* named MctC (monocarboxylic acid transporter) is known (see, for example, Jolkver et al. (2009) *J. Bacteriol.* 191(3): 940-8). The putP_6 propionate transporter from *Virgibacillus* species (UniProt A0A024QGU1) has also been identified.

Propionate transporters, may be expressed or modified in the bacteria of the invention in order to enhance propionate transport into the cell. Specifically, when the propionate transporter is expressed in the recombinant bacterial cells of the invention, the bacterial cells import more propionate into the cell when the transporter is expressed than unmodified bacteria of the same bacterial subtype under the same conditions. Thus, the genetically engineered bacteria comprising a heterologous gene encoding an propionate transporter may be used to import propionate into the bacteria and can be used to treat diseases associated with the catabolism of propionate, such as organic acidurias (including PA and MMA) and vitamin $B_{12}$ deficiencies. In one embodiment, the bacterial cell of the invention comprises a heterologous gene encoding an propionate transporter.

The uptake of propionate into bacterial cells is mediated by proteins well known to those of skill in the art. In one embodiment, the at least one gene encoding a propionate transporter is a gene selected from the group consisting of metC, PutP_6, mctB, mctC, dip0780, dip0791, ce0909, ce0910, ce1091, ce1092, sco1822, sco1823, sco1218, sco1219, ce1091, sco5827, m_5160, m_5161, m_5165, m_5166, nfa 17930, nfa 17940, nfa 17950, nfa 17960, actP, yjcH, ywcB, and ywcA. In one embodiment, the bacterial cell described herein has been genetically engineered to comprise at least one heterologous gene selected from the group consisting of metC, PutP_6, mctB, mctC, dip0780, dip0791, ce0909, ce0910, ce1091, ce1092, sco1822, sco1823, sco1218, sco1219, ce1091, sco5827, m_5160, m_5161, m_5165, m_5166, nfa 17930, nfa 17940, nfa 17950, nfa 17960, actP, yjcH, ywcB, and ywcA. In one embodiment, the at least one gene encoding a propionate transporter is the metC gene. In one embodiment, the at least one gene encoding a propionate transporter is the putP_6 gene.

In some embodiments, the propionate transporter is encoded by a propionate transporter gene derived from a bacterial genus or species, including but not limited to, *Bacillus, Campylobacter, Clostridium, Corynebacterium, Escherichia, Lactobacillus, Mycobacterium, Pseudomonas, Salmonella, Staphylococcus, Streptomyces, Bacillus subtilis, Campylobacter jejuni, Clostridium perfringens, Escherichia coli, Lactobacillus delbrueckii, Mycobacterium smegmatis, Nocardia farcinica, Pseudomonas aeruginosa, Salmonella typhimurium, Virgibacillus,* or *Staphylococcus aureus.* In some embodiments, the propionate transporter gene is derived from *Virgibacillus.* In some embodiments, the propionate transporter gene is derived from *Corynebacterium.* In one embodiment, the propionate transporter gene is derived from *Corynebacterium glutamicum.* In another embodiment, the propionate transporter gene is derived from *Corynebacterium diphtheria.* In another embodiment, the propionate transporter gene is derived from *Corynebacterium efficiens.* In another embodiment, the propionate transporter gene is derived from *Streptomyces coelicolor.* In another embodiment, the propionate transporter gene is derived from *Mycobacterium smegmatis.* In another embodiment, the propionate transporter gene is derived from *Nocardia farcinica.* In another embodiment, the propionate transporter gene is derived from *E. coli.* In another embodiment, the propionate transporter gene is derived from *B. subtilis.* In some embodiments, the bacterial species is *Escherichia coli.* In some embodiments, the bacterial species is *Escherichia coli* strain Nissle.

Assays for testing the activity of a propionate transporter, a functional variant of a propionate transporter, or a functional fragment of transporter of propionate are well known to one of ordinary skill in the art. For example, propionate import can be assessed by expressing the protein, functional variant, or fragment thereof, in a recombinant bacterial cell that lacks an endogenous propionate transporter. Propionate import can also be assessed using mass spectrometry. Propionate import can also be expressed using gas chromatography. For example, samples can be injected into a Perkin Elmer Autosystem XL Gas Chromatograph containing a Supelco packed column, and the analysis can be performed according to manufacturing instructions (see, for example, Supelco I (1998) Analyzing fatty acids by packed column gas chromatography, Bulletin 856B:2014). Alternatively, samples can be analyzed for propionate import using high-pressure liquid chromatography (HPLC). For example, a computer-controlled Waters HPLC system equipped with a model 600 quaternary solvent delivery system, and a model 996 photodiode array detector, and components of the sample can be resolved with an Aminex HPX-87H (300 by 7.8 mm) organic acid analysis column (Bio-Rad Laboratories) (see, for example, Palacios et al., 2003, *J. Bacteriol.*, 185(9):2802-2810).

Propionate transporters may be expressed or modified in the bacteria in order to enhance propionate transport into the cell. Specifically, when the propionate transporter is expressed in the recombinant bacterial cells, the bacterial cells import more propionate into the cell when the transporter is expressed than unmodified bacteria of the same bacterial subtype under the same conditions. In one embodiment, the bacterial cell comprises a heterologous gene encoding a propionate transporter. In one embodiment, the bacterial cell comprises a heterologous gene encoding a propionate transporter and a genetic modification that reduces export of a propionate, e.g., a genetic mutation in an exporter gene or promoter.

In one embodiment, the bacterial cell comprises at least one gene encoding a propionate transporter from a different organism, e.g., a different species of bacteria. In one embodiment, the bacterial cell comprises at least one native gene encoding a propionate transporter. In some embodiments, the at least one native gene encoding a propionate transporter is not modified. In another embodiment, the bacterial cell comprises more than one copy of at least one native gene encoding a propionate transporter. In yet another embodiment, the bacterial cell comprises a copy of at least one gene encoding a native propionate transporter, as well as at least one copy of at least one heterologous gene encoding a propionate transporter from a different bacterial species. In one embodiment, the bacterial cell comprises at least one, two, three, four, five, or six copies of the at least one heterologous gene encoding a propionate transporter. In one embodiment, the bacterial cell comprises multiple copies of the at least one heterologous gene encoding a propionate transporter.

In one embodiment, the recombinant bacterial cell comprises a heterologous gene encoding a propionate transporter, wherein said propionate transporter comprises a propionate sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the propionate sequence of a polypeptide encoded by a propionate transporter gene disclosed herein.

The present disclosure further comprises genes encoding functional fragments of a propionate transporter or functional variants of a propionate transporter. As used herein, the term "functional fragment thereof" or "functional variant thereof" of a propionate transporter relates to an element having qualitative biological activity in common with the wild-type propionate transporter from which the fragment or variant was derived. For example, a functional fragment or a functional variant of a mutated propionate transporter is one which retains essentially the same ability to import propionate into the bacterial cell as does the propionate transporter protein from which the functional fragment or functional variant was derived. In one embodiment, the recombinant bacterial cell comprises at least one heterologous gene encoding a functional fragment of a propionate transporter. In another embodiment, the recombinant bacterial cell comprises a heterologous gene encoding a functional variant of a propionate transporter.

In one embodiment, the genes encoding the propionate transporter have been codon-optimized for use in the host organism, e.g., a bacterial cell disclosed herein. In one embodiment, the genes encoding the propionate transporter have been codon-optimized for use in *Escherichia coli*.

The present disclosure also encompasses genes encoding a propionate transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a propionate transporter is mutagenized; mutants exhibiting increased propionate import are selected; and the mutagenized at least one gene encoding a propionate transporter is isolated and inserted into the bacterial cell. In some embodiments, the at least one gene encoding a propionate transporter is mutagenized; mutants exhibiting decreased propionate import are selected; and the mutagenized at least one gene encoding a propionate transporter is isolated and inserted into the bacterial cell. The transporter modifications described herein may be present on a plasmid or chromosome.

In some embodiments, the bacterial cell comprises a heterologous gene encoding a propionate transporter operably linked to a promoter. In one embodiment, the at least one gene encoding a propionate transporter is directly operably linked to the promoter. In another embodiment, the at least one gene encoding a propionate transporter is indirectly operably linked to the promoter.

In one embodiment, the promoter is not operably linked with the at least one gene encoding a propionate transporter in nature. In some embodiments, the at least one gene encoding the propionate transporter is controlled by its native promoter. In some embodiments, the at least one gene encoding the propionate transporter is controlled by an inducible promoter. In some embodiments, the at least one gene encoding the propionate transporter is controlled by a promoter that is stronger than its native promoter. In some embodiments, the at least one gene encoding the propionate transporter is controlled by a constitutive promoter.

In another embodiment, the promoter is an inducible promoter. Inducible promoters are described in more detail infra.

In one embodiment, the at least one gene encoding a propionate transporter is located on a plasmid in the bacterial cell. In some embodiments, the plasmid is a high copy number plasmid. In some embodiments, the plasmid is a low copy number plasmid. In another embodiment, the at least one gene encoding a propionate transporter is located in the chromosome of the bacterial cell. In yet another embodiment, a native copy of the at least one gene encoding a propionate transporter is located in the chromosome of the bacterial cell, and a copy of at least one gene encoding a propionate transporter from a different species of bacteria is located on a plasmid in the bacterial cell. In yet another embodiment, a native copy of the at least one gene encoding a propionate transporter is located on a plasmid in the bacterial cell, and a copy of at least one gene encoding a propionate transporter from a different species of bacteria is located on a plasmid in the bacterial cell. In yet another embodiment, a native copy of the at least one gene encoding a propionate transporter is located in the chromosome of the bacterial cell, and a copy of the at least one gene encoding a propionate transporter from a different species of bacteria is located in the chromosome of the bacterial cell.

In some embodiments, the at least one native gene encoding the propionate transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the propionate transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the propionate transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the propionate transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In one embodiment, the propionate transporter is MctC. In one embodiment, the mctC gene has at least about 80% identity to SEQ ID NO:129. Accordingly, in one embodiment, the mctC gene has at least about 90% identity to SEQ ID NO:129. Accordingly, in one embodiment, the mctC gene has at least about 95% identity to SEQ ID NO:12. Accordingly, in one embodiment, the mctC gene has at least about 70%, 75%, 80%, 85%, 86%, 87%, 88%, 89%, 90%, 91%, 92%, 93%, 94%, 95%, 96%, 97%, 98%, or 99% identity to SEQ ID NO:129. In another embodiment, the mctC gene comprises the sequence of SEQ ID NO:129. In yet another embodiment the mctC gene consists of the sequence of SEQ ID NO:129.

In another embodiment, the propionate transporter is PutP_6. In one embodiment, the putP_6 gene has at least about 80% identity to SEQ ID NO:130. Accordingly, in one embodiment, the putP_6 gene has at least about 90% identity to SEQ ID NO:130. Accordingly, in one embodiment, the putP_6 gene has at least about 95% identity to SEQ ID NO:130. Accordingly, in one embodiment, the putP_6 gene has at least about 70%, 75%, 80%, 85%, 86%, 87%, 88%, 89%, 90%, 91%, 92%, 93%, 94%, 95%, 96%, 97%, 98%, or 99% identity to SEQ ID NO:130. In another embodiment, the putP_6 gene comprises the sequence of SEQ ID NO:130. In yet another embodiment the putP_6 gene consists of the sequence of SEQ ID NO:130.

Other propionate transporter genes are known to those of ordinary skill in the art. See, for example, Jolker et al., *J. Bacteriol.*, 2009, 191(3):940-948. In one embodiment, the propionate transporter comprises the mctBC genes from *C. glutamicum*. In another embodiment, the propionate transporter comprises the dip0780 and dip0791 genes from *C. diphtheria*. In another embodiment, the propionate transporter comprises the ce0909 and ce0910 genes from *C. efficiens*. In another embodiment, the propionate transporter comprises the ce1091 and ce1092 genes from *C. efficiens*. In another embodiment, the propionate transporter comprises the sco1822 and sco1823 genes from *S. coelicolor*. In another embodiment, the propionate transporter comprises the sco1218 and sco1219 genes from *S. coelicolor*. In another embodiment, the propionate transporter comprises the ce1091 and sco5827 genes from *S. coelicolor*. In another embodiment, the propionate transporter comprises the m_5160, m_5161, m_5165, and m_5166 genes from *M. smegmatis*. In another embodiment, the propionate transporter comprises the nfa 17930, nfa 17940, nfa 17950, and nfa 17960 genes from *N. farcinica*. In another embodiment, the propionate transporter comprises the actP and yjcH genes from *E. coli*. In another embodiment, the propionate transporter comprises the ywcB and ywcA genes from *B. subtilis*.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the propionate transporter is expressed in the recombinant bacterial cells, the bacterial cells import 10% more propionate into the bacterial cell when the transporter is expressed than unmodified bacteria of the same bacterial subtype under the same conditions. In another embodiment, when the propionate transporter is expressed in the recombinant bacterial cells, the bacterial cells import 20%, 30%, 40%, 50%, 60%, 70%, 80%, 90% or 100% more propionate, into the bacterial cell when the transporter is expressed than unmodified bacteria of the same bacterial subtype under the same conditions. In yet another embodiment, when the propionate transporter is expressed in the recombinant bacterial cells, the bacterial cells import two-fold more propionate into the cell when the transporter is expressed than unmodified bacteria of the same bacterial subtype under the same conditions. In yet another embodiment, when the propionate transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more propionate into the cell when the transporter is expressed than unmodified bacteria of the same bacterial subtype under the same conditions.

In one embodiment, the recombinant bacterial cells described herein comprise a first heterologous propionate transporter and a second heterologous propionate transporter. In one embodiment, said first propionate transporter is derived from a different organism than said second propionate transporter. In some embodiments, said first propionate transporter is derived from the same organism as said second propionate transporter. In some embodiments, said first propionate transporter is a wild-type propionate transporter and said second propionate transporter is a mutagenized version of said first propionate transporter. In some embodiments, the recombinant bacterial cells described herein comprise at least a third heterologous propionate transporter. In some embodiments, the recombinant bacterial cells described herein comprise at least four heterologous propionate transporters. In some embodiments, the recombinant bacterial cells described herein comprise at least five heterologous propionate transporters or more.

In some embodiment, the recombinant bacterial cell comprising a heterologous gene encoding an propionate transporter may be used to treat a disease, condition, and/or symptom associated with the catabolism of propionate in a subject. In some embodiments, the recombinant bacterial cells described herein may be used to reduce, ameliorate, or eliminate one or more symptom(s) associated with these diseases or disorders. In one embodiment, the disorder associated with the catabolism of propionate is a metabolic disorder involving the abnormal catabolism of propionate. Metabolic diseases associated with abnormal catabolism of propionate include propionic acidemia (PA) and methylmalonic acidemia (MMA), as well as severe nutritional vitamin $B_{12}$ deficiencies. In one embodiment, the disease associated with abnormal catabolism of propionate is propionic acidemia. In one embodiment, the disease associated with abnormal catabolism of propionate is methylmalonic acidemia. In another embodiment, the disease associated with abnormal catabolism of propionate is a vitamin $B_{12}$ deficiency.

G. Bile Salt Acid Transporters

In one embodiment, the recombinant bacterial cell of the invention comprises a heterologous gene encoding a substrate transporter, wherein the substrate transporter is a bile salt transporter. In one embodiment, the bile salt transporter transports bile salt into the cell.

The uptake of bile salt into bacterial cells is mediated by proteins well known to those of skill in the art. For example, the uptake of bile salts into the *Lactobacillus* and *Bifidobacterium* has been found to occur via the bile salt transporters CbsT1 and CbsT2 (see, e.g., Elkins et al., *Microbiology*, 147(Pt. 12):3403-3412 (2001), the entire contents of which are expressly incorporated herein by reference). Other proteins that mediate the import of bile salts into cells are well known to those of skill in the art.

In one embodiment, the at least one gene encoding a bile salt transporter is a cbsT1 or a cbsT2 gene. In one embodiment, the bacterial cell described herein has been genetically engineered to comprise at least one heterologous gene selected from a cbsT1 or a cbsT2 gene. In one embodiment, the at least one gene encoding a bile salt transporter is the cbsT1 gene. In one embodiment, the at least one gene encoding a bile salt transporter is the cbsT2 gene. In one embodiment, the bile acid transporter is the bile acid sodium symporter $ASBT_{NM}$ (NMB0705 gene of Neisseria meningitides).

In some embodiments, the bile salt transporter is encoded by a bile salt transporter gene derived from a bacterial genus or species, including but not limited to, *Lactobacillus*, for example, *Lactobacillus johnsonni* (e.g., *Lactobacillus johnsonni* strain 100-100). In some embodiments, the bacterial species is *Escherichia coli*. In some embodiments, the bacterial species is *Escherichia coli* strain Nissle.

Assays for testing the activity of an transporter of a bile salt, a functional variant of an transporter of a bile salt, or a functional fragment of an transporter of a bile salt are well known to one of ordinary skill in the art. For example, bile salt import can be assessed as described in Elkins et al. (2001) *Microbiology*, 147:3403-3412, the entire contents of which are expressly incorporated herein by reference.

Bile salt transporters may be expressed or modified in the bacteria in order to enhance bile salt transport into the cell. Specifically, when the bile salt transporter is expressed in the recombinant bacterial cells, the bacterial cells import more bile salt into the cell when the transporter is expressed than unmodified bacteria of the same bacterial subtype under the same conditions. In one embodiment, the bacterial cell comprises a heterologous gene encoding a bile salt transporter. In one embodiment, the bacterial cell comprises a heterologous gene encoding a bile salt transporter and a genetic modification that reduces export of a bile salt, e.g., a genetic mutation in an exporter gene or promoter.

In one embodiment, the bacterial cell comprises at least one gene encoding a bile salt transporter from a different organism, e.g., a different species of bacteria. In one embodiment, the bacterial cell comprises at least one native gene encoding a bile salt transporter. In some embodiments, the at least one native gene encoding a bile salt transporter is not modified. In another embodiment, the bacterial cell comprises more than one copy of at least one native gene encoding a bile salt transporter. In yet another embodiment, the bacterial cell comprises a copy of at least one gene encoding a native bile salt transporter, as well as at least one copy of at least one heterologous gene encoding a bile salt transporter from a different bacterial species. In one embodiment, the bacterial cell comprises at least one, two, three, four, five, or six copies of the at least one heterologous gene encoding a bile salt transporter. In one embodiment, the bacterial cell comprises multiple copies of the at least one heterologous gene encoding a bile salt transporter.

In one embodiment, the recombinant bacterial cell comprises a heterologous gene encoding a bile salt transporter, wherein said bile salt transporter comprises a bile salt sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the bile salt sequence of a polypeptide encoded by a bile salt transporter gene disclosed herein.

The present disclosure further comprises genes encoding functional fragments of a bile salt transporter or functional variants of a bile salt transporter. As used herein, the term "functional fragment thereof" or "functional variant thereof" of a bile salt transporter relates to an element having qualitative biological activity in common with the wild-type bile salt transporter from which the fragment or variant was derived. For example, a functional fragment or a functional variant of a mutated bile salt transporter is one which retains essentially the same ability to import bile salt into the bacterial cell as does the bile salt transporter protein from which the functional fragment or functional variant was derived. In one embodiment, the recombinant bacterial cell comprises at least one heterologous gene encoding a functional fragment of a bile salt transporter. In another embodiment, the recombinant bacterial cell comprises a heterologous gene encoding a functional variant of a bile salt transporter.

In one embodiment, the genes encoding the bile salt transporter have been codon-optimized for use in the host organism, e.g., a bacterial cell disclosed herein. In one embodiment, the genes encoding the bile salt transporter have been codon-optimized for use in *Escherichia coli*.

The present disclosure also encompasses genes encoding a bile salt transporter comprising amino acids in its sequence that are substantially the same as an amino acid sequence described herein. Amino acid sequences that are substantially the same as the sequences described herein include sequences comprising conservative amino acid substitutions, as well as amino acid deletions and/or insertions.

In some embodiments, the at least one gene encoding a bile salt transporter is mutagenized; mutants exhibiting increased bile salt import are selected; and the mutagenized at least one gene encoding a bile salt transporter is isolated and inserted into the bacterial cell. In some embodiments, the at least one gene encoding a bile salt transporter is mutagenized; mutants exhibiting decreased bile salt import are selected; and the mutagenized at least one gene encoding a bile salt transporter is isolated and inserted into the bacterial cell. The transporter modifications described herein may be present on a plasmid or chromosome.

In some embodiments, the bacterial cell comprises a heterologous gene encoding a bile salt transporter operably linked to a promoter. In one embodiment, the at least one gene encoding a bile salt transporter is directly operably linked to the promoter. In another embodiment, the at least one gene encoding a bile salt transporter is indirectly operably linked to the promoter.

In one embodiment, the promoter is not operably linked with the at least one gene encoding a bile salt transporter in nature. In some embodiments, the at least one gene encoding the bile salt transporter is controlled by its native promoter. In some embodiments, the at least one gene encoding the bile salt transporter is controlled by an inducible promoter. In some embodiments, the at least one gene encoding the bile salt transporter is controlled by a promoter that is stronger than its native promoter. In some embodiments, the at least one gene encoding the bile salt transporter is controlled by a constitutive promoter.

In another embodiment, the promoter is an inducible promoter. Inducible promoters are described in more detail infra.

In one embodiment, the at least one gene encoding a bile salt transporter is located on a plasmid in the bacterial cell. In some embodiments, the plasmid is a high copy number plasmid. In some embodiments, the plasmid is a low copy number plasmid. In another embodiment, the at least one gene encoding a bile salt transporter is located in the chromosome of the bacterial cell. In yet another embodiment, a native copy of the at least one gene encoding a bile salt transporter is located in the chromosome of the bacterial cell, and a copy of at least one gene encoding a bile salt transporter from a different species of bacteria is located on a plasmid in the bacterial cell. In yet another embodiment, a native copy of the at least one gene encoding a bile salt transporter is located on a plasmid in the bacterial cell, and a copy of at least one gene encoding a bile salt transporter from a different species of bacteria is located on a plasmid in the bacterial cell. In yet another embodiment, a native copy of the at least one gene encoding a bile salt transporter is located in the chromosome of the bacterial cell, and a copy of the at least one gene encoding a bile salt transporter from a different species of bacteria is located in the chromosome of the bacterial cell.

In some embodiments, the at least one native gene encoding the bile salt transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the bile salt transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the bile salt transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the bile salt transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In one embodiment, the bile salt transporter is the bile salt transporter CbsT1. In one embodiment, the cbsT1 gene has at least about 80% identity to SEQ ID NO:131. Accordingly, in one embodiment, the cbsT1 gene has at least about 90% identity to SEQ ID NO:131. Accordingly, in one embodiment, the cbsT1 gene has at least about 95% identity to SEQ ID NO:131. Accordingly, in one embodiment, the cbsT1 gene has at least about 70%, 75%, 80%, 85%, 86%, 87%, 88%, 89%, 90%, 91%, 92%, 93%, 94%, 95%, 96%, 97%, 98%, or 99% identity to SEQ ID NO:131. In another embodiment, the cbsT1 gene comprises the sequence of SEQ ID NO:131. In yet another embodiment the cbsT1 gene consists of the sequence of SEQ ID NO:131.

In one embodiment, the bile salt transporter is the bile salt transporter CbsT2. In one embodiment, the cbsT2 gene has at least about 80% identity to SEQ ID NO:132. Accordingly, in one embodiment, the cbsT2 gene has at least about 90% identity to SEQ ID NO:132. Accordingly, in one embodiment, the cbsT2 gene has at least about 95% identity to SEQ ID NO:132. Accordingly, in one embodiment, the cbsT2 gene has at least about 70%, 75%, 80%, 85%, 86%, 87%, 88%, 89%, 90%, 91%, 92%, 93%, 94%, 95%, 96%, 97%, 98%, or 99% identity to SEQ ID NO:132. In another embodiment, the cbsT2 gene comprises the sequence of SEQ ID NO:132. In yet another embodiment the cbsT2 gene consists of the sequence of SEQ ID NO:132.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the bile salt transporter is expressed in the recombinant bacterial cells, the bacterial cells import 10% more bile salt into the bacterial cell when the transporter is expressed than unmodified bacteria of the same bacterial subtype under the same conditions. In another embodiment, when the bile salt transporter is expressed in the recombinant bacterial cells, the bacterial cells import 20%, 30%, 40%, 50%, 60%, 70%, 80%, 90% or 100% more bile salt, into the bacterial cell when the transporter is expressed than unmodified bacteria of the same bacterial subtype under the same conditions. In yet another embodiment, when the bile salt transporter is expressed in the recombinant bacterial cells, the bacterial cells import two-fold more bile salt into the cell when the transporter is expressed than unmodified bacteria of the same bacterial subtype under the same conditions. In yet another embodiment, when the bile salt transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more bile salt into the cell when the transporter is expressed than unmodified bacteria of the same bacterial subtype under the same conditions.

In one embodiment, the recombinant bacterial cells described herein comprise a first heterologous bile salt transporter and a second heterologous bile salt transporter. In one embodiment, said first bile salt transporter is derived from a different organism than said second bile salt transporter. In some embodiments, said first bile salt transporter is derived from the same organism as said second bile salt transporter. In some embodiments, said first bile salt transporter imports the same bile salt as said second bile salt transporter. In other embodiment, said first bile salt transporter imports a different bile salt from said second bile salt transporter. In some embodiments, said first bile salt transporter is a wild-type bile salt transporter and said second bile salt transporter is a mutagenized version of said first bile salt transporter. In some embodiments, the recombinant bacterial cells described herein comprise at least a third heterologous bile salt transporter. In some embodiments, the recombinant bacterial cells described herein comprise at least four heterologous bile salt transporters. In some embodiments, the recombinant bacterial cells described herein comprise at least five heterologous bile salt transporters or more.

In some embodiment, the recombinant bacterial cell comprising a heterologous gene encoding an bile salt transporter may be used to treat a disease, condition, and/or symptom associated with bile salts. In some embodiments, the recombinant bacterial cells described herein may be used to reduce, ameliorate, or eliminate one or more symptom(s) associated with these diseases or disorders. In some embodiments, the disease or disorder associated with bile salts is cardiovascular disease, metabolic disease, liver disease, such as cirrhosis or NASH, gastrointestinal cancer, and/or *C. difficile* infection. In some embodiments, the disclosure provides methods for reducing, ameliorating, or eliminating one or more symptom(s) associated with these diseases, including but not limited to chest pain, heart failure, or weight gain. In some embodiments, the disease is secondary to other conditions, e.g., cardiovascular disease or liver disease.

H. Ammonia Transporters

In one embodiment, the recombinant bacterial cell of the invention comprises a heterologous gene encoding a substrate transporter, wherein the substrate transporter is an ammonia transporter. In one embodiment, the ammonia transporter transports ammonia into the cell.

The uptake of ammonia into bacterial cells is mediated by proteins well known to those of skill in the art. For example, the ammonium/methylammonium transport B (AmtB) protein is a membrane transport protein that transports ammonia into bacterial cells. In one embodiment, the at least one gene encoding an ammonia transporter is an amtB gene. In one embodiment, the bacterial cell described herein has been genetically engineered to comprise at least one heterologous an amtB gene.

In some embodiments, the ammonia transporter is encoded by an ammonia transporter gene derived from a bacterial genus or species, including but not limited to, *Corynebacterium*, e.g., *Corynebacterium glutamicum*, *Escherichia*, e.g., *Escherichia coli*, *Streptomyces*, e.g., *Streptomyces coelicolor*, or *Ruminococcus*, e.g., *Ruminococcus albus*. In some embodiments, the bacterial species is *Escherichia coli*. In some embodiments, the bacterial species is *Escherichia coli* strain Nissle.

Assays for testing the activity of an ammonia transporter, a functional variant of an ammonia transporter, or a functional fragment of transporter of ammonia are well known to one of ordinary skill in the art. For example, import of ammonia may be determined using a methylammonium uptake assay, as described in Soupene et al. (1998) *Proc. Natl. Acad. Sci. U.S.A.* 95(12): 7030-4, the entire contents of each of which are expressly incorporated by reference herein.

Ammonia transporters may be expressed or modified in the bacteria in order to enhance ammonia transport into the cell. Specifically, when the ammonia transporter is expressed in the recombinant bacterial cells, the bacterial cells import more ammonia into the cell when the transporter is expressed than unmodified bacteria of the same bacterial subtype under the same conditions. In one embodiment, the bacterial cell comprises a heterologous gene encoding an ammonia transporter. In one embodiment, the bacterial cell comprises a heterologous gene encoding an ammonia transporter and a genetic modification that reduces export of a ammonia, e.g., a genetic mutation in an exporter gene or promoter.

In one embodiment, the bacterial cell comprises at least one gene encoding an ammonia transporter from a different organism, e.g., a different species of bacteria. In one embodiment, the bacterial cell comprises at least one native gene encoding an ammonia transporter. In some embodiments, the at least one native gene encoding an ammonia transporter is not modified. In another embodiment, the bacterial cell comprises more than one copy of at least one native gene encoding an ammonia transporter. In yet another embodiment, the bacterial cell comprises a copy of at least one gene encoding a native ammonia transporter, as well as at least one copy of at least one heterologous gene encoding an ammonia transporter from a different bacterial species. In one embodiment, the bacterial cell comprises at least one, two, three, four, five, or six copies of the at least one heterologous gene encoding an ammonia transporter. In one embodiment, the bacterial cell comprises multiple copies of the at least one heterologous gene encoding an ammonia transporter.

In one embodiment, the recombinant bacterial cell comprises a heterologous gene encoding an ammonia transporter, wherein said ammonia transporter comprises an ammonia sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the ammonia sequence of a polypeptide encoded by an ammonia transporter gene disclosed herein.

The present disclosure further comprises genes encoding functional fragments of an ammonia transporter or functional variants of an ammonia transporter. As used herein, the term "functional fragment thereof" or "functional variant thereof" of an ammonia transporter relates to an element having qualitative biological activity in common with the wild-type ammonia transporter from which the fragment or variant was derived. For example, a functional fragment or a functional variant of a mutated ammonia transporter is one which retains essentially the same ability to import ammonia into the bacterial cell as does the ammonia transporter protein from which the functional fragment or functional variant was derived. In one embodiment, the recombinant bacterial cell comprises at least one heterologous gene encoding a functional fragment of an ammonia transporter. In another embodiment, the recombinant bacterial cell comprises a heterologous gene encoding a functional variant of an ammonia transporter.

In one embodiment, the genes encoding the ammonia transporter have been codon-optimized for use in the host organism, e.g., a bacterial cell disclosed herein. In one embodiment, the genes encoding the ammonia transporter have been codon-optimized for use in *Escherichia coli*.

The present disclosure also encompasses genes encoding an ammonia transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding an ammonia transporter is mutagenized; mutants exhibiting increased ammonia import are selected; and the mutagenized at least one gene encoding an ammonia transporter is isolated and inserted into the bacterial cell. In some embodiments, the at least one gene encoding an ammonia transporter is mutagenized; mutants exhibiting decreased ammonia import are selected; and the mutagenized at least one gene encoding an ammonia transporter is isolated and inserted into the bacterial cell. The transporter modifications described herein may be present on a plasmid or chromosome.

In some embodiments, the bacterial cell comprises a heterologous gene encoding an ammonia transporter operably linked to a promoter. In one embodiment, the at least one gene encoding an ammonia transporter is directly operably linked to the promoter. In another embodiment, the at least one gene encoding an ammonia transporter is indirectly operably linked to the promoter.

In one embodiment, the promoter is not operably linked with the at least one gene encoding an ammonia transporter in nature. In some embodiments, the at least one gene encoding the ammonia transporter is controlled by its native promoter. In some embodiments, the at least one gene encoding the ammonia transporter is controlled by an inducible promoter. In some embodiments, the at least one gene encoding the ammonia transporter is controlled by a promoter that is stronger than its native promoter. In some embodiments, the at least one gene encoding the ammonia transporter is controlled by a constitutive promoter.

In another embodiment, the promoter is an inducible promoter. Inducible promoters are described in more detail infra.

In one embodiment, the at least one gene encoding an ammonia transporter is located on a plasmid in the bacterial cell. In some embodiments, the plasmid is a high copy number plasmid. In some embodiments, the plasmid is a low copy number plasmid. In another embodiment, the at least one gene encoding an ammonia transporter is located in the chromosome of the bacterial cell. In yet another embodiment, a native copy of the at least one gene encoding an ammonia transporter is located in the chromosome of the bacterial cell, and a copy of at least one gene encoding an ammonia transporter from a different species of bacteria is located on a plasmid in the bacterial cell. In yet another embodiment, a native copy of the at least one gene encoding an ammonia transporter is located on a plasmid in the bacterial cell, and a copy of at least one gene encoding an ammonia transporter from a different species of bacteria is located on a plasmid in the bacterial cell. In yet another embodiment, a native copy of the at least one gene encoding an ammonia transporter is located in the chromosome of the bacterial cell, and a copy of the at least one gene encoding an ammonia transporter from a different species of bacteria is located in the chromosome of the bacterial cell.

In some embodiments, the at least one native gene encoding the ammonia transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the ammonia transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the ammonia transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the ammonia transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In one embodiment, the ammonia transporter is the ammonia transporter AmtB, for example the *Escherichia coli* AmtB. In one embodiment the ammonia transporter is encoded by a amtB gene. In one embodiment, the amtB gene has at least about 80% identity with the sequence of SEQ ID NO:133. Accordingly, in one embodiment, the amtB gene has at least about 90% identity with the sequence of SEQ ID NO:133. Accordingly, in one embodiment, the amtB gene has at least about 95% identity with the sequence of SEQ ID NO:133. Accordingly, in one embodiment, the amtB gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:133. In another embodiment, the amtB gene comprises the sequence of SEQ ID NO:133. In yet another embodiment the amtB gene consists of the sequence of SEQ ID NO:133.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the ammonia transporter is expressed in the recombinant bacterial cells, the bacterial cells import 10% more ammonia into the bacterial cell when the transporter is expressed than unmodified bacteria of the same bacterial subtype under the same conditions. In another embodiment, when the ammonia transporter is expressed in the recombinant bacterial cells, the bacterial cells import 20%, 30%, 40%, 50%, 60%, 70%, 80%, 90% or 100% more ammonia, into the bacterial cell when the transporter is expressed than unmodified bacteria of the same bacterial subtype under the same conditions. In yet another embodiment, when the ammonia transporter is expressed in the recombinant bacterial cells, the bacterial cells import two-fold more ammonia into the cell when the transporter is expressed than unmodified bacteria of the same bacterial subtype under the same conditions. In yet another embodiment, when the ammonia transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more ammonia into the cell when the transporter is expressed than unmodified bacteria of the same bacterial subtype under the same conditions.

In one embodiment, the recombinant bacterial cells described herein comprise a first heterologous ammonia transporter and a second heterologous ammonia transporter. In one embodiment, said first ammonia transporter is derived from a different organism than said second ammonia transporter. In some embodiments, said first ammonia transporter is derived from the same organism as said second ammonia transporter. In some embodiments, said first ammonia transporter is a wild-type ammonia transporter and said second ammonia transporter is a mutagenized version of said first ammonia transporter. In some embodiments, the recombinant bacterial cells described herein comprise at least a third heterologous ammonia transporter. In some embodiments, the recombinant bacterial cells described herein comprise at least four heterologous ammonia transporters. In some embodiments, the recombinant bacterial cells described herein comprise at least five heterologous ammonia transporters or more.

In some embodiment, the recombinant bacterial cell comprising a heterologous gene encoding an ammonia transporter may be used to treat a disease, condition, and/or symptom associated with hyperammonenia. In some embodiment, the recombinant bacterial cells described herein can be used to treat hepatic encephalopathy. In some embodiment, the recombinant bacterial cells described herein can be used to treat Huntington's disease. In some embodiments, the invention provides methods for reducing, ameliorating, or eliminating one or more symptom(s) associated with hepatic encephalopathy and Huntington's disease. In some embodiments, the symptom(s) associated thereof include, but are not limited to, seizures, ataxia, stroke-like lesions, coma, psychosis, vision loss, acute encephalopathy, cerebral edema, as well as vomiting, respiratory alkalosis, and hypothermia.

I. γ-Aminobutyric Acid (GABA) Transporters

γ-aminobutyric acid (GABA) is the predominant inhibitory neurotransmitter ($C_4H_9NO_2$) in the mammalian central nervous system. In humans, GABA is also directly responsible for regulating muscle tone. GABA is capable of activating the GABAA receptor, which is part of a ligand-gated ion channel complex, as well as the GABAs metabotropic G protein-coupled receptor. Neurons that produce GABA are known as "GABAergic" neurons, and activation of GABA receptors is described as GABAergic tone (i.e., increased activation of GABA receptors refers to increased GABAergic tone).

γ-Aminobutyric acid (GABA) is the predominant inhibitory neurotransmitter in the mammalian central nervous system. In humans, GABA activates the postsynaptic GABAA receptor, which is part of a ligand-gated chloride-specific ion channel complex. Activation of this complex on a post-synaptic neuron allows chloride ions to enter the neuron and exert an inhibitory effect. Alterations of such GABAergic neurotransmission have been implicated in the pathophysiology of several neurological disorders, including epilepsy (Jones-Davis and MacDonald (2003) *Curr. Opin. Pharmacol.* 3(1): 12-8), Huntington's disease (Krogsgaard-Larsen (1992) *Pharmacol Toxicol.* 70(2):95-104), and hepatic encephalopathy (Jones and Basile (1997) *Adv. Exp. Med. Biol.* 420: 75-83). Neurons in the brain that are modulated by GABA are said to be under inhibitory GABAergic tone. This inhibitory tone prevents neuronal firing until a sufficiently potent stimulatory stimulus is received, or until the inhibitory tone is otherwise released. Increased GABAergic tone in hepatic encephalopathy (HE) was initially described in the early 1980s, based on a report of similar visual response patterns in rabbits with galactosamine-induced liver failure and rabbits treated with allosteric modulators of the GABAA receptor (e.g., pentobarbital, diazepam) (Jones and Basile, 1997). Clinical improvements in hepatic encephalopathy patients treated with a highly selective benzodiazapene antagonist at the GABAA receptor, flumazenil, further confirmed these observations (Banksy et al. (1985) *Lancet* 1: 1324-5; Scollo-Lavizzari and Steinmann (1985) *Lancet* 1: 1324. Increased GABAergic tone in HE has since been proposed as a consequence of one or more of the following: (1) increased GABA concentrations in the brain, (2) altered integrity of the GABAA receptor, and/or (3) increased concentrations of endogenous modulators of the GABAA receptor (Ahboucha and Butterworth (2004) *Metab. Brain Dis.* 1 9(3-4):331-343).

In one embodiment, the recombinant bacterial cell of the invention comprises a heterologous gene encoding a substrate transporter, wherein the substrate transporter is a GABA transporter. In one embodiment, the GABA transporter transports GABA into the cell.

The uptake of GABA into bacterial cells is mediated by proteins well known to those of skill in the art. For example, GABA uptake in *E. coli* is driven by membrane potential and facilitated by the membrane transport protein, GabP (Li et al. (2001) *FEBS Lett.* 494(3): 165-169. GabP is a member of the amino acid/polymaine/organocation (APC) transporter superfamily, one of the two largest families of secondary active transporters (Jack et al. (2000) *Microbiology* 146: 1797-1814). GabP protein, encoded by the gabP gene, consists of 466 amino acids and 12 transmembrane alpha helices, wherein both N- and C-termini face the cytosol (Hu and King, (1998) *Biochem J.* 336(Pt 1): 69-76. The GabP residue sequence also includes a consensus amphipathic region (CAR), which is conserved between members of the APC family from bacteria to mammals (Hu and King, 1998). Upon entry into the cell, GABA is converted to succinyl semialdehyde (SSA) by GABA a-ketoglutarate transaminase (GSST). Succinate-semialdehyde dehydrogenase (SSDH) then catalyzes the second and only other specific step in GABA catabolism, the oxidation of succinyl semialdehyde to succinate (Dover and Halpern (1972) *J. Bacteriol.* 109 (2):835-43). Ultimately, succinate becomes a substrate for the citric acid (TCA) cycle. In one embodiment, the at least one gene encoding a GABA transporter is encoded by an gabP gene. In one embodiment, the bacterial cell described herein has been genetically engineered to comprise at least one heterologous an gabP gene.

In some embodiments, the GABA transporter is encoded by a GABA transporter gene derived from a bacterial genus or species, including but not limited to, *Bacillus*, e.g., *Bacillus subtilis*, or *Escherichia*, e.g., *Escherichia coli*. In some embodiments, the bacterial species is *Escherichia coli*. In some embodiments, the bacterial species is *Escherichia coli* strain Nissle.

Assays for testing the activity of a GABA transporter, a functional variant of a GABA transporter, or a functional fragment of transporter of GABA are well known to one of ordinary skill in the art.

GABA transporters may be expressed or modified in the bacteria in order to enhance GABA transport into the cell. Specifically, when the GABA transporter is expressed in the recombinant bacterial cells, the bacterial cells import more GABA into the cell when the transporter is expressed than unmodified bacteria of the same bacterial subtype under the same conditions. In one embodiment, the bacterial cell comprises a heterologous gene encoding a GABA transporter. In one embodiment, the bacterial cell comprises a heterologous gene encoding a GABA transporter and a genetic modification that reduces export of a GABA, e.g., a genetic mutation in an exporter gene or promoter.

In one embodiment, the bacterial cell comprises at least one gene encoding a GABA transporter from a different organism, e.g., a different species of bacteria. In one embodiment, the bacterial cell comprises at least one native gene encoding a GABA transporter. In some embodiments, the at least one native gene encoding a GABA transporter is not modified. In another embodiment, the bacterial cell comprises more than one copy of at least one native gene encoding a GABA transporter. In yet another embodiment, the bacterial cell comprises a copy of at least one gene encoding a native GABA transporter, as well as at least one copy of at least one heterologous gene encoding a GABA transporter from a different bacterial species. In one embodiment, the bacterial cell comprises at least one, two, three, four, five, or six copies of the at least one heterologous gene encoding a GABA transporter. In one embodiment, the bacterial cell comprises multiple copies of the at least one heterologous gene encoding a GABA transporter.

In one embodiment, the recombinant bacterial cell comprises a heterologous gene encoding a GABA transporter, wherein said GABA transporter comprises a GABA sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the GABA sequence of a polypeptide encoded by a GABA transporter gene disclosed herein.

The present disclosure further comprises genes encoding functional fragments of a GABA transporter or functional variants of a GABA transporter. As used herein, the term "functional fragment thereof" or "functional variant thereof" of a GABA transporter relates to an element having qualitative biological activity in common with the wild-type GABA transporter from which the fragment or variant was derived. For example, a functional fragment or a functional variant of a mutated GABA transporter is one which retains essentially the same ability to import GABA into the bacterial cell as does the GABA transporter protein from which the functional fragment or functional variant was derived. In one embodiment, the recombinant bacterial cell comprises at least one heterologous gene encoding a functional fragment of a GABA transporter. In another embodiment, the recombinant bacterial cell comprises a heterologous gene encoding a functional variant of a GABA transporter.

In one embodiment, the genes encoding the GABA transporter have been codon-optimized for use in the host organism, e.g., a bacterial cell disclosed herein. In one embodiment, the genes encoding the GABA transporter have been codon-optimized for use in *Escherichia coli*.

The present disclosure also encompasses genes encoding a GABA transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a GABA transporter is mutagenized; mutants exhibiting increased GABA import are selected; and the mutagenized at least one gene encoding a GABA transporter is isolated and inserted into the bacterial cell. In some embodiments, the at least one gene encoding a GABA transporter is mutagenized; mutants exhibiting decreased GABA import are selected; and the mutagenized at least one gene encoding a GABA transporter is isolated and inserted into the bacterial cell. The transporter modifications described herein may be present on a plasmid or chromosome.

In some embodiments, the bacterial cell comprises a heterologous gene encoding a GABA transporter operably linked to a promoter. In one embodiment, the at least one gene encoding a GABA transporter is directly operably linked to the promoter. In another embodiment, the at least one gene encoding a GABA transporter is indirectly operably linked to the promoter.

In one embodiment, the promoter is not operably linked with the at least one gene encoding a GABA transporter in nature. In some embodiments, the at least one gene encoding the GABA transporter is controlled by its native promoter. In some embodiments, the at least one gene encoding the GABA transporter is controlled by an inducible promoter. In some embodiments, the at least one gene encoding the GABA transporter is controlled by a promoter that is stronger than its native promoter. In some embodiments, the at least one gene encoding the GABA transporter is controlled by a constitutive promoter.

In another embodiment, the promoter is an inducible promoter. Inducible promoters are described in more detail infra.

In one embodiment, the at least one gene encoding a GABA transporter is located on a plasmid in the bacterial cell. In some embodiments, the plasmid is a high copy number plasmid. In some embodiments, the plasmid is a low copy number plasmid. In another embodiment, the at least one gene encoding a GABA transporter is located in the chromosome of the bacterial cell. In yet another embodiment, a native copy of the at least one gene encoding a GABA transporter is located in the chromosome of the bacterial cell, and a copy of at least one gene encoding a GABA transporter from a different species of bacteria is located on a plasmid in the bacterial cell. In yet another embodiment, a native copy of the at least one gene encoding a GABA transporter is located on a plasmid in the bacterial cell, and a copy of at least one gene encoding a GABA transporter from a different species of bacteria is located on a plasmid in the bacterial cell. In yet another embodiment, a native copy of the at least one gene encoding a GABA transporter is located in the chromosome of the bacterial cell, and a copy of the at least one gene encoding a GABA transporter from a different species of bacteria is located in the chromosome of the bacterial cell.

In some embodiments, the at least one native gene encoding the GABA transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the GABA transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the GABA transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the GABA transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In one embodiment, the GABA transporter is the GABA transporter GabP, for example the *Escherichia coli* GabP. In one embodiment the GABA transporter is encoded by a amtB gene. In one embodiment, the gabP gene has at least about 80% identity with the sequence of SEQ ID NO:134. Accordingly, in one embodiment, the gabP gene has at least about 90% identity with the sequence of SEQ ID NO:134.

Accordingly, in one embodiment, the gabP gene has at least about 95% identity with the sequence of SEQ ID NO:134. Accordingly, in one embodiment, the gabP gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:134. In another embodiment, the gabP gene comprises the sequence of SEQ ID NO:134. In yet another embodiment the gabP gene consists of the sequence of SEQ ID NO:134.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the GABA transporter is expressed in the recombinant bacterial cells, the bacterial cells import 10% more GABA into the bacterial cell when the transporter is expressed than unmodified bacteria of the same bacterial subtype under the same conditions. In another embodiment, when the GABA transporter is expressed in the recombinant bacterial cells, the bacterial cells import 20%, 30%, 40%, 50%, 60%, 70%, 80%, 90% or 100% more GABA, into the bacterial cell when the transporter is expressed than unmodified bacteria of the same bacterial subtype under the same conditions. In yet another embodiment, when the GABA transporter is expressed in the recombinant bacterial cells, the bacterial cells import two-fold more GABA into the cell when the transporter is expressed than unmodified bacteria of the same bacterial subtype under the same conditions. In yet another embodiment, when the GABA transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more GABA into the cell when the transporter is expressed than unmodified bacteria of the same bacterial subtype under the same conditions.

In one embodiment, the recombinant bacterial cells described herein comprise a first heterologous GABA transporter and a second heterologous GABA transporter. In one embodiment, said first GABA transporter is derived from a different organism than said second GABA transporter. In some embodiments, said first GABA transporter is derived from the same organism as said second GABA transporter. In some embodiments, said first GABA transporter is a wild-type GABA transporter and said second GABA transporter is a mutagenized version of said first GABA transporter. In some embodiments, the recombinant bacterial cells described herein comprise at least a third heterologous GABA transporter. In some embodiments, the recombinant bacterial cells described herein comprise at least four heterologous GABA transporters. In some embodiments, the recombinant bacterial cells described herein comprise at least five heterologous GABA transporters or more.

In some embodiment, the recombinant bacterial cell comprising a heterologous gene encoding an GABA transporter may be used to treat a disease, condition, and/or symptom associated with hyperammonenia. In some embodiment, the recombinant bacterial cells described herein can be used to treat hepatic encephalopathy. In some embodiment, the recombinant bacterial cells described herein can be used to treat Huntington's disease. In some embodiments, the invention provides methods for reducing, ameliorating, or eliminating one or more symptom(s) associated with hepatic encephalopathy and Huntington's disease. In some embodiments, the symptom(s) associated thereof include, but are not limited to, seizures, ataxia, stroke-like lesions, coma, psychosis, vision loss, acute encephalopathy, cerebral edema, as well as vomiting, respiratory alkalosis, and hypothermia.

J. Manganese Transporters

In biological systems, manganese ($Mn^{2+}$) is an essential trace metal and plays an important role in enzyme-mediated catalysis, but can also have deleterious effects. Manganese is a biologically important trace metal and is required for the survival of most living organisms. Cells maintain manganese under tight homeostatic control in order to avoid toxicity. In mammals, manganese is excreted in the bile, but its disposal is affected by the impaired flow of bile from the liver to the duodenum (i.e., cholestasis) that accompanies liver failure Similar to ammonia, elevated concentrations of manganese play a role in the development of hepatic encephalopathy (Rivera-Manda et al. (2012) *Neurochem. Res.* 37(5): 1074-1084). Astrocytes in the brain which detoxify ammonia in a reaction catalyzed by glutamine synthetase, require manganese as a cofactor and thus have a tendency to accumulate this metal (Aschner et al. (1999) *Neurotoxicology* 20(2-3): 173-180). In vitro studies have demonstrated that manganese can result in the inhibition of glutamate transport (Hazell and Norenberg, 1997), abnormalities in astrocyte morphology (Hazell et al. (2006) *Neurosci. Lett.* 396(3): 167-71), and increased cell volume (Rama Rao et al., 2007). Some disorders associated with hyperammonemia may also be characterized by elevated levels of manganese; manganese may contribute to disease pathogenesis (e.g., hepatic encephalopathy) (Rivera-Manda et al., 2012). Manganese and ammonia have also been shown to act synergistically in the pathogenesis of hepatic encephalopathy (Jayakumar et al. (2004) *Neurochem. Res.* 29(11): 2051-6).

In one embodiment, the recombinant bacterial cell of the invention comprises a heterologous gene encoding a substrate transporter, wherein the substrate transporter is a manganese transporter. In one embodiment, the manganese transporter transports manganese into the cell.

The uptake of manganese into bacterial cells is mediated by proteins well known to those of skill in the art. For example, the manganese transporter MntH is a membrane transport protein capable of transporting manganese into bacterial cells (see, e.g., Jensen and Jensen (2014) Chapter 1: Manganese transport, trafficking and function in invertebrates. In: Manganese in Health and Disease, pp. 1-33). In *Escherichia coli*, the mntH gene encodes a proton-stimulated, divalent metal cation uptake system involved in manganese transport (Porcheron et al. (2013) *Front. Cell. Infect. Microbiol.* 3: 90). In one embodiment, the manganese transporter is selected from the group consisting of mntH, MntABCD, SitABCD, PsaABCD, YfeABCD. In one embodiment, the at least one gene encoding a manganese transporter is encoded by an mntH gene. In one embodiment, the at least one gene encoding a manganese transporter is encoded by an MntABCD operon. In one embodiment, the at least one gene encoding a manganese transporter is encoded by an sitABCD operon. In one embodiment, the at least one gene encoding a manganese transporter is encoded by an PsaABCD operon. In one embodiment, the at least one gene encoding a manganese transporter is encoded by an YfeABCD operon. In one embodiment, the bacterial cell described herein has been genetically engineered to comprise at least one heterologous mntH gene.

Metal ion homeostasis in prokaryotic cells, which lack internal compartmentalization, is maintained by the tight regulation of metal ion flux across in cytoplasmic membrane (Jensen and Jensen, 2014). Manganese uptake in bacteria predominantly involves two major types of transporters: proton-dependent Nramprelated transporters, and/or ATP-dependent ABC transporters. The Nramp (Natural resistance-§.ssociated macrophage Qrotein) transporter family was first described in plants, animals, and yeasts (Cellier et al. (1996) *Trends Genet.* 12(6): 201-4), but MntH has since been characterized in several bacterial species (Porcheron et al., 2013). Selectivity of the Nramp1 transporter for manganese has been shown in metal accumulation studies, wherein overexpression of *Staphylococcus aureus* mntH resulted in increased levels of cell-associated manganese, but no accumulation of calcium, copper, iron, magnesium, or zinc (Horsburgh et al. (2002) *Mol. Microbiol.* 44(5): 1269-86). Additionally, *Bacillus subtilis* strains comprising a mutation in the mntH gene exhibited impaired growth in metal-free medium that was rescued by the addition of manganese (Que and Heimann (2000) *Mol. Microbiol.* 35(6): 1454-68).

High-affinity manganese uptake may also be mediated by ABC (ATP-binding cassette) transporters. Members of this transporter superfamily utilize the hydrolysis of ATP to fuel the import or export of diverse substrates, ranging from ions to macromolecules, and are well characterized for their role in multi-drug resistance in both prokaryotic and eukaryotic cells. Non-limiting examples of bacterial ABC transporters involved in manganese import include MntABCD (*Bacilis subtilis, Staphylococcus aureus*), SitABCD (*Salmonella typhimurium, Shigella flexneri*), PsaABCD (*Streptococcus pneumoniae*), and YfeABCD (*Yersinia pestis*) (Bearden and Perry (1999) *Mol. Microbiol.* 32(2):403-14; Kehres et al. (2002) *J. Bacteriol.* 184(12): 3159-66; McAllister et al. (2004) *Mol. Microbiol.* 53(3): 889-901; Zhou et al. (1999) *Infect. Immun.* 67(4): 1974-81). The MntABCD transporter complex consists of three subunits, wherein MntC and MntD are integral membrane proteins that comprise the permease subunit mediate cation transport, MntB is the ATPase, and MntA binds and delivers manganese to the permease submit. Other ABC transporter operons, such as sitABCD, psaABCD, and yfeABCD, exhibit similar subunit organization and function (Higgins, 1992; Rees et al. (2009) *Nat. Rev. Mol. Cell Biol.* 10(3): 218-227).

In some embodiments, the manganese transporter is encoded by a manganese transporter gene derived from a bacterial genus or species, including but not limited to, *Bacillus*, e.g., *Bacillus subtilis, Staphylococcus*, e.g., *Staphylococcus aureus, Salmonella*, e.g., *Salmonella typhimurium, Shigella*, e.g., *Shigella flexneri, Yersinia*, e.g., *Yersinia pestis*, or *Escherichia*, e.g., *Escherichia coli*. In some embodiments, the bacterial species is *Escherichia coli*. In some embodiments, the bacterial species is *Escherichia coli* strain Nissle.

Assays for testing the activity of a manganese transporter, a functional variant of a manganese transporter, or a functional fragment of transporter of manganese are well known to one of ordinary skill in the art.

Manganese transporters may be expressed or modified in the bacteria in order to enhance manganese transport into the cell. Specifically, when the manganese transporter is expressed in the recombinant bacterial cells, the bacterial cells import more manganese into the cell when the transporter is expressed than unmodified bacteria of the same bacterial subtype under the same conditions. In one embodiment, the bacterial cell comprises a heterologous gene encoding a manganese transporter. In one embodiment, the bacterial cell comprises a heterologous gene encoding a manganese transporter and a genetic modification that reduces export of a manganese, e.g., a genetic mutation in an exporter gene or promoter.

In one embodiment, the bacterial cell comprises at least one gene encoding a manganese transporter from a different organism, e.g., a different species of bacteria. In one embodiment, the bacterial cell comprises at least one native gene encoding a manganese transporter. In some embodiments, the at least one native gene encoding a manganese transporter is not modified. In another embodiment, the bacterial cell comprises more than one copy of at least one native gene encoding a manganese transporter. In yet another embodiment, the bacterial cell comprises a copy of at least one gene encoding a native manganese transporter, as well as at least one copy of at least one heterologous gene encoding a manganese transporter from a different bacterial species. In one embodiment, the bacterial cell comprises at least one, two, three, four, five, or six copies of the at least one heterologous gene encoding a manganese transporter. In one embodiment, the bacterial cell comprises multiple copies of the at least one heterologous gene encoding a manganese transporter.

In one embodiment, the recombinant bacterial cell comprises a heterologous gene encoding a manganese transporter, wherein said manganese transporter comprises a manganese sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the manganese sequence of a polypeptide encoded by a manganese transporter gene disclosed herein.

The present disclosure further comprises genes encoding functional fragments of a manganese transporter or functional variants of a manganese transporter. As used herein, the term "functional fragment thereof" or "functional variant thereof" of a manganese transporter relates to an element having qualitative biological activity in common with the wild-type manganese transporter from which the fragment or variant was derived. For example, a functional fragment or a functional variant of a mutated manganese transporter is one which retains essentially the same ability to import manganese into the bacterial cell as does the manganese transporter protein from which the functional fragment or functional variant was derived. In one embodiment, the recombinant bacterial cell comprises at least one heterologous gene encoding a functional fragment of a manganese transporter. In another embodiment, the recombinant bacterial cell comprises a heterologous gene encoding a functional variant of a manganese transporter.

In one embodiment, the genes encoding the manganese transporter have been codon-optimized for use in the host organism, e.g., a bacterial cell disclosed herein. In one embodiment, the genes encoding the manganese transporter have been codon-optimized for use in *Escherichia coli*.

The present disclosure also encompasses genes encoding a manganese transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a manganese transporter is mutagenized; mutants exhibiting increased manganese import are selected; and the mutagenized at least one gene encoding a manganese transporter is isolated and inserted into the bacterial cell. In some embodiments, the at least one gene encoding a manganese transporter is mutagenized; mutants exhibiting decreased manganese import are selected; and the mutagenized at least one gene encoding a manganese transporter is isolated and inserted into the bacterial cell. The transporter modifications described herein may be present on a plasmid or chromosome.

In some embodiments, the bacterial cell comprises a heterologous gene encoding a manganese transporter operably linked to a promoter. In one embodiment, the at least one gene encoding a manganese transporter is directly operably linked to the promoter. In another embodiment, the at least one gene encoding a manganese transporter is indirectly operably linked to the promoter.

In one embodiment, the promoter is not operably linked with the at least one gene encoding a manganese transporter in nature. In some embodiments, the at least one gene encoding the manganese transporter is controlled by its native promoter. In some embodiments, the at least one gene encoding the manganese transporter is controlled by an inducible promoter. In some embodiments, the at least one gene encoding the manganese transporter is controlled by a promoter that is stronger than its native promoter. In some embodiments, the at least one gene encoding the manganese transporter is controlled by a constitutive promoter.

In another embodiment, the promoter is an inducible promoter. Inducible promoters are described in more detail infra.

In one embodiment, the at least one gene encoding a manganese transporter is located on a plasmid in the bacterial cell. In some embodiments, the plasmid is a high copy number plasmid. In some embodiments, the plasmid is a low copy number plasmid. In another embodiment, the at least one gene encoding a manganese transporter is located in the chromosome of the bacterial cell. In yet another embodiment, a native copy of the at least one gene encoding a manganese transporter is located in the chromosome of the bacterial cell, and a copy of at least one gene encoding a manganese transporter from a different species of bacteria is located on a plasmid in the bacterial cell. In yet another embodiment, a native copy of the at least one gene encoding a manganese transporter is located on a plasmid in the bacterial cell, and a copy of at least one gene encoding a manganese transporter from a different species of bacteria is located on a plasmid in the bacterial cell. In yet another embodiment, a native copy of the at least one gene encoding a manganese transporter is located in the chromosome of the bacterial cell, and a copy of the at least one gene encoding a manganese transporter from a different species of bacteria is located in the chromosome of the bacterial cell.

In some embodiments, the at least one native gene encoding the manganese transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the manganese transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the manganese transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the manganese transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In one embodiment, the manganese transporter is the manganese transporter GabP, for example the *Escherichia coli* mntH gene. In one embodiment the manganese transporter is encoded by a mntH gene. In one embodiment, the mntH gene has at least about 80% identity with the sequence of SEQ ID NO:135. Accordingly, in one embodiment, the mntH gene has at least about 90% identity with the sequence of SEQ ID NO:135. Accordingly, in one embodiment, the mntH gene has at least about 95% identity with the sequence of SEQ ID NO:135. Accordingly, in one embodiment, the mntH gene has at least about 70%, 75%, 80%, 85%, 86%, 87%, 88%, 89%, 90%, 91%, 92%, 93%, 94%, 95%, 96%, 97%, 98%, or 99% identity with the sequence of SEQ ID NO:135. In another embodiment, the mntH gene comprises the sequence of SEQ ID NO:135. In yet another embodiment the mntH gene consists of the sequence of SEQ ID NO:135.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the manganese transporter is expressed in the recombinant bacterial cells, the bacterial cells import 10% more manganese into the bacterial cell when the transporter is expressed than unmodified bacteria of the same bacterial subtype under the same conditions. In another embodiment, when the manganese transporter is expressed in the recombinant bacterial cells, the bacterial cells import 20%, 30%, 40%, 50%, 60%, 70%, 80%, 90% or 100% more manganese, into the bacterial cell when the transporter is expressed than unmodified bacteria of the same bacterial subtype under the same conditions. In yet another embodiment, when the manganese transporter is expressed in the recombinant bacterial cells, the bacterial cells import two-fold more manganese into the cell when the transporter is expressed than unmodified bacteria of the same bacterial subtype under the same conditions. In yet another embodiment, when the manganese transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more manganese into the cell when the transporter is expressed than unmodified bacteria of the same bacterial subtype under the same conditions.

In one embodiment, the recombinant bacterial cells described herein comprise a first heterologous manganese transporter and a second heterologous manganese transporter. In one embodiment, said first manganese transporter is derived from a different organism than said second manganese transporter. In some embodiments, said first manganese transporter is derived from the same organism as said second manganese transporter. In some embodiments, said first manganese transporter is a wild-type manganese transporter and said second manganese transporter is a mutagenized version of said first manganese transporter. In some embodiments, the recombinant bacterial cells described herein comprise at least a third heterologous manganese transporter. In some embodiments, the recombinant bacterial cells described herein comprise at least four heterologous manganese transporters. In some embodiments, the recombinant bacterial cells described herein comprise at least five heterologous manganese transporters or more.

In some embodiment, the recombinant bacterial cell comprising a heterologous gene encoding an manganese transporter may be used to treat a disease, condition, and/or symptom associated with hyperammonenia. In some embodiment, the recombinant bacterial cells described herein can be used to treat hepatic encephalopathy. In some embodiment, the recombinant bacterial cells described herein can be used to treat Huntington's disease. In some embodiments, the invention provides methods for reducing, ameliorating, or eliminating one or more symptom(s) associated with hepatic encephalopathy and Huntington's disease. In some embodiments, the symptom(s) associated thereof include, but are not limited to, seizures, ataxia, stroke-like lesions, coma, psychosis, vision loss, acute encephalopathy, cerebral edema, as well as vomiting, respiratory alkalosis, and hypothermia.

K. Toxin Transporters

In one embodiment, the recombinant bacterial cell of the invention comprises a heterologous gene encoding a substrate transporter, wherein the substrate transporter is a toxin transporter. In one embodiment, the toxin transporter transports toxin into the cell.

In some embodiments, the toxin transporter is encoded by a toxin transporter gene derived from a bacterial genus or species, including but not limited to, *Escherichia, Corynebacterium, Escherichia coli, Saccharomyces cerevisiae* or *Corynebacterium glutamicum*. In some embodiments, the bacterial species is *Escherichia coli*. In some embodiments, the bacterial species is *Escherichia coli* strain Nissle.

Assays for testing the activity of a toxin transporter, a functional variant of a toxin transporter, or a functional fragment of transporter of toxin are well known to one of ordinary skill in the art.

Toxin transporters may be expressed or modified in the bacteria in order to enhance toxin transport into the cell. Specifically, when the toxin transporter is expressed in the recombinant bacterial cells, the bacterial cells import more toxin into the cell when the transporter is expressed than unmodified bacteria of the same bacterial subtype under the same conditions. In one embodiment, the bacterial cell comprises a heterologous gene encoding a toxin transporter. In one embodiment, the bacterial cell comprises a heterologous gene encoding a toxin transporter and a genetic modification that reduces export of a toxin, e.g., a genetic mutation in an exporter gene or promoter.

In one embodiment, the bacterial cell comprises at least one gene encoding a toxin transporter from a different organism, e.g., a different species of bacteria. In one embodiment, the bacterial cell comprises at least one native gene encoding a toxin transporter. In some embodiments, the at least one native gene encoding a toxin transporter is not modified. In another embodiment, the bacterial cell comprises more than one copy of at least one native gene encoding a toxin transporter. In yet another embodiment, the bacterial cell comprises a copy of at least one gene encoding a native toxin transporter, as well as at least one copy of at least one heterologous gene encoding a toxin transporter from a different bacterial species. In one embodiment, the bacterial cell comprises at least one, two, three, four, five, or six copies of the at least one heterologous gene encoding a toxin transporter. In one embodiment, the bacterial cell comprises multiple copies of the at least one heterologous gene encoding a toxin transporter.

In one embodiment, the recombinant bacterial cell comprises a heterologous gene encoding a toxin transporter, wherein said toxin transporter comprises a toxin sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the toxin sequence of a polypeptide encoded by a toxin transporter gene disclosed herein.

The present disclosure further comprises genes encoding functional fragments of a toxin transporter or functional variants of a toxin transporter. As used herein, the term "functional fragment thereof" or "functional variant thereof" of a toxin transporter relates to an element having qualitative biological activity in common with the wild-type toxin transporter from which the fragment or variant was derived. For example, a functional fragment or a functional variant of a mutated toxin transporter is one which retains essentially the same ability to import toxin into the bacterial cell as does the toxin transporter protein from which the functional fragment or functional variant was derived. In one embodiment, the recombinant bacterial cell comprises at least one heterologous gene encoding a functional fragment of a toxin transporter. In another embodiment, the recombinant bacterial cell comprises a heterologous gene encoding a functional variant of a toxin transporter.

In one embodiment, the genes encoding the toxin transporter have been codon-optimized for use in the host organism, e.g., a bacterial cell disclosed herein. In one embodiment, the genes encoding the toxin transporter have been codon-optimized for use in *Escherichia coli*.

The present disclosure also encompasses genes encoding a toxin transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a toxin transporter is mutagenized; mutants exhibiting increased toxin import are selected; and the mutagenized at least one gene encoding a toxin transporter is isolated and inserted into the bacterial cell. In some embodiments, the at least one gene encoding a toxin transporter is mutagenized; mutants exhibiting decreased toxin import are selected; and the mutagenized at least one gene encoding a toxin transporter is isolated and inserted into the bacterial cell. The transporter modifications described herein may be present on a plasmid or chromosome.

In some embodiments, the bacterial cell comprises a heterologous gene encoding a toxin transporter operably linked to a promoter. In one embodiment, the at least one gene encoding a toxin transporter is directly operably linked to the promoter. In another embodiment, the at least one gene encoding a toxin transporter is indirectly operably linked to the promoter.

In one embodiment, the promoter is not operably linked with the at least one gene encoding a toxin transporter in nature. In some embodiments, the at least one gene encoding the toxin transporter is controlled by its native promoter. In some embodiments, the at least one gene encoding the toxin transporter is controlled by an inducible promoter. In some embodiments, the at least one gene encoding the toxin transporter is controlled by a promoter that is stronger than its native promoter. In some embodiments, the at least one gene encoding the toxin transporter is controlled by a constitutive promoter.

In another embodiment, the promoter is an inducible promoter. Inducible promoters are described in more detail infra.

In one embodiment, the at least one gene encoding a toxin transporter is located on a plasmid in the bacterial cell. In some embodiments, the plasmid is a high copy number plasmid. In some embodiments, the plasmid is a low copy number plasmid. In another embodiment, the at least one gene encoding a toxin transporter is located in the chromosome of the bacterial cell. In yet another embodiment, a native copy of the at least one gene encoding a toxin transporter is located in the chromosome of the bacterial cell, and a copy of at least one gene encoding a toxin transporter from a different species of bacteria is located on a plasmid in the bacterial cell. In yet another embodiment, a native copy of the at least one gene encoding a toxin transporter is located on a plasmid in the bacterial cell, and a copy of at least one gene encoding a toxin transporter from a different species of bacteria is located on a plasmid in the bacterial cell. In yet another embodiment, a native copy of the at least one gene encoding a toxin transporter is located in the chromosome of the bacterial cell, and a copy of the at least one gene encoding a toxin transporter from a different species of bacteria is located in the chromosome of the bacterial cell.

In some embodiments, the at least one native gene encoding the toxin transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the toxin transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the toxin transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the toxin transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the toxin transporter is expressed in the recombinant bacterial cells, the bacterial cells import 10% more toxin into the bacterial cell when the transporter is expressed than unmodified bacteria of the same bacterial subtype under the same conditions. In another embodiment, when the toxin transporter is expressed in the recombinant bacterial cells, the bacterial cells import 20%, 30%, 40%, 50%, 60%, 70%, 80%, 90% or 100% more PGE2, into the bacterial cell when the transporter is expressed than unmodified bacteria of the same bacterial subtype under the same conditions. In yet another embodiment, when the toxin transporter is expressed in the recombinant bacterial cells, the bacterial cells import two-fold more toxin into the cell when the transporter is expressed than unmodified bacteria of the same bacterial subtype under the same conditions. In yet another embodiment, when the toxin transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more toxin into the cell when the transporter is expressed than unmodified bacteria of the same bacterial subtype under the same conditions.

In one embodiment, the recombinant bacterial cells described herein comprise a first heterologous toxin transporter and a second heterologous toxin transporter. In one embodiment, said first toxin transporter is derived from a different organism than said second toxin transporter. In some embodiments, said first toxin transporter is derived from the same organism as said second toxin transporter. In some embodiments, said first toxin transporter imports the same toxin as said second toxin transporter. In other embodiment, said first toxin transporter imports a different toxin from said second toxin transporter. In some embodiments, said first toxin transporter is a wild-type toxin transporter and said second toxin transporter is a mutagenized version of said first toxin transporter. In some embodiments, the recombinant bacterial cells described herein comprise at least a third heterologous toxin transporter. In some embodiments, the recombinant bacterial cells described herein comprise at least four heterologous toxin transporters. In some embodiments, the recombinant bacterial cells described herein comprise at least five heterologous toxin transporters or more.

L. Peptide Transporters

In one embodiment, the recombinant bacterial cell of the invention comprises a heterologous gene encoding a substrate transporter, wherein the substrate transporter is a peptide transporter.

In some embodiments, the peptide transporter is encoded by a peptide transporter gene derived from a bacterial genus or species, including but not limited to, *Escherichia, Corynebacterium, Escherichia coli, Saccharomyces cerevisiae* or *Corynebacterium glutamicum*. In some embodiments, the bacterial species is *Escherichia coli*. In some embodiments, the bacterial species is *Escherichia coli* strain Nissle.

Assays for testing the activity of a peptide transporter, a functional variant of a peptide transporter, or a functional fragment of transporter of peptide are well known to one of ordinary skill in the art.

Peptide transporters may be expressed or modified in the bacteria in order to enhance peptide transport into the cell. Specifically, when the peptide transporter is expressed in the recombinant bacterial cells, the bacterial cells import more peptide into the cell when the transporter is expressed than unmodified bacteria of the same bacterial subtype under the same conditions. In one embodiment, the bacterial cell comprises a heterologous gene encoding a peptide transporter. In one embodiment, the bacterial cell comprises a heterologous gene encoding a peptide transporter and a genetic modification that reduces export of a peptide, e.g., a genetic mutation in an exporter gene or promoter.

In one embodiment, the bacterial cell comprises at least one gene encoding a peptide transporter from a different organism, e.g., a different species of bacteria. In one embodiment, the bacterial cell comprises at least one native gene encoding a peptide transporter. In some embodiments, the at least one native gene encoding a peptide transporter is not modified. In another embodiment, the bacterial cell comprises more than one copy of at least one native gene encoding a peptide transporter. In yet another embodiment, the bacterial cell comprises a copy of at least one gene encoding a native peptide transporter, as well as at least one copy of at least one heterologous gene encoding a peptide transporter from a different bacterial species. In one embodiment, the bacterial cell comprises at least one, two, three, four, five, or six copies of the at least one heterologous gene encoding a peptide transporter. In one embodiment, the bacterial cell comprises multiple copies of the at least one heterologous gene encoding a peptide transporter.

In one embodiment, the recombinant bacterial cell comprises a heterologous gene encoding a peptide transporter, wherein said peptide transporter comprises a peptide sequence that has at least 70%, 75%, 80%, 81%, 82%, 83% 84%, 85%, 86%, 87%, 88%, 89%, 90%, 91%, 92%, 93%, 94%, 95%, 96%, 97%, 98%, 99%, or 100% identity to the peptide sequence of a polypeptide encoded by a peptide transporter gene disclosed herein.

The present disclosure further comprises genes encoding functional fragments of a peptide transporter or functional variants of a peptide transporter. As used herein, the term "functional fragment thereof" or "functional variant thereof" of a peptide transporter relates to an element having qualitative biological activity in common with the wild-type peptide transporter from which the fragment or variant was derived. For example, a functional fragment or a functional variant of a mutated peptide transporter is one which retains essentially the same ability to import peptide into the bacterial cell as does the peptide transporter protein from which the functional fragment or functional variant was derived. In one embodiment, the recombinant bacterial cell comprises at least one heterologous gene encoding a functional fragment of a peptide transporter. In another embodiment, the recombinant bacterial cell comprises a heterologous gene encoding a functional variant of a peptide transporter.

In one embodiment, the genes encoding the peptide transporter have been codon-optimized for use in the host organism, e.g., a bacterial cell disclosed herein. In one embodiment, the genes encoding the peptide transporter have been codon-optimized for use in *Escherichia coli*.

The present disclosure also encompasses genes encoding a peptide transporter comprising amino acids in its sequence that are substantially the same as an amino acid sequence described herein Amino acid sequences that are substantially the same as the sequences described herein include sequences comprising conservative amino acid substitutions, as well as amino acid deletions and/or insertions.

In some embodiments, the at least one gene encoding a peptide transporter is mutagenized; mutants exhibiting increased peptide import are selected; and the mutagenized at least one gene encoding a peptide transporter is isolated and inserted into the bacterial cell. In some embodiments, the at least one gene encoding a peptide transporter is mutagenized; mutants exhibiting decreased peptide import are selected; and the mutagenized at least one gene encoding a peptide transporter is isolated and inserted into the bacterial cell. The transporter modifications described herein may be present on a plasmid or chromosome.

In some embodiments, the bacterial cell comprises a heterologous gene encoding a peptide transporter operably linked to a promoter. In one embodiment, the at least one gene encoding a peptide transporter is directly operably linked to the promoter. In another embodiment, the at least one gene encoding a peptide transporter is indirectly operably linked to the promoter.

In one embodiment, the promoter is not operably linked with the at least one gene encoding a peptide transporter in nature. In some embodiments, the at least one gene encoding the peptide transporter is controlled by its native promoter. In some embodiments, the at least one gene encoding the peptide transporter is controlled by an inducible promoter. In some embodiments, the at least one gene encoding the peptide transporter is controlled by a promoter that is stronger than its native promoter. In some embodiments, the at least one gene encoding the peptide transporter is controlled by a constitutive promoter.

In another embodiment, the promoter is an inducible promoter. Inducible promoters are described in more detail infra.

In one embodiment, the at least one gene encoding a peptide transporter is located on a plasmid in the bacterial cell. In some embodiments, the plasmid is a high copy number plasmid. In some embodiments, the plasmid is a low copy number plasmid. In another embodiment, the at least one gene encoding a peptide transporter is located in the chromosome of the bacterial cell. In yet another embodiment, a native copy of the at least one gene encoding a peptide transporter is located in the chromosome of the bacterial cell, and a copy of at least one gene encoding a peptide transporter from a different species of bacteria is located on a plasmid in the bacterial cell. In yet another embodiment, a native copy of the at least one gene encoding a peptide transporter is located on a plasmid in the bacterial cell, and a copy of at least one gene encoding a peptide transporter from a different species of bacteria is located on a plasmid in the bacterial cell. In yet another embodiment, a native copy of the at least one gene encoding a peptide transporter is located in the chromosome of the bacterial cell, and a copy of the at least one gene encoding a peptide transporter from a different species of bacteria is located in the chromosome of the bacterial cell.

In some embodiments, the at least one native gene encoding the peptide transporter in the recombinant bacterial cell is not modified, and one or more additional copies of the native transporter are inserted into the genome. In alternate embodiments, the at least one native gene encoding the transporter is not modified, and one or more additional copies of the transporter from a different bacterial species is inserted into the genome of the recombinant bacterial cell. In some embodiments, the at least one native gene encoding the peptide transporter in the recombinant bacterial cell is modified, and one or more additional copies of the native transporter are inserted into the genome. In alternate embodiments, the at least one native gene encoding the transporter is modified, and one or more additional copies of the transporter from a different bacterial species is inserted into the genome of the recombinant bacterial cell.

In some embodiments, at least one native gene encoding the peptide transporter in the bacterial cell is not modified, and one or more additional copies of at least one native gene encoding the transporter are present in the bacterial cell on a plasmid. In alternate embodiments, the at least one native gene encoding the transporter is not modified, and a copy of at least one gene encoding the transporter from a different bacterial species is present in the bacteria on a plasmid. In some embodiments, at least one native gene encoding the peptide transporter in the bacterial cell is modified, and one or more additional copies of at least one native gene encoding the transporter are present in the bacterial cell on a plasmid. In alternate embodiments, the at least one native gene encoding the transporter is modified, and a copy of at least one gene encoding the transporter from a different bacterial species is present in the bacteria on a plasmid.

In some embodiments, the bacterium is *E. coli* Nissle, and the at least one native gene encoding the transporter in *E. coli* Nissle is not modified; one or more additional copies at least one native gene encoding the transporter from *E. coli* Nissle is inserted into the *E. coli* Nissle genome. In an alternate embodiment, the at least one native gene encoding the transporter in *E. coli* Nissle is not modified, and a copy of at least one gene encoding the transporter from a different bacterial species is inserted into the *E. coli* Nissle genome.

In one embodiment, when the peptide transporter is expressed in the recombinant bacterial cells, the bacterial cells import 10% more peptide into the bacterial cell when the transporter is expressed than unmodified bacteria of the same bacterial subtype under the same conditions. In another embodiment, when the peptide transporter is expressed in the recombinant bacterial cells, the bacterial cells import 20%, 30%, 40%, 50%, 60%, 70%, 80%, 90% or 100% more PGE2, into the bacterial cell when the transporter is expressed than unmodified bacteria of the same bacterial subtype under the same conditions. In yet another embodiment, when the peptide transporter is expressed in the recombinant bacterial cells, the bacterial cells import two-fold more peptide into the cell when the transporter is expressed than unmodified bacteria of the same bacterial subtype under the same conditions. In yet another embodiment, when the peptide transporter is expressed in the recombinant bacterial cells, the bacterial cells import three-fold, four-fold, five-fold, six-fold, seven-fold, eight-fold, nine-fold, ten-fold, fifteen-fold, twenty-fold, thirty-fold, forty-fold, or fifty-fold more peptide into the cell when the transporter is expressed than unmodified bacteria of the same bacterial subtype under the same conditions.

In one embodiment, the recombinant bacterial cells described herein comprise a first heterologous peptide transporter and a second heterologous peptide transporter. In one embodiment, said first peptide transporter is derived from a different organism than said second peptide transporter. In some embodiments, said first peptide transporter is derived from the same organism as said second peptide transporter. In some embodiments, said first peptide transporter imports the same peptide as said second peptide transporter. In other embodiment, said first peptide transporter imports a different peptide from said second peptide transporter. In some embodiments, said first peptide transporter is a wild-type peptide transporter and said second peptide transporter is a mutagenized version of said first peptide transporter. In some embodiments, the recombinant bacterial cells described herein comprise at least a third heterologous peptide transporter. In some embodiments, the recombinant bacterial cells described herein comprise at least four heterologous peptide transporters. In some embodiments, the recombinant bacterial cells described herein comprise at least five heterologous peptide transporters or more.

Inducible Promoters

In some embodiments, the bacterial cell comprises a stably maintained plasmid or chromosome carrying the gene(s) encoding the tranporter(s), such that the tranporter(s) can be expressed in the host cell, and the host cell is capable of survival and/or growth in vitro, e.g., in medium, and/or in vivo, e.g., in the gut. In some embodiments, bacterial cell comprises two or more distinct tranporters or operons, e.g., two or more tranporter genes. In some embodiments, bacterial cell comprises three or more distinct transporters or operons, e.g., three or more tranporter genes. In some embodiments, bacterial cell comprises 4, 5, 6, 7, 8, 9, 10, or more distinct tranporters or operons, e.g., 4, 5, 6, 7, 8, 9, 10, or more tranporter genes.

In some embodiments, the genetically engineered bacteria comprise multiple copies of the same tranporter gene(s). In some embodiments, the gene encoding the tranporter is present on a plasmid and operably linked to a directly or indirectly inducible promoter. In some embodiments, the gene encoding the tranporter is present on a plasmid and operably linked to a promoter that is induced under low-oxygen or anaerobic conditions. In some embodiments, the gene encoding the tranporter is present on a chromosome and operably linked to a directly or indirectly inducible promoter. In some embodiments, the gene encoding the tranporter is present in the chromosome and operably linked to a promoter that is induced under low-oxygen or anaerobic conditions. In some embodiments, the gene encoding the tranporter is present on a plasmid and operably linked to a promoter that is induced by exposure to tetracycline or arabinose.

In some embodiments, the promoter that is operably linked to the gene encoding the tranporter is directly induced by exogenous environmental conditions. In some embodiments, the promoter that is operably linked to the gene encoding the tranporter is indirectly induced by exogenous environmental conditions. In some embodiments, the promoter is directly or indirectly induced by exogenous environmental conditions specific to the gut of a mammal. In some embodiments, the promoter is directly or indirectly induced by exogenous environmental conditions specific to the small intestine of a mammal. In some embodiments, the promoter is directly or indirectly induced by low-oxygen or anaerobic conditions such as the environment of the mammalian gut. In some embodiments, the promoter is directly or indirectly induced by molecules or metabolites that are specific to the gut of a mammal. In some embodiments, the promoter is directly or indirectly induced by a molecule that is co-administered with the bacterial cell.

In certain embodiments, the bacterial cell comprises a gene encoding an tranporter expressed under the control of a fumarate and nitrate reductase regulator (FNR) responsive promoter. In E. coli, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. FNR responsive promoters include, but are not limited to, the FNR responsive promoters listed in the chart, below. Underlined sequences are predicted ribosome binding sites, and bolded sequences are restriction sites used for cloning.

In some embodiments, the bacterial cell comprises an oxygen-level dependent transcriptional regulator, e.g., FNR, ANR, or DNR, and corresponding promoter from a different bacterial species. The heterologous oxygen-level dependent transcriptional regulator and promoter increase the transcription of genes operably linked to said promoter, e.g., the gene encoding the tranporter, in a low-oxygen or anaerobic environment, as compared to the native gene(s) and promoter in the bacteria under the same conditions. In certain embodiments, the non-native oxygen-level dependent transcriptional regulator is an FNR protein from N. gonorrhoeae (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

| FNR Responsive Promoter | Sequence |
| --- | --- |
| SEQ ID NO: | GTCAGCATAACACCCTGACCTCTCATTAATTGTTCATGCCGGGCGGCACTAT CGTCGTCCGGCCTTTTCCTCTCTTACTCTGCTACGTACATCTATTTCTATAAA TCCGTTCAATTTGTCTGTTTTTTGCACAAACATGAAATATCAGACAATTCCGT GACTTAAGAAAATTTATACAAATCAGCAATATACCCCTTAAGGAGTATATAAA GGTGAATTTGATTTACATCAATAAGCGGGGTTGCTGAATCGTTAAGGTAGGC GGTAATAG<u>AAAAGAAATCGAGGCAAAA</u> |
| SEQ ID NO: | ATTTCCTCTCATCCCATCCGGGGTGAGAGTCTTTTCCCCCGACTTATGGCTC ATGCATGCATCAAAAAAGATGTGAGCTTGATCAAAAACAAAAAATATTTCACT CGACAGGAGTATTTATATTGCGCCCGTTACGTGGGCTTCGACTGTAAATC<u>AG AAAGGAGAAAACACCT</u> |
| SEQ ID NO: | GTCAGCATAACACCCTGACCTCTCATTAATTGTTCATGCCGGGCGGCACTAT CGTCGTCCGGCCTTTTCCTCTCTTACTCTGCTACGTACATCTATTTCTATAAA TCCGTTCAATTTGTCTGTTTTTTGCACAAACATGAAATATCAGACAATTCCGT GACTTAAGAAAATTTATACAAATCAGCAATATACCCCTTAAGGAGTATATAAA GGTGAATTTGATTTACATCAATAAGCGGGGTTGCTGAATCGTTAAGGATCCC <u>TCTAGAAATAATTTTGTTTAACTTTAAGAAGGAGATATACAT</u> |
| SEQ ID NO: | CATTTCCTCTCATCCCATCCGGGGTGAGAGTCTTTTCCCCCGACTTATGGCT CATGCATGCATCAAAAAAGATGTGAGCTTGATCAAAAACAAAAAATATTTCAC TCGACAGGAGTATTTATATTGCGCCCGGATCCCTCTAGAAATAATTTTGTTTA <u>ACTTTAAGAAGGAGATATACAT</u> |
| SEQ ID NO: | AGTTGTTCTTATTGGTGGTGTTGCTTTATGGTTGCATCGTAGTAAATGGTTGT AACAAAAGCAATTTTTCCGGCTGTCTGTATACAAAAACGCCGTAAAGTTTGAG CGAAGTCAATAAACTCTCTACCCATTCAGGGCAATATCTCTCTTGGATCCC<u>T CTAGAAATAATTTTGTTTAACTTTAAGAAGGAGATATACAT</u> |

In one embodiment, the FNR responsive promoter comprises SEQ ID NO:1. In another embodiment, the FNR responsive promoter comprises SEQ ID NO:2. In another embodiment, the FNR responsive promoter comprises SEQ ID NO:3. In another embodiment, the FNR responsive promoter comprises SEQ ID NO:4. In yet another embodiment, the FNR responsive promoter comprises SEQ ID NO:5.

In some embodiments, multiple distinct FNR nucleic acid sequences are inserted in the genetically engineered bacteria. In alternate embodiments, the genetically engineered bacteria comprise a gene encoding an tranporter expressed under the control of an alternate oxygen level-dependent promoter, e.g., DNR (Trunk et al., 2010) or ANR (Ray et al., 1997). In these embodiments, expression of the tranporter gene is particularly activated in a low-oxygen or anaerobic environment, such as in the gut. In some embodiments, gene expression is further optimized by methods known in the art, e.g., by optimizing ribosomal binding sites and/or increasing mRNA stability. In one embodiment, the mammalian gut is a human mammalian gut.

In some embodiments, the genetically engineered bacteria comprise a wild-type oxygen-level dependent transcriptional regulator, e.g., FNR, ANR, or DNR, and corresponding promoter that is mutated relative to the wild-type promoter from bacteria of the same subtype. The mutated promoter enhances binding to the wild-type transcriptional regulator and increases the transcription of genes operably linked to said promoter, e.g., the gene encoding the tranporter, in a low-oxygen or anaerobic environment, as compared to the wild-type promoter under the same conditions. In some embodiments, the genetically engineered bacteria comprise a wild-type oxygen-level dependent promoter, e.g., FNR, ANR, or DNR promoter, and corresponding transcriptional regulator that is mutated relative to the wild-type transcriptional regulator from bacteria of the same subtype. The mutated transcriptional regulator enhances binding to the wild-type promoter and increases the transcription of genes operably linked to said promoter, e.g., the gene encoding the tranporter, in a low-oxygen or anaerobic environment, as compared to the wild-type transcriptional regulator under the same conditions. In certain embodiments, the mutant oxygen-level dependent transcriptional regulator is an FNR protein comprising amino acid substitutions that enhance dimerization and FNR activity (see, e.g., Moore et al., (2006).

In some embodiments, the bacterial cells comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding the tranporter are present on different plasmids. In some embodiments, the gene encoding the oxygen level-sensing transcriptional regulator and the gene encoding the tranporter are present on the same plasmid. In some embodiments, the gene encoding the oxygen level-sensing transcriptional regulator is present on a chromosome. In some embodiments, the gene encoding the oxygen level-sensing transcriptional regulator and the gene encoding the tranporter are present on different chromosomes. In some embodiments, the gene encoding the oxygen level-sensing transcriptional regulator and the gene encoding the tranporter are present on the same chromosome. In some instances, it may be advantageous to express the oxygen level-sensing transcriptional regulator under the control of an inducible promoter in order to enhance expression stability. In some embodiments, expression of the transcriptional regulator is controlled by a different promoter than the promoter that controls expression of the gene encoding the tranporter. In some embodiments, expression of the transcriptional regulator is controlled by the same promoter that controls expression of the tranporter. In some embodiments, the transcriptional regulator and the tranporter are divergently transcribed from a promoter region.

RNS-Dependent Regulation

In some embodiments, the genetically engineered bacteria or genetically engineered virus comprise a gene encoding an tranporter that is expressed under the control of an inducible promoter. In some embodiments, the genetically engineered bacterium or genetically engineered virus that expresses an tranporter under the control of a promoter that is activated by inflammatory conditions. In one embodiment, the gene for producing the tranporter is expressed under the control of an inflammatory-dependent promoter that is activated in inflammatory environments, e.g., a reactive nitrogen species or RNS promoter.

As used herein, "reactive nitrogen species" and "RNS" are used interchangeably to refer to highly active molecules, ions, and/or radicals derived from molecular nitrogen. RNS can cause deleterious cellular effects such as nitrosative stress. RNS includes, but is not limited to, nitric oxide (NO.), peroxynitrite or peroxynitrite anion (ONOO—), nitrogen dioxide (•NO2), dinitrogen trioxide (N2O3), peroxynitrous acid (ONOOH—), and nitroperoxycarbonate (•ONOOCO2-) (unpaired electrons denoted by •). Bacteria have evolved transcription factors that are capable of sensing RNS levels. Different RNS signaling pathways are triggered by different RNS levels and occur with different kinetics.

As used herein, "RNS-inducible regulatory region" refers to a nucleic acid sequence to which one or more RNS-sensing transcription factors is capable of binding, wherein the binding and/or activation of the corresponding transcription factor activates downstream gene expression; in the presence of RNS, the transcription factor binds to and/or activates the regulatory region. In some embodiments, the RNS-inducible regulatory region comprises a promoter sequence. In some embodiments, the transcription factor senses RNS and subsequently binds to the RNS-inducible regulatory region, thereby activating downstream gene expression. In alternate embodiments, the transcription factor is bound to the RNS-inducible regulatory region in the absence of RNS; in the presence of RNS, the transcription factor undergoes a conformational change, thereby activating downstream gene expression. The RNS-inducible regulatory region may be operatively linked to a gene or genes, e.g., an tranporter gene sequence(s), e.g., any of the tranporters described herein. For example, in the presence of RNS, a transcription factor senses RNS and activates a corresponding RNS-inducible regulatory region, thereby driving expression of an operatively linked gene sequence. Thus, RNS induces expression of the gene or gene sequences.

As used herein, "RNS-derepressible regulatory region" refers to a nucleic acid sequence to which one or more RNS-sensing transcription factors is capable of binding, wherein the binding of the corresponding transcription factor represses downstream gene expression; in the presence of RNS, the transcription factor does not bind to and does not repress the regulatory region. In some embodiments, the RNS-derepressible regulatory region comprises a promoter sequence. The RNS-derepressible regulatory region may be operatively linked to a gene or genes, e.g., an tranporter gene sequence(s). For example, in the presence of RNS, a transcription factor senses RNS and no longer binds to and/or represses the regulatory region, thereby derepressing an operatively linked gene sequence or gene cassette. Thus, RNS derepresses expression of the gene or genes.

As used herein, "RNS-repressible regulatory region" refers to a nucleic acid sequence to which one or more RNS-sensing transcription factors is capable of binding, wherein the binding of the corresponding transcription factor represses downstream gene expression; in the presence of RNS, the transcription factor binds to and represses the regulatory region. In some embodiments, the RNS-repressible regulatory region comprises a promoter sequence. In some embodiments, the transcription factor that senses RNS is capable of binding to a regulatory region that overlaps with part of the promoter sequence. In alternate embodiments, the transcription factor that senses RNS is capable of binding to a regulatory region that is upstream or downstream of the promoter sequence. The RNS-repressible regulatory region may be operatively linked to a gene sequence or gene cassette. For example, in the presence of RNS, a transcription factor senses RNS and binds to a corresponding RNS-repressible regulatory region, thereby blocking expression of an operatively linked gene sequence or gene sequences. Thus, RNS represses expression of the gene or gene sequences.

As used herein, a "RNS-responsive regulatory region" refers to a RNS-inducible regulatory region, a RNS-repressible regulatory region, and/or a RNS-derepressible regulatory region. In some embodiments, the RNS-responsive regulatory region comprises a promoter sequence. Each regulatory region is capable of binding at least one corresponding RNS-sensing transcription factor. Examples of transcription factors that sense RNS and their corresponding RNS-responsive genes, promoters, and/or regulatory regions include, but are not limited to, those shown in Table 3.

Examples of RNS-Sensing Transcription Factors and RNS-Responsive Genes

| RNS-sensing transcription factor: | Primarily capable of sensing: | Examples of responsive genes, promoters, and/or regulatory regions: |
|---|---|---|
| NsrR | NO | norB, aniA, nsrR, hmpA, ytfE, ygbA, hcp, hcr, nrfA, aox |
| NorR | NO | norVW, norR |
| DNR | NO | norCB, nir, nor, nos |

In some embodiments, the genetically engineered bacteria of the invention comprise a tunable regulatory region that is directly or indirectly controlled by a transcription factor that is capable of sensing at least one reactive nitrogen species. The tunable regulatory region is operatively linked to a gene or genes capable of directly or indirectly driving the expression of an tranporter, thus controlling expression of the tranporter relative to RNS levels. For example, the tunable regulatory region is a RNS-inducible regulatory region, and the payload is an tranporter, such as any of the tranporters provided herein; when RNS is present, e.g., in an inflamed tissue, a RNS-sensing transcription factor binds to and/or activates the regulatory region and drives expression of the tranporter gene or genes. Subsequently, when inflammation is ameliorated, RNS levels are reduced, and production of the tranporter is decreased or eliminated.

In some embodiments, the tunable regulatory region is a RNS-inducible regulatory region; in the presence of RNS, a transcription factor senses RNS and activates the RNS-inducible regulatory region, thereby driving expression of an operatively linked gene or genes. In some embodiments, the transcription factor senses RNS and subsequently binds to the RNS-inducible regulatory region, thereby activating downstream gene expression. In alternate embodiments, the transcription factor is bound to the RNS-inducible regulatory region in the absence of RNS; when the transcription factor senses RNS, it undergoes a conformational change, thereby inducing downstream gene expression.

In some embodiments, the tunable regulatory region is a RNS-inducible regulatory region, and the transcription factor that senses RNS is NorR. NorR "is an NO-responsive transcriptional activator that regulates expression of the norVW genes encoding flavorubredoxin and an associated flavoprotein, which reduce NO to nitrous oxide" (Spiro 2006). The genetically engineered bacteria of the invention may comprise any suitable RNS-responsive regulatory region from a gene that is activated by NorR. Genes that are capable of being activated by NorR are known in the art (see, e.g., Spiro 2006; Vine et al., 2011; Karlinsey et al., 2012; Table 1). In certain embodiments, the genetically engineered bacteria of the invention comprise a RNS-inducible regulatory region from norVW that is operatively linked to a gene or genes, e.g., one or more tranporter gene sequence(s). In the presence of RNS, a NorR transcription factor senses RNS and activates to the norVW regulatory region, thereby driving expression of the operatively linked gene(s) and producing the tranporter.

In some embodiments, the tunable regulatory region is a RNS-inducible regulatory region, and the transcription factor that senses RNS is DNR. DNR (dissimilatory nitrate respiration regulator) "promotes the expression of the nir, the nor and the nos genes" in the presence of nitric oxide (Castiglione et al., 2009). The genetically engineered bacteria of the invention may comprise any suitable RNS-responsive regulatory region from a gene that is activated by DNR. Genes that are capable of being activated by DNR are known in the art (see, e.g., Castiglione et al., 2009; Giardina et al., 2008; Table 1). In certain embodiments, the genetically engineered bacteria of the invention comprise a RNS-inducible regulatory region from norCB that is operatively linked to a gene or gene cassette, e.g., a butyrogenic gene cassette. In the presence of RNS, a DNR transcription factor senses RNS and activates to the norCB regulatory region, thereby driving expression of the operatively linked gene or genes and producing one or more tranporters. In some embodiments, the DNR is *Pseudomonas aeruginosa* DNR.

In some embodiments, the tunable regulatory region is a RNS-derepressible regulatory region, and binding of a corresponding transcription factor represses downstream gene expression; in the presence of RNS, the transcription factor no longer binds to the regulatory region, thereby derepressing the operatively linked gene or gene cassette.

In some embodiments, the tunable regulatory region is a RNS-derepressible regulatory region, and the transcription factor that senses RNS is NsrR. NsrR is "an Rrf2-type transcriptional repressor [that] can sense NO and control the expression of genes responsible for NO metabolism" (Isabella et al., 2009). The genetically engineered bacteria of the invention may comprise any suitable RNS-responsive regulatory region from a gene that is repressed by NsrR. In some embodiments, the NsrR is Neisseria gonorrhoeae NsrR. Genes that are capable of being repressed by NsrR are known in the art (see, e.g., Isabella et al., 2009; Dunn et al., 2010; Table 1). In certain embodiments, the genetically engineered bacteria of the invention comprise a RNS-derepressible regulatory region from norB that is operatively linked to a gene or genes, e.g., an tranporter gene or genes. In the presence of RNS, an NsrR transcription factor senses RNS and no longer binds to the norB regulatory region, thereby derepressing the operatively linked an tranporter gene or genes and producing the encoding an tranporter(s).

In some embodiments, it is advantageous for the genetically engineered bacteria to express a RNS-sensing transcription factor that does not regulate the expression of a significant number of native genes in the bacteria. In some embodiments, the genetically engineered bacterium of the invention expresses a RNS-sensing transcription factor from a different species, strain, or substrain of bacteria, wherein the transcription factor does not bind to regulatory sequences in the genetically engineered bacterium of the invention. In some embodiments, the genetically engineered bacterium of the invention is *Escherichia coli*, and the RNS-sensing transcription factor is NsrR, e.g., from is Neisseria gonorrhoeae, wherein the *Escherichia coli* does not comprise binding sites for said NsrR. In some embodiments, the heterologous transcription factor minimizes or eliminates off-target effects on endogenous regulatory regions and genes in the genetically engineered bacteria.

In some embodiments, the tunable regulatory region is a RNS-repressible regulatory region, and binding of a corresponding transcription factor represses downstream gene expression; in the presence of RNS, the transcription factor senses RNS and binds to the RNS-repressible regulatory region, thereby repressing expression of the operatively linked gene or gene cassette. In some embodiments, the RNS-sensing transcription factor is capable of binding to a regulatory region that overlaps with part of the promoter sequence. In alternate embodiments, the RNS-sensing transcription factor is capable of binding to a regulatory region that is upstream or downstream of the promoter sequence.

In these embodiments, the genetically engineered bacteria may comprise a two repressor activation regulatory circuit, which is used to express an tranporter. The two repressor activation regulatory circuit comprises a first RNS-sensing repressor and a second repressor, which is operatively linked to a gene or gene cassette, e.g., encoding an tranporter. In one aspect of these embodiments, the RNS-sensing repressor inhibits transcription of the second repressor, which inhibits the transcription of the gene or gene cassette. Examples of second repressors useful in these embodiments include, but are not limited to, TetR, C1, and LexA. In the absence of binding by the first repressor (which occurs in the absence of RNS), the second repressor is transcribed, which represses expression of the gene or genes. In the presence of binding by the first repressor (which occurs in the presence of RNS), expression of the second repressor is repressed, and the gene or genes, e.g., an tranporter gene or genes is expressed.

RNS-responsive transcription factor may induce, derepress, or repress gene expression depending upon the regulatory region sequence used in the genetically engineered bacteria. One or more types of RNS-sensing transcription factors and corresponding regulatory region sequences may be present in genetically engineered bacteria. In some embodiments, the genetically engineered bacteria comprise one type of RNS-sensing transcription factor, e.g., NsrR, and one corresponding regulatory region sequence, e.g., from norB. In some embodiments, the genetically engineered bacteria comprise one type of RNS-sensing transcription factor, e.g., NsrR, and two or more different corresponding regulatory region sequences, e.g., from norB and aniA. In some embodiments, the genetically engineered bacteria comprise two or more types of RNS-sensing transcription factors, e.g., NsrR and NorR, and two or more corresponding regulatory region sequences, e.g., from norB and norR, respectively. One RNS-responsive regulatory region may be capable of binding more than one transcription factor. In some embodiments, the genetically engineered bacteria comprise two or more types of RNS-sensing transcription factors and one corresponding regulatory region sequence. Nucleic acid sequences of several RNS-regulated regulatory regions are known in the art (see, e.g., Spiro 2006; Isabella et al., 2009; Dunn et al., 2010; Vine et al., 2011; Karlinsey et al., 2012).

In some embodiments, the genetically engineered bacteria of the invention comprise a gene encoding a RNS-sensing transcription factor, e.g., the nsrR gene, that is controlled by its native promoter, an inducible promoter, a promoter that is stronger than the native promoter, e.g., the GlnRS promoter or the P(Bla) promoter, or a constitutive promoter. In some instances, it may be advantageous to express the RNS-sensing transcription factor under the control of an inducible promoter in order to enhance expression stability. In some embodiments, expression of the RNS-sensing transcription factor is controlled by a different promoter than the promoter that controls expression of the therapeutic molecule. In some embodiments, expression of the RNS-sensing transcription factor is controlled by the same promoter that controls expression of the therapeutic molecule. In some embodiments, the RNS-sensing transcription factor and therapeutic molecule are divergently transcribed from a promoter region.

In some embodiments, the genetically engineered bacteria of the invention comprise a gene for a RNS-sensing transcription factor from a different species, strain, or substrain of bacteria. In some embodiments, the genetically engineered bacteria comprise a RNS-responsive regulatory region from a different species, strain, or substrain of bacteria. In some embodiments, the genetically engineered bacteria comprise a RNS-sensing transcription factor and corresponding RNS-responsive regulatory region from a different species, strain, or substrain of bacteria. The heterologous RNS-sensing transcription factor and regulatory region may increase the transcription of genes operatively linked to said regulatory region in the presence of RNS, as compared to the native transcription factor and regulatory region from bacteria of the same subtype under the same conditions.

In some embodiments, the genetically engineered bacteria comprise a RNS-sensing transcription factor, NsrR, and corresponding regulatory region, nsrR, from Neisseria gonorrhoeae. In some embodiments, the native RNS-sensing transcription factor, e.g., NsrR, is left intact and retains wild-type activity. In alternate embodiments, the native RNS-sensing transcription factor, e.g., NsrR, is deleted or mutated to reduce or eliminate wild-type activity.

In some embodiments, the genetically engineered bacteria of the invention comprise multiple copies of the endogenous gene encoding the RNS-sensing transcription factor, e.g., the nsrR gene. In some embodiments, the gene encoding the RNS-sensing transcription factor is present on a plasmid. In some embodiments, the gene encoding the RNS-sensing transcription factor and the gene or gene cassette for producing the therapeutic molecule are present on different plasmids. In some embodiments, the gene encoding the RNS-sensing transcription factor and the gene or gene cassette for producing the therapeutic molecule are present on the same plasmid. In some embodiments, the gene encoding the RNS-sensing transcription factor is present on a chromosome. In some embodiments, the gene encoding the RNS-sensing transcription factor and the gene or gene cassette for producing the therapeutic molecule are present on different chromosomes. In some embodiments, the gene encoding the RNS-sensing transcription factor and the gene or gene cassette for producing the therapeutic molecule are present on the same chromosome.

In some embodiments, the genetically engineered bacteria comprise a wild-type gene encoding a RNS-sensing transcription factor, e.g., the NsrR gene, and a corresponding regulatory region, e.g., a norB regulatory region, that is mutated relative to the wild-type regulatory region from bacteria of the same subtype. The mutated regulatory region increases the expression of the tranporter in the presence of RNS, as compared to the wild-type regulatory region under the same conditions. In some embodiments, the genetically engineered bacteria comprise a wild-type RNS-responsive regulatory region, e.g., the norB regulatory region, and a corresponding transcription factor, e.g., NsrR, that is mutated relative to the wild-type transcription factor from bacteria of the same subtype. The mutant transcription factor increases the expression of the tranporter in the presence of RNS, as compared to the wild-type transcription factor under the same conditions. In some embodiments, both the RNS-sensing transcription factor and corresponding regulatory region are mutated relative to the wild-type sequences from bacteria of the same subtype in order to increase expression of the tranporter in the presence of RNS.

In some embodiments, the gene or gene cassette for producing the anti-inflammation and/or gut barrier function enhancer molecule is present on a plasmid and operably linked to a promoter that is induced by RNS. In some embodiments, expression is further optimized by methods known in the art, e.g., by optimizing ribosomal binding sites, manipulating transcriptional regulators, and/or increasing mRNA stability.

In some embodiments, any of the gene(s) of the present disclosure may be integrated into the bacterial chromosome at one or more integration sites. For example, one or more copies of one or more encoding an tranporter gene(s) may be integrated into the bacterial chromosome. Having multiple copies of the gene or gen(s) integrated into the chromosome allows for greater production of the tranporter(s) and also permits fine-tuning of the level of expression. Alternatively, different circuits described herein, such as any of the secretion or exporter circuits, in addition to the therapeutic gene(s) or gene cassette(s) could be integrated into the bacterial chromosome at one or more different integration sites to perform multiple different functions.

ROS-Dependent Regulation

In some embodiments, the genetically engineered bacteria or genetically engineered virus comprise a gene for producing an tranporter that is expressed under the control of an inducible promoter. In some embodiments, the genetically engineered bacterium or genetically engineered virus that expresses an tranporter under the control of a promoter that is activated by conditions of cellular damage. In one embodiment, the gene for producing the tranporter is expressed under the control of an cellular damaged-dependent promoter that is activated in environments in which there is cellular or tissue damage, e.g., a reactive oxygen species or ROS promoter.

As used herein, "reactive oxygen species" and "ROS" are used interchangeably to refer to highly active molecules, ions, and/or radicals derived from molecular oxygen. ROS can be produced as byproducts of aerobic respiration or metal-catalyzed oxidation and may cause deleterious cellular effects such as oxidative damage. ROS includes, but is not limited to, hydrogen peroxide ($H_2O_2$), organic peroxide (ROOH), hydroxyl ion (OH—), hydroxyl radical (•OH), superoxide or superoxide anion (•O2-), singlet oxygen (1O2), ozone (O3), carbonate radical, peroxide or peroxyl radical (•O2-2), hypochlorous acid (HOCl), hypochlorite ion (OCl—), sodium hypochlorite (NaOCl), nitric oxide (NO•), and peroxynitrite or peroxynitrite anion (ONOO—) (unpaired electrons denoted by •). Bacteria have evolved transcription factors that are capable of sensing ROS levels. Different ROS signaling pathways are triggered by different ROS levels and occur with different kinetics (Marinho et al., 2014).

As used herein, "ROS-inducible regulatory region" refers to a nucleic acid sequence to which one or more ROS-sensing transcription factors is capable of binding, wherein the binding and/or activation of the corresponding transcription factor activates downstream gene expression; in the presence of ROS, the transcription factor binds to and/or activates the regulatory region. In some embodiments, the ROS-inducible regulatory region comprises a promoter sequence. In some embodiments, the transcription factor senses ROS and subsequently binds to the ROS-inducible regulatory region, thereby activating downstream gene expression. In alternate embodiments, the transcription factor is bound to the ROS-inducible regulatory region in the absence of ROS; in the presence of ROS, the transcription factor undergoes a conformational change, thereby activating downstream gene expression. The ROS-inducible regulatory region may be operatively linked to a gene sequence or gene sequence, e.g., a sequence or sequences encoding one or more tranporter(s). For example, in the presence of ROS, a transcription factor, e.g., OxyR, senses ROS and activates a corresponding ROS-inducible regulatory region, thereby driving expression of an operatively linked gene sequence or gene sequences. Thus, ROS induces expression of the gene or genes.

As used herein, "ROS-derepressible regulatory region" refers to a nucleic acid sequence to which one or more ROS-sensing transcription factors is capable of binding, wherein the binding of the corresponding transcription factor represses downstream gene expression; in the presence of ROS, the transcription factor does not bind to and does not repress the regulatory region. In some embodiments, the ROS-derepressible regulatory region comprises a promoter sequence. The ROS-derepressible regulatory region may be operatively linked to a gene or genes, e.g., one or more genes encoding one or more tranporter(s). For example, in the presence of ROS, a transcription factor, e.g., OhrR, senses ROS and no longer binds to and/or represses the regulatory region, thereby derepressing an operatively linked gene sequence or gene cassette. Thus, ROS derepresses expression of the gene or gene cassette.

As used herein, "ROS-repressible regulatory region" refers to a nucleic acid sequence to which one or more ROS-sensing transcription factors is capable of binding, wherein the binding of the corresponding transcription factor represses downstream gene expression; in the presence of ROS, the transcription factor binds to and represses the regulatory region. In some embodiments, the ROS-repressible regulatory region comprises a promoter sequence. In some embodiments, the transcription factor that senses ROS is capable of binding to a regulatory region that overlaps with part of the promoter sequence. In alternate embodiments, the transcription factor that senses ROS is capable of binding to a regulatory region that is upstream or downstream of the promoter sequence. The ROS-repressible regulatory region may be operatively linked to a gene sequence or gene sequences. For example, in the presence of ROS, a transcription factor, e.g., PerR, senses ROS and binds to a corresponding ROS-repressible regulatory region, thereby blocking expression of an operatively linked gene sequence or gene sequences. Thus, ROS represses expression of the gene or genes.

As used herein, a "ROS-responsive regulatory region" refers to a ROS-inducible regulatory region, a ROS-repressible regulatory region, and/or a ROS-derepressible regulatory region. In some embodiments, the ROS-responsive regulatory region comprises a promoter sequence. Each regulatory region is capable of binding at least one corresponding ROS-sensing transcription factor. Examples of transcription factors that sense ROS and their corresponding ROS-responsive genes, promoters, and/or regulatory regions include, but are not limited to, those shown in Table 4.

Examples of ROS-Sensing Transcription Factors and ROS-Responsive Genes

| ROS-sensing transcription factor: | Primarily capable of sensing: | Examples of responsive genes, promoters, and/or regulatory regions: |
|---|---|---|
| OxyR | $H_2O_2$ | ahpC; ahpF; dps; dsbG; fhuF; flu; fur; gor; grxA; hemH; katG; oxyS; sufA; sufB; sufC; sufD; sufE; sufS; trxC; uxuA; yaaA; yaeH; yaiA; ybjM; ydcH; ydeN; ygaQ; yljA; ytfK |
| PerR | $H_2O_2$ | katA; ahpCF; mrgA; zoaA; fur; hemAXCDBL; srfA |
| OhrR | Organic peroxides NaOCl | ohrA |

| ROS-sensing transcription factor: | Primarily capable of sensing: | Examples of responsive genes, promoters, and/or regulatory regions: |
|---|---|---|
| SoxR | •$O_2^-$ NO• (also capable of sensing $H_2O_2$) | soxS |
| RosR | $H_2O_2$ | rbtT; tnp16a; rluC1; tnp5a; mscL; tnp2d; phoD; tnp15b; pstA; tnp5b; xylC; gabD1; rluC2; cgtS9; azlC; narKGHJI; rosR |

In some embodiments, the genetically engineered bacteria comprise a tunable regulatory region that is directly or indirectly controlled by a transcription factor that is capable of sensing at least one reactive oxygen species. The tunable regulatory region is operatively linked to a gene or gene cassette capable of directly or indirectly driving the expression of an tranporter, thus controlling expression of the tranporter relative to ROS levels. For example, the tunable regulatory region is a ROS-inducible regulatory region, and the molecule is an tranporter; when ROS is present, e.g., in an inflamed tissue, a ROS-sensing transcription factor binds to and/or activates the regulatory region and drives expression of the gene sequence for the tranporter, thereby producing the tranporter. Subsequently, when inflammation is ameliorated, ROS levels are reduced, and production of the tranporter is decreased or eliminated.

In some embodiments, the tunable regulatory region is a ROS-inducible regulatory region; in the presence of ROS, a transcription factor senses ROS and activates the ROS-inducible regulatory region, thereby driving expression of an operatively linked gene or gene cassette. In some embodiments, the transcription factor senses ROS and subsequently binds to the ROS-inducible regulatory region, thereby activating downstream gene expression. In alternate embodiments, the transcription factor is bound to the ROS-inducible regulatory region in the absence of ROS; when the transcription factor senses ROS, it undergoes a conformational change, thereby inducing downstream gene expression.

In some embodiments, the tunable regulatory region is a ROS-inducible regulatory region, and the transcription factor that senses ROS is OxyR. OxyR "functions primarily as a global regulator of the peroxide stress response" and is capable of regulating dozens of genes, e.g., "genes involved in H2O2 detoxification (katE, ahpCF), heme biosynthesis (hemH), reductant supply (grxA, gor, trxC), thiol-disulfide isomerization (dsbG), Fe—S center repair (sufA-E, sufS), iron binding (yaaA), repression of iron import systems (fur)" and "OxyS, a small regulatory RNA" (Dubbs et al., 2012). The genetically engineered bacteria may comprise any suitable ROS-responsive regulatory region from a gene that is activated by OxyR. Genes that are capable of being activated by OxyR are known in the art (see, e.g., Zheng et al., 2001; Dubbs et al., 2012; Table 1). In certain embodiments, the genetically engineered bacteria of the invention comprise a ROS-inducible regulatory region from oxyS that is operatively linked to a gene, e.g., an tranporter gene. In the presence of ROS, e.g., H2O2, an OxyR transcription factor senses ROS and activates to the oxyS regulatory region, thereby driving expression of the operatively linked tranporter gene and producing the tranporter. In some embodiments, OxyR is encoded by an E. coli oxyR gene. In some embodiments, the oxyS regulatory region is an E. coli oxyS regulatory region. In some embodiments, the ROS-inducible regulatory region is selected from the regulatory region of katG, dps, and ahpC.

In alternate embodiments, the tunable regulatory region is a ROS-inducible regulatory region, and the corresponding transcription factor that senses ROS is SoxR. When SoxR is "activated by oxidation of its [2Fe—2S] cluster, it increases the synthesis of SoxS, which then activates its target gene expression" (Koo et al., 2003). "SoxR is known to respond primarily to superoxide and nitric oxide" (Koo et al., 2003), and is also capable of responding to H2O2. The genetically engineered bacteria of the invention may comprise any suitable ROS-responsive regulatory region from a gene that is activated by SoxR. Genes that are capable of being activated by SoxR are known in the art (see, e.g., Koo et al., 2003; Table 1). In certain embodiments, the genetically engineered bacteria of the invention comprise a ROS-inducible regulatory region from soxS that is operatively linked to a gene, e.g., an tranporter. In the presence of ROS, the SoxR transcription factor senses ROS and activates the soxS regulatory region, thereby driving expression of the operatively linked an tranporter gene and producing the an tranporter.

In some embodiments, the tunable regulatory region is a ROS-derepressible regulatory region, and binding of a corresponding transcription factor represses downstream gene expression; in the presence of ROS, the transcription factor no longer binds to the regulatory region, thereby derepressing the operatively linked gene or gene cassette.

In some embodiments, the tunable regulatory region is a ROS-derepressible regulatory region, and the transcription factor that senses ROS is OhrR. OhrR "binds to a pair of inverted repeat DNA sequences overlapping the ohrA promoter site and thereby represses the transcription event," but oxidized OhrR is "unable to bind its DNA target" (Duarte et al., 2010). OhrR is a "transcriptional repressor [that] . . . senses both organic peroxides and NaOCl" (Dubbs et al., 2012) and is "weakly activated by H2O2 but it shows much higher reactivity for organic hydroperoxides" (Duarte et al., 2010). The genetically engineered bacteria of the invention may comprise any suitable ROS-responsive regulatory region from a gene that is repressed by OhrR. Genes that are capable of being repressed by OhrR are known in the art (see, e.g., Dubbs et al., 2012; Table 1). In certain embodiments, the genetically engineered bacteria of the invention comprise a ROS-derepressible regulatory region from ohrA that is operatively linked to a gene or gene cassette, e.g., an tranporter gene. In the presence of ROS, e.g., NaOCl, an OhrR transcription factor senses ROS and no longer binds to the ohrA regulatory region, thereby derepressing the operatively linked tranporter gene and producing the an tranporter.

OhrR is a member of the MarR family of ROS-responsive regulators. "Most members of the MarR family are transcriptional repressors and often bind to the −10 or −35 region in the promoter causing a steric inhibition of RNA polymerase binding" (Bussmann et al., 2010). Other members of this family are known in the art and include, but are not limited to, OspR, MgrA, RosR, and SarZ. In some embodiments, the transcription factor that senses ROS is OspR, MgRA, RosR, and/or SarZ, and the genetically engineered bacteria of the invention comprises one or more corresponding regulatory region sequences from a gene that is repressed by OspR, MgRA, RosR, and/or SarZ. Genes that are capable of being repressed by OspR, MgRA, RosR, and/or SarZ are known in the art (see, e.g., Dubbs et al., 2012).

In some embodiments, the tunable regulatory region is a ROS-derepressible regulatory region, and the corresponding transcription factor that senses ROS is RosR. RosR is "a MarR-type transcriptional regulator" that binds to an "18-bp inverted repeat with the consensus sequence TTGTTGAY-RYRTCAACWA" and is "reversibly inhibited by the oxidant H2O2" (Bussmann et al., 2010). RosR is capable of repressing numerous genes and putative genes, including but not limited to "a putative polyisoprenoid-binding protein (cg1322, gene upstream of and divergent from rosR), a sensory histidine kinase (cgtS9), a putative transcriptional regulator of the Crp/FNR family (cg3291), a protein of the glutathione S-transferase family (cg1426), two putative FMN reductases (cg1150 and cg1850), and four putative monooxygenases (cg0823, cg1848, cg2329, and cg3084)" (Bussmann et al., 2010). The genetically engineered bacteria of the invention may comprise any suitable ROS-responsive regulatory region from a gene that is repressed by RosR. Genes that are capable of being repressed by RosR are known in the art (see, e.g., Bussmann et al., 2010; Table 1). In certain embodiments, the genetically engineered bacteria of the invention comprise a ROS-derepressible regulatory region from cgtS9 that is operatively linked to a gene or gene cassette, e.g., an tranporter. In the presence of ROS, e.g., H2O2, a RosR transcription factor senses ROS and no longer binds to the cgtS9 regulatory region, thereby derepressing the operatively linked tranporter gene and producing the tranporter.

In some embodiments, it is advantageous for the genetically engineered bacteria to express a ROS-sensing transcription factor that does not regulate the expression of a significant number of native genes in the bacteria. In some embodiments, the genetically engineered bacterium of the invention expresses a ROS-sensing transcription factor from a different species, strain, or substrain of bacteria, wherein the transcription factor does not bind to regulatory sequences in the genetically engineered bacterium of the invention. In some embodiments, the genetically engineered bacterium of the invention is *Escherichia coli*, and the ROS-sensing transcription factor is RosR, e.g., from *Corynebacterium glutamicum*, wherein the *Escherichia coli* does not comprise binding sites for said RosR. In some embodiments, the heterologous transcription factor minimizes or eliminates off-target effects on endogenous regulatory regions and genes in the genetically engineered bacteria.

In some embodiments, the tunable regulatory region is a ROS-repressible regulatory region, and binding of a corresponding transcription factor represses downstream gene expression; in the presence of ROS, the transcription factor senses ROS and binds to the ROS-repressible regulatory region, thereby repressing expression of the operatively linked gene or gene cassette. In some embodiments, the ROS-sensing transcription factor is capable of binding to a regulatory region that overlaps with part of the promoter sequence. In alternate embodiments, the ROS-sensing transcription factor is capable of binding to a regulatory region that is upstream or downstream of the promoter sequence.

In some embodiments, the tunable regulatory region is a ROS-repressible regulatory region, and the transcription factor that senses ROS is PerR. In *Bacillus subtilis*, PerR "when bound to DNA, represses the genes coding for proteins involved in the oxidative stress response (katA, ahpC, and mrgA), metal homeostasis (hemAXCDBL, fur, and zoaA) and its own synthesis (perR)" (Marinho et al., 2014). PerR is a "global regulator that responds primarily to H2O2" (Dubbs et al., 2012) and "interacts with DNA at the per box, a specific palindromic consensus sequence (TTATAATNATTATAA) residing within and near the promoter sequences of PerR-controlled genes" (Marinho et al., 2014). PerR is capable of binding a regulatory region that "overlaps part of the promoter or is immediately downstream from it" (Dubbs et al., 2012). The genetically engineered bacteria of the invention may comprise any suitable ROS-responsive regulatory region from a gene that is repressed by PerR. Genes that are capable of being repressed by PerR are known in the art (see, e.g., Dubbs et al., 2012; Table 1).

In these embodiments, the genetically engineered bacteria may comprise a two repressor activation regulatory circuit, which is used to express an tranporter. The two repressor activation regulatory circuit comprises a first ROS-sensing repressor, e.g., PerR, and a second repressor, e.g., TetR, which is operatively linked to a gene or gene cassette, e.g., an tranporter. In one aspect of these embodiments, the ROS-sensing repressor inhibits transcription of the second repressor, which inhibits the transcription of the gene or gene cassette. Examples of second repressors useful in these embodiments include, but are not limited to, TetR, C1, and LexA. In some embodiments, the ROS-sensing repressor is PerR. In some embodiments, the second repressor is TetR. In this embodiment, a PerR-repressible regulatory region drives expression of TetR, and a TetR-repressible regulatory region drives expression of the gene or gene cassette, e.g., an tranporter. In the absence of PerR binding (which occurs in the absence of ROS), tetR is transcribed, and TetR represses expression of the gene or gene cassette, e.g., an tranporter. In the presence of PerR binding (which occurs in the presence of ROS), tetR expression is repressed, and the gene or gene cassette, e.g., an tranporter, is expressed.

A ROS-responsive transcription factor may induce, derepress, or repress gene expression depending upon the regulatory region sequence used in the genetically engineered bacteria. For example, although "OxyR is primarily thought of as a transcriptional activator under oxidizing conditions . . . OxyR can function as either a repressor or activator under both oxidizing and reducing conditions" (Dubbs et al., 2012), and OxyR "has been shown to be a repressor of its own expression as well as that of fhuF (encoding a ferric ion reductase) and flu (encoding the antigen 43 outer membrane protein)" (Zheng et al., 2001). The genetically engineered bacteria of the invention may comprise any suitable ROS-responsive regulatory region from a gene that is repressed by OxyR. In some embodiments, OxyR is used in a two repressor activation regulatory circuit, as described above. Genes that are capable of being repressed by OxyR are known in the art (see, e.g., Zheng et al., 2001; Table 1). Or, for example, although RosR is capable of repressing a number of genes, it is also capable of activating certain genes, e.g., the narKGHJI operon. In some embodiments, the genetically engineered bacteria comprise any suitable ROS-responsive regulatory region from a gene that is activated by RosR. In addition, "PerR-mediated positive regulation has also been observed . . . and appears to involve PerR binding to distant upstream sites" (Dubbs et al., 2012). In some embodiments, the genetically engineered bacteria comprise any suitable ROS-responsive regulatory region from a gene that is activated by PerR.

One or more types of ROS-sensing transcription factors and corresponding regulatory region sequences may be present in genetically engineered bacteria. For example, "OhrR is found in both Gram-positive and Gram-negative bacteria and can coreside with either OxyR or PerR or both" (Dubbs et al., 2012). In some embodiments, the genetically engineered bacteria comprise one type of ROS-sensing transcription factor, e.g., OxyR, and one corresponding regulatory region sequence, e.g., from oxyS. In some embodiments, the genetically engineered bacteria comprise one type of ROS-sensing transcription factor, e.g., OxyR, and two or more different corresponding regulatory region sequences, e.g., from oxyS and katG. In some embodiments, the genetically engineered bacteria comprise two or more types of ROS-sensing transcription factors, e.g., OxyR and PerR, and two or more corresponding regulatory region sequences, e.g., from oxyS and katA, respectively. One ROS-responsive regulatory region may be capable of binding more than one transcription factor. In some embodiments, the genetically engineered bacteria comprise two or more types of ROS-sensing transcription factors and one corresponding regulatory region sequence.

Nucleic acid sequences of several exemplary OxyR-regulated regulatory regions are shown in Table 5. OxyR binding sites are underlined and bolded. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 46, 47, 48, or 49, or a functional fragment thereof.

Nucleotide Sequences of Exemplary OxyR-Regulated Regulatory Regions promoter that controls expression of the therapeutic molecule. In some embodiments, expression of the ROS-sensing transcription factor is controlled by the same promoter that controls expression of the therapeutic molecule. In some embodiments, the ROS-sensing transcription factor and therapeutic molecule are divergently transcribed from a promoter region.

In some embodiments, the genetically engineered bacteria of the invention comprise a gene for a ROS-sensing transcription factor from a different species, strain, or substrain of bacteria. In some embodiments, the genetically engineered bacteria comprise a ROS-responsive regulatory region from a different species, strain, or substrain of bacteria. In some embodiments, the genetically engineered bacteria comprise a ROS-sensing transcription factor and corresponding ROS-responsive regulatory region from a different species, strain, or substrain of bacteria. The heterologous ROS-sensing transcription factor and regulatory region may increase the transcription of genes operatively linked to said regulatory region in the presence of ROS, as compared to the native transcription factor and regulatory region from bacteria of the same subtype under the same conditions.

In some embodiments, the genetically engineered bacteria comprise a ROS-sensing transcription factor, OxyR, and corresponding regulatory region, oxyS, from *Escherichia*

| Regulatory sequence | 01234567890123456789012345678901234567890123456789 |
|---|---|
| katG (SEQ ID NO:) | TGTGGCTTTTATGAAAATCACACAGTGATCACAAATTTTAAACA GAGCACAAAATGCTGCCTCGAAATGAGGGCGGGAAAATAAGGT TATCAGCCTTGTTTTCTCCCTCATTACTTGAAGGATATGAAGCTA AAACCCTTTTTTATAAAGCATTTGTCCGAATTCGGACATAATCA AAAAAGCTTAATTAAGATCAATTTGATCTACATCTCTTTAACCA ACAATATGTAAGATCTCAACTATCGCATCCGTGGATTAATTC AATTATAACTTCTCTCTAACGCTGTGTATCGTAACGGTAACACT GTAGAGGGGAGCACATTGATGCGAATTCATTAAAGAGGAGAAA GGTACC |
| dps (SEQ ID NO:) | TTCCGAAAATTCCTGGCGAGCAGATAAATAAGAATTGTTCTTAT CAATATATCTAACTCATTGAATCTTTATTAGTTTTGTTTTTCACG CTTGTTACCACTATTAGTGTGATAGGAACAGCCAGAATAGCG GAACACATAGCCGGTGCTATACTTAATCTCGTTAATTACTGGGA CATAACATCAAGAGGATATGAAATTCGAATTCATTAAAGAGGA GAAAGGTACC |
| ahpC (SEQ ID NO:) | GCTTAGATCAGGTGATTGCCCTTTGTTTATGAGGGTGTTGTAATC CATGTCGTTGTTGCATTTGTAAGGGCAACACCTCAGCCTGCAGG CAGGCACTGAAGATACCAAAGGGTAGTTCAGATTACACGGTCA CCTGGAAAGGGGGCCATTTTACTTTTTATCGCCGCTGGCGGTGC AAAGTTCACAAAGTTGTCTTACGAAGGTTGTAAGGTAAAACTT ATCGATTTGATAATGGAAACGCATTAGCCGAATCGGCAAAAAT TGGTTACCTTACATCTCATCGAAAACACGGAGGAAGTATAGATG CGAATTCATTAAAGAGGAGAAAGGTACC |
| oxyS (SEQ ID NO:) | CTCGAGTTCATTATCCATCCTCCATCGCCACGATAGTTCATGGC GATAGGTAGAATAGCAATGAACGATTATCCCTATCAAGCATTC TGACTGATAATTGCTCACACGAATTCATTAAAGAGGAGAAAGGT ACC |

In some embodiments, the genetically engineered bacteria of the invention comprise a gene encoding a ROS-sensing transcription factor, e.g., the oxyR gene, that is controlled by its native promoter, an inducible promoter, a promoter that is stronger than the native promoter, e.g., the GlnRS promoter or the P(Bla) promoter, or a constitutive promoter. In some instances, it may be advantageous to express the ROS-sensing transcription factor under the control of an inducible promoter in order to enhance expression stability. In some embodiments, expression of the ROS-sensing transcription factor is controlled by a different promoter than the

*coli*. In some embodiments, the native ROS-sensing transcription factor, e.g., OxyR, is left intact and retains wild-type activity. In alternate embodiments, the native ROS-sensing transcription factor, e.g., OxyR, is deleted or mutated to reduce or eliminate wild-type activity.

In some embodiments, the genetically engineered bacteria of the invention comprise multiple copies of the endogenous gene encoding the ROS-sensing transcription factor, e.g., the oxyR gene. In some embodiments, the gene encoding the ROS-sensing transcription factor is present on a plasmid. In some embodiments, the gene encoding the ROS-sensing transcription factor and the gene or gene cassette for producing the therapeutic molecule are present on different plasmids. In some embodiments, the gene encoding the ROS-sensing transcription factor and the gene or gene cassette for producing the therapeutic molecule are present on the same. In some embodiments, the gene encoding the ROS-sensing transcription factor is present on a chromosome. In some embodiments, the gene encoding the ROS-sensing transcription factor and the gene or gene cassette for producing the therapeutic molecule are present on different chromosomes. In some embodiments, the gene encoding the ROS-sensing transcription factor and the gene or gene cassette for producing the therapeutic molecule are present on the same chromosome.

In some embodiments, the genetically engineered bacteria comprise a wild-type gene encoding a ROS-sensing transcription factor, e.g., the soxR gene, and a corresponding regulatory region, e.g., a soxS regulatory region, that is mutated relative to the wild-type regulatory region from bacteria of the same subtype. The mutated regulatory region increases the expression of the tranporter in the presence of ROS, as compared to the wild-type regulatory region under the same conditions. In some embodiments, the genetically engineered bacteria comprise a wild-type ROS-responsive regulatory region, e.g., the oxyS regulatory region, and a corresponding transcription factor, e.g., OxyR, that is mutated relative to the wild-type transcription factor from bacteria of the same subtype. The mutant transcription factor increases the expression of the tranporter in the presence of ROS, as compared to the wild-type transcription factor under the same conditions. In some embodiments, both the ROS-sensing transcription factor and corresponding regulatory region are mutated relative to the wild-type sequences from bacteria of the same subtype in order to increase expression of the tranporter in the presence of ROS.

In some embodiments, the gene or gene cassette for producing the tranporter is present on a plasmid and operably linked to a promoter that is induced by ROS. In some embodiments, the gene or gene cassette for producing the tranporter is present in the chromosome and operably linked to a promoter that is induced by ROS. In some embodiments, the gene or gene cassette for producing the tranporter is present on a chromosome and operably linked to a promoter that is induced by exposure to tetracycline. In some embodiments, the gene or gene cassette for producing the tranporter is present on a plasmid and operably linked to a promoter that is induced by exposure to tetracycline. In some embodiments, expression is further optimized by methods known in the art, e.g., by optimizing ribosomal binding sites, manipulating transcriptional regulators, and/or increasing mRNA stability.

In some embodiments, the genetically engineered bacteria may comprise multiple copies of the gene(s) capable of producing an tranporter(s). In some embodiments, the gene(s) capable of producing an tranporter(s) is present on a plasmid and operatively linked to a ROS-responsive regulatory region. In some embodiments, the gene(s) capable of producing an tranporter is present in a chromosome and operatively linked to a ROS-responsive regulatory region.

Thus, in some embodiments, the genetically engineered bacteria or genetically engineered virus produce one or more tranporters under the control of an oxygen level-dependent promoter, a reactive oxygen species (ROS)-dependent promoter, or a reactive nitrogen species (RNS)-dependent promoter, and a corresponding transcription factor.

In some embodiments, the genetically engineered bacteria comprise a stably maintained plasmid or chromosome carrying a gene for producing an tranporter, such that the tranporter can be expressed in the host cell, and the host cell is capable of survival and/or growth in vitro, e.g., in medium, and/or in vivo. In some embodiments, a bacterium may comprise multiple copies of the gene encoding the tranporter. In some embodiments, the gene encoding the tranporter is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the gene encoding the tranporter is expressed on a high-copy plasmid. In some embodiments, the high-copy plasmid may be useful for increasing expression of the tranporter. In some embodiments, the gene encoding the tranporter is expressed on a chromosome.

In some embodiments, the bacteria are genetically engineered to include multiple mechanisms of action (MOAs), e.g., circuits producing multiple copies of the same product (e.g., to enhance copy number) or circuits performing multiple different functions. For example, the genetically engineered bacteria may include four copies of the gene encoding a particular tranporter inserted at four different insertion sites. Alternatively, the genetically engineered bacteria may include three copies of the gene encoding a particular tranporter inserted at three different insertion sites and three copies of the gene encoding a different tranporter inserted at three different insertion sites.

In some embodiments, under conditions where the tranporter is expressed, the genetically engineered bacteria of the disclosure produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more of the tranporter, and/or transcript of the gene(s) in the operon as compared to unmodified bacteria of the same subtype under the same conditions.

In some embodiments, quantitative PCR (qPCR) is used to amplify, detect, and/or quantify mRNA expression levels of the tranporter gene(s). Primers specific for tranporter the gene(s) may be designed and used to detect mRNA in a sample according to methods known in the art. In some embodiments, a fluorophore is added to a sample reaction mixture that may contain tranporter mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the tranporter gene(s).

In some embodiments, quantitative PCR (qPCR) is used to amplify, detect, and/or quantify mRNA expression levels of the tranporter gene(s). Primers specific for tranporter the gene(s) may be designed and used to detect mRNA in a sample according to methods known in the art. In some embodiments, a fluorophore is added to a sample reaction mixture that may contain tranporter mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the tranporter gene(s).

Essential Genes and Auxotrophs

As used herein, the term "essential gene" refers to a gene that is necessary to for cell growth and/or survival. Bacterial essential genes are well known to one of ordinary skill in the art, and can be identified by directed deletion of genes and/or random mutagenesis and screening (see, for example, Zhang and Lin, 2009, DEG 5.0, a database of essential genes in both prokaryotes and eukaryotes, *Nucl. Acids Res.*, 37:D455-D458 and Gerdes et al., Essential genes on metabolic maps, *Curr. Opin. Biotechnol.*, 17(5):448-456, the entire contents of each of which are expressly incorporated herein by reference).

An "essential gene" may be dependent on the circumstances and environment in which an organism lives. For example, a mutation of, modification of, or excision of an essential gene may result in the recombinant bacteria of the disclosure becoming an auxotroph. An auxotrophic modification is intended to cause bacteria to die in the absence of an exogenously added nutrient essential for survival or growth because they lack the gene(s) necessary to produce that essential nutrient.

An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is a DNA synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thiI, as long as the corresponding wild-type gene product is not produced in the bacteria. For example, thymine is a nucleic acid that is required for bacterial cell growth; in its absence, bacteria undergo cell death. The thyA gene encodes thimidylate synthetase, an enzyme that catalyzes the first step in thymine synthesis by converting dUMP to dTMP (Sat et al. (2003) *J Bacteriol*. (2003) 185(6):1803-7). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro. Without sufficient amounts of thymine, the thyA auxotroph dies. In some embodiments, the auxotrophic modification is used to ensure that the bacterial cell does not survive in the absence of the auxotrophic gene product, e.g., outside of the hypoxic tumor environment.

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which the dapD gene is deleted and/or replaced with an unrelated gene. A dapD auxotroph can grow only when sufficient amounts of DAP are present, e.g., by adding DAP to growth media in vitro. Without sufficient amounts of DAP, the dapD auxotroph dies. In some embodiments, the auxotrophic modification is used to ensure that the bacterial cell does not survive in the absence of the auxotrophic gene product.

In other embodiments, the genetically engineered bacterium of the present disclosure is a uraA auxotroph in which the uraA gene is deleted and/or replaced with an unrelated gene. The uraA gene codes for UraA, a membrane-bound transporter that facilitates the uptake and subsequent metabolism of the pyrimidine uracil (Andersen et al., 1995). A uraA auxotroph can grow only when sufficient amounts of uracil are present, e.g., by adding uracil to growth media in vitro. Without sufficient amounts of uracil, the uraA auxotroph dies. In some embodiments, auxotrophic modifications are used to ensure that the bacteria do not survive in the absence of the auxotrophic gene product.

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria of the invention comprise a deletion or mutation in two or more genes required for cell survival and/or growth.

Other examples of essential genes include, but are not limited to yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, mc, ftsB, eno, pyrG, chpR, lgt, fbaA, pgk, yqgD, metK, yqgF, plsC, ygiT, pare, ribB, cca, ygjD, tdcF, yraL, yihA, ftsN, murl, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, lspA, ispH, dapB, folA, imp, yabQ, ftsL, ftsI, murE, murF, mraY, murD, ftsW, murG, murC, ftsQ, ftsA, ftsZ, lpxC, secM, secA, can, folK, hemL, yadR, dapD, map, rpsB, infB, nusA, ftsH, obgE, rpmA, rplU, ispB, murA, yrbB, yrbK, yhbN, rpsl, rplM, degS, mreD, mreC, mreB, accB, accC, yrdC, def fmt, rplQ, rpoA, rpsD, rpsK, rpsM, entD, mrdB, mrdA, nadD, hlepB, rpoE, pssA, yfiO, rplS, trmD, rpsP, ffh, grpE, yfjB, csrA, ispF, ispD, rplW, rplD, rplC, rpsJ, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsL, rplV, rpsS, rplB, cdsA, yaeL, yaeT, lpxD, fabZ, lpxA, lpxB, dnaE, accA, tilS, proS, yafF, tsf, pyrH, olA, rlpB, leuS, int, glnS, fldA, cydA, infA, cydC, ftsK, A, serS, rpsA, msbA, lpxK, kdsB, mukF, mukE, mukB, asnS, fabA, mviN, me, yceQ, fabD, fabG, acpP, tmk, holB, C, D, E, purB, ymfK, minE, mind, pth, rsA, ispE, lolB, hemA, prfA, prmC, kdsA, topA, ribA, fabI, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson "Synthetic Auxotrophs with Ligand-Dependent Essential Genes for a BL21 (DE3 Biosafety Strain," ACS Synthetic Biology (2015) DOI: 10.1021/acssynbio.5b00085, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG, and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A, and F40G. In some embodiments, the essential gene is tyrS comprising the mutations L36V, C38A, and F40G. In some embodiments, the essential gene is metG comprising one or more of the following mutations: E45Q, N47R, I49G, and A51C. In some embodiments, the essential gene is metG comprising the mutations E45Q, N47R, I49G, and A51C. In some embodiments, the essential gene is adk comprising one or more of the following mutations: I4L, L5I, and L6G. In some embodiments, the essential gene is adk comprising the mutations I4L, L5I, and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51C) are complemented by benzothiazole, indole, 2-aminobenzothiazole, indole-3-butyric acid, indole-3-acetic acid or L-histidine methyl ester. Bacterial cells comprising mutations in dnaN (H191N, R240C, I317S, F319V, L340T, V347I, and S345C) are complemented by benzothiazole, indole or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I, and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

In some embodiments, the genetically engineered bacterium is a conditional auxotroph whose essential gene(s) is replaced using an arabinose system.

In some embodiments, the genetically engineered bacterium of the disclosure is an auxotroph and also comprises kill switch circuitry, such as any of the kill switch components and systems described herein. For example, the recombinant bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as low oxygen levels) or regulated by one or more recombinases that are expressed upon sensing an exogenous environmental condition(s) and/or signal(s) (such as the recombinase systems described herein). Other embodiments are described in Wright et al., "GeneGuard: A Modular Plasmid System Designed for Biosafety," ACS Synthetic Biology (2015) 4: 307-16, the entire contents of which are expressly incorporated herein by reference). In some embodiments, the genetically engineered bacterium of the disclosure is an auxotroph and also comprises kill switch circuitry, such as any of the kill switch components and systems described herein, as well as another biosecurity system, such a conditional origin of replication (see Wright et al., supra). In other embodiments, auxotrophic modifications may also be used to screen for mutant bacteria that produce the substrate transporter.

Genetic Regulatory Circuits

In some embodiments, the genetically engineered bacteria comprise multilayered genetic regulatory circuits for expressing the constructs described herein (see, e.g., U.S. Provisional Application No. 62/184,811, incorporated herein by reference in its entirety). The genetic regulatory circuits are useful to screen for mutant bacteria that produce a substrate transporter or rescue an auxotroph. In certain embodiments, the invention provides methods for selecting genetically engineered bacteria that produce one or more genes of interest.

In some embodiments, the invention provides genetically engineered bacteria comprising a gene or gene cassette for producing a payload and a T7 polymerase-regulated genetic regulatory circuit. For example, the genetically engineered bacteria comprise a first gene encoding a T7 polymerase, wherein the first gene is operably linked to a fumarate and nitrate reductase regulator (FNR)-responsive promoter; a second gene or gene cassette for producing a payload, wherein the second gene or gene cassette is operably linked to a T7 promoter that is induced by the T7 polymerase; and a third gene encoding an inhibitory factor, lysY, that is capable of inhibiting the T7 polymerase. In the presence of oxygen, FNR does not bind the FNR-responsive promoter, and the payload is not expressed. LysY is expressed constitutively (P-lac constitutive) and further inhibits T7 polymerase. In the absence of oxygen, FNR dimerizes and binds to the FNR-responsive promoter, T7 polymerase is expressed at a level sufficient to overcome lysY inhibition, and the payload is expressed. In some embodiments, the lysY gene is operably linked to an additional FNR binding site. In the absence of oxygen, FNR dimerizes to activate T7 polymerase expression as described above, and also inhibits lysY expression.

In some embodiments, the invention provides genetically engineered bacteria comprising a gene or gene cassette for producing a payload, and a protease-regulated genetic regulatory circuit. For example, the genetically engineered bacteria comprise a first gene encoding an mf-lon protease, wherein the first gene is operably linked to a FNR-responsive promoter; a second gene or gene cassette for producing a payload operably linked to a tet regulatory region (tetO); and a third gene encoding an mf-lon degradation signal linked to a tet repressor (tetR), wherein the tetR is capable of binding to the tet regulatory region and repressing expression of the second gene or gene cassette. The mf-lon protease is capable of recognizing the mf-lon degradation signal and degrading the tetR. In the presence of oxygen, FNR does not bind the FNR-responsive promoter, the repressor is not degraded, and the payload is not expressed. In the absence of oxygen, FNR dimerizes and binds the FNR-responsive promoter, thereby inducing expression of mf-lon protease. The mf-lon protease recognizes the mf-lon degradation signal and degrades the tetR, and the payload is expressed.

In some embodiments, the invention provides genetically engineered bacteria comprising a gene or gene cassette for producing a payload, and a repressor-regulated genetic regulatory circuit. For example, the genetically engineered bacteria comprise a first gene encoding a first repressor, wherein the first gene is operably linked to a FNR-responsive promoter; a second gene or gene cassette for producing a payload operably linked to a first regulatory region comprising a constitutive promoter; and a third gene encoding a second repressor, wherein the second repressor is capable of binding to the first regulatory region and repressing expression of the second gene or gene cassette. The third gene is operably linked to a second regulatory region comprising a constitutive promoter, wherein the first repressor is capable of binding to the second regulatory region and inhibiting expression of the second repressor. In the presence of oxygen, FNR does not bind the FNR-responsive promoter, the first repressor is not expressed, the second repressor is expressed, and the payload is not expressed. In the absence of oxygen, FNR dimerizes and binds the FNR-responsive promoter, the first repressor is expressed, the second repressor is not expressed, and the payload is expressed.

Examples of repressors useful in these embodiments include, but are not limited to, ArgR, TetR, ArsR, AscG, LacI, CscR, DeoR, DgoR, FruR, GalR, GatR, CI, LexA, RafR, QacR, and PtxS (US20030166191).

In some embodiments, the invention provides genetically engineered bacteria comprising a gene or gene cassette for producing a payload and a regulatory RNA-regulated genetic regulatory circuit. For example, the genetically engineered bacteria comprise a first gene encoding a regulatory RNA, wherein the first gene is operably linked to a FNR-responsive promoter, and a second gene or gene cassette for producing a payload. The second gene or gene cassette is operably linked to a constitutive promoter and further linked to a nucleotide sequence capable of producing an mRNA hairpin that inhibits translation of the payload. The regulatory RNA is capable of eliminating the mRNA hairpin and inducing payload translation via the ribosomal binding site. In the presence of oxygen, FNR does not bind the FNR-responsive promoter, the regulatory RNA is not expressed, and the mRNA hairpin prevents the payload from being translated. In the absence of oxygen, FNR dimerizes and binds the FNR-responsive promoter, the regulatory RNA is expressed, the mRNA hairpin is eliminated, and the payload is expressed.

In some embodiments, the invention provides genetically engineered bacteria comprising a gene or gene cassette for producing a payload, and a CRISPR-regulated genetic regulatory circuit. For example, the genetically engineered bacteria comprise a Cas9 protein; a first gene encoding a CRISPR guide RNA, wherein the first gene is operably linked to a FNR-responsive promoter; a second gene or gene cassette for producing a payload, wherein the second gene or gene cassette is operably linked to a regulatory region comprising a constitutive promoter; and a third gene encoding a repressor operably linked to a constitutive promoter, wherein the repressor is capable of binding to the regulatory region and repressing expression of the second gene or gene cassette. The third gene is further linked to a CRISPR target sequence that is capable of binding to the CRISPR guide RNA, wherein said binding to the CRISPR guide RNA induces cleavage by the Cas9 protein and inhibits expression of the repressor. In the presence of oxygen, FNR does not bind the FNR-responsive promoter, the guide RNA is not expressed, the repressor is expressed, and the payload is not expressed. In the absence of oxygen, FNR dimerizes and binds the FNR-responsive promoter, the guide RNA is expressed, the repressor is not expressed, and the payload is expressed.

In some embodiments, the invention provides genetically engineered bacteria comprising a gene or gene cassette for producing a payload and a recombinase-regulated genetic regulatory circuit. For example, the genetically engineered bacteria comprise a first gene encoding a recombinase, wherein the first gene is operably linked to a FNR-responsive promoter, and a second gene or gene cassette for producing a payload operably linked to a constitutive promoter. The second gene or gene cassette is inverted in orientation (3' to 5') and flanked by recombinase binding sites, and the recombinase is capable of binding to the recombinase binding sites to induce expression of the second gene or gene cassette by reverting its orientation (5' to 3'). In the presence of oxygen, FNR does not bind the FNR-responsive promoter, the recombinase is not expressed, the payload remains in the 3' to 5' orientation, and no functional payload is produced. In the absence of oxygen, FNR dimerizes and binds the FNR-responsive promoter, the recombinase is expressed, the payload is reverted to the 5' to 3' orientation, and functional payload is produced.

In some embodiments, the invention provides genetically engineered bacteria comprising a gene or gene cassette for producing a payload and a polymerase- and recombinase-regulated genetic regulatory circuit. For example, the genetically engineered bacteria comprise a first gene encoding a recombinase, wherein the first gene is operably linked to a FNR-responsive promoter; a second gene or gene cassette for producing a payload operably linked to a T7 promoter; a third gene encoding a T7 polymerase, wherein the T7 polymerase is capable of binding to the T7 promoter and inducing expression of the payload. The third gene encoding the T7 polymerase is inverted in orientation (3' to 5') and flanked by recombinase binding sites, and the recombinase is capable of binding to the recombinase binding sites to induce expression of the T7 polymerase gene by reverting its orientation (5' to 3'). In the presence of oxygen, FNR does not bind the FNR-responsive promoter, the recombinase is not expressed, the T7 polymerase gene remains in the 3' to 5' orientation, and the payload is not expressed. In the absence of oxygen, FNR dimerizes and binds the FNR-responsive promoter, the recombinase is expressed, the T7 polymerase gene is reverted to the 5' to 3' orientation, and the payload is expressed.

Host-Plasmid Mutual Dependency

In some embodiments, the genetically engineered bacteria of the invention also comprise a plasmid that has been modified to create a host-plasmid mutual dependency. In certain embodiments, the mutually dependent host-plasmid platform is GeneGuard (Wright et al., 2015). In some embodiments, the GeneGuard plasmid comprises (i) a conditional origin of replication, in which the requisite replication initiator protein is provided in trans; (ii) an auxotrophic modification that is rescued by the host via genomic translocation and is also compatible for use in rich media; and/or (iii) a nucleic acid sequence which encodes a broad-spectrum toxin. The toxin gene may be used to select against plasmid spread by making the plasmid DNA itself disadvantageous for strains not expressing the anti-toxin (e.g., a wild-type bacterium). In some embodiments, the GeneGuard plasmid is stable for at least 100 generations without antibiotic selection. In some embodiments, the GeneGuard plasmid does not disrupt growth of the host. The GeneGuard plasmid is used to greatly reduce unintentional plasmid propagation in the genetically engineered bacteria of the invention.

The mutually dependent host-plasmid platform may be used alone or in combination with other biosafety mechanisms, such as those described herein (e.g., kill switches, auxotrophies). In some embodiments, the genetically engineered bacteria comprise a GeneGuard plasmid. In other embodiments, the genetically engineered bacteria comprise a GeneGuard plasmid and/or one or more kill switches. In other embodiments, the genetically engineered bacteria comprise a GeneGuard plasmid and/or one or more auxotrophies. In still other embodiments, the genetically engineered bacteria comprise a GeneGuard plasmid, one or more kill switches, and/or one or more auxotrophies.

Kill Switch

In some embodiments, the genetically engineered bacteria of the invention also comprise a kill switch (see, e.g., U.S. Provisional Application Nos. 62/183,935 and 62/263,329 incorporated herein by reference in their entireties). The kill switch is intended to actively kill engineered microbes in response to external stimuli. As opposed to an auxotrophic mutation where bacteria die because they lack an essential nutrient for survival, the kill switch is triggered by a particular factor in the environment that induces the production of toxic molecules within the microbe that cause cell death.

Bacteria engineered with kill switches have been engineered for in vitro research purposes, e.g., to limit the spread of a biofuel-producing microorganism outside of a laboratory environment. Bacteria engineered for in vivo administration to treat a disease or disorder may also be programmed to die at a specific time after the expression and delivery of a heterologous gene or genes, for example, a therapeutic gene(s) or after the subject has experienced the therapeutic effect. For example, in some embodiments, the kill switch is activated to kill the bacteria after a period of time following oxygen level-dependent expression of the substrate transporter. In some embodiments, the kill switch is activated in a delayed fashion following oxygen level-dependent expression of the substrate transporter. Alternatively, the bacteria may be engineered to die if the bacteria have spread outside of a target site (e.g., a tumor site). Specifically, it may be useful to prevent the spread of the microorganism outside the area of interest (for example, outside of the tumor site) within the subject, or spread of the microorganism outside of the subject into the environment (for example, spread to the environment through the blood or stool of the subject). Examples of such toxins that can be used in kill switches include, but are not limited to, bacteriocins, lysins, and other molecules that cause cell death by lysing cell membranes, degrading cellular DNA, or other mechanisms. Such toxins can be used individually or in combination. The switches that control their production can be based on, for example, transcriptional activation (toggle switches; see, e.g., Gardner et al. (2000) Nature 403: 339-42), translation (riboregulators), or DNA recombination (recombinase-based switches), and can sense environmental stimuli such as anaerobiosis or reactive oxygen species. These switches can be activated by a single environmental factor or may require several activators in AND, OR, NAND and NOR logic configurations to induce cell death. For example, an AND riboregulator switch is activated by tetracycline, isopropyl β-D-1-thiogalactopyranoside (IPTG), and arabinose to induce the expression of lysins, which permeabilize the cell membrane and kill the cell. IPTG induces the expression of the endolysin and holin mRNAs, which are then derepressed by the addition of arabinose and tetracycline. All three inducers must be present to cause cell death. Examples of kill switches are known in the art (Callura et al. (2010) *Proc. Natl. Acad. Sci. USA* 107(36): 15898-903.). In some embodiments, the kill switch is activated to kill the bacteria after a period of time following oxygen level-dependent expression of the substrate transporter. In some embodiments, the kill switch is activated in a delayed fashion following oxygen level-dependent expression of the substrate transporter.

Kill switches can be designed such that a toxin is produced in response to an environmental condition or external signal (e.g., the bacteria is killed in response to an external cue) or, alternatively designed such that a toxin is produced once an environmental condition no longer exists or an external signal is ceased.

Thus, in some embodiments, the genetically engineered bacteria of the disclosure are further programmed to die after sensing an exogenous environmental signal, for example, in a low oxygen environment. In some embodiments, the genetically engineered bacteria of the present disclosure comprise one or more genes encoding one or more recombinase(s), whose expression is induced in response to an environmental condition or signal and causes one or more recombination events that ultimately leads to the expression of a toxin which kills the cell. In some embodiments, the at least one recombination event is the flipping of an inverted heterologous gene encoding a bacterial toxin which is then constitutively expressed after it is flipped by the first recombinase. In one embodiment, constitutive expression of the bacterial toxin kills the genetically engineered bacterium. In these types of kill switch systems, once the engineered bacterial cell senses the exogenous environmental condition and expresses the heterologous gene of interest, the recombinant bacterial cell is no longer viable.

In another embodiment in which the genetically engineered bacteria of the present disclosure express one or more recombinase(s) in response to an environmental condition or signal causing at least one recombination event, the genetically engineered bacterium further expresses a heterologous gene encoding an anti-toxin in response to an exogenous environmental condition or signal. In one embodiment, the at least one recombination event is flipping of an inverted heterologous gene encoding a bacterial toxin by a first recombinase. In one embodiment, the inverted heterologous gene encoding the bacterial toxin is located between a first forward recombinase recognition sequence and a first reverse recombinase recognition sequence. In one embodiment, the heterologous gene encoding the bacterial toxin is constitutively expressed after it is flipped by the first recombinase. In one embodiment, the anti-toxin inhibits the activity of the toxin, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In another embodiment, the at least one recombination event is flipping of an inverted heterologous gene encoding a second recombinase by a first recombinase, followed by the flipping of an inverted heterologous gene encoding a bacterial toxin by the second recombinase. In one embodiment, the inverted heterologous gene encoding the second recombinase is located between a first forward recombinase recognition sequence and a first reverse recombinase recognition sequence. In one embodiment, the inverted heterologous gene encoding the bacterial toxin is located between a second forward recombinase recognition sequence and a second reverse recombinase recognition sequence. In one embodiment, the heterologous gene encoding the second recombinase is constitutively expressed after it is flipped by the first recombinase. In one embodiment, the heterologous gene encoding the bacterial toxin is constitutively expressed after it is flipped by the second recombinase. In one embodiment, the genetically engineered bacterium is killed by the bacterial toxin. In one embodiment, the genetically engineered bacterium further expresses a heterologous gene encoding an anti-toxin in response to the exogenous environmental condition. In one embodiment, the anti-toxin inhibits the activity of the toxin when the exogenous environmental condition is present, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In one embodiment, the at least one recombination event is flipping of an inverted heterologous gene encoding a second recombinase by a first recombinase, followed by flipping of an inverted heterologous gene encoding a third recombinase by the second recombinase, followed by flipping of an inverted heterologous gene encoding a bacterial toxin by the third recombinase.

In one embodiment, the at least one recombination event is flipping of an inverted heterologous gene encoding a first excision enzyme by a first recombinase. In one embodiment, the inverted heterologous gene encoding the first excision enzyme is located between a first forward recombinase recognition sequence and a first reverse recombinase recognition sequence. In one embodiment, the heterologous gene encoding the first excision enzyme is constitutively expressed after it is flipped by the first recombinase. In one embodiment, the first excision enzyme excises a first essential gene. In one embodiment, the programmed recombinant bacterial cell is not viable after the first essential gene is excised.

In one embodiment, the first recombinase further flips an inverted heterologous gene encoding a second excision enzyme. In one embodiment, the wherein the inverted heterologous gene encoding the second excision enzyme is located between a second forward recombinase recognition sequence and a second reverse recombinase recognition sequence. In one embodiment, the heterologous gene encoding the second excision enzyme is constitutively expressed after it is flipped by the first recombinase. In one embodiment, the genetically engineered bacterium dies or is no longer viable when the first essential gene and the second essential gene are both excised. In one embodiment, the genetically engineered bacterium dies or is no longer viable when either the first essential gene is excised or the second essential gene is excised by the first recombinase.

In one embodiment, the genetically engineered bacterium dies after the at least one recombination event occurs. In another embodiment, the genetically engineered bacterium is no longer viable after the at least one recombination event occurs.

In any of these embodiment, the recombinase can be a recombinase selected from the group consisting of: BxbI, PhiC31, TP901, BxbI, PhiC31, TP901, HK022, HP1, R4, Int1, Int2, Int3, Int4, Int5, Int6, Int1, Int8, Int9, Int10, Int11, Int12, Int13, Int14, Int15, Int16, Int17, Int18, Int19, Int20, Int21, Int22, Int23, Int24, Int25, Int26, Int27, Int28, Int29, Int30, Int31, Int32, Int33, and Int34, or a biologically active fragment thereof.

In the above-described kill switch circuits, a toxin is produced in the presence of an environmental factor or signal. In another aspect of kill switch circuitry, a toxin may be repressed in the presence of an environmental factor (not produced) and then produced once the environmental condition or external signal is no longer present. Such kill switches are called repression-based kill switches and represent systems in which the bacterial cells are viable only in the presence of an external factor or signal, such as arabinose or other sugar. Exemplary kill switch designs in which the toxin is repressed in the presence of an external factor or signal (and activated once the external signal is removed) are shown in FIGS. 12-16. The disclosure provides recombinant bacterial cells which express one or more heterologous gene(s) upon sensing arabinose or other sugar in the exogenous environment. In this aspect, the recombinant bacterial cells contain the araC gene, which encodes the AraC transcription factor, as well as one or more genes under the control of the araBAD promoter. In the absence of arabinose, the AraC transcription factor adopts a conformation that represses transcription of genes under the control of the araBAD promoter. In the presence of arabinose, the AraC transcription factor undergoes a conformational change that allows it to bind to and activate the AraBAD promoter, which induces expression of the desired gene, for example tetR, which represses expression of a toxin gene. In this embodiment, the toxing gene is repressed in the presence of arabinose or other sugar. In an environment where arabinose is not present, the tetR gene is not activated and the toxin is expressed, thereby killing the bacteria. The arbinoase system can also be used to express an essential gene, in which the essential gene is only expressed in the presence of arabinose or other sugar and is not expressed when arabinose or other sugar is absent from the environment.

Thus, in some embodiments in which one or more heterologous gene(s) are expressed upon sensing arabinose in the exogenous environment, the one or more heterologous genes are directly or indirectly under the control of the araBAD promoter. In some embodiments, the expressed heterologous gene is selected from one or more of the following: a heterologous therapeutic gene, a heterologous gene encoding an antitoxin, a heterologous gene encoding a repressor protein or polypeptide, for example, a TetR repressor, a heterologous gene encoding an essential protein not found in the bacterial cell, and/or a heterologous encoding a regulatory protein or polypeptide.

Arabinose inducible promoters are known in the art, including $P_{ara}$, $P_{araB}$, $P_{araC}$, and $P_{araBAD}$. In one embodiment, the arabinose inducible promoter is from $E.$ $coli$. In some embodiments, the $P_{araC}$ promoter and the $P_{araBAD}$ promoter operate as a bidirectional promoter, with the $P_{araBAD}$ promoter controlling expression of a heterologous gene(s) in one direction, and the $P_{araC}$ (in close proximity to, and on the opposite strand from the $P_{araBAD}$ promoter), controlling expression of a heterologous gene(s) in the other direction. In the presence of arabinose, transcription of both heterologous genes from both promoters is induced. However, in the absence of arabinose, transcription of both heterologous genes from both promoters is not induced.

In one exemplary embodiment of the disclosure, the genetically engineered bacteria of the present disclosure contains a kill-switch having at least the following sequences: a $P_{araBAD}$ promoter operably linked to a heterologous gene encoding a Tetracycline Repressor Protein (TetR), a $P_{araC}$ promoter operably linked to a heterologous gene encoding AraC transcription factor, and a heterologous gene encoding a bacterial toxin operably linked to a promoter which is repressed by the Tetracycline Repressor Protein ($P_{TetR}$). In the presence of arabinose, the AraC transcription factor activates the $P_{araBAD}$ promoter, which activates transcription of the TetR protein, which, in turn, represses transcription of the toxin. In the absence of arabinose, however, AraC suppresses transcription from the the $P_{araBAD}$ promoter and no TetR protein is expressed. In this case, expression of the heterologous toxin gene is activated, and the toxin is expressed. The toxin builds up in the recombinant bacterial cell, and the recombinant bacterial cell is killed. In one embodiment, the AraC gene encoding the AraC transcription factor is under the control of a constitutive promoter and is therefore constitutively expressed.

In one embodiment of the disclosure, the genetically engineered bacterium further comprises an antitoxin under the control of a constitutive promoter. In this situation, in the presence of arabinose, the toxin is not expressed due to repression by TetR protein, and the antitoxin protein builds-up in the cell. However, in the absence of arabinose, TetR protein is not expressed, and expression of the toxin is induced. The toxin begins to build-up within the recombinant bacterial cell. The recombinant bacterial cell is no longer viable once the toxin protein is present at either equal or greater amounts than that of the anti-toxin protein in the cell, and the recombinant bacterial cell will be killed by the toxin.

In another embodiment of the disclosure, the genetically engineered bacterium further comprises an antitoxin under the control of the $P_{araBAD}$ promoter. In this situation, in the presence of arabinose, TetR and the anti-toxin are expressed, the anti-toxin builds up in the cell, and the toxin is not expressed due to repression by TetR protein. However, in the absence of arabinose, both the TetR protein and the antitoxin are not expressed, and expression of the toxin is induced. The toxin begins to build-up within the recombinant bacterial cell. The recombinant bacterial cell is no longer viable once the toxin protein is expressed, and the recombinant bacterial cell will be killed by the toxin.

In another exemplary embodiment of the disclosure, the genetically engineered bacteria of the present disclosure contain a kill-switch having at least the following sequences: a $P_{araBAD}$ promoter operably linked to a heterologous gene encoding an essential polypeptide not found in the recombinant bacterial cell (and required for survival), and a $P_{araC}$ promoter operably linked to a heterologous gene encoding AraC transcription factor. In the presence of arabinose, the AraC transcription factor activates the $P_{araBAD}$ promoter, which activates transcription of the heterologous gene encoding the essential polypeptide, allowing the recombinant bacterial cell to survive. In the absence of arabinose, however, AraC suppresses transcription from the $P_{araBAD}$ promoter and the essential protein required for survival is not expressed. In this case, the recombinant bacterial cell dies in the absence of arabinose. In some embodiments, the sequence of $P_{araBAD}$ promoter operably linked to a heterologous gene encoding an essential polypeptide not found in the recombinant bacterial cell can be present in the bacterial cell in conjunction with the TetR/toxin kill-switch system described directly above. In some embodiments, the sequence of $P_{araBAD}$ promoter operably linked to a heterologous gene encoding an essential polypeptide not found in the recombinant bacterial cell can be present in the bacterial cell in conjunction with the TetR/toxin/anto-toxin kill-switch system described directly above.

In yet other embodiments, the bacteria may comprise a plasmid stability system with a plasmid that produces both a short-lived anti-toxin and a long-lived toxin. In this system, the bacterial cell produces equal amounts of toxin and anti-toxin to neutralize the toxin. However, if/when the cell loses the plasmid, the short-lived anti-toxin begins to decay. When the anti-toxin decays completely the cell dies as a result of the longer-lived toxin killing it.

In some embodiments, the engineered bacteria of the present disclosure that are capable of producing a substrate transporter further comprise the gene(s) encoding the components of any of the above-described kill switch circuits.

In any of the above-described embodiments, the bacterial toxin is selected from the group consisting of a lysin, Hok, Fst, TisB, LdrD, Kid, SymE, MazF, FlmA, Ibs, XCV2162, dinJ, CcdB, MazF, ParE, YafO, Zeta, hicB, relB, yhaV, yoeB, chpBK, hipA, microcin B, microcin B17, microcin C, microcin C7-C51, microcin J25, microcin ColV, microcin 24, microcin L, microcin D93, microcin L, microcin E492, microcin H47, microcin 147, microcin M, colicin A, colicin E1, colicin K, colicin N, colicin U, colicin B, colicin Ia, colicin Ib, colicin 5, colicin10, colicin S4, colicin Y, colicin E2, colicin E7, colicin E8, colicin E9, colicin E3, colicin E4, colicin E6; colicin E5, colicin D, colicin M, and cloacin DF13, or a biologically active fragment thereof.

In any of the above-described embodiments, the anti-toxin is selected from the group consisting of an anti-lysin, Sok, RNAII, IstR, Rd1D, Kis, SymR, MazE, FlmB, Sib, ptaRNA1, yafQ, CcdA, MazE, ParD, yafN, Epsilon, HicA, relE, prlF, yefM, chpBI, hipB, MccE, $MccE^{CTD}$, MccF, Cai, ImmE1, Cki, Cni, Cui, Cbi, Iia, Imm, Cfi, Im10, Csi, Cyi, Im2, Im7, Im8, Im9, Im3, Im4, ImmE6, cloacin immunity protein (Cim), ImmE5, ImmD, and Cmi, or a biologically active fragment thereof.

In one embodiment, the bacterial toxin is bactericidal to the genetically engineered bacterium. In one embodiment, the bacterial toxin is bacteriostatic to the genetically engineered bacterium.

In some embodiments, provided herein are genetically engineered bacteria comprising a heterologous gene encoding a substrate transporter, wherein the gene or gene cassette for producing the substrate transporter is controlled by a promoter that is induced under low-oxygen or anaerobic conditions. In some embodiments, the promoter is selected from the fumarate and nitrate reductase regulator (FNR) promoter, arginine deiminiase and nitrate reduction (ANR) promoter, and dissimilatory nitrate respiration regulator (DNR) promoter.

In some embodiments, the genetically engineered bacteria comprising a heterologous gene encoding a substrate transporter is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments, the genetically engineered bacteria comprising a heterologous gene encoding a substrate transporter further comprises a kill switch circuit, such as any of the kill switch circuits provided herein. For example, in some embodiments, the genetically engineered bacteria further comprise one or more genes encoding one or more recombinase(s) under the control of an inducible promoter and an inverted toxin sequence. In some embodiments, the genetically engineered bacteria further comprise one or more genes encoding an anti-toxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an anti-toxin.

In some instances, basal or leaky expression from an inducible promoter may result in the activation of the kill switch, thereby creating strong selective pressure for one or more mutations that disable the switch and thus the ability to kill the cell. In some embodiments, an environmental factor, e.g. arabinose, is present during manufacturing, and activates the production of a repressor that shuts down toxin production. Mutations in this circuit, with the exception of the toxin gene itself, will result in death with reduced chance for negative selection. When the environmental factor is absent, the repressor stops being made, and the toxin is produced. When the toxin concentration overcomes that of the antitoxin, the cell dies. In some embodiments, variations in the promoter and ribosome binding sequences of the antitoxin and the toxin allow for tuning of the circuit to produce variations in the timing of cell death. In alternate embodiments, the circuit comprises recombinases that are repressed by tetR and produced in the absence of tetR. These recombinases are capable of flipping the toxin gene or its promoter into the active configuration, thereby resulting in toxin production.

Figure 21:
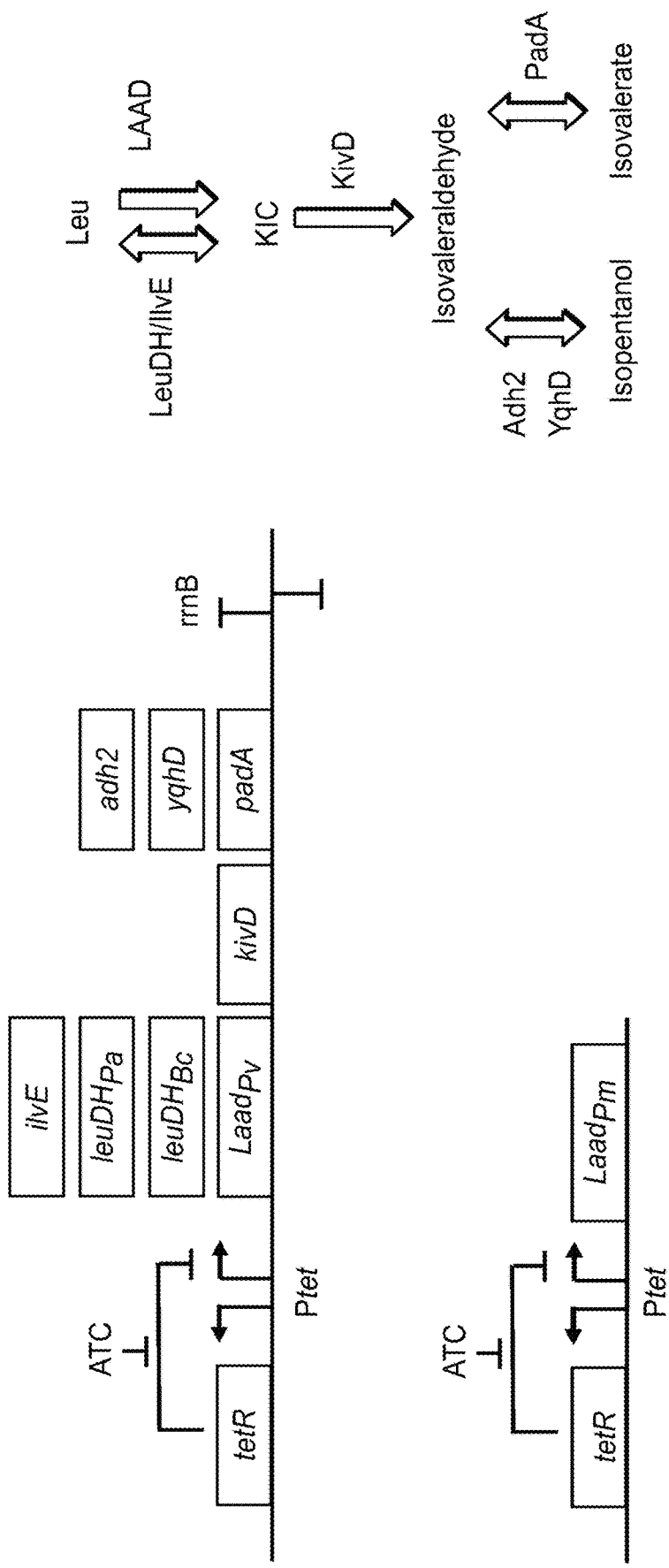
FIG. 21 depicts exemplary components of a branched chain amino acid synthetic biotic disclosed herein for leucine degradation.
Figure 23:
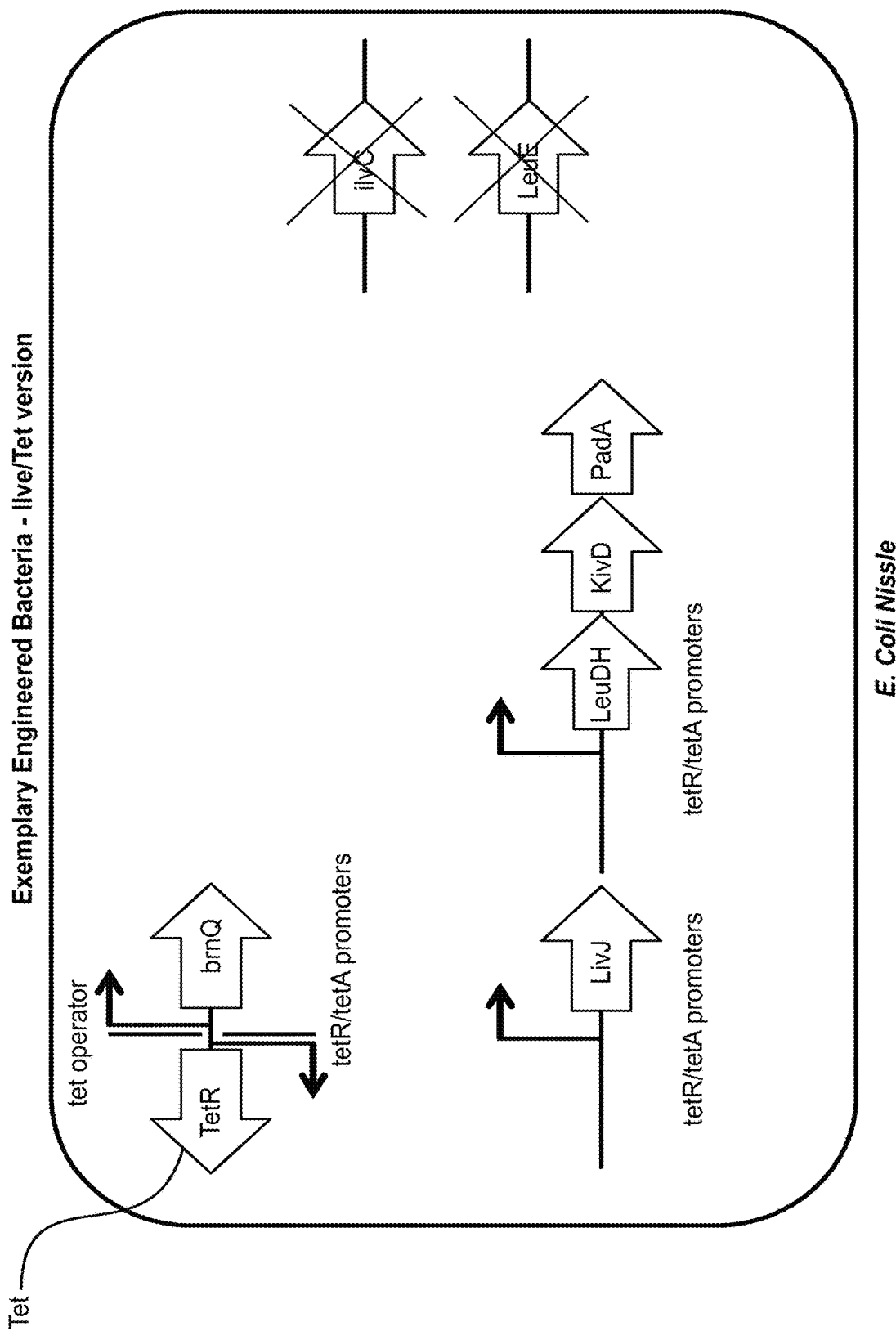
FIG. 23 depicts one exemplary branched chain amino acid circuit. Genes shown are low affinity BCAA transporter (BrnQ), the branched chain a-ketoacid decarboxylase (KivD) from *Lactococcus lactis*, aldehyde dehydrogenase from *E. Coli* K-12 (PadA), and leuDH derived from *Pseudomonas aeruginosa* PA01 or *Bacillus cereus*. The genes for the leucine exporter (LeuE) and ilvC have been deleted. The gene for ilvJ is added.
Figure 24:
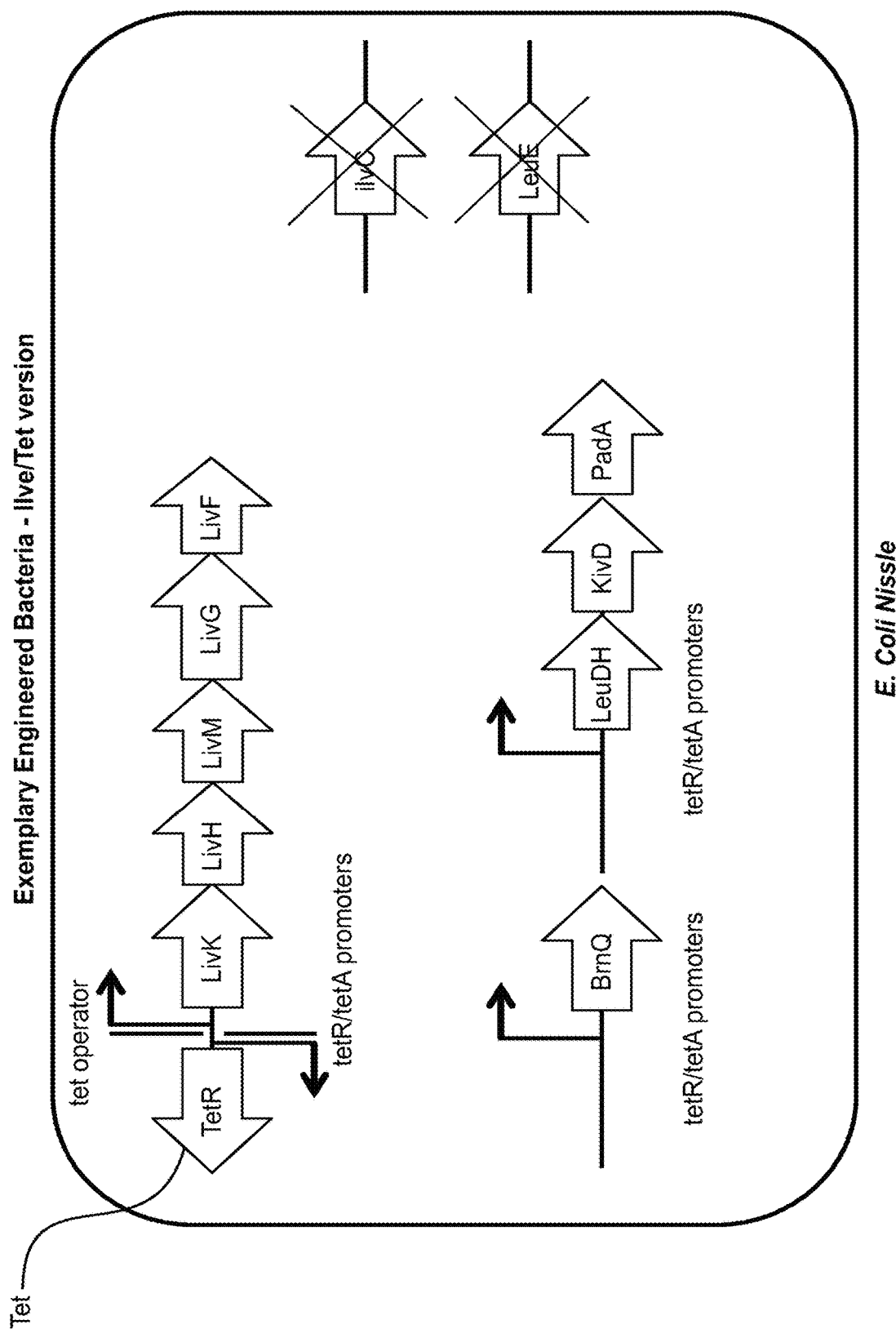
FIG. 24 depicts one exemplary branched chain amino acid circuit. Genes shown are high affinity leucine transporter complex (LivKHMGF), the branched chain a-ketoacid decarboxylase (KivD) from *Lactococcus lactis*, aldehyde dehydrogenase from *E. Coli* K-12 (PadA), and leuDH derived from *Pseudomonas aeruginosa* PA01 or *Bacillus cereus*. The genes for the leucine exporter (LeuE) and ilvC have been deleted. The gene for BrnQ is added.
Figure 25:
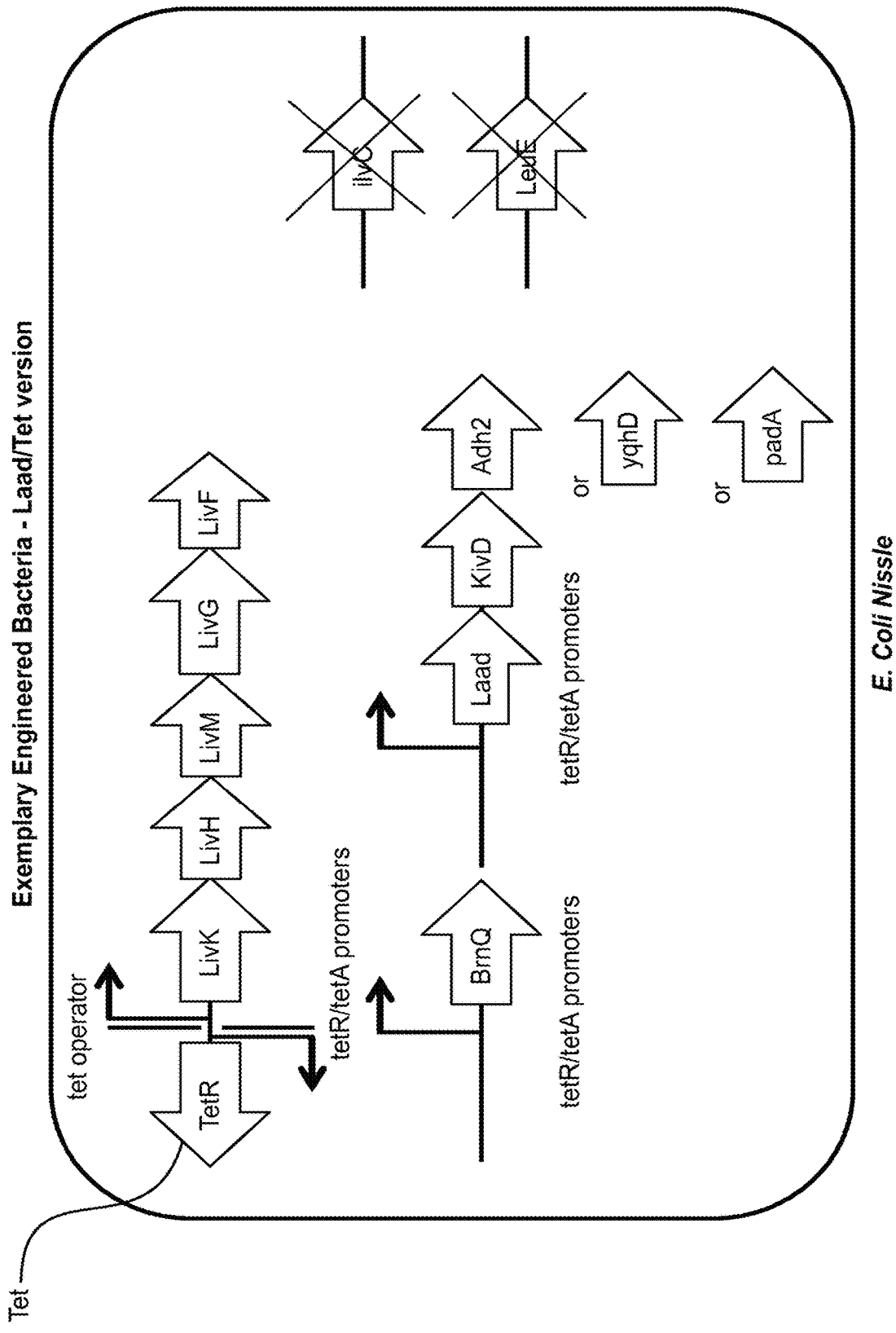
FIG. 25 depicts one exemplary branched chain amino acid circuit. Genes shown are high affinity leucine transporter complex (LivKHMGF), the branched chain a-ketoacid decarboxylase (KivD) from *Lactococcus lactis*, either aldehyde dehydrogenase from *E. Coli* K-12 (PadA), alcohol dehydrogenase YqhD from *E. Coli*, or alcohol dehydrogenase Adh2 from *S. cerevisiae*, and L-AAD derived from *Proteus vulgaris* or *Proteus mirabilis*. The genes for the leucine exporter (LeuE) and ilvC have been deleted. The gene for BrnQ is added.
Figure 26:
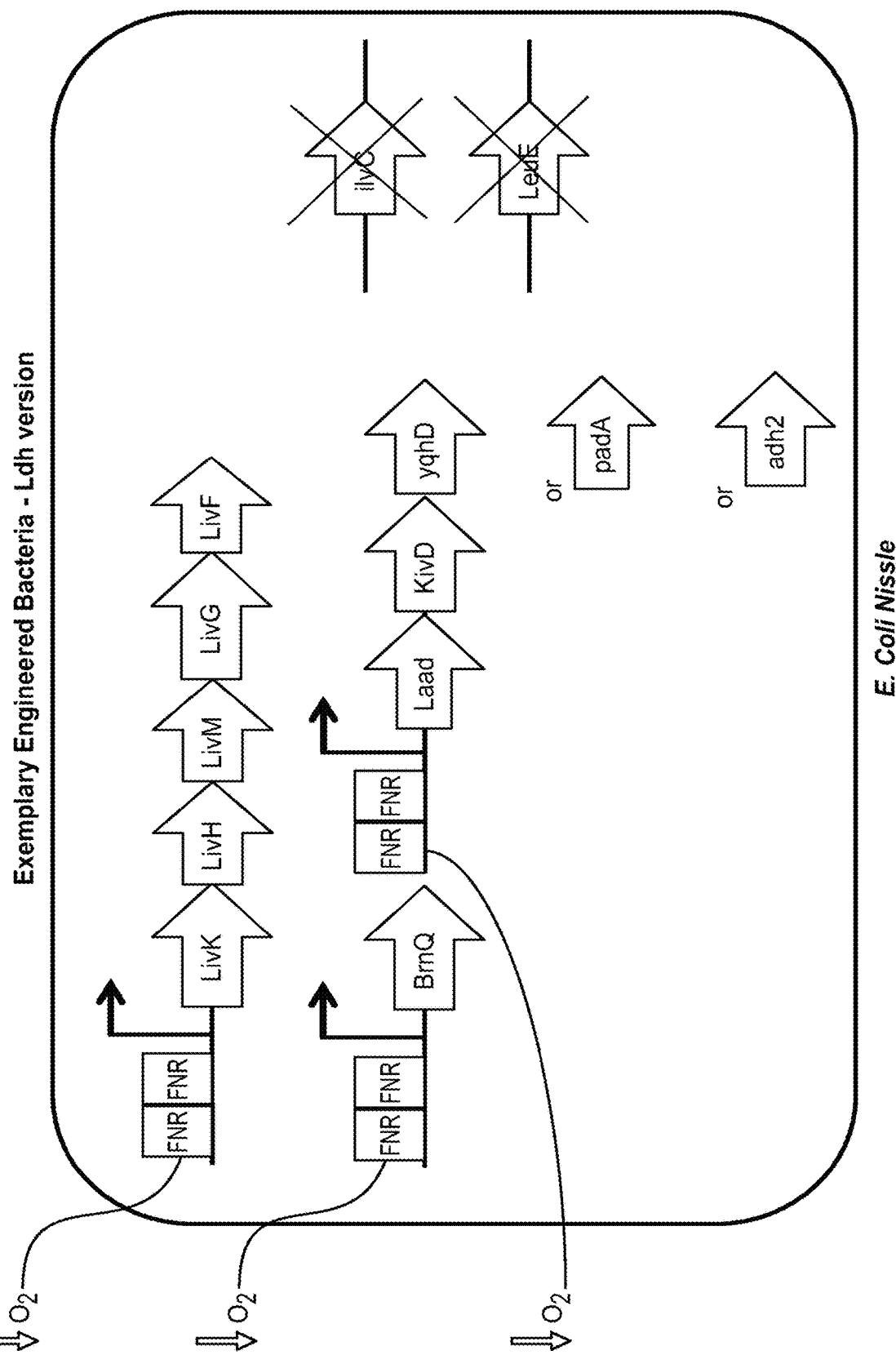
FIG. 26 depicts one exemplary branched chain amino acid circuit. Genes shown are high affinity leucine transporter complex (LivKHMGF), the branched chain a-ketoacid decarboxylase (KivD) from *Lactococcus lactis*, either aldehyde dehydrogenase from *E. Coli* K-12 (PadA), alcohol dehydrogenase YqhD from *E. Coli*, or alcohol dehydrogenase Adh2 from *S. cerevisiae*, and L-AAD derived from *Proteus vulgaris* or *Proteus mirabilis*. The genes for the leucine exporter (LeuE) and ilvC have been deleted. The gene for BrnQ is added. The genes are under the control of the FNR promoter.
Figure 27:
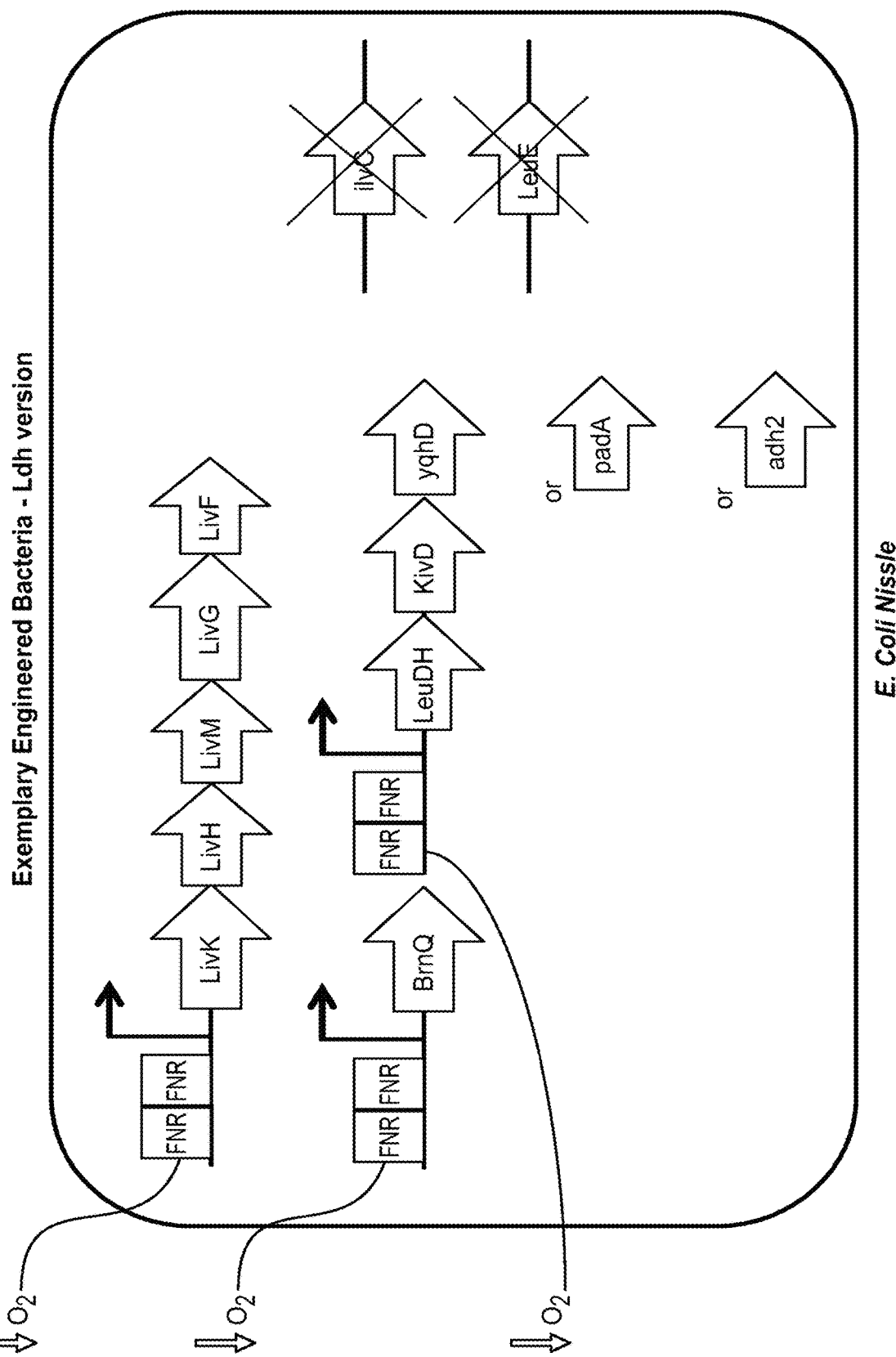
FIG. 27 depicts one exemplary branched chain amino acid circuit. Genes shown are high affinity leucine transporter complex (LivKHMGF), the branched chain a-ketoacid decarboxylase (KivD) from *Lactococcus lactis*, either aldehyde dehydrogenase from *E. Coli* K-12 (PadA), alcohol dehydrogenase YqhD from *E. Coli*, or alcohol dehydrogenase Adh2 from *S. cerevisiae*, and LeuDh derived from *Pseudomonas aeruginosa* PA01 or *Bacillus cereus*. The genes for the leucine exporter (LeuE) and ilvC have been deleted. The gene for BrnQ is added. The genes are under the control of the FNR promoter.
Figure 28:
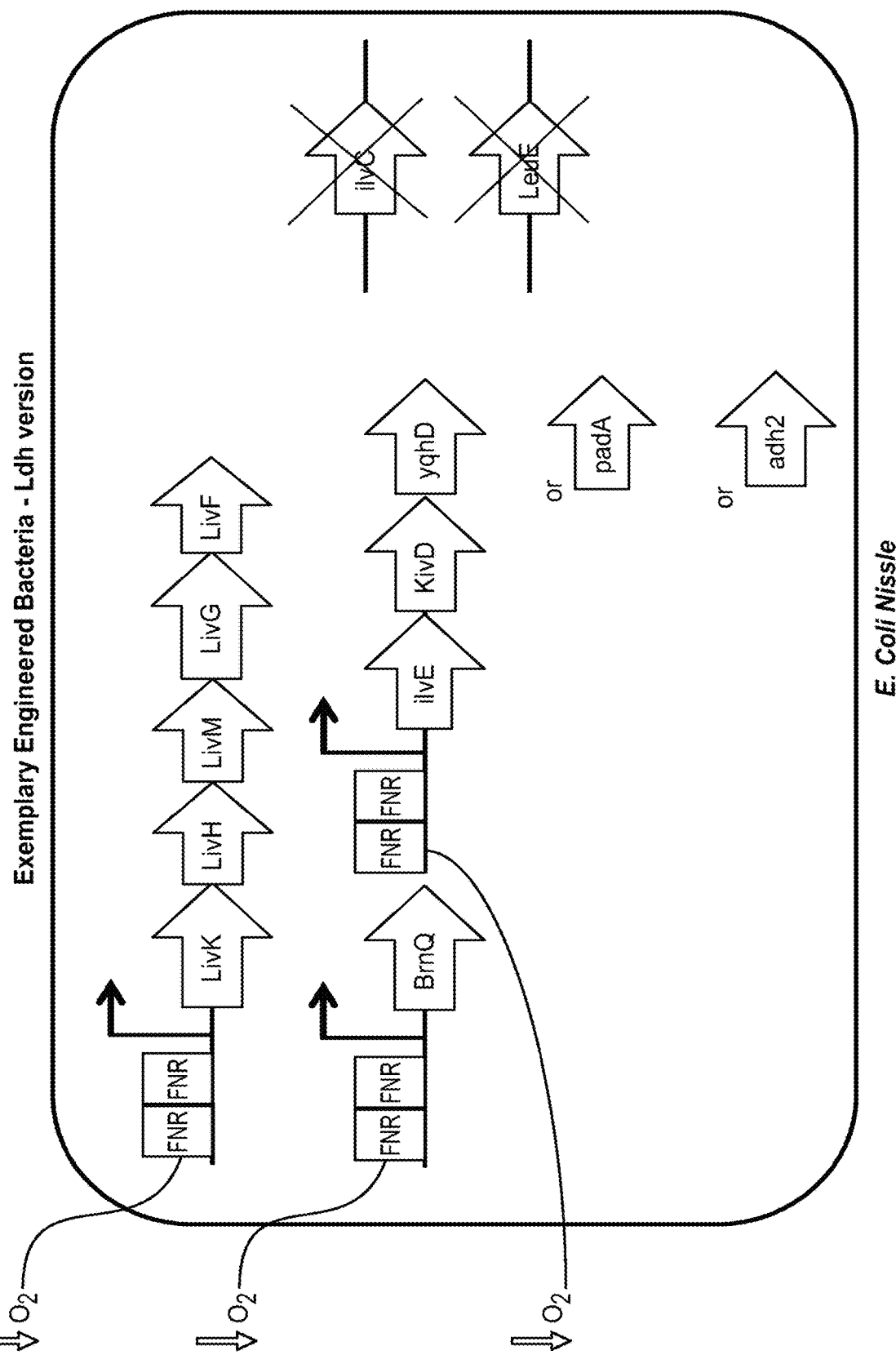
FIG. 28 depicts one exemplary branched chain amino acid circuit. Genes shown are high affinity leucine transporter complex (LivKHMGF), the branched chain a-ketoacid decarboxylase (KivD) from *Lactococcus lactis*, either aldehyde dehydrogenase from *E. Coli* K-12 (PadA), alcohol dehydrogenase YqhD from *E. Coli*, or alcohol dehydrogenase Adh2 from *S. cerevisiae*, and BCAA aminotransferase ilvE. The genes for the leucine exporter (LeuE) and ilvC have been deleted. The gene for BrnQ is added. The genes are under the control of the FNR promoter.
Figure 30:
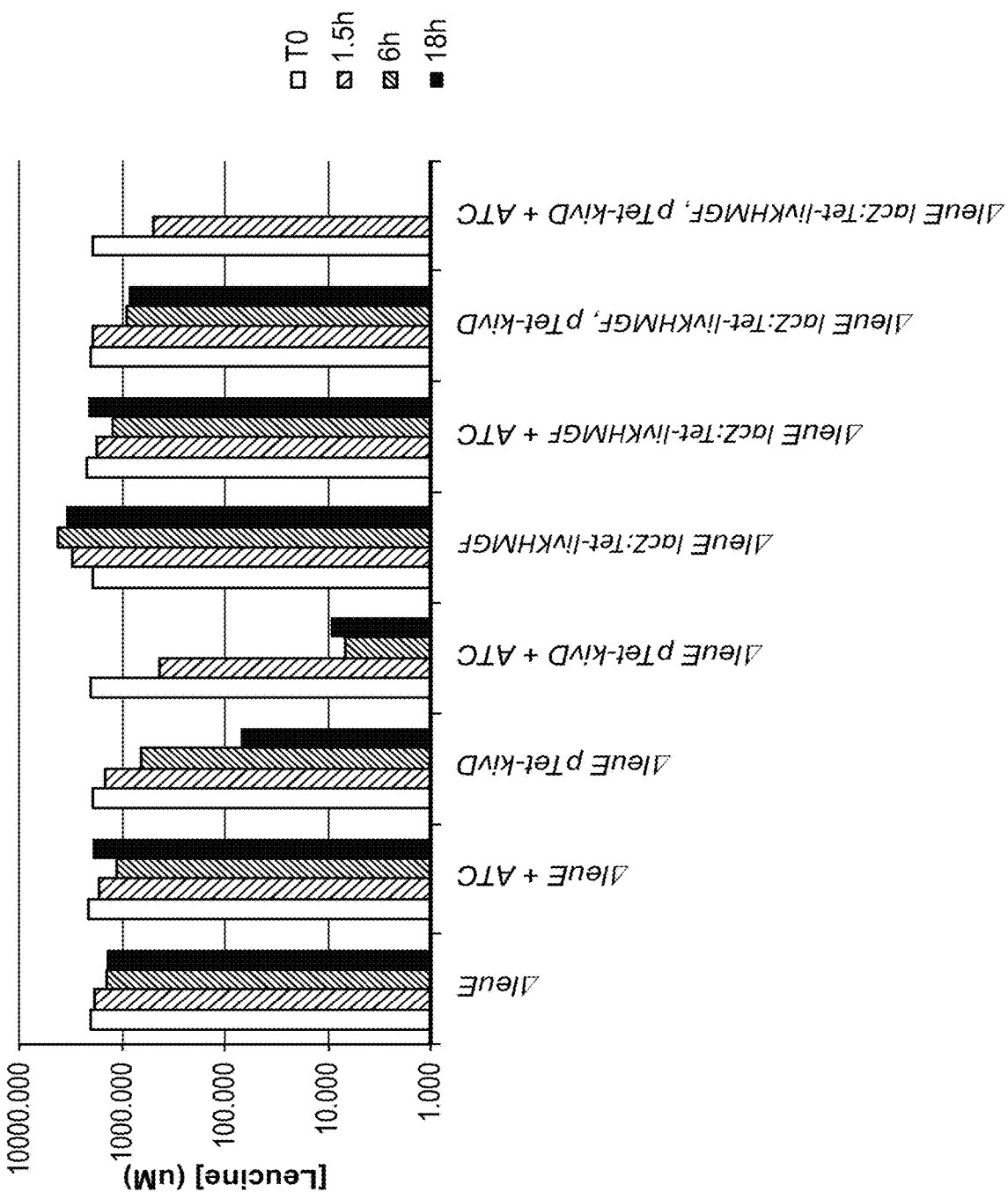
FIG. 30 depicts leucine levels in the Nissle ΔleuE deletion strain harboring a high-copy plasmid expressing kivD from the Tet promoter or further with a copy of the livKHMGF operon driven by the Tet promoter integrated into the chromosome at the lacZ locus, which were induced with ATC and incubated in culture medium supplemented with 2 mM leucine. Samples were removed at 0, 1.5, 6 and 18 h, and leucine concentration was determined by liquid chromatography tandem mass spectrometry.
Figure 31:
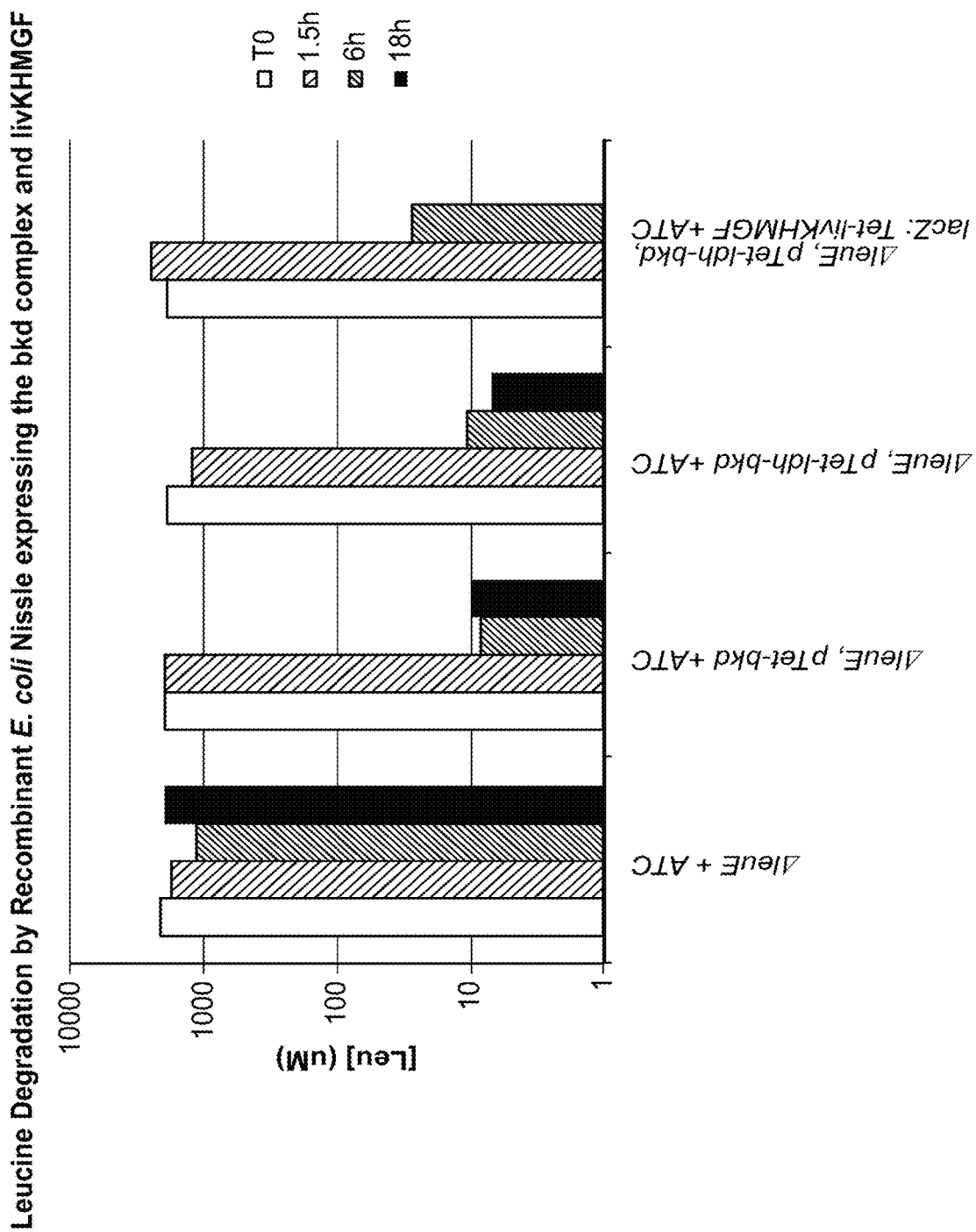
FIG. 31 depicts leucine degradation in the Nissle ΔleuE deletion strain harboring a high-copy plasmid expressing the branch-chain keto-acid dehydrogenase (bkd) complex with or without expression of a leucine dehydrogenase (ldh) from the Tet promoter or further with a copy of the leucine importer livKHMGF driven by the Tet promoter integrated into the chromosome at the lacZ locus, which were induced with ATC and incubated in culture medium supplemented with 2 mM leucine. Samples were removed at 0, 1.5, 6 and 18 h, and leucine concentration was determined by liquid chromatography tandem mass spectrometry.

Synthetic gene circuits express on plasmids may function well in the short term but lose ability and/or function in the long term, e.g., in the stringent conditions found in a tumor microenvironment (Danino et al. (2015) Sci. Transl. Med. 7(289):289ra84). In some embodiments, the genetically engineered bacteria comprise stable circuits for expressing genes of interest, e.g., a substrate transporter, over prolonged periods. In some embodiments, the genetically engineered bacteria are capable of targeting cancerous cells and producing a substrate transporter and further comprise a toxin-antitoxin system that simultaneously produces a toxin (hok) and a short-lived antitoxin (sok), wherein loss of the plasmid causes the cell to be killed by the long-lived toxin (Danino et al., 2015; FIG. 21). In some embodiments, the genetically engineered bacteria further comprise alp7 from *B. subtilis* plasmid pL20 and produces filaments that are capable of pushing plasmids to the poles of the cells in order to ensure equal segregation during cell division (Danino et al., 2015).

In some embodiments, the genetically engineered bacteria comprising a heterologous gene encoding a substrate transporter is an auxotroph and further comprises a kill switch circuit, such as any of the kill switch circuits described herein.

In some embodiments of the above described genetically engineered bacteria, the gene encoding the substrate transporter is present on a plasmid in the bacterium and operatively linked on the plasmid to the promoter that is induced under low-oxygen or anaerobic conditions. The genetically engineered bacteria are capable of local and tumor-specific delivery of the substrate transporter, e.g., an amino acid transporter. In other embodiments, the gene encoding the substrate transporter is present in the bacterial chromosome and is operatively linked in the chromosome to the promoter that is induced under low-oxygen or anaerobic conditions. The genetically engineered bacteria are capable of local and tumor-specific delivery of the substrate transporter.

Pharmaceutical Compositions and Formulations

Pharmaceutical compositions comprising the genetically engineered microrganisms of the invention may be used to treat, manage, ameliorate, and/or prevent a disease or condition disclosed herein. Pharmaceutical compositions of the invention comprising one or more genetically engineered bacteria with prophylactic agents, therapeutic agents, and/or pharmaceutically acceptable carriers are provided.

In certain embodiments, the pharmaceutical composition comprises one species, strain, or subtype of bacteria that are engineered to comprise the genetic modifications described herein, e.g., one or more genes encoding one or more substrate transporters. In alternate embodiments, the pharmaceutical composition comprises two or more species, strains, and/or subtypes of bacteria that are each engineered to comprise the genetic modifications described herein, e.g., one or more genes encoding one or more substrate transporters.

In some embodiments, the genetically engineered bacteria are administered systemically or intratumorally as spores. As a non-limiting example, the genetically engineered bacteria are *Clostridia*, and administration results in a selective colonization of hypoxic/necrotic areas within a tumor. In some embodiments, the spores germinate exclusively in the hypoxic/necrotic regions present in solid tumours and nowhere else in the body.

The pharmaceutical compositions of the invention may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered microorganisms may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, intravenous, subcutaneous, intratumoral, peritumor, immediate-release, pulsatile-release, delayed-release, or sustained release). Suitable dosage amounts for the genetically engineered bacteria may range from about $10^4$ to $10^{12}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In on embodiment, the pharmaceutical composition is administered after the subject eats a meal.

The genetically engineered bacteria or genetically engineered virus may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered microorganisms may be administered intravenously, e.g., by infusion or injection. Alternatively, the genetically engineered microorganisms may be administered intratumorally and/or peritumorally. In other embodiments, the genetically engineered microorganisms may be administered intra-arterially, intramuscularly, or intraperitoneally. In some embodiments, the genetically engineered bacteria colonize about 20%, 30%, 40%, 50%, 60%, 70%, 80%, 90% or more of the target site (e.g., a tumor). In some embodiments, the genetically engineered bacteria are co-administered with a PEGylated form of rHuPH20 (PEGPH20) or other agent in order to destroy the tumor septae in order to enhance penetration of the tumor capsule, collagen, and/or stroma. In some embodiments, the genetically engineered bacteria are capable of producing a substrate transporter as well as one or more enzymes that degrade fibrous tissue.

The genetically engineered mircroroganisms of the disclosure may be administered via intratumoral injection, resulting in bacterial cells that are directly deposited within the target tissue (e.g., a tumor). Intratumoral injection of the engineered bacteria may elicit a potent localized inflammatory response as well as an adaptive immune response against tumor cells. Bacteria are suspended in solution before being withdrawn into a 1-ml syringe. In some embodiments, the tumor is injected with an 18-gauge multipronged needle (Quadra-Fuse, Rex Medical). The injection site is aseptically prepared. If available, ultrasound or CT may be used to identify a necrotic region of the tumor for injection. If a necrotic region is not identified, the injection can be directed to the center of the tumor. The needle is inserted once into a predefined region, and dispensed with even pressure. The injection needle is removed slowly, and the injection site is sterilized.

Direct intratumoral injection of the genetically engineered bacteria of the invention into a target tissue (e.g., a solid tumor) may be advantageous as compared to intravenous administration. Using an intravenous injection method, only a small proporation of the bacteria may reach the target tumor. For example, following *E. coli* Nissle injection into the tail vein of 4T1 tumor-bearing mice, most bacteria (>99%) are quickly cleared from the animals and only a small percentage of the administered bacteria colonize the tumor (Stritzker et al., 2007). In particular, in large animals and human patients, which have relatively large blood volumes and relatively small tumors compared to mice, intratumoral injection may be especially beneficial. Injection directly into the tumor allows the delivery of a higher concentration of therapeutic agent and avoids the toxicity, which can result from systemic administration. In addition, intratumoral injection of bacteria induces robust and localized immune responses within the tumor.

Depending on the location, tumor type, and tumor size, different administration techniques may be used, including but not limited to, cutaneous, subcutaneous, and percutaneous injection, therapeutic endoscopic ultrasonography, or endobronchial intratumor delivery. Prior to the intratumor administration procedures, sedation in combination with a local anesthetic and standard cardiac, pressure, and oxygen monitoring, or full anesthesia of the patient is performed.

For some tumors, percutaneous injection can be employed, which is the least invasive administration method. Ultrasound, computed tomography (CT) or fluoroscopy can be used as guidance to introduce and position the needle. Percutaneous intratumoral injection is for example described for hepatocellular carcinoma in Lencioni et al. (2010) *J. Vasc Interv Radiol.* 21(10): 1533-8). Intratumoral injection of cutaneous, subcutaneous, and nodal tumors is for example described in WO/2014/036412 (Amgen) for late stage melanoma.

Single insertion points or multiple insertion points can be used in percutaneous injection protocols. Using a single insertion point, the solution may be injected percutaneously along multiple tracks, as far as the radial reach of the needle allows. In other embodiments, multiple injection points may be used if the tumor is larger than the radial reach of the needle. The needle can be pulled back without exiting, and redirected as often as necessary until the full dose is injected and dispersed. To maintain sterility, a separate needle is used for each injection. Needle size and length varies depending on the tumor type and size.

In some embodiments, the tumor is injected percutaneously with an 18-gauge multipronged needle (Quadra-Fuse, Rex Medical). The device consists of an 18 gauge puncture needle 20 cm in length. The needle has three retractable prongs, each with four terminal side holes and a connector with extension tubing clamp. The prongs are deployed from the lateral wall of the needle. The needle can be introduced percutaneously into the center of the tumor and can be positioned at the deepest margin of the tumor. The prongs are deployed to the margins of the tumor. The prongs are deployed at maximum length and then are retracted at defined intervals. Optionally, one or more rotation-injection-rotation maneuvers can be performed, in which the prongs are retracted, the needle is rotated by a 60 degrees, which is followed by repeat deployment of the prongs and additional injection.

Therapeutic endoscopic ultrasonography (EUS) is employed to overcome the anatomical constraints inherent in gaining access to certain other tumors (Shirley et al. (2013) *Gastroenterol Res. Pract.* 2013: 207129). EUS-guided fine needle injection (EUS-FNI) has been successfully used for antitumor therapies for the treatment of head and neck, esophageal, pancreatic, hepatic, and adrenal masses (Verna et al. (2008) *Therap. Adv Gastroenterol.* 1(2): 103-9). EUS-FNI has been extensively used for pancreatic cancer injections. Fine-needle injection requires the use of the curvilinear echoendoscope. The esophagus is carefully intubated and the echoendoscope is passed into the stomach and duodenum where the pancreatic examination occurs and the target tumor is identified. The largest plane is measured to estimate the tumor volume and to calculate the injection volume. The appropriate volume is drawn into a syringe. A primed 22-gauge fine needle aspiration (FNA) needle is passed into the working channel of the echoendoscope. Under ultrasound guidance, the needle is passed into the tumor. Depending on the size of the tumor, administration can be performed by dividing the tumor into sections and then injecting the corresponding fractions of the volume into each section. Use of an installed endoscopic ultrasound processor with Doppler technology assures there are no arterial or venous structures that may interfere with the needle passage into the tumor (Shirley et al., 2013). In some embodiments, 'multiple injectable needle' (MIN) for EUS-FNI can be used to improvement the injection distribution to the tumor in comparison with straight-type needles (Ohara et al. (2013) *Mol. Clin. Oncol.* 1(2): 231-4).

Intratumoral administration for lung cancer, such as non-small cell lung cancer, can be achieved through endobronchial intratumor delivery methods, as described in Celikoglu et al., 2008. Bronchoscopy (trans-nasal or oral) is conducted to visualize the lesion to be treated. The tumor volume can be estimated visually from visible length-width height measurements over the bronchial surface. The needle device is then introduced through the working channel of the bronchoscope. The needle catheter, which consists of a metallic needle attached to a plastic catheter, is placed within a sheath to prevent damage by the needle to the working channel during advancement. The needle size and length varies and is determined according to tumor type and size of the tumor. Needles made from plastic are less rigid than metal needles and are ideal, since they can be passed around sharper bends in the working channel. The needle is inserted into the lesion and the genetically engineered bacteria of the invention are in injected. Needles are inserted repeatedly at several insertion points until the tumor mass is completely perfused. After each injection, the needle is withdrawn entirely from the tumor and is then embedded at another location. At the end of the bronchoscopic injection session, removal of any necrotic debris caused by the treatment may be removed using mechanical dissection, or other ablation techniques accompanied by irrigation and aspiration.

In some embodiments, the genetically engineered bacteria are administrated directly into the tumor using methods, including but not limited to, percutaneous injection, EUS-FNI, or endobronchial intratumor delivery methods. In some cases other techniques, such as laproscopic or open surgical techniques are used to access the target tumor, however, these techniques are much more invasive and bring with them much greater morbidity and longer hospital stays.

In some embodiments, bacteria, e.g., *E. coli* Nissle, or spores, e.g., *Clostridium novyi* NT, are dissolved in sterile phosphate buffered saline (PBS) for systemic or intratumor injection.

The dose to be injected is derived from the type and size of the tumor. The dose of a drug or the genetically engineered bacteria or virus of the invention is typically lower, e.g., orders of magniture lower, than a dose for systemic intravenous administration.

The volume injected into each lesion is based on the size of the tumor. To obtain the tumor volume, a measurement of the largest plane can be conducted. The estimated tumor volume can then inform the determination of the injection volume as a percentage of the total volume. For example, an injection volume of approximately 20-40% of the total tumor volume can be used.

For example, as is described, for example, in WO 2014/036412, for tumors larger than 5 cm in their largest dimension, up to 4 ml can be injected. For tumors between 2.5 and 5 cm in their largest dimension, up to 2 ml can be injected. For tumors between 2.5 and 5 cm in their largest dimension, up to 2 ml can be injected. For tumors between 1.5 and 2.5 cm in their largest dimension, up to 1 ml can be injected. For tumors between 0.5 and 1.5 cm in their largest dimension, up to 0.5 ml can be injected. For tumors equal or small than 0.5 in their largest dimension, up to 0.1 ml can be injected. Alternatively, ultrasound scan can be used to determine the injection volume that can be taken up by the tumor without leakage into surrounding tissue.

In some embodiments, the treatment regimen will include one or more intratumoral administrations. In some embodiments, a treatment regimen will include an initial dose, which followed by at least one subsequent dose. One or more doses can be administered sequentially in two or more cycles.

For example a first dose may be administered at day 1, and a second dose may be administered after 1, 2, 3, 4, 5, 6, days or 1, 2, 3, or 4 weeks or after a longer interval. Additional doses may be administered after 1, 2, 3, 4, 5, 6, days or after 1, 2, 3, or 4 weeks or longer intervals. In some embodiments, the first and subsequent administrations have the same dosage. In other embodiments, different doses are administered. In some embodiments, more than one dose is administered per day, for example, two, three or more doses can be administered per day.

The routes of administration and dosages described are intended only as a guide. The optimum route of administration and dosage can be readily determined by a skilled practitioner. The dosage may be determined according to various parameters, especially according to the location of the tumor, the size of the tumor, the age, weight and condition of the patient to be treated and the route and method of administration.

In one embodiment, *Clostridium* spores are delivered systemically. In another embodiment, *Clostridium* spores are delivered via intratumor injection. In one embodiment, *E. coli* Nissle are delivered via intratumor injection In other embodiments, *E. coli* Nissle, which is known to hone to tumors, is administered via intravenous injection or orally, as described in a mouse model in for example in Danino et al. 2015, or Stritzker et al., 2007, the contents of which is herein incorporated by reference in its entirety. *E. coli* Nissle mutations to reduce toxicity include but are not limited to msbB mutants resulting in non-myristoylated LPS and reduced endotoxin activity, as described in Stritzker et al., 2010 (Stritzker et al, Bioengineered Bugs 1:2, 139-145; Myroystoation negative msbB-mutants of probiotic *E. coli* Nissle 1917 retain tumor specific colonization properties but show less side effects in immunocompetent mice.

For intravenous injection a preferred dose of bacteria is the dose in which the greatest number of bacteria is found in the tumor and the lowest amount found in other tissues. In mice, Stritzker et al. (2007) *Int. J. Med. Microbiol.* 297 (2007) 151-162) found that the lowest number of bacteria needed for successful tumor colonization was $2\times10^4$ CFU, in which half of the mice showed tumor colonization. Injection of $2\times10^5$ and $2\times10^6$ CFU resulted in colonization of all tumors, and numbers of bacteria in the tumors increased. However, at higher concentrations, bacterial counts became detectable in the liver and the spleen.

In some embodiments, the genetically engineered microorganisms of the invention may be administered orally. In some embodiments the genetically engineered bacteria may be useful in the prevention, treatment or management of liver cancer or liver metastases. For example, Danino et al. showed that orally administered *E. coli* Nissle is able to colonize liver metastases by crossing the gastrointestinal tract in a mouse model of liver metastases (Danino et al., *Science Translational Medicine* 7 (289): 1-10, the contents of which is herein incorporated by reference in its entirety).

Tumor types into which the engineered bacteria of the current invention are intratumorally delivered include locally advanced and metastatic tumors, including but not limited to, B, T, and NK cell lymphomas, colon and rectal cancers, melanoma, including metastatic melanoma, mycosis fungoides, Merkel carcinoma, liver cancer, including hepatocellular carcinoma and liver metastasis secondary to colorectal cancer, pancreatic cancer, breast cancer, follicular lymphoma, prostate cancer, refractory liver cancer, and Merkel cell carcinoma.

The genetically engineered microorganisms disclosed herein may be administered topically and formulated in the form of an ointment, cream, transdermal patch, lotion, gel, shampoo, spray, aerosol, solution, emulsion, or other form well known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered microorganisms disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered microorganisms are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered microorganisms described herein.

In one embodiment, the genetically engineered microorganisms of the disclosure may be formulated in a composition suitable for administration to pediatric subjects. As is well known in the art, children differ from adults in many aspects, including different rates of gastric emptying, pH, gastrointestinal permeability, etc. (Ivanovska et al., *Pediatrics*, 134(2):361-372, 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered microorganisms may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. For example, see U.S. 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered microorganisms described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered microorganisms may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{50}/ED_{50}$) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

In some embodiments, the genetically engineered microorganisms and composition thereof is formulated for intravenous administration, intratumor administration, or peritumor administration. The genetically engineered microorganisms may be formulated as depot preparations. Such long acting formulations may be administered by implantation or by injection. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In another embodiment, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

The genetically engineered bacteria of the invention may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Methods of Treatment

In one aspect of the invention provides methods of treating a disease, disorder and/or a symptom of a disease or disorder described herein. In one aspect aspect of the invention provides methods of treating cancer. In some embodiments, the invention provides methods for reducing, ameliorating, or eliminating one or more symptom(s) associated with cancer. In some embodiments, the cancer is selected from adrenal cancer, adrenocortical carcinoma, anal cancer, appendix cancer, bile duct cancer, bladder cancer, bone cancer (e.g., Ewing sarcoma tumors, osteosarcoma, malignant fibrous histiocytoma), brain cancer (e.g., astrocytomas, brain stem glioma, craniopharyngioma, ependymoma), bronchial tumors, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, gestational trophoblastic disease, heart cancer, Kaposi sarcoma, kidney cancer, largyngeal cancer, hypopharyngeal cancer, leukemia (e.g., acute lymphoblastic leukemia, acute myeloid leukemia, chronic lymphocytic leukemia, chronic myelogenous leukemia), liver cancer, lung cancer, lymphoma (e.g., AIDS-related lymphoma, Burkitt lymphoma, cutaneous T cell lymphoma, Hogkin lymphoma, Non-Hogkin lymphoma, primary central nervous system lymphoma), malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer (e.g., basal cell carcinoma, melanoma), small intestine cancer, stomach cancer, teratoid tumor, testicular cancer, throat cancer, thymus cancer, thyroid cancer, unusual childhood cancers, urethral cancer, uterine cancer, uterine sarcoma, vaginal cancer, vulvar cancer, Waldenström macroglublulinemia, and Wilms tumor. In some embodiments, the symptom(s) associated thereof include, but are not limited to, anemia, loss of appetite, irritation of bladder lining, bleeding and bruising (thrombocytopenia), changes in taste or smell, constipation, diarrhea, dry mouth, dysphagia, edema, fatigue, hair loss (alopecia), infection, infertility, lymphedema, mouth sores, nausea, pain, peripheral neuropathy, tooth decay, urinary tract infections, and/or problems with memory and concentration.

The method may comprise preparing a pharmaceutical composition with at least one genetically engineered species, strain, or subtype of bacteria described herein, and administering the pharmaceutical composition to a subject in a therapeutically effective amount. The genetically engineered microorganisms may be administered locally, e.g., intratumorally or peritumorally into a tissue or supplying vessel, or systemically, e.g., intravenously by infusion or injection. In some embodiments, the genetically engineered bacteria are administered intravenously, intratumorally, intra-arterially, intramuscularly, intraperitoneally, orally, or topically. In some embodiments, the genetically engineered microorganisms are administered intravenously, i.e., systemically.

In certain embodiments, administering the pharmaceutical composition to the subject reduces cell proliferation, tumor growth, and/or tumor volume in a subject. In some embodiments, the methods of the present disclosure may reduce cell proliferation, tumor growth, and/or tumor volume by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing cell proliferation, tumor growth, and/or tumor volume in a subject before and after administration of the pharmaceutical composition. In some embodiments, the method of treating or ameliorating a cancer in a subject allows one or more symptoms of the cancer to improve by at least about 10%, 20%, 30%, 40%, 50%, 60%, 70%, 80%, 90%, 95%, or more.

Before, during, and after the administration of the pharmaceutical composition, cancerous cells and/or biomarkers in a subject may be measured in a biological sample, such as blood, serum, plasma, urine, peritoneal fluid, and/or a biopsy from a tissue or organ. In some embodiments, the methods may include administration of the compositions of the invention to reduce tumor volume in a subject to an undetectable size, or to less than about 1%, 2%, 5%, 10%, 20%, 25%, 30%, 40%, 50%, 60%, 70%, 75%, 80%, or 90% of the subject's tumor volume prior to treatment. In other embodiments, the methods may include administration of the compositions of the invention to reduce the cell proliferation rate or tumor growth rate in a subject to an undetectable rate, or to less than about 1%, 2%, 5%, 10%, 20%, 25%, 30%, 40%, 50%, 60%, 70%, 75%, 80%, or 90% of the rate prior to treatment.

The genetically engineered bacteria may be destroyed, e.g., by defense factors in tissues or blood serum (Sonnenborn et al. (2009) Microbial Ecology in Health and Disease 21: 122-58), or by activation of a kill switch, several hours or days after administration. Thus, the pharmaceutical composition comprising the genetically engineered bacteria comprising a heterologous gene encoding a substrate transporter may be re-administered at a therapeutically effective dose and frequency. In alternate embodiments, the genetically engineered bacteria are not destroyed within hours or days after administration and may propagate and colonize the tumor.

The pharmaceutical composition may be administered alone or in combination with one or more additional therapeutic agents, e.g., a chemotherapeutic drug such a methotrexate. An important consideration in selecting the one or more additional therapeutic agents is that the agent(s) should be compatible with the genetically engineered bacteria of the invention, e.g., the agent(s) must not kill the bacteria. In some studies, the efficacy of anticancer immunotherapy, e.g., CTLA-4 or PD-1 inhibitors, requires the presence of particular bacterial strains in the microbiome (Ilda et al., 2013; Vetizou et al., 2015; Sivan et al., 2015). In some embodiments, the pharmaceutical composition is administered with one or more commensal or probiotic bacteria, e.g., *Bifidobacterium* or *Bacteroides*.

In some embodiments, the genetically engineered microorganisms may be administered as part of a regimen, which includes other treatment modalities or combinations of other modalities. Non-limiting examples of these modalities or agents are conventional therapies (e.g., radiotherapy, chemotherapy), other immunotherapies, stem cell therapies, and targeted therapies, (e.g., BRAF or vascular endothelial growth factor inhibitors; antibodies or compounds), bacteria described herein, and oncolytic viruses. Therapies also include related to antibody-immune engagement, including Fc-mediated ADCC therapies, therapies using bispecific soluble scFvs linking cytotoxic T cells to tumor cells (e.g., BiTE), and soluble TCRs with effector functions. Immunotherapies include vaccines (e.g., viral antigen, tumor associated antigen, neoantigen, or combinations thereof), checkpoint inhibitors, cytokine therapies, adoptive cellular therapy (ACT). ACT includes but is not limited to, tumor infiltrating lymphocyte (TIL) therapies, native or engineered TCR or CAR-T therapies, natural killer cell therapies, and dendritic cell vaccines or other vaccines of other antigen presenting cells. Targeted therapies include antibodies and chemical compounds, and include for example antiangiogenic strategies and BRAF inhibition.

The immunostimulatory activity of bacterial DNA is mimicked by synthetic oligodeoxynucleotides (ODNs) expressing unmethylated CpG motifs (see, e.g., Bode et al. (2011) Expert Rev Vaccines 10(4): 499-511). CpG DNA as a vaccine adjuvant. When used as vaccine adjuvants, CpG ODNs improve the function of professional antigen-presenting cells and boost the generation of humoral and cellular vaccine-specific immune responses. In some embodiments, CpG can be administered in combination with the genetically engineered bacteria of the invention.

In one embodiment, the genetically engineered microorganisms are administered in combination with tumor cell lysates.

The dosage of the pharmaceutical composition and the frequency of administration may be selected based on the severity of the symptoms and the progression of the cancer. The appropriate therapeutically effective dose and/or frequency of administration can be selected by a treating clinician.

Treatment In Vivo

The genetically engineered bacteria may be evaluated in vivo, e.g., in an animal model. Any suitable animal model of a disease or condition associated with cancer may be used, e.g., a tumor syngeneic or xenograft mouse models (see, e.g., Yu et al., 2015). The genetically engineered bacteria may be administered to the animal systemically or locally, e.g., via oral administration (gavage), intravenous, or subcutaneous injection or via intratumoral injection, and treatment efficacy determined, e.g., by measuring tumor volume.

Non-limiting examples of animal models include mouse models, as described in Dang et al., 2001, Heap et al., 2014 and Danino et al., 2015).

Pre-clinical mouse models determine which immunotherapies and combination immunotherapies will generate the optimal therapeutic index (maximal anti-tumor efficacy and minimal immune related adverse events (irAEs)) in different cancers.

Implantation of cultured cells derived from various human cancer cell types or a patient's tumor mass into mouse tissue sites has been widely used for generations of cancer mouse models (xenograft modeling). In xenograft modeling, human tumors or cell lines are implanted either subcutaneously or orthotopically into immune-compromised host animals (e.g., nude or SCID mice) to avoid graft rejection. Because the original human tumor microenvironment is not recapitulated in such models, the activity of anti-cancer agents that target immune modulators may not be accurately measured in these models, making mouse models with an intact immune system more desirable.

Accordingly, implantation of murine cancer cells in a syngeneic immunocompetent host (allograft) are used to generate mouse models with tumor tissues derived from the same genetic background as a given mouse strain. In syngeneic models, the host immune system is normal, which may more closely represent the real life situation of the tumor's micro-environment. The tumor cells or cancer cell lines are implanted either subcutaneously or orthotopically into the syngeneic immunocompetent host animal (e.g., mouse). Representative murine tumor cell lines, which can be used in syngeneic mouse models for immune checkpoint benchmarking include, but are not limited to the cell lines listed in Table 32.

TABLE 32

Selected cell lines for use in syngeneic mouse models

| Cancer Types | Cell LInes |
| --- | --- |
| Bladder | MBT-2 |
| Breast | 4T1, EMT6, JC |
| Colon | CT-26, Colon26, MC38 |
| Kidney | Renca |
| Leukemia | L1210, C1498 |
| Mastocytoma P815 | P815 |
| Neuroblastoma Neuro-2-A | Neuro-2a |
| Myeloma | MPC-11 |
| Liver | H22 |
| Lung | LL/2, KLN205 |
| Lymphoma | A20, EL4, P388D1, L15178-R, E.G7-OVA |
| Melanoma | B16-BL6, B16-F10, S91 |
| Pancreatic | Pan02 |
| Prostate | RM-1 |
| Fibrosarcom | WHI-164 |
| Plasmacytoma | J558 |

Additional cell lines include, but are not limited to those in Table 33, which are described with respect to CTLA-4 benchmarking in Joseph F. Grosso and Maria N. Jure-Kunkel et al., 2013, the contents of which is herein incorporated by reference in its entirety.

TABLE 33

Murine cell lines and CTLA-4 antibodies for syngenic mouse models

| Murine Tumor | Tumor type/Mouse strain | Anti-CTLA-4 Ab/Tx regimen |
| --- | --- | --- |
| Brain | SMA-560 Glioma/Vm/Dk) | 9H10; d7* (100 µg), d10 (50 µg), d13 (50 µg) post-implant |
| | GL-261 Glioma/C57BL/6) | 9H10; d0 (100 µg), d3 (50 µg), d6 (50 µg), |
| Ovarian | OV-HM/C57BL/6 × C3H/He) | UC10-4F10-11; 1 mg/mouse |
| Bladder | MB49/C57BL/6 | 9D9; d7, d10, d13 (200 µg each) |
| Sarcoma | Meth-A/BALB/c | 9H10; d6 (100 µg), d9 (50 µg), d12 (50 µg) |
| | MC38, 11A1 BALB/c, C57BL/6 | 9H10; d14 (100 µg), d17 (50 µg), d20 (50 µg) |
| Breast | TSA/BALB/c (62 | 9H10; d12, d14, d16 (200 µg each) |
| | 4T1 BALB/c | 9H10; d14, d18, d21 (200 µg each) |
| | 4T1 BALB/c | 9H10; d14, d18, d21 (200 µg each) |
| | 4T1 BALB/c | UC10-4F10-11; d7, d11, d15, d19 (100 µg each) |
| | SM1/BALB/c | 9H10; d4, d7, d10 (100 µg each) |
| | EMT6/BALB/c | UC10-4F10-11; d4, d8, d12 (400 µg each) Ixa: d3, d7, d11 |
| Colon | MC38/C57BL/6 | UC10-4F10-11; d7, d11, d16 (100 µg each) |
| | MC38 | K4G4, L1B11, L3D10 |
| | CT26 BALB/c | 9H10; d10 (100 µg), d13 (50 µg), d15 (50 µg) |
| | CT26 BALB/c | UC10-4F10-11; d5, d9, d13 (400 µg each) Ixa: d4, d8, d12 |
| | MC38/C57BL/6 | UC10-4F10-11; d14, d21, d28 (800 µg each) |

TABLE 33-continued

Murine cell lines and CTLA-4 antibodies for syngenic mouse models

| Murine Tumor | Tumor type/Mouse strain | Anti-CTLA-4 Ab/Tx regimen |
|---|---|---|
| Lymphoma | BW5147.3/AKR | UC10-4F10-11; d-1 (250 µg), d0 (250 µg), d4 [100 µg), d8 (100 µg), d12 (100 µg) |
|  | EL4/C57BL/6 | 9H10; d3, d5 (100 µg each) |
| Fibrosarcoma | SA1N/A/J | 9H10; every 4 days (200 µg each) |
|  | SA1N | UC10-4F10-11; d12, d16, d20 (400 µg each) Ixa: d11, d15, d15 |
| Prostata | TRAMP C1[pTC1]/C57BU6 | 9H10; d7, d10, d13 (100 µg each) |
|  | TRAMP C2/C57BL/6 | 9H10; d4, d7, d10 (100 µg each) |
|  | TRAMP/C57BL | 9H10; 14-16 week old mice d7, d10, d16 post-tR tx (100 µg each) |
|  | TRAMP C2/C57BL/6 | 9H10; d29, d33, d40, d50 (100 µg each) d29 = 1d post-cryoablation |
| Melanoma | B16/C57BL/6 | 9H10; d0, d3, d6 (200 µg each) |
|  | B16/C57BL/6 | 9H10; d6 (100 µg), d8 [50 µg), d10 (50 µg) |
|  | B16/C57BL/6 | 9D9; d3, d6, d9 |
|  | B16/C57BL/6 | 9H10; d3, d6, d9 (100 µg each) |
|  | B16.F10/C57BL/6 | 9H10; d5 (100 µg), d7 (50 µg), d9 (50 µg) |
| Lung | M109/BALB/c | UC10-4F10-11; d4, d8, d12(400 µg each) Ixa: d3, d7, d11 |
| Plasmacytoma | MOPC-315/BALB/cANnCrlBr | UC10-4F10-11; 20 mm tumors tx daily for 10 days (100 µg each) |

For tumors derived from certain cell lines, ovalbumin can be added to further stimulate the immune response, thereby increasing the response baseline level.

Examples of mouse strains that can be used in syngeneic mouse models, depending on the cell line include C57BL/6, FVB/N, Balb/c, C3H, HeJ, C3H/HeJ, NOD/ShiLT, A/J, 129S1/SvlmJ, NOD. Additionally, several further genetically engineered mouse strains have been reported to mimic human tumorigenesis at both molecular and histologic levels. These genetically engineered mouse models also provide excellent tools to the field and additionally, the cancer cell lines derived from the invasive tumors developed in these models are also good resources for cell lines for syngeneic tumor models Examples of genetically engineered strains are provided in Table 34.

TABLE 34

Exemplary genetic engineered mouse strains of interest

| Animal strain | Strain background | Predicted cancer type |
|---|---|---|
| C57BL/6-Tg(TRAMP)8247Ng/JNju | C57BL/6 | Prostate cancer |
| FVB/N-Tg☐MMTV-PyVT)634Mul/Jnju | FVB/N | Breast cancer |
| C57BL/6J-Apc$^{Min}$/JNju | C57BL/6 | Colorectal cancer |
| STOCK Ptch1$^{tm1Mps}$/JNju | C57BL/6JNju | Medulloblastoma |
| NOD-Prkdc$^{em26Cd52}$Il2rg$^{em26Cd22}$Nju | NOD/ShiLt | Not specific |
| C57BL/6J-Apc$^{Min}$/JNju | C57BL/6 | Colorectal cancer |
| BALB/cJNju | BALB/c | Lung cancer |
| C3H/HeJNju (Urethane induced lung cancer model) | C3H/HeJ | Lung cancer |
| A/JNju | A/J | Lung cancer |
| A/Jnju (Urethane induced lung cancer model) | A/J | Lung cancer |
| C3H/HeJSlac | C3H/HeJ | Lung cancer |
| 129S1/SvlmJNju (Urethane induced lung cancer model) | 129S1/SvlmJ | Lung cancer |
| Kras$^{LSL-G12D/WT}$ | C57BL/6 | Lung cancer |
| Kras$^{LSL-G12D/WT}$;P53$^{KO/KO}$ | C57BL/6 | Lung cancer |
| Pdx1-cre; Kras$^{LSL-G12D/WT}$;P53$^{KO/KO}$ | C57BL/6 | Pancreatic cancer |
| Kras$^{LSL-G12D/WT}$;P16$^{KO/KO}$ | C57BL/6; FVB/N | Pancreaticc cancer; Lung cancer |
| Kras$^{LSL-G12D/WT}$; PTEN$^{CKO/CKO}$ | C57BL/6 | Ovarian cancer; Prostate cancer; Brain cancer |
| Pbsn-cre;Kras$^{LSL-G12D/WT}$;PTEN$^{CKO/CKO}$ | C57BL/6 | Prostate cancer |
| P53$^{KO/KO}$;PTEN$^{CKO/CKO}$ | C57BL/6 | Prostate cancer |
| Pbsn-cre;PTEN$^{CKO/CKO}$ | C57BL/6 | Prostate cancer |
| NOD | NOD | Leukemia |
| B6.Cg-Tg(IghMyc)22Bri/JNju | C57BL/6 | B cell Lymphoma |
| PTEN$^{CKO/CKO}$ | C57BL/6 | Ovarian cancer (Female); Prostate cancer (Male); Tes/s cancer (Male) |
| NASH-HCC (Streptozotocin and high-fat diet induced liver cancer model) | C57BL/6 | Hepatocellular Carcinoma |

TABLE 34-continued

Exemplary genetic engineered mouse strains of interest

| Animal strain | Strain background | Predicted cancer type |
|---|---|---|
| BALB/c nude | BALB/c | Not specific |
| C3H/He | C3H/He | Hepatocellular Carcinoma |
| B6N | C57BL/6 | Not specific |
| B6/N-Akr1c12$^{tm1a}$Nju | C57BL/6 | Not specific |
| P53 null from VitalStar | C57BL/6 | Not specific |
| P53 null from VitalStar | C57BL/6 | Not specific |
| P53 null from VitalStar | C57BL/6 | Not specific |
| Pdx1-cre;Kras$^{LSL-G12D/WT}$;p53$^{KO/KO}$ | C57BL/6 | Pancrea/c cancer |
| Kras$^{LSL-G12D/WT}$;P16$^{KO/KO}$ | C57BL/6; FVB/N | Pancrea/c cancer; Lung cancer |
| Kras$^{LSL-G12D/WT}$;PTEN$^{CKO/CKO}$ | C57BL/6 | Ovarian cancer; |
| Kras$^{LSL-G12D/WT}$;PTEN$^{CKO/CKO}$ | C57BL/6 | Prostate cancer; |
| Kras$^{LSL-G12D/WT}$;PTEN$^{CKO/CKO}$ | C57BL/6 | Brain cancer |
| Pbsn-cre; Kras$^{LSL-G12D/WT}$;PTEN$^{CKO/CKO}$ | C57BL/6 | Prostate cancer |
| P53$^{KO/KO}$;PTEN$^{CKO/CKO}$ | C57BL/6 | Prostate cancer |
| Pbsn-cre;PTEN$^{CKO/CKO}$ | C57BL/6 | Prostate cancer |
| Kras$^{LSL-G12D/WT}$ | C57BL/6 | Lung cancer |
| NOD | NOD | Leukemia |
| B6.Cg-Tg(IghMyc)22Bri/JNju | C57BL/6 | B cell Lymphoma |
| PTENCKO/CKO | C57BL/6 | Ovarian cancer (Female); Prostate cancer (Male); Tes/s cancer (Male) |
| NASH-HCC (Streptozotocin and high-fat diet induced liver cancer model) | C57BL/6 | Hepatocellular Carcinoma |
| BALB/c nude | BALB/c | Not specific |
| C3H/He | C3H/He | Hepatocellular Carcinoma |
| B6N | C57BL/6 | Not specific |
| B6/N-Akr1c12$^{tm1a}$Nju | C57BL/6 | Not specific |
| P53 null from VitalStar | C57BL/6 | Not specific |
| P53 null from VitalStar | C57BL/6 | Not specific |
| P53 null from VitalStar | C57BL/6 | Not specific |
| Kras$^{LSL-G12D/WT}$;p53$^{KO/KO}$ | C57BL/6 | Not specific |

Often antibodies directed against human proteins do not detect their murine counterparts. In studying antibodies, including those directed against human immune checkpoint molecules, it is necessary to take this in consideration. For example, Ipilimumab did not show cross-reactivity with or binding to CTLA-4 from rats, mice or rabbits.

In some cases, mice transgenic for the gene of interest can used to overcome this issue, as was done for ipilimumab. However, in syngeneic mouse models without a human transgene, mouse protein reactive antibodies must be used to test therapeutic antibody strategies. For example, suitable CTLA-4 antibodies for expression by the genetically engineered bacteria of interest include, but are not limited to, 9H10, UC10-4F10-11, 9D9, and K4G4 (Table 33).

More recently, "humanized" mouse models have been developed, in which immunodeficient mice are reconstituted with a human immune system, and which have helped overcome issues relating to the differences between the mouse and human immune systems, allowing the in vivo study of human immunity. Severely immunodeficient mice which combine the IL2 receptor null and the severe combined immune deficiency mutation (scid) (NOD-scid IL2Rgnull mice) lack mature T cells, B cells, or functional NK cells, and are deficient in cytokine signaling. These mice can be engrafted with human hematopoietic stem cells and peripheral-blood mononuclear cells. CD34+ hematopoietic stem cells (hu-CD34) are injected into the immune deficient mice, resulting in multi-lineage engraftment of human immune cell populations including very good T cell maturation and function for long-term studies. This model has a research span of 12 months with a functional human immune system displaying T-cell dependent inflammatory responses with no donor cell immune reactivity towards the host. Patient derived xenografts can readily be implanted in these models and the effects of immune modulatory agents studied in an in vivo setting more reflective of the human tumor microenvironment (both immune and non-immune cell-based) (Baia et al., 2015).

Human cell lines of interest for use in the humanized mouse models include but are not limited to HCT-116 and HT-29 colon cancer cell lines.

A rat F98 glioma model and the utility of spontaneous canine tumors, as described in Roberts et al 2014, the contents of each of which are herein incorporated by reference in their entireties. Locally invasive tumors generated by implantation of F98 rat glioma cells engineered to express luciferase were intratumorally injected with C. novyi-NT spores, resulting in germination and a rapid fall in luciferase activity. C. novyi-NT germination was demonstrated by the appearance of vegetative forms of the bacterium. In these studies, C. novyi-NT precisely honed to the tumor sparing neighboring cells.

Canine soft tissue sarcomas for example are common in many breeds and have clinical, histopathological, and genetically features similar to those in humans (Roberts et al, 2014; Staedtke et al., 2015), in particular, in terms of genetic alterations and spectrum of mutations. Roberts et al. conducted a study in dogs, in which C. novyi-NT spores were intrtatumorally injected ($1 \times 10^8$ C. novyi-NT spores) into spontaneously occurring solid tumors in one to 4 treatment cycles and followed for 90 days. A potent inflammatory response was observed, indicating that the intratumoral injections mounted an innate immune response.

In some embodiments, the genetically engineered microorganisms of the invention are administered systemically, e.g., orally, subcutaneously, intraveneously or intratumorally into any of the models described herein to assess anti-tumor efficacy and any treatment related adverse side effects.

EXAMPLES

Figure 4:
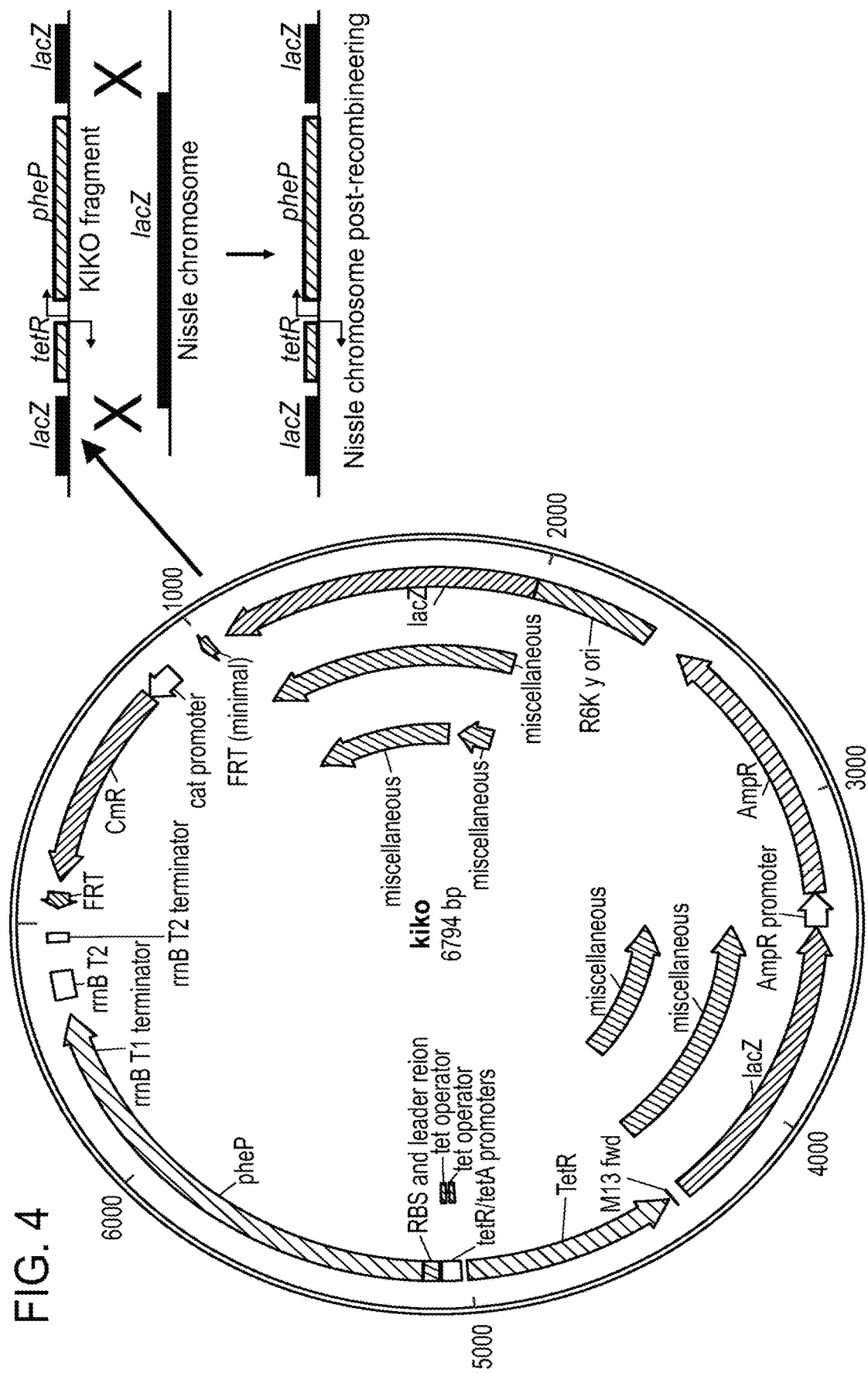
FIG. 4 depicts a schematic representation of the construction of a pheP knock-in strain, wherein recombineering is used to insert a $2^{nd}$ copy of pheP into the Nissle lacZ gene.
Figure 5:
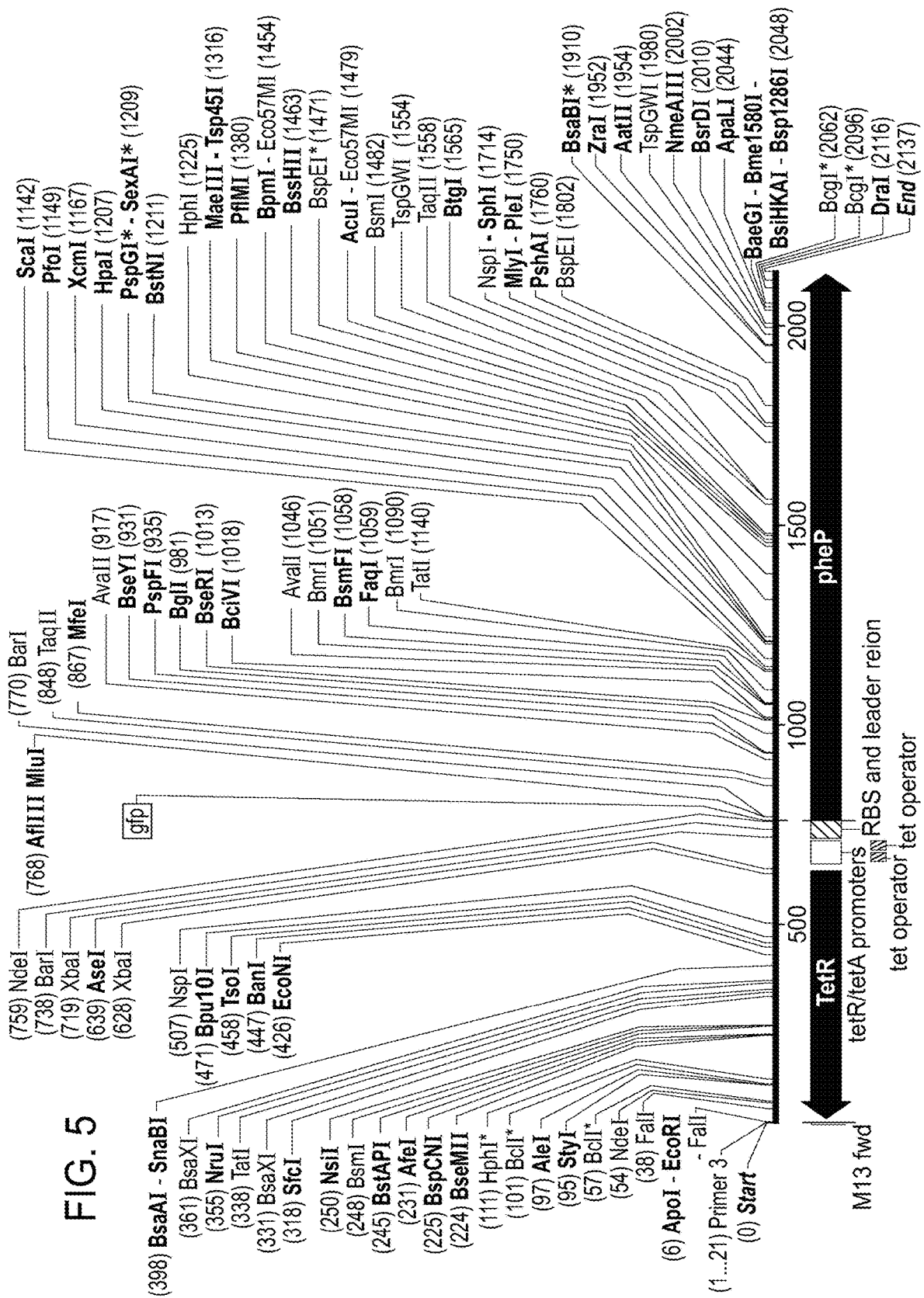
FIG. 5 depicts the gene organization of an exemplary construct comprising a gene encoding PheP, a gene coding TetR, and a Tet promoter sequence for chromosomal insertion e.g., as for example comprised in SYN-PKU203, SYN-PKU401, SYN-PKU402, SYN-PKU302, and SYN-PKU303.
Figure 6A:
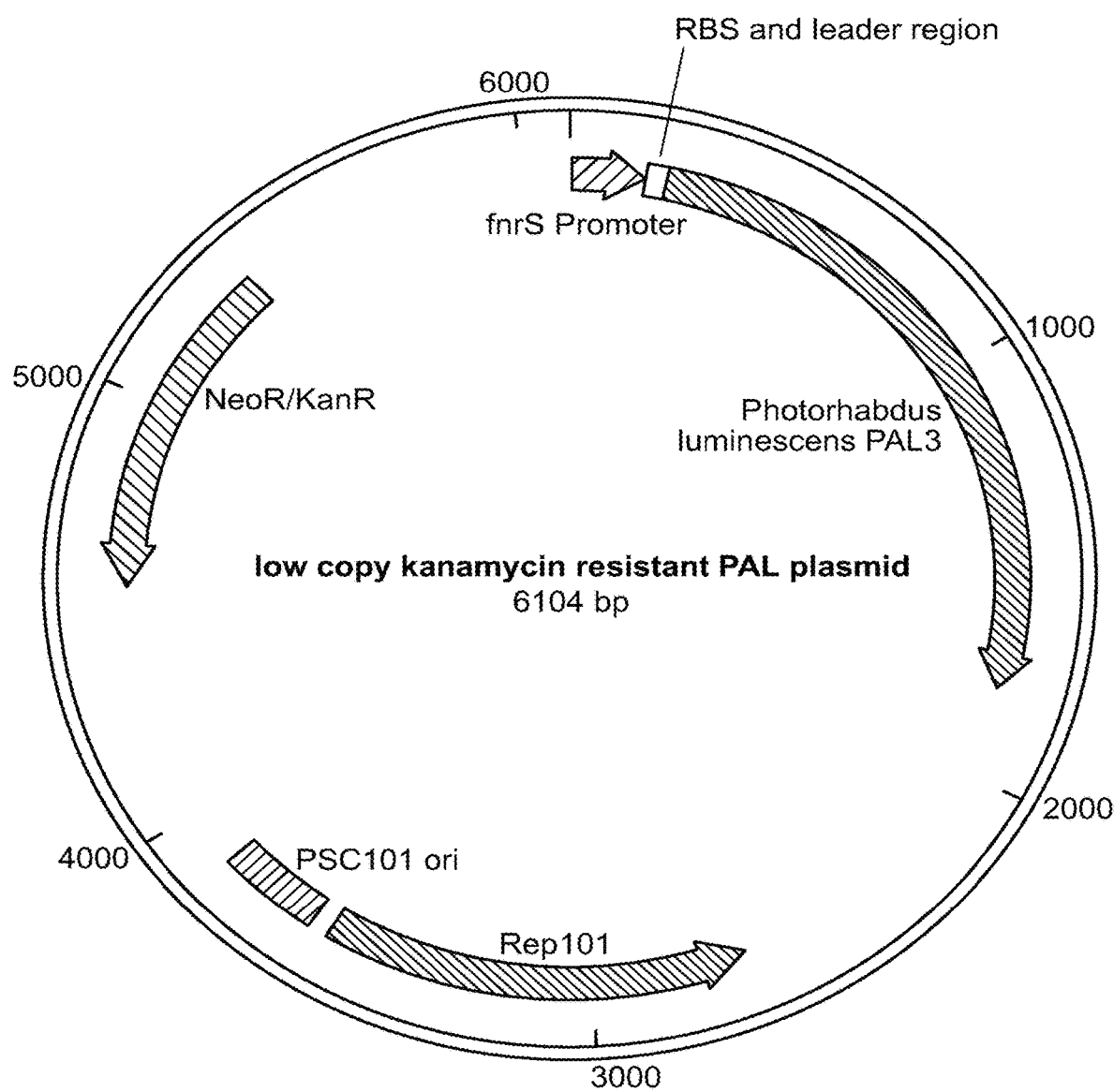
FIGS. 6A and 6B depict the gene organization of an exemplary construct, comprising a cloned PAL3 gene under the control of an FNR promoter sequence, on a low-copy, kanamycin-resistant plasmid (pSC101 origin of replication, (FIG. 6A). Under anaerobic conditions, PAL3 degrades phenylalanine to non-toxic trans-cinnamate.
Figure 6B:
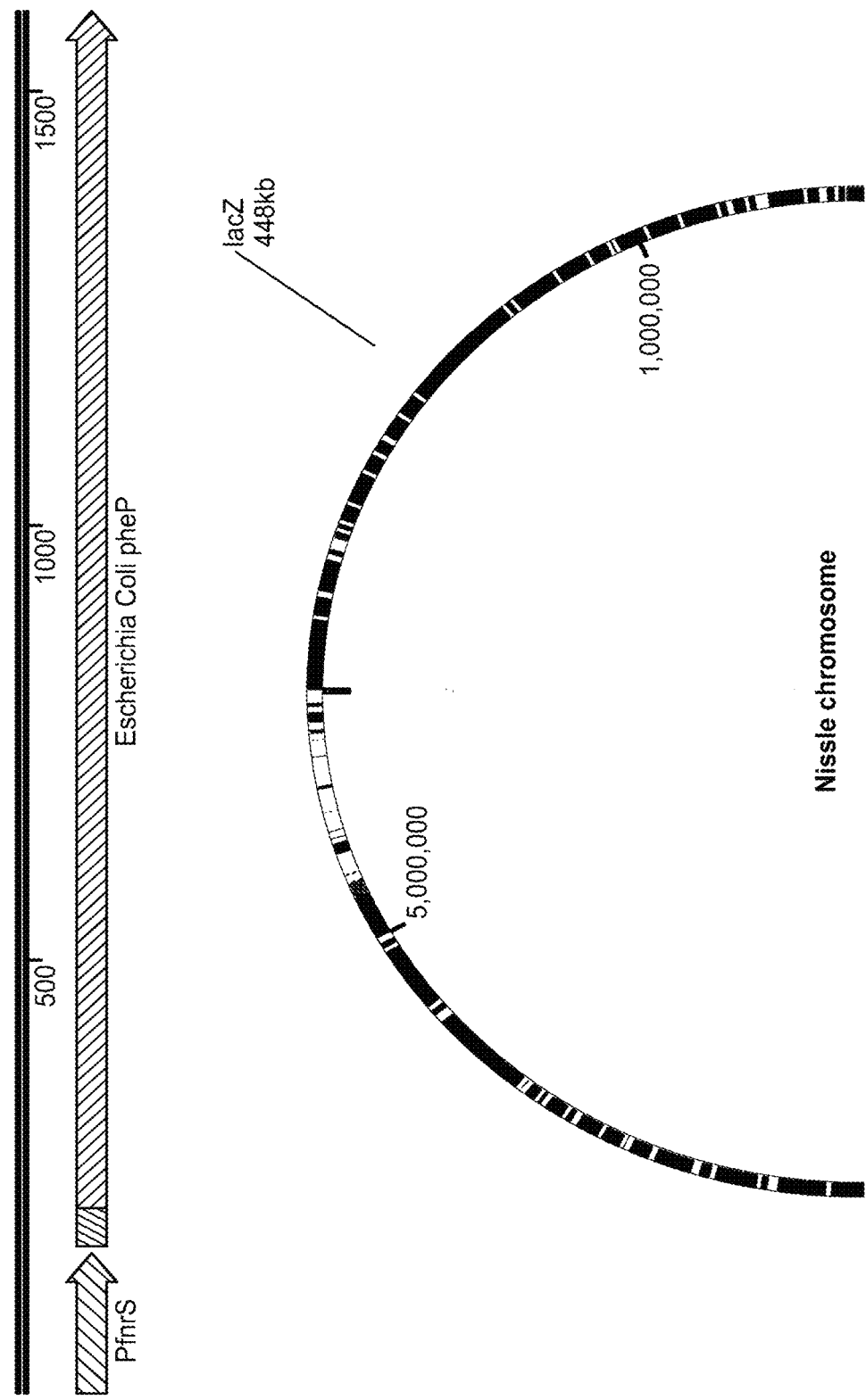
Figure 7A:
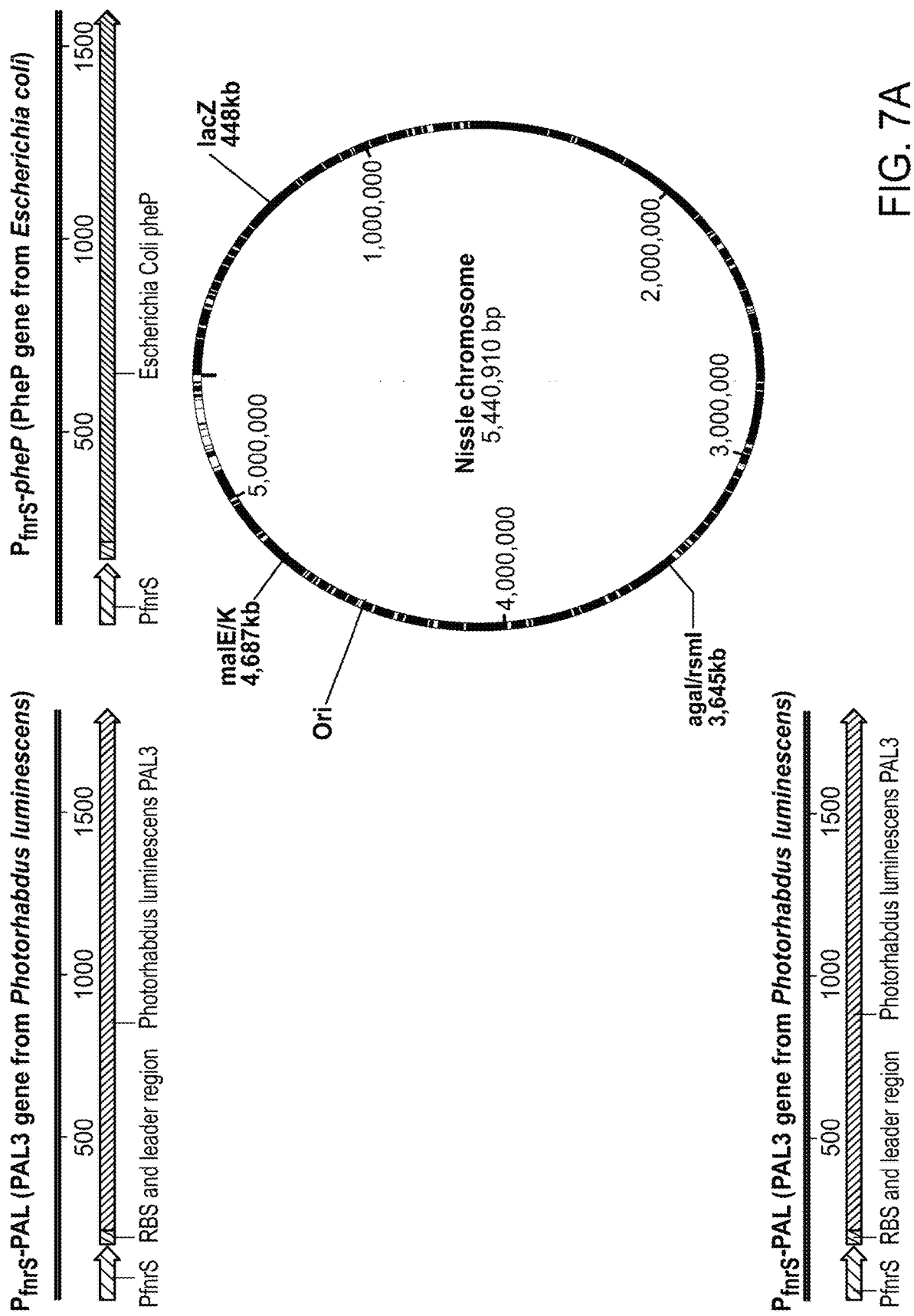
FIGS. 7A, 7B, and 7C depict schematic diagrams of non-limiting embodiments of the disclosure.
Figure 7B:
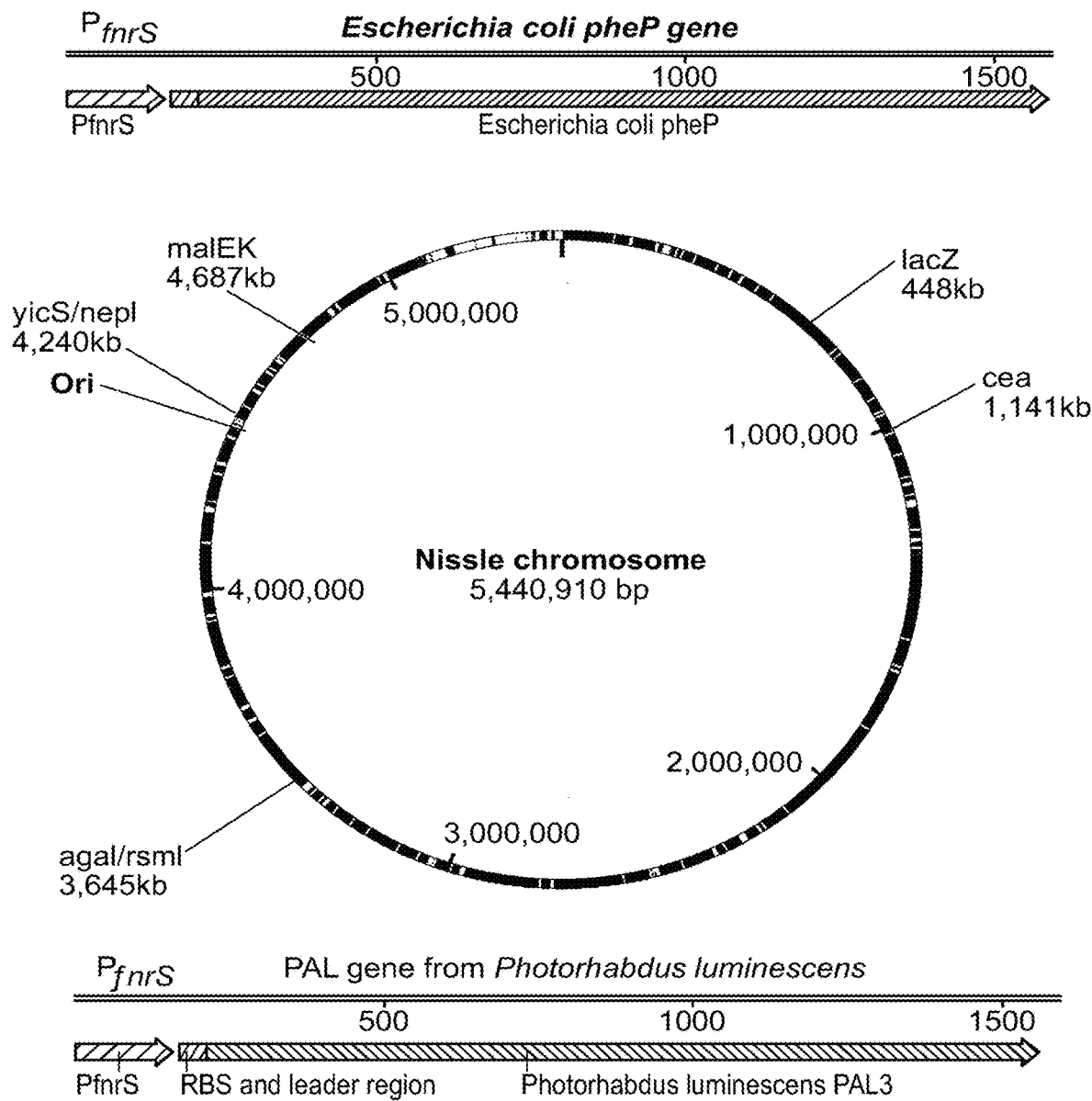
Figure 7C:
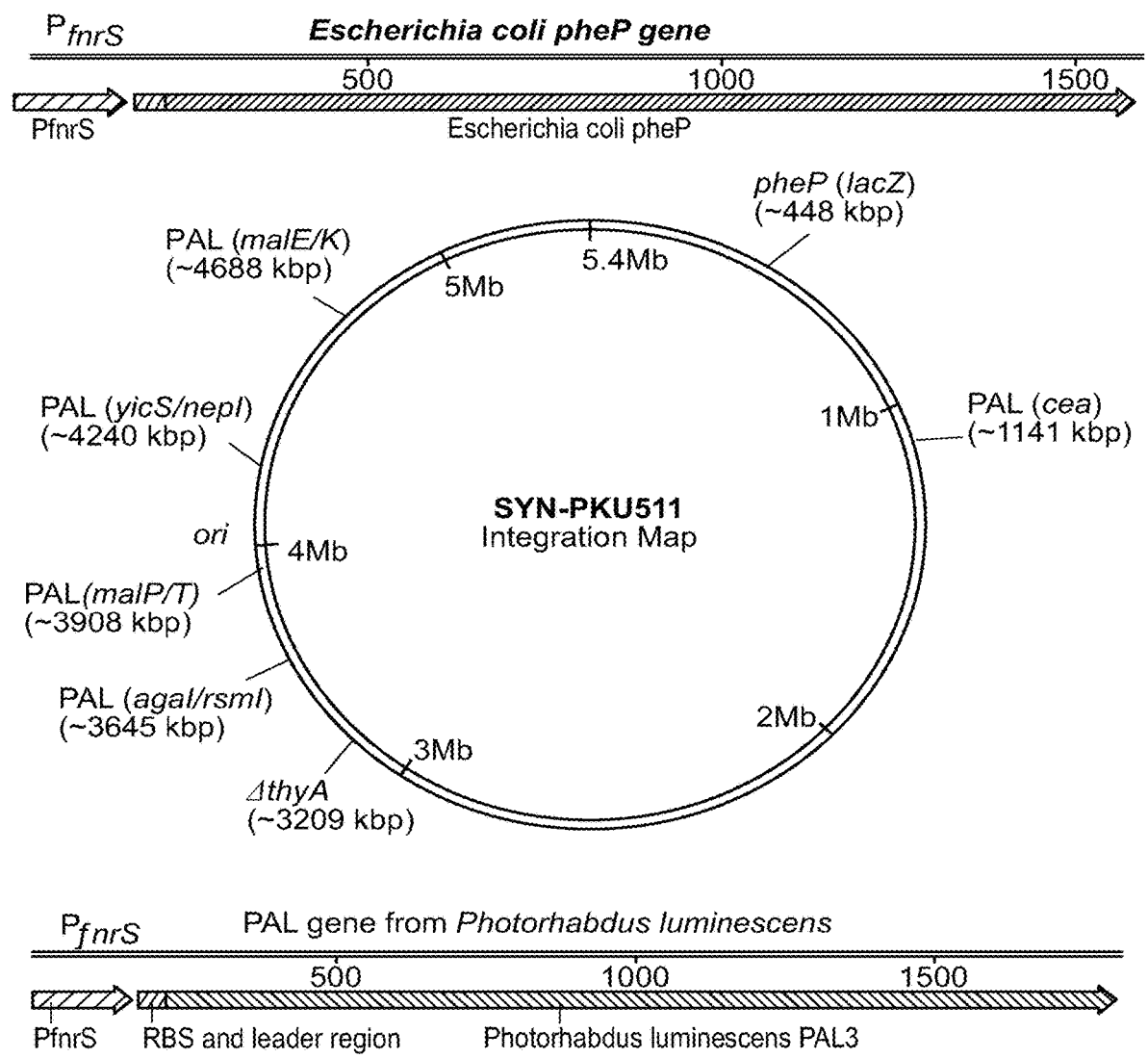

Example 1. Phenylalanine Transporter—Integration of PheP into the Bacterial Chromosome In some embodiments, it may be advantageous to increase phenylalanine transport into the cell, thereby enhancing phenylalanine metabolism. Therefore, a second copy of the native high affinity phenylalanine transporter, PheP, driven by an inducible promoter, was inserted into the Nissle genome through homologous recombination. Organization of the construct is shown in FIG. 4. The pheP gene was placed downstream of the $P_{tet}$ promoter, and the tetracycline repressor, TetR, was divergently transcribed (see, e.g., FIG. 4). This sequence was synthesized by Genewiz (Cambridge, Mass.). To create a vector capable of integrating the synthesized TetR-PheP construct into the chromosome, Gibson assembly was first used to add 1000 bp sequences of DNA homologous to the Nissle lacZ locus into the R6K origin plasmid pKD3. This targets DNA cloned between these homology arms to be integrated into the lacZ locus in the Nissle genome. Gibson assembly was used to clone the TetR-PheP fragment between these arms. PCR was used to amplify the region from this plasmid containing the entire sequence of the homology arms, as well as the pheP sequence between them. This PCR fragment was used to transform electrocompetent Nissle-pKD46, a strain that contains a temperature-sensitive plasmid encoding the lambda red recombinase genes. After transformation, cells were grown for 2 hrs before plating on chloramphenicol at 20 μg/mL at 37° C. Growth at 37° C. cures the pKD46 plasmid. Transformants containing anhydrous tetracycline (ATC)-inducible pheP were lac-minus (lac-) and chloramphenicol resistant.

Example 2. Effect of the Phenylalanine Transporter on Phenylalanine Degradation

To determine the effect of the phenylalanine transporter on phenylalanine degradation, phenylalanine degradation and trans-cinnamate accumulation achieved by genetically engineered bacteria expressing PAL1 or PAL3 on low-copy (LC) or high-copy (HC) plasmids in the presence or absence of a copy of pheP driven by the Tet promoter integrated into the chromosome was assessed.

Figure 8A:
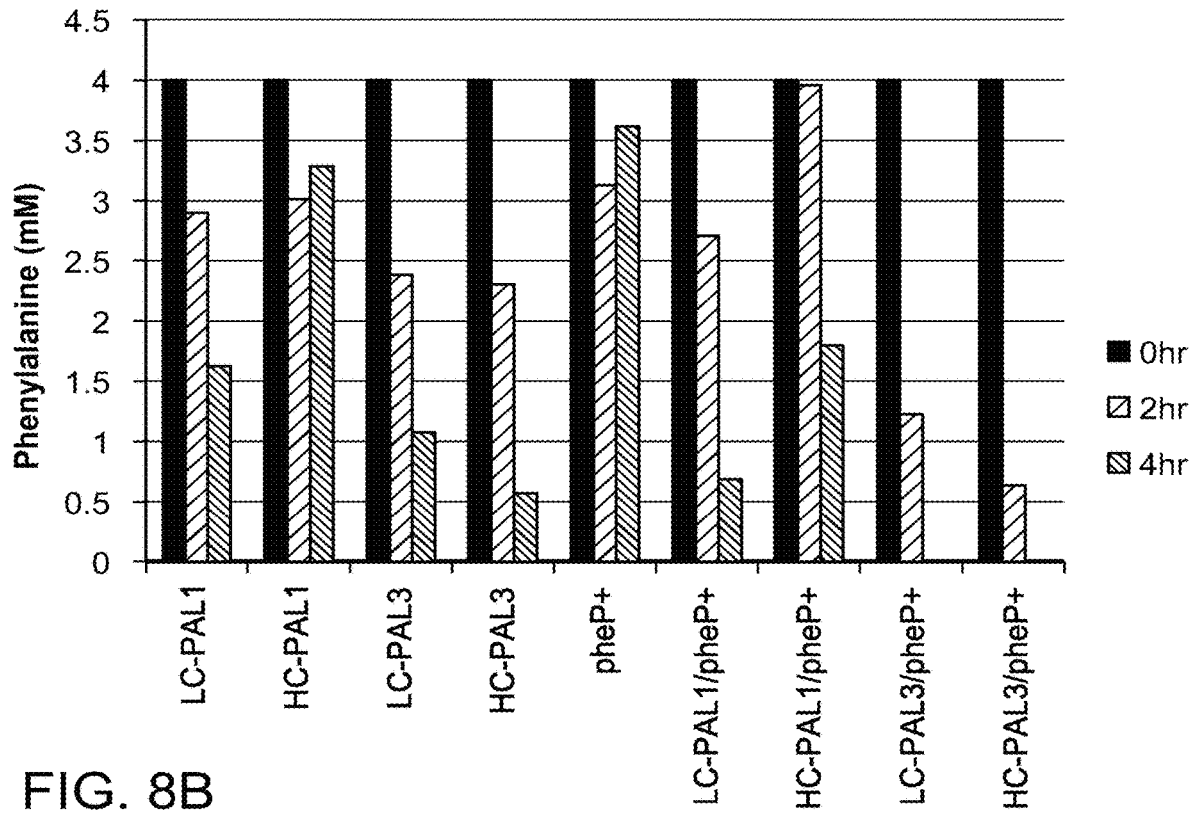
FIG. 8A depicts phenylalanine concentrations in samples comprising bacteria expressing PAL1 or PAL3 on low-copy (LC) or high-copy (HC) plasmids, or further comprising a copy of pheP driven by the Tet promoter integrated into the chromosome. Bacteria were induced with ATC, and then grown in culture medium supplemented with 4 mM (660,000 ng/mL) of phenylalanine to an $OD_{600}$ of 2.0. Samples were removed at 0 hrs, 2 hrs, and 4 hrs post-induction and phenylalanine concentrations were determined by mass spectrometry. Notably, the additional copy of pheP permitted the degradation of phenylalanine (4 mM) in 4 hrs.
Figure 8B:
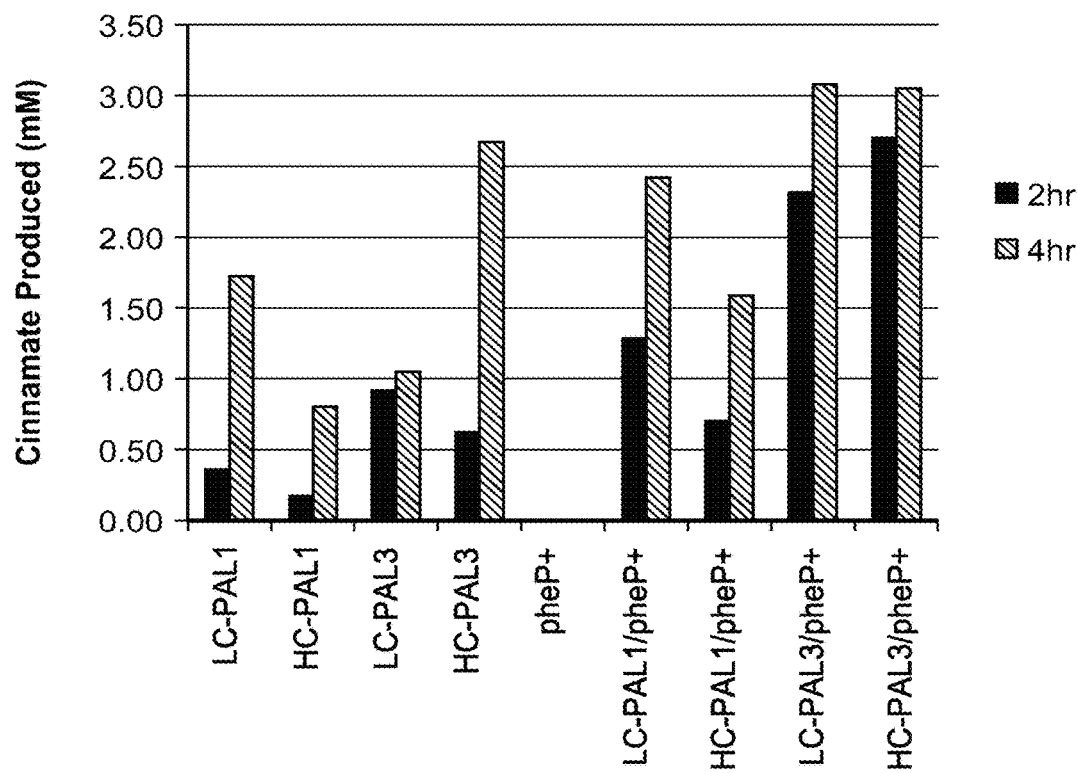
FIG. 8B depicts cinnamate levels in samples at 2 hrs and 4 hrs post-induction. In some embodiments, cinnamate may be used as an alternative biomarker for strain activity. PheP overexpression improves phenylalanine metabolism in engineered bacteria. Strains analyzed in this data set are SYN-PKU101, SYN-PKU102, SYN-PKU202, SYN-PKU201, SYN-PKU401, SYN-PKU402, SYN-PKU203, SYN-PKU302, SYN-PKU303.

For in vitro studies, all incubations were performed at 37° C. Cultures of E. coli Nissle transformed with a plasmid comprising the PAL gene driven by the Tet promoter were grown overnight and then diluted 1:100 in LB. The cells were grown with shaking (200 rpm) to early log phase. Anhydrous tetracycline (ATC) was added to cultures at a concentration of 100 ng/mL to induce expression of PAL, and bacteria were grown for another 2 hrs. Bacteria were then pelleted, washed, and resuspended in minimal media, and supplemented with 4 mM phenylalanine. Aliquots were removed at 0 hrs, 2 hrs, and 4 hrs for phenylalanine quantification (FIG. 8A), and at 2 hrs and 4 hrs for cinnamate quantification (FIG. 8B), by mass spectrometry, as described in Examples 24-26. As shown in FIG. 8, expression of pheP in conjunction with PAL significantly enhances the degradation of phenylalanine as compared to PAL alone or pheP alone. Notably, the additional copy of pheP permitted the complete degradation of phenylalanine (4 mM) in 4 hrs (FIG. 8A). FIG. 8B depicts cinnamate levels in samples at 2 hrs and 4 hrs post-induction. Since cinnamate production is directly correlated with phenylalanine degradation, these data suggest that phenylalanine disappearance is due to phenylalanine catabolism, and that cinnamate may be used as an alternative biomarker for strain activity. PheP overexpression improves phenylalanine metabolism in engineered bacteria.

In conclusion, in conjunction with pheP, even low-copy PAL-expressing plasmids are capable of almost completely eliminating phenylalanine from a test sample (FIGS. 8A and 8B). Furthermore, without wishing to be bound by theory, in some embodiments, that incorporate pheP, there may be additional advantages to using a low-copy PAL-expressing plasmid in conjunction in order to enhance the stability of PAL expression while maintaining high phenylalanine metabolism, and to reduce negative selection pressure on the transformed bacterium. In alternate embodiments, the phenylalanine transporter is used in conjunction with a high-copy PAL-expressing plasmid.

Example 3. Phenylalanine Degradation in Recombinant E. Coli with and without pheP Overexpression The SYN-PKU304 and SYN-PKU305 strains contain low-copy plasmids harboring the PAL3 gene, and a copy of pheP integrated at the lacZ locus. The SYN-PKU308 and SYN-PKU307 strains also contain low-copy plasmids harboring the PAL3 gene, but lack a copy of pheP integrated at the lacZ locus. In all four strains, expression of PAL3 and pheP (when applicable) is controlled by an oxygen level-dependent promoter.

To determine rates of phenylalanine degradation in engineered E. coli Nissle with and without pheP on the chromosome, overnight cultures of SYN-PKU304 and SYN-PKU307 were diluted 1:100 in LB containing ampicillin, and overnight cultures of SYN-PKU308 and SYN-PKU305 were diluted 1:100 in LB containing kanamycin. All strains were grown for 1.5 hrs before cultures were placed in a Coy anaerobic chamber supplying 90% $N_2$, 5% $CO_2$, and 5% $H_2$. After 4 hrs of induction, bacteria were pelleted, washed in PBS, and resuspended in 1 mL of assay buffer. Assay buffer contained M9 minimal media supplemented with 0.5% glucose, 8.4% sodium bicarbonate, and 4 mM of phenylalanine.

Figure 10:
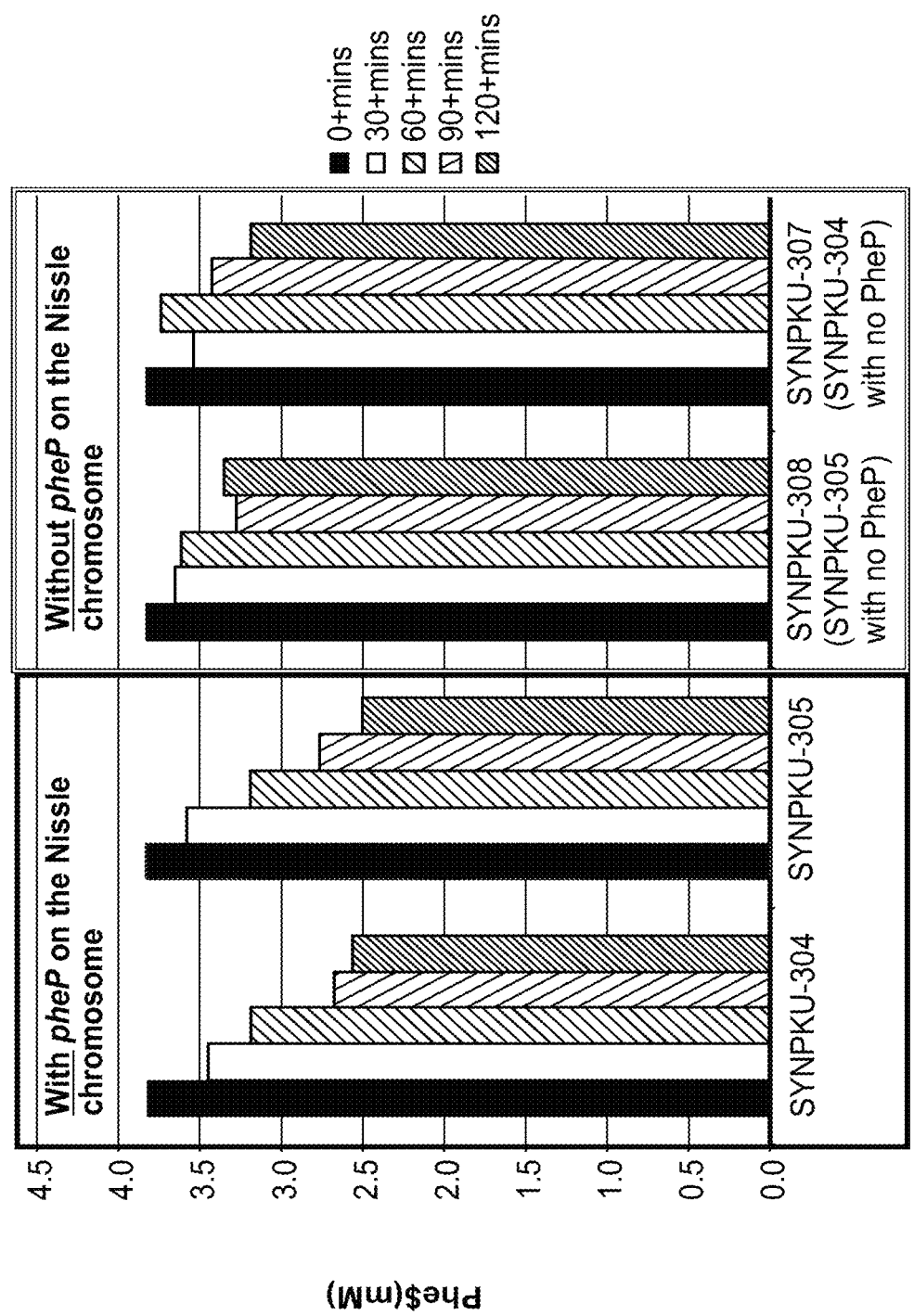
FIG. 10 depicts phenylalanine concentrations in cultures of synthetic probiotic strains, with and without an additional copy of pheP inserted on the chromosome. After 1.5 hrs of growth, cultures were placed in Coy anaerobic chamber supplying 90% $N_2$, 5% $CO_2$, and 5% $H_2$. After 4 hrs of induction, bacteria were resuspended in assay buffer containing 4 mM phenylalanine. Aliquots were removed from cell assays every 30 min for 3 hrs for phenylalanine quantification by mass spectrometry. Phenylalanine degradation rates in strains comprising an additional copy of pheP (SYN-PKU304 and SYN-PKU305; left) were higher than strains lacking an additional copy of pheP (SYN-PKU308 and SYN-PKU307; right).
Figure 11:
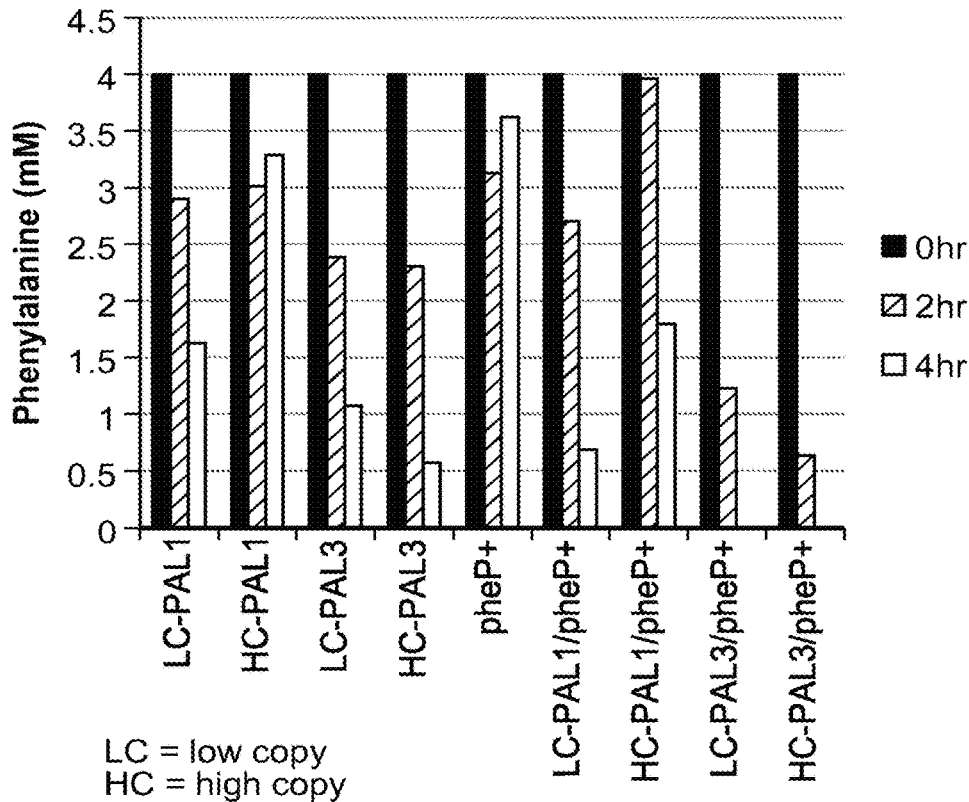
FIG. 11. shows that pheP Overexpression Improves Phe Degradation. Strains containing different PAL genes and an additional copy of the gene encoding the pheP transporter were compared with strains lacking the additional pheP gene. Notably, the additional pheP copy permitted the complete degradation of 4 mM Phe in 4 hours in this experiment.
Figure 12:
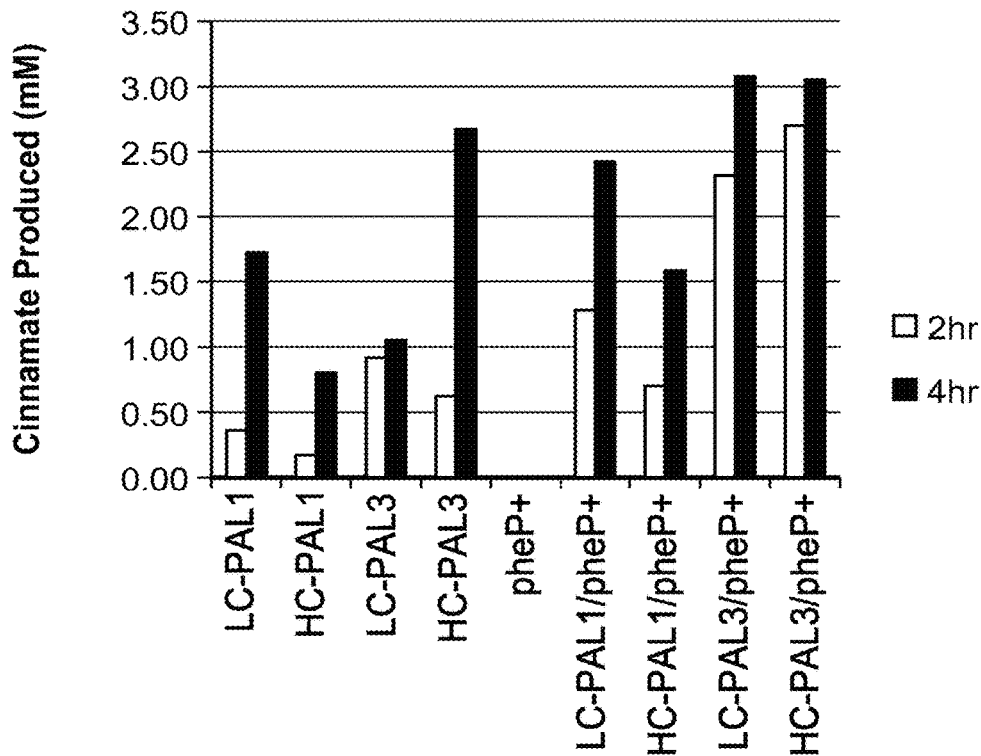
FIG. 12. Shows that cinnamate production is enhanced in pheP+ Strains. Cinnamate production is directly correlated with Phe degradation. pheP+ refers to the Nissle parent strain containing an additional integrated copy of the pheP gene but lacking a PAL circuit.
Figure 13:
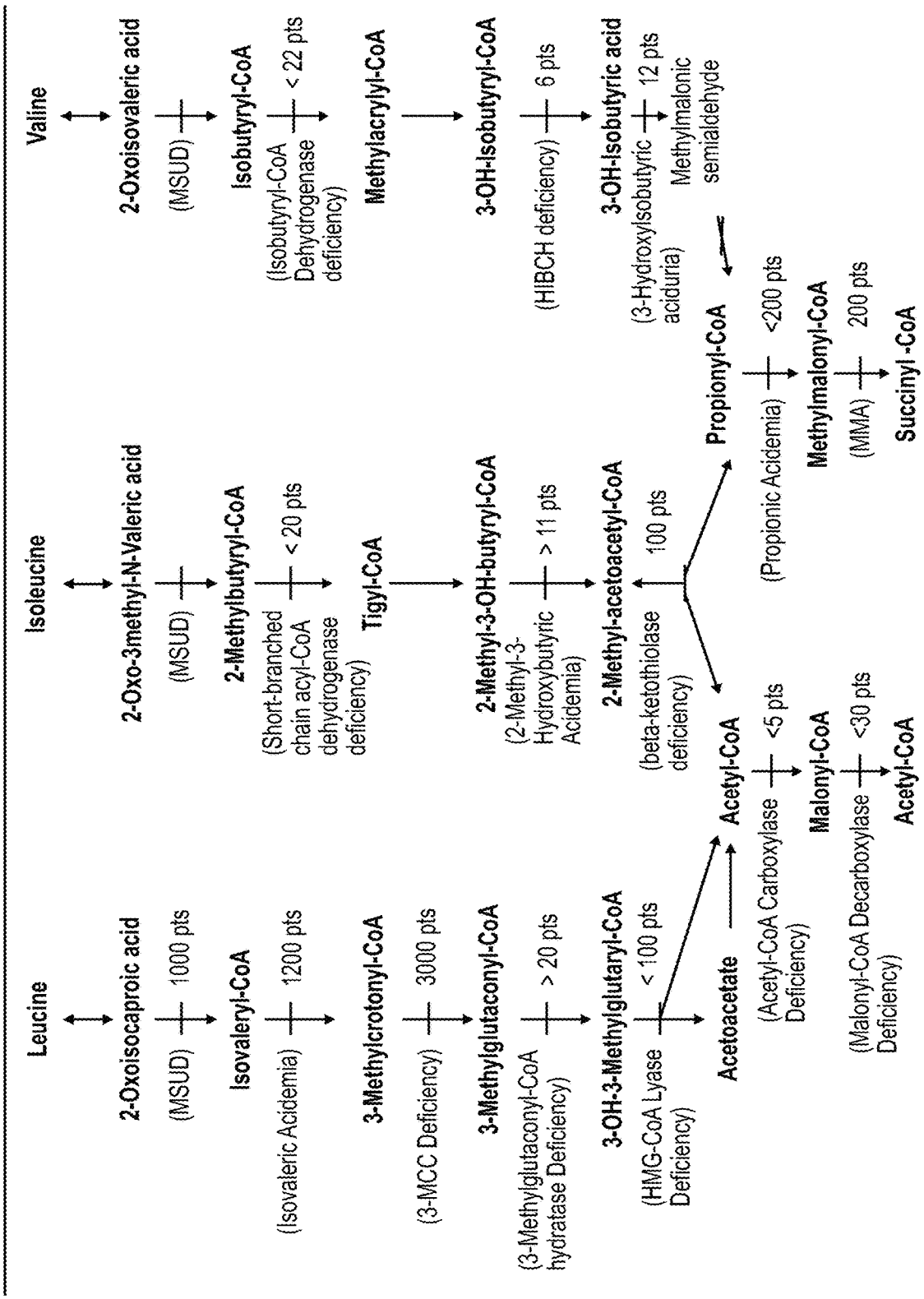
FIG. 13 depicts diseases associated with branched chain amino acid degradative pathways.
Figure 14:
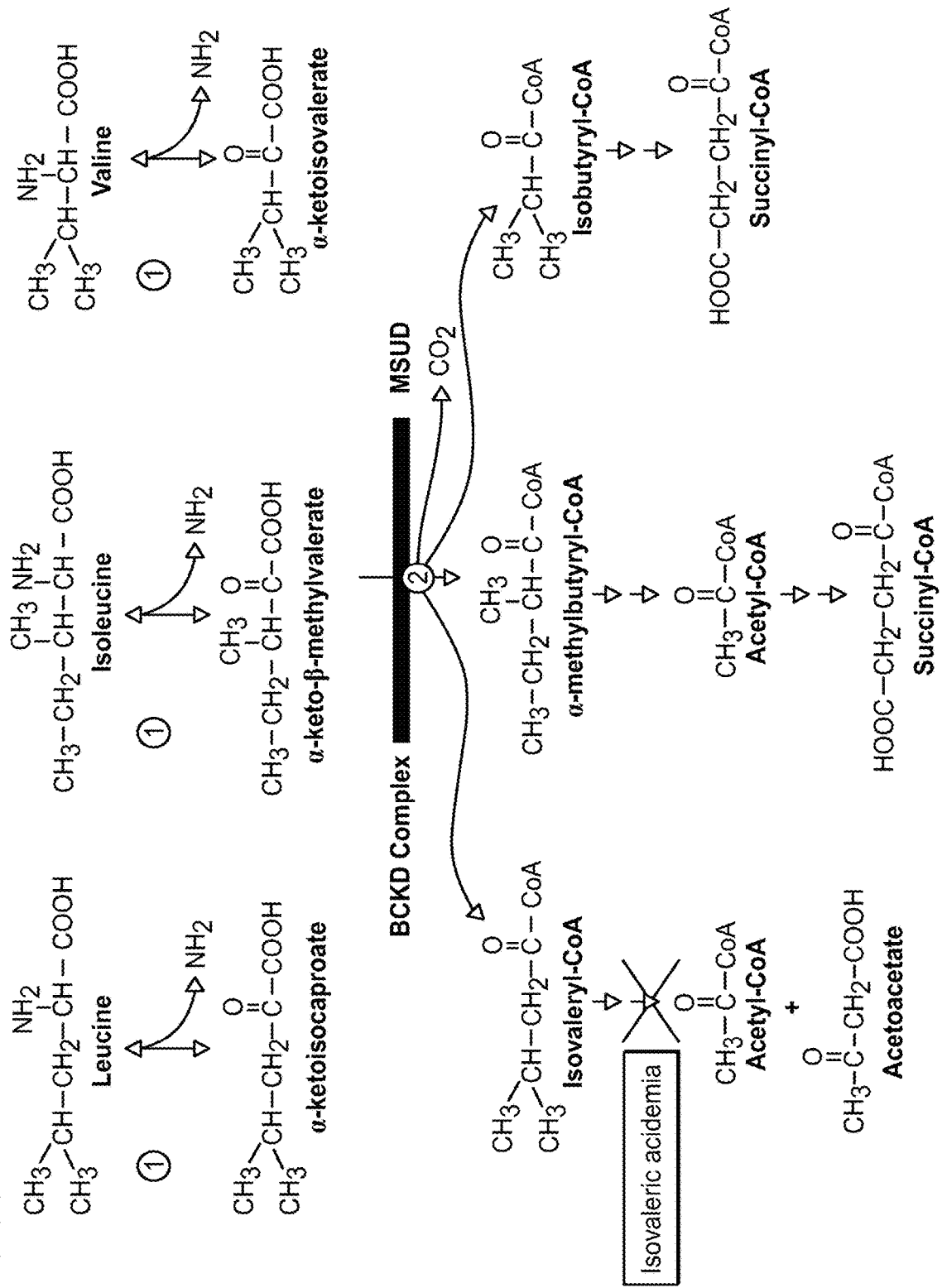
FIG. 14 depicts aspects of the branched chain amino acid degradative pathway
Figure 15:
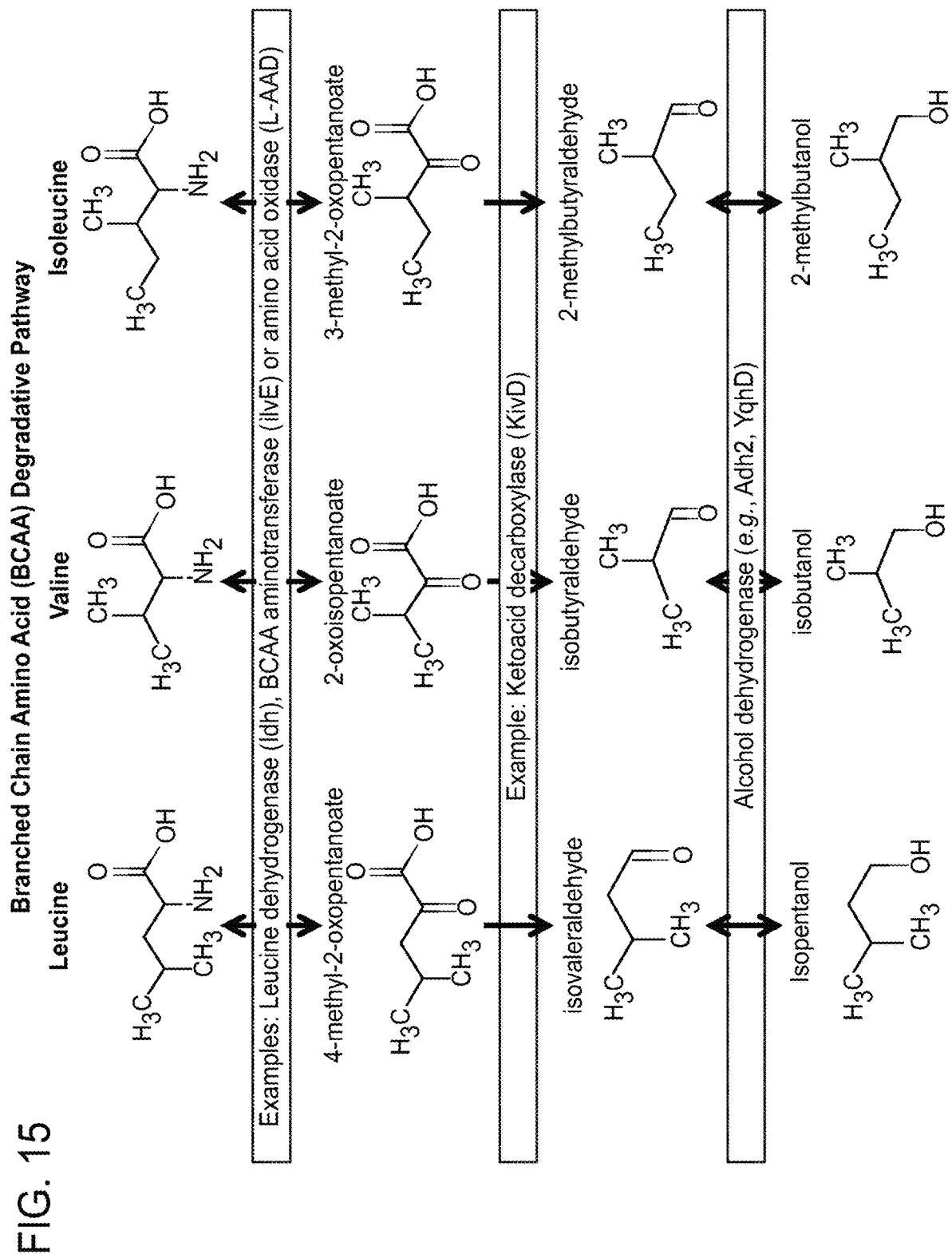
FIG. 15 depicts aspects of the branched chain amino acid degradative pathway
Figure 16:
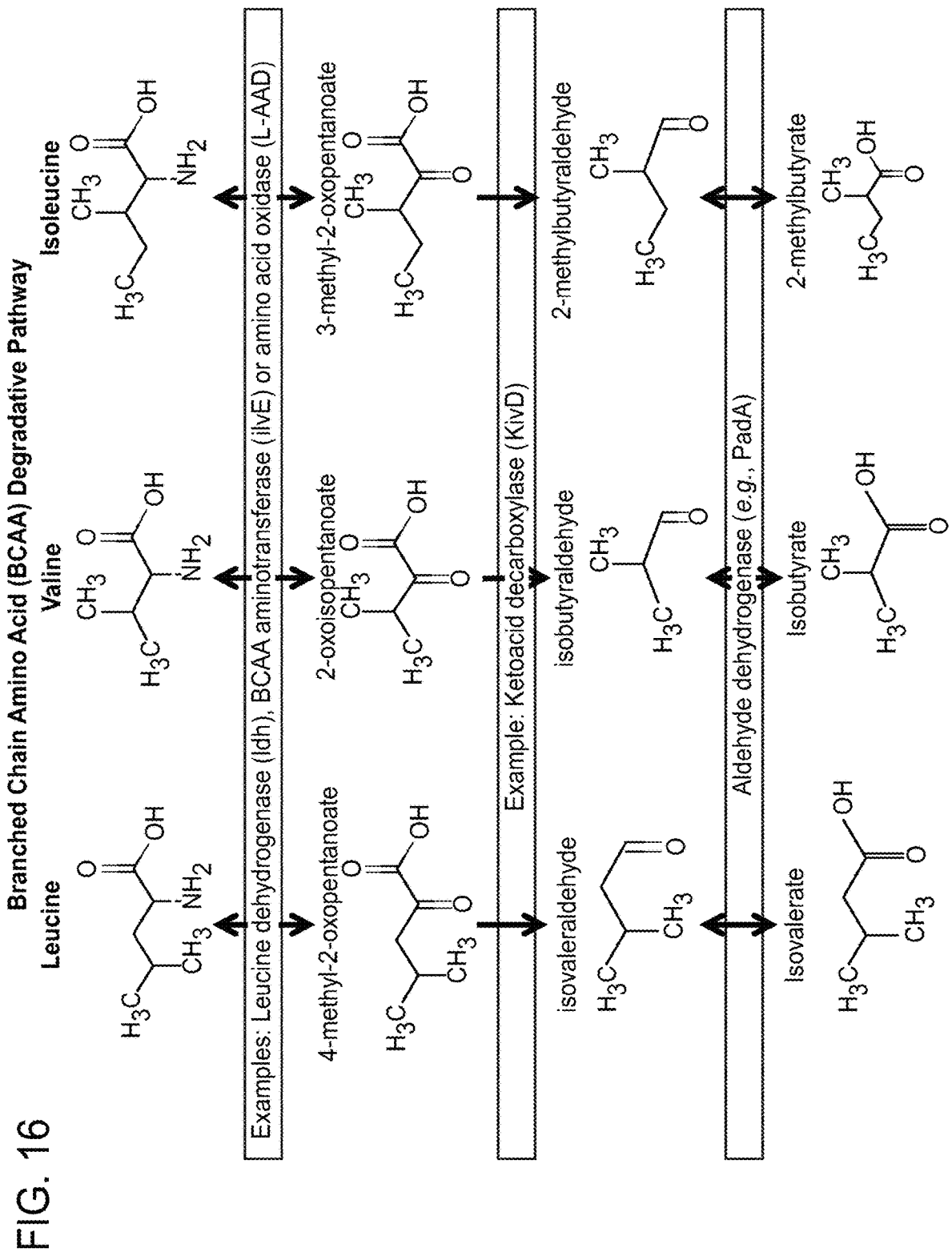
FIG. 16 depicts aspects of the branched chain amino acid degradative pathway
Figure 20:
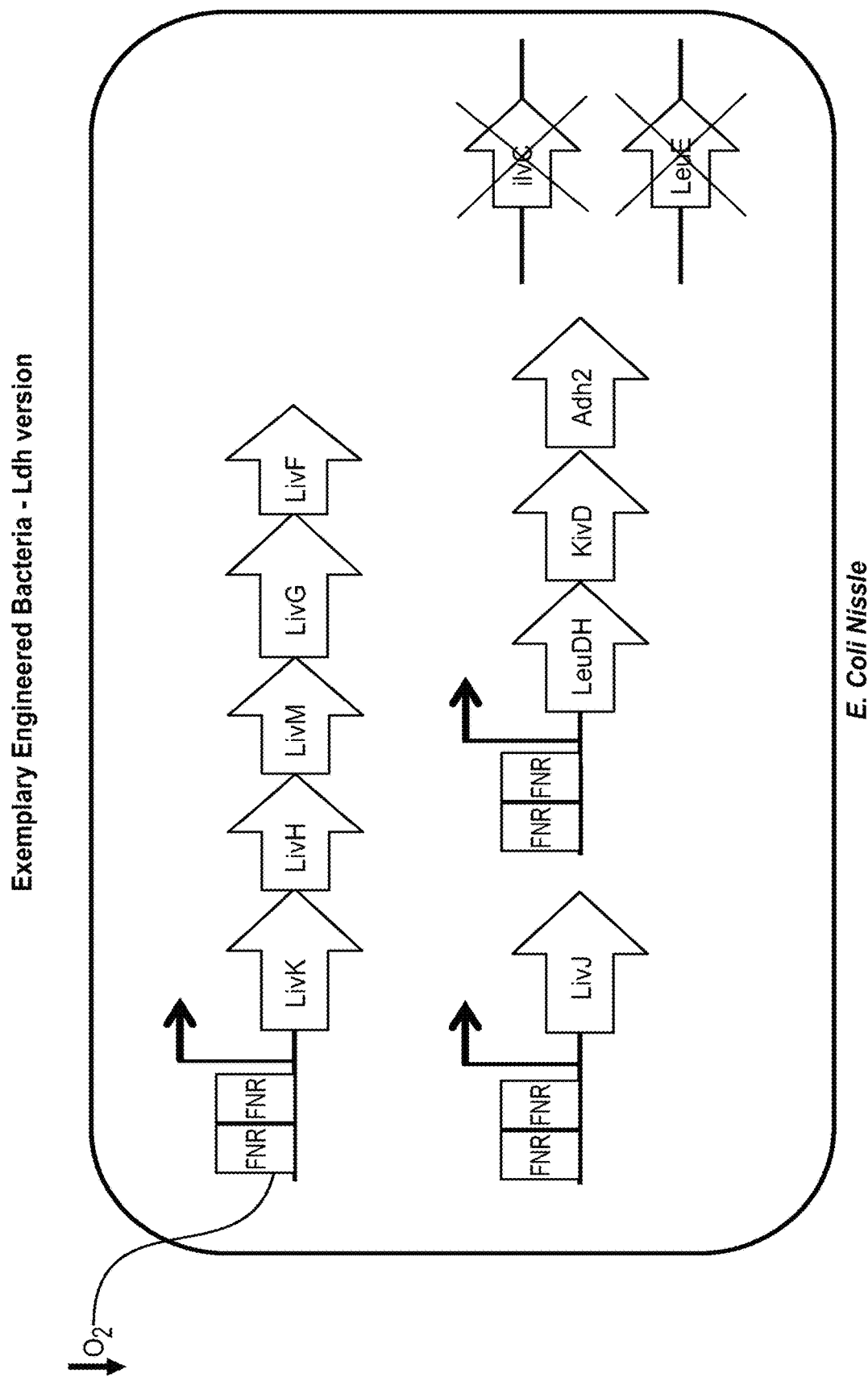
FIG. 20 depicts one exemplary branched chain amino acid circuit. Genes shown are high affinity leucine transporter complex (LivKHMGF), the branched chain a-ketoacid decarboxylase (KivD) from *Lactococcus lactis*, aldehyde dehydrogenase 2 (Adh2) from *Saccharomyces cerevisiae*, and leucine dehydrogenase (Ldh) from *Pseudomonas aeruginosa*. The genes for the leucine exporter (LeuE) and ilvC have been deleted. The gene for ilvJ is added which can be under the control of the native, FNR, or constitutive promoter Ptac

For the activity assay, starting counts of colony-forming units (cfu) were quantified using serial dilution and plating. Aliquots were removed from each cell assay every 30 min for 3 hrs for phenylalanine quantification by mass spectrometry. Specifically, 150 μL of bacterial cells were pelleted and the supernatant was harvested for LC-MS analysis, with assay media without cells used as the zero-time point. FIG. 10 shows the observed phenylalanine degradation for strains with pheP on the chromosome (SYN-PKU304 and SYN-PKU305; left), as well as strains lacking pheP on the chromosome (SYN-PKU308 and SYN-PKU307; right). These data show that pheP overexpression is important in order to increase rates of phenylalanine degradation in synthetic probiotics.

Strains Used in the Experiments

| Strain Name | Strain Name | Genotype | PAL Activity (umol/hr/10^9 cells) |
|---|---|---|---|
| SYN025 | SYN-PKU101 | Low copy pSC101-Ptet::PAL1, ampicillin resistant | ND |
| SYN026 | SYN-PKU102 | High copy pColE1-Ptet::PAL1, ampicillin resistant, | ND |
| SYN065 | SYN-PKU201 | Low copy pSC101-Ptet::PAL3, ampicillin resistant | ND |
| SYN063 | SYN-PKU202 | High copy pColE1-Ptet::PAL3, ampicillin resistant, | ND |
| SYN107 | SYN-PKU203 | lacZ::Ptet-pheP::cam | 0 |
| SYN108 | SYN-PKU401 | Low copy pSC101-Ptet::PAL1, ampicillin resistant, chromosomal lacZ::Ptet-pheP::cam | 1.1 |
| SYN109 | SYN-PKU402 | High copy pColE1-Ptet::PAL1, ampicillin resistant, chromosomal lacZ::Ptet-pheP::cam | 0.8 |
| SYN110 | SYN-PKU302 | Low Copy pSC101-Ptet::PAL3, ampicillin resistant; chromosomal lacZ::Ptet-pheP::cam | 2.2 |
| SYN111 | SYN-PKU303 | High copy pColE1-Ptet::PAL3, ampicillin resistant, chromosomal lacZ::Ptet-pheP::cam | 7.1 |
| SYN340 | SYN-PKU304 | Low Copy pSC101-PfnrS::PAL3, ampicillin resistant; chromosomal lacZ::PfnrS-pheP::cam | 3 |
| SYN958 | SYN-PKU305 | Low Copy pSC101-PfnrS::PAL3, kanamycin resistant; chromosomal lacZ::PfnrS-pheP::cam | 3 |
| SYN959 | SYN-PKU307 | Low Copy pSC101-PfnrS::PAL3, ampicillin resistant; | 0.3 |
| SYN837 | SYN-PKU308 | Low Copy pSC101-PfnrS::PAL3, kanamycin resistant; | 0.3 |

Example 4. Construction of Plasmids Encoding Branched Chain Amino Acid Importers and Branched Chain Amino Acid Catabolism Enzyme The kivD gene of *Lactococcus lactis* IFPL730 was synthesized (Genewiz), fused to the Tet promoter, cloned into the high-copy plasmid pUC57-Kan by Gibson assembly and transformed into *E. coli* DH5α to generate the plasmid pTet-kivD. The bkd operon of *Pseudomonas aeruginosa* PA01 fused to the Tet promoter was synthesized (Genewiz) and cloned into the high-copy plasmid pUC57-Kan to generate the plasmid pTet-bkd. The bkd operon of *Pseudomonas aeruginosa* PA01 fused to the ldh gene from PA01 and the Tet promoter was synthesized (Genewiz) and cloned into the high-copy plasmid pUC57-Kan to generate the plasmid pTet-ldh-bkd. The livKHMGF operon from *E. coli* Nissle fused to the Tet promoter was synthesized (Genewiz), cloned into the pKIKO-lacZ plasmid by Gibson assembly and transformed into *E. coli* PIR1 as described in Example 3 to generate the pTet-livKHMGF.

Example 5. Generation of Recombinant Bacterial Cell Comprising a Genetic Modification that Reduces Export of a Branched Chain Amino Acid

*E. coli* Nissle was transformed with the pKD46 plasmid encoding the lambda red proteins under the control of an arabinose-inducible promoter as follows. An overnight culture of *E. coli* Nissle grown at 37° C. was diluted 1:100 in 4 mL of lysogeny broth (LB) and grown at 37° C. until it reached an $OD_{600}$ of 0.4-0.6. 1 mL of the culture was then centrifuged at 13,000 rpm for 1 min in a 1.5 mL microcentrifuge tube and the supernatant was removed. The cells were then washed three times in pre-chilled 10% glycerol and resuspended in 40 uL pre-chilled 10% glycerol. The electroporator was set to 1.8 kV. 1 uL of a pKD46 miniprep was added to the cells, mixed by pipetting, and pipetted into a sterile, chilled 1 mm cuvette. The cuvette was placed into the sample chamber, and the electric pulse was applied. 500 uL of room-temperature SOC media was immediately added, and the mixture was transferred to a culture tube and incubated at 30° C. for 1 hr. The cells were spread out on an LB plate containing 100 ug/mL carbenicillin and incubated at 30° C.

A ΔleuE deletion construct with 77 bp and a 100 bp flanking leuE homology regions and a kanamycin resistant cassette flanked by FRT recombination site was generated by PCR, column-purified and transformed into *E. coli* Nissle pKD46 as follows. An overnight culture of *E. coli* Nissle pKD46 grown in 100 ug/mL carbenicillin at 30° C. was diluted 1:100 in 5 mL of LB supplemented with 100 ug/mL carbenicillin, 0.15% arabinose and grown until it reaches an $OD_{600}$ of 0.4-0.6. The bacteria were aliquoted equally in five 1.5 mL microcentrifuge tubes, centrifuged at 13,000 rpm for 1 min and the supernatant was removed. The cells were then washed three times in pre-chilled 10% glycerol and combined in 50 uL pre-chilled 10% glycerol. The electroporator was set to 1.8 kV. 2 uL of a the purified ΔleuE deletion PCR fragment are then added to the cells, mixed by pipetting, and pipetted into a sterile, chilled 1 mm cuvette. The cuvette was placed into the sample chamber, and the electric pulse was applied. 500 uL of room-temperature SOC media was immediately added, and the mixture was transferred to a culture tube and incubated at 37° C. for 1 hr. The cells were spread out on an LB plate containing 50 ug/mL kanamycin. Five kanamycin-resistant transformants were then checked by colony PCR for the deletion of the leuE locus.

The kanamycin cassette was then excised from the ΔleuE deletion strain as follows. ΔleuE was transformed with the pCP20 plasmid encoding the Flp recombinase gene. An overnight culture of ΔleuE grown at 37° C. in LB with 50 ug/mL kanamycin was diluted 1:100 in 4 mL of LB and grown at 37° C. until it reaches an $OD_{600}$ of 0.4-0.6. 1 mL of the culture was then centrifuged at 13,000 rpm for 1 min in a 1.5 mL microcentrifuge tube and the supernatant was removed. The cells were then washed three times in pre-chilled 10% glycerol and resuspended in 40 uL pre-chilled 10% glycerol. The electroporator was set to 1.8 kV. 1 uL of a pCP20 miniprep was added to the cells, mixed by pipetting, and pipetted into a sterile, chilled 1 mm cuvette. The dry cuvette was placed into the sample chamber, and the electric pulse was applied. 500 uL of room-temperature SOC media was immediately added, and the mixture was transferred to a culture tube and incubated at 30° C. for 1 hr. The cells were spread out on an LB plate containing 100 ug/mL carbenicillin and incubated at 30° C. Eight transformants were then streaked on an LB plate and were incubated overnight at 43° C. One colony per transformant was picked and resuspended in 10 uL LB and 3 uL of the suspension were pipetted on LB, LB with 50 ug/mL Kanamycin or LB with 100 ug/mL carbenicillin. The LB and LB Kanamycin plates were incubated at 37° C. and the LB Carbenicillin plate was incubated at 30° C. Colonies showing growth on LB alone were selected and checked by PCR for the excision of the Kanamycin cassette.

Example 6. Generation of Recombinant Bacteria Comprising an Importer of a Branched Chain Amino Acid and/or a Branched Chain Amino Acid Catabolism Enzyme and Lacking an Exporter of a Branched Chain Amino Acid pTet-kivD, pTet-bkd, pTet-ldh-bkd and pTet-livKHFGF plasmids described above were transformed into *E. coli* Nissle (pTet-kivD), Nissle (pTet-kivD, pTet-bkd, pTet-ldh-bkd), DH5α (pTet-kivD, pTet-bkd, pTet-ldh-bkd) or PIR1 (pTet-livKHMGF). All tubes, solutions, and cuvettes were pre-chilled to 4° C. An overnight culture of *E. coli* (Nissle, ΔleuE, DH5α or PIR1) was diluted 1:100 in 4 mL of LB and grown until it reached an $OD_{600}$ of 0.4-0.6. 1 mL of the culture was then centrifuged at 13,000 rpm for 1 min in a 1.5 mL microcentrifuge tube and the supernatant was removed. The cells were then washed three times in pre-chilled 10% glycerol and resuspended in 40 uL pre-chilled 10% glycerol. The electroporator was set to 1.8 kV. 1 uL of a pTet-kivD, pTet-bkd, pTet-ldh-bkd or pTet-livKHMGF miniprep was added to the cells, mixed by pipetting, and pipetted into a sterile, chilled 1 mm cuvette. The dry cuvette was placed into the sample chamber, and the electric pulse was applied. 500 uL of room-temperature SOC media was immediately added, and the mixture was transferred to a culture tube and incubated at 37° C. for 1 hr. The cells were spread out on an LB plate containing 50 ug/mL Kanamycin for pTet-kivD, pTet-bkd and pTet-ldh-bkd or 100 ug/mL carbenicillin for pTet-livKHMGF.

Example 7. Generation of Recombinant Bacteria Comprising an Importer of a Branched Chain Amino Acid and a Genetic Modification that Reduces Export of a Branched Chain Amino Acid

*E. coli* Nissle ΔleuE was transformed with the pKD46 plasmid encoding the lambda red proteins under the control of an arabinose-inducible promoter as follows. An overnight culture of *E. coli* Nissle ΔleuE grown at 37° C. was diluted 1:100 in 4 mL of LB and grown at 37° C. until it reached an $OD_{600}$ of 0.4-0.6. 1 mL of the culture was then centrifuged at 13,000 rpm for 1 min in a 1.5 mL microcentrifuge tube and the supernatant was removed. The cells were then washed three times in pre-chilled 10% glycerol and resuspended in 40 uL pre-chilled 10% glycerol. The electroporator was set to 1.8 kV. 1 uL of a pKD46 miniprep was added to the cells, mixed by pipetting, and pipetted into a sterile, chilled 1 mm cuvette. The dry cuvette was placed into the sample chamber, and the electric pulse was applied. 500 uL of room-temperature SOC media was immediately added, and the mixture was transferred to a culture tube and incubated at 30° C. for 1 hr. The cells were spread out on an LB plate containing 100 ug/mL carbenicillin and incubated at 30° C.

The DNA fragment used to integrate Tet-livKHMGF into *E. coli* Nissle lacZ was amplified by PCR from the pTet-livKHMGF plasmid, column-purified and transformed into ΔleuE pKD46 as follows. An overnight culture of the *E. coli* Nissle ΔleuE pKD46 strain grown in LB at 30° C. with 100 ug/mL carbenicillin was diluted 1:100 in 5 mL of lysogeny broth (LB) supplemented with 100 ug/mL carbenicillin, 0.15% arabinose and grown at 30° C. until it reached an $OD_{600}$ of 0.4-0.6. The bacteria were aliquoted equally in five 1.5 mL microcentrifuge tubes, centrifuged at 13,000 rpm for 1 min and the supernatant was removed. The cells were then washed three times in pre-chilled 10% glycerol and combined in 50 uL pre-chilled 10% glycerol. The electroporator was set to 1.8 kV. 2 uL of a the purified Tet-livKHMGF PCR fragment were then added to the cells, mixed by pipetting, and pipetted into a sterile, chilled 1 mm cuvette. The dry cuvette was placed into the sample chamber, and the electric pulse was applied. 500 uL of room-temperature SOC media was immediately added, and the mixture was transferred to a culture tube and incubated at 37° C. for 1 hr. The cells were spread out on an LB plate containing 20 ug/mL chloramphenicol, 40 ug/mL X-Gal and incubated overnight at 37° C. White chloramphenicol resistant transformants were then checked by colony PCR for integration of Tet-livKHMGF into the lacZ locus.

Example 8. Functional Assay Demonstrating that the Recombinant Bacterial Cells Decrease Branched Chain Amino Acid Concentration For in vitro studies, all incubations were performed at 37° C. Cultures of *E. coli* Nissle ΔleuE, ΔleuE+pTet-kivD, ΔleuE+pTet-bkd, ΔleuE+pTet-ldh-bkd, ΔleuE lacZ:Tet-livKHMGF, ΔleuE lacZ:Tet-livKHMGF+pTet-kivD, ΔleuE lacZ:Tet-livKHMGF+pTet-bkd, ΔleuE lacZ:Tet-livKHMGF+pTet-ldh-bkd were grown overnight in LB, LB 50 ug/mL Kanamycin or LB 50 ug/mL Kanamycin 20 ug/mL chloramphenicol and then diluted 1:100 in LB. The cells were grown with shaking (250 rpm) to early log phase with the appropriate antibiotics. Anhydrous tetracycline (ATC) was added to cultures at a concentration of 100 ng/mL to induce expression of KivD, Bkd, Ldh and LivKHFMG, and bacteria were grown for another 3 hours. Bacteria were then pelleted, washed, and resuspended in minimal media, and supplemented with 0.5% glucose and 2 mM leucine. Aliquots were removed at 0 h, 1.5 h, 6 h and 18 h for leucine quantification by liquid chromatography-mass spectrometry (LCMS) using a Thermo TSQ Quantum Max triple quadrupole instrument. Briefly, 100 uL aliquots were centrifuged at 4,500 rpm for 10 min 10 uL of the supernatant was resuspended in 90 uL water with 1 ug/mL L-leucine-5,5,5-$d_3$ (isotope used as internal standard). 10 uL of the samples was then resuspended in 90 uL 10% acetonitrile, 0.1% formic acid and placed in the LCMS autosampler. A C18 column 100×2 mm, 3 um particles was used (Luna, Phenomenex). The mobile phases used were water 0.1% formic acid (solvent A) and acetonitrile 0.1% (solvent B). The gradient used was:

0 min: 95% A, 5% B
0.5 min: 95% A, 5% B
1 min: 10% A, 90% B
2.5 min: 10% A, 90% B
2.51 min: 95% A, 5% B
3.5 min: 95% A, 5% B The Q1/Q3 transitions used for leucine and L-leucine-5,5,5-$d_3$ were 132.1/86.2 and 135.1/89.3 respectively.

Leucine was rapidly graded by the expression of kivD in the Nissle ΔleuE strain. After 6 h of incubation, leucine concentration dropped by over 99% in the presence of ATC. This effect was even more pronounced in the case of ΔleuE expressing both kivD and the leucine transporter livKHMGF where leucine is undetectable after 6 h of incubation. The expression of the bkd complex also leads rapidly to the degradation of leucine. After 6 h of incubation, 99% of leucine was degraded. The expression of the leucine transporter livKHMGF, in parallel with the expression of ldh and bkd leads to the complete degradation of leucine after 18 h.

Example 9. Simultaneous Degradation of Branched Chain Amino Acids by Recombinant Bacteria Expressing a Branched Chain Amino Acid Catabolism Enzyme and an Importer of a Branched Chain Amino Acid In these studies, all incubations were performed at 37° C. Cultures of E. coli Nissle, Nissle+pTet-kivD, ΔleuE+pTet-kivD, ΔleuE lacZ:Tet-livKHMGF+pTet-kivD were grown overnight in LB, LB 50 ug/mL Kanamycin or LB 50 ug/mL Kanamycin 20 ug/mL chloramphenicol and then diluted 1:100 in LB. The cells were grown with shaking (250 rpm) to early log phase with the appropriate antibiotics. Anhydrous tetracycline (ATC) was added to cultures at a concentration of 100 ng/mL to induce expression of KivD and LivKHFMG, and bacteria were grown for another 3 hours. Bacteria were then pelleted, washed, and resuspended in minimal media, and supplemented with 0.5% glucose and the three branched chain amino acids (leucine, isoleucine and valine, 2 mM each). Aliquots were removed at 0 h, 1.5 h, 6 h and 18 h for leucine, isoleucine and valine quantification by liquid chromatography-mass spectrometry (LCMS) using a Thermo TSQ Quantum Max triple quadrupole instrument. Briefly, 100 uL aliquots were centrifuged at 4,500 rpm for 10 min 10 uL of the supernatant was resuspended in 90 uL water with 1 ug/mL L-leucine-5,5,5-d$_3$ (isotope used as internal standard). 10 uL of the samples was then resuspended in water, 0.1% formic acid and placed in the LCMS autosampler. A C18 column 100×2 mm, 3 um particles was used (Luna, Phenomenex). The mobile phases used were water 0.1% formic acid (solvent A) and acetonitrile 0.1% (solvent B). The gradient used was:

0 min: 100% A, 0% B
0.5 min: 100% A, 0% B
1.5 min: 10% A, 90% B
3.5 min: 10% A, 90% B
3.51 min: 100% A, 0% B
4.5 min: 100% A, 0% B
The Q1/Q3 transitions used are:
Leucine: 132.1/86.2
L-leucine-5,5,5-d$_3$: 135.1/89.3
Isoleucine: 132.1/86.2
Valine: 118.1/72

Figure 32A:
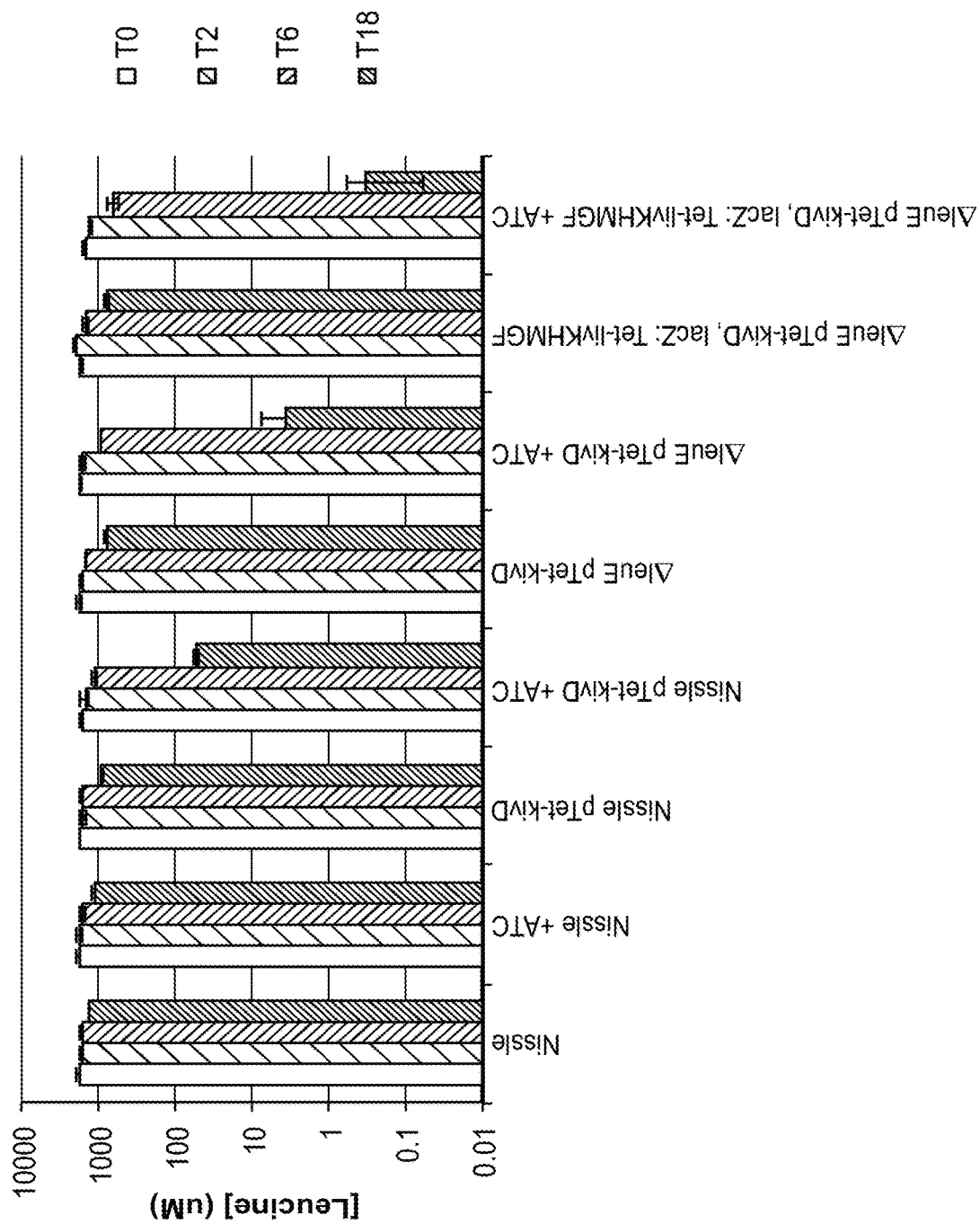
FIGS. 32A, 32B, and 32C depict the simultaneous degradation of leucine (FIG. 32A), isoleucine (FIG. 32B), and valine (FIG. 32C) by *E. coli* Nissle and its ΔleuE deletion strain harboring a high-copy plasmid expressing the keto-acid decarboxylase kivD from the Tet promoter or further with a copy of the livKHMGF operon driven by the Tet promoter integrated into the chromosome at the lacZ locus, which were induced with ATC and incubated in culture medium supplemented with 2 mM leucine, 2 mM isoleucine and 2 mM valine. Samples were removed at 0, 1.5, 6 and 18 h, and leucine concentration was determined by liquid chromatography tandem mass spectrometry.
Figure 32B:
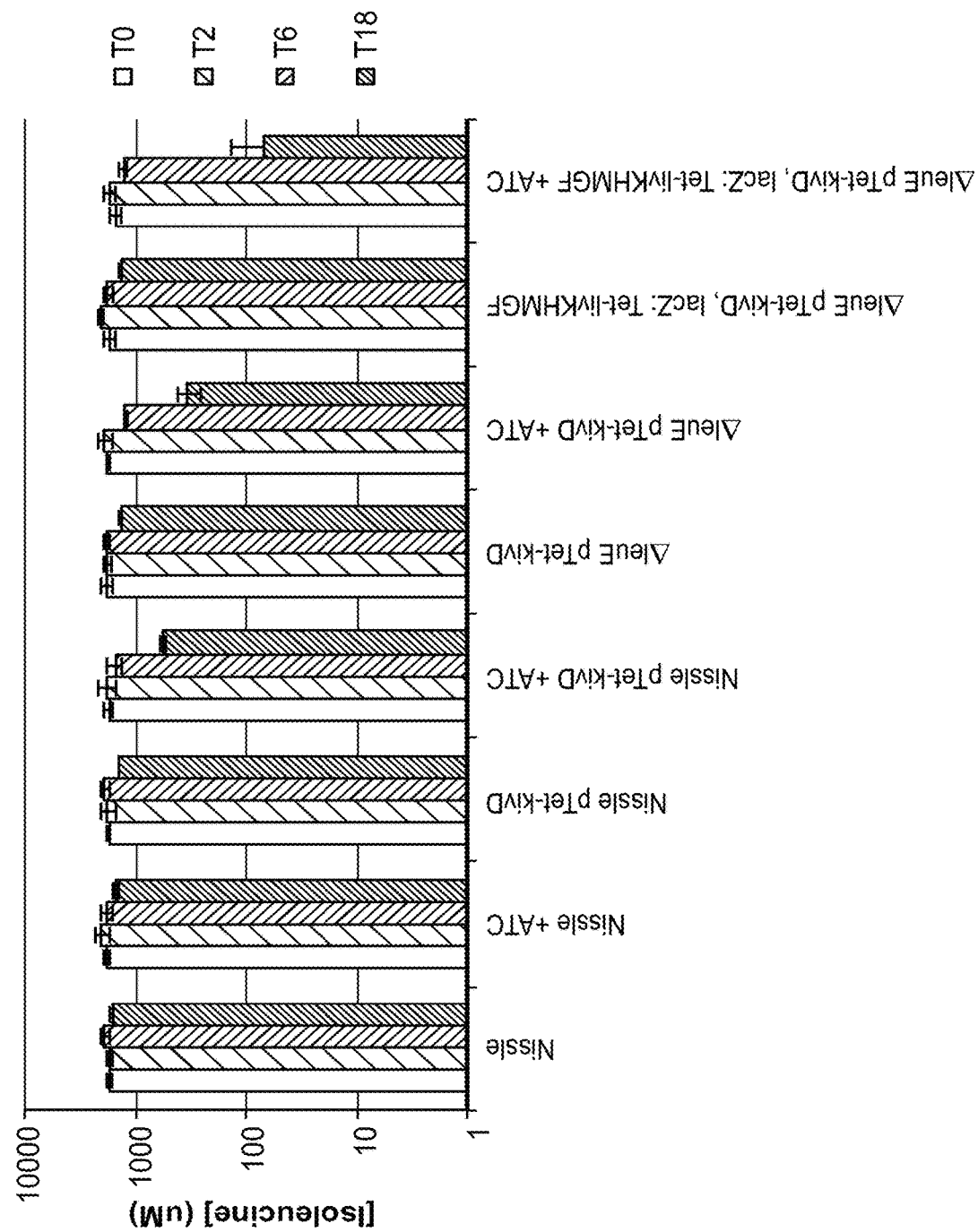
Figure 32C:
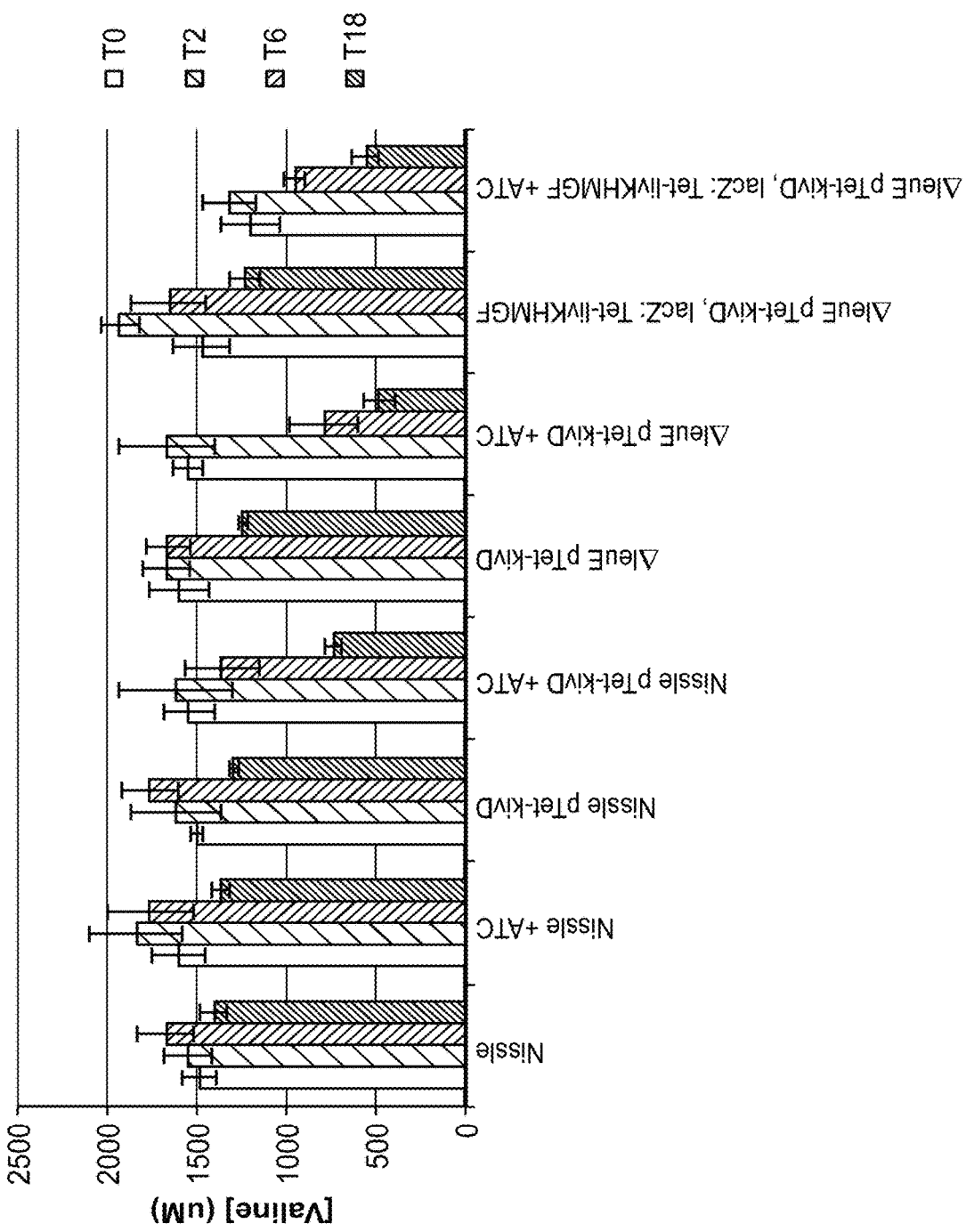
Figure 33:
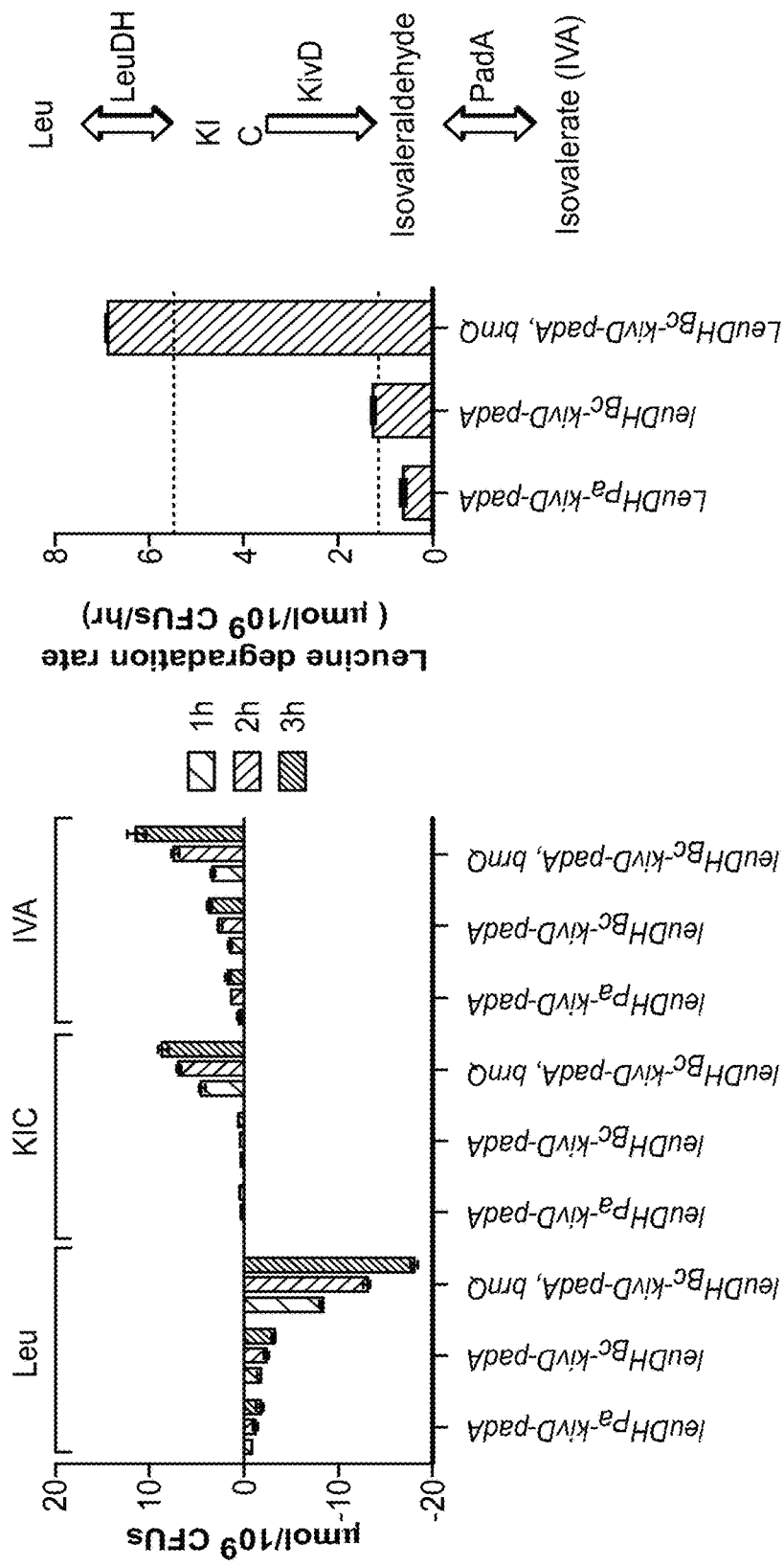
FIG. 33 shows that overexpression of the low-affinity BCAA transporter BrnQ greatly improves the rate of leucine degradation in a LeuE and ilvC knockout bacterial strain having either LeuDH derived from *P. aeruginosa* or LeuDH derived from *Bacillus cereus*, kivD, and padA with and without the BCAA transporter brnQ under the control of tet promoter as measured by leucine degradation, KIC production, and isovalerate production.

As shown in FIGS. 32A-32C, leucine, isoleucine and valine were all degraded by the expression of kivD in E. coli Nissle. At 18 h, 96.8%, 67.2% and 52.1% of leucine, isoleucine and valine respectively were degraded in Nissle expressing kivD in the presence of ATC. The efficiency of leucine and isoleucine degradation was further improved by expressing kivD in the ΔleuE background strain with a 99.8% leucine and 80.6% isoleucine degradation at 18 h Finally, an additional increase in leucine and isoleucine degradation was achieved by expressing the leucine transporter livKHMGF in the Nissle ΔleuE pTet-kivD strain with a 99.98% leucine and 95.5% isoleucine degradation at 18 h. No significant improvement in valine degradation was observed in the ΔleuE deletion strain expressing livKHMGF.

Example 10. Increase of BCAA Import by Overexpressing the High Affinity BCAA Transporters livKHMGF and livJHMGF In Vitro Study Objective
BCAA accumulate to toxic levels in MSUT) patients
Different synthetic probiotic E. coli Nissle strains were engineered to efficiently import BCAA into the bacterial cell to be degraded
The objective of this study was to determine if expressing the two BCAA transporters livKHMGF and livJHMGF increase the import of valine, a BCAA naturally secreted to high levels by E. coli Nissle.
Description of the Different Probiotic Strains
All strains are derived from the human probiotic: strain E. coli Nissle 1917. A ΔleuE deletion strain (deleted for the leucine exporter leuE) was generated by lambda red-recombination
A copy of the high-affinity leucine ABC transporter livKHMGF under the control of a tetracycline-inducible promoter (Ptet) was inserted into the lacZ locus of the ΔleuE deletion strain by lambda-red recombination to generate the ΔleuE, lacZ:Ptet-livKHMGF strain. In this strain, the BCAA transporter livKHMGF can get induced in the presence of anhydrotetracycline (ATC)
Finally, the endogenous promoter of livJ was swapped with the constitutive promoter Ptac by lambda-red recombination to generate the ΔleuE, lacZ:Ptet-livKHMGF, Ptac-livJ strain. In this strain, livJ is constitutively induced. In the presence of ATC, both BCAA transporters livKHMGF and livJHMGF are expressed
Experimental Procedure
The three strains tested (ΔleuE; ΔleuE, lacZ:Ptet-livKHMGF; ΔleuE, lacZ:Ptet-livKHMGF, Ptac-livJ) were grown overnight at 37° C. and 250 rpm in 4 mL of LB
Cells were diluted 100 fold in 4 mL LB and grown for 2 h at 37° C. and 250 rpm
Cells were split in two 2 mL culture tubes
One 2 mL culture tube was induced with 100 ng/mL anhydrotetracycline (ATC) to activate the Ptet promoter
After 1 h induction, 1 mL of cells was spun down at maximum speed for 30 seconds in a microcentrifuge
The supernatant was removed and the pellet re-suspended in 1 mL M9 medium 0.5% glucose
The cells were spun down again at maximum speed for 30 seconds and resuspended in 1 mL M9 medium 0.5% glucose
The cells were transferred to a culture tube and incubated at at 37° C. and 250 rpm for 5.5 h
150 μL of cells were collected at 0 h, 2 h and 5.5 h
The concentration of valine in the cell supernatant at the different time points was determined by LC-MS/MS.
Results
The natural secretion of valine by E. coli Nissle is observed for the ΔleuE strain. The secretion of valine is strongly reduced for ΔleuE, lacZ:Ptet-livKHMGF in the presence of ATC. This strongly suggests that the secreted valine is efficiently imported back into the cell by livKHMGF. The secretion of valine is abolished in the ΔleuE, lacZ:Ptet-livKHMGF, Ptac-livJ strain, with or without ATC. This strongly suggests that the constitutive expression of livJ is sufficient to import back the entire amount of valine secreted by the cell via the livJHMGF transporter. E. coli Nissle was engineered to efficiently import BCAA, in this case valine, using both an inducible promoter (Ptet), and a constitutive promoter (Ptac), controlling the expression of livKHMGF and livJ respectively.

Example 11. Generation of Bacterial Strains with Enhance Ability to Transport Biomolecules Due to their ease of culture, short generation times, very high population densities and small genomes, microbes can be evolved to unique phenotypes in abbreviated timescales. Adaptive laboratory evolution (ALE) is the process of passaging microbes under selective pressure to evolve a strain with a preferred phenotype. Most commonly, this is applied to increase utilization of carbon/energy sources or adapting a strain to environmental stresses (e.g., temperature, pH), whereby mutant strains more capable of growth on the carbon substrate or under stress will outcompete the less adapted strains in the population and will eventually come to dominate the population.

This same process can be extended to any essential metabolite by creating an auxotroph. An auxotroph is a strain incapable of synthesizing an essential metabolite and must therefore have the metabolite provided in the media to grow. In this scenario, by making an auxotroph and passaging it on decreasing amounts of the metabolite, the resulting dominant strains should be more capable of obtaining and incorporating this essential metabolite.

For example, if the biosynthetic pathway for producing an amino acid is disrupted a strain capable of high-affinity capture of said amino acid can be evolved via ALE. First, the strain is grown in varying concentrations of the auxotrophic amino acid, until a minimum concentration to support growth is established. The strain is then passaged at that concentration, and diluted into lowering concentrations of the amino acid at regular intervals. Over time, cells that are most competitive for the amino acid—at growth-limiting concentrations—will come to dominate the population. These strains will likely have mutations in their amino acid-transporters resulting in increased ability to import the essential and limiting amino acid.

Similarly, by using an auxotroph that cannot use an upstream metabolite to form an amino acid, a strain can be evolved that not only can more efficiently import the upstream metabolite, but also convert the metabolite into the essential downstream metabolite. These strains will also evolve mutations to increase import of the upstream metabolite, but may also contain mutations which increase expression or reaction kinetics of downstream enzymes, or that reduce competitive substrate utilization pathways.

In the previous examples, a metabolite innate to the microbe was made essential via mutational auxotrophy and selection was applied with growth-limiting supplementation of the endogenous metabolite. However, phenotypes capable of consuming non-native compounds can be evolved by tying their consumption to the production of an essential compound. For example, if a gene from a different organism is isolated which can produce an essential compound or a precursor to an essential compound this gene can be recombinantly introduced and expressed in the heterologous host. This new host strain will now have the ability to synthesize an essential nutrient from a previously non-metabolizable substrate. Hereby, a similar ALE process can be applied by creating an auxotroph incapable of converting an immediately downstream metabolite and selecting in growth-limiting amounts of the non-native compound with concurrent expression of the recombinant enzyme. This will result in mutations in the transport of the non-native substrate, expression and activity of the heterologous enzyme and expression and activity of downstream native enzymes. It should be emphasized that the key requirement in this process is the ability to tether the consumption of the non-native metabolite to the production of a metabolite essential to growth.

Once the basis of the selection mechanism is established and minimum levels of supplementation have been established, the actual ALE experimentation can proceed. Throughout this process several parameters must be vigilantly monitored. It is important that the cultures are maintained in an exponential growth phase and not allowed to reach saturation/stationary phase. This means that growth rates must be check during each passaging and subsequent dilutions adjusted accordingly. If growth rate improves to such a degree that dilutions become large, then the concentration of auxotrophic supplementation should be decreased such that growth rate is slowed, selection pressure is increased and dilutions are not so severe as to heavily bias subpopulations during passaging. In addition, at regular intervals cells should be diluted, grown on solid media and individual clones tested to confirm growth rate phenotypes observed in the ALE cultures.

Predicting when to halt the stop the ALE experiment also requires vigilance. As the success of directing evolution is tied directly to the number of mutations "screened" throughout the experiment and mutations are generally a function of errors during DNA replication, the cumulative cell divisions (CCD) acts as a proxy for total mutants which have been screened. Previous studies have shown that beneficial phenotypes for growth on different carbon sources can be isolated in about $10^{11.2}$ CCD[1]. This rate can be accelerated by the addition of chemical mutagens to the cultures—such as N-methyl-N-nitro-N-nitrosoguanidine (NTG)—which causes increased DNA replication errors. However, when continued passaging leads to marginal or no improvement in growth rate the population has converged to some fitness maximum and the ALE experiment can be halted.

At the conclusion of the ALE experiment, the cells should be diluted, isolated on solid media and assayed for growth phenotypes matching that of the culture flask. Best performers from those selected are then prepped for genomic DNA and sent for whole genome sequencing. Sequencing with reveal mutations occurring around the genome capable of providing improved phenotypes, but will also contain silent mutations (those which provide no benefit but do not detract from desired phenotype). In cultures evolved in the presence of NTG or other chemical mutagen, there will be significantly more silent, background mutations. If satisfied with the best performing strain in its current state, the user can proceed to application with that strain. Otherwise the contributing mutations can be deconvoluted from the evolved strain by reintroducing the mutations to the parent strain by genome engineering techniques. See Lee, D.-H., Feist, A. M., Barrett, C. L. & Palsson, B. Ø. Cumulative Number of Cell Divisions as a Meaningful Timescale for Adaptive Laboratory Evolution of *Escherichia coli*. PLoS ONE 6, e26172 (2011).

These methods were used to generate *E. Coli* Nissle mutants that consume kynurenine and over-produce tryptophan as described elsewhere herein.

Example 12. Engineered Bacteria Engineered to Efficiently Import KYN

In the tumor microenvironment the amino acid tryptophan (TRP) and its degradation product kynurenine (KYN) play pivotal roles as immunomodulatory signals. Tumors often degrade TRP (which has proinflammatory properties) into KYN, which possesses anti-inflammatory characteristics, thereby promoting evasion from immune surveillance.

E. coli Nissle can be engineered to efficiently import KYN and convert it to TRP. While Nissle does not typically utilize KYN, by introducing the Kynureninase (KYNase) from *Pseudomonas fluorescens* (kynU) on a medium-copy plasmid under the control of the tetracycline promoter (Ptet) a new strain with this plasmid (Ptet-KYNase) is able to convert L-kynurenine into anthranilate.

E. coli naturally utilizes anthranilate in its TRP biosynthetic pathway. Briefly, the TrpE (in complex with TrpD) enzyme converts chorismate into anthranilate. TrpD, TrpC, TrpA and TrpB then catalyze a five-step reaction ending with the condensation of an indole with serine to form tryptophan. By replacing the TrpE enzyme via lambda-RED recombineering, the subsequent strain of Nissle (ΔtrpE::Cm) is an auxotroph unable to grow in minimal media without supplementation of TRP or anthranilate. By expressing kynureninase in ΔtrpE::Cm (KYNase-trpE), this auxotrophy can be alternatively rescued by providing KYN.

Leveraging the growth-limiting nature of KYN in KYNase-trpE, adaptive laboratory evolution was employed to evolve a strain capable of increasingly efficient utilization of KYN. First a lower limit of KYN concentration was established and mutants were evolved by passaging in lowering concentrations of KYN. While this can select for mutants capable of increasing KYN import, the bacterial cells still prefer to utilize free, exogenous TRP. In the tumor environment, dual-therapeutic functions can be provided by depletion of KYN and increasing local concentrations of TRP. Therefore, to evolve a strain which prefers KYN over TRP, a toxic analogue of TRP—5-fluoro-L-tryptophan (Tox-TRP)—can be incorporated into the ALE experiment. The resulting best performing strain is then whole genome sequenced in order to deconvolute the contributing mutations. Lambda-RED can be performed in order to reintroduce TrpE, to inactivate Trp regulation (trpR, tyrR, transcriptional attenuators) to up-regulate TrpABCDE expression and increase chorismate production. The resulting strain is now insensitive to external TRP, efficiently converts KYN into TRP, and also now overproduces TRP.

Kynureninase Protein Sequences

| Description | ID | Sequence |
|---|---|---|
| *Pseudomonas kynureninase* | P83788 | MTTRNDCLALDAQDSLAPLRQQFALPEGVIYLDGNS LGARPVAALARAQAVIAEEWGNGLIRSWNSAGWRD LSERLGNRLATLIGARDGEVVVTDTTSINLFKVLSAA LRVQATRSPERRVIVTETSNFPTDLYIAEGLADMLQQ GYTLRLVDSPEELPQAIDQDTAVVMLTHVNYKTGYM HDMQALTALSHECGALAIWDLAHSAGAVPVDLHQA GADYAIGCTYKYLNGGPGSQAFVWVSPQLCDLVPQP LSGWFGHSRQFAMEPRYEPSNGIARYLCGTQPITSLA MVECGLDVFAQTDMASLRRKSLALTDLFIELVEQRC AAHELTLVTPREHAKRGSHVSFEHPEGYAVIQALIDR GVIGDYREPRIMRFGFTPLYTTFTEVWDAVQILGEILD RKTWAQAQFQVRHSVT* |
| Human | Q16719 | MEPSSLELPADTVQRIAAELKCHPTDERVALHLDEED KLRHFRECFYIPKIQDLPPVDLSLVNKDENAIYFLGNS LGLQPKMVKTYLEEELDKWAKIAAYGHEVGKRPWI TGDESIVGLMKDIVGANEKEIALMNALTVNLHLLML SFFKPTPKRYKILLEAKAFPSDHYAIESQLQLHGLNIE ESMRMIKPREGEETLRIEDILEVIEKEGDSIAVILFSGV HFYTGQHFNIPAITKAGQAKGCYVGFDLAHAVGNVE LYLHDWGVDFACWCSYKYLNAGAGGIAGAFIHEKH AHTIKPALVGWFGHELSTRFKMDNKLQLIPGVCGFRI SNPPILLVCSLHASLEIFKQATMKALRKKSVLLTGYLE YLIKHNYGKDKAATKKPVVNIITPSHVEERGCQLTITF SVPNKDVFQELEKRGVVCDKRNPNGIRVAPVPLYNS FHDVYKFTNLLTSILDSAETKN* |
| *Shewanella* | Q8E973 | MLLNVKQDFCLAGPGYLLNHSVGRPLKSTEQALKQA FFAPWQESGREPWGQWLGVIDNFTAALASLFNGQPQ DFCPQVNLSSALTKIVMSLDRLTRDLTRNGGAVVLM SEIDFPSMGFALKKALPASCELRFIPKSLDVTDPNVW DAHICDDVDLVFVSHAYSNTGQQAPLAQIISLARERG CLSLVDVAQSAGILPLDLAKLQPDFMIGSSVKWLCSG PGAAYLWVNPAILPECQPQDVGWFSHENPFEFDIHDF RYHPTALRFWGGTPSIAPYAIAAHSIEYFANIGSQVM REHNLQLMEPVVQALDNELVSPQEVDKRSGTIILQFG ERQPQILAALAAANISVDTRSLGIRVSPHIYNDEADIA RLLGVIKANR* |

*designates the position of the stop codon

Selected Codon-Optimized Sequences for Kynureninase

| Kynureninase protein sequences | Kynureninase protein sequences |
|---|---|
| Ptet-kynU (Pseudomonas) | atctaatctagacatcattaattcctaattttttgttgacactctatcattgatagagttat<br>tttaccactccctatcagtgatagagaaaagtgaattatataaaagtgggaggtgccc<br>gaatgacgacccgaaatgattgcctagcgttggatgcacaggacagtctggctccgctg<br>cgccaacaatttgcgctgccggagggtgtgatatacctggatggcaattcgctgggcgca<br>cgtccggtagctgcgctggctcgcgcgcaggctgtgatcgcagaagaatggggcaacg<br>ggttgatccgttcatggaactctgcgggctggcgtgatctgtctgaacgcctgggtaatcg<br>cctggctaccctgattggtgcgcgcgatggggaagtagttgttactgataccacctcgatt<br>aatctgtttaaagtgctgtcagcggcgctgcgcgtgcaagctacccgtagcccggagcg<br>ccgtgttatcgtgactgagacctcgaatttcccgaccgacctgtatattgcggaagggttg<br>gcggatatgctgcaacaaggttacactctgcgtttggtggattcaccggaagagctgcca<br>caggctatagatcaggacaccgcggtggtgatgctgacgcacgtaaattataaaaccggt<br>tatatgcacgacatgcaggctctgaccgcgttgagccacgagtgtgggctctggcgatt<br>tgggatctggcgcactctgctggcgctgtgccggtggacctgcaccaagcgggcgcgg<br>actatgcgattggctgcacgtacaaatacctgaatggcggcccgggttcgcaagcgtttgt<br>ttgggtttcgccgcaactgtgcgacctggtaccgcagccgctgtctggttggttcggccat<br>agtcgccaattcgcgatggagccgcgctacgaaccttctaacggcattgctcgctatctgt<br>gcggcactcagcctattactagcttggctatggtggagtgcggcctggatgtgtttgcgca<br>gacggatatgcgcttcgctgcgccgtaaaagtctggcgctgactgatctgttcatcgagctg<br>gttgaacaacgctgcgctgcacacgaactgaccctggttactccacgtgaacacgcgaa<br>acgcggctctcacgtgtcttttgaacaccccgagggttacgctgttattcaagctctgattg<br>atcgtggcgtgatcggcgattaccgtgagccacgtattatgcgtttcggtttcactcctctgt<br>atactactttttacggaagtttgggatgcagtacaaatcctgggcgaaatcctggatcgtaag<br>acttgggcgcaggctcagtttcaggtgcgccactctgttacttaaaaataaaacgaaag<br>gctcagtcgaaagactgggcctttcgttttatctgttg |
| Ptet-kynU (Human) | atctaatctagacatcattaattcctaattttttgttgacactctatcattgatagagttat<br>tttaccactccctatcagtgatagagaaaagtgaatatcaagacacgaggaggtaag<br>attatggagccttcatctttagaactgccagcggacacggtgcagcgcatcgcggcgga<br>actgaagtgccatccgactgatgagcgtgtggcgctgcatctggacgaagaagataaac<br>tgcgccactttcgtgaatgatttatattcctaaaattcaagacttgccgccggtagatttgagt<br>ctcgttaacaaagatgaaaacgcgatctactttctgggcaactctctgggtctgcaaccaa<br>aaatggttaaaacgtacctggaggaagaactggatataatgggcaaaaatcgcggcttatg<br>gtcacgaagtgggcaagcgtccttggattactggcgacgagtctattgtgggtttgatgaa<br>agatattgtgggcgcgaatgaaaaggaaattgcactgatgaatgctctgaccgttaatctg<br>cacctgctgatgctgtctttttttaaaccgaccccgaaacgctacaaaatactgctggaagc<br>gaaagcgtttccgtcggatcactatgctatagaaagtcaactgcagttgcatggtctgaata<br>tcgaggaatctatgcgcatgattaaaccgcgtgagggtgaaagaaacgctgcgtattgaag<br>acattctggaagttattgaaaaagaaggtgattctatcgcagttatactgttttctggcgtgca<br>cttttatacaggtcagcacttcaatatcccggcaatcactaaagcggggcaggcaaaagg<br>ctgctatgttggttttgacctggcgcatgcagtggggaatgttgaactgtatctgcacgattg<br>gggcgttgatttcgcgtgttggtgtagctacaaatatctgaacgctggcgcgggtggcatt<br>gctggcgcttttattcacgaaaaaacacgcgcacaccattaaaccggctctggttggctggt<br>tcggtcatgagctgagtactcgctttaaaatggataacaaactgcaattgattccgggtgttt<br>gcggcttccgtatcagcaatccgccgattctgctggttttgcagcctgcacgctagtctgga<br>aatctttaagcaggcgactatgaaagcgctgcgcaaaaaatctgtgctgctgaccggctat<br>ctggagtatctgatcaaacacaattatggcaaagataaagctgcaactaaaaaaccggta<br>gtgaacattatcaccccctcacacgtggaggagcgcggttgtcagctgactattactttca<br>gtgtacctaataaagatgtgttccaggaactggaaaaacgcggcgttgtttgtgataaacg<br>taacccgaatggtattcgcgtggctcctgtgccgctgtacaattcattccacgatgtttataa<br>attcaccaacctgctgacttctattctcgacagtgctgagactaaaaattaaaaataaaac<br>gaaaggctcagtcgaaagactgggcctttcgttttatctgttg |
| ptet-kynU (Shewanella) | atctaatctagacatcattaattectaattttttgttgacactctatcattgatagagttat<br>tttaccactccctatcagtgatagagaaaagtgaatggttcaccaccacaaggaggg<br>attatgctgctgaatgtaaaacaggacttttgcctggcaggccccgggctacctgctgaatc<br>actcggttggccgtccgctgaaatcaactgagcaagcgctgaaacaagcatttttttgctcc<br>gtggcaagagagcggtcgtgaaccgtggggccagtggctgggtgttattgataatttcac<br>tgctgcgctggcatctctgtttaatggtcaaccgcaggattttttgtccgcaggttaacctgag<br>cagcgcgctgactaaaattgtgatgtcactggatcgtctgactcgcgatctgacccgcaat<br>ggcggtgctgttgtgctgatgtctgaaatcgatttcccatctatgggcttcgcgttgaaaaa<br>agcgctgccagcgagctgcgaactgcgtttttatcccgaaaagtctggacgtgactgatcc<br>gaacgtatgggatgcacacatctgtgatgatgtagacctggttttttgtgtctcacgcctatag<br>taatacgggccaacaggctccgctggcgcaaatcatctctctgcgcgtgaacgtggct<br>gcctgtcactggtggatgtagcgcaatcagcggggattttgccgctggatctggcgaaac<br>tgcaaccggacttcatgatcggcagttcggttaaatggctgtgctcgggccctggtgcgg<br>catatctgtgggttaatccggcgattctgccggaatgtcagccgcaggatgtgggctggtt<br>ttcacatgagaatccctttgaattcgacatccacgatttccgctaccaccccgactgcactgc<br>gcttttggggtggtacgccgtcgatcgcgccttatgcgatcgcggcgcactcgatcgaat<br>attttgccaatatcggctcgcaagtgatgcgtgaacacaacctgcaactgatggaaccggt<br>ggttcaggcgctggacaatgaactggtgagcccgcaggaagtggataaacgctcaggc<br>actattattctgcaattcggtgaacgtcaaccgcaaattctggcggctctggctgcggcga<br>acatttcggtggacactcgttctttggggattcgtgttagtccgcacatttataatgatgagg<br>cggacattgcgcgcctgctgggtgtgatcaaagcaaatcgctaaaaataaaacgaaagg<br>ctcagtcgaaagactgggcctttcgttttatctgttg |

The ptet-promoter is in bold, designed Ribosome binding site is underlined, codon-optimized protein coding sequence is in plain text, and the terminator is in italics.

Generation of E. Coli Mutants with increased ability to consume L-Kynurenine

Example 13. Results

Adaptive Laboratory Evolution was used to produce mutant bacterial strains that consume Kynurenine and produce tryptophan. First, a ΔtrpE strain was constructed that expresses kynureninase and is capable of converting L-kynurenine to anthranilate to rescue the auxotrophic tryptophan background (KYNase). E. coli Nissle can be engineered to efficiently import KYN and convert it to TRP. While Nissle does not typically utilize KYN, by introducing the Kynureninase (KYNase) from *Pseudomonas fluorescens* (kynU) on a medium-copy plasmid under the control of the tetracycline promoter (Ptet) a new strain with this plasmid (Ptet-KYNase) is able to convert L-kynurenine into anthranilate.

E. coli naturally utilizes anthranilate in its TRP biosynthetic pathway. Briefly, the TrpE (in complex with TrpD) enzyme converts chorismate into anthranilate. TrpD, TrpC, TrpA and TrpB then catalyze a five-step reaction ending with the condensation of an indole with serine to form tryptophan. By replacing the TrpE enzyme via lambda-RED recombineering, the subsequent strain of Nissle (ΔtrpE::Cm) is an auxotroph unable to grow in minimal media without supplementation of TRP or anthranilate. By expressing kynureninase in ΔtrpE::Cm (KYNase-trpE), this auxotrophy can be alternatively rescued by providing KYN.

First a lower limit of KYN concentration was established and mutants were evolved by passaging in lowering concentrations of KYN. While this can select for mutants capable of increasing KYN import, the bacterial cells still prefer to utilize free, exogenous TRP. In the tumor environment, dual-therapeutic functions can be provided by depletion of KYN and increasing local concentrations of TRP. Therefore, to evolve a strain which prefers KYN over TRP, a toxic analogue of TRP—5-fluoro-L-tryptophan (ToxTRP)—can be incorporated into the ALE experiment. The resulting best performing strain is then whole genome sequenced in order to deconvolute the contributing mutations. Lambda-RED can be performed in order to reintroduce TrpE, to inactivate Trp regulation (trpR, tyrR, transcriptional attenuators) to up-regulate TrpABCDE expression and increase chorismate production. The resulting strain is now insensitive to external TRP, efficiently converts KYN into TRP, and also now overproduces TRP.

To establish the minimum concentration of L-kynurenine and maximum concentration of 5-fluoro-L-tryptophan (ToxTrp) capable of sustaining growth of the KYNase strain, using a checkerboard assay, the following protocol was used. Using a 96-well plate with M9 minimal media with glucose, KYNU is supplemented decreasing across columns in 2-fold dilutions from 2000 ug/mL down to ~1 ug/mL. In the rows, ToxTrp concentration decreases by 2-fold from 200 ug/mL down to ~1.5 ug/mL. In one plate, Anhydrous Tetracycline (aTc) was added to a final concentration of 100 ng/uL to induce production of the KYNase. From an overnight culture cells were diluted to an OD600=0.5 in 12 mL of TB (plus appropriate antibiotics and inducers, where applicable) and grown for 4 hours. 100 uL of cells were spun down and resuspended to an OD600=1.0. These were diluted 2000-fold and 25 uL was added to each well to bring the final volumes in each well to 100 uL. Cells were grown for roughly 20 hours with static incubation at 37 C then growth was assessed by OD600, making sure readings fell within linear range (0.05-1.0).

Once identified, the highest concentrations of ToxTrp and lowest concentration of kynurenine capable of supporting growth becomes the starting point for ALE. The ALE parental strain was chosen by culturing the KYNase strain on M9 minimal media supplemented with glucose and L-kynurenine (referred to as M9+KYNU from here on). A single colony was selected, resuspended in 20 uL of sterile phosphate-buffered saline solution. This colony was then used to inoculate three cultures of M9+KYNU, grown into late-logarithmic phase and optical density determined at 600 nm. These cultures were then diluted to $10^3$ in 4 rows of a 96-well deep-well plate with 1 mL of M9+KYNU. Each one of the four rows has a different ToxTrp (increasing 2-fold), while each column has decreasing concentrations of KYNU (by 2-fold). Each morning and evening this plate is diluted back to $10^3$ using the well in which the culture has grown to just below saturation so that the culture is always in logarithmic growth. This process is repeated until a change in growth rate is no longer detected. Once no growth rate increases are detected (usually around $10^{11}$ Cumulative Cell Divisions) the culture is plated onto M9+KYNU. Phillips, R. S. Structure and mechanism of kynureninase. *Archives of Biochemistry and Biophysics* 544, 69-74 (2014). Individual colonies are selected and screened in M9+KYNU+ToxTrp media to confirm increased growth rate phenotype. Once mutants with significantly increased growth rate on M9+KYNU are isolated, genomic DNA can be isolated and sent for whole genome sequencing to reveal the mutations responsible for phenotype.

All culturing is done shaking at 350 RPM at 37° C.

| STRAIN | Rich Media | Min Media | Min + Anthranilate | Min + KYNU + aTc |
|---|---|---|---|---|
| SYN094 | + | + | + | + |
| trpE | + | − | + | − |
| trpE pseudoKYNase | + | − | + | + |
| trpE hKYNase | + | − | + | − |

In a preliminary assay, wildtype Nissle (SYN094), Nissle with a deletion of trpE, and trpE mutants expressing either the human kynureninase (hKYNase) or the *Pseudomonas fluorescens* kynureninase (pseudoKYNase) from a Ptet promoter on a medium-copy plasmid were grown in either rich media, minimal media (min media), minimal media with 5 mM anthranilate (Min+anthranilate) or minimal media with 10 mM kynurenine and 100 ng/uL aTc (Min+KYNU+aTc). These were grown in 1 mL of media in a deep well plate with shaking at 37° C. A positive for growth (+) in the above table indicates a change in optical density of >5-fold from inoculation.

The results show that in a mutant trpE (which is typically used in the tryptophan biosynthetic pathway to convert chorismate into anthranilate) background, Nissle is unable to grow in minimal media without supplementation with anthranilate (or tryptophan). When minimal media was supplemented with KYNU, the trpE mutant was also unable to grow. However, when the pseudoKYNase was expressed in the trpE tryptophan-auxotroph the cells were able to grow in Min+KYNU. This indicates that Nissle is able to import L-kynurenine from the media and convert it into anthranilate using the pseudoKYNase. The hKYNase homolog was unable to support growth on M9+KYNU, most likely due to differences in substrate specificity as it has been documented that the human kynureninase prefers 3-hydroxykynurenine as a substrate. Lee, D.-H., Feist, A. M., Barrett, C. L. & Palsson, B. Ø. Cumulative Number of Cell Divisions as a Meaningful Timescale for Adaptive Laboratory Evolution of Escherichia coli. PLoS ONE 6, e26172 (2011).

Moving forward with the knowledge that Nissle is able to grow on KYNU supplemented minimal media in a trpE auxotroph by importing and converting kynurenine, the next step was to establish the minimal concentrations of kynurenine capable of supporting growth. Additionally, in our selection experiment if 5-fluoro-L-tryptophan (ToxTrp) was employed the concentrations of both KYNU and ToxTrp capable of still sustaining growth. A growth assay was performed in 96-well plates using SYN094, trpE and trpE pseudoKYNase with and without induction of pseudoKYNase expression using 100 ng/uL aTc. These strains were inoculated at very dilute concentrations into M9 minimal media with varying concentrations of KYNU across columns (2-fold dilutions starting at 2000 ug/mL) and varying concentrations of ToxTrp across rows (2-fold dilutions starting at 200 ug/mL). On a separate plate, the strains were grown in M9+KYNU (at the same concentrations) in the absence of ToxTrp.

Figure 36:
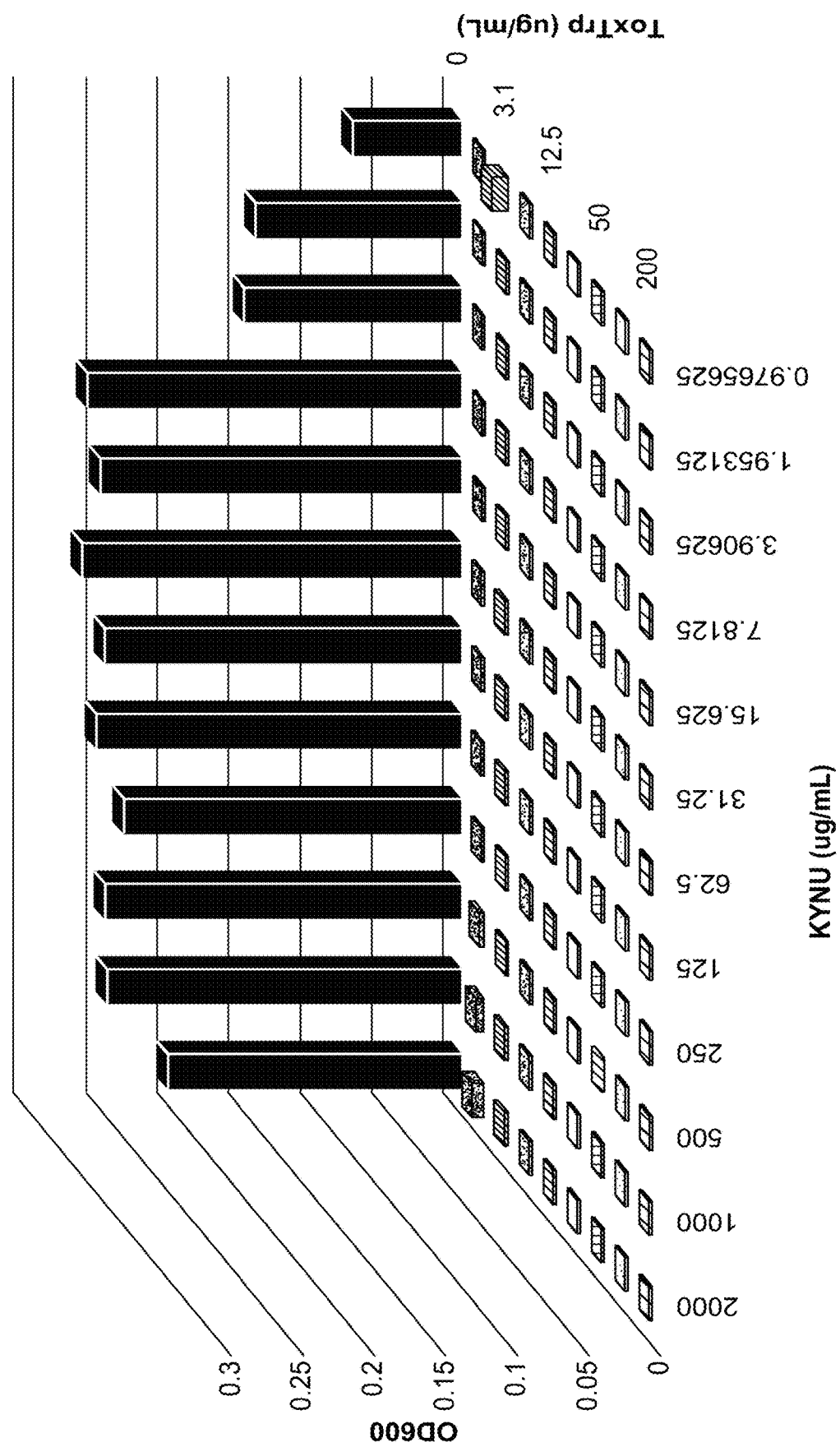
FIG. 36. shows the results of an adaptive laboratory evolution to select a bacterial mutant with enhanced kynurenine import into the cell. The results of the initial checkerboard assay are displayed as a function of optical density at 600 nm. The X-axis shows decreasing KYNU concentration from left-to-right, while the Z-axis shows decreasing ToxTrp concentration from front-to-back with the very back row representing media with no ToxTrp.
Figure 37:
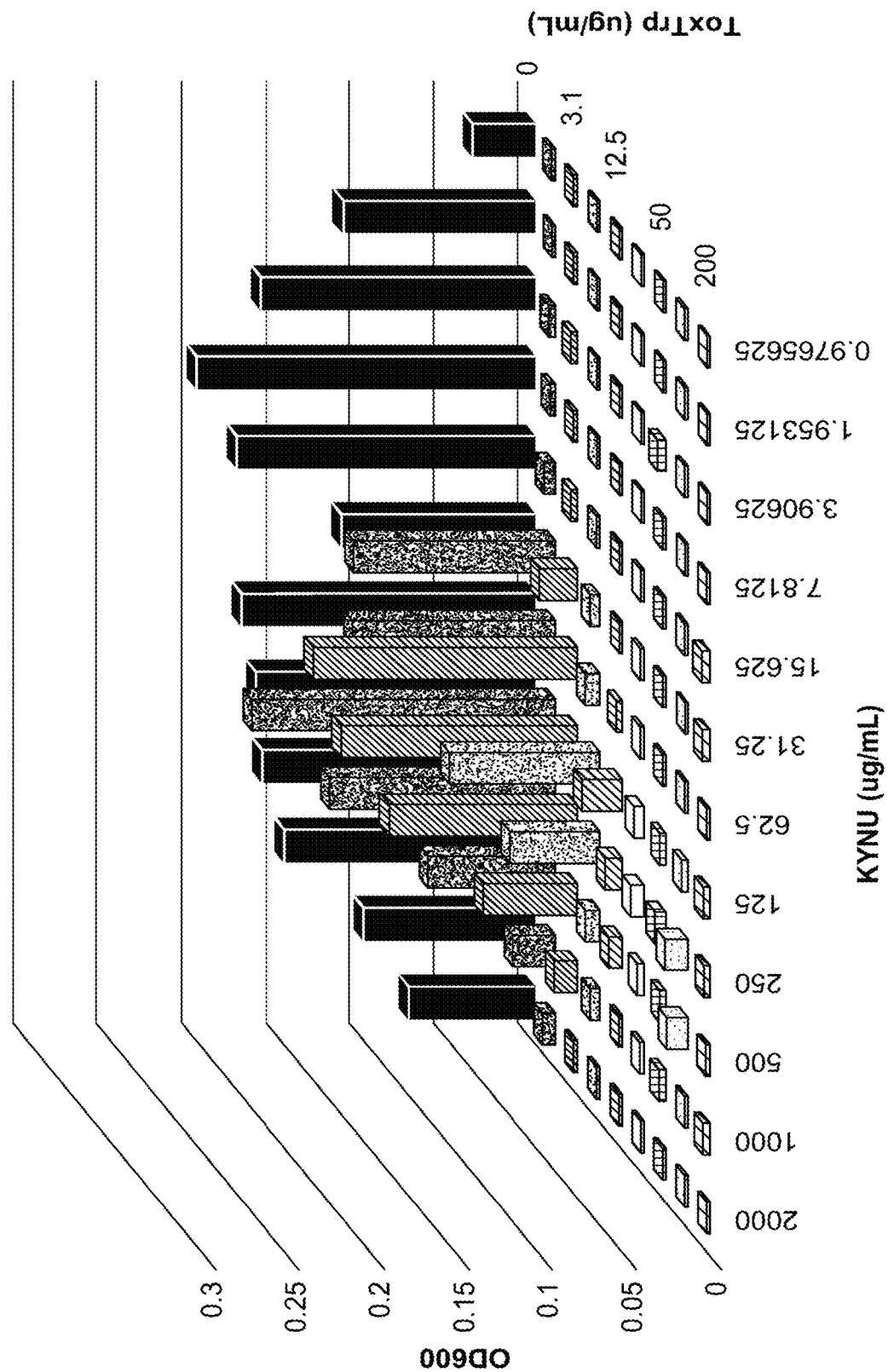
FIG. 37. shows the results of an adaptive laboratory evolution to select a bacterial mutant with enhanced kynurenine import into the cell.
Figure 38:
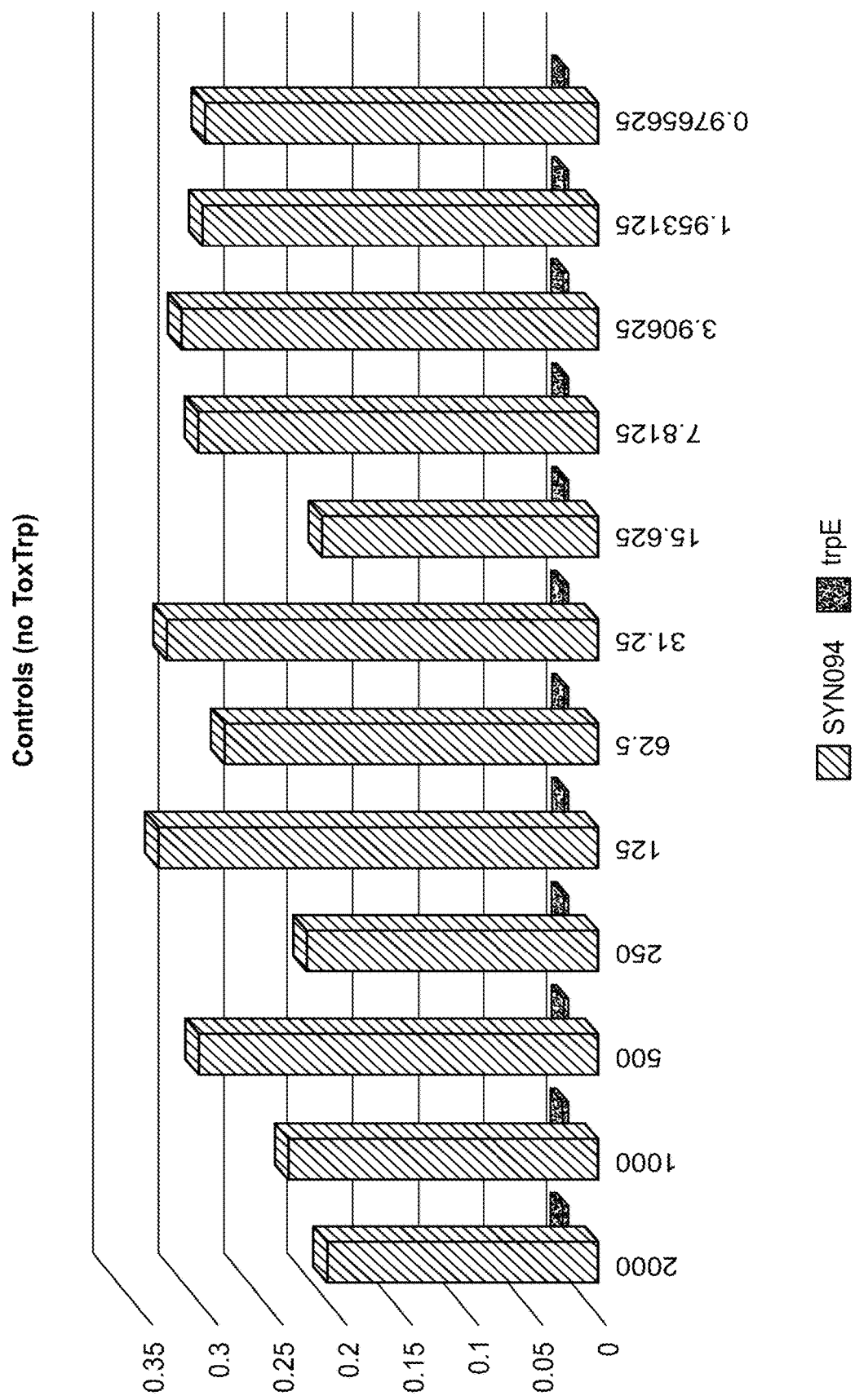
FIG. 38. shows the results of an adaptive laboratory evolution to select a bacterial mutant with enhanced kynurenine import into the cell. The control strains SYN094 and trpE are shown in M9+KYNU without any ToxTrp, as there was no growth detected from either strain at any concentration of ToxTrp. The results of the assay show that expression of the pseudoKYNase provides protection against toxicity of ToxTrp and shows that growth is permitted between 250-62.5 ug/mL of KYNU and 6.3-1.55 ug/mL of ToxTrp.
Figure 39:
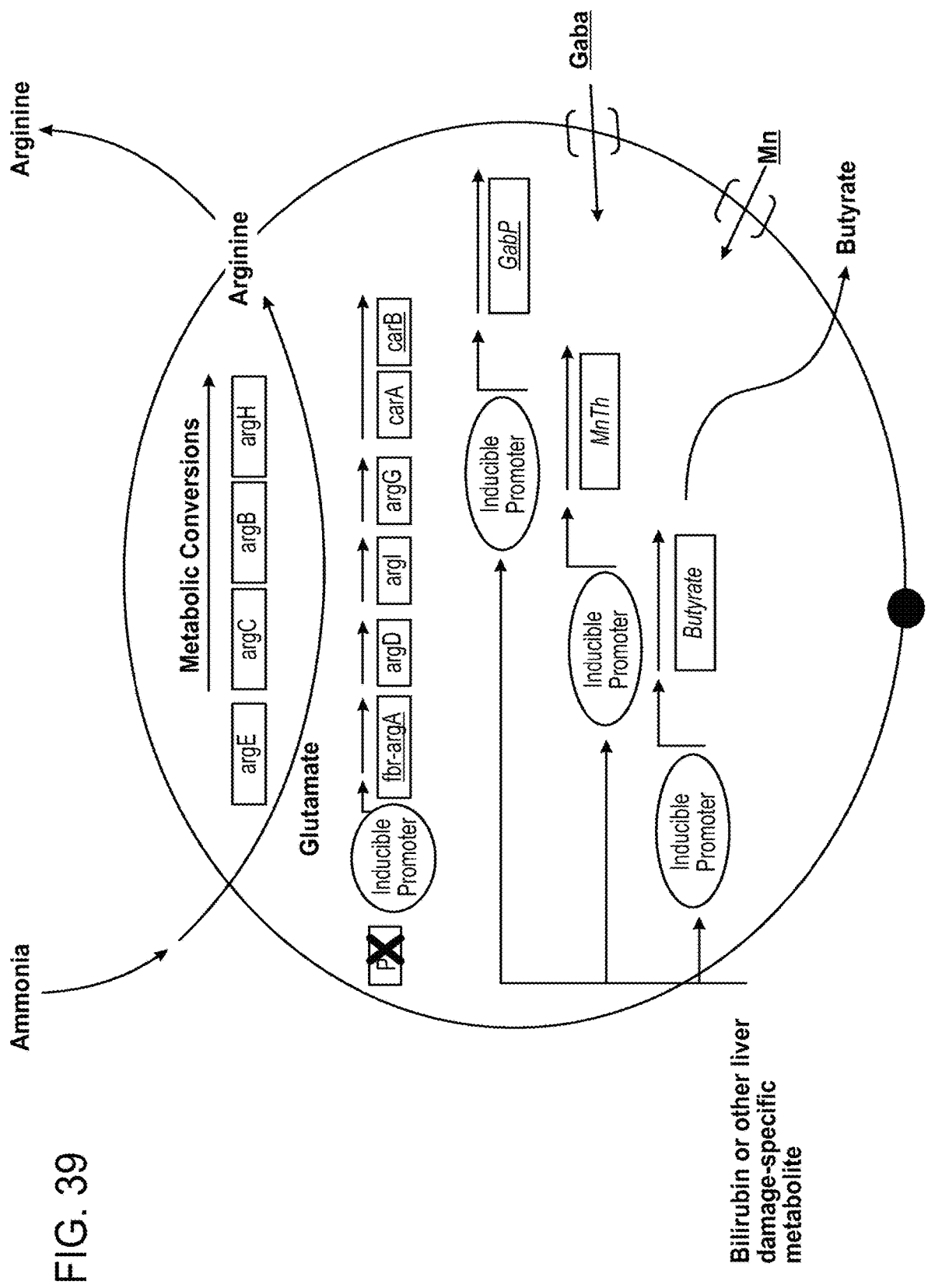
FIG. 39. is a schematic depicting an exemplary circuit for treating hepatic encephalopathy.
Figure 40:
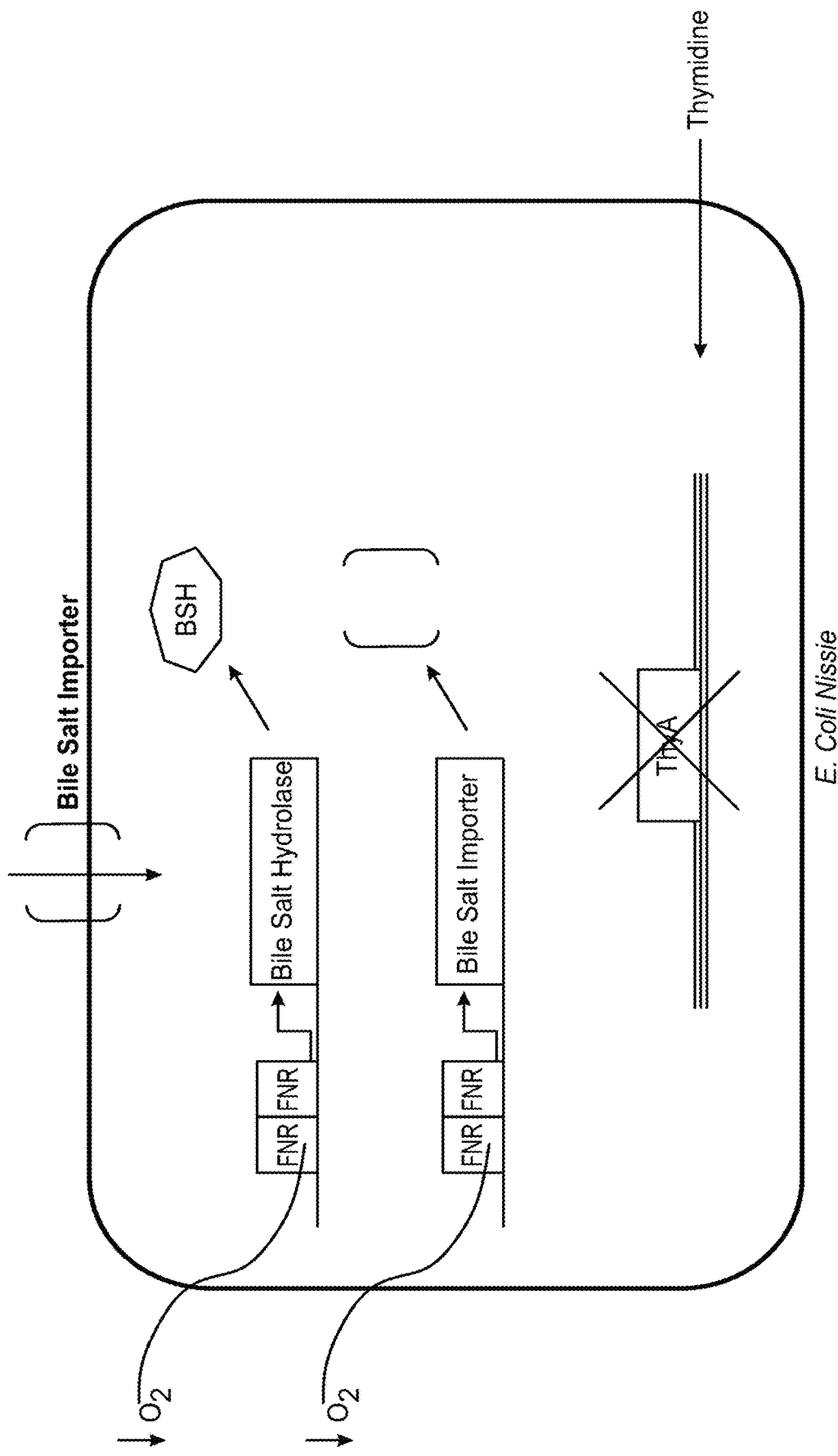
FIG. 40. is a schematic depicting an exemplary circuit for depleting bile salts.

The results of the initial checkerboard assay are displayed in FIGS. 36-38 as a function of optical density at 600 nm (normalized to a media blank). In FIGS. 36 and 37, the X-axis shows decreasing KYNU concentration from left-to-right, while the Z-axis shows decreasing ToxTrp concentration from front-to-back with the very back row representing media with no ToxTrp. In FIG. 38. the control strains SYN094 and trpE are shown in M9+KYNU without any ToxTrp, as there was no growth detected from either strain at any concentration of ToxTrp. The results of the assay show that expression of the pseudoKYNase provides protection against toxicity of ToxTrp. More importantly, growth is permitted between 250-62.5 ug/mL of KYNU and 6.3-1.55 ug/mL of ToxTrp.

Together these experiments establish that expression of the Pseudomonas fluorescens kynureninase is sufficient to rescue a trpE auxotrophy in the presence of kynurenine. In addition, the pseudoKYNase is also capable of providing increased resistance to the toxic tryptophan, 5-fluoro-L-tryptophan Using the information attained here it is possible to proceed to an adaptive laboratory evolution experiment to select for mutants with highly efficient and selective conversion of kynurenine to tryptophan.

Sequence Listing

| SEQ ID NO: | Gene or Operon | Sequence |
|---|---|---|
| 6 | kivD (Lactococcus lactis IFPL730) | ATGTATACAGTAGGAGATTACCTATTAGACCGATTACACGAGTTAGGAATTGAAGAAATTTTT GGAGTCCCTGGAGACTATAACTTACAATTTTTAGATCAAATTATTTCCCACAAGGATATGAAA TGGGTCGGAAATGCTAATGAATTAAATGCTTCATATATGGCTGATGGCTATGCTCGTACTAAA AAAGCTGCCGCATTTCTTACAACCTTTGGAGTAGGTGAATTGAGTGCAGTTAATGGATTAGCA GGAAGTTACGCCGAAAATTTACCAGTAGTAGAAATAGTGGGATCACCTACATCAAAAGTTCAA AATGAAGGAAAATTTGTTCATCATACGCTGGCTGACGGTGATTTTAAACACTTTATGAAAATG CACGAACCTGTTACAGCAGCTCGAACTTTACTGACAGCAGAAAATGCAACCGTTGAAATTGAC CGAGTACTTTCTGCACTATTAAAAGAAAGAAAACCTGTCTATATCAACTTACCAGTTGATGTT GCTGCTGCAAAAGCAGAGAAACCCTCACTCCCTTTGAAAAAGGAAAACTCAACTTCAAATACA AGTGACCAAGAAATTTTGAACAAAATTCAAGAAAGCTTGAAAAATGCCAAAAAACCAATCGTG ATTACAGGACATGAAATAATTAGTTTTGGCTTAGAAAAAACAGTCACTCAATTTATTTCAAAG ACAAAACTACCTATTACGACATTAAACTTTGGTAAAAGTTCAGTTGATGAAGCCCTCCCTTCA TTTTTAGGAATCTATAATGGTACACTCTCAGAGCCTAATCTTAAAGAATTCGTGGAATCAGCC GACTTCATCTTGATGCTTGGAGTTAAACTCACAGACTCTTCAACAGGAGCCTTCACTCATCAT TTAAATGAAAATAAAATGATTTCACTGAATATAGATGAAGGAAAAATATTTAACGAAAGAATC CAAAATTTTGATTTTGAATCCCTCATCTCCTCTCTCTTAGACCTAAGCGAAATAGAATACAAA GGAAAATATATCGATAAAAAGCAAGAAGACTTTGTTCCATCAAATGCGCTTTTATCACAAGAC CGCCTATGGCAAGCAGTTGAAAACCTAACTCAAAGCAATGAAACAATCGTTGCTGAACAAGGG ACATCATTCTTTGGCGCTTCATCAATTTTCTTAAAATCAAAGAGTCATTTTATTGGTCAACCC TTATGGGGATCAATTGGATATACATTCCCAGCAGCATTAGGAAGCCAAATTGCAGATAAAGAA AGCAGACACCTTTTATTTATTGGTGATGGTTCACTTCAACTTACAGTGCAAGAATTAGGATTA GCAATCAGAGAAAAAATTAATCCAATTTGCTTTATTATCAATAATGATGGTTATACAGTCGAA AGAGAAATTCATGGACCAAATCAAAGCTACAATGATATTCCAATGTGGAATTACTCAAAATTA CCAGAATCGTTTGGAGCAACAGAAGATCGAGTAGTCTCAAAAATCGTTAGAACTGAAAATGAA TTTGTGTCTGTCATGAAAGAAGCTCAAGCAGATCCAAATAGAATGTACTGGATTGAGTTAATT TTGGCAAAAGAAGGTGCACCAAAAGTACTGAAAAAAATGGGCAAACTATTTGCTGAACAAAAT AAATCATAA |
| 7 | Tet-bkd construct sequence (Gene coding regions are shown in uppercase) | gtaaaacgacggccagtgaattcgTTAAGACCCACTTTCACATTTAAGTTGTTTTTCTAATCC GCATATGATCAATTCAAGGCCGAATAAGAAGGCTGGCTCTGCACCTTGGTGATCAAATAATTC GATAGCTTGTCGTAATAATGGCGGCATACTATCAGTAGTAGGTGTTTCCCTTTCTTCTTTAGC GACTTGATGCTCTTGATCTTCCAATACGCAACCTAAAGTAAAATGCCCCACAGCGCTGAGTGC ATATAATGCATTCTCTAGTGAAAAACCTTGTTGGCATAAAAAGGCTAATTGATTTTCGAGAGT TTCATACTGTTTTTCTGTAGGCCGTGTACCTAAATGTACTTTTGCTCCATCGCGATGACTTAG TAAAGCACATCTAAAACTTTTAGCGTTATTACGTAAAAAATCTTGCCAGCTTTCCCCTTCTAA AGGGCAAAAGTGAGTATGGTGCCTATCTAACATCTCAATGGCTAAGGCGTCGAGCAAAGCCCG CTTATTTTTTACATGCCAATACAATGTAGGCTGCTCTACACCTAGCTTCTGGGCGAGTTTACG GGTTGTTAAACCTTCGATTCCGACCTCATTAAGCAGCTCTAATGCGCTGTTAATCACTTTACT TTTATCTAATCTAGACATcattaattcctaattttttgttgacactctatcattgatagagtta ttttaccactccctatcagtgatagagaaaagtgaactctagaaataattttgtttaacttta agaaggagatatacatATGAGTGATTACGAGCCGTTGCGTCTGCATGTCCCGGAGCCCACCGG GCGTCCTGGCTGCAAGACCGACTTTTCCTATCTGCACCTGTCCCCGCCGGCGAGGTACGCAA GCCGCCGGTGGATGTCGAGCCCGCCGAAACCAGCGACCTGGCCTACAGCCTGGTACGTGTGCT CGACGACGACGGCCACGCCGTCGGTCCCTGGAATCCGCAGCTCAGCAACGAACAACTGCTGCG |

| Sequence Listing | | |
|---|---|---|
| SEQ ID NO: | Gene or Operon | Sequence |
| | | CGGCATGCGGGCGATGCTCAAGACCCGCCTGTTCGACGCGCGCATGCTCACCGCGCAACGGCA
GAAAAAGCTTTCCTTCTATATGCAATGCCTCGGCGAGGAAGCCATCGCCACCGCCCACACCCT
GGCCCTGCGCGACGGCGACATGTGCTTTCCGACCTATCGCCAGCAAGGCATCCTGATCACCCG
CGAATACCCGCTGGTGGACATGATCTGCCAGCTTCTCTCCAACGAGGCCGACCCGCTCAAGGG
CCGCCAGCTGCCGATCATGTACTCGAGCAAGGAGGCAGGTTTCTTCTCCATCTCCGGCAACCT
CGCCACCCAGTTCATCCAGGCGGTCGGCTGGGGCATGGCCTCGGCGATCAAGGGCGACACGCG
CATCGCCTCGGCCTGGATCGGCGACGGCGCCACCGCCGAGTCGGACTTCCACACCGCCCTCAC
CTTCGCCCATGTCTACCGCGCGCGGTAATCCTCAACGTGGTCAACAACCAGTGGGCGATCTC
CACCTTCCAGGCCATCGCCGGCGGCGAAGGCACCACCTTCGCCAACCGTGGCGTGGGCTGCGG
GATCGCCTCGCTGCGGGTCGACGGCAATGACTTCCTGGCGGTCTACGCCGCCTCCGAGTGGGC
CGCCGAGCGCGCCCGGCGCAACCTCGGGCCGAGCCTGATCGAATGGGTCACCTACCGCGCCGG
CCCGCACTCGACTTCGGACGACCCGTCCAAGTACCGCCCCGCCGACGACTGGACCAACTTCCC
GCTGGGCGACCCGATCGCCCGCCTGAAGCGGCACATGATCGGCCTCGGCATCTGGTCGGAGGA
ACAGCACGAAGCCACCCACAAGGCCCTCGAAGCCGAAGTACTGGCCGCGCAGAAACAGGCGGA
GAGCCATGGCACCCTGATCGACGGCCGGGTGCCGAGCGCCGCCAGCATGTTCGAGGACGTCTA
TGCAGAACTGCCGGAGCATCTGCGCGCAACGCCAGGAGCTCGGGGTATGAATGCCATGAAC
CCGCAACACGAGAACGCCCAGACGGTCACCAGCATGACCATGATCCAGGCGCTGCGCTCGGCG
ATGGACATCATGCTCGAGCGCGACGACGACGTGGTGGTATTCGGCCAGGACGTCGGCTACTTC
GGCGGCGTGTTCCGCTGCACCGAAGGCCTGCAGAAGAAATACGGCACCTCGCGGGTGTTCGAT
GCGCCGATCTCCGAGAGCGGCCATCATCGGCGCCGCGGTCGGCATGGGTGCCTACGGCCTGCGC
CCGGTGGTGGAGATCCAGTTCGCCGACTACGTCTACCCGGCCTCCGACCAGTTGATCTCCGAG
GCGGCGCGCCTGCGCTATCGCTCGGCCGGCGACTTCATCGTGCCGATGACCGTACGCATGCCC
TGTGGCGGCGGCATCTACGGCGGGCAAACGCACAGCCAGAGCCCGGAGGCGATGTTCACCCAG
GTCTGCGGCCTGCGCACGGTGATGCCGTCCAACCCCTACGACGCCAAGGGCCTGCTGATCGCC
TGCATCGAGAACGACGACCCGGTGATCTTCCTCGAGCCCAAGCGCCTCTACAACGGCCCGTTC
GATGGCCACCACGACCGCCCGGTGACGCCCTGGTCCAAGCATCCGGCCAGCCAGGTGCCGGAC
GGCTACTACAAGGTGCCGCTGGACAAGGCGGCGATCGTCCGCCCCGGCGCGGCGCTGACCGTG
CTGACCTACGGCACCATGGTCTACGTGGCCCAGGCCGCGGCCGACGAAACCGGCCTGGACGCC
GAGATCATCGACCTGCGCAGCCTCTGGCCGCTGGACCTGGAAACCATCGTCGCCTCGGTCGAAG
AAGACCGGCCGCTGCGTCATCGCCCACGAGGCGACCCGCACCTGTGGGTTCGGCGCCGAGCTG
ATGTCGCTGGTGCAGGAGCACTGCTTCCACCACCTGGAGGCGCCGATCGAGCGCGTCACCGGT
TGGGACACCCCCTACCCGCATGCCCAGGAGTGGGCGTATTTCCCCGGCCCCGCGCGCGTCGGC
GCGGCATTCAAGCGTGTGATGGAGGTCTGAATGGGTACCCATGTGATCAAGATGCCGGACATC
GGGGAAGGCATCGCCGAGGTCGAACTGGTGGAGTGGCATGTCCAGGTCGGCGACTCGGTCAAT
GAAGACCAGGTCCTCGCCGAGGTGATGACCGACAAGGCCACGGTGGAGATTCCCTCGCCGGTG
GCCGGACGCATCCTCGCCCTCGGCGGCCAGCCGGGCCAGGTGATGGCGGTGGGCGGCGAACTG
ATCCGCCTGGAGGTGGAAGGCGCCGGCAACCTCGCCGAGAGTCCGGCCGCGGCGACGCCGGCC
GCGCCCGTCGCCGCCACCCCGGAGAAACCGAAGGAAGCCCCGGTCGCGGCGCCGAAAGCCGCC
GCCGAAGCGCCGCGCGCCTTGCGCGACAGCGAGGCGCCACGGCAGCGGCGCCAGCCCGGCGAA
CGCCCGCTGGCCTCCCCCGCGGTGCGCCAGCGCGCCCGCGACCTGGGCATCGAGTTGCAGTTC
GTGCAGGGCAGCGGTCCCGCCGGACGCGTCCTCACGAGGACGCTCGATGCCTACCTGACCCAG
GATGGCAGCGTCGCGCGCAGCGGCGGCGCCGCGCAGGGGTATGCCGAGCGACACGACGAACAG
GCGGTGCCGGTGATCGGCCTGCGTCGCAAGATCGCCAGAAGATGCAGGACGCCAAGCGACGC
ATCCCGCATTTCAGCTATGTCGAGGAAATCGACGTCACCGATCTGGAAGCCCTGCGCGCCCAT
CTCAACCAGAAATGGGGTGGCCAGCGCGGCAAGCTGACCCTGCTGCCGTTCCTGGTCCGCGCC
ATGGTCGTGGCGCTGCGCGACTTCCCGCAGTTGAACGCGCGCTACGACGACGAGGCCGAGGTG
GTCACCCGCTACGGCGCGGTGCACGTCGGCATCGCCACCCAGAGCGACAACGGCCTGATGGTG
CCGGTGCTGCGCCACGCCGAATCGCGCGACCTCTGGGGCAACGCCAGCGAAGTGGCGCGCCTG
GCCGAAGCCGCACGCAGCGGCAAGGCGCAACGCCAGGAGCTGTCCGGCTCGACCATCACCCTG
AGCAGCCTCGGCGTGCTCGGCGGGATCGTCAGCACACCGGTGATCAACCATCCGGAGGTTGGCC
ATCGTCGGCGTCAACCGCATCGTCGAGCGACCGATGGTGGTCGGCGGCAACATCGTCGTGCGC
AAGATGATGAACCTCTCCTCCTCCTTCGACCACCGGGTGGTCGACGGGATGGACGCGGCGGCC
TTCATCCAGGCCGTGCGGGCGCTGCTCGAACTAAGCGATG
AGCCAGATCCTGAAGACTTCCCTGCTGATCGTCGGCGGCGGTCCCGGCGGCTACGCTCGCGGCG
ATCCGTGCCGGGCAACTGGGCATTCCCACCGTACTGGTGGAGGGCGCCGCCCTCGGCGGCACC
TGTCTGAACGTCGGCTGCATCCCGTCGAAGGCGCTGATCCACGCCGCCGAGGAATACCTCAAG
GCCCGCCACTATGCCAGCCGGTCGGCGCTGGGCATCCAGGTACAGGCGCCGAGCATCGACATC
GCCCGCACCGTGAATGGAAGGACGCCATCGTCGACCGCCTCACCAGCGGCGTCGCCGCGCTG
CTGAAGAAACACGGGGTCGATGTCGTCCAGGGCTGGGCGAGGATCCTCGACGGCAAAAGCGTG
GCGGTCGAACTCGCCGGCGGCGGCAGCCAGCGCATCGAGTGCGAGCATCTGCTGCTGGCCGCC
GGCTCGCAGAGCGTCGAGCTACCGATCCTGCCGCTGGGCGGCAAGGTGATCTCCTCCACCGAG
GCGCTGGCGCCCGGCAGCCTGCCCAAGCGCCTGGTGGTGGTCGGCGGCGGCTACATCGGCCTG
GAGCTGGGTACCGCCTACCGCAAGCTCGGCGTCGAGGTGGCGGTGGTGGAAGCGCAACCACGC
ATCCTGCCGGGCTACGACGAAGAACTGACCAAGCCGGTGGCCCAGGCCTTGCGCAGGCTGGGC
GTCGAGCTGTACCTCGGGCACAGCCTGCTGGGCCCGAGCGAGAACGGCGTGCGGGTCCGCGAC
GGCGCCGGCGAGGAGCGCGAGATCGCCGCCGACCAGGTACTGGTGGCGGTCGGCCGCAAGCCG
CGCAGCGAAGGCTGGAACCTGGAAAGCCTGGGCCTGGACATGAACCGGCCGGGCGGTGAAGGTC
GACGACCAGTGCCGCACCTCGATGCGCAATGTCTGGGCCATAGGCGATCTCGCCGGCGAGCCG
ATGCTCGCGCACCGGGCCATGGCCCAGGGCGAGATGGTCGCCGAGCTGATCGCCGGCAAGCGT
CGCCAGTTCGCCCCGGTGCGCGATCCCCGCGGTGTGCTTCACCGATCCGGAAGTGGTGGTCGCC
GGGTTGTCCCCGGAGCAGGCGAAGGATGCCGGCCTGGACTGCCTGGTGGCGAGCTTCCCGTTC
GCCGCCAACGGTCGCGCCATGACCCTGGAGGCCAACGAAGGCTTCGTCCGCGTGGTGGCGCGT
CGCGACAACCACCTGGTCGTCGGCTGGCAGGCGGTGGGCAAGGCGGTTTCGGAACTGTCCACG |

Sequence Listing

| SEQ ID NO: | Gene or Operon | Sequence |
|---|---|---|
| | | GCCTTCGCCCAGTCGCTGGAGATGGGCGCCCGCCTGGAAGACATCGCCGGCACCATCCACGCC<br>CATCCGACCCTCGGCGAAGCGGTCCAGGAAGCCGCCCTGCGCGCGCTGGGACACGCCCTGCAC<br>ATCTGA |
| 8 | Tet-ldh-bkd construct (gene coding regions are shown in uppercase) | gtaaaacgacggccagtgaattcgTTAAGACCCACTTTCACATTTAAGTTGTTTTTCTAATCC<br>GCATATGATCAATTCAAGGCCGAATAAGAAGGCTGGCTCTGCACCTTGGTGATCAAATAATTC<br>GATAGCTTGTCGTAATAATGGCGGCATACTATCAGTAGTAGGTGTTTCCCTTTCTTCTTTAGC<br>GACTTGATGCTCTTGATCTTCCAATACGCAACCTAAAGTAAAATGCCCCACAGCGCTGAGTGC<br>ATATAATGCATTCTCTAGTGAAAAACCTTGTTGGCATAAAAAGGCTAATTGATTTTCGAGAGT<br>TTCATACTGTTTTTCTGTAGGCCGTGTACCTAAATGTACTTTTGCTCCATCGCGATGACTTAG<br>TAAAGCACATCTAAAACTTTTAGCGTTATTACGTAAAAAATCTTGCCAGCTTTCCCCTTCTAA<br>AGGGCAAAAGTGAGTATGGTGCCTATCTAACATCTCAATGGCTAAGGCGTCGAGCAAAGCCCG<br>CTTATTTTTTACATGCCAATACAATGTAGGCTGCTCTACACCTAGCTTCTGGGCGAGTTTACG<br>GGTTGTTAAACCTTCGATTCCGACCTCATTAAGCAGCTCTAATGCGCTGTTAATCACTTTACT<br>TTTATCTAATCTAGACATcattaattcctaattttgttgacactctatcattgatagagtta<br>ttttaccactccctatcagtgatagagaaaagtgaactctagaaataatttttgtttaactta<br>agaaggagatatacatATGTTCGACATGATGGACGCGGCCCGGCTCGAGGGTCTgCACCTCGC<br>CCAAGGACCCGGCCACGGGACTCAAGGCCATTATCGCCATCCACAGCACGCGACTCGGCCCGGC<br>GCTGGGTGGTTGTCGCTACCTGCCTTACCCCAACGACGAAGCCGCCATCGGCGACGCCATCCG<br>CCTGGCCCAGGGCATGAGCTACAAGGCGGCCCTGGCCGGGCTGGAGACAGGGCGGCGGCAAGGC<br>GGTGATCATCCGCCCGCCGCACCTGGACAATCGCGGCGCGCTGTTCGAGGCCTTCGGGCGCTT<br>CATCGAAAGCCTCGGCGGACGCTACATCACTGCGGTGGACAGCGGTACCTCCAGCGCCGACAT<br>GGACTGCATCGCCCAGCAGACCCGCCACGTCACCAGCACCACCCAGGCCGGCGACCCCTCGCC<br>GCATACCGCCCTCGGCGTGTTCGCCGGGATTCGCGCCAGCGCCCAGGCGCGCCTCGGCAGCGA<br>CGACCTGGAAGGCCTGCGGGTCGCGGTGCAGGGGCTCGGCCACGTCGGCTACGCATTGGCCGA<br>GCAACTGCGGCGGTCGGCGCCGAGCTGCTGGTCTGCGACCTCGATCCCGGCCGGGTGCAACT<br>GGCCGTCGAGCAGCTCGGTGCCCATCCGCTGGCGCCGGAGGCATTGCTCTCCACCCCTTGCGA<br>CATCCTCGCGCCCTGCGGCCTGGGCGGCGTGCTCACCAGCCAGAGCGTCAGCCAGTTGCGCTG<br>CGCGGCGGTGGCCGGGCGGCGAACAACCAGTTGGAGCGGCCGGAGGTCGCCGACGAGCTGGA<br>GGCGCGCGGCATCCTCTATGCGCCGGACTACGTGATCAACTCCGGCGGCCTGATCTACGTCGC<br>CCTCAAGCACCGCGGCGCCGATCCGCACAGCATCACCGCGCACCTGGCGCGGATTCCCGCGCG<br>GCTCACCGAGATCTATGCCCATGCCCAGGCCGACCACCAGTCGCCGGCGCGGATCGCCGACCG<br>TCTGGCGGAACGGATTCTCTACGGCCCGCAGTGAgaaggagatatacatATGAGTGATTACGA<br>GCCGTTGCGTCTGCATGTCCCGGAGCCCACCGGGCGTCCTGGCTGCAAGACCGACTTTTCCTA<br>TCTGCACCTGTCCCCCGCCGGCGAGGTACGCAAGCCGCCGGTGGATGTCGAGCCCGCCGAaAC<br>CAGCGACCTGGCCTACAGCCTGGTACGTGTGCTCGACGACGACGGCCACGCCGTCGGTCCCTG<br>GAATCCGCAGCTCAGCAACGAACAACTGCTGCGCGGCATGCGGGCGATGCTCAAGACCCGCCT<br>GTTCGACGCGCGCATGCTCACCGCGCAACGGCAGAAAAAGCTTTCCTTCTATATGCAATGCCT<br>CGGCGAGGAAGCCATCGCCACCGCCCACACCCTGGCCCTGCGCGACGGCGACATGTGCTTTCC<br>GACCTATCGCCAGCAAGGCATCCTGATCACCCGCGAATACCCGCTGGTGGACATGATCTGCCA<br>GCTTCTCTCCAACGAGGCCGACCCGCTCAAGGGCCGCCAGCTGCCGATCATGTACTCGAGCAA<br>GGAGGCAGGTTTCTTCTCCATCTCCGGCAACCTCGCCACCCAGTTCATCCAGGCGGTCGGCTG<br>GGGCATGGCCTCGGCGATCAAGGGCGACACGCGCATCGCCTCGGCCTGGATCGGCGACGGCGC<br>CACCGCCGAGTCGGACTTCCACACCGCCCTCACCTTCGCCCATGTCTACCGCGCGCCGGTAAT<br>CCTCAACGTGGTCAACAACCAGTGGGCGATCTCCACCTTCCAGGCCATCGCCGGCGGCGAAGG<br>CACCACCTTCGCCAACCGTGGCGTGGGCTGCGGGATCGCCTCGCTGCGGGTCGACGGCAATGA<br>CTTCCTGGCGGTCTACGCCGCCTCCGAGTGGGCGCCGAGCGCGCCCGGCGCAACCTCGGGCC<br>GAGCCTGATCGAATGGGTCACCTACCGCGCCGGCCCGCACTCGACTTCGGACGACCCGTCCAA<br>GTACCGCCCCGCCGACGACTGGACCAACTTCCCGCTGGGCGACCCGATCGCCCGCCTGAAGCG<br>GCACATGATCGGCCTCGGCATCTGGTCGGAGGAACAGCACGAAGCCACCCACAAGGCCCTCGA<br>AGCCGAAGTACTGGCCGCGCAGAAACAGGCGGAGAGCCATGGCACCCTGATCGACGGCCGGGT<br>GCCGAGCGCCGCCAGCATGTTCGAGGACGTCTATGCAGAACTGCCGGAGCAtCTGCCGGCA<br>ACGCCAGGAGCTCGGGGTATGAATGCCATGAACCCGCAACACGAGAACGCCCAGACGGTCACC<br>AGCATGACCATGATCCAGGCGCTGCGCTCGGCGATGGACATCATGCTCGAGCGCGACGACGAC<br>GTGGTGGTATTCGGCCAGGACGTCGGCTACTTCGGCGGCGTGTTCCGCTGCACCGAAGGCCTG<br>CAGAAGAAATACGGCACCTCGCGGGTGTTCGATGCGCCGATCTCCGAGAGCGGCATCATCGGC<br>GCCGCGGTCGGCATGGGTGCCTACGGCCTGCGCCCGGTGGTGGAGATCCAGTTCGCCGACTAC<br>GTCTACCCGGCCTCCGACCAGTTGATCTCCGAGGCGGCGCGCCTGCGCTATCGCTCGGCCGGC<br>GACTTCATCGTGCCGATGACCGTACGCATGCCCGTGGCGGCGGCATCTACGGCGGGCAAACG<br>CACAGCCAGAGCCCGGAGGCGATGTTCACCCAGGTCTGCGGCCTGCGCACGGTGATGCCGTCC<br>AACCCCTACGACGCCAAGGGCCTGCTGATCGCCTGCATCGAGAACGACGACCCGGTGATCTTC<br>CTCGAGCCCAAGCGCCTCTACAACGGCCCGTTCGATGGCCACCACGACCGCCCGGTGACGCCC<br>TGGTCCAAGCATCCGGCCAGCCAGGTGCCGGACGGCTACTACAAGGTGCCGCTGGACAAGGCG<br>GCGATCGTCCGCCCCGGCGCGGCGCTGACCGTGCTGACCTACGGCACCATGGTCTACGTGGCC<br>CAGGCCGCGGCCGACGAaCCGGCCTGGACGCCGAGATCATCGACCTGCGCAGCCTCTGGCCG<br>CTGGACCTGGAAACCATCGTCGCCTCGGTGAAGAAGACCGGCCGCTGCGTCATCGCCCACGAG<br>GCGACCCGCACCTGtGGGTTCGGCGCCGAGCTGATGTCGCTGGTGCAGGAGCACTGCTTCCAC<br>CACCTGGAGGCGCCGATCGAGCGCGTCACCGGTTGGGACACCCCCTACCCGCATGCCCAGGAG<br>TGGGCGTATTTCCCCGGCCCCGCGCGCGTCGGCGCGGCATTCAAGCGTGTGATGGAGGTCTGA<br>ATGGGTACCCATGTGATCAAGATGCCGGACATCGGGGAAGGCATCGCCGAGGTCGAACTGGTG<br>GAGTGGCATGTCCAGGTCGGCGACTCGGTCAATGAAGACCAGGTCCTCGCCGAGGTGATGACC<br>GACAAGGCCACGGTGGAGATTCCCTCGCCGGTGGCCGGACGCATCCTCGCCCTCGGCGGCCAG<br>CCGGGCCAGGTGATGGCGGTGGGCGGCGAACTGATCCGCCTGGAGGTGGAAGGCGCCGGCAAC |

| SEQ ID NO: | Gene or Operon | Sequence |
|---|---|---|
| | | CTCGCCGAGAGTCCGGCCGCGGCGACGCCGGCCGCGCCCGTCGCCGCCACCCCGGAGAAACCG<br>AAGGAAGCCCCGGTCGCGGCGCCGAAAGCCGCCGCCGAAGCGCCGCGCGCCTTGCGCGACAGC<br>GAGGCGCCACGGCAGCGGCGCCAGCCCGGCGAACGCCCGCTGGCCTCCCCCGCGGTGCGCCAG<br>CGCGCCCGCGACCTGGGCATCGAGTTGCAGTTCGTGCAGGGCAGCGGTCCCGCCGGACGCGTC<br>CTCCACGAGGACCTCGATGCCTACCTGACCCAGGATGGCAGCGTCGCGCGCAGCGGCGGCGCC<br>GCGCAGGGGTATGCCGAGCGACACGACGAACAGGCGGTGCCGGTGATCGGCCTGCGTCGCAAG<br>ATCGCCCAGAAGATGCAGGACGCCAAGCGACGCATCCCGCATTTCAGCTATGTCGAGGAAATC<br>GACGTCACCGATCTGGAAGCCCTGCGCGCCCATCTCAACCAGAAATGGGGTGGCCAGCGCGGC<br>AAGCTGACCCTGCTGCCGTTCCTGGTCCGCGCCATGGTCGTGGCGCTGCGCGACTTCCCGCAG<br>TTGAACGCGCGCTACGACGACGAGGCCGAGGTGGTCACCCGCTACGGCGCGGTGCACGTCGGC<br>ATCGCCACCCAGAGCGACAACGGCCTGATGGTGCCGGTGCTGCGCCACGCCGAATCGCGCGAC<br>CTCTGGGGCAACGCCAGCGAAGTGGCGCGCTGGCCGAAGCCGCACGCAGCGGCAAGGCGCAA<br>CGCCAGGAGCTGTCCGGCTCGACCATCACCCTGAGCAGCCTCGGCGTGCTCGGCGGGATCGTC<br>AGCACACCGGTGATCAACCATCCGGAGGTGGCCATCGTCGGCGTCAACCGCATCGTCGAGCGA<br>CCGATGGTGGTCGGCGGCAACATCGTCGTGCGCAAGATGATGAACCTCTCCTCCTCCTTCGAC<br>CACCGGGTGGTCGACGGGATGGACGCGGCCTTCATCCAGGCCGTGCGCGGCCTGCTCGAA<br>CATCCCGCCACCCGTGTTCCTGGAGTAAgcgATGAGCCAGATCCTGAAGACTTCCCTGCTGATC<br>GTCGGCGGCGGTCCCGGCGGCTACGTCGCGGCGATCCGTGCCGGGCAACTGGGCATTCCCACC<br>GTACTGGTGGAGGGCGCCGCCCTCGGCGGCACCTGtCTGAACGTCGGCTGCATCCCGTCGAAG<br>GCGCTGATCCACGCCGCCGAGGAATACCTCAAGGCCCGCCACTATGCCAGCCGGTCGGCGCTG<br>GGCATCCAGGTACAGGCGCCGAGCATCGACATCGCCCGCACCGTGGAATGGAAGGACGCCATC<br>GTCGACCGCCTCACCAGCGGCGTCGCCGCGCTGCTGAAGAAACACGGGGTCGATGTCGTCCAG<br>GGCTGGGCGAGGATCCTCGACGGCAAAAGCGTGGCGGTCGAACTCGCCGGCGGCGGCAGCCAG<br>CGCATCGAGTGCGAGCAtCTGCTGCTGGCCGCCGGCTCGCAGAGCGTCGAGCTACCGATCCTG<br>CCGCTGGGCGGCAAGGTGATCTCCTCCACCGAGGCGCTGGCGCCCGGCAGCCTGCCCAAGCGC<br>CTGGTGGTGGTCGGCGGCGGCTACATCGGCCTGGAGCTGGGTACCGCCTACCGCAAGCTCGGC<br>GTCGAGGTGGCCGGTGGTGGAAGCGCAACCACGCATCCTGCCGGGCTACGACGAAGAACTGACC<br>AAGCCGGTGGCCCAGGCCTTGCGCAGGCTGGGCGTCGAGCTGTACCTCGGGCACAGCCTGCTG<br>GGCCCGAGCGAGAACGGCGTGCGGGTCCGCGACGGCGCCGGCGAGGAGCGCGAGATCGCCGCC<br>GACCAGGTACTGGTGGCGGTCGGCCGCAAGCCGCGCAGCGAAGGCTGGAACCTGGAAAGCCTG<br>GGCCTGGACATGAACGGCCGGGCGGTGAAGGTCGACGACCAGTGCCGCACCTCGATGCGCAAT<br>GTCTGGGCCATAGGCGATCTCGCCGGCCAGGCCGATGCTCGCGCACCGGGCCATGGCCCAGGGC<br>GAGATGGTCGCCGAGCTGATCGCCGGCCAAGCGTCGCCAGTTCGCCCCGGTGGCGATCCCCGCG<br>GTGTGCTTCACCGATCCGGAAGTGGTGGTCGCCGGGTTGTCCCCGGAGCAGGCGAAGGATGCC<br>GGCCTGGACTGCCTGGTGGCGAGCTTCCCGTTCGCCGCCAACGGTCGCGCCATGACCCTGGAG<br>GCCAACGAAGGCTTCGTCCGCGTGGTGGCGCGTCGCGACAACCACCTGGTCGTCGGCTGGCAG<br>GCGGTGGGCAAGGCGGTtTCGGAACTGTCCACGGCCTTCGCCCAGTCGCTGGAGATGGGCGCC<br>CGCCTGGAAGACATCGCCGGCACCATCCACGCCCATCCGACCCTCGGCGAAGCGGTCCAGGAA<br>GCCGCCCTGCGCGCGCTGGGACACGCCCTGCACATCTGA |
| 9 | Tet-livKHMGF construct (gene coding regions are shown in uppercase) | ccagtgaattcgTTAAGACCCCACTTTCACATTTAAGTTGTTTTTCTAATCCGCATATGATCAA<br>TTCAAGGCCGAATAAGAAGGCTGGCTCTGCACCTTGGTGATCAAATAATTCGATAGCTTGTCG<br>TAATAATGGCGGCATACTATCAGTAGTAGGTGTTTCCCTTTCTTCTTTAGCGACTTGATGCTC<br>TTGATCTTCCAATACGCAACCTAAAGTAAAATGCCCCACAGCGCTGAGTGCATATAATGCATT<br>CTCTAGTGAAAAACCTTGTTGGCATAAAAAGGCTAATTGATTTTCGAGAGTTTCATACTGTTT<br>TTCTGTAGGCCGTGTACCTAAATGTACTTTTGCTCCATCGCGATGACTTAGTAAAGCACATCT<br>AAAACTTTTAGCGTTATTACGTAAAAAATCTTGCCAGCTTTCCCCTTCTAAAGGGCAAAAGTG<br>AGTATGGTGCCTATCTAACATCTCAATGGCTAAGGCGTCGAGCAAAGCCCGCTTATTTTTTAC<br>ATGCCAATACAATGTAGGCTGCTCTACACCTAGTTCTGGGCGAGTTTACGGGTTGTTAAACC<br>TTCGATTCCGACCTCATTAAGCAGCTCTAATGCGCTGTTAATCACTTTACTTTTATCTAATCT<br>AGACATcattaattcctaattttgttgacactctatcattgatagagtttattttaccactcc<br>ctatcagtgatagagaaagtgaactctagaaataattttgtttaactttaagaaggagatat<br>acatATGAAACGGAATGCGAAAACTATCATCGCAGGGATGATTGCACTGGCAATTTCACACAC<br>CGCTATGGCTGACGATATTAAAGTCGCCGTTGTCGGCGCGATGTCCGGCCCGATTGCCCAGTG<br>GGGCGATATGGAATTTAACGGCGCGCGTCAGGCAATTAAAGACATTAATGCCAAAGGGGAAT<br>TAAGGGCGATAAACTGGTTGGCGTGGAATATGACGACGCATGCGACCCGAAACAAGCCGTTGC<br>GGTCGCCAACAAAATCGTTAATGACGGCATTAAATACGTTATTGGTCATCTGTGTTCTTCTTC<br>TACCCAGCCTGCGTCAGATATCTATGAAGACGAAGGTATTCTGATGATCTCGCCGGGAGCGAC<br>CAACCCGGAGCTGACCCAACGCGGTTATCAACACATTATGCGTACTGCCGGGCTGGACTCTTC<br>CCAGGGGCAACGGCGGCAAAATACATTCTTGAGACGGTGAAGCCCAGCGCATCGCCATCAT<br>TCACGACAAACAACAGTATGGCGAAGGGCTGGCGCGTTCGGTGCAGGACGGGCTGAAAGCGGC<br>TAACGCCAACGTCGTCTTCTTCGACGGTATTACCGCCGGGGAGAAAGATTTCTCCGCGCTGAT<br>CGCCCGCCTGAAAAAAGAAAACATCGACTTCGTTTACTACGGCGGTTACTACCCGGAAATGGG<br>GCAGATGCTGCGCCAGGCCCGTTCCGTTGGCCTGAAAACCCAGTTTATGGGGCCGGAAGGTGT<br>GGGTAATGCGTCGTTGTCGAACATTGCCGGTGATGCCGCCGAAGGCATGTTGGTCACTATGCC<br>AAAACGCTATGACCAGGATCCGGCAAACCAGGGCATCGTTGATGCGCTGAAAGCAGACAAGAA<br>AGATCCGTCCGGGCCTTATGTCTGGATCACCTACGCGGCGGTGCAATCTCTGGCGACTGCCT<br>TGAGCGTACCGGCAGCGATGAGCCGCTGGCGCTGGTGAAAGATTTAAAAGCTAACGGTGCAAA<br>CACCGTGATTGGGCCGCTGAACTGGGATGAAAAAGGCGATCTTAAGGGATTTGATTTTGGTGT<br>CTTCCAGTGGCACGCCGACGGTTCATCCACGGCAGCCAAGTGAtcatcccaccgcccgtaaaa<br>tgcgggcgggtttagaaaggttaccttATGTCTGAGCAGTTTTTGTATTTCTTGCAGCAGATG<br>TTTAACGGCGTCACGCTGGGCAGTACCTACGCGCTGATAGCCATCGGCTACACCATGGTTTAC<br>GGCATTATCGGCATGATCAACTTCGCCCACGGCGAGGTTTATATGATTGGCAGCTACGTCTCA |

| SEQ ID NO: | Gene or Operon | Sequence |
|---|---|---|
| | | TTTATGATCATCGCCGCGCTGATGATGATGGGCATTGATACCGGCTGGCTGCTGGTAGCTGCG<br>GGATTCGTCGGCGCAATCGTCATTGCCAGCGCCTACGGCTGGAGTATCGAACGGGTGGCTTAC<br>CGCCCGGTGCGTAACTCTAAGCGCCTGATTGCACTCATCTCTGCAATCGGTATGTCCATCTTC<br>CTGCAAAACTACGTCAGCCTGACCGAAGGTTCGCGCGACGTGGCGCTGCCGAGCCTGTTTAAC<br>GGTCAGTGGGTGGTGGGGCATAGCGAAAACTTCTCTGCCTCTATTACCACCATGCAGGCGGTG<br>ATCTGGATTGTTACCTTCCTCGCCATGCTGGCGCTGACGATTTTCATTCGCTATTCCCGCATG<br>GGTCGCGCGTGTCGTGCCTGCGCGGAAGATCTGAAAATGGCGAGTCTGCTTGGCATTAACACC<br>GACCGGGTGATTGCGCTGACCTTTGTGATTGGCGCGGCGATGGCGGCGGTGGCGGGTGTGCTG<br>CTCCGGTCAGTTCTACGGCGTCATTAACCCCTACATCGGCTTTATGGCCGGGATGAAAGCCTTT<br>ACCGCGGCGGTGCTCGGTGGGATTGGCAGCATTCCGGGAGCGATGATTGGCGGCCTGATTCTG<br>GGGATTGCGGAGGCGCTCTCTTCTGCCTATCTGAGTACGGAATATAAAGATGTGGTgTCATTC<br>GCCCTGCTGATTCTGGTGCTGCTGGTGATGCCGACCGGTATTCTGGGTCGCCCGGAGGTAGAG<br>AAAGTATGAAACCGATGCATATTGCAATGGCGCTGCTCTCTGCCGCGATGTTCTTTGTGCTGG<br>CGGGCGTCTTTATGGGCGTGCAACTGGAGCTGGATGGCACCAAACTGGTGGTCGACACGGCTT<br>CGGATGTCCGTTGGCAGTGGGTGTTTATCGGCACGGCGGTGGTCTTTTTCTTCCAGCTTTTGC<br>GACCGGCTTTCCAGAAAGGGTTGAAAAGCGTTTCCGGACCGAAGTTTATTCTGCCCGCCATTG<br>ATGGCTCCACGGTGAAGCAGAAACTGTTCCTCGTGGCGCTGTTGGTGCTTGCGGTGGCGTGGC<br>CGTTTATGGTTTCACGCGGGACGGTGGATATTGCCACCCTGACCATGATCTACATTATCCTCG<br>GTCTgGGGCTGAACGTGGTTGTTGGTCTTTCTGGTCTGCTGGTGCTGGGGTACGGCGGTTTTT<br>ACGCCATCGGCGCTTACACTTTTGCGCTGCTCAATCACTATTACGGCTTGGGCTTCTGGACCT<br>GCCTGCCGATTGCTGGATTAATGGCAGCGGCGGCGGGCTTCCTGCTCGGTTTTCCGGTGCTGC<br>GTTTGCGCGGTGACTATCTGGCGATCGTTACCCTCGGTTTCGGCGAAATTGTGCGCATATTGC<br>TGCTCAATAACACCGAAATTACCGGCGGCCCGAACGGAATCAGTCAGATCCCGAAACCGACAC<br>TCTTCGGACTCGAGTTCAGCCGTACCGCTCGTGAAGGCGGCTGGGACACGTTCAGTAATTTCT<br>TTGGCCTGAAATACGATCCCTCCGATCGTGTCATCTTCCTCTACCTGGTGGCGTTGCTGCTGG<br>TGGTGCTAAGCCTGTTTGTCATTAACCGCCTGCTGCGGATGCCGCTGGGGCGTGCGTGGGAAG<br>CGTTGCGTGAAGATGAAATCGCCTGCCGTTCGCTGGGCTTAAGCCCGCGTCGTATCAAGCTGA<br>CTGCCTTTACCATAAGTGCCGCGTTTGCCGGTTTTGCCGGAACGCTGTTTGCGGCGCGTCAGG<br>GCTTTGTCAGCCCGGAATCCTTCACCTTTGCCGAATCGGCGTTTGTGCTGGCGATAGTGGTGC<br>TCGGCGGTATGGGCTCGCAATTTGCGGTGATTCTGGCGGCAATTTTGCTGGTGGTGTCGCGCG<br>AGTTGATGCGTGATTTCAACGAATACAGCATGTTAATGCTCGGTGGTTTGATGGTGCTGATGA<br>TGATCTGGCGTCCGCAGGGCTTGCTGCCCATGAACGCGCCCGCAACTGAAGCTGAAAAACGGCG<br>CAGCGAAAGGAGAGCAGGCATGAGTCAGCCATTATTATCTGTTAACGGCCTGATGATGCGCTT<br>CGGCGGCCTGCTGGCGGTGAACAACGTCAATCTTGAACTGTACCCGCAGGAGATCGTCTCGTT<br>AATCGGCCCTAACGGTGCCGGAAAAACCACGGTTTTTAACTGTCTGACCGGATTCTACAAACC<br>CACCGGCGGCACCATTTTACTGCGCGATCAGCACCTGGAAGGTTTACCGGGGCAGCAAATTGC<br>CCGCATGGGCGTGGTGCGCACCTTCCAGCATGTGCGTCTGTTCCGTGAAATGACGGTAATTGA<br>AAACCTGCTGGTGGCGCAGCATCAGCAACTGAAAACCGGGCTGTTCTCTGGCCTGTTGAAAAC<br>GCCATCCTTCCGTCGCGCCCAGAGCGAAGCGCTCGACCGCGCCGCGACCTGGCTTGAGCGCAT<br>TGGTTTGCTGGAACACGCCAACCGTCAGGCGAGTAACCTGGCCTATGGTGACCAGCGCCGTCT<br>TGAGATTGCCCGCTGCATGGTGACGCAGCCGGAGATTTTAATGCTCGACGAACCTGCGGCAGG<br>TCTTAACCCGAAAGAGACGAAAGAGCTGGATGAGCTGATTGCCGAACTGCGCAATCATCACAA<br>CACCACTATCTTGTTGATTGAACACGATATGAAGCTGGTGATGGGAATTTCGGACCGAATTTA<br>CGTGGTCAATCAGGGGACGCCGCTGGCAAACGGTACGCCGGAGCAGATCCGTAATAACCCGGA<br>CGTGATCCGTGCCTATTTAGGTGAGGCATAAGATGGAAAAAGTCATGTTGTCCTTTGACAAAG<br>TCAGCGCCCACTACGGCAAAATCCAGGCGCTGCATGAGGTGAGCCTGCATATCAATCAGGGCG<br>AGATTGTCACGCTGATTGGCGCGAACGGGCGGGGAAAACCACCTTGCTCGGCACGTTATGCG<br>GCGATCCGCGTGCCACCAGCGGGCGAATTGTGTTTGATGATAAAGACATTACCGACTGGCAGA<br>CAGCGAAAATCATGCGCGAAGCGGTGGCGATTGTCCCGGAAGGGCGTCGCGTCTTCTCGGA<br>TGACGGTGGAAGAGAACCTGGCGATGGGCGGTTTTTTTGCTGAACGCGACCAGTTCCAGGAGC<br>GCATAAAGTGGGTGTATGAGCTGTTTCCACGTCTGCATGAGCGCCGTATTCAGCGGGCGGGCA<br>CCATGTCCGGCGGTGAACAGCAGATGCTGGCGATTGGTCGTGCGCTGATGAGCAACCCGCGTT<br>TGCTACTGCTTGATGAGCCATCGCTCGGTCTTGCGCCGATTATCATCCAGCAAATTTTCGACA<br>CCATCGAGCAGCTGCGCGAGCAGGGGATGACTATCTTTCTCGTCGAGCAGAACGCCAACCAGG<br>CGCTAAAGCTGGCGGATCGCGGCTACGTGCTGGAAAACGGCCATGTAGTGCTTTCCGATACTG<br>GTGATGCGCTGCTGGCGAATGAAGCGGTGAGAAGTGCGTATTTAGGCGGGTAA |
| 10 | livJ (Escherichia coli) | ATGAACATAAAGGGTAAAGCGTTACTGGCAGGATGTATCGCGCTGGCATTCAGCAATATGGCT<br>CTGGCAGAAGATATTAAAGTCGCGGTCGTGGGCGCAATGTCCGGTCCGGTTGCGCAGTACGGT<br>GACCAGGAGTTTACCGGCGCAGAGCAGGCGGTTGCGGATATCAACGCTAAAGGCGGCATTAAA<br>GGCAACAAACTGCAAATCGTAAAATATGACGATGCCTGTGACCCGAAACAGGCGGTTGCGGTG<br>GCGAACAAAGTCGTTAACGACGGCATTAAATATGTGATTGGTCACCTCTGTTCTTCATCAACG<br>CAGCCTGCGTCTGACATCTACGAAGACGAAGGCATTTTAATGATCACCCCAGCGGCAACCGCG<br>CCGGAGCTGACCGCCCGTGGCTATCAGCTGATCCTGCGCACCACCGGCCTGGACTCCGACCAG<br>GGGCCGACGGCGGCGAAATATATTCTTGAGAAAGTGAAACCGCAGCGTATTGCTATCGTTCAC<br>GACAAACAGCAATACGGCGAAGGTCTGGCGCGAGCGGTGCAGGACGGCCTGAAGAAGGCAAT<br>GCAAACGTGGTGTTCTTTGATGGCATCACCGCCGGGGAAAAAGATTTCTCAACGCTGGTGGCG<br>CGTCTGAAAAAAGAGAATATCGACTTCGTTTTACTACGGCGGTTATCACCCGGAAATGGGGCAA<br>ATCCTGCGTCAGGCACGCGCGGCAGGGCTGAAAACTCAGTTTATGGGGCCGGAAGGTGTGGCT<br>AACGTTTCGCTGTCTAACATTGCGGGCGAATCAGCGGAAGGGCTGCTGGTGACCAAGCCGAAG<br>AACTACGATCAGGTTCCGGCGAACAAACCCATTGTTGACGCGATCAAAGCGAAAAAACAGGAC<br>CCAAGTGGCGCATTCGTTTGGACCACCTACGCCGCGCTGCAATCTTTGCAGGCGGGCCTGAAT<br>CAGTCTGACGATCCGGCTGAAATCGCCAAATACCTGAAAGCGAACTCCGTGGATACCGTAATG |

| SEQ ID NO: | Gene or Operon | Sequence |
|---|---|---|
| | | GGACCGCTGACCTGGGATGAGAAAGGCGATCTGAAAGGCTTTGAGTTCGGCGTATTTGACTGG CACGCCAACGGCACGGCGACCGATGCGAAGTAA |
| 11 | leucine exporter gene leuE (*Escherichia coli* Nissle 1917) | GTGTTCGCTGAATACGGGGTTCTGAATTACTGGACCTATCTGGTTGGGGCCATTTTTATTGTG TTGGTGCCAGGGCCAAATACCCTGTTTGTACTCAAAAATAGCGTCAGTAGCGGTATGAAAGGC GGTTATCTTGCGGCCTGTGGTGTATTTATTGGCGATGCGGTATTGATGTTTCTGGCATGGGCT GGAGTGGCGACATTAATTAAGACCACCCCGATATTATTCAACATCGTACGTTATCTTGGTGCG TTTTATTTGCTCTATCTGGGGAGTAAAATTCTCTACGCGACCCTGAAAGGTAAAAATAGCGAG ACCAAATCCGATGAGCCCAATACGGTGCCATTTTTAAACGCGCGTTAATTTTGAGCCTGACT AATCCGAAAGCCATTTTGTTCTATGTGTCGTTTTTCGTACAGTTTATCGATGTTAATGCCCCA CATACGGGAATTTCATTCTTTATTCTGGCGACGACGCTGGAACTGGTGAGTTTCTGCTATTTG AGCTTCCTGATTATTTCTGGGGCTTTTGTCACGCAGTACATACGTACCAAAAAGAAACTGGCT AAAGTGGGCAACTCACTGATTGGTTTGATGTTCGTGGGTTTCGCCGCCCGACTGGCGACGCTG CAATCCTGA |
| 12 | Arginine decarboxylase (*Escherichia coli*) | ATGATGAAAG TGTTAATCGT GGAATCTGAA TTTCTGCACC AGGATACGTG GGTCGGTAAC GCTGTTGAAC GTCTGGCCGA TGCTTTAAGC CAGCAAAATG TGACAGTTAT CAAATCCACC TCTTTTGACG ATGGCTTTGC CATTCTGTCA AGCAATGAAG CCATCGATTG TCTGATGTTC TCGTACCAGA TGGAACACCC CGATGAGCAC CAAAATGTTC GTCAGCTGAT CGGCAAACTT CACGAACGTC AACAGAACGT ACCGGTCTTT CTGTTAGGCG ACCGCGAAAA GGCCTTGGCG GCTATGGATC GCGATCTGCT GGAGTTGGTC GACGAGTTTG CCTGGATTCT CGAGGATACG GCGGATTTTA TTGCCGGTCG CGCAGTCGCC GCCATGACGC GCTACCGCCA ACAGCTGCTC CCGCCGCTGT TTTCTGCCCT GATGAAATAC TCGGACATTC ACGAATACAG CTGGGCAGCT CCCGGGCACC AGGGCGGCGT TGGCTTCACG AAAACCCCAG CTGGTCGCTT TTATCATGAC TACTACGGCG AGAATTTATT TCGTACCGAC ATGGGCATTG AACGTACCAG CCTGGGCTCG CTGCTGGACC ACACGGGCGC TTTTGGGGAA TCAGAGAAAT ATGCAGCACG CGTGTTCGGT GCGGACCGCA GTTGGTCCGT CGTGGTGGGC ACCAGTGGTA GCAACCGCAC CATTATGCAG GCGTGCATGA CCGATAATGA TGTGGTAGTG GTGGATCGCA ATTGTCATAA GAGCATCGAA CAAGGCTTGA TGCTGACTGG CGCTAAACCA GTCTATATGG TGCCGTCCCG TAATCGCTAT GGTATTATCG GCCCGATTTA TCCTCAGGAG ATGCAGCCGG AAACCCTCCA GAAGAAAATC TCAGAGTCCC CGTTAACTAA AGATAAAGCT GGGCAAAAAC CGAGTTATTG TGTAGTAACT AATTGTACGT ATGATGGTGT TTGCTATAAC GCTAAGGAGG CCCAAGATCT TCTGGAAAAA ACAAGTGATC GTCTTCATTT TGATGAAGCT TGGTACGGTT ATGCGCGTTT CAACCCTATT TACGCCGACC ACTATGCGAT GCGTGGTGAA CCTGGGGATC ATAATGGCCC TACTGTGTTT GCCACCCATT CTACGCATAA ACTCCTGAAT GCGTTGTCAC AGGCGAGTTA CATCCACGTA CGCGAAGGCC GTGGCGCTAT TAATTTTAGC CGCTTTAACC AGGCCTATAT GATGCACGCG ACGACAAGTC CGCTGTATGC GATTTGCGCG TCCAACGATG TTGCGGTCAG CATGATGGAC GGCAACAGCG GTCTGTCGTT AACCCAGGAA GTGATTGATG AAGCGGTCGA CTTTCGCCAG GCGATGGCCC GTCTGTACAA AGAATTCACC GCCGATGGCT CGTGGTTCTT CAAACCCTGG AATAAAGAAG TCGTGACTGA CCCGCAGACG GGCAAAACTT ATGATTTTGC AGATGCCCCG ACGAAGCTTC TTACTACGGT CCAGGATTGC TGGGTGATGC ACCCGGGGGA GTCTTGGCAT GGCTTCAAAG ATATCCCTGA TAACTGGTCT ATGCTCGACC CAATCAAAGT TTCAATTTTA GCTCCAGGCA TGGGCGAAGA TGGCGAACTG GAAGAGACGG GGGTACCAGC TGCGTTGGTT ACCGCTGGT TAGGCGCCA TGGTATTGTT CCAACACGTA CCACTGATTT TCAGATTATG TTTCTGTTCA GTATGGGTGT GACGCGCGGT AAATGGGGGA CGCTGGTCAA CACTCTCTGC TCCTTTAAAC GCCATTATGA TGCGAACACG CCCCTGGCGC AAGTCATGCC AGAGCTGGTG GAACAATACC CTGATACTTA TGCGAACATG GGTATCCACG ATCTGGGAGA TACTATGTTC CGCCTGGCTTA AAGAAAATAA CCCGGGGGCC CGCCTGAACG AAGCATATAG TGGCCTGCCC ATGGCGGAAA TTACTCCGCG TGAAGCCTAT AATGCCATCG TTGATAATAA CGTCGAATTA GTATCCATCG AGAACCTCCC CGGTCGTATT GCGGCAAATA GCGTAATCCC GTACCCGCCG GGTATTCCCA TGCTGCTCAG CGGCGAAAAC TTCGGTGATA AAAATTCCCC GCAAGTTTCT TATCTGCGCA GCCTGCAATC GTGGGACCAT CACTTTCCCG GGTTTGAGCA TGAAACTGAA GGGACAGAGA TCATCGATGG CATTTATCAT GTGATGTGCG TCAAGGCG |
| 13 | ArgT (*Escherichia coli*) | ATGAAAAAA GCATCCTCGC GCTGTCACTG TTAGTGGGTC TCAGCGCCGC GGCCAGCAGC TATGCTGCTC TTCCTGAAAC GGTGCGCATC GGGACGGATA CCACTTATGC ACCGTTTAGC AGCAAAGATG CTAAAGGAGA CTTCGTAGGG TTTGATATCG ATTTAGGCAA CGAGATGTGC AAACGTATGC AAGTGAAATG TACCTGGGTG GCTTCAGACT TTGATGCATT AATCCCGAGT TTGAAAGCAA AAAAATTGA CGCAATTATT TCGAGCCTGA GCATTACAGA TAAGCGCCAA CAAGAAATTG CCTTCTCAGA TAAATTATAT GCCGCTGATT CGCGTCTTAT CGCGGCTAAA GGCTCCCCTA TCCAACCAAC GTTGGACAGC CTGAAGGGA AACATGTAGG GGTTCTGCAA GGGTCCACGC AGGAAGCTTA CGCCAATGAA ACCTGGCGTT CGAAAGGGGT CGATGTGGTG GCGTACGCCA ATCAGGACTT GGTGTATTCC GATCTGGCCG CAGGTCGTCT GGACGCAGCT CTGCAGGACG |

| SEQ ID NO: | Gene or Operon | Sequence |
|---|---|---|
| | | AAGTGGCGGC GAGTGAGGGT TTCCTGAAAC AGCCAGCAGG CAAAGATTTT<br>GCGTTCGCCG GCTCGAGTGT AAAGGATAAA AAATATTTCG GGGATGGCAC<br>GGGTGTCGGT TTACGCAAAG ATGATGCAGA ACTGACCGCG GCGTTTAATA<br>AAGCCCTTGG CGAACTGCGC CAAGACGGCA CATATGATAA AATGGCGAAA<br>AAGTACTTTG ACTTCAATGT TTATGGTGAT |
| 14 | artP<br>(*Escherichia coli*) | ATGTCTATTC AATTAAATGG CATCAACTGT TTCTACGGTG CACATCAAGC<br>CTTATTTGAC ATCACGCTTG ATTGCCCGCA AGGGGAGACA CTGGTGCTGC<br>TGGGCCCGAG TGGAGCCGGC AAATCGTCGT TGCTGCGGGT GTTGAACCTG<br>TTGGAGATGC CGCGCTCAGG CACCCTGAAT ATCGCGGGCA ACCATTTCGA<br>TTTTACGAAA ACACCGTCCG ATAAAGCTAT TCGTGATCTT CGTCGCAACG<br>TCGGCATGGT GTTTCAGCAG TATAATTTAT GTGCTCATCT GACGGTTCAG<br>CAAAATCTGA TCGAAGCACC GTGTCGTGTG TTGGGCCTGA GCAAAGACCA<br>AGCCCTGGCC AGCGCAGAAA AATTATTAGA GCGCCTGCGC TTGAAACCAT<br>ATTCGGATCG GTACCCACTT CACTTAAGCG GGGGCCAGCA ACAGCGCGTT<br>GCCATCGCTC GTGCGCTGAT GATGGAGCCG CAAGTTCTCC TTTTTGATGA<br>ACCTACCGCA GCGCTTGATC CGGAGATCAC GGCGCAGATC GTCAGCATCA<br>TTCGTGAACT CGCTGAGACG AATATTCAC AAGTTATTGT GACACATGAG<br>GTAGAAGTGG CTCGCAAGAC CGCGTCTCGC GTAGTGTATA TGGAAAACGG<br>TCATATCGTG GAGCAAGGGG ACGCCTCATG TTTTACAGAG CCGCAGACAG<br>AGGCATTCAA AAATTATCTG AGCCAC |
| 15 | artI<br>(*Escherichia coli*) | ATGAAAAAAG TGCTTATTGC CGCCCTGATT GCGGGCTTCT CTCTGTCTGC<br>CACCGCGGCC GAAACCATCC GTTTTGCCAC TGAAGCGTCA TATCCCCCTT<br>TCGAAAGCAT TGACGCCAAC AACCAAATTG TCGGTTTCGA CGTTGACCTC<br>GCGCAGGCCC TGTGCAAAGA AATTGATGCC ACCTGCACCT TCTCTAACCA<br>AGCGTTTGAC TCATTGATTC CTTCGCTGAA ATTTCGTCGC GTGGAAGCCG<br>TCATGGGCGG CATGGATATC ACCCCCGAGC GCGAAAAACA GGTCTTGTTT<br>ACTACACCGT ACTACGACAA CTCGGCTTTG TTTGTCGGCC AGCAAGGCAA<br>GTATACTTCT GTCGACCAGC TGAAAGGTAA AAAAGTCCGT TCAGTCCAGA<br>ACGGCACCAC TCACCAGAAA TTCATCATGG ACAAACATCC TGAGATCACT<br>ACCGTGCCGT ATGATTCTTA CCAGAACGCG AAGTTAGATC TGGAAAATGG<br>TCGGATTGAT GGCGTCTTTG GCGACACCGC TGTGGTACAT GAATGGCTGA<br>AAGACAATCC TAAATTAGTG GTTGTGGGAG ATAAGGTTAC GGATAAGGAT<br>TATTTTGGCA CCGGTCTCGG CATTGCAGTC CGCCAAGGTA ATACCGAATT<br>GCAACAGAAA TTGAATACCG CGCTGGAAAA AGTGAAAAAA GACGGTACAT<br>ACGAAACCAT TTACAACAAA TGGTTTCAAA AA |
| 16 | artQ<br>(*Escherichia coli*) | ATGAACGAAT TCTTCCCTCT CGCGTCTGCG GCAGGTATGA CCGTGGGTTT<br>GGCGGTTTGT GCGCTGATTG TCGGTCTCGC TCTGGCAATG TTCTTTGCCG<br>TATGGGAGTC AGCGAAATGG CGTCCGGTCG CCTGGGCAGG TTCCGCCCTG<br>GTAACCATTC TGCGTGGTCT GCCAGAGATC CTGGTAGTTC TGTTTATCTA<br>CTTTGGCTCT TCTCAGTTAC TGTTAACACT GTCTGACGGG TTTACGATTA<br>ACCTGGGTTT TGTCCAGATT CCGGTCCAGA TGGATATTGA AAATTTCGAC<br>GTCTCCCCTT TTCTCTGTGG CGTCATCGCG CTGAGCTTGC TCTACGCTGC<br>ATATGCATCA CAGACCCTTC GTGGTGCATT AAAAGCGGTG CCAGTAGGAC<br>AGTGGGAAAG CGGCCAGGCC CTTGGCCTGA GCAAGAGCGC AATTTTTTTC<br>CGCCTTGTTA TGCCGGCCGA TGTCCGCCAT GCGTTACCAG GTCTGGGTAA<br>TCAATGGCTG GTGTTGTTGA AAGACACCGC CCTTGTCTCG CTGATTAGCG<br>TGAACGATTT AATGCTGCAA ACCAAATCGA TTGCAACCCG CACTCAGGAA<br>CCGTTTACCT GGTACATCGT GGCGGCAGCA ATCTATCTGG TGATCACACT<br>TCTGAGCCAG TATATTTTAA AACGTATTGA CCTGCGTGCC ACCCGCTTTG<br>AGCGCCGCCC TAGC |
| 17 | artM<br>(*Escherichia coli*) | ATGTTTGAAT ATCTGCCGGA ACTGATGAAA GGTTTGCATA CTAGTCTGAC<br>GCTGACCGTC GCGAGTCTGA TCGTTGCGCT TATCCTGGCA CTGATCTTCA<br>CCATTATTCT GACTCTCAAG ACCCCGGTCC TGGTGTGGCT GGTCGGCGGT<br>TACATTACCT TATTCACCGG GACCCCGCTC TTGGTTCGCA TTTTTCTTAT<br>TTACTATGGT CCGGGTCAGT TTCCGACCTT GCAAGAATAT CCTGCGTTAT<br>GGCACCTGCT GTCTGAACCG TGGCTGTGCG CTCTGATTGC TCTGAGTGTT<br>AACTCGGCGG CCTATACGAC ACAGCTGTTC TACGGTGCTA TTCGTGCGAT<br>CCCAGAAGGT CAATGGCAGT CTTGTAGCGC ACTGGGCATG TCAAAGAAAG<br>ATACTCTTGC TATTCTGCTG CCGTACGCTT TTAAACGCTC TCTGAGCTCG<br>TACAGCAATG AAGTTGTCCT GGTTTTCAAA AGCACTAGCT AGCGTATAC<br>GATCACGCTG ATGGAAGTCA TGGGTTATAG CCAGTTATTA TATGGTCGCA<br>CGTACGACGT CATGGTGTTT GGTGCAGCGG GCATTATCTA TCTTGTAGTT<br>AATGGATTAC TGACGTTAAT GATGCGCTTG ATCGAACGCA AAGCCGTGGC<br>ATTCGAGCGG CGTAAT |
| 18 | artJ<br>(*Escherichia coli*) | ATGAAAAAAT TGGTGCTTGC AGCACTGCTG GCCAGTTTCA CTTTCGGCGC<br>TTCGGCGGCC GAAAAGATTA ATTTCGGTGT CAGCGCAACT TACCCACCGT<br>TCGAAAGCAT CGGTGCGAAC AATGAGATTG TAGGATTTGA TATCGATCTG<br>GCCAAAGCGT TATGCAAACA AATGCAAGCG AGTGCACTT TTACCAATCA |

Sequence Listing

| SEQ ID NO: | Gene or Operon | Sequence |
|---|---|---|
| | | TGCGTTTGAT AGCCTGATCC CGTCGCTGAA GTTCCGTAAA TACGACGCCG<br>TGATTTCGGG GATGGACATC ACCCCTGAGC GCTCGAAACA GGTGAGCTTC<br>ACCACTCCAT ATTATGAAAA CTCAGCGGTG GTGATTGCGA AAAAAGACAC<br>CTATAAAACA TTTGCCGACC TGAAAGGGAA ATGTATTGGT ATGGAGAACG<br>GCACCACCCA TCAGAAGTAT ATTCAAGACC AGCACCCGGA GGTTAAGACC<br>GTAAGCTACG ACTCCTACCA GAATGCTTTC ATTGATTTAA AAAATGGTCG<br>TATTGATGGT GTATTCGGAG ATACAGCCGT GGTGAATGAG TGGCTGAAAA<br>CCAATCCGCA GTTGGGTGTT GCGACCGAAA AAGTGACAGA TCCACAATAC<br>TTTGGGACTG GCCTGGGCAT CGCGGTGCGC CCGGATAACA AAGCCCTGTT<br>GGAGAAACTG AACAACGCGT TAGCTGCGAT TAAAGCGGAT GGGACCTATC<br>AGAAGATTTC AGACCAATGG TTCCCGCAA |
| 19 | ArgO<br>(Escherichia coli) | ATGTTCTCGT ACTATTTCCA AGGCTTAGCA CTGGGTGCGG CCATGATCTT<br>ACCGCTGGGC CCACAAAACG CTTTTGTTAT GAACCAGGGA ATCCGCCGGC<br>AGTACCATAT CATGATTGCG CTGCTGTGTG CCATCTCGGA TCTGGTCCTG<br>ATTTGCGCCG GTATTTTTGG CGGGTCGGCG TTACTTATGC AAAGCCCTTG<br>GCTGCTGGCG CTGGTAACGT GGGGCGGCGT AGCATTTCTG CTTTGGTATG<br>GATTCGGCGC CTTCAAAACT GCGATGAGTT CGAATATCGA GCTTGCGAGT<br>GCTGAGGTAA TGAAACAGGG CCGTTGGAAA ATTATTGCGA CCATGTTAGC<br>CGTGACTTGG TTGAACCCGC ACGTGTACCT GGATACTTTT GTGGTGTTGG<br>GTTCACTCGG TGGGCAATTA GATGTGAAC CGAAACGCTG GTTTGCCTTG<br>GGCACAATCT CGGCCAGTTT TTTGTGGTTC TTCGGGCTGG CGCTGCTGGC<br>CGCGTGGCTG GCACCACGTT TACGCACCGC CAAGGCCCAG CGCATCATCA<br>ACTTAGTCGT GGGCTGTGTG ATGTGGTTCA TTGCTCTGCA ACTGGCGCGC<br>GATGGCATTG CGCACGCCCA GGCCCTGTTC TCA |
| 20 | [001] mono-functional lysine-ketoglutarate reductase (Flavobacterium limnosedimin is JC2902) | ATGATGCGCT TTGGCATCAT TAAAGAACGT AAGAACCCGC CAGATCGTCG<br>TGTAGTGTTT ACACCGTCCG AACTGATCAA ACTGAAAGAA CAGTTTCCGC<br>TGGCCGAAAT TAAGGTGGAA TCCTCAGATA TTCGCATTTT TTCTGATGAT<br>GAGTATCGTA AACTTGGATT TGAAGTAACC GATGACCTGA GTGATTGTGA<br>TGTCTTGATT GGCGTGAAAG AAGTACCGAT CGATGCCCTG CTGCCCGGGA<br>AAAAGTATTT TTTTTTCTCT CACACAATTA AAAAACAGCC TTACAATAAA<br>AAACTGCTGA TCGCCTGCTT GGAAAAAAAC ATCCGTCTGA TTGATCATGA<br>GACGATCGTG AATGAAGATA ATCATCGTTT GATTGGGTTC GGCCGTTACG<br>CAGGTATCGT GGGGGCCTAT AACGGTTTCC GTGCTTTTGG TATTAAGTAC<br>GAGCTCTTTA ACCTGCCCAA AGCGGAAACC TTAGCGGACA AAACGGCACT<br>TGTGGAACGC CTGCGTCGGC CGATGCTGCC GCCAATCAAA ATTGTGTTGA<br>CCGGTCACGG CAAAGTAGGG ATGGGTGCAA AAGAGATTCT GGATGCCATG<br>AAAATCAAAC AAGTTTCCGT GGAGGACTAC TTAACAAAAA CCTATGACAA<br>GCCGGTGTAT ACGCAGATCG ACGTTCTGGA CTATAACAAG CGGAAAGATG<br>GCAAACCGGC GGAACGTGAA CACTTTTATG CCAATCCGCA GGAGTATGTC<br>TCGGACTTCG AACGCTTTAC CAAGGTGTCG GATCTGTTCA TCGCAGGCCA<br>TTTCTATGGC AACGGTGCAC CGGTAATTCT GACTCGCACC ATGCTTAACG<br>CTTCTGATAA TAAAATTAAA GTAGTTGCGG ATATTAGCTG TGATGTCGGT<br>GGCCCTATCG AATGTACGCT GCGCAGCAGC ACCATCGCAG AGCCGTTTTA<br>TGGTTATTAT CCTTCCGAAG GTAAAGAAGT CGACGTCAAC CATCCGGGCG<br>CGGTGGTTGT GATGGCGGTG GACAATCTGC CCTGCGAGCT GCCTAAAGAT<br>GCCAGCGAGG GTTTCGGAGA ATGTTTCTC AAACATGTGA TTCCAGCCTT<br>CTACAACAAC GATAAGGACG GCATTCTTGA GCGGGCCAAA ATCACCGAAA<br>ACGGCAAATT AACAAAACGC TTCTCCTACT TACAGGACTA TGTCGATGGT GAA |
| 21 | saccharopine dehydrogenase (Flavobacterium sp. EM1321) [002] | ATGCGTAATA TTTTGATTAT CGGCGCCGGT CGGTCCGCTT CCTCGCTGAT<br>TCAGTACTTA TTGAATAAGT CCCAAGAAGA ACAGCTGCAT TTAACCATTG<br>CCGATTTATC ACTCGAACTG GCTCAGAAGA AAACCAATAA CCATCCGAAC<br>GCTACCGCGC TGGCGCTGGA TATTTATAAT AAGGATGAAC GTCGTGCGGC<br>CATCGAGAAA GCGGCCATTG TGATCAGCAT GTTGCCAGCG CATCTGCATA<br>TCGAAATCGC CCGGGATTGC CTGTATTTTA AAAAGAACCT TGTTACGGCG<br>AGCTATATTA GTGACGCGAT GCAGGAGCTT GATGCGGAAG TAAAGAGAA<br>CAAACTGATC TTTATGAATG AGGTCGGTTT AGACCCGGGT ATTGATCATA<br>TGAGCGCCAT GAAAGTCATC GATGAAATTC GGGAACAAGG CGGCAAAATG<br>CTTCTCTTCG AAAGTTTTTG CGGCGGCCTG GTGGCACCAG AATCAGATAA<br>CAATTTATGG AACTATAAAT TTACCTGGGC CCCACGTAAC GTAGTTCTGG<br>CTGGCCAGGG TGGTGTGGCA AAATTCATTC AAGAAGGCAC CTATAAAATAT<br>ATCCCGTATG ACAGCTTATT TCGCCGGACC GAGTTTCTGG AAGTAGAAGG<br>ATACGGGCGT TTCGAAGCTT ATTCGAATCG CGATTCTCTC AAATATCGGA<br>GTATTTATGG GCTCGATGAC GTTCTCACCC TGTTTCGTGG TACAATCCGT<br>CGCGTTGGCT TCTCCAAAGC TTGGAACATG TTTGTGCAAC TGGGCATGAC<br>GGACGACAGC TATGTTATGG AAGATTCTGA GAATATGTCC TATCGTCAAT<br>TTATTAACTC ATTCCTGCCT TATCACCCAA CCGATAGCGT TGAAATTAAG<br>ACCCGTTTTT TGTTAAAAAT CGATCAGGAT GATATCATGT GGGACAAACT<br>GCTGGAACTG GATCTTTTCA ACGATAAAAA AATGGTTGGG TTGAAAAATG<br>CGACGCCGGC ACAGATCCTG GAGAAAATCC TGAACGATTC GTGGACCCTG<br>CAACCGGAAG ATAAAGATAT GATCGTGATG TATCATAAAT TTGGTTACCA |

Sequence Listing

| SEQ ID NO: | Gene or Operon | Sequence |
|---|---|---|
| | | GATCAACGGC GAAAAAGTGC AGATGGATTC ACAGATGGTG TGTATCGGCC AGGACCAAAC GTATACCGCG ATGGCAAAAA CCGTCGGCCT GCCTGTGGCA ATGGCAACTC TGCTGATTCT GAACGGTAAA ATCAAAACAA CGGGAGTTCA GTTGCCAATC AATAAAGAAG TTTACCTGCC GGTCCTGGAG GAACTGGAGA AATATGGCGT TGTGTTCAAA GAACAGATGC TCCCATATCT TGGATACAAA TATAGT |
| 22 | Lysine aminotransferase (*Bacillus methanolicus* PB1) [003] | ATG AAG AAA AAT CAT TCC TTG CAG TCG CTT AAA AAC CAA GAT GAG CGT TTC ATT TGG CAC TCG ATG AAG CCG TAT AAC CCC GAC AAG ACG ATC GT T GTCACC AAG GCC GAA GGA TCA TGG ATT ACA ACG AGT GAT GGA AAG AA G TAT CTT GAC GCA ATG GCC GGT CTT TGG TGC GTT AAC GTG GGG TAT G GA CGC AAAGAG CTT GCC GAT GCC GCG TAC GAA CAG ATG ATG GAA ATG G CA TAC TAT CCA CTG ACT CAG TCA CAT GTA CCC GCC ATT CAG TTA GCG GAG AAG TTG AACGAT CTG CTG GAA GAC GAA TAC GTA ATC TTT TTT AGC AAT TCG GGG AGT GAG GCG AAC GAG GCT GCT TTT AAA ATT GCT CGT CAG TAT CAT CAA CAA AAAGGA GAC CAC AAT CGC TAT AAG ATT GTT GCA CGC TAC CGT GCA TAT CAT GGG AAC TCA ATT GGA GCC TTG GCA GCG ACA GG G CAG GCC CAG CGT AAA TATAAG TAT GAG CCT CTG GCC TTT GGA TTC GT C CAT GTT GCC CCT CCT GAC TCC TAC CGT GAT GAA ACT AAC GTA TCC G AT CCT TCG CAG TTG TCC GCA GTCAAA GAA ATT GAC CGT GTA ATG ACG T GG GAG CTT TCG GAA ACT ATC GCC GCA ATG ATC ATG GAA CCG ATT ACT GGT GGA GGC ATC TTA GTG CCC CCAGAG GGG TAT ATG AAA GCG GCT AAG GAG GTT TGT GAA AAG CAC GGG GCT CTT TGT ATT GTG GAC GAG GTG ATT TGC GGG TTT GGT CGT ACG GGT AAG CCGTTC GGA TTC ATG AAC TAT GGA GTC AAG CCG GAC ATT ATC ACC ATG GCT AAA GGC ATC ACC AGT GC G TAT CTT CCG TTG TCA GCA ACT GCA GTC AAA AAGGAA ATC TAT GAT GC C TTT AAA GGT GAG GAC GAA TAT GAG TTC TTC CGT CAT GTC AAC ACT T TC GGA GGG TCA CCC GCC GCA TGT GCG CTG GCT ATC AAGAAC ATT CAG A TT TTG GAG GAG GAA AAG CTG TTT GAC CGC TCG GGC ATG GGC GAA AAA GTT TTA ACA GAA CTT CAG AAC TTG TTA CGC GAT CAC CCCTAC GTT GGC GAC GTT CGT GGA AAG GGT CTG TTA ATC GGA ATT GAA TTG GTT AAA GAC AAG CAG ACG AAA GAG CCC TTA AAT ACA AGC AAA GTT GAC GAAGTA ATC GCT CTT TGT AAA CAG GAA GGA CTT CTG ATT GGA AAA AAT GGC AT G ACC GTG GCA GGC TAT AAC AAC GTC CTT ACA CTG TCC CCT CCG CTT A ATATC CCA GAG ACC GAC TTA GAC TTT TTG ATC AAA GTA CTG ACG GCG T CC TTG GAG AAG ATT AAG |
| 23 | [004] lysine dehydrogenase (*Agrobacterium tumefaciens*) | ATG AAA AAT ATC GTA GTG ATC GGG GCA GGG AAT ATT GGC AGC GCC ATT GCG TGG ATG TTG GCA GCT AGC GGG GAT TAT CGC ATT ACT GTA GCA GA C CGCAGC GCG GAT CAG TTA GCT AAT GTA CCG GCT CAT GAA CGT GTC GA C ATT GTT GAC ATT ACC GAC CGC CCC GCG CTG GAA GCA CTG TTA AAA G GG AAA TTTGCG GTA CTT AGC GCC GCT CCC ACC GAG TTT CAT TTG ACT G CC GGA ATT GCG GAA GCG GCC GTC GCG GTA GGC ACG CAC TAC TTA GAC TTA ACA GAA GATGTG GAG TCT ACC CGC AAG GTA AAA GCG CTG GCT GAG ACG GCC GAG ACA GCT TTA ATC CCC CAA TGT GGG CTG GCA CCA GGT TTT ATT TCG ATT GTT GCTGCC GAT TTG GCT GTG AAG TTT GAT AAA TTA GAT TCT GTT CGT ATG CGC GTC GGG GCG CTG CCT CAG TAT CCC AGT AAC GC A TTG AAT TAC AAT TTG ACTTGG AGC ACA GAT GGC CTT ATC AAC GAG TA C ATT GAG CCT TGC GAG GGG TTT GTA GAA GGT CGC TTG ACC GCG GTC C CG GCT TTA GAG GAA CGC GAG GAATTT AGT CTT GAT GGG ATC ACC TAC G AG GCA TTC AAC ACC TCG GGC GGA CTT GGG ACC TTG TGC GCC ACC CTT GAG GGT AAG GTG CGC ACA ATG AAC TACCGT ACC ATC CGC TAT CCG GGT CAT GTA GCA ATC ATG AAG GCA CTT CTT AAT GAC TTG AAC CTG CGT AAT CGC CGT GAC GTT TTG AAA GAT CTT TTT GAAAAT GCA CTG CCT GGA ACG ATG CAA GAT GTC GTA ATT GTT TTT GTA ACA GTG TGT GGC ACT CGC AA C GGA CGC TTT CTG CAA GAG ACT TAT GCC AAT AAAGTG TAC GCG GGG CC T GTG TCA GGC CGC ATG ATG TCC GCG ATC CAG ATC ACA ACA GCT GCT G GA ATT TGC ACA GTC CTG GAT TTG TTG GCC GAA GGC GCGCTT CCG CAG A AG GGC TTC GTT CGT CAA GAG GAG GTC GCA CTG CCT AAG TTT TTG GAA AAT CGT TTC GGA CGT TAT TAT GGT TCT CAC GAA CCG TTG GCTCGT GTT GGT |
| 24 | lysine racemase (uncultured bacterium) [005] | ATG GCA CAT ACA GGC CGT ATG TTT AAG ATC GAA GCC GCG GAG ATC GTA GTG GCT CGC CTG CCG CTG AAA TTT CGT TTT GAG ACA TCT TTC GGT GT C CAGACA CAT AAA GTG GTG CCT TTA CTG ATC TTA CAT GGC GAA GGT GT T CAA GGG GTC GCG GAG GGG ACA ATG GAA GCT CGC CCC ATG TAC CGC G AA GAA ACGATT GCC GGA GCC CTT GAT TTG TTG CGT GGA ACT TTT TTA C CT GCG ATT CTG GGC CAA ACC TTT GCC AAT CCA GAA GCG GTA AGT GAT GCC CTG GGC TCTTAC CGC GGC AAT GCC ATG GCA CGC GCT ATG GTG GAG ATG GCA GCT TGG GAC TTG TGG GCC CGC ACC CTT GGT GTG CCT TTG GGC ACA CTG TTG GGT GGTCAC AAG GAA CAA GTC GAG GTG GGT GTA TCG TTG GGA ATC CAG GCA GAT GAG CAA GCT ACA GTA GAC TTA GTG CGT CGT CA T GTT GAA CAA GGA TAT CGTCGC ATT AAG TTG AAG ATT AAG CCT GGG TG G GAC GTT CAA CCT GTA CGT GCG ACC CGT GAG GCA TTC ATG TTA AAC A |

-continued

| SEQ ID NO: | Gene or Operon | Sequence |
|---|---|---|
| | | CG CTT AAT GTC GGC GCC TCT GGTTAC GCG GGC GCA GAA CTG GTT ACA T AC GTG AAC CGC CAC CCC CAT ATG AAC ATT ACG GCG TTG ACC GTA TCA GCA CAG TCA AAC GAT GCA GGG AAG TTAATC TCC GAT TTG CAT CCC CAA TTA AAG GGC ATC GTT GAC TTA CCA TTG CAG CCG ATG TCC GAC ATC TCT GAA TTC AGC CCC GGG GTA GAT GTA GTG TTCCTG GCT ACA GCT CAC GAA GTT TCA CAC GAC CTG GCC CCG CAA TTT TTG GAG GCG GGT TGT GTG GT C TTT GAT CTG TCC GGC GCT TTT CGC GTT AAC GATGCT ACA TTT TAC GA G AAG TAT TAC GGT TTC ACC CAC CAA TAC CCA GAG CTG CTG GAA CAG G CG GCC TAC GGG CTT GCT GAG TGG TGT GGC AAC AAA CTTAAG GAA GCT A AT CTT ATT GCA GTT CCT GGA TGT TAC CCT ACC GCC GCA CAG CTG GCG CTG AAG CCG TTA ATT GAT GCT GAC CTG CTG GAC CTG AAC CAATGG CCG GTG ATC AAT GCG ACC AGT GGC GTA TCT GGG GCG GGT CGT AAA GCC GCA ATT TCA AAC TCC TTC TGC GAG GTT AGC TTA CAA CCG |
| 25 | Lysine transporter yvsh (*Bacillus subtilis*) [006] | ATG GAG CAG ACG AAG AAA TGG GGA TTT TGG TTA CTG ACG GCC TTC GTC GTG GGC AAC ATG GTG GGT AGT GGA ATC TTT TCT CTT CCA TCC TCC CT G GCGAGC ATC GCG TCG CCT TTC GGA GCT ACG TCC GCT TGG CTT CTG AC A GGT GCG GGG GTG TTA ATG ATC GCC TTA GTA TTC GGA CAT TTG TCC A TT CGT AAACCC GAA TTG ACT GCC GGG CCT CAA TCA TAC GCC CGT GCA T TG TTC AGC GAT CCA AAA AAG GGG AAT GCG GCC GGG TTT ACT ATG GTT TGG GGT TAC TGGGTC GCG AGC TGG ATC AGT AAC GTA GCA ATC ATT ACA TCT CTG GCG GGG TAT CTG ACC AGC TTC TTC CCC ATC CTG GTA GAC AAA CGC GAA ATG TTT TCTATT GGG GGT CAA GAG GTC ACC CTG GGG CAG CTG CTG ACT TTT GCC GTT TGC ACC ATT CTG TTG TGG GGC ACC CAT GCG AT T TTG GTC GCA TCG ATC AATGGC GCA AGC AAG CTG AAT TTT GTG ACC AC A TTA TCC AAG GTC TTG GGA TTC GTG TTT TTC ATT GTG GCA GGG TTA T TC GTC TTC CAG ACG ACG CTT TTTGGT CAT TTC TAT TTC CCG GTC CAA G GC GAG AAT GGA ACG AGC ATC GGT ATT GGG GGA CAG GTG CAT GAC GCT GCG ATT TCT ACA CTT TGG GCT TTC GTCGGA ATC GAA AGC GCC GTT ATC TTG TCT GGC CGC GCG CGC AGC CAG CGC GAT GTT AAA CGT GCT ACC ATT ACC GGA CTT CTG ATT GCA CTG TCG ATC TATATT ATC GTC ACG TTA ATC ACG ATG GGT GTT TTA CCC CAC GAC AAA TTA GTA GGA AGT GAA AAG CC A TTT GTC GAT GTT TTA TAT GCA ATC GTC GGG AACGCT GGT TCA GTA AT C ATG GCA CTG CTG GCC ATC TTG TGC CTT TTT GGA ACC ATG TTG GGG T GG ATT TTA CTG GCT CGA GAG GTG CCC TAC CAA GCA GCCAAA GCT GGT G AT TTC CCC GCC TTC TTT GCC AAA ACT AAT AAG AAA GGT TCT CCA GTG ATT GCG CTT ATT ACC AAT GTC ATG TCA CAG GTT TTC ATTTTT AGC GTG ATC AGT CGT ACA ATT TCC GAT GCT TTT ACT TTT TTG ACT ACA GCG GCC ACG TTG GCC TAT CTG ATT CCC TAC TTA GTT TCA GCG ATT TATAGT TTG AAA GTG GTT ATT AAA GGC GAA ACC TAT GAC CAG TTG AAA GGC AG T CGT GTA CGT GAT GGT CTT ATC GCT ATC TTG GCA TGT GCA TAC TCA G TCTTC GTA ATC GTG ACG GGT ACC GCC GAT TTG ACG ACC TTT ATT TTA G GT ATT GGG CTT TTT TTT GTG GGC CTT ATC GTG TAC CCA TTT GTC TCG AAG AAGTTT CAA AAG GAG AAG CAG GAA |
| 26 | Lysine Transporter LysP (*Klebsiella*) [007] | ATG ACC ATG ATT GCT ATT GGC GGG TCG ATC GGC ACA GGG CTT TTC GTT GCA TCC GGA GCA ACG ATT AGT CAA GCA GGT CCA GGC GGG GCT CTG CT G TCTTAT ATT CTT ATC GGC TTA ATG GTG TAT TTT CTG ATG ACC TCT CT T GGA GAG CTG GCC GCT TTT ATG CCA GTC TCC GGA TCG TTC GCT ACA A AT GGG CAAAAC TAC GTA GAG GAG GGT TTC GGG TTT GCG CTG GGT GGA A AT TAC TGG TAT AAT TGG GCT GTG ACG ATC GCA GTT GAC TTG GTG GCT TCG CAG CTT GTGATG AGC TAT GGG TTC CCT GAC ACT CCG GGC TGG ATT TGG TCT GCT TTG TTT TTG GGC ATC ATG TTC TTG CTT AAC TGG ATC TCC GTT CGC GGG TTC GGTGAA GCT GAG TAC TGG TTC AGT CTG ATT AAA GTT GCG ACC GTT ATT ATC TTC ATC ATC GTT GGC GTG ATG ATG ATT GTC GG C ATT TTC AAA GGG GCG CAACCG GCT GGA TGG TCC AAC TGG GGT ATC GC T GAC GCC CCA TTT GCG GGG GGC TTC TCG GCG ATG ATT GGC GTT GCC A TG ATT GTC GGT TTT TCC TTT CAGGGT ACA GAG TTA ATT GGA ATT GCT G CT GGT GAA TCC GAG AAT CCT GAG AAA AAT ATT CCA CGT GCG GTA CGT CAG GTA TTC TGG CGC ATT TTA CTG TTTTAT GTT TTT GCA ATC TTG ATT ATC TCG TTG ATC ATC CCT TAT ACT GAC CCA TCC TTA TTG CGT AAC GAT GTG AAG GAT ATT TCC GTG TCT CCC TTC ACGTTG GTA TTT CAG TAT GCT GGG CTG CTT AGT GCC GCT GCG ATC ATG AAC GCA GTC ATT CTT ACG GC T GTA CTG AGC GCT GGA AAC TCG GGA ATG TAC GCTTCA ACA CGC ATG TT A TAT ACC TTG GCA TGT GAC GGG AAA GCA CCG CGT ATC TTT AGC AAG C TT TCC CGT GGC GGT GTG CCA CGC AAT GCT CTG TAT GCAACA ACT GTA A TT GCT GCC TTA TGC TTT CTT ACC AGC ATG TTC GGC AAC CAA ACG GTT TAT CTG TGG TTG CTG AAC ACT TCG GGA ATG ACA GGG TTC ATCGCC TGG CTG GGT ATT GCT ATT TCT CAC TAT CGT TTC CGT CGC GGC TAC GTG CTG CAG GGG AAT GAT ATC AAT AAT CTT CCG TAT CGT TCA GGA TTT TTTCCT CTT GGA CCC ATT TTT GCA TTT GTA TTG TGT TTG ATT ATT ACT CTT GG C CAA AAT TAT GAG GCG TTC TTA AAA GAT ACT ATC GAT TGG GGT GGG G TAGCC GCA ACC TAC ATC GGG ATT CCC TTG TTC CTT GTT ATT TGG TTT G |

-continued

| Sequence Listing | | |
|---|---|---|
| SEQ ID NO: | Gene or Operon | Sequence |
| | | GA TAT AAG TTG GCT AAG GGT ACC CGC TTT GTC CGT TAT TCC GAA ATG ACC TTCCCA GAT CGT TTT AAA CGC |
| 27 | Lysine Exporter (*Pseudomonas*) | ATG AGT ATG GAA GTC TGG CTG GGG TTT TTT GCA GCG TGT TGG GTG ATT AGT TTG TCA CCG GGA GCC GGA GCC ATC GCC TCT ATG TCA TCG GGT TT A CAATAT GGC TTC TGG CGT GGC TAC TGG AAT GCA CTT GGA TTG CAG CT T GGT TTA ATT ATG CAA ATT GCA ATT ATC GCT GCG GGC GTC GGA GCC G TC TTG GCGGCC TCG GCT ACG GCC TTC CAG GTA ATT AAA TGG TTC GGA G TT GGG TAT CTT GTG TAT TTA GCA TAC AAA CAA TGG CGT GCA CTG CCC ATG GAT ATG TCGGAT GAA AGC GGG GTG CGT CCA ATC GGC AAA CCA TTA TCG CTG GTA TTT CGT GGA TTT TTG GTG AAT ATC TCC AAC CCA AAA GCT TTA GTA TTC ATG TTGGCC GTT TTA CCC CAG TTC CTG AAT CCC CAC GCC CCC TTG TTA CCC CAA TAC GTG GCT ATC ACT GTG ACA ATG GTT ACA GT T GAC TTG TTA GTG ATG GCCGGA TAC ACA GGT TTA GCA TCT CAT GTA TT A CGT ATG CTT CGT ACC CCA AAA CAG CAA AAA CGC CTG AAC CGC ACC T TC GCC GGT TTA TTC ATC GGA GCGGCC ACA TTC CTT GCC ACT TTG CGC C GC GCA CCA GTA |
| 28 | Asparaginase (*Escherichia coli*) | ATG CAG AAG AAA TCG ATC TAC GTC GCG TAC ACG GGC GGC ACC ATT GGG ATG CAG CGT TCG GAG CAG GGT TAC ATC CCC GTT TCC GGT CAC TTG CA G CGCCAG CTG GCC TTG ATG CCC GAG TTC CAT CGC CCC GAG ATG CCA GA T TTT ACC ATT CAT GAG TAC ACT CCA CTT ATG GAT TCA TCG GAC ATG A CG CCG GAAGAC TGG CAA CAC ATT GCA GAA GAT ATC AAG GCT CAC TAT G AT GAT TAT GAC GGC TTT GTT ATT TTA CAC GGT ACT GAC ACA ATG GCA TAC ACA GCT TCTGCA CTT TCC TTT ATG CTT GAG AAC CTT GGT AAG CCC GTG ATC GTG ACC GGG TCG CAG ATC CCC CTT GCC GAA TTG CGC AGT GAC GGG CAG ATC AAT CTTCTT AAT GCG TTA TAT GTG GCC GCT AAC TAT CCG ATC AAT GAA GTG ACT TTA TTC TTC AAT AAC CGC TTG TAC CGT GGA AA C CGC ACT ACG AAA GCC CATGCT GAT GGC TTT GAC GCC TTT GCA TCC CC A AAT CTG CCT CCC CTT TTG GAA GCC GGG ATT CAC ATC CGT CGT TTA A AT ACA CCC CCC GCC CCA CAT GGAGAG GGG GAG CTT ATC GTA CAT CCA A TT ACC CCT CAA CCT ATC GGA GTT GTA ACG ATT TAC CCT GGT ATT AGT GCC GAC GTA GTC CGC AAT TTC CTT CGCCAG CCC GTG AAA GCA TTG ATC TTA CGT TCC TAC GGT GTA GGG AAC GCG CCA CAG AAT AAG GCA TTT CTG CAA GAA TTA CAA GAG GCA TCG GAT CGT GGTATC GTG GTA GTC AAC CTG ACA CAG TGC ATG TCA GGT AAA GTT AAT ATG GGT GGA TAC GCA ACC GG G AAT GCA TTA GCT CAT GCA GGG GTA ATT GGA GGCGCT GAT ATG ACG GT C GAA GCT ACC CTG ACG AAG CTT CAT TAT CTG TTA TCC CAG GAG TTG G AC ACC GAG ACC ATT CGC AAA GCT ATG TCT CAG AAC CTTCGC GGT GAG C TT ACT CCC GAT GAC |
| 29 | Asparagine transporter ansp2 (*Mycobacterium bovis*) | ATG CCG CCT CTG GAC ATC ACC GAC GAA CGC TTG ACT CGC GAA GAT ACA GGA TAT CAC AAA GGC CTT CAC TCC CGT CAG CTT CAG ATG ATC GCT CT T GGAGGT GCT ATT GGG ACC GGA CTT TTT CTG GGG GCA GGC GGA CGT CT G GCT TCT GCC GGA CCG GGA TTA TTC TTG GTT TAT GGT ATC TGT GGC A TT TTT GTCTTT CTT ATT CTT CGT GCC TTG GGA GAA CTT GTG CTT CAC C GC CCT AGT TCA GGA TCA TTT GTA TCC TAC GCG GGG GAA TTT TAT GGT GAA AAG GTC GCGTTC GTC GCG GGG TGG ATG TAT TTT TTG AAT TGG GCA ATG ACT GGG ATT GTG GAC ACT ACA GCC ATC GCC CAC TAT TGC CAC TAT TGG CGC GCT TTT CAACCA ATT CCA CAG TGG ACG TTG GCC CTT ATT GCG TTG TTA GTT GTA TTA TCC ATG AAT CTG ATC TCC GTC CGC TTA TTC GG G GAA CTT GAG TTT TGG GCCTCG CTT ATT AAA GTA ATT GCG CTT GTT AC G TTC CTG ATT GTA GGG ACT GTA TTC CTG GCG GGG CGT TAC AAG ATT G AC GGG CAA GAA ACT GGT GTA TCATTA TGG TCA TCT CAT GGC GGA ATC G TT CCT ACG GGG TTA CTG CCC ATT GTC CTT GTG ACC TCT GGA GTT GTG TTC GCA TAC GCA GCC ATC GAG CTG GTAGGA ATC GCA GCC GGG GAG ACG GCC GAA CCA GCC AAA ATC ATG CCC CGC GCA ATC AAT TCG GTC GTC CTT CGT ATT GCG TGT TTT TAT GTG GGA TCT ACGGTG CTT CTG GCG TTG CTT TTA CCA TAC ACG GCT TAT AAG GAG CAC GTA AGT CCC TTC GTA ACA TT T TTC AGC AAA ATT GGA ATT GAT GCC GCG GGG AGTGTA ATG AAC TTG GT A GTG CTT ACG GCA GCG TTA TCT AGT TTG AAC GCT GGT TTG TAT TCC A CA GGA CGC ATC CTG CGC TCA ATG GCG ATC AAC GGC AGCGGA CCA CGC T TT ACG GCA CCC ATG AGT AAA ACC GGT GTT CCT TAT GGC GGT ATC TTG CTT ACA GCA GGT ATC GGT TTA TTG GGA ATC ATT CTT AAT GCGATC AAA CCC TCG CAG GCG TTC GAA ATC GTT TTA CAC ATC GCT GCT ACC GGC GTA ATC GCA GCC TGG GCT ACG ATC GTG GCT TGT CAG TTG CGC TTA CATCGC ATG GCC AAC GCT GGC CAA CTT CAG CGC CCT AAG TTC CGT ATG CCC TT G TCA CCT TTT AGC GGG TAC CTG ACT TTG GCG TTT CTG GCG GGC GTG C TGATT CTG ATG TAT TTC GAT GAG CAG CAC GGG CCC TGG ATG ATC GCC G CG ACA GTA ATT GGG GTT CCT GCC CTT ATT GGG GGT TGG TAC TTG GTT CGT AACCGT GTG ACT GCC GTC GCT CAT CAC GCT ATT GAC CAC ACT AAG AGT GTA GCT GTG GTT CAT TCG GCA GAT CCC ATT |

| SEQ ID NO: | Gene or Operon | Sequence |
|---|---|---|
| 30 | Serine ammonia lyase (Bacillus subtilis) | ATG TCC ATT AAT CAG GAG GCG CTT CAC GTA CTG TTG AAG GAT CCT TTT ATT CAT CGT CTT ATT GAT GCT GAG CCA GTG TTT TGG GCA AAT CCA GG T ATGAAG GAG GGG CTG CTT TTT CAC GCT GAC GAG TGG GAA AGT GAG AT T GCC GAA GCA GAG AAA CGC TTG CGT CGT TTT GCG CCT TAT ATC GCG G AG GTT TTCCCA GAG ACC AAA GAT GCA AAG GGC ATG ATC GAG TCT CCA C TG TTT GAG ATG CAA CAT ATG AAA AAG AAA CTG GAG GCA GCA TAC CAA CAA CCT TTC CCCGGA CGT TGG CTG CTT AAG TGT GAC CAT GAA CTT CCC ATT TCC GGG TCG ATT AAG GCC CGC GGA GGT ATC TAT GAA GTC TTG AAA CAT GCC GAA AAG CTGGCT CTT CAG GAG GGG ATG CTT CAA GAG TCG GAC GAT TAT CGT ATG TTG CAA GAA GAT CGT TTC GCG GCC TTC TTC AGC CG C TAT TCT ATC GCA GTG GGCTCC ACG GGC AAT TTA GGT TTA AGT ATC GG G ATT ATT GGC GCT GCT CTT GGT TTC CGC GTA ACA GTT CAC ATG AGT G CT GAC GCT AAG CAA TGG AAG AAAGAT CTG TTA CGT CAG AAA GGG GTA A CC GTA ATG GAA TAT GAG AGC GAT TAT TCA GAA GCA GTT AAA GAA GGT CGT CGC CAA GCA GAA CAA GAC CCA TTCTGT TAC TTC ATT GAT GAT GAA CAT AGC CGT CAA TTG TTC CTG GGC TAC GCA GTT GCC GCG TCC CGC CTT AAG ACA CAA CTG GAT TGC ATG GAA ATC CAACCT GGT CCC GAA ACA CCC CTG TTC GTG TAT CTT CCC TGT GGC GTA GGT GGG GGG CCA GGA GGT GT C GCT TTC GGG TTG AAA CTG CTG TAT GGA GAT CACGTC CAT GTA TTT TT C GGA GAA CCG ACG CAA TCC CCG TGC ATG CTT TTA GGC TTA TAT TCT G GC TTA CAC GAG CAG ATT TCA GTT CAA GAC ATT GGA TTGGAC AAC CGT A CC GCG GCG GAT GGC TTG GCG GTA GGG CGT CCC TCA GGA TTC GTA GGA AAA TTA ATC GAA CCA CTG CTG TCG GGC TGC TAT ACT GTA GAAGAC GAT ACA CTG TAT GCT TTA CTG CAC ATG CTG GCA GCT TCG GAA TCC AAG TAT CTT GAA CCT AGC GCC TTG GCG GGG ATG TTC GGC CCG ATC CAG CTGTTC AGC ACA GAA GAA GGA CGT CGC TAT TCT CAG AAA CAT AAA ATG GAG CA T GCG GTG CAC GTT ATC TGG GGG ACG GGG GGT AGC ATG GTG CCA AAG G AGGAG ATG GCC GCA TAC AAC CGC ATC GGG GCG GAT CTG TTA AAA AAT G AA ATG AAG AAG |
| 31 | SdaA (Pseudomonas fluorescens F113) | ATG TCC CTT TCA GTG TTT GAT CTT TTT AAG ATC GGA ATT GGT CCC TCG TCC TCT CAT ACC GTA GGA CCT ATG CGT GCG GCC GCT CGT TTT GCC GA A GGTCTG CGC CGC GAC GAC CTG CTG AAC TGT ACT ACT AGC GTG AAA GT C GAG CTG TAC GGA TCT CTG GGC GCG ACT GGT AAA GGG CAC GGT TCG G AC AAA GCAGTG TTA CTG GGA TTG GAG GGA GAA CAC CCT GAC ACT GTC G AC ACC GAG ACG GTT GAC GCT CGT TTA CAG GCG ATC CGC AGT TCA GGC CGC CTG AAT TTATTG GGG GAG CAT AGC ATT GAG TTT AAT GAA AAG CTG CAC TTG GCA ATG ATT CGC AAG CCG TTA GCT TTC CAT CCG AAT GGC ATG ATT TTC CGT GCG TTTGAT GCT GCG GGC TTA CAG GTA CGT TCC CGT GAG TAT TAC TCC GTC GGC GGA GGG TTC GTT GTA GAC GAG GAC GCA GCG GG T GCC GAC CGT ATC GTC GAGGAT GCA ACA CCT TTG ACA TTC CCC TTC AA G AGC GCG AAG GAT CTT TTA GGT CAT TGT TCT ACT TAT GGT TTA AGC A TC AGC CAA GTC ATG CTT ACA AACGAG TCT GCG TGG CGT CCG GAA GCG G AG ACC CGC GCA GGG CTT CTT AAA ATT TGG CAG GTG ATG CAA GAC TGC GTT GCC GCG GGG TGT CGC AAT GAG GGCATC CTT CCA GGA GGT CTT AAA GTA AAG CGC CGC GCG GCT GCG TTG CAT CGT CAA TTG TGT AAG AAC CCC GAG GCT GCC CTG CGC GAT CCG TTA AGT GTATTA GAT TGG GTG AAT TTG TAT GCG TTA GCG GTA AAT GAA GAG AAC GCC TAC GGT GGA CGC GTG GT C ACG GCG CCC ACT AAT GGA GCC GCA GGA ATC ATTCCT GCC GTA TTG CA T TAC TAC ATG CGC TTT ATT CCG GGG GCA TCT GAG GAC GGA GTA GTC C GC TTC CTT CTT ACA GCG GCG GCA ATC GGG ATC TTG TATAAA GAG AAC G CC TCT ATT AGT GGG GCT GAG GTT GGC TGT CAG GGC GAA GTA GGA GTG GCA TGC TCC ATG GCA GCG GGG GCG TTG TGC GAA GTC TTG GGAGGC TCG GTC CAA CAA GTA GAA AAC GCA GCA GAA ATC GGA ATG GAG CAT AAC CTT GGC TTG ACA TGT GAT CCT ATC GGC GGG TTA GTA CAG GTC CCG TGTATC GAG CGT AAC GCA ATG GGA TCT GTT AAA GCC ATT AAC GCA GTA CGC AT G GCT ATG CGC GGG GAC GGT CAC CAT TTC GTC TCC CTT GAC AAA GTA A TTCGT ACC ATG CGT CAA ACT GGG GCC GAC ATG AAA AGC AAG TAC AAG G AA ACC GCG CGT GGT GGA CTT GCT GTC AAC ATC ATC GAG TGT |
| 32 | sdaB (Klebsiella pneumoniae) | ATG ATT AGT GTG TTT GAC ATC TTT AAA ATC GGT ATC GGT CCG TCT TCT TCC CAT ACG GTT GGT CCC ATG AAA GCA GGG AAG CAG TTT ACC GAC GA C TTAATT GCT CGT GGA CTG CTG GCA GAG GTC AGT AAG GCG GTG GTT GA T GTT TAT GGC TCC CTT TCA TTG ACG GGC AAA GGT CAC CAT ACT GAC A TT GCT ATCATT ATG GGT CTG GCG GGA AAC TTG CCA GAC ACC GTT GAC A TC GAC GCC ATC CCC GGC TTC ATC CAA GAT GTT AAC ACT CAC GGA CGT CTG ATG TTA GCGAAT GGG CAG CAT GAA GTT GAT TTC CCG GTA GAC GAG TGT ATG AAT TTT CAC GCT GAC AAC CTG TCC TTG CAC GAG AAT GGA ATG CGT ATT ACG GCT CTTGCG GGA GAC AAA GTG TTG TAC TCT CAG ACT TAC TAC TCA ATC GGC GGC GGA TTC ATT GTT GAT GAG GAA CAT TTT GGC CA A ACA ACG GAG GCT CCT GTAGCC GTC CCA TAT CCA TAC AAA AAC GCC GC T GAT TTG CAG CGT CAT TGC CGT GAA ACT GGT TTG AGT TTA TCT GGA C TT ATG ATG CAA AAC GAA CTT GCATTG CAT AGC AAA GAA GCT CTG GAA C |

| SEQ ID NO: | Gene or Operon | Sequence |
|---|---|---|
| | | AG CAC TTT GCT GCA GTT TGG GAG GTT ATG TCT GCC GGC ATT GAG CGC GGC ATT ACA ACT GAA GGT GTG TTG CCTGGC AAA TTA CGT GTA CCC CGC CGC GCC GCG GCA CTG CGT CGT ATG TTA GTC TCG CAA GAC ACG ACG AAC TCG GAC CCT ATG GCT GTT GTA GAT TGG ATCAAT ATG TTC GCG TTG GCC GTC AAC GAG GAG AAC GCG GCG GGC GGT CGC GTT GTT ACA GCC CCC AC A AAT GGC GCG TGC GGA ATT GTT CCG GCC GTG CTGGCA TAT TAT GAC AA A TTT ATC CGC AAA GTC AAC TCC AAC AGT CTG GCG CGT TAT ATG CTG G TG GCA AGT GCA ATC GGC TCA CTT TAT AAG ATG AAT GCGAGC ATC TCC G GC GCA GAA GTT GGC TGC CAA GGT GAA GTG GGG GTC GCC TGC TCT ATG GCA GCG GCT GGC TTG GCA GAG CTG TTG GGC GGG TCG CCA GGGCAA GTG TGC ATT GCG GCT GAA ATT GCG ATG GAG CAT AAC TTG GGC CTT ACG TGC GAT CCC GTA GCT GGC CAA GTG CAG GTA CCG TGT ATC GAA CGC AATGCA ATT GCA GCC GTA AAA GCA GTA AAT GCG GCT CGC ATG GCC TTA CGT CG T ACT TCC GAG CCC CGT GTG TGC TTG GAT AAG GTG ATC GAA ACC ATG T ATGAG ACA GGT AAG GAC ATG AAT GCA AAG TAT CGT GAA ACG TCT CGT G GA GGC CTG GCC ATG AAG ATC GTC GCG TGT GAC |
| 33 | tdcG L-serine dehydratase (*Escherichia coli* O157: H7 str. SS17) | ATG ATT AGT GCA TTC GAT ATT TTC AAG ATT GGA ATC GGC CCC TCG TCA TCG CAC ACG GTG GGC CCA ATG AAC GCA GGT AAG TCC TTC ATT GAT CG C CTTGAG TCG AGT GGC TTA TTG ACA GCG ACA AGC CAC ATT GTC GTG GA C CTG TAC GGG AGT CTG TCG TTG ACG GGC AAA GGC CAT GCG ACC GAT G TT GCT ATTATC ATG GGA TTG GCC GGG AAT TCA CCG CAG GAC GTA GTA A TC GAT GAA ATC CCG GCC TTC ATT GAG CTG GTA ACT CGT TCG GGC CGT CTG CCA GTC GCAAGC GGA GCT CAT ATC GTT GAC TTC CCA GTT GCC AAG AAC ATT ATT TTT CAC CCT GAA ATG TTA CCT CGC CAT GAG AAC GGA ATG CGT ATC ACA GCA TGGAAA GCT CAG GAA GAA TTA TTG AGT AAG ACG TAT TAC TCG GTT GGT GGC GGG TTC ATC GTC GAG GAA GAG CAC TTC GGT TT A TCT CAT GAC GTA GAA ACACCA GTA CCA TAC GAC TTC CAT TCA GCA GG T GAG TTG TTG AAA ATG TGC GAT TAC AAT GGC CTT AGT ATT TCG GGA C TT ATG ATG CAT AAC GAA TTA GCGCTT CGT TCG AAG GCC GAA ATT GAC G CC GGC TTC GCA CGT ATC TGG CAA GTT ATG CAT GAT GGC ATC GAA CGT GGT ATG AAC ACC GAA GGT GTG TTA CCAGGA CCC TTG AAT GTT CCG CGT CGT GCA GTC GCA CTG CGT CGT CAA CTT GTT AGT AGT GAC AAC ATT TCC AAT GAT CCA ATG AAC GTG ATT GAC TGG ATCAAC ATG TAC GCG CTG GCG GTC TCG GAG GAA AAC GCC GCT GGG GGT CGC GTG GTA ACA GCA CCT AC G AAT GGG GCT TGC GGG ATC ATC CCT GCG GTA TTGGCC TAT TAC GAT AA G TTT CGC CGT CCA GTC AAT GAG CGC TCA ATC GCT CGT TAC TTC CTG G CG GCG GGG GCT ATC GGC GCT TTA TAC AAG ATG AAC GCCTCT ATT TCA G GG GCG GAG GTC GGT TGT CAA GGA GAG ATT GGG GTC GCG TGC TCT ATG GCA GCT GCA GGT TTG ACA GAA TTA TTA GGC GGC AGC CCA GCCCAA GTT TGC AAC GCG GCT GAA ATC GCA ATG GAA CAT AAT CTT GGT CTG ACC TGT GAC CCT GTC GCA GGT CAG GTA CAG ATT CCT TGC ATT GAG CGT AATGCA ATC AAC GCA GTA AAA GCT GTT AAT GCG GCG CGT ATG GCT ATG CGT CG C ACA TCA GCC CCG CGT GTG AGC CTG GAT AAG GTA ATC GAG ACC ATG T ACGAA ACC GGT AAA GAC ATG AAT GAC AAA TAC CGC GAA ACC TCT CGC G GG GGT CTT GCA ATT AAA GTC GTG TGT GGC |
| 34 | glyA (*Escherichia coli* EPEC C342-62) | ATG TTG AAA CGT GAG ATG AAT ATT GCC GAC TAT GAT GCA GAA TTA TGG CAA GCT ATG GAA CAA GAG AAA GTC CGC CAG GAA GAA CAT ATT GAA TT A ATCGCC TCT GAA AAT TAC ACT AGT CCC CGC GTT ATG CAA GCC CAA GG C AGC CAA TTA ACT AAC AAA TAT GCC GAG GGA TAT CCT GGG AAA CGC T AC TAT GGAGGT TGC GAG TAT GTA GAT ATT GTC GAA CAG TTA GCA ATC G AC CGC GCG AAA GAG CTT TTC GGC GCA GAC TAT GCA AAC GTG CAG CCC CAT TCG GGT AGCCAA GCG AAT TTT GCG GTC TAT ACC GCA CTG CTG GAA CCG GGA GAC ACG GTA CTG GGT ATG AAT TTA GCT CAT GGT GGT CAC TTA ACG CAC GGG TCC CCCGTT AAT TTC TCT GGA AAA CTG TAC AAC ATC GTC CCC TAT GGA ATC GAT GCT ACC GGC CAC ATT GAT TAC GCG GAT CTT GA G AAG CAA GCT AAG GAA CATAAA CCA AAG ATG ATC ATT GGC GGT TTT TC A GCT TAT AGT GGT GTC GTC GAC TGG GCT AAG ATG CGT GAA ATT GCA G AC TCT ATT GGC GCG TAC CTT TTTGTC GAC ATG GCC CAC GTG GCT GGC T TG GTG GCG GCA GGG GTC TAC CCG AAC CCC GTT CCC CAT GCG CAT GTC GTG ACC ACC ACG ACA CAT AAG ACA CTGGCT GGG CCT CGT GGT GGC TTA ATC TTG GCC AAG GGG GGG TCT GAG GAA TTA TAC AAA AAA CTT AAC TCA GCC GTT TTT CCA GGC GGA CAG GGT GGT CCGTTG ATG CAC GTG ATT GCT GGA AAG GCG GTC GCT CTT AAG GAA GCC ATG GAA CCT GAA TTC AAA AC G TAC CAA CAG CAG GTT GCA AAA AAC GCC AAA GCGATG GTT GAG GTT TT C CTG GAA CGT GGT TAC AAA GTC GTT AGT GGG GGT ACC GAT AAT CAT C TT TTC TTA GTT GAC CTG GTA GAT AAA AAT TTG ACC GGAAAG GAG GCG G AC GCT GCC TTA GGC CGT GCG AAT ATT ACC GTC AAT AAA AAC TCG GTG CCA AAT GAT CCC AAG TCG CCT TTC GTG ACT TCA GGA ATC CGCGTA GGA ACT CCC GCA ATT ACA CGC CGC GGG TTC AAG GAA GCT GAG GCG AAG GAG |

| SEQ ID NO: | Gene or Operon | Sequence |
|---|---|---|
| | | TTA GCA GGA TGG ATG TGT GAT GTT TTA GAC TCG ATT AAC GAT GAGGCG GTG ATC GAA CGT ATC AAA GGT AAA GTA TTA GAT ATT TGC GCC CGT TA T CCA GTT TAT GCC |
| 35 | SdaC serine STP transporter (*Escherichia coli* BL21 (DE3) | ATG GAG ACC ACG CAG ACT TCT ACA ATT GCG AGC AAA GAT AGC CGT TCT GCT TGG CGC AAA ACT GAT ACT ATG TGG ATG TTG GGC CTG TAT GGA ACA GCTATT GGG GCC GGG GTA CTG TTT TTG CCA ATC AAT GCT GGA GTG GGG GGT ATG ATC CCG CTG ATC ATT ATG GCG ATT CTT GCT TTC CCA ATG ACA TTT TTTGCA CAT CGC GGT CTT ACA CGC TTT GTC CTT TCA GGA AAG AAT CCT GGG GAG GAC ATT ACG GAG GTT GTA GAA GAA CAT TTT GGC ATT GGG GCT GGG AAACTT ATC ACA TTG CTG TAT TTT TTT GCA ATC TAT CCC ATT TTG CTT GTC TAT AGC GTA GCA ATC ACG AAC ACC GTA GAA TCA TTC ATG TCG CAC CAG TTAGGC ATG ACA CCT CCG CCA CGT GCG ATT CTG TCA TTG ATC TTG ATC GTG GGA ATG ATG ACA ATT GTT CGT TTC GGA GAG CAA ATG ATC GTG AAA GCC ATGTCA ATT TTG GTA TTT CCG TTC GTG GGA GTC TTA ATG TTG CTG GCA TTG TAT TTA ATT CCC CAG TGG AAT GGT GCC GCT CTG GAG ACC TTG TCG TTG GATACG GCG TCA GCG ACC GGT AAT GGT CTT TGG ATG ACG CTT TGG TTG GCC ATT CCG GTC ATG GTT TTT TCA TTT AAC CAC TCA CCG ATC ATT AGC TCG TTCGCT GTG GCG AAA CGC GAA GAA TAC GGT GAT ATG GCT GAA CAA AAG TGC TCG AAG ATT TTG GCA TTC GCC GAC ATC ATG ATG GTA CTT ACG GTC ATG TTCTTC GTG TTT TCT TGC GTC CTT AGT TTA ACC CCA GCG GAC CTG GCG GCT GCA AAG GAA CAA AAT ATC AGC ATC TTA AGC TAT TTG GCG AAT CAT TTC AACGCG CCT GTT ATC GCA TGG ATG GCA CCC ATT ATC GCT ATC ATT GCA ATT ACC AAA TCT TTC TTA GGG CAC TAC TTG GGT GCG CGC GAA GGA TTT AAC GGGATG GTT ATC AAG TCG CTT CGT GGG AAA GGA AAG AGT ATC GAG ATC AAT AAA CTT AAT CGC ATC ACC GCC TTG TTC ATG TTA GTA ACA ACG TGG ATC GTCGCT ACA CTT AAT CCC TCC ATT CTG GGG ATG ATT GAA ACG CTT GGG GGT CCA ATC ATC GCA ATG ATC TTG TTT CTG ATG CCG ATG TAC GCT ATC CAG AAGGTA CCC GCA ATG CGT AAA TAC TCT GGG CAT ATC TCC AAC GTG TTT GTT GTT GTT ATG GGA TTA ATC GCT ATT TCT GCT ATC TTC TAT AGT CTG TTC TCC |
| 36 | threonine Serine Exporter (*Lactobacillus saniviri* JCM 17471 = DSM 24301) | ATG GCG TAT TCT GTC CAG TTC CTG ATC CAA CTG TCC TTC TCG TAC CTT GCC ACT GTG GCT TTT GCT ATC TGC ATC AAC GTT CCA CGT CGT GCG TT A AATTTT GCC GGA TGG GCC GGT GCC ATC GGG TGG ATC TGC TAC TGG CT G CTG AAC ACA CAT GGC ACG GGC CGC ATG TTC GCT AAC CTG ATT GGC G CT GTC GCAGTT GGG GTA TGT GGT ATC ATT TTC GCT CGC ATC AAG AAG A TG CCC GTG ATT ATT TTC AAT ATT CCG GGG CTG GTG CCA TTA GTG CCT GGA GCA ACC GCCTAC CAG GCA GTT CGC GCT CTT GCG TTG GGA AAT ATG GAC CTT GCT ATC CAG CTT GGA GTT CGT GTT ATT ATG GTC GCA GGG GCA ATC GCG GTG GGA TTCATG GTT AGT CAG CTT CTG TCA GAG TTG ACT TAC CGC TTG CAC |
| 37 | glutaminase YbaS (*Escherichia coli* ST131) | ATG CTG GAT GCT AAT AAG CTG CAG CAG GCT GTC GAT CAG GCT TAT ACT CAA TTT CAT TCT TTG AAT GGT GGG CAG AAT GCC GAT TAC ATT CCT TT C TTGGCT AAT GTC CCA GGG CAA TTA GCA GCC GTA GCT ATT GTA ACA TC C GAT GGC AAC GTG TAT TCT GCC GGG GAC TCG GAC TAC CGC TTC GCA C TT GAG TCTATC AGT AAA GTC TGC ACT TTG GCA CTG GCG CTG GAG GAC G TT GGG CCT CAG GCC GTG CAG GAC AAG GTT GGG GCT GAT CCT ACA GGG CTG CCA TTC AACTCA GTA ATT GCT TTG GAA TTA CAC GGT GGA AAA CCA CTG TCA CCG CTG GTG AAC GCG GGG GCA ATC GCT ACC ACG TCT TTG ATT AAT GCA GAA AAT ACGGAA CAG CGT TGG CAA CGT ATT TTG CAT ATT CAG CAG CAG CTT GCT GGT GAG CAA GTC GCA CTT TCT GAT GAA GTG AAC CA A AGT GAA CAA ACT ACT AATTTT CAC AAC CGT GCA ATT GCT TGG TTA CT G TAC AGT GCT GGC TAC TTG TAC TGT GAC GCA ATG GAA GCC TGT GAT G TT TAT ACA CGT CAG TGC AGT ACTTTG ATC AAC ACA ATC GAA TTG GCA A CA TTG GGA GCT ACG TTA GCC GCT GGG GGC TTG ACA CAT AAA CGC GTT CTG CAA GCG GAC AAT GTGCCC TAT ATT TTG GCT GAA ATG ATG ATG GAA GGG CTT TAT GGC CGC TCT GGG GAC TGG GCC TAC CGT GTA GGC TTG CCA GGA AAG TCG GGG GTC GGA GGAGGG ATT CTG GCC GTG GTG CCC GGC GTA ATG GGA ATT GCC GCG TTT CGC CCT CCC TTA GAC GAA GA A GGT AAC AGC GTG CGC GGA CAA AAG ATG GTT GCGAGC GTT GCA AAG CA G CTT GGG TAT AAC GTA TTT AAA GGG |
| 38 | Glutaminase (*Escherichia coli* o145: H28 str. RM12581) | ATG GCC GTC GCA ATG GAT AAC GCC ATT TTA GAG AAT ATC CTG CGC AA GTG CGC CCA TTA ATC GGA CAA GGC AAG GTT GCG GAT TAC ATT CCG GC C TTAGCT ACA GTG GAT GGG AGT CTG CGA ATC GCT ATT TGC ACT GT T GAC GGC CAA TTG TTT CAG GCA GGC GAC GCA CAA GAG CGC TTC TCC A TC CAG AGCATT TCT AAA GTG TTG TCA TTG GTT GTT GCT ATG CGT CAC T AC TCT GAG GAG GAA ATT TGG CAG CGC GTG GGG AAG GAC CCG TCC GGC AGT CCA TTT AATTCG TTG GTA CAG TTG GAG ATG GAA CAA GGA ATC CCT CGT AAT CCC TTC ATC AAT GCA GGT GCT CTT GTA GTC TGC GAC ATG TTA CAA GGT CGT TTA TCTGCC CCT CGC CAA CGC ATG TTG GAA GTT GTG CGT |

| SEQ ID NO: | Gene or Operon | Sequence |
|---|---|---|
| | | GGT TTG TCT GGA GTT AGC GAT ATC AGC TAC GAC ACG TCG TGG CTC CG<br>C AGT GAA TTT GAA CAC TCAGCA CGC AAT GCA GCG ATT GCG TGG TTA AT<br>G AAG TCG TTT GGG AAT TTT CAT CAC GAT GTG ACG ACA GTC CTT CAA A<br>AT TAT TTC CAC TAC TGC GCA TTGAAG ATG TCG TGC GTA GAG CTT GCC C<br>GT ACG TTC GTC TTT CTT GCG AAC CAG GGC AAG GCC ATC CAT ATC GAC<br>GAG CCC GTC GTA ACC CCG ATG CAG GCGCGT CAA ATC AAT GCG CTG ATG<br>GCG ACA TCG GGA ATG TAT CAG AAT GCG GGG GAG TTC GCC TGG CGT GTC<br>GGA TTA CCA GCT AAA TCC GGT GTA GGC GGTGGA ATC GTT GCC ATT GTG<br>CCC CAT GAA ATG GCT ATC GCT GTG TGG TCC CCA GAA TTA GAT GAC GC<br>A GGA AAT TCG TTA GCA GGT ATT GCG GTT TTA GAACAA CTT ACG AAA CA<br>A TTA GGA CGC TCG GTG TAT |
| 39 | ylaM<br>(Bacillus<br>subtilis<br>subsp.<br>subtilis<br>str. 168) | ATG GTG TGT CAG CAT AAT GAT GAA TTA GAG GCT CTT GTC AAG AAG GCA<br>AAA AAG GTT ACG GAT AAG GGG GAG GTG GCT AGT TAC ATT CCA GCT CT<br>G GCTAAG GCG GAC AAA CAC GAC TTA AGT GTC GCA ATC TAC TAT AGC AA<br>T AAT GTG TGC CTG TCC GCA GGG GAC GTT GAA AAG ACG TTC ACT CTG C<br>AA TCC ATCAGC AAA GTT CTG TCG TTA GCT CTG GTA CTT ATG GAG TAT G<br>GG AAG GAT AAG GTA TTC AGT TAT GTT GGG CAG GAA CCT ACA GGT GAT<br>CCC TTT AAC AGCATC ATT AAA CTG GAG ACA GTC AAC CCC TCT AAG CCA<br>TTA AAT CCG ATG ATC AAT GCG GGC GCG TTA GTA GTG ACC AGT CTT ATC<br>CGC GGA CGT ACG GTGAAG GAG CGT CTT GAC TAT CTT CTT AGC TTT ATC<br>CGT CGT CTG ACT AAT AAT CAA GAA ATT ACA TAC TGC CGC GAG GTA GC<br>G GAA AGC GAA TAT TCT ACTTCA ATG ATT AAC CGT GCG ATG TGC TAT TA<br>T ATG AAA CAG TAT GGA ATT TTC GAA GAT GAC GTT GAA GCG GTT ATG G<br>AC CTT TAT ACA AAG CAA TGC GCTATT GAA ATG AAC TCA CTT GAT TTG G<br>CT AAG ATC GGT TCG GTT TTC GCC TTG AAC GGA CGC CAT CCT GAA ACC<br>GGG GAG CAA GTG ATT TCG AAG GAT GTAGCC CGT ATC TGT AAG ACG TTT<br>ATG GTG ACG TGT GGA ATG TAT AAT GCC TCT GGT GAA TTT GCG ATC AAA<br>GTT GGT ATC CCT GCG AAA TCG GGA GTG TCAGGT GGG ATT ATG GGT ATC<br>TCC CCT TAC GAT TTC GGA ATC GGG ATC TTT GGA CCC GCG CTG GAC GA<br>G AAG GGG AAT AGT ATT GCT GGT GTG AAG CTT TTAGAA ATC ATG AGC GA<br>G ATG TAC CGT CTT AGT ATC TTT |
| 40 | ybgJ (Bacillus<br>subtilis) | ATG AAA GAG TTG ATT AAA GAG CAT CAA AAG GAT ATC AAT CCT GCA TTA<br>CAA CTG CAT GAC TGG GTA GAA TAC TAC CGT CCA TTT GCG GCA AAT GG<br>C CAAAGT GCA AAC TAT ATC CCC GCT TTA GGG AAG GTG AAC GAC AGC CA<br>G TTA GGG ATC TGC GTA CTG GAA CCG GAT GGC ACC ATG ATT CAC GCT G<br>GG GAT TGGAAT GTG TCC TTT ACC ATG CAG TCG ATT TCA AAA GTA ATT A<br>GC TTC ATT GCT GCC TGC ATG TCG CGT GGA ATC CCG TAT GTC TTG GAT<br>CGT GTA GAC GTGGAA CCC ACA GGA GAT GCT TTT AAT AGT ATC ATC CGT<br>TTA GAG ATC AAC AAA CCA GGA AAG CCT TTC AAT CCT ATG ATT AAT GCC<br>GGA GCT TTG ACT ATCGCT AGC ATT CTT CCA GGA GAG TCC GCT TAC GAA<br>AAA CTT GAG TTT TTG TAT AGC GTG ATG GAG ACT TTA ATC GGT AAA CG<br>C CCC CGT ATT CAC GAA GAAGTA TTC CGT TCT GAA TGG GAG ACC GCT CA<br>T CGC AAT CGC GCC TTA GCC TAC TAT CTT AAA GAA ACA AAC TTC TTA G<br>AG GCC GAG GTC GAA GAG ACA CTGGAA GTA TAT TTG AAA CAA TGC GCG A<br>TG GAA TCG ACC ACG GAA GAC ATC GCC CTG ATC GGG TTG ATC CTG GCC<br>CAC GAT GGG TAT CAT CCT ATC CGT CATGAG CAG GTC ATT CCC AAG GAT<br>GTT GCC AAG TTG GCT AAA GCG TTA ATG TTG ACC TGT GGC ATG TAT AAC<br>GCT TCT GGA AAG TAT GCG GCT TTC GTT GGAGTA CCC GCA AAA TCT GGA<br>GTT TCG GGT GGT ATT ATG GCC TTG GTG CCT CCA AGT GCG CGT CGC GA<br>A CAG CCG TTC CAG AGC GGG TGC GGT ATC GGG ATTTAT GGA CCT GCA AT<br>T GAT GAG TAC GGG AAT AGC CTG ACG GGC GGC ATG CTT TTA AAA CAC A<br>TG GCC CAA GAG TGG GAA CTG AGT ATT TTC |
| 41 | Glutamine<br>permease<br>glnHPQ<br>operon<br>(Escherichia<br>coli)<br>GenBank:<br>X14180.1 | CCATGGCAGAACGTGCAGTGCAGCTGGGCGGTGTAGCTCTGGGGACCACTCAAGTTATCAACA<br>GCAAAACCCCGCTGAAAAGTTACCCGCTGGACATCCACAACGTTCAGGATCACCTGAAAGAAC<br>TGGCTGACCGTTACGCAATCGTCGCTAATGACGTACGCAAAGCGATTGGCGAAGCGAAAGATG<br>ACGACACCGCAGATATCCTGACCGCCGCGTCTCGCGACCTGGATAAATTCCTGTGGTTTATCG<br>AGTCTAACATCGAATAAATCCATCGCTGATGGTGCAGAACTTTAGTACCCGATAAAAGCGGCT<br>TCCTGACAGGAGGCCGTTTTGTTTTGCAGCCCACCTCAACGCACTTATTTAGTGCATCCATCT<br>GCTATCTCCAGCTGATTAAGTAAATTTTTTGTATCCACATCATCACACATCGTTACATAAAG<br>ATTGTTTTTTCATCAGGTTTTACGCTAAATAATCACTGTGTTGAGTGCACAATTTTAGCGCAC<br>CAGATTGGTGCCCCAGAATGGTGCATCTTCAGGGTATTGCCCTATAAATCGTGCATCACGTTT<br>TTGCCGCATCTCGAAAAATCAAGGAGTTGCAAAACTGGCACGATTTTTTCATATATGTGAATG<br>TCACGCAGGGGATCGTCCCGTGGATAGAAAAAAGGAAATGCTATGAAGTCTGTATTAAAAGTT<br>TCACTGGCTGCACTGACCCTGGCTTTTGCGGTTTCTTCTCATGCCGCGGATAAAAAATTAGTT<br>GTCGCGACGGATACCGCCTTCGTTCCGTTTGAATTTAAACAGGGCGATAAATATGTGGGCTTT<br>GACGTTGATCTGTGGGCTGCCATCGCTAAAGAGCTGAAGCTGGATTACGAACTGAAGCCGATG<br>GATTTCAGTGGGATCATTCCGGCACTGCAAACCAAAACGTCGATCTGGCGCTGGCGGGCATT<br>ACCATCACCGACGAGCGTAAAAAAGCGATCGATTTCTCTGACGGCTACTACAAAAGCGGCCTG<br>TTAGTGATGGTGAAAGCTAACAATAACGATGTGAAAGCGTGAAAGATCTCGACGGGAAGTG<br>GTTGCTGTGAAGAGCGGTACTGGCTCCGTTGATTACGCGAAAGCAAACATCAAAACTAAAGAT |

| SEQ ID NO: | Gene or Operon | Sequence |
|---|---|---|
| | | CTGCGTCAGTTCCCGAACATCGATAACGCCTATATGGAACTGGGCACCAACCGCGCAGACGCC<br>GTTCTGCACGATACGCCAAACATTCTGTACTTCATCAAAACCGCCGGTAACGGTCAGTTCAAA<br>GCGGTAGGTGACTCTCTGGAAGCGCAGCAATACGGTATTGCGTTCCCGAAAGGTAGCGACGAG<br>CTGCGTGACAAAGTCAACGGCGCGTTGAAAACCCTGCGCGAGAACGGAACTTACAACGAAATC<br>TACAAAAAATGGTTCGGTACTGAACCGAAATAATAACGCTACACCTGTAAAACGCACTGGCAG<br>TTCCCTCTCCCTATGGGGAGAGGATTAGGGTGAGGGGCGCAAACCCGCTCCGGGGCCATTAA<br>TTACCCTGAATTTGATTATTTACACCACGGTAACAGGAACAACATATGCAGTTTGACTGGAGT<br>GCCATCTGGCCTGCCATTCCGCTTCTGATTGAAGGTGCCAAAATGACCCTGTGGATTTCGGTC<br>CTCGGTCTGGCAGGCGGTCTGGTAATCGGATTGCTGGCAGGTTTTGCACGCACCTTCGGAGGT<br>TGGATAGCCAACCACGTCGCGCTGGTCTTTATTGAAGTGATCCGCGGCACACCTATCGTCGTC<br>CAGGTGATGTTTATTTATTTCGCCCTGCCGATGCGCGTTTAACGACTTACGCATCGACCCATTT<br>ACTGCGGCGGTGGTCACCATCATGATCAACTCCGGCGCGTATATTGCGGAAATCACGCGTGGT<br>GCGGTGCTGTCTATCCACAAAGGTTTTCGTGAAGCAGGACTGGCGCTCGGTCTTTCACGTTGG<br>GAAACCATTCGCTACGTCATTTTACCGCTGGCACTGCTCGTATGCTGCCGCCGCTGGGTAAC<br>CAGTGGATCATCAGCATTAAAGACACCTCGCTGTTTATTGTGATCGGCGTGGCGGAACTGACC<br>CGTCAGGGGCAAGAAATTATTGCCGGTAACTTCCGCGCCCTTGAGATCTGGAGCGCCGTGGCG<br>GTGTTCTATCTGATTATTACCCTGGTGCTGAGCTTTATTCTGCGTCGTCTGGAAAGAAGGATG<br>AAAATCCTGTGATTGAATTTAAAAACGTCTCCAAGCACTTTGGCCCAACCCAGGTGCTGCACA<br>ATATCGATTTGAACATTGCCCAGGGCGAAGTCGTGGTGATTATCGGGCCGTCCGGTTCCGGTA<br>AATCGACCCTGCTCGCGCTGCATCAACAAACTGGAAGAAATCACCTCCGGCGATCTGATTGTCG<br>ATGGCCTGAAGGTTAACGATCCGAAAGTTGACGAGCGCCTGATTCGCCAGGAAGCAGGTATGG<br>TGTTCCAGCAGTTTTACCTCTTCCCGCATCTGACAGCGCTGGAAAACGTCATGTTTGGCCCGC<br>TACGCGTGCGTGGCGCGAACAAAGAAGAGGCGGAAAAACTGGCACGTGAGCTGCTGGCGAAAG<br>TCGGTCTGGCAGAACGTGCACATCACTACCCTTCCGAACTTTCTGGTGGTCAACAGCAGCGTG<br>TGGCGATTGCCCGCGCGCTGGCGGTGAAGCCGAAAATGATGCTGTTTGATGAACCGACTTCCG<br>CTCTTGACCCGGAACTGCGCCATGAAGTGCTGAAGGTTATGCAGGATCTGGCTGAAGAAGGGA<br>TGACGATGGTGATCGTGACCCACGAAATCGGTTTTGCCGAGAAAGTAGCTTCGCGGCTGATCT<br>TTATCGACAAAGGCCGGATTGCGGAAGATGGCAATCCGCAGGTGTTGATCAAGAACCCGCCGA<br>GCCAGCGCTTGCAGGAATTTTTGCAGCACGTCTCTTAATAAGACACATTGCCTGATCGTACGC<br>TTATCAGGCCTACAGGATATCTGGCAACTTATTAAAATTGCATGAACTTGTAGGACGGATAAG<br>GCGTTCACGCGCATCCGGCAAAAAGCCCGCACGTTGTCAGCAACCTGCTTAATATCCCTTCC<br>TCCCTTTCACCCGAAAGGGAGGCACACCAGATTCCTCTCATTTAAAATCGCCCCTCCTCCAGC<br>ATCTATACTTATCTTTTTGCTCTATTTTCTCACTGGAGGAGTCATGCGGTGGATCCTGTTCAT<br>CCTCTTCTGCCTGCTGGGCGCACCTGCCCACGCGGTATCCATACCCGGCGTTACAACCACAAC<br>GACAACGGACTCAACGACTGAACCGGCCCCGGAACCGGATATCGAACAAAAAAAAGCGGCCTA<br>TGCGCACTGGCGGATGTGCTGGATAATGACACCTCGCGTAAAGAGTTGATCGACCAGTTGCGC<br>ACCGTTGCCGCTACGCCCCTGCTGAACCGGTACC |
| 42 | Glutamine permease H glnH (*Escherichia coli* EPEC C342-62) | ATG AAA AGT GTA CTT AAA GTG TCA TTG GCA GCA CTG ACA CTT GCA TTT<br>GCA GTC TCC AGT CAT GCT GCG GAC AAA AAG TTA GTC GTA GCG ACT GA<br>C ACTGCG TTT GTT CCT TTC GAA TTC AAG CAG GGC GAT AAG TAC GTC GG<br>C TTT GAC GTA GAC CTT TGG GCC GCC ATT GCA AAA GAG CTT AAG TTG G<br>AT TAC GAGTTA AAG CCT ATG GAC TTC AGT GGT ATC ATT CCC GCC CTG C<br>AA ACG AAA AAC GTG GAT CTT GCG CTT GCA GGC ATT ACT ATT ACC GAC<br>GAA CGC AAG AAGGCG ATT GAC TTC AGC GAC GGC TAT TAT AAG TCG GGT<br>CTT TTA GTT ATG GTA AAA GCC AAC AAT AAT GAT GTG AAA AGC GTG AAA<br>GAT TTG GAC GGG AAAGTA GTG GCA GTT AAA TCA GGT ACA GGG AGT GTG<br>GAT TAC GCG AAA GCT AAT ATC AAA ACC AAA GAC TTA CGT CAA TTC CC<br>G AAT ATC GAC AAT GCG TATATG GAA CTG GGG ACG AAC CGT GCG GAT GC<br>G GTG CTG CAC GAT ACA CCC AAC ATC CTT TAT TTC ATT AAA ACA GCT G<br>GT AAT GGT CAA TTT AAA GCT GTAGGC GAC AGC CTG GAA GCC CAG CAA T<br>AC GGG ATC GCG TTC CCT AAG GGC TCT GAT GAG CTT CGT GAC AAG GTA<br>AAC GGG GCG CTT AAA ACG CTG CGT GAAAAC GGA ACG TAC AAT GAA ATC<br>TAT AAG AAG TGG TTC GGA ACC GAG CCC AAA |
| 43 | Glutamine permease P glnP (*Escherichia coli* B354) | ATG CAA TTC GAT TGG AGT GCG ATT TGG CCT GCC ATT CCC CTT CTG ATT<br>GAG GGT GCA AAA ATG ACT CTG TGG ATT TCA GTG CTG GGG TTA GCC GG<br>A GGTCTT GTT ATT GGG TTA TTA GCA GGG TTT GCA CGC ACT TTC GGG GG<br>A TGG ATT GCA AAT CAT GTT GCG CTG GTC TTC ATC GAA GTC ATT CGT G<br>GC ACC CCCATC GTG GTC CAA GTG ATG TTT ATT TAC TTC GCG TTG CCA A<br>TG GCA TTT AAC GAT CTT CGT ATT GAT CCA TTT ACT GCG GCA GTG GTG<br>ACT ATC ATG ATTAAT AGT GGG GCG TAC ATT GCG GAG ATT ACT CGC GGC<br>GCT GTT CTT TCC ATT CAC AAA GGT TTT CGT GAG GCC GGT TTA GCT CTT<br>GGG CTT TCC CGC TGGGAA ACA ATT CGT TAT GTT ATC TTG CCG CTT GCC<br>TTG CGC CGT ATG TTG CCG CCG CTG GGT AAC CAA TGG ATC ATT TCT AT<br>C AAA GAT ACT TCG CTT TTCATT GTT ATT GGA GTG GCT GAA TTA ACA CG<br>C CAA GGT CAA GAA ATC ATC GCG GGG AAT TTC CGT GCA TTA GAG ATC T<br>GG AGT GCT GTC GCC GTT TTC TACTTG ATC ATT ACG CTG GTG CTG TCC T<br>TT ATT TTG CGC CGC TTG GAG CGT CGC ATG AAG ATT CTT |
| 44 | Glutamine Permease Q glnQ | ATG ATT GAA TTT AAG AAT GTG TCG AAG CAT TTC GGC CCC ACC CAA GTA<br>CTT CAC AAC ATT GAC CTT AAC ATC GCC CAG GGC GAG GTT GTA GTA AT<br>C ATCGGT CCA TCT GGT AGT GGC AAG TCC ACC TTG CTG CGT TGT ATC AA |

-continued

| SEQ ID NO: | Gene or Operon | Sequence |
|---|---|---|
| | (*Escherichia coli* EPEC C342-62) | T AAA CTT GAG GAA ATC ACC AGC GGA GAC TTA ATT GTG GAC GGT CTT A AA GTC AACGAT CCA AAA GTG GAC GAA CGC TTG ATT CGT CAG GAA GCG G GT ATG GTT TTC CAG CAG TTC TAC TTG TTT CCG CAC CTT ACG GCT CTT GAG AAC GTC ATGTTC GGA CCG TTA CGC GTG CGC GGG GCC AAT AAG GAG GAG GCG GAG AAG TTG GCA CGC GAG CTG TTA GCA AAA GTT GGC TTG GCT GAA CGT GCA CAT CATTAC CCT TCT GAG CTG TCA GGT GGG CAA CAG CAA CGT GTC GCC ATC GCA CGC GCG CTT GCT GTA AAA CCA AAG ATG ATG CT G TTC GAT GAG CCA ACG TCGGCG CTT GAC CCG GAG TTG CGC CAT GAG GT C CTT AAG GTT ATG CAA GAC TTA GCT GAA GAG GGA ATG ACG ATG GTA A TC GTG ACG CAC GAG ATT GGA TTCGCA GAG AAG GTA GCA TCT CGT TTG A TC TTC ATC GAC AAA GGT CGC ATT GCA GAA GAC GGC GAC CCA CAA GTT CTG ATT AAG AAC CCC CCT TCA CAG CGCCTG CAA GAA TTT CTG CAA CAT GTC TCC |

Tryptophan

| 45 | tryptophan amino transferase (transaminase) (*Ustilago maydis* 521) | ATG AGT TCC GCC ACA AGT CCG GCA CTG GAT TAT GCA TTG CTG TTG TCT TCT TCT GCT CGT AAC CGT ATG CCT TCT GCA ATC CGT TCC CTG TTC CC G GCAGAA TTA ATT CCA GGC ATG GTC TCT CTT TTG TCA GGT AAA CCG AA T TCG GAG ACC TTT CCC TTC CAG CGC ATC AGT TTG GAA CTT AAA CCC T CC ATC CATCTG GAG GGA CAG ACC GAG ACA GTG AGC ATC GAA GGT AGC G AT TTA GAC ATC GCT CTT CAG TAT TCA GCA ACG AGT GGG TTG CCA AAG TTG GTA GAC TGGATC ATT AAA TTT CAA TCT CGC GTT CAC GCT CGT AAG CAG GTC GAT GAG GGC AAT AAG CCG GGT GAA GTA TGG CGC TGT AGC TTT GGC AAC GGA TCT CAAGAC CTG CTG ACC AAG ACA TTT GAG GCT TTA GTT GAC GCC GGT GAT TCA GTA GTC CTG GAA AGT CCG GCT TAC AGT GGA AT T TTG CCG TCG TTG GTT GCGCAT AAA GCC AAC CTT TTC GAG GCA GAA AC T GAC GCC GAG GGC GTT GAG CCC ACG GCT TTA GAC ACA TTG CTG ACT A AC TGG AAG ACT GAC AGT GCA ACACGT GAC TCT CGT TTT CCC AAG TTT T TA TAT ACT ACC CCG ACT GGT GCA AAT CCG TCC GGG ACA TCA GCC TCT GAT AAT CGC AAG CGT GCG ATC CTT GATATT ATC CGC AAG CAC AAT TTA CTT CTG CTG GAG GAT GAT CCT TAC TAT TTT TTG TCA TTC CAA GGG TTG GAA CCG GGG GCT GAC GCG GTC AAA CGC ACTCGT GGG AAG AGC TAT TTT CAG TTG GAA GCT CAG GAC GAC TAT GGC GTC GGC CGT GTT GTT CGC TT T GAT TCA TTT AGT AAG ATC TTG TCT GCC GGA TTACGC CTG GGT TTC GT T ACA GGA CCC AAA GAG ATT CTG GAC GCC ATC GAC CTG GAC ACT TCC T CC CGC AAT TTG CAG ACA AGT GGC ACT TCC CAG GCA ATCGCC TAT GCT T TG TTG TCT AAG TGG GGA ATT GAC GGT TTT TTA CAT CAT GCG GAC AAT GTC GCA CGT TTT TAC CAA AAT CGC TTA GAA CGC TTT GAA GCCAGT GCC CAG GCA ATC TTA ACC GGA AGC CCT AGC ATC GCC TCG TGG GTT CGT CCT TCG GCA GGG ATG TTC CTG TGG ATC AAG TTA AAG TTG CCT CCG TCGCCC GAC TCG GCG GAG GGT GAT AGT TTT GAC CTG ATC TCT AAT AAA GCT AA G GCA GCT GGG GTA TTG GCT TTA CCC GGT GTG GCC TTC AAA CCA CCG A GCAGT TCA AGT ACG GGT GGC AAA CGT AAG ACA TCG GCA TAT GTC CGC A CG TCA TTC TCC CAG GTG CCT CTG GAC CAA GTG GAT ACC GCA TTC ACA CGC CTGCGT CAG GTG GTA GAG GAG GCC TGG CGT GAG GCT GGA CTT CAA ATC CCC GCG |
| 46 | Mtr tryptophan ArAAP transporter (*Escherichia coli* BL21(DE3)) | ATG GCT ACC CTT ACT ACT ACT CAA ACT TCC CCA TCG CTT CTT GGA GGA GTC GTT ATC ATC GGT GGA ACT ATC ATC GGA GCA GGG ATG TTT TCA CT G CCGGTT GTG ATG TCG GGA GCA TGG TTC TTT TGG TCA ATG GCG GCT CT T ATC TTC ACG TGG TTC TGT ATG TTG CAT AGT GGC CTG ATG ATC CTG G AA GCA AATCTG AAC TAC CGT CTG ATT GGG TCC TCT TTT GAT ACA ATT ACA A AG GAC CTT CTG GGG AAA GGA TGG AAT GTA GTT AAT GGA ATT AGT ATC GCG TTC GTC CTTTAC ATC TTG ACC TAC GCG TAT ATC TCT GCC TCA GGG AGC ATC TTG CAT CAC ACT TTT GCC GAG ATG TCA TTG AAC GTG CCC GCA CGC GCT GCT GCT GGC TTTGGT TTT GCA CTG CTT GTG GCA TTC GTA GTC TGG TTA AGT ACG AAG GCT GTG AGC CGT ATG ACC GCT ATC GTC CTT GGG GC T AAA GTA ATT ACC TTC TTTTTA ACA TTC GGC TCG CTG TTA GGA CAC GT G CAG CCT GCC ACT TTG TTC AAT GTG GCT GAA TCA AAC GCC TCG TAT G CC CCC TAT TTA CTT ATG ACT TTGCCG TTT TGT CTG GCT TCC TTC GGT T AT CAC GGA AAC GTG CCA TCA CTG ATG AAA TAT TAT GGT AAG GAT CCT AAA ACA ATT GTG AAG TGC TTG GTA TACGGG ACC TTA ATG GCA CTT GCC CTT TAC ACG ATC TGG CTT CTT GCA ACG ATG GGC AAT ATT CCT CGC CCT GAA TTT ATC GGG ATC GCA GAA AAA GGG GGGAAT ATT GAC GTG CTG GTC CAG GCT TTA TCG GGT GTC TTG AAT AGC CGC TCT TTG GAT CTT TTG TT A GTT GTC TTT TCC AAT TTT GCC GTG GTA TCG AGTTTC TTA GGT GTG AC G CTG GGT CTT TTT GAT TAC CTG GCC GAT CTG TTC GGA TTC GAC GAC A GC GCG GTG GGC CGT CTT AAA ACT GCT TTA TTA ACA TTTGCG CCC CCT G TA GTG GGA GGT CTT CTG TTT CCT AAC GGA TTC TTA TAC GCC ATC GGC TAC GCC GGA TTG GCG GCC ACG ATT TGG GCA GCT ATC GTC CCGGCT TTA TTG GCA CGT GCC TCA CGC AAA CGC TTC GGG AGT CCT AAA TTC CGT GTT TGG GGC GGG AAG CCT ATG ATT GCC CTT ATT TTA GTG TTT GGA GTCGGT |

| SEQ ID NO: | Gene or Operon | Sequence |
|---|---|---|
| | | AAT GCA CTT GTG CAC ATC TTG TCA TCG TTC AAT CTG CTT CCC GTT TA T CAA |
| 47 | tryptophan permease Tna B (*Escherichia coli* str. K-12 substr. MC4100) | ATG ACC GAC CAA GCT GAA AAG AAG CAT TCG GCA TTC TGG GGA GTA ATG GTC ATT GCC GGT ACC GTG ATC GGC GGT GGG ATG TTT GCT TTA CCT GT G GACTTA GCA GGC GCG TGG TTT TTT TGG GGG GCG TTC ATT CTG ATT AT T GCT TGG TTT TCC ATG CTG CAT AGT GGC TTG CTG CTT CTT GAA GCG A AT CTT AACTAT CCG GTG GGG TCA GTT TTC AAT ACC ATT ACA AAG GAC C TG ATT GGT AAC ACA TGG AAT ATC ATT TCG GGA TCA ACG GTA GCA TTT GTA TTG TAT ATTCTT ACA TAT GCT TAT ATC AGT GCG AAT GGC GCA ATC ATT TCC GAG ACG ATC TCC ATG AAC CTG GGG TAT CAC GCG AAT CCC GTT ATT GTC GGC ATC TGCACA GCG ATT TTT GTT GCG AGC GTA TTA TGG CTG AGT TCG TTG GCA GCT TCG CGT ATT ACT TCC CTT TTC CTT GGT TTG AA A ATC ATC AGC TTC GTA ATTGTG TTT GGG AGT TTT TTT TTC CAG GTC GA C TAC TCC ATT CTT CGC GAT GCA ACA AGT AGC ACA GCA GGC ACC AGT T AC TTC CCA TAT ATC TTT ATG GCCTTA CCG GTT TGT TTA GCG TCT TTT G GT TTT CAT GGT AAT ATC CCC TCA TTA ATT ATT TGC TAC GGC AAG CGC AAG GAC AAA TTA ATT AAG TCT GTT GTTTTC GGC TCC TTG TTG GCG CTT GTA ATC TAT TTA TTT TGG CTT TAT TGT ACG ATG GGG AAC ATC CCT CGC GAA TCC TTT AAG GCT ATT ATT TCT TCA GGAGGC AAC GTA GCA AGT TTG GTA AAA AGT TTT TTG GGT ACG AAG CAG CAT GGT ATC ATC GAG TTT TG T TTA CTT GTT TTC AGT AAT CTT GCC GTT GCT TCCTCA TTC TTT GGC GT G ACT CTG GGG CTT TTT GAT TAT CTG GCA GAT TTA TTC AAG ATC GAC A AC TCG CAT GGC GGG CGC TTC AAA ACG GTT CTG CTT ACATTT CTT CCT C CA GCT TTA CTT TAC CTG ATC TTT CCG AAT GGT TTT ATC TAT GGT ATT GGG GGG GCA GGC CTG TGC GCC ACT ATC TGG GCA GTT ATC ATTCCT GCT GTA TTG GCT ATC AAG GCA CGC AAA AAG TTT CCC AAC CAG ATG TTC ACC GTG TGG GGC GGC AAT TTG ATT CCG GCA ATC GTG ATC TTA TTT GGTATC ACG GTT ATT CTT TGC TGG TTC GGC AAT GTG TTT AAC GTC CTG CCT AA G TTT GGA |
| 48 | aroP (*Escherichia coli* O104:H4 str. C227-11) | ATG GAA GGG CAG CAG CAT GGC GAA CAG CTT AAG CGT GGC CTG AAG AAT CGT CAT ATC CAG CTT ATC GCA TTA GGC GGA GCT ATT GGG ACC GGC TT G TTCTTA GGC TCT GCT TCA GTC ATT CAG TCT GCG GGG CCA GGC ATT AT T TTA GGC TAC GCG ATT GCG GGC TTC ATC GCC TTT TTA ATT ATG CGC C AG CTT GGCGAG ATG GTG GTG GAG GAA CCC GTG GCA GGC AGT TTC TCT C AC TTT GCA TAC AAG TAT TGG GGA AGT TTT GCA GGC TTT GCG AGC GGT TGG AAC TAC TGGGTT CTG TAC GTT CTG GTG GCC ATG GCG GAA CTG ACA GCA GTC GGT AAA TAT ATT CAA TTC TGG TAC CCT GAA ATT CCC ACT TGG GTC TCT GCC GCT GTCTTC TTT GTC GTC ATT AAT GCA ATC AAC TTG ACC AAC GTC AAA GTA TTC GGC GAG ATG GAG TTT TGG TTC GCT ATT ATC AA A GTC ATT GCT GTT GTG GCCATG ATC ATT TTC GGA GGC TGG CTG CTT TT C AGC GGC AAC GGA GGT CCC CAG GCA ACT GTA TCG AAT CTT TGG GAC C AG GGT GGT TTC TTG CCA CAT GGGTTC ACG GGG TTA GTT ATG ATG ATG G CC ATT ATT ATG TTC TCG TTT GGA GGG CTT GAA TTG GTG GGC ATC ACT GCT GCT GAA GCT GAT AAC CCG GAG CAAAGC ATT CCT AAG GCC ACA AAT CAA GTG ATC TAT CGC ATC CTT ATC TTT TAC ATT GGA TCG TTG GCA GTA TTG CTG AGT TTG ATG CCC TGG ACC CGT GTCACC GCT GAT ACA AGC CCT TTT GTT TTG ATT TTT CAT GAA TTA GGG GAT ACT TTT GTG GCA AAT GC G TTA AAC ATC GTC GTA TTA ACT GCT GCC TTG TCAGTA TAT AAC TCC TG C GTA TAC TGT AAT AGC CGT ATG CTG TTC GGC TTG GCT CAG CAG GGG A AC GCT CCG AAA GCA CTG GCC AGT GTC GAC AAG CGT GGAGTA CCT GTG A AT ACG ATT TTA GTT TCT GCT CTG GTC ACT GCA CTT TGT GTA TTG ATC AAC TAC CTG GCG CCT GAG TCG GCG TTT GGC CTG CTG ATG GCGCTG GTG GTT AGC GCA TTG GTC ATC AAT TGG GCG ATG ATC TCC TTG GCA CAC ATG AAA TTC GCC CGT GCT AAA CAA GAA CAG GGT GTG GTT ACA CAC TTCCCA GCA TTA TTA TAC CCT CTG GGC AAC TGG ATT TGC TTA CTT TTT ATG GC A GCG GTT CTG GTC ATC ATG CTG ATG ACG CCT GGT ATG GCT ATT TCT G TTTAT CTG ATT CCG GTT TGG TTA ATC GTA TTA GGG ATT GGC TAT TTA T TC AAG GAA AAA ACT GCA AAG GCT GTC AAA GCG CAT |
| 49 | Aromatic amino acid exporter Ydd G (*Escherichia coli* TW10598) | ATG ACC CGC CAG AAG GCG ACT CTG ATC GGT TTG ATT GCT ATC GTA TTA TGG TCC ACA ATG GTT GGT TTA ATT CGT GGG GTT TCT GAG GGG CTT GG C CCGGTG GGC GGA GCA GCA GCT ATC TAC TCC CTG AGC GGT CTG TTA TT G ATC TTT ACA GTT GGG TTT CCG CGT ATC CGT CAA ATC CCC AAG GGA T AC TTA TTGGCG GGG AGT TTA CTT TTT GTG AGC TAT GAA ATT GCC TTT G CC TTG TCT CTG GGC TAC GCA GCG ACA CGC CAT CAA GCA ATT GAG GTA GGG ATG GTT AATTAC CTT TGG CCG TCA TTG ACG ATT CTT TTC GCA ATC TTA TTT AAC GGT CAG AAG ACT AAT TGG TTG ATT GTA CCG GGT TTA TTA TTA GCG TTG GTG GGAGTA TGC TGG GTG TTG GGA GGT GAC AAT GGT CTG CAT TAT GAC GAG ATT ATT AAT AAT ATC ACA ACA TCG CCC TTA TCC TA C TTT CTG GCT TTC ATT GGTGCC TTT ATC TGG GCC GCC TAT TGC ACC GT G ACG AAT AAG TAC GCT CGT GGC TTC AAC GGA ATT ACA GTA TTT GTC T |

| SEQ ID NO: | Gene or Operon | Sequence |
|---|---|---|
| | | TG CTT ACT GGT GCA TCT TTG TGGGTA TAT TAT TTC TTG ACC CCT CAA C<br>CA GAG ATG ATC TTC TCC ACC CCG GTT ATG ATC AAA TTA ATT TCA GCA<br>GCT TTC ACT TTG GGA TTC GCA TAC GCAGCT TGG AAT GTC GGC ATT CTT<br>CAT GGG AAT GTG ACG ATT ATG GCA GTC GGT TCC TAC TTC ACG CCC GTA<br>CTT AGT TCC GCT TTA GCA GCG GTA CTG CTGTCG GCG CCT TTG AGT TTT<br>AGT TTC TGG CAG GGT GCC CTG ATG GTG TGT GGG GGC TCC CTT TTG TG<br>C TGG CTT GCT ACC CGC CGT GGT |
| 50 | S-adenosyl-methionine synthase (UniProtKB/Swiss-Prot: P0A817.2) | ATG GCA AAG CAC CTT TTC ACG TCG GAA TCT GTA TCT GAA GGG CAT CCC<br>GAC AAA ATT GCA GAT CAA ATC TCC GAC GCG GTA CTT GAT GCT ATT CT<br>G GAACAA GAT CCC AAA GCC CGC GTC GCT TGC GTC GAA ACT TAT GTC AAG AC<br>A GGC ATG GTG TTA GTC TGC GGC GAG ATC ACT ACC TCT GCG TGG GTG G<br>AT ATC GAGGAA ATC ACG CGC AAT ACG GTG CGT GAG ATT GGC TAT GTA C<br>AC TCG GAC ATG GGG TTC GAC GCC AAC AGT TGT GCG GTT TTA AGT GCC<br>ATT GGG AAA CAGTCA CCT GAT ATT AAT CAG GGG GTG GAT CGT GCG GAC<br>CCT CTT GAA CAA GGT GCT GGT GAC CAA GGT CTG ATG TTC GGT TAT GCT<br>ACG AAC GAA ACC GATGTG TTG ATG CCC GCC CCG ATC ACA TAC GCC CAC<br>CGT CTG GTC CAA CGC CAG GCG GAG GTC CGT AAA AAC GGC ACG CTT CC<br>T TGG CTT CGT CCA GAT GCTAAG TCG CAG GTC ACT TTC CAA TAC GAC GA<br>C GGG AAG ATT GTC GGA ATC GAC GCC GTG GTC TTG TCA ACT CAG CAT T<br>CA GAG GAG ATC GAT CAA AAG AGCCTT CAG GAA GCC GTC ATG GAA GAG A<br>TC ATC AAG CCG ATT CTG CCT GCA GAA TGG TTA ACT TCC GCG ACC AAG<br>TTC TTT ATT AAC CCC ACC GGG CGT TTTGTC ATT GGC GGT CCT ATG GGC<br>GAC TGT GGG TTG ACC GGC CGT AAA ATT ATT GTC GAC ACT TAT GGC GGA<br>ATG GCT CGT CAT GGC GGT GGG GCA TTC AGTGGC AAG GAC CCG TCA AAG<br>GTA GAT CGT TCA GCC GCC TAT GCC GCC CGT TAC GTA GCC AAG AAC AT<br>T GTT GCT GCA GGA CTT GCT GAC CGC TGT GAA ATCCAA GTG AGC TAC GC<br>G ATC GGC GTA GCA GAA CCC ACC TCC ATT ATG GTG GAA ACT TTT GGC A<br>CC GAA AAA GTC CCC AGT GAG CAA CTG ACC TTA TTG GTTCGT GAG TTT T<br>TT GAT TTG CGC CCT TAC GGA CTT ATC CAA ATG TTA GAC CTT TTG CAC<br>CCA ATC TAC AAA GAA ACT GCA GCA TAC GGT CAC TTT GGA CGCGAG CAT<br>TTT CCC TGG GAG AAG ACA GAC AAA GCA CAG CTG TTA CGT GAC GCG GCC<br>GGA TTG AAA |
| 51 | adenosylhomo cysteinase (Anabaena cylindrica PCC 7122) GenBank: AFZ60429.1 | ATG ACG GCT ACG ACG CCA CGC CTG AAA CAT GAA GTG AAG GAC CTT GCG<br>CTT GCG CCT TTA GGT CGT CAG CGT CAT GAG TGG GCG GGG CGC GAA AT<br>G CCTGTT TTA AAG CAA ATC CGC GAC CGC TTT GAA AAA GAA AAG CCC TT<br>C GCG GGC CTG CGT ATC TCG GCT TGT GCA CAT GTT ACA ACA GAG ACG G<br>CT CAT TTAGCA ATT GCC CTG AAG GCC GGG GGA GCT GAT GCC GTA TTG A<br>TC GCA AGC AAC CCA CTG TCT ACG CAG GAT GAC GTA GCA GCC TCG CTT<br>GTC GCT GAT CATGAG ATC TCT GTG TTT GCA CAA AAG GGC GAA GAC GCC<br>GCG ACG TAC TCG CGT CAC GTC CAA ATT GCG TTG GGC CAC CGC CCC AAT<br>ATC ATC GTT GAT GACGGT TCC GAC GTA GTA GCT GAA TTA GTA CAG CAC<br>CGT CAG AAT CAG ATC GCG GAT CTT ATT GGA TCC ACT GAA GAA ACT AC<br>A ACT GGG ATT GTT CGC CTTCGC GCT ATG TTC AAC GAG GGG GTT TTG AC<br>G TTT CCC GCG ATG AAT GTC AAC GAC GCA GAC ACA AAA CAT TTT TTT G<br>AC AAC CGC TAC GGT ACA GGA CAATCT ACC TTG GAC GGG ATC ATT CGT G<br>CA ACC AAC ATC TTG CTT GCC GGC AAA ACT ATC GTA GTT GTA GGC TAT<br>GGC TGG TGC GGA AAG GGG ACC GCA TTACGC GCC CGC GGG ATG GGA GCT<br>AAT GTC ATT GTT ACC GAG ATC GAT CAC ATT AAG GCA ATT GAG GCG GTG<br>ATG GAT GGG TTT CGC GTT CTG CCC ATG GCTGAA GCC GCA CCG CAT GGT<br>GAT ATC TTT ATC ACT GTA ACG GGT AAT AAA CAC GTA GTT CGT GGT GA<br>A CAC TTT GAT GTC ATG AAA GAC GGC GCC ATT GTTTGC AAC TCA GGT CA<br>C TTC GAT TTG GAG TTG GAT TTA AAA TAT TTA GCA GCA AAT GCC AAG G<br>AA ATC AAA GAT GTG CGC CCA TTC ACA CAA GAA TAT AAATTA ACC AAC G<br>GC AAA AGC GTA GTG GTA TTA GGA GAG GGG CGT TTG ATT AAT CTT GCA<br>GCG GCA GAA GGT CAT CCG TCG GCA GTT ATG GAC ATG TCT TTCGCC AAT<br>CAA GCC TTA GCA GTC GAG TAT TTA GTG AAA AAT AAA GGC TCC TTG GCG<br>GCT GGA TTA CAT TCG ATC CCC CGC GAG GTT GAT GAG GAA ATC GCTCGT<br>TTA AAA TTG CAA GCG ATG GGG ATT TTT ATC GAT TCC CTG ACA GCA GA<br>T CAA ATC GAT TAT ATT AAT TCT TGG CAG TCA GGG ACG |
| 52 | Cystathionine-beta-synthase (Klebsiella quasipneumoniae subsp. Quasipneumoniae) GenBank: CDQ16225.1 | ATG GTA ATG TCG TTA TTC CAC AGT GTT AGC GAT TTA ATC GGT CAC ACA<br>CCT TTA TTA CAA TTG CAT AAG CTT GAT ACA GGA CCC TGT AGT TTG TT<br>C TTGAAA CTT GAG AAT CAA AAC CCA GGA GGG TCA ATT AAA GAT CGT GT<br>A GCG CTT AGC ATG ATT AAC GAA GCG GAA CGT CAG GGA AAA CTT GCG C<br>CA GGA GGAACT ATC ATC GAG GCT ACG GCG GGA AAT ACT GGG TTG GGG C<br>TT GCT TTG ATC GCA GCC CAG AAA AAC TAC CGT CTT ATC CTT GTA GTT<br>CCC GAC AAG ATGTCA CGT GAA AAA ATT TTC CAC TTG CGT GCC TTA GGC<br>GCA ACC GTG CTT TTG ACC CGT TCA GAC GTG AAC AAG GGG CAC CCG GCA<br>TAT TAT CAG GAC TATGCT CGC CGC TTG GCA GAT GAG ACT CCA GGG GCG<br>TTC TAC ATT GAC CAA TTC AAT AAT GAT GCC AAT CCT TTA GCA CAT GC<br>A ACA AGC ACG GCC CCT GAGCTG TTC CAA CAA TTA GAA GGG GAC ATC GA |

Sequence Listing

| SEQ ID NO: | Gene or Operon | Sequence |
|---|---|---|
| | | T GCC ATT GTG GTT GGT GTT GGG TCG GGT GGA ACG TTG GGC GGC TTG C AG GCC TGG TTC GCA GAA CAC TCTCCC AAA ACA GAG TTC ATC TTG GCT G AT CCA GCT GGG TCG ATT CTT GCC GAC CAG GTA GAC ACA GGC CGC TAC GGG GAA ACG GGA AGC TGG CTT GTA GAGGGT ATT GGC GAG GAT TTT ATC CCA CCA CTT GCT CGC CTG GAA GGA GTT CAT ACC GCA TAT CGT GTA TCT GAT CGC GAA GCC TTT CTT ACA GCC CGT CAACTG CTT CAG GTA GAG GGT GTA TTA GCG GGC TCG TCA ACG GGA ACA TTG TTA TCT GCG GCC TTG CG C TAT TGC CGT GCC CAG TCT CGC CCA AAG CGT GTGGTT ACC TTC GCA TG T GAC TCT GGA AAT AAG TAC TTG AGT AAG ATG TTC AAT GAC GAC TGG A TG CGC CAA CAG GGA CTT ATT GCG CGC CCG GAA CAG GGAGAT CTG AGT G AT TTC ATC GCC TTA CGT CAC GAC GAG GGG GCC ACG GTC ACC GCC GCG CCC GAC GAC ACA CTG GCG GCT GTA TTT ACT CGC ATG CGC TTGTAC GAT ATC TCC CAG CTT CCG GTC TTG GAA GAC GGT CGT GTC GTT GGC ATT GTG GAC GAA TGG GAT TTA ATT CGC CAT GTA CGT GGC GAC CGT CAA CGCTTT TCC CTG CCA GTC AGC GAG GCT ATG TCC CGT CAC GTA GAA ACG TTA GA C AAA CGC GCC CCC GAA TCC GAA TTG CAA GCT ATC TTA GAC CGT GGA C TGGTA GCA GTC ATT GCA GAC AAT GCG CGC TTT CTG GGA CTG GTT ACA C GT TCA GAT GTC TTA ACG GCA TGG CGC AAT CGT GTG GCG CAA |
| 53 | cystathionine-gamma-lyase (Klebsiella pneumoniae subsp. pneumoniae HS11286) NCBI Reference Sequence: YP_005228837.1 | ATG TCG TCT ATT CAC ACC CTG TCT GTT CAT AGT GGC ACC TTC ACG GAC TCA CAT GGC GCG GTG ATG CCC CCA ATC TAT GCC ACC TCC ACG TTC GC G CAACCT GCG CCC GGA CAG CAC ACC GGA TAT GAA TAC TCG CGC AGT GG A AAT CCT ACT CGT CAT GCC TTA GAG ACT GCG ATC GCA GAC CTG GAG A AT GGA ACGCGC GGG TAC GCA TTT GCC TCG GGC TTG GCA GCG ATC TCG A CT GTC CTT GAA TTG TTG GAT AAG GAC AGC CAT TTA GTT GCA GTG GAT GAT GTC TAT GGTGGG ACC TAC CGT TTA CTT GAA AAC GTT CGT CGT CGT TCT GCT GGG CTG CAA GTG TCG TGG GTC AAG CCA GAC GAT TTA GCG GGG ATT GAG GCG GCT ATCCGT CCT GAC ACC CGT ATG ATC TGG GTC GAA ACA CCT ACT AAT CCT TTG CTG AAA TTA GCC GAT TTG AGC GCC ATC GCA GC T ATC GCA CGC CGT CAC AATCTT ATT TCA GTT GCG GAT AAC ACG TTC GC T TCA CCA GCC ATC CAC CGT CCT CTT GAA CAC GGT TTC GAC ATT GTG G TG CAT TCT GCG ACA AAA TAC TTAAAT GGA CAT TCC GAT GTG GTT GCG G GG TTA GCT GTC GTC GGA GAT AAC TCC GGC TTA GCC GAG AAA TTA GGT TAT TTA CAA AAT GCA GTT GGC GGG GTATTA GAC CCC TTT TCC TCG TTC CTT ACA TTG CGC GGC ATC CGC ACT CTG GCA CTG CGT ATG GAA CGT CAT AGC GCG AAT GCA CTG CAG TTA GCC GAA TGGTTG GAA CAA CAG CCC GAA GTA GAG CGT GTA TGG TTT CCT TGG CTG GCC TCC CAT CAT CAT CA A TTG GCA CGT CAG CAG ATG GCA TTA CCT GGC GGGATG ATT AGC GTA GT A GTC AAA GGA GAT GAG GGA TAT GCT GAG CGC ATC ATC AGT AAA CTG C GT TGG TTC ACT CTT GCC GAG TCT TTA GGC GGC GTC GAGTCG TTA GTT T CC CAG CCG TTC TCA ATG ACA CAT GCT TCG ATC CCA CTT GAA AAG CGT CTT GCG AAC GGC ATT ACG CCC CAG CTT ATT CGC CTT AGT GTGGGG ATC GAA GAC CCA CAT GAT CTT ATC GCG GAT TGG CAA CAA GCC CTG CGT GCC GAA |
| 54 | cysteine dioxygenase (Bacillus subtilis sub sp. subtilis str. BAB-1) GenBank: AGI30235.1 | ATG GAG TTA TAC GAG TGC ATC CAG GAC ATC TTC TCG GGG TTG AAA AAC CCT TCC GTG AAA GAT CTG GCA ACA TCC CTG AAA CAA ATC CCG AAT GC A GCTAAA TTA TCT CAG CCT TAC ATT AAA GAG CCT GAC CAG TAT GCA TA C GGT CGC AAT GCC ATC TAC CGT AAC AAC GAG TTG GAG ATT ATT GTT A TC AAC ATTCCT CCC AAC AAA GAG ACA ACC GTA CAC GAT CAC GGA CAA T CC ATT GGA TGC GCA ATG GTT CTG GAA GGT AAA TTA CTT AAT AGC ATT TAT CGT TCT GCTGGT GAG CAC GCC GAG CTG TCC AAC TCT TAC TTT GTT CAC GAG GGG GAA TGC CTT ATC TCG ACT AAA GGC TTG ATT CAC AAA ATG AGC AAC CCC ACA AGCGAG CGC ATG GTA TCG TTG CAT GTT TAT TCG CCA CCG CTT GAG GAC ATG ACA GTA TTT GAG GAA CAG AAA GAG GTG TTA AA G AAC TCT |
| 55 | Glutamate Oxaloacetate Transaminase (Caenorhabditis elegans) NCBI Reference Sequence: NP_741811.1 | ATG AGC GTT AGT AAA AAA CTG TTC TCT ACG GCT GTG CGT GGT AAG AGC TGG TGG TCA CAC GTC GAG ATG GGC CCT CCT GAT GCG ATT TTG GGG GT G ACTGAA GCT TTC AAA GCT GAT TCT AAC CCC AAG AAG ATC AAT TTG GG C GTG GGA GCG TAC CGT GAT GAC CAA GGA AAA CCG TTC GTA CTT CCT A GC GTC AAGGAA GCC GAA CGT CAA GTT ATT GCA GCA AAT TTT GAC AAG G AG TAC GCC GGG ATC GTT GGC CTG CCT GAA TTC ACG AAA CTT AGT GCT CAG TTA GCA TTAGGG GAA AAC AGT GAC GTA ATC AAA AAC AAG CGT ATT TTT ACG ACG CAA AGT ATT TCT GGG ACT GGT GCG CTG CGT ATT GGA AGT GAG TTC CTG AGT AAATAT GCA AAG ACT AAG GTT ATC TAT CAA CCC ACG CCT ACA TGG GGA AAC CAC GTG CCT ATC TTC AAG TTC GCG GGC GTG GA T GTG AAA CAG TAT CGT TATTAT GAC AAG TCT ACA TGT GGA TTT GAT GA G ACG GGG GCA TTG GCT GAT ATT GCG CAA ATC CCC GAA GGT AGC ACT A TT TTG CTG CAC GCG TGC GCA CATAAC CCA ACG GGG GTC GAC CCT AGT C GT GAC CAA TGG AAA AAG ATT TCA GAT ATT GTT AAG AAA CGC AAT TTG TTC GTG TTT TTT GAC ATG GTG AAT GAGTCA GTC CTG AGT CCG TTA CTG CCT CGC ACG CTT ATG CGC CTG CTT GTG TTG TTA CTG AAA TCC GCA GT |

-continued

Sequence Listing

| SEQ ID NO: | Gene or Operon | Sequence |
|---|---|---|
| | | CTT TTC GCC CAC TCA ACA CCC ACC CAT CAGTCG ATG GAA TTA GCT CTT TTG CCG GCC TCG TCG CGT ATC CAA CTT TCT ACC TCC AAT GGG TCA GA A ATG TCC AGC TCT TGG CTT ATC GTC AGC AGC CCT |
| 56 | methionine gamma lyase (*Bacillus halodurans* C-125) GenBank: BAB04518.1 | ATG AAA CGC GAC CAA CAT TTT GAA ACA CGC GCG ATC CAT ACT GGT TAC AAG CCG AAC GAG CAT TTT GAT AGC TTG ACT CCC CCT ATT TAC CAA AC C AGCACG TTC ACA TTT GCA TCA ATG GAG CAA GGT GGC AAC CGT TTC GC A GGC GAG GAA GCA GGA TAT GTT TAT TCA CGC CTG GGG AAC CCC ACC G TG CAA ATTTTG GAA CAA CGC ATT GCT GAG TTG GAG GGT GGG GAG GCA G CT CTT GCC TTT GGA TCT GGC ATG GCT GCT GTC AGT GCG ATT TTG GTG GGG CTT ACG AAGGCC AAC GAC CAC ATC TTA GTG AGC AAT GGA GTG TAT GGT TGT ACG TTT GGG TTG TTA ACG ATG TTA AAG GAA AAA TAC AAC ATC GAC GCC ACT TTC AGTCCG ATG GAC AGC GTA GAG GAA ATC CTG GCA AAC ATC CAG GAT AAT ACC ACG TGC ATT TAT GTG GAA ACA CCT ATC AAC CC C ACC ATG CAG TTA ATC GATTTG GAA CTG GTT GTG CGC GTA GCG AAG GA A AAG GGT ATT AAG GTA ATC GTT GAT AAC ACG TTT GCC ACA CCA TAC T TA CAA CAA CCG ATT GCT CTG GGATGT GAC TTC GTT GTC CAT TCG GCC A CG AAA TAC ATC GGG GGT CAT GGG GAC GTG GTC GCC GGA GTG CTG ATT GGA GAC AAG GAA ACA ATT CAG TTG ATCCGT AAG ACC ACC CAG AAG GAT ATG GGG GGC GTA ATT TCT CCA TTT GAT GCG TGG CTG CTG TTG CGC GGA TTG AAA ACA CTT GCA GTA CGT ATG GAT CGCCAT TGC GAG AAT GCT GAA AAA TTG GCC GAG AAA CTG AAA GAG CAT CCA AAA GTA AGT ACG GTT CT G TAC CCG GGA GAC TTT GAG CAT CCC GAT CAC TCCATC GTC GCC AAA CA G ATG AAA AAG GGA GGC GGT TTA TTA AGC TTT GAG ATC AAG GGG ACT G AG GCG GAC ATC GCC AAA GTT GTA AAT CAG TTA AAA CTGATT CGT ATT G CT GTT AGT TTG GGT GAC GCA GAG ACC TTG ATT CAG CAT CCT GCA ACC ATG ACC CAT GCA GTA GTA CCC GAA AAG CGC CGC ACT CAA ATGGGT ATT AGT AAA AAG TTG TTA CGC ATG TCG GCC GGG TTA GAG GCC TGG CAA GAT GTC TGG GCT GAC TTA GAG CAG GCG TTA AAT CAA CTG |
| 57 | Methionine aminotransferase (*Methylobacterium aquaticum*) GenBank: BAQ48233.1 | ATG ACC GCG ATT CCG GCC TTG GCA GAC CTG CAG GCT CGT TAT GCC GAC TTA CAA GGG CGT GGT CTG AAG TTA GAT ATG ACG CGC GGT GCA AAA CCG GC G CCAGAG CAG TTG GAT TTA TCG GAC GAT CTT TTC ACT TTA CCA GGT AA C CGC GAT CAC CGC ACA GAG AGC GGA GAA GAC GCG CGT AAT TAC GGC G GA GTA CAGGGC CTG GCT GAG GTC CGT GCC TTA TTC GCC CCT GTG CTT G GT GCG TCA CCC GAT CGC ATT GCC GTA GGT AAT AAC TCA TCG TTG GCA TTG ATG CAT GACTGC ATT GCC TAT GCA TTG CTT AAG GGT GTA CCC GGC GGC GCT CGT CCT TGG GCA AAG GAA GAG GAG ATT CGT TTT TTA TGC CCA GTC CCA GGG TAC GACCGT CAC TTC GCT CTG TGC GAG ACC TAC GGG ATT GGA ATG ATT CCA GTC CCT ATG ACC GCT GAC GGG CCT GAT ATG GAA AT G GTT GAA CGT GAG GTA CGCGAT CCA CGC GTC AAA GGT ATG TGG GCG GT G CCG CAG TAT AGT AAC CCA GGC GGT GAG ACA TAC TCC GAC GCG ACT G TT GAG CGC CTG GCT CGT ATG GAAACC GGT GCC CCT GAC TTC CGT CTT T TT TGG GAC AAC GCG TAT GCA CTT CAC CAT TTG ACC GAA CGT CGC CCA ACC CTT CGT AAT GTG TTA GAT GCC TGTGCG GAA GCC GGG TCA CCG GAT CGT GCT ATT GTG TTT GCT AGT ACG TCG AAA GTT ACA CTG GCG GGG GCA GGC CTT GCG ATG CTT GCG TCC AGC GAG GGCAAT ATT CGC TGG TAT TTA GCT AAC GCC GGC AAA CGC TCA ATT GGT CCA GAT AAG CTT AAC CAG TT G CGC CAT GTT CGC TTT CTG CGT GAC CAG GGC GGACTT GAT GCA TTA AT G GAC GGC CAC CGC CGT CTT TTA GCT CCT AAG TTC CGC GCT GTA ACG G AA ACC CTT GCT CGT CAT CTG GGC GGG ACT GGA GTA GCGCGC TGG AGC G AG CCG GAA GGG GGG TAC TTT ATC CTG CTG GAA GTC CCT GAG GGC TGT GCG ACA CGC GTA GTT AAG CTT GCTGCT GCT TGC GGA CTG GCTCTG ACG CCC GCA GGG GCG ACG CAC CCA TAC GGG CGT GAC CCT CAA GAT AAG CTG TTA CGT CTT GCC CCG TCA TAC CCG AAA CCA GCG GAG GTC GAG GCAGCC GCT GAG GTA GTC GCT GTG TGC GTT TTA CTT GCG GCA GCT GAA AGC CG C GAA GCT GGC GGT TCG GGG CAG GTT GCT GCA |
| 58 | Aro10p decarboxylase (*Saccharomyces cerevisiae* YJM1615) GenBank: AJV21157.1 | ATG GCA CCC GTC ACT ATT GAG AAA TTC GTG AAT CAA GAA GAG CGT CAT TTA GTG AGC AAT CGT TCC GCC ACG ATC CCT TTT GGA GAA TAT ATT TT C AAGCGC CTT CTT TCC ATT GAC ACC AAA AGC GTC TTC GGG GTT CCC GG C GAC TTC AAT TTA TCT TTA TTG GAA TAT TTA TAC TCG CCC TCG GTG G AA TCT GCGGGT CTT CGT TGG GTT GGC ACC TGT AAC GAG TTA AAT GCA G CC TAC GCT GCA GAT GGA TAT TCC CGC TAC TCT AAT AAA ATT GGA TGC TTA ATC ACC ACATAC GGC GTA GGA GAA CTG AGT GCG CTT AAT GGA ATC GCG GGG TCA TTC GCT GAA AAT GTA AAG GTT CTG CAT ATC GTA GGG GTC GCC AAG TCC ATT GATTCC CGT TCG TCT AAC TTC TCG GAT CGT AAC TTA CAT CAC TTG GTC CCG CAG TTA CAT GAT TCG AAC TTT AAA GGA CCC AA C CAT AAG GTC TAT CAC GACATG GTT AAA GAT CGT GTC GCA TGT TCC GT C GCC TAC CTG GAG GAT ATT GAG ACG GCC TGT GAC CAA GTT GAT AAC G TG ATC CGT GAC ATT TAT AAG TATTCA AAA CCT GGT TAC ATT TTC GTC C CA GCC GAC TTT GCC GAC ATG TCC GTA ACC TGC GAC AAC TTG GTC AAT GTA CCG CGT ATC AGC CAA CAA GAT TGTATT GTC TAC CCC AGC GAG AAC |

-continued

Sequence Listing

| SEQ ID NO: | Gene or Operon | Sequence |
|---|---|---|
| | | CAA CTG TCA GAC ATC ATT AAT AAA ATC ACT AGC TGG ATC TAC TCG TCT AAG ACT CCA GCA ATC CTT GGA GAC GTC TTAACT GAT CGT TAT GGG GTA TCA AAC TTT CTG AAC AAA CTG ATC TGC AAA ACC GGT ATC TGG AAC TT C TCC ACC GTG ATG GGA AAA TCA GTC ATT GAC GAGAGT AAC CCA ACT TA T ATG GGT CAA TAC AAC GGC AAA GAA GGT CTT AAA CAG GTC TAT GAA C AT TTC GAG CTG TGT GAT TTG GTT TTA CAC TTC GGA GTAGAT ATT AAC G AG ATC AAT AAT GGT CAC TAC ACG TTC ACT TAC AAG CCA AAT GCG AAA ATT ATT CAA TTC CAC CCT AAT TAT ATT CGT TTA GTA GAC ACTCGT CAG GGG AAT GAA CAA ATG TTC AAA GGC ATC AAT TTT GCG CCA ATC TTG AAA GAG TTG TAT AAG CGT ATC GAC GTC TCT AAA TTA TCG TTG CAA TACGAT TCC AAT GTA ACA CAA TAC ACC AAT GAG ACT ATG CGT CTG GAG GAC CC A ACG AAT GGT CAA TCG AGC ATC ATT ACC CAA GTA CAC CTG CAA AAG A CCATG CCG AAA TTT TTG AAT CCC GGC GAC GTC GTC GTG TGT GAG ACT G GT AGT TTC CAA TTC AGT GTA CGC GAC TTC GCA TTC CCC AGT CAG TTG AAA TATATC AGC CAG GGT TTC TTT TTA TCC ATT GGT ATG GCC TTG CCT GCC GCG TTG GGG GTT GGG ATC GCA ATG CAG GAT CAT TCC AAC GGG CAT ATT AAC GGAGGG AAC GTC AAA GAA GAC TAC AAG CCC CGC TTA ATT TTG TTT GAA GGT GAC GGC GCC GCG CAG ATG ACC ATC CAG GAG CTT AGC AC G ATC CTT AAA TGCAAT ATC CCT TTG GAG GTC ATT ATC TGG AAT AAC AA T GGA TAC ACT ATC GAG CGT GCC ATC ATG GGT CCA ACA CGT TCA TAT A AC GAT GTG ATG TCG TGGAAA TGG ACA AAG TTG TTC GAA GCC TTT GGG G AT TTC GAT GGT AAG TAT ACG AAT TCG ACT TTA ATT CAG TGT CCT AGC AAA TTA GCG TTA AAA CTT GAAGAA TTG AAG AAT TCT AAT AAG CGT TCG GGG ATC GAA CTG TTA GAA GTG AAG CTG GGT GAG CTT GAC TTC CCA GAG CAA TTG AAG TGT ATG GTA GAG GCCGCA GCT CTT AAA CGT AAT AAG |
| 59 | Methionine import system permease protein MetP (Bacillus subtilis) GenBank: KIX81758.1 | ATG TTT GAG AAG TAT TTT CCA AAT GTT GAC TTG ACC GAG TTA TGG AAT GCC ACA TAT GAA ACT CTG TAT ATG ACA TTG ATT TCC TTA CTG TTT GC C TTCGTA ATC GGC GTC ATC CTG GGA TTG CTG TTA TTC TTA ACA TCT AA G GGG TCT CTT TGG CAA AAT AAA GCA GTA AAT TCC GTT ATC GCA GCC G TT GTC AACATC TTT CGT TCA ATT CCC TTC CTT ATT TTA ATC ATC CTG C TT CTT GGT TTC ACT AAA TTC TTA GTG GGA ACA ATT TTG GGA CCA AAT GCG GCT CTT CCCGCG TTA GTC ATC GGT AGT GCT CCC TTT TAT GCT CGT CTG GTC GAA ATC GCA CTT CGT GAA GTG GAC AAA GGA GTG ATT GAG GCG GCG AAA TCG ATG GGGGCT AAG ACG AGC ACT ATT ATT TTT AAG GTT CTT ATC CCC GAG TCC ATG CCC GCG CTG ATT TCC GGA ATT ACA GTG ACT GC G ATT GCA TTG ATC GGG TCAACC GCC ATC GCA GGA GCT ATT GGT TCT GG T GGA TTG GGA AAC TTA GCA TAC GTT GAA GGC TAT CAA TCG AAT AAT G CG GAT GTG ACC TTC GTG GCC ACAGTT TTC ATC CTG ATT ATT GTT TTC A TC ATT CAG ATC ATT GGT GAC CTT ATT ACC AAC ATC ATC GAT AAA CGC |
| 60 | DL-methionine transporter subunit MetN (Escherichia coli K-12]) GenBank: CQR79802.1 | ATG ATT AAA CTG AGC AAC ATT ACT AAG GTG TTC CAC CAA GGT ACA CGT ACG ATC CAG GCT CTT AAT AAT GTG TCA CTG CAC GTT CCT GCT GGT CA G ATTTAT GGG GTT ATC GGT GCC AGT GGG GCT GGG AAG AGC ACT CTG AT C CGC TGC GTC AAT CTG TTA GAG GCC ACA GAG GGC TCG GTA CTG G TG GAC GGTCAA GAG TTG ACT ACT CTG TCG GAG TCC GAG TTG ACA AAA G CA CGC CGC CAG ATT GGC ATG ATT TTC CAA CAT TTC AAT TTG TTA TCG AGC CGT ACA GTTTTC GGG AAC GTG GCC TTA CCA CTG GAG TTG GAC AAT ACT CCC AAA GAC GAA GTC AAA CGT CGT GTG ACC GAA TTA TTG TCC TTG GTG GGT CTT GGT GACAAA CAC GAC AGT TAT CCC AGT AAT TTG AGT GGC GGG CAA AAA CAG CGT GTT GCC ATC GCA CGC GCA TTA GCT TCG AAT CC C AAG GTG CTG TTA TGT GATGAA GCG ACC AGC GCC CTT GAC CCA GCC AC A ACT CGT AGC ATC CTG GAG CTT TTG AAA GAT ATC AAT CGT CGC CTG G GT TTG ACC ATC TTA TTG ATT ACGCAC GAG ATG GAC GTT GTA AAG CGT A TC TGT GAC TGT GTA GCG GTG ATC TCC AAC GGT GAA TTA ATC GAA CAG GAC ACC GTA TCG GAG GTC TTC TCA CATCCT AAG ACA CCC CTT GCA CAA AAA TTC ATC CAA AGC ACG CTG CAT TTA GAT ATT CCT GAA GAT TAT CAG GAA CGC CTG CAG GCT GAA CCG TTT ACT GATTGC GTT CCA ATG CTT CGC TTA GAG TTC ACA GGG CAA TCG GTT GAC GCT CCC TTA TTG AGT GAA AC C GCC CGC CGT TTC AAT GTT AAT AAC AAC ATC ATTTCC GCG CAA ATG GA C TAC GCG GGG GGT GTT AAA TTT GGA ATC ATG TTA ACC GAA ATG CAC G GC ACA CAG CAG GAT ACA CAG GCG GCG ATC GCA TGG CTGCAG GAA CAT C AT GTT AAA GTA GAA GTC CTT GGG TAT GTG |
| 61 | metI (Escherichia coli) | ATGTCTGAGCCGATGATGTGGCTGCTGGTTCGTGGCGTATGGGAAACGCTGGCAATGACCTTC GTATCCGGTTTTTTTGGCTTTGTGATTGGTCTGCCGGTTGGCGTTCTGCTTTATGTCACGCGT CCGGGGCAAATTATTGCTAACGCGAAGCTGTATCGTACCGTTTCTGCGATTGTGAACATTTTC CGTTCCATCCCGTTCATTATCTTGCTTGTATGGATGATTCCGTTTACCCGCGTTATTGTCGGT ACATCGATTGGTTTGCAGGCAGCGATTGTTCCGTTAACCGTTGGTGCAGCACCGTTTATTGCC CGTATGGTCGAGAACGCTCTGCTGGAGATCCCAACCGGGTTAATTGAAGCTTCCCGCGCAATG GGTGCCACGCCGATGCAGATCGTCCGTAAGGTGCTGTTACCGGAAGCGCTGCCGGGTCTGGTG AATGCGGCAACTATCACCCTGATTACCCTGGTCGGTTATTCCGCGATGGGTGTGCAGTCGGT GCCGGTGGTTTAGGTCAGATTGGCTATCAGTATGGCTACATCGGCTATAACGCGACGGTGATG |

-continued

Sequence Listing

| SEQ ID NO: | Gene or Operon | Sequence |
|---|---|---|
| | | AATACGGTACTGGTATTGCTGGTCATTCTGGTTTATTTAATTCAGTTCGCAGGCGACCGCATC<br>GTCCGGGCTGTCACTCGCAAGTAA |
| 62 | metQ<br>(*Escherichia coli*) | ATGGCGTTCAAATTCAAAACCTTTGCGGCAGTGGGAGCCCTGATCGGATCACTGGCACTGGTA<br>GGCTGCGGTCAGGATGAAAAAGATCCAAACCACATTAAAGTCGGCGTGATTGTTGGTGCCGAA<br>CAGCAGGTTGCAGAAGTCGCGCAGAAAGTTGCGAAAGACAAATATGGCCTGGACGTTGAGCTG<br>GTAACCTTCAACGACTATGTTCTGCCAAACGAAGCATTGAGCAAAGGCGATATCGACGCCAAC<br>GCCTTCCAGCATAAACCGTACCTTGATCAGCAACTGAAAGATCGTGGCTACAAACTGGTCGCA<br>GTAGGCAACACTTTTGTTTATCCGATTGCTGGTTACTCCAAGAAAATCAAATCACTGGATGAA<br>CTGCAGGATGGTTCGCAGGTTGCCGTGCCAAACGACCCAACTAACCTTGGTCGTTCACTGCTG<br>CTGCTGCAAAAGTGGGCTTGATCAAACTGAAAGATGGCGTTGGCCTGCTGCCGACCGTTCTT<br>GATGTTGTTGAGAACCCCAAAAATCTGAAAATTGTTGAACTGGAAGCACCGCAACTGCCGCGT<br>TCTCTGGACGACGCGCAAATCGCTCTGGCAGTTATCAATACCACCTATGCCAGCCAGATTGGC<br>CTGACTCCGGCGAAAGACGGTATCTTTGTTGAAGATAAAGAGTCCCCGTACGTAAACCTGATC<br>GTGACGCGTGAAGATAACAAAGACGCCGAGAACGTGAAGAAATTCGTCCAGGCTTATCAGTCT<br>GACGAAGTTTACGAAGCAGCAAACAAAGTGTTTAACGGCGGAGCTGTTAAAGGCTGGTAA |
| 63 | MetE<br>(*Bacillus atrophaeus* UCMB-5137)<br>GenBank: AKL84080.1 | ATG ACG ACT ATC AAA ACA TCA AAT CTG GGC TTC CCT CGC ATT GGA CTT<br>AAT CGC GAA TGG AAA AAA TCA CTG GAA GCG TTT TGG AAA GGT AAC AG<br>C GACAAA GAT ACA TTT CTT AAG CAG ATG GAT GAG TTA TTT CTT ACT GC<br>C GTA AAA ACC CAG ATT GAT CAA AAA ATC GAC ATC GTG CCC GTG AGC G<br>AC TTC ACTCAC TAC GAC CAC GTT CTT GAC ACA GCT ATC TCT TTT AAT T<br>GG ATT CCA GAA CGC TTT AAA CAC ATT ACG GAT GCG ACT GAT ACA TAT<br>TTC GCG CTG GCACGT GGC ATT AAG GAT GCT GTT AGT TCG GAA ATG ACT<br>AAG TGG TTT AAT ACC AAT TAC CAC TAT ATC GTT CCG GAA TAC AAT AAA<br>GAC ATC GAA TTC CGTTTA ACC CGC AAC AAG CAG TTA GAG GAC TAC CGC<br>CGC GTC AAA CAA GCG TTT GGC GTC GAA ACT AAA CCC GTC ATT GTC GG<br>T CCT TAC ACA TTC GTG ACGCTT GCC AAG GGC TAC GAA CAA AGT GAG GC<br>C AAA GAA ATC CAA AAG CGT TTA GTC CCA TTG TAT GTG CAA TTA TTG A<br>AA GAA TTG GAA CAA GAG GGC GTGCAG TGG GTA CAA ATC GAT GAG CCA G<br>CA CTT GTG ACA GCC TCA TCC GAG GAT GTT AGC GCG GCC AAG GAG TTA<br>TAC CAG GCC ATT ACG AAT GAG TTA TCCGGC TTG AAT GTC CTT TTG CAG<br>ACT TAC TTC GAT TCT GTT GAT GCT TAT GAG GAG TTA ATC AGC TAC CCG<br>GTA CAG GGT ATC GGC TTG GAT TTT GTA CACGAT AAA GGG CGC AAC TTG<br>GAG CAA TTA AAA GCG CAT GGA TTT CCG AAG GAT AAG GTA TTA GCA GC<br>T GGT GTT ATT GAT GGT CGT AAC ATT TGG AAG ACGGAT TTA GAT GAG CG<br>C TTG GAC GCC ATC CTT GCG CTG TTA TCT TCG ACG GAC ATT GAC GAA T<br>TA TGG ATT CAA CCA AGC AAT TCG CTT CTT CAT GTA CCAGTA GCA AAG C<br>AC CCA GAC GAG CAC CTG GAG AAG GAT CTG TTG AAT GGC TTG AGT TAC<br>GCA AAA GAA AAG CTG GCA GAA CTG TCC GCT TTA AAA GAG GGTTTG TTA<br>TCG GGT AAA GCG GCA ATC TCG GCC GCG CAT TCG CAG GCC AAA GCG GAT<br>TTA CAG GCC CTG AAG CAA TTC GCC ACC GGG GCT AAC AGT GAG CAGAAA<br>GAG GAA TTA AAT CAG TTG ACC GAG AAA GAC TTT AAG CGC CCG ATC CC<br>C TTC GAA GAG CGC CTG AAA ATC CAG AAT GAA TCC TTG GGG CTT CCC C<br>TGCTT CCT ACT ACG ACT ATT GGT TCT TTT CCT CAA AGC GCC GAG GTG C<br>GT TCG GCG CGC CAA AAG TGG CGC AAA AGT GAG TGG AGC GAC GAG CAA<br>TAT CAAGAA TTT ATC AAC GCG GAA ACG AAG CGC TGG ATC GAC ATT CAG<br>GAA GAG CTT GAT CTT GAC GTT TTA GTA CAT GGA GAG TTC GAG CGC ACC<br>GAC ATG GTCGAA TAT TTC GGT GAG AAA CTG GCT GGA TTC GCG TTT ACT<br>AAA TAC GCA TGG GTC CAG AGC TAC GGA TCC CGC TGT GTA CGC CCT CC<br>C GTC ATC TAT GGGGAC GTG GAG TTT ATT GAA CCT ATG ACT GTC AAG GA<br>C ACA GTG TAC GCT CAA TCT TTA ACG AGT AAG CAG GTT AAA GGG ATG T<br>TG ACT GGC CCG GTC ACAATC TTG AAT TGG AGC TTC CCG CGT AAC GAC A<br>TT AGC CGT AAG GAG ATC GCC TTC CAA ATC GGG TTA GCT CTT CGC AAA<br>GAG GTC AAG GCG TTG GAA GATGCT GGT ATT CAA ATC ATC CAA GTT GAC<br>GAA CCG GCC CTG CGT GAA GGG CTG CCT CTG AAA GAA AAC GAT TGG GAA<br>GAG TAT TTA ACG TGG GCC GCG GAGGCG TTC CGC TTA ACT ACT TCG GCT<br>GTG AAA AAC GAC ACT CAG ATT CAT ACA CAC ATG TGT TAT TCC AAT TT<br>T GAG GAC ATT GTC GAC ACA ATT AAT GACTTG GAT GCG GAC GTC ATT AC<br>A ATC GAA CAC TCC CGC AGT CAC GGT GGG TTC TTG GAC TAC TTG CGC G<br>AT CAT CCG TAT CTT AAA GGT TTA GGT CTT GGCGTG TAC GAT ATT CAC A<br>GC CCT CGT GTA CCC CCG ACA GAG GAA ATT TAT AAG ATC ATT GAC GAA<br>GCC CTG ACC GTA TGT CCT ACT GAC CGC TTC TGG GTAAAC CCA GAC TGC<br>GGG CTG AAG ACC CGT CAC CAG GAG GAA ACG ATT GCC GCG TTG AAG AAC<br>ATG GTC GAG GCT GCT AAA CAG GCT CGT GCC AAA CAG AGTCAA CTT GTC |
| 64 | BrnF<br>(*Corynebacterium glutamicum*)<br>GenBank: AAM46686.1 | ATG CAG AAA ACA CAG GAG ATT CAC AGC TCG TTA GAG GTT AGC CCC AGT<br>AAA GCT GCT CTG GAG CCC GAC GAT AAG GGG TAT CGT CGT TAC GAA AT<br>C GCACAA GGC CTG AAG ACC TCT CTT GCT GCA GGC CTG GGA ATG TAT CC<br>T ATC GGA ATT GCA TTC GGC TTA CTG GTG ATT CAA TAT GGT TAT GAA T<br>GG TGG GCCGCT CCA CTG TTC TCC GGC CTG ATT TTT GCG GGG TCT ACG G<br>AG ATG CTT GTA ATT GCA CTT GTG GTC GGC GCT GCT CCG CTG GGT GCC<br>ATT GCC CTT ACGACC TTA CTT GTT AAT TTC CGT CAT GTT TTC TAT GCC |

| SEQ ID NO: | Gene or Operon | Sequence |
|---|---|---|
| | | TTT TCC TTT CCC TTG CAC GTT GTT AAA AAC CCT ATT GCG CGC TTC TAT TCT GTA TTC GCT CTTATT GAT GAA GCA TAC GCT GTT ACA GCC GCT CGT CCC GCC GGT TGG AGT GCA TGG CGT CTG ATT TCA ATG CAG ATT GCG TT C CAC TCC TAC TGG GTA TTTGGA GGC TTG ACC GGT GTA GCA ATC GCA GA G TTA ATT CCT TTC GAG ATC AAA GGC CTG GAG TTC GCA CTT TGT TCG T TA TTT GTA ACT CTT ACT TTA GACAGT TGT CGC ACT AAG AAA CAA ATT C CG AGT TTG TTA TTG GCT GGA CTG AGC TTT ACT ATC GCG TTA GTA GTG ATC CCC GGC CAA GCT CTG TTC GCT GCGTTA CTT ATC TTT CTG GGG CTT CTG ACA ATC CGT TAT TTT TTC TTA GGG AAG GCA GCC AAA |
| 65 | BrnE (*Corynebacterium glutamicum*) GenBank: AAM46685.1 | ATG ACG ACT GAT TTC TCC TGC ATC CTG TTG GTG GTC GCG GTA TGT GCA GTC ATT ACA TTT GCG CTT CGT GCC GTA CCT TTT CTG ATC TTG AAA CC C TTGCGT GAA TCG CAA TTT GTG GGA AAA ATG GCC ATG TGG ATG CCT GC G GGC ATT CTG GCA ATC CTG ACG GCT TCT ACC TTC CGT TCA AAC GCC A TC GAT TTAAAG ACG TTG ACG TTC GGT CTG ATT GCC GTG GCA ATC ACA G TC GTA GCC CAC TTA TTA GGA GGC GTC GCA CCT TTA TTA TCT GTT GGC GCT GGA ACA ATTGTG TTT GTA GGT CTT GTT AAT TTG TTT |

Threonine

| 66 | threonine 3-dehydrogenase (*Salmonella enterica* subsp. *enterica* serovar Typhistr. CT18) GenBank: CAD03286.1 | ATG AAG GCC CTG AGC AAA TTG AAA GCC GAG GAG GGG ATC TGG ATG ACC GAT GTT CCT GAA CCA GAA GTG GGG CAC AAC GAC CTT TTA ATC AAA AT T CGCAAG ACT GCA ATC TGC GGG ACA GAC GTA CAT ATC TAT AAC TGG GA C GAG TGG AGT CAA AAA ACT ATT CCC GTC CCT ATG GTG GTC GGG CAC G AG TAT GTCGGA GAG GTT GTA GGA ATC GGA CAA GAA GTC AAA GGA TTT A AA ATC GGG GAT CGT GTG AGT GGG GAG GGT CAC ATT ACC TGT GGG CAT TGC CGC AAT TGCCGT GGA GGA CGC ACA CAT TTG TGC CGT AAC ACT ACA GGC GTA GGC GTG AAT CGT CCC GGA CCA TGT TTC GCG GAA TAC CTT GTC ATT CCA GCG TTT AAC GCCTTT AAG ATC CCT GAC AAC ATT TCA GAT GAT TTA GCA TCC ATT TTT GAC CCA TTC GGT AAC GCG GTC CAT ACT GCG TTG AG C TTC GAC TTA GTT GGA GAAGAT GTA TTA GTT TCC GGC GCC GGA CCG AT T GGC GTC ATG GCA GCT GCC GTT GCG AAG CAC GTG GGC GCA CGT CAT G TG GTA ATT ACG GAC GTA AAT GAGTAT CGT CTG GAG CTG GCA CGT AAA A TG GGG GTT ACA CGT GCC GTA AAC GTT GCG AAA GAG TCT TTA AAC GAT GTC ATG GCT GAA CTG GGC ATG ACG GAAGGG TTT GAT GTC GGA CTG GAA ATG TCC GGT GCC CCG CCA GCC TTC CGT ACC ATG TTG GAC ACC ATG AAC CAT GGG GGC CGT ATC GCA ATG TTG GGA ATTCCC CCG AGC ACG ATG TCT ATC GAC TGG ACA AAG GTA ATT TTT AAA GGC CTG TTC ATT AAG GGG AT T TAC GGT CGT GAG ATG TTT GAG ACG TGG TAC AAGATG GCT GCC TTG AT T CAA TCG GGG TTG GAT CTG AGC CCT ATC ATC ACA CAC CGT TTT TCA G TG GAT GAC TTT CAA AAA GGG TTT GAC GCC ATG TGC AGCGGT CAA TCA G GG AAA GTA ATT CTT TCT TGG GAC |
| 67 | threonine aldolase (*Escherichia coli* O26: H11 str. CVM10026) GenBank: EIL35157.1 | ATG ATT GAC CTT CGT TCG GAC ACC GTA ACC CGC CCA TCT CAC GCA ATG TTG GAA GCT ATG ATG GCC GCG CCT GTG GGG GAT GAT GCT TAT GGG GA T GACCCG ACC GTC AAC GCT TTA CAA GAT TAC GCT GCT GAA TTG TCG GG C AAA GAA GCA GCA ATC TTC TTA CCT ACA GGT ACA CAA GCT AAT CTT G TC GCC CTGCTT AGT CAC TGT GAG CGT GGC GAA GAA TAC ATT GTT GGT C AA GCA GCG CAT AAT TAC CTG TTC GAA GCT GGA GGG GCT GCT GTT CTT GGT AGC ATT CAGCCC CAA CCC ATT GAT GCT GCT GCC GAT GGT ACT CTT CCT CTG GAT AAA GTC GCT ATG AAA ATT AAG CCA GAC GAC ATT CAC TTC GCA CGC ACA AAG CTGCTG TCG CTT GAG AAT ACA CAC AAT GGA AAA GTC CTG CCC CGT GAG TAC CTG AAA GAG GCT TGG GAA TTT ACA CGC GAA CG C AAC CTG GCT CTG CAC GTAGAC GGT GCT CGC ATC TTC AAC GCC GTT GT C GCC TAC GGT TGC GAA TTG AAA GAG ATT ACG CAA TAC TGT GAC TCC T TC ACG ATT TGC TTG TCC AAA GGCTTA GGC ACC CCG GTG GGT TCA TTG T TG GTA GGA AAC CGT GAC TAT ATT AAG CGC GCC ATC CGC TGG CGT AAA ATG GCA GGG GGT GGA ATG CGT CAA TCAGGG ATT CTT GCG GCA GCT GGC ATG TAC GCG CTG AAA AAT AAT GTG GCT CGC CTT CAA GAG GAT CAC GAT AAT GCT GCG TGG ATG GCT GAG CAA TTA CGTGAG GCG GGT GCA GAC GTA ATG CGC CAA GAT ACC AAT ATG CTG TTC GTA CGT GTT GGG GAA GAA AA C GCT GCG GCC TTA GGA GAA TAC ATG AAG GCG CGTAAC GTG TTG ATC AA C GCA TCC CCT ATT GTT CGC CTT GTA ACT CAC CTT GAT GTT TCA CGT G AA CAA TTG GCG GAA GTT GCC GCC CAC TGG CGT GCC TTTCTT GCT CGC |
| 68 | serine hydroxymethyl-transferase (*Escherichia coli*) GenBank: AAA23912.1 | ATG CTT AAA CGT GAG ATG AAT ATC GCC GAC TAC GAC GCC GAA TTA TGG CAG GCG ATG GAG CAG GAG GTC CGC CAA AGG GAA CAC GAT ATT GAG CT T ATTGCG TCG GAG AAC TAT ACA TCC CCT CGC GTT ATG CAG GCG CAA CG C TCA CAG TTG ACG AAC AAA TAC GCT GAG GGA TAT CCG GGA AAG CGT T AT TAT GGCGGT TGC GAG TAC GTT GAC ATT GTT GAA CAG TTA GCG ATT G AT CGT GCT AAG GAG TTA TTT GGA GCG GAT TAT GCC AAT GTT CAA CCT CAC TCG GGC AGCCAG GCT AAC TTT GCT GTA TAC ACC GCA CTT TTA GAA CCT GGT GAC ACG TCC CTG GGT ATG AAT TTG GCC CAT GGA GGC CAC TTA |

| SEQ ID NO: | Gene or Operon | Sequence |
|---|---|---|
| | | ACT CAT GGA AGC CCTGTG AAT TTT AGT GGG AAG TTG TAT AAC ATC GTG CCC TAC GGG ATC GAC GCC ACA GGA CAC ATT GAT TAC GCA GAT TTG GA G AAA CAA GCC AAG GAA CATAAG CCT AAA ATG ATC ATC GGC GGA TTT TC A GCA TAT AGC GGA GTG GTA GAC TGG GCC AAA ATG CGC GAG ATT GCT G AT TCG ATT GGT GCT TAC CTG TTTGTC GAT ATG GCG CAT GTC GCT GGT C TG GTC GCT GCG GGA GTT TAT CCT AAC CCC GTG CCT CAC GCT CAC GTC GTG ACG ACT ACT ACA CAT AAG ACT TTAGCG GGT CCT CGT GGG GGT TTG ATT CTT GCG AAG GGG GGC TCA GAG GAA CTT TAT AAG AAG CTT AAC TCT GCC GTA TTT CCC GGC GGT CAG GGG GGC CCTCTT ATG CAC GTC ATC GCA GGA AAG GCG GTG GCT CTG AAG GAA GCG ATG GAA CCC GAA TTC AAG AC T TAC CAA CAG CAA GTA GCC AAA AAC GCC AAA GCCATG GTG GAG GTA TT C CTG GAG CGC GGC TAC AAG GTA GTT AGC GGG GGG ACG GAC AAC CAT T TG TTC TTA GTC GAT TTA GTG GAC AAA AAC CTT ACT GGTAAG GAG GCT G AT GCT GCT CTT GGG CGT GCA AAT ATC ACA GTC AAT AAG AAT AGC GTG CCC AAT GAC CCA AAG TCG CCA TTT GTG ACT TCT GGC ATC CGCGTT GGG ACT CCG GCA ATC ACC CGT CGT GGC TTT AAG GAG GCA GAG GCC AAG GAG CTG GCA GGG TGG ATG TGT GAC GTA CTG GAC TCT ATT AAT GAT GAGGCA GTT ATC GAA CGT ATT AAA GGC AAA GTG CTT GAC ATT TGT GCG CGC TA C CCC GTG TAT GCC |
| 69 | tdcC (Escherichia coli) GenBank: AAA24662.1 | ATG TCT ACT TCG GAC TCT ATT GTT TCA TCG CAA ACA AAA CAG TCA TCC TGG CGT AAA TCA GAT ACC ACC TGG ACT TTG GGT CTG TTT GGT ACC GC G ATCGGG GCT GGT GTA TTG TTT TTC CCG ATC CGC GCT GGA TTT GGT GG T TTA ATT CCT ATC CTG CTG ATG CTT GTA CTG GCA TAT CCT ATT GCT T TT TAT TGTCAT CGC GCA GCG CGC TTG TGT TTA AGC GGA AGC AAC CCC T CG GGT AAT ATC ACA GAG ACG GTG GAG GAG CAT TTC GGG AAA ACA GGA GGG GTC GTA ATCACA TTT CTG TAC TTT TTT GCT ATT TGT CCC CTG TTG TGG ATT TAT GGG GTT ACG ATC ACC AAT ACT TTT ATG ACG TTT TGG GAG AAT CAA CTG GGC TTTGCA CCG CTT AAC CGC GGA TTC GTG GCG CTG TTC CTT TTA CTG TTG ATG GCG TTT GTC ATC TGG TTC GGT AAA GAC TTA AT G GTG AAA GTC ATG TCT TATTTG GTA TGG CCT TTC ATT GCT TCA CTT GT C TTA ATT AGT CTG TCA TTA ATC CCT TAT TGG AAC TCG GCA GTA ATC G AT CAA GTA GAT CTG GGT AGC CTGTCT TTG ACC GGA CAT GAT GGG ATC T TA ATT ACC GTA TGG CTG GGC ATT TCT ATT ATG GTC TTT AGT TTT AAC TTT TCA CCT ATC GTG TCC TCC TTT GTGGTG TCC AAG CGC GAG GAA TAT GAG AAG GAT TTT GGT CGT GAT TTT ACG GAA CGT AAG TGC TCA CAA ATT ATT AGC CGC GCG TCT ATG CTT ATG GTG GCTGTC GTT ATG TTC TTT GCT TTC TCC TGC TTA TTT ACC TTG TCA CCG GCG AAC ATG GCG GAA GCG AA G GCG CAA AAC ATT CCA GTT TTA TCA TAT CTT GCTAAT CAT TTC GCT TC T ATG ACA GGG ACC AAA ACT ACT TTT GCC ATC ACA TTG GAG TAT GCG G CG TCT ATC ATT GCA TTA GTG GCC ATT TTT AAG TCG TTCTTT GGC CAT T AT TTA GGT ACT TTA GAA GGG TTG AAT GGC TTA GTC TTG AAA TTC GGA TAC AAG GGG GAC AAA ACT AAA GTT TCC TTG GGT AAG TTG AACACA ATC TCG ATG ATC TTT ATT ATG GGG AGT ACA TGG GTC GTT GCG TAT GCA AAT CCA AAC ATT CTG GAT TTA ATT GAG GCG ATG GGA GCA CCG ATT ATCGCG TCA TTG TTG TGC CTT TTG CCG ATG TAC GCC ATC CGT AAG GCG CCT TC A CTG GCC AAA TAT CGT GGG CGC TTG GAT AAC GTG TTC GTA ACC GTC A TCGTT TGC |
| 70 | Threonine/ homoserine exporter Rht A UniProtKB/ Swiss-Prot: P0AA67.1 | ATG CCT GGT TCC TTG CGT AAA ATG CCG GTT TGG TTG CCG ATT GTT ATT CTT CTG GTT GCA ATG GCT AGC ATC CAA GGA GGC GCT AGT TTA GCA AA A AGTCTG TTT CCT TTG GTG GGG GCA CCG GGT GTG ACC GCG CTG CGT TT G GCT TTG GGC ACT TTA ATT TTG ATT GCC TTC TTT AAG CCC TGG CGC C TT CGT TTTGCT AAA GAA CAA CGT TTG CCG CTT TTG TTC TAC GGC GTC T CA CTT GGT GGC ATG AAC TAT CTT TTT TAT TTA AGC ATC CAA ACC GTA CCC CTG GGT ATTGCG GTG GCT TTG GAG TTC ACG GGT CCA TTG GCA GTT GCC CTT TTC AGC TCG CGT CGC CCA GTC GAT TTC GTC TGG GTA GTG CTT GCG GTA CTT GGA CTGTGG TTC TTA CTG CCC TTA GGC CAA GAC GTG AGT CAC GTA GAC CTT ACC GGG TGT GCG CTG GCT TTG GGA GCC GGT GCT TG T TGG GCA ATT TAC ATC CTGTCG GGA CAG CGT GCG GGA GCA GAG CAC GG G CCT GCG ACA GTA GCG ATT GGG TCG CTG ATC GCA GCC CTG ATT TTC G TC CCC ATT GGT GCC TTA CAG GCAGGA GAG GCG TTG TGG CAC TGG TCA G TG ATT CCC TTA GGT TTG GCG GTA GCA ATC CTG TCT ACC GCA CTT CCT TAT TCT TTA GAG ATG ATT GCC TTA ACCCGT CTG CCG ACA CGT ACG TTT GGC ACC TTA ATG TCG ATG GAA CCG GCA TTG GCT GCC GTT TCA GGT ATG ATC TTC CTG GGA GAG ACG TTA ACT CCC ATTCAG TTG TTA GCT CTT GGG GCA ATC ATC GCT GCG AGT ATG GGA TCG ACC CTT ACG GTT CGT AAA GA G TCG AAG ATT AAA GAA TTG GAC ATC AAT |
| 71 | htB r (Escherichia coli FVEC130 2) | ATG ACG CTG GAG TGG TGG TTC GCA TAC TTG CTG ACA TCC ATC ATC CTG AGT TTA AGC CCC GGA TCT GGT GCA ATC AAC ACG ATG ACT ACG TCT TT G AATCAC GGC TAT CGT GGT GCT GTT GCA TCC ATT GCC GGC TTG CAG AC G GGA TTA GCC ATC CAT ATT GTT TTA GTG GGT GTA GGA CTT GGA ACA T |

-continued

Sequence Listing

| SEQ ID NO: | Gene or Operon | Sequence |
|---|---|---|
| | GenBank: EFI17945.1 | TA TTC AGTCGC TCG GTT ATC GCC TTT GAG GTC TTA AAG TGG GCT GGT G CC GCT TAT TTG ATT TGG CTG GGA ATT CAG CAA TGG CGT GCA GCC GGT GCG ATT GAC TTGAAG AGC CTT GCG TCC ACA CAG AGC CGC CGT GTC ACC TTG TTT CAA CGT GCA GTA TTC GTC AAT TTG ACC AAC CCC AAA AGT ATC GTC TTT CTG GCG GCA CTGTTT CCC CAG TTC ATT ATG CCT CAA CAG CCG CAG TTG ATG CAG TAC ATC GTC TTG GGC GTC ACC ACC ATC GTA GTG GAC AT T ATT GTA ATG ATT GGA TACGCC ACT CTG GCC CAA CGT ATT GCG CTG TG G ATC AAG GGC CCG AAA CAG ATG AAG GCA CTG AAC AAA ATT TTT GGT T CT TTG TTT ATG TTG GTT GGG GCACTT CTT GCC AGT GCA CGT CAC GCG |
| 72 | RhtC threonine Rht Transporter (Escherichia coli BL21(DE3)) GenBank: CAQ34168.1 | ATG CTG ATG CTT TTT TTA ACA GTA GCA ATG GTG CAT ATC GTC GCA TTG ATG TCA CCG GGA CCT GAC TTT TTT TTT GTT TCA CAA ACA GCA GTA TC A CGCTCA CGT AAG GAG GCA ATG ATG GGT GTC TTA GGG ATC ACT TGC GG C GTA ATG GTA TGG GCC GGT ATT GCA CTT CTG GGA CTG CAT TTA ATT A TT GAG AAGATG GCC TGG CTT CAC ACA TTA ATC ATG GTA GGC GGT GGG C TT TAT TTA TGT TGG ATG GGC TAT CAA ATG CTG CGT GGA GCT CTT AAG AAA GAA GCC GTGTCC GCA CCG GCT CCC CAA GTG GAA CTT GCG AAA TCA GGT CGC TCC TTC TTG AAG GGG TTG TTG ACT AAT CTT GCG AAC CCT AAG GCC ATC ATT TAT TTCGGT TCT GTG TTT AGT TTG TTC GTT GGG GAT AAT GTG GGA ACC ACG GAA CGC TGG GGA ATC TTC GCA TTA ATC ATT GA G ACG TTA GCT TGG TTC ACCGTC GTG GCC TCC CTT TTT GCT CTG CCG CA A ATG CGC CGT GGT TAC CAA CGT TTA GCA AAG TGG ATC GAC GGT TTT G CT GGA GCT TTA TTT GCG GGT TTCGGC ATT CAT CTG ATT ATT AGC CGT |
| 73 | cysteine desulfhydrase (Escherichia coli) GenBank: ALI49110.1 | ATG CCC CTG CAC AAC TTA ACA CGT TTT CCA CGC CTG GAA TTC ATT GGT GCA CCG ACT CCC TTG GAA TAT CTG CCT CGC TTT TCG GAC TAC TTA GG C CGCGAG ATT TTC ATT AAG CGC GAT GAT GTT ACA CCG ATG GCT ATG GG G GGT AAC AAA TTG CGT TTT GAA TTT CTT GCA GCG GAT GAT GTT ACA CC GT GAA GGCGCG GAC ACT TTA ATT ACC GCT GGT GCA ATT CAG TCA AAT C AC GTA CGC CAA ACT GCG GCA GTT GCT GCG AAG TTA GGT CTT CAT TGT GTC GCC CTT TTGGAA AAT CCA ATT GGC ACA ACG GCA GAA AAT TAC CTT ACC AAC GGG AAC CGT TTG TTG CTT GAC CTT TTT AAC ACA CAG AAT GAA ATG TGC GAC GCT TTAACT GAT CCC AAC GCT CAA TTG GAG GAG CTT GCG ACT CGC GTG GAA GCT CAA GGC TTC CGT CCG TAT GTT ATT CCG GTC GG C GGC AGC AAT GCT CTT GGGGCA TTA GGG TAT GTA GAG TCC GCT CTG GA G ATC GCG CAA CAA TGT GAG GGC GCG GTT AAC ATT TCG AGT GTA GTT G TG GCC TCT GGA AGT GCG GGC ACCCAC GCC GGG CTG GCT GTG GGT CTT G AG CAC TTA ATG CCT GAA TCT GAA CTG ATC GGG GTC ACA GTC TCG CGT TCC GTC GCA GAT CAG TTA CCT AAG GTAGTA AAC TTA CAG CAA GCC ATT GCG AAA GAA TTA GAA TTA ACC GCT AGT GCA GAA ATC TTA TTA TGG GAT GAT TAC TTT GCG CCT GGG TAC GGT GTC CCCAAT GAT GAA GGA ATG GAA GCA GTC AAG CTT TTA GCT CGT TTG GAG GGG ATC TTG CTG GAC CCT GT T TAC ACC GGC AAA GCA ATG GCA GGC TTA ATT GACGGT ATC AGT CAG AA A CGC TTC AAA GAC GAG GGA CCA ATT CTG TTC ATC CAT ACC GGC GGC G CT CCT GCC CTT TTT GCC TAC CAC CCT CAC GTT |
| 74 | tnaA (Escherichia coli DH1) GenBank: BAJ45452.1 | ATG GAG AAT TTC AAG CAT TTG CCC GAG CCG TTC CGC ATT CGT GTC ATT GAG CCT GTC AAG CGT ACT ACT CGC GCG TAT CGC GAA GAG GCG ATT AT C AAATCG GGT ATG AAT CAT CCA TTT TTA CTT GAT TCA GAA GAT GTG TCA T C GAT TTA CTT ACA GAT TCT GGG ACA GGC GCG GTA ACG CAA TCG ATG C AA GCA GCGATG ATG CGC GGT GAC GAA GCC TAT TCT GGC TCG CGC TCC T AT TAT GCT CTG GCC GAA TCA GTC AAA AAC ATT TTT GGT TAC CAA TAT ACG ATT CCC ACGCAT CAG GGA CGC GGA GCA GCA GCA TTT TAT ATC CCA GTC TTA ATC AAA AAG CGC GAG CAA GAA AAG GGA TTG GAC CGC TCG AAA ATG GTA GCC TTC TCAAAT TAC TTC TTC GAC ACT ACT CAG GGG CAC TCG CAA ATC AAC GGC TGC ACT GTT GCG AAT GTG TAT ATC AAG GAA GCC TT T GAT ACA GGC GTA CGT TACGAT TTC AAG GGG AAC TTT GAC CTG GAA GG T CTT GAA CGT GGC ATT GAA GAA GTA GGA CCC AAC AAC GTA CCC TAT A TC GTC GCC ACG ATC ACA TCT AATAGC GCA GGA GGT CAG CCT GTG TCT T TG GCG AAT CTG AAA GCG ATG TAT TCG ATC GCC AAA AAG TAT GAT ATC CCC GTC GTA ATG GAT TCT GCA CGT TTTGCA GAG AAC GCC TAC TTC ATT AAA CAG CGT GAA GCG GAG TAC AAA GAT TGG ACC ATC GAA CAG ATC ACT CGT GAG ACT TAT AAA TAT GCT GAC ATG CTGGCT ATG TCG GCT AAG AAG GAC GCT ATG GTC CCA ATG GGA GGC TTT TTA GCG ATG AAG GAC GAT AG T TTT TTT GAC GTT TAT ACG GAA TGT CGC ACC CTTTGT GTA GTG CAG GA A GGA TTC CCC ACT TAT GGC GGC TTG GAA GGT GGA GCG ATG GAA CGT T TA GCT GTT GGA CTG TAT GAT GGT ATG AAT CTG GAT TGGCTG GCA TAT C GT ATT GCG CAG GTG CAG TAC CTG GTA GAC GGG TTA GAG GAG ATC GTT GTG TGC CAG CAG GCC GGG GGC CAT GCG GCG TTC GTG GACGCA GGA AAA CTG CTT CCC CAC ATT CCC GCC GAT CAG TTC CCT GCG CAG GCA CTT GCT TGC GAG TTA TAC AAG GTG GCC GGT ATC CGT GCG GTA GAG ATCGGC TCG TTT CTT TTG GGG CGC GAC CCT AAA ACA GGA AAA CAA TTG CCC TG C CCT GCC GAA CTT CTT CGC CTT ACT ATC CCT CGT GCG ACC TAC ACT C |

Sequence Listing

| SEQ ID NO: | Gene or Operon | Sequence |
|---|---|---|
| | | AAACC CAC ATG GAC TTT ATT ATC GAG GCC TTC AAA CAT GTG AAG GAG A AT GCT GCT AAT ATC AAG GGC CTG ACC TTT ACC TAC GAG CCA AAG GTT TTG CGCCAC TTT ACA GCA AAA CTT AAA GAA GTT |
| 75 | cysK (*Escherichia coli* O104: H4 str. C227-11) GenBank: EGT66151.1 | ATG TCA AAA ATT TTC GAG GAT AAC TCG TTA ACG ATC GGC CAC ACT CCC TTG GTT CGT CTG AAT CGT ATC GGT AAC GGG CGC ATT CTG GCA AAG GT T GAATCA CGC AAT CCG TCC TTC TCA GTT AAG TGC CGT ATT GGA GCG AA T ATG ATT TGG GAT GCT GAG AAG CGC GGA GTC CTG AAG CCT GGG GTG G AG TTG GTGGAG CCA ACC TCT GGG AAT ACA GGT ATC GCG CTG GCT TAT G TA GCT GCA GCG CGT GGC TAC AAA TTA ACA CTT ACC ATG CCC GAG ACC ATG TCA ATC GAACGT CGT AAG TTG TTG AAG GCA TTA GGA GCG AAT CTG GTA CTG ACC GAA GGA GCT AAG GGA ATG AAG GGC GCT ATT CAA AAA GCG GAA GAA ATT GTC GCAAGT AAC CCC GAA AAG TAT CTT TTA CTG CAA CAG TTT TCT AAC CCT GCA AAT CCT GAG ATC CAC GAA AAA ACA ACA GGT CC C GAA ATC TGG GAA GAC ACCGAC GGT CAA GTT GAC GTA TTT ATC GCC GG G GTA GGA ACT GGA GGA ACC TTA ACG GGG GTC AGT CGT TAT ATT AAG G GT ACG AAG GGA AAG ACT GAT TTGATT AGC GTA GCA GTG GAG CCA ACG G AT AGT CCT GTT ATT GCC CAA GCC CTG GCG GGG GAG GAA ATC AAA CCG GGA CCT CAC AAA ATC CAA GGG ATT GGTGCG GGT TTT ATC CCA GCC AAT CTG GAT CTG AAA CTT GTC GAC AAG GTC ATT GGA ATT ACT AAT GAA GAG GCG ATC TCC ACT GCG CGC CGT TTG ATG GAGGAA GAA GGG ATT TTG GCA GGG ATT TCA AGC GGT GCG GCG GTG GCA GCA GCT TTG AAA TTG CAA GA A GAC GAG TCA TTC ACT AAT AAG AAT ATT GTT GTTATT TTA CCA AGC AG C GGT GAG CGC TAC TTA TCA ACC GCT TTG TTC GCT GAT TTA TTT ACG G AA AAA GAG TTA CAA CAA |
| 76 | cysm (*Escherichia coli* FVEC1412) GenBank: EFF01099.1 | ATG TCA ACA TTA GAA CAG ACA ATT GGT AAT ACC CCC CTG GTC AAA TTG CAG CGC ATG GGG CCA AAC AAT GGA AGC GAG GTT TGG CTG AAA TTG GA A GGCAAC AAC CCG GCG GGA TCT GTG AAA GAC CGT GCC GCA CTG TCC AT G ATC GTA GAA GCT GAG AAA CGT GGC GAG ATT AAA CCT GGG GAT GTT T TA ATC GAGGCT ACA AGT GGG AAC ACT GGA ATC GCC CTT GCC ATG ATT G CG GCT TTA AAG GGT TAT CGT ATG AAG TTA CTT ATG CCC GAT AAC ATG AGC CAG GAG CGCCGT GCC GCT ATG CGT GCC TAT GGT GCT GAA CTT ATC TTA GTT ACC AAG GAG CAA GGC ATG GAA GGT GCG CGT GAC TTG GCA TTA GAA ATG GCG AAT CGTGGC GAA GGG AAG CTG CTT GAC CAA TTT AAT AAT CCA GAT AAC CCT TAT GCA CAC TAT ACC ACG ACC GGC CCG GAA ATC TG G CAA CAA ACC GGC GGG CGCATC ACC ACC CAC TTT GTA TCA TCC ATG GGC AC A ACT GGT ACA ATT ACG GGC GTT TCT CGT TTC ATG CGC GAG CAG AGT A AA CCT GTT ACA ATC GTG GGA CTTCAA CCT GAG GAG GGA TCT TCG ATC C CA GGC ATT CGT CGT TGG CCT GCT GAG TAC TTA CCT GGC ATT TTC AAC GCA TCC TTA GTG GAT GAA GTT CTT GACATT CAT CAG CGC GAA GCA GAG AAT ACC ATG CGC GAG TTG GCA GTA CGT GAG GGC ATT TTC TGC GGG GTT TCT TCT GGG GGG GCC GTG GCG GGT GCT TTACGT GTC GCC AAA GCA AAC CCC GGA GCA GTA GTT GTT GCC ATT ATT TGT GAT CGT GGT GAC CGC TA C TTA TCT ACG GGA GTC TTC GGA GAG GAA CAC TTTTCA CAA GGG GCC GG A ATT |
| 77 | malY (*Escherichia coli*) GenBank: AAA24099.1 | ATG TTC GAT TTT TCG AAA GTC GTC GAT CGT CAT GGG ACC TGG TGC ACT CAA TGG GAC TAC GTG GCA GAC CGC TTT GGG ACA GCA GCA GAT TTC GAC G TTCACT ATT AGC GAC ATG GAT TTT GCC ACA GCA CCT TGC ATT ATC GA G GCA CTG AAT CAG CGC TTA ATG CAT GGG GTT TTC GGT TAT AGC CGT T GG AAG AACGAT GAG TTC CTT GCA GCA ATT GCA CAT GGT TCA GTA CCC C AA CAT TAT ACC GCT ATC GAT TCC CAG ACG GTT GTG TAC GGC CCC AGC GTT ATT TAC ATGGTG AGC GAA TTG ATC CGT CAG TGG TCT GAA ACA GGA GAA GGT GTA GTA ATC CAT ACT CCC GCC TAT GAC GCG TTC TAC AAA GCC ATT GAG GGG AAT CAACGT ACA GTA ATG CCC GTT GCC TTA GAA AAA CAG GCA GAC GGA TGG TTT TGC GAT ATG GGA AAA TTA GAG GCG GTA CTT GC A AAA CCC GAG TGC AAA ATCATG CTT TTA TGC AGT CCG CAA AAC CCA AC A GGC AAG GTC TGG ACC TGT GAT GAA TTA GAG ATT ATG GCG GAT TTG T GC GAG CGT CAC GGA GTC CGT GTCATC TCT GAC GAG ATT CAC ATG GAC A TG GTC TGG GGG GAA CAG CCG CAC ATT CCT TGG TCT AAT GTC GCA CGT GGT GAT TGG GCC CTT TTG ACA TCG GGTTCG AAA AGC TTT AAC ATT CCA GCC CTG ACC GGG GCA TAT GGA ATT ATC GAG AAC TCG TCG AGC CGT GAC GCG TAT TTA TCT GCC CTT AAG GGA CGT GATGGA CTT TCG AGC CCG TCG GTT CTT GCC TTG ACG GCA CAC ATT GCT GCT TAC CAA CAG GGA GCG CC G TGG CTG GAC GCT CTT CGC ATT TAC CTG AAG GATAAC CTT ACT TAC AT T GCG GAT AAG ATG AAT GCG GCC TTC CCA GAA CTT AAC TGG CAG ATT C CC CAG TCA ACG TAT TTA GCC TGG CTT GAC CTT CGT CCCTTA AAC ATT G AT GAC AAC GCA CTG CAA AAG GCA CTG ATC GAA CAG GAA AAG GTA GCC ATC ATG CCT GGC TAT ACC TAC GGC GAG GAG GGC CGT GGG TTCGTC CGC CTG AAC GCA GGA TGT CCC CGC TCG AAA CTT GAA AAA GGG GTA GCT GGT CTT ATT AAT GCT ATT CGC GCT GTG CGC |

Sequence Listing

| SEQ ID NO: | Gene or Operon | Sequence |
|---|---|---|
| 78 | MetC (*Escherichia coli*) GenBank: ADK47401.1 | ATG GCC GAC AAG AAG TTG GAT ACT CAA CTG GTG AAC GCC GGG CGT TCC AAA AAA TAT ACC TTG GGA GCT GTT AAT AGC GTT ATC CAA CGT GCA TC A AGTTTA GTT TTC GAT AGT GTC GAA GCA AAG AAG CAT GCG ACA ACG CG AA T CGC GCA AAT GGG GAA TTA TTT TAT GGA CGC CGC GGG ACC TTG ACC C AC TTC TCTTTA CAG CAG GCC ATG TGT GAG CTG GAA GGG GGA GCC GGT T GT GTA TTG TTC CCC TGC GGA GCC GCG GCG GTG GCT AAC AGT ATC CTG GCG TTC GTG GAGCAG GGT GAT CAC GTC CTG ATG ACG AAC ACC GCG TAC GAA CCC TCG CAA GAC TTC TGC AGT AAA ATC TTA TCC AAA TTA GGT GTG ACT ACC TCG TGG TTTGAC CCG TTG ATC GGG GCG GAC ATT GTG AAA CAT CTG CAG CCC AAC ACG AAA ATT GTT TTT TTG GAG TCT CCC GGT TCG AT T ACT ATG GAG GTA CAC GACGTG CCA GCT ATC GTT GCA GCA GTT CGT TC C GTG GCG CCC GCA GCA ATT ATC ATG GAC AAT ACA TGG GCC GCA G GC GTC CTT TTT AAA GCC TTA GATTTT GGC ATT GAT GTA AGT ATC CAA G CG GCT ACC AAG TAC TTG GTC GGA CAT TCC GAT GCG ATG ATT GGT ACA GCA GTA TGC AAT GCA CGC TGC TGG GAGCAA TTG CGT GAA AAC GCT TAC CTG ATG GGG CAA ATG GTA GAC GCA GAT ACC GCT TAT ATT ACC AGT CGT GGG TTG CGT ACA TTA GGA GTG CGT TTG CGTCAA CAC CAC GAG TCA TCC CTG AAA GTG GCT GAA TGG CTG GCT GAA CAT CCC CAG GTT GCT CGC GT A AAC CAC CCC GCA CTT CCG GGA TCA AAG GGC CATGAA TTT TGG AAG CG C GAC TTC ACG GGC TCC AGT GGA TTG TTT TCT TTC GTA CTT AAG AAA A AG TTG TCT AAT GAA GAA TTG GCG AAT TAC CTT GAT AACTTT AGC TTG T TT AGT ATG GCA TAT AGT TGG GGG GGA TAT GAA TCA CTG ATT TTG GCA AAT CAA CCA GAA CAT ATT GCT GCG ATT CGT CCT CAA GGC GAAATT GAT TTT AGC GGA ACG TTA ATT CGT CTG CAC ATC GGG CTT GAG GAT GTG GAC GAT TTA ATT GCA GAT TTG GAT GCG GGA TTT GCA CGT ATT GTG |
| 79 | cystathione gamma lyase (*Trypanosoma grayi*) NCBI Reference Sequence: XP_009313447.1 | ATG TCA GGT GCC CAG CAC TTG TTC GCA GAT TTC AGC GAA GGA TCA GGA TCG TGG CAA CCC CAG GCC CAG GGG TTT GAG ACG CTT CTG GTA CAT GG T GGCGTA AAG CCA GAT CCC GTC ACG GGG GCA ATC CTG ACC CCC GTC TA C CAG TCT ACG ACG TTC GTG CAA GAG AGT ATC GAA CGT TAT CAA GCA A AG GGC TATAGC TAT ACC CGT TCA GCC AAT CCT ACC GTA TCT GCA TTG G AA GAG AAA TTG TGC GCA ATC GAG CAC GGC GAA TAT GCC ACT GTG TAT AGC ACC GGC ATGTCC GCT ACG ACA ACG GCC ATC AGT AGT TTT ATG TCT GCT GGC GAC CAC GCT ATT GTG ACC GAA TGT AGC TAT GGC GGA ACC AAT CGT GCC TGC CGT GTCTTC TTC ACG CGC TTA GGT ATG TCT TTT ACA TTC GTA GAT ATG CGC GAC GTT AAA AAT GTA GAG GCT GCC ATC AAA CCC AA T ACC AAG CTG GTT ATC TCAGAA TCG CCA GCA AAC CCT ACA CTG ACG CT T ACT GAT ATT GAC GCA CTT AGC TCG CTT TGC AAG GCT AAG GGT ATT A TT CAC ATG TGT GAC AAC ACT TTCGCA ACC GCT TTC ATT ATG CGT CCG C TT GAT CAC GGA GCA GAC GTG ACC CTG ATC TCC ACG ACT AAG TTT GTT GAT GGC CAC AAT ATG ACC GTC GGA GGGGCC TTG GTC ACT AAA TCC AAG GAA TTA GAC GGA AAG GTA CGT TTA ACG CAA AAT ATC TTA GGT AAC TGT ATG AGT CCA TTT GTT GCG TTC CTT CAA TTACAA ACG GTG AAG ACG ATG AGC CTT CGC ATT TCT CGT CAA TCA GAA AAC GCC CAG AAA GTA GCG GA A TTT CTT GAG ACC CAC CCC GCA GTG GAA CGC GTAATG TAT CCA GGT CT T AAA TCT TTC CCA CAG AAG GCC TTA GCG GAT CGT CAG CAC GCA AAC A AT TTA CAT GGC GGT ATG TTA TGG TTT GAA GTG CGC GGAGGA ACA GCG G CA GGG CGT CGC TTG ATG GAC ACC GTT CAG CGC CCG TGG AGC TTA TGC GAG AAT CTG GGT GCG ACG GAA TCC ATC ATT ACT TGC CCG AGTGTC ATG ACC CAC GCG AAC ATG ACT ACT GAG GAC CGT ATG AAG GTC GGT ATC ACC GAC GGA TTT GTA CGT GTC AGC TGC GGG ATC GAA GAT GCA GCC GATCTT ATC TCA GCT TTG AAG GCC GCA CTG GAT GCC TTG GGC AAG |
| 80 | Cystathione beta-synthase (*Helicobacter pylori* 2017) GenBank: ADZ49193.1 | ATG ATC TTA ACA GCA ATG CAA GAT GCA ATC GGG CGT ACA CCT ATC TTC AAG TTT ACA CGT AAA GAT TAC CCA ATT CCA TTG AAG TCG GCA ATT TA C GCGAAA TTG GAA CAC TTA AAC CCG GGG GGA TCC GTG AAA GAT CGC CT T GGG CAG TAT CTT ATT AAG GAG GCC TTC CGT ACA CAC AAG ATT ACC T CT ACT ACCACT ATC ATC GAA CCT ACT GCT GGG AAT ACT GGC ATC GCC C TT GCC CTT GTA GCT ATC AAA CAT CAT CTT AAA ACG ATC TTT GTT GTT CCC GAA AAA TTTTCG GTT GAG AAA CAA CAG ATC ATG CGT GCT CTT GGT GCC TTA GTA ATC AAT ACG CCT ACC TCA GAG GGT ATC TCA GGG GCC ATT AAA AAA AGC AAA GAGTTA GCC GAG TCT ATC CCG GAC AGC TAC TTG CCT CTT CAA TTT GAG AAT CCC GAC AAT CCG GCT GCT TAT TAC CAC ACT CT T GCT CCT GAA ATT GTA AAGGAA CTG GGG ACG AAT TTT ACC TCT TTT GT A GCG GGC ATC GGT TCT GGA GGA ACT TTC GCA GGC ACC GCC AAG TAC C TT AAA GAA CGT ATC CCG AAC ATCCGC TTG ATT GGA GTT GAA CCA GAA G GT TCT ATT TTA AAT GGG GGT GAA CCG GGG CCC ACC GAA ATC GAA GGA ATT GGA GTA GAG TTC ATC CCA CCA TTCTTC GCT AAT TTG GAT ATT GAT GGG TTT GAG ACG ATT TCA GAC GAA GAG GGC TTC AGT TAT ACG CGC AAA TTA GCC AAA AAG AAC GGA TTA TTA GTG GGTAGT TCG TCC GGA GCA GCG TTC GCC GCG GCT CTT AAG GAA GTA CAA CGT CTG CCC GAA GGG TCA CA A GTG TTG ACG ATT TTC CCA GAT ATG GCT GAT CGCTAC CTT AGT AAA GG C ATT TAT TCC |

Sequence Listing

| SEQ ID NO: | Gene or Operon | Sequence |
|---|---|---|
| 81 | putative amino transferase (*Helicobacter pylori* 2017) GenBank: ADZ50111.1 | ATG CAA GCT TTC TTG AAC CGT TCG TTC GCG CCC CTT TTA AAC CCA AAT GAG AAC CTG CTG GAT CAA GTT AAG AGT TCG ATT ATT TTG AAG AAA GG T GTTAGC TAC TTT GAC TGG GGT GCT AGT GGG CTG GCC AGT GCA TTG GT C GAG AAA CGT GTT AAG TCC CTG CTT CCA TAT TAT GCC AAT GCC CAC A GC GTA GCAAGT AAA CAT GCC ATC TTA ATG GGC ATG TTA CTT AAA GAA T GC CAA GAG AAG CTG AAA CGC TCG TTA AAC CTT AGT ACT AAC CAT GC GTG CTT AGC GCCGGG TAT GGC GCG AGC TCA GCG ATC AAG AAA TTC CAA GAG ATC CTG GGA GTT GCA TCC CCT AAA ACC AAA AAG AAT CTG GAA CCT TAT TTA AAA GACATG GCG CTG AAA CGC GTA ATC GTA GGT CCT TAT GAA CAT CAC TCT AAC GAG GTC TCT TGG CGC GAG TCT CTT TGT GAG GT G GTG CGC ATT CCA CTT AACGAA CAT GGA CTG CTG GAT TTG GAG ATT TT A GAG CAG ATC TTA AAG AAA TCC CCC AAT TCT CTG GTC TCC GTC TCG G CC GCA AGT AAT GTA ACG GGG ATTCTG ACA CCC CTG AAA GAA ATT AGC T CA CTG TGC AAG GAG TAT CGC GCG ATC CTG GCG CTT GAT CTG GCC AAC TTT TCC GCA CAC GCG AAC CCG AAA GACTGC GAG TAC ACA ACG GGG TTC TAT GCA CCA CAC AAG TTG TTG GGT GGT ATT GGG GGA TGC GGG CTT CTT GGA ATC TCC AAA GAC TTG ATC GAT ACA CAGATC CCA CCT AGT TTT TCA GCC GGA GGA GTC ATT AAG TAC GCA AAC CGC ACG CGT CAC GAA TTT AT T GAT GAG CTG CCG TTG CGT GAG GAG TTC GGA ACTCCG GGA CTG CTG CA A TTT TAT CGC TCA GTG TTA GCC TAC CAG TTA CGT GAC GAA TGC GGT T TG GAT TTC ATT CAT AAG AAG GAG AAT AAT CTG CTT CGTGTG TTA ATG C AT GGC TTG AAA GAT CTG CCA GCT ATC AAC ATT TAC GGC AAT TTA ACC GCA AGC CGC GTA GGA GTA GTC GCG TTT AAC ATC GGA GGC ATTAGT CCA TAC GAT CTT GCC CGT GTC CTG AGT TAC GAA TAT GCT ATT GAG ACT CGC GCA GGG TGC TCT TGT GCC GGC CCG TAT GGA CAT GAC TTA CTG AATTTG AAT GCA CAA AAG TCT TCC GAT TTC AAT GCA AAA CCT GGA TGG TTG CG C GTC TCA CTT CAT TTT ACA CAC AGT ATT AAT GAC ATT GAC TAT CTG T TGGAC TCT CTG AAG AAA GCT GTT AAG AAA CTG CGT |
| 82 | YdeD (*Bacillus atrophaeus* UCMB-5137) GenBank: AKL87093.1 | ATG AAC GGT GAA CAC GCC GCG TTG GCC CAC TCC CGC ACA AAA GGG ATT GCT TTG GTT TTA ACG GGC AAT ACT TTA TGG GGC GTT TCA GGG ACA GT T GCGCAG TAC TTA TTC CAA CAA CAA CAT TTT AAC GTA GAG TGG TTG AC C GTC GTT CGC TTG TTG CTG TCT GGT ATC TTG CTG CTT GGC CTT GCC T AT CGT AAGGAA AAG CAA CGC ATC TGG GCT GTC TGG AAA GAC AAG ACA G AT GGT CTG AAT CTG GTT CTG TTC GGG ATT TTG GGG ATG TTG TCC GTC CAG TAC ACA TACTTT GCG GCT ATC CAG CAT GGT AAT GCG GCG ACG GCA ACT GTA CTT CAG TAT CTG GCC CCG GCA CTT ATT ACC TGC TAC GTA GCC ATT CGC TCT AAG CGTCTT CCA ACC GTC AAA GAG TTG ATC GCA GTT TTC CTG GCT ATT ATT GGA ACG TTT TTT TTA GTC ACC CAT GGG GAC ATC CA C AGT CTT AGT ATC TCA GGGTGG GCT TTA TTC TGG GGA TTA AGT TCG GC G TTT GCC CTG GCG TTT TAC ACT TTG CAC CCT CAT AAA CTT CTG GCC A AG TGG GGG GCG GCT ATC GTT GTTGGC TGG GGT ATG CTT ATC GGA GGG C TT GGT CTT TCC TTA ATC CAT CCT CCA TGG AAA TTT GAG GGA CAG TGG TCG GTC TCG GCT TAT GCC GCC GTT ATTTTC ATT GTC CTG TTT GGG ACC CTG ACT GCC TTC TAC TGC TAC CTG GAA TCT TTA AAG TAC TTA ACT GCC AGC GAA ACT TCA TTA ATC GCC TGC GCG GAGCCC TTA AGT GCT GCG TTC TTA AGC GTG ATT TGG TTG CAT GTG ACT TTT GGT ATC AGC GAG TGG CT T GGT ACT TGT TGT ATT TTA TCT ACG ATT ATG ATCTTA TCG ATT AAG GA G AAG AAG CTG AAG |
| 83 | protein YfiK (*Escherichia coli*) GenBank: AJE57139.1 | ATG ACA CCC ACG TTG CTT AGC GCC TTC TGG ACG TAC ACC CTT ATT ACA GCC ATG ACG CCT GGG CCA AAT AAT ATC CTT GCC TTA TCA TCC GCA AC G TCGCAT GGG TTC GCC CAG TCC ACC CGT GTG CTT GCA GGT ATG TCT CT T GGC TTT TTA ATC GTT ATG CTG TTG TGC GCG GGA ATC AGT TTC TCC T TG GCG GTAATC GAC CCC GCC GCC GTA CAT TTA TTG TCT TGG GCT GGT G CC GCG TAT ATT GTT TGG CTG GCT TGG AAA ATT GCC ACG TCT CCG ACT AAG GAA GAT GGTTTA CAA GCA AAA CCC ATC TCG TTT TGG GCT TCA TTT GCA CTT CAG TTC GTG AAT GTC AAG ATT ATT CTT TAC GGG GTA ACA GCC CTG TCC ACT TTC GTTTTA CCC CAG ACG CAG GCG TTG TCA TGG GTA GTC GGA GTG TCC GTC TTA TTA GCC ATG ATC GGT ACG TTT GGG AAT GTG TG C TGG GCG CTG GCG GGC CACTTG TTT CAA CAA TTA TTC CGT CAG TAC GG T CGC CAG TTA AAT ATC GTT CTT GCT TTA TTA CTG GTG TAT TGT GCA G TC CGC ATC TTC TAT |
| 84 | multidrug efflux transporter. Bcr (*Escherichia coli*) GenBank: CDZ21005.1 | ATG ACG ACC CGC CAG CAT AGC TCG TTC GCA ATC GTA TTT ATT CTT GGA TTG CTT GCT ATG TTG GCC TTA TCA ATC GAC ATG TAC TTA CCA GC C CTGCCT GTT ATT TCG GCC CAA TTT GGA GTA CCC GCT GGG TCA ACC CA A ATG ACA TTA TCA ACA TAC ATT CTG GGG TTC GCT TTA GGA CAG TTG A TT TAT GGTCCA ATG GCT GAC TCG TTT GGG CGC AAA CCA GTG GTC TTG G GC GGG ACA CTG GTC TTT GCG GCC GCA GCC GTT GCG TGT GCC TTG GCT AAC ACG ATC GACCAG CTT ATT GTA ATG CGT TTC TTC CAT GGC TTA GCT GCG GCG GCT GCC AGT GTA GTG ATT AAT GCG CTT ATG CGT GAC ATC TAT |

| SEQ ID NO: | Gene or Operon | Sequence |
|---|---|---|
| | | CCG AAG GAG GAA TTCAGC CGC ATG ATG AGC TTC GTA ATG TTG GTA ACG ACC ATC GCT CCA TTA ATG GCC CCT ATT GTT GGG GGT TGG GTC TTA GT C TGG CTT TCA TGG CAT TACATT TTT TGG ATC CTT GCC CTG GCG GCT AT T CTG GCC TCA GCG ATG ATT TTC TTC CTG ATT AAA GAA ACC CTT CCT C CG GAG CGC CGT CAG CCT TTC CATATT CGC ACT ACT ATC GGT AAT TTT G CG GCC TTG TTT CGC CAT AAA CGC GTG CTG TCA TAC ATG TTG GCA AGC GGC TTT TCT TTC GCG GGT ATG TTC TCGTTT TTA AGT GCT GGT CCC TTC GTG TAT ATC GAA ATC AAT CAC GTA GCC CCG GAG AAC TTC GGC TAT TAC TTC GCA TTA AAT ATC GTG TTT CTT TTC GTCATG ACC ATC TTC AAC TCT CGC TTC GTC CGT CGT ATC GGT GCC TTA AAT ATG TTT CGT TCG GGG CT G TGG ATC CAA TTT ATC ATG GCT GCG TGG ATG GTGATC TCC GCA CTG TT G GGG CTT GGG TTT TGG TCG CTT GTG GTG GGC GTG GCT GCA TTC GTT G GA TGT GTC AGC ATG GTA TCT TCT AAC GCG ATG GCT GTAATT TTG GAT G AG TTC CCA CAT ATG GCA GGG ACT GCT TCC TCT CTG GCT GGC ACA TTT CGC TTC GGA ATT GGT GCA ATC GTA GGC GCG TTG CTG AGC TTAGCG ACA TTC AAT TCG GCG TGG CCC ATG ATT TGG TCC ATT GCG TTT TGT GCG ACC AGC AGC ATC CTG TTC TGC CTT TAT GCT TCC CGT CCA AAG AAG CGT |
| 85 | TolC (*Pseudomonas fluorescens* R124) GenBank: EJZ58348.1 | ATG AAC AAA CTT AGT ATG CTG GGA GCT GCC TTC GCG TTG TTG GCA GGG AAC TCA GCA TTG GCA GCA ATG GGG CCT TTC GAA ATC TAC GAA CAG GC T CTTCGC AAT GAC CCA GTT TTC TTA GGG GCC ATT AAG GAG CGT GAC GC C GGA TTG GAA AAC CGC ATC ATC GGC CGC GCA GGA TTG TTA CCA CGC T TG GGG TACAAC TAC AAT CGT GGC CAT AAC ACC TCT AAA GCG ACC CAG T TG ACA AAT CGT GGC TCT CTG ACT GAA GAC CGT AAC TAT AAT TCG TAT GGT TCA ACT CTTACA TTA CAG CAA CCC TTA TTA GAC TAT GAG GCC TAT GCC GCC TAC CGT AAG GGA GTA GCG CAA AGC TTG TTC GCC GAT GAA GCC TTT CGC GGT AAG TCACAG GAA TTA TTG GTT CGC GTC TTA GAT AAT TAC ACG AAA GCG TTG TTC GCA CAA GAC CAA ATC GAT ATC GCA CAG GCG AA A AAA AAA GCT TAT GAA CAACAA TTT CAG CAG AAC GAA CAT ATG TTC AA A CAA GGC GAG GGG ACG CGC ACT GAC ATT TTG GAA GCT GAA AGT CGT T AT GAA CTT GCC ACG GCA GAA GAAATC GAG GCG CGT AAC GAA CAG GAT G CC GCT CTT CGC GAG CTT GGT GCG CTT GTC GGT CTG CCA CAC ACT GTC GAC ATT TCT GAA CTT GCA CCC TTA GAC CAGAAT TTT CAA ACG TTC GCG CTG ATG CCT GCT AAC TAT GAT ACG TGG CAC GAG TTA GCA ATT TCT AAT AAT CCG AAC CTG GCA TCA CAG CGT CAG GCC GTGGAA GTA GCA AAA TAC GAA GTT GAA CGT AAC CGT GCA GGA CAT TTA CCC AAG GTC TCA GCA TAT GC C AGC ATT CGT CAG ACT GAG TCT GAC AGT GGT AATACC TAC AAT CAA CG T TAT GAT ACG AAC ACC ATT GGC TTT GAG GTA AAC GTC CCT CTG TAT G CA GGA GGA GGA GTC TCA GCA AGT ACA CGC CAA GCA TCACGC ACG ATG G AG CAG GCG GAG TAT GAA TTA GAT GGA AAG ACG CGT GAG ACG TTA ATT GAA TTA CGT CGT CAG TTC AGC GCG TGC CTT AGT GGA GTT AATAAG TTA CGC GCC TAT CAG AAA GCC CTG GCC TCG GCC GAA GCA CTG GTG GTC TCA ACC AAG CAG AGC ATT CTT GGC GGC GAA CGC ACC AAC TTG GAC GCGCTT AAC GCG GAA CAG CAG CTG TTC ACC ACG CGT CGC GAC CTT GCA CAG GC C CGC TAT GAC TAC TTG ATG GCG TGG ACG AAA CTG CAT TAT TAC GCA G GAACC CTG AAC GAA CAA GAT TTA GCG CGT GTG GAC GAG GCA TTT GGC C AA GGG CCC AAA TCA AAT CCT CGC |
| 86 | Tyrosine transaminase (*Sinorhizobium meliloti* AK83) GenBank: AEG55340.1 | ATG TTC GAT GCG CTG GCG CGT CAA GCG GAT GAT CCG CTT TTG GCG CTG ATC GGA CTG TTT CGC AAA GAC GAG CGC CCC GGT AAA GTG GAC TTA GG T GTGGGA GTT TAC CGC GAC GAA ACT GGC CGC ACT CCG ATC TTT CGC GC G GTT AAA GCA GCC GAA AAA CGC TTG CTT GAG ACT CAG GAC TCG AAG G CC TAC ATCGGC CCG GAA GGA GAC CTG GTT TTT CTT GAC CGT TTG TGG G AA CTT GTT GGG GGG GAT ACC ATT GAA CGT TCT CAC GTA GCT GGT GTA CAA ACA CCT GGCGGG AGC GGC GCA CTT CGT TTG GCG GCA GAT TTA ATC GCC CGC ATG GGC GGT CGC GGG ATT TGG TTG GGG TTG CCA TCC TGG CCG AAT CAC GCT CCC ATTTTC AAA GCG ACT GGA CTG GAT ATC GCG ACT TAC GAT TTC TTT GAT ATC CCG AGT CAA TCC GTT ATT TTT GAT AAC CTG GT G TCT GCC CTG GAA GGT GCAGCA TCT GGC GAT GCC GTC TTA TTG CAT GC T AGC TGC CAC AAT CCA ACT GGA GGG GTA TTA TCC GAG GCA CAG TGG A TG GAA ATT GCC GCG CTG GTC GCCGAA CGC GGA CTG TTA CCA CTT GTT G AT CTT GCG TAT CAA GGG TTC GGA CGT GGG CTG GAT CAA GAC GTC GCG GGC TTA CGC CAT TTA TTA GGT GTA GTTCCC GAA GCC CTT GTC GCC GTT AGC TGC TCT AAA TCG TTC GGC TTG TAC CGC GAA CGC GCT GGA GCC ATC TTC GCC CGT ACA TCA TCT ACC GCT TCA GCCGAC CGC GTC CGC AGT AAC TTA GCT GGC CTT GCT CGC ACA TCG TAT AGT ATG CCC CCC GAT CAC GG G GCC GCG GTT GTC CGT ACG ATC TTA GAC GAC CCAGAG CTG CGT CGT GA C TGG ACC GAG GAA TTA GAG ACA ATG CGC TTG CGT ATG ACG GGT CTT C GC CGC TCT CTT GCA GAG GGC TTG CGC ACC CGT TGG CAGTCT CTT GGC G CC GTA GCT GAC CAA GAA GGG ATG TTC TCG ATG CTG CCG TTG TCC GAA GCA GAG GTT ATG CGC CTT CGC ACT GAG CAT GGA ATT TAC ATGCCC GCA TCA GGA CGC ATT AAC ATT GCG GGG TTA AAA ACG GCG GAG GCT GCC GAA ATT GCA GGT AAA TTT ACG AGT TTG |

| SEQ ID NO: | Gene or Operon | Sequence |
|---|---|---|
| 87 | tyrosine transporter TyrP (*Escherichia coli* W) GenBank: AFH11702.1 | ATG AAG AAC CGC ACT CTT GGA TCA GTA TTC ATT GTT GCG GGG ACC ACC ATC GGT GCA GGT ATG CTT GCC ATG CCC CTG GCT GCA GCT GGC GTC GG G TTCAGC GTT ACC CTG ATT TTA CTG ATT GGT CTG TGG GCT CTG ATG TG T TAC ACG GCA TTG CTT TTG CTT GAA GTG TAC CAG CAT GTA CCC GCA G AC ACC GGTCTT GGC ACT CTG GCG AAA CGT TAT TTA GGA CGT TAT GGT C AA TGG CTG ACC GGT TTC TCC ATG ATG TTT CTG ATG TAT GCG CTG ACG GCC GCA TAC ATTAGT GGT GCA GGT GAA CTG CTG GCA AGT TCA ATT TCT GAC TGG ACG GGC ATC TCT ATG AGC GCG ACT GCT GGG GTT TTA TTG TTT ACA TTT GTG GCT GGCGGT GTA GTG TGT GTA GGG ACG TCA TTA GTT GAT CTG TTT AAC CGC TTC CTT TTC AGT GCA AAA ATC ATT TTC CTT GTA GT A ATG CTT GTC TTA TTA TTACCA CAT ATT CAT AAG GTA AAT CTT TTG AC A TTA CCA TTG CAG CAG GGA TTG GCG TTA TCA GCC ATC CCT GTA ATC T TC ACA TCC TTC GGA TTC CAC GGGTCC GTC CCA TCC ATC GTG TCC TAC A TG GAC GGC AAT GTA CGC AAG TTA CGT TGG GTC TTT ATC ACA GGG AGC GCC ATT CCC CTT GTA GCG TAT ATT TTTTGG CAA GTT GCT ACT CTG GGG TCA ATC GAC TCT ACC ACC TTC ATG GGT TTA CTT GCG AAC CAC GCG GGG TTG AAC GGA CTG TTA CAG GCT TTG CGT GAAATG GTT GCC TCG CCA CAT GTT GAG TTG GCG GTT CAT CTT TTT GCT GAC TTA GCC TTA GCT ACC TC T TTC CTT GGG GTT GCG CTG GGA TTA TTC GAC TATCTG GCT GAT CTT TT T CAA CGC TCC AAC ACC GTA GGT GGA CGT TTA CAG ACT GGA GCC ATT A CT TTC TTG CCC CCT TTA GCC TTT GCG CTG TTT TAT CCACGT GGG TTT G TT ATG GCC TTG GGG TAT GCT GGA GTC GCC TTA GCT GTA CTT GCT CTT ATT ATT CCA TCG TTA TTA ACG TGG CAA TCG CGT AAA CAC AACCCC CAA GCA GGG TAC CGC GTG AAG GGA GGA CGC CCC GCG CTG GTG GTT GTT TTT CTG TGC GGG ATT GCC GTC ATC GGC GTG CAA TTT TTG ATT GCA GCAGGT TTG TTG CCG GAG GTG GGG |

Phenylalanine

| SEQ ID NO: | Gene or Operon | Sequence |
|---|---|---|
| 88 | Beta-phenylalanine transaminase (Aromatic beta-amino acid aminotransferase; Beta-phenylalanine-aminotransferase; VpAT) UniProtKB/ Swiss-Prot: H8WR05.1 | ATG ACT CAT GCT GCA ATT GAC CAG GCG TTG GCA GAC GCC TAT CGT CGT TTT ACT GAC GCA AAC CGT GCC AGC CAG CGC CAG CGT CAG TTT GAA GCG CAA GCC CGCTAT ATG CCC GGG GCT AAC TCT CGC TCT GTT TTG TTT TAT GCA CCC TTT CCA TTG ACG ATC GCA CGT GGG GAA GGC GCC GCT CTT TGG GAT GCG GAC GGCCAC CGT TAC GCT GAC TTT ATC GCG GAA TAC ACA GCT GGG GTG TAT GGA CAC AGT GCC CCA GCA CCA CGA GAG ATT CGT GAC GCA GTA ATC GAA GCT ATG CAG GGT GGGGATT AAT TTG ACG GGT CAT AAT TTG TTG GAA GGC CGC TTA GCC CGC CTT ATT TGT GAG CGT TTC CCA CAG ATC GAA CAG TTG CGT TTC ACG AAT AGC GGAACA GAG GCC AAT CTG ATG GCC CTT ACC GCG GCG CTT CAT TTT ACT GGT CGC CGC AAA ATC GTC GTA TTT AGT GGA GGT TAT CAT GGG GGG GTT CTT GGGTTC GGT GCC CGT CCT AGC CCT ACA CCA GTA CCA TTT GAC TTC CTT GTG CTG CCT TAC AAC GAT GCT CAG ACG GCT CGT GCT CAG ATC GAG CGC CAC GGCCCG GAG ATC GCG GTC GTG TTA GTC GAG CCC ATG CAA GGT GCT TCT GGC TGC ATC CCA GGT CAG CCC GAC TTT CTG CAA GCC CTG CGC GAA TCC GCT ACTCAG GTA CGG GCG CTG TTA GTT TTT GAC GAA GTG ATG ACT AGT CGC TTA GCG CCA CAT GGT TTA GCT AAC AAA TTG GGG ATC CGT TCG GAT TTG ACA ACCCTG GGT AAG TAC ATT GGC GGC GGT ATG TCA TTT GGG GCC TTT GGC GGT CGT GCT GAT GTC ATG GCC CTG TTC GAC CCT CGC ACT GGA CCT TTG GCT CATTCC GGT ACG TTT AAC AAC AAT GTG ATG ACG ATG GCT GCC GGT TAT GCT GGC TTA ACG AAA TTA TTC ACT CCG GAA GCG GCA GGG GCA TTG GCA GAG CGTGGA GAA GCG CTT CGC GCA CGT CTT AAC GCC CTG TGT GCT AAC GAA GGA GTA GCA ATG CAG TTC ACT GGC ATC GGC TCG CTG ATG AAT GCC CAC TTC GTCCAG GGA GAC GTT CGT AGC TCT GAG GAT CTG GCC GCA GTT GAT GGG CGT TTA CGT CAG TTG TTG TTC TTT CAT TTA TTG AAT GAA GAT ATT TAC TCT TCACCG CGT GGG TTT GTT GTA TTA TCG TTG CCA TTG ACT GAC GCT GAT ATT GAC CGC TAC GTT GCT GCG ATC GGT TCA TTT ATT GGC GGT CAT GGG GCG TTGTTA CCG CGC GCT AAC |
| 89 | gadA glutamate decarboxylase (*Escherichia coli*) | ATGGACCAGAAGCTGTTAACGGATTTCCGCTCAGAACTACTCGATTCACGTTTTGGCGCAAAG GCCATTTCTACTATCGCGGAGTCAAAACGATTTCCGCTGCACGAAATGCGCGATGATGTCGCA TTTCAGATTATCAATGATGAATTATATCTTGATGGCAACGCTCGTCAGAACCTGGCCACTTTC TGCCAGACCTGGGACGACGAAAACGTTCCATAAATTGATGGATTTGTCGATCAATAAAAACTGG ATCGACAAAGAAGAATATCCGCAATCCGCAGCCATCGACCTGCGTTGCGTAAATATGGTTGCC GATCTGTGGCATGCGCCTGCGCCGAAAAATGGTCAGGCCGTTGGCACCAACACCATTGGTTCT TCCGAGGCCTGTATGCTCGGCGGGATGGCGATGAAATGGCGTTGGCGCAAGCGTATGGAAGCT GCAGGCAAACCAACGGATAAACCAAACCTGGTGTGCGGTCCGGTACAAATCTGCTGGCATAAA TTCGCCCGCTACTGGGATGTGGAGCTGCGTGAGATCCCTATGCGCCCCGGTCAGTTGTTTATG GACCCGAAACGCATGATTGAAGCCTGTGACGAAAACACCATCGGCGTGGTGCCGACTTTCGGC GTGACCTACACCGGTAACTATGAGTTCCCACAACCGCTGCACGATGCGCTGGATAAATTCCAG GCCGACACCGGTATCGACATCGACATGCACATCGACGCTGCCAGCGGTGGCTTCCTGGCACCG TTCGTCGCCCCGGATATCGTCTGGGACTTCCGCCTGCCGCGTGTGAAATCGATCAGTGCTTCA GGCCATAAATTCGGTCTGGCTCCGCTGGGCTGCGGCTGGGTTATCTGGCGTGACGAAGAAGCG |

Sequence Listing

| SEQ ID NO: | Gene or Operon | Sequence |
|---|---|---|
| | | CTGCCGCAGGAACTGGTGTTCAACGTTGACTACCTGGGTGGTCAAATTGGTACTTTTGCCATC<br>AACTTCTCCCGCCCGGCGGGTCAGGTAATTGCACAGTACTATGAATTCCTGCGCCTCGGTCGT<br>GAAGGCTATACCAAAGTACAGAACGCCTCTTACCAGGTTGCCGCTTATCTGGCGGATGAAATC<br>GCCAAACTGGGGCCGTATGAGTTCATCTGTACGGGTCGCCCGGACGAAGGCATCCCGGCGGTT<br>TGCTTCAAACTGAAAGATGGTGAAGATCCGGGATACACCCTGTACGACCTCTCTGAACGTCTG<br>CGTCTGCGCGGCTGGCAGGTTCCGGCCTTCACTCTCGGCGGTGAAGCCACCGACATCGTGGTG<br>ATGCGCATTATGTGTCGTCGCGGCTTCGAAATGGACTTTGCTGAACTGTTGCTGGAAGACTAC<br>AAAGCCTCCCTGAAATATCTCAGCGATCACCCGAAACTGCAGGGTATTGCCCAGCAGAACAGC<br>TTTAAACACACCTGA |
| 90 | glutamate decarboxylase (Escherichia coli KO11FL) GenBank: ADX50933.1 | ATG GAT AAA AAG CAA GTG ACG GAC CTG CGC TCT GAA CTT CTT GAC AGT CGT TTT GGG GCA AAG AGT ATT AGT ACC ATT GCT GAG TCA AAG CGT TT T CCTTTG CAT GAG ATG CGC GAT GAC GTC GCA TTC CAG ATT ATC AAC GA C GAG CTG TAT TTG GAC GGC AAT GCC CGC CAA AAC TTG GCC ACG TTT T GT CAG ACTTGG GAT GAC GAG AAT GTT CAT AAA CTT ATG GAC CTT TCA A TT AAC AAA AAT TGG ATT GAC AAA GAA GAG TAC CCC CAA TCT GCC GCA ATT GAT TTA CGTTGT GTT AAT ATG GTG GCC GAC TTA TGG CAT GCA CCA GCC CCT AAA AAC GGC CAA GCG GTG GGA ACC AAC ACG ATC GGG TCT AGT GAG GCA TGT ATG TTAGGC GGG ATG GCC ATG AAG TGG CGT TGG CGT AAA CGC ATG GAG GCA GCA GGG AAA CCA ACC GAT AAA CCT AAT TTA GTC TG C GGA CCG GTT CAG ATC TGTTGG CAT AAA TTT GCG CGC TAC TGG GAT GT G GAA TTA CGC GAA ATT CCG ATG CGT CCG GGC CAA CTG TTC ATG GAT C CC AAA CGT ATG ATC GAA GCA TGTGAC GAA AAC ACG ATT GGG GTG GTA C CC ACC TTT GGG GTC ACA TAT ACA GGT AAC TAC GGA TTT CCA CAA CCG TTG CAT GAT GCT CTG GAC AAG TTT CAAGCT GAC ACC GGG ATC GAC ATT GAT ATG CAC ATT GAC GCT GCC TCC GGC GGA TTC TTG GCC CCA TTT GTA GCC CCT GAC ATT GTC TGG GAC TTT CGT CTTCCC CGT GTG AAA TCC ATC AGC GCA TCC GGT CAC AAG TTT GGG CTT GCC CCA TTA GGG TGT GGA TG G GTC ATC TGG CGT GAT GAG GAA GCA TTA CCC CAAGAA CTT GTC TTC AA T GTA GAT TAC CTT GGG GGA CAG ATT GGC ACT TTT GCC ATC AAC TTT T CT CGC CCA GCG GGT CAA GTG ATC GCC CAG TAT TAC GAGTTT CTG CGC C TG GGA CGT GAG GGA TAT ACA AAA GTG CAG AAC GCA TCG TAC CAG GTA GCG GCT TAC CTT GCG GAC GAA ATT GCA AAG CTG GGG CCA TACGAG TTT ATC TGT ACC GGG CGT CCA GAT GAA GGT ATT CCG GCT GTG TGT TTT AAG CTG AAA GAC GGG GAA GAT CCC GGA TAT ACG CTG TAT GAT CTG TCTGAA CGT TTA CGT TTG CGC GGT TGG CAA GTT CCA GCC TTC ACG TTG GGT GG C GAA GCC ACT GAT ATT GTA GTC ATG CGT ATC ATG TGT CGT CGC GGC T TTGAA ATG GAT TTC GCA GAG TTA CTT CTG GAA GAC TAC AAA GCG AGC T TA AAA TAT TTG TCT GAC CAT CCC AAG TTG CAA GGG ATC GCA CAG CAA AAT TCGTTT AAA CAC ACT |
| 91 | GltT (Bacillus atrophaeus UCMB-5137) GenBank: AKL83763.1 | ATG AAG AAA TTA CGC TTC GGA CTG GCG ACT CAA ATC TTT GTG GGG CTG ATT CTT GGG GTA GTA GTG GGC GTT ATC TGG TAC GGT AAT CCG GCG GT G GTAACT TAT TTG CAG CCA GTT GGG GAC CTT TTT TTA CGT TTG ATT AA A ATG ATC GTT ATT CCT ATC GTG TCT TCT TTG ATC ATT GGC GTC G CG GGA GCTGGG TCC GGA AAA CAG GTC GGA AAG CTG GGC TTT CGT ACT A TT CTG TAC TTC GAG ATC ATC ACT ACC TTT GCC ATC ATT CTG GGA CTT GCT CTG GCG AATCTT TTC CAG CCT GGT ACA GGA GTA AAT ATC GAG AGC GCG CAG AAA AGT GAC ATT TCC CAG TAC GTG GAG ACT GAA AAA GAG CAA TCC ACC AAA TCC GTAGCT GAG ACT TTC CTG CAT ATC GTG CCC ACC AAT TTC TTT CAA TCA CTT GCG GAA GGT GAT CTT CTT GCT ATT ATC TGC TT T ACC GTA CTT TTC GCC CTTGGC ATT TCG GCT ATC GGT GAA CGT GGC AA A CCG GTG CTT GCT TTC TTT GAC GGA GTA TCC CAC GCG ATG TTT CAT G TA GTG AAC CTT GTG ATG AAG GTTGCT CCG TTC GGC GTA TTT GCT CTG A TT GGA GTA ACA GTA AGC AAA TTT GGA CTG GGT TCT TTA CTG AGC CTG GGT AAA CTT GTG GGG CTG GTA TAT GTTGCT CTG GCA TTT TTT CTT ATT GTA ATC TTT GGT ATT GTT GGA AAG CTG GCT GGC GTG AAT ATC TTC AAG TTT TTA GCT TAC ATG AAG GAT GAA ATC TTATTA GCG TTC TCG ACC TCA TCG TCC GAG ACT GTG TTG CCC CGC ATC ATG GAG AAA ATG GAG AAG AT C GGG TGT CCA AAG GGA ATT GTA AGC TTT GTA GTCCCC ATC GGT TAC AC A TTC AAT CTT GAC GGC TCG GTC TTA TAC CAA TCT ATT GCT GCG CTG T TC TTG GCA CAG GTT TAC GGA ATC GAC CTG ACT ATT TGGCAT CAG ATT A CT CTG GTG TTA GTT CTG ATG GTC ACT AGC AAA GGC ATG GCA GCC GTT CCT GGA ACT AGC TTT GTA GTC CTG CTG GCA ACC TTA GGT ACCATT GGT GTT CCA GCG GAA GGG CTT GCA TTC ATT GCG GGG GTT GAC CGC ATT ATG GAC ATG GCT CGC ACT GTG GTC AAT TTA ACA GGC AAT GCT CTT GCGAGT GTC GTA ATG AGC AAG TGG GAG GGT CAG TAC GAC CCG GTG AAA GGT GC A GAG ATT ATG AGC CGC AGC AAG ACG GAA CAG GAC GCT ACT ATC TCC G GA |
| 92 | mechanosensitive channel Msc S (Escherichia | ATG GAG GAC TTG AAC GTA GTA GAT AGC ATT AAT GGA GCG GGC TCA TGG TTA GTA GCC AAC CAA GCC CTG TTG TTA TCG TAT GCT GTA AAT ATC GT C GCAGCC TTA GCC ATC ATT ATC GTT GGG TTA ATC ATC GCC CGT ATG AT |

Sequence Listing

| SEQ ID NO: | Gene or Operon | Sequence |
|---|---|---|
| | coli) GenBank: CTX26261.1 | T TCT AAT GCG GTG AAT CGC TTA ATG ATC TCG CGC AAG ATC GAC GCC A CT GTC GCGGAT TTC TTG TCC GCC CTG GTG CGT TAC GGT ATC ATC GCG T TC ACA TTG ATT GCG GCA TTA GGG CGC GTA GGA GTC CAG ACA GCT TCT GTG ATT GCG GTATTA GGT GCA GCA GGA TTA GCT GTG GGA TTG GCG TTA CAG GGG TCT CTT TCC AAT CTG GCG GCC GGC GTA CTT CTG GTT ATG TTT CGC CCC TTT CGC GCCGGA GAG TAT GTG GAT TTG GGA GGA GTG GCC GGA ACA GTG CTG TCA GTG CAA ATC TTT TCT ACC ACG ATG CGT ACA GCA GA T GGA AAA ATC ATC GTG ATCCCC AAT GGC AAG ATC ATC GCG GGT AAC AT T ATC AAC TTC TCC CGC GAA CCT GTT CGC CGC AAC GAA TTT ATC ATC G GT GTT GCC TAT GAT TCA GAC ATCGAT CAG GTC AAA CAA ATT CTT ACG A AC ATC ATT CAG TCA GAG GAC CGT ATT CTG AAA GAC CGC GAA ATG ACG GTG CGT TTG AAT GAG TTA GGG GCT TCAAGT ATC AAC TTC GTA GTC CGC GTG TGG AGC AAT TCC GGT GAT TTG CAA AAC GTG TAT TGG GAC GTC CTT GAG CGC ATT AAG CGT GAA TTC GAT GCT GCCGGG ATC TCC TTT CCG TAT CCT CAG ATG GAT GTG AAT TTC AAG CGT GTA AAG GAA GAT AAG GCT GC C |
| 93 | HutH (Bacillus amyloliquefaciens subsp. plantarum str. FZB42) GenBank: ABS75970.1 | ATG ATG GTC ACC TTG GAT GGG TCT TCA TTA ACG ACG GCT GAT GCA CAA CGT GTA CTT TTC GAT TTT GAA GAG GTA CAG GCA TCG GCT GAA TCG AT G GAGCGC GTA AAA AAG GCT GCC GCC GTG GAA CGC ATT GTA CAA GA A GAA AAA ACT ATC TAC GGA ATC ACT ACG GGG TTT GGT AAG TTT TCC G AT GTG CTGATC CAA AAA GAG GAC GCT GCG GAT TTA CAA TTG AAT TTG A TC TTG TCA CAT GCA TGT GGA GTC GGC GAT CCT TTC CCA GAG TCA GTC TCC CGC GCC ATGCTG CTT CTG GCT GCA AAC GCA TTG TTA AAA GGC TTC TCC GGT GTT CGT ACG GAA TTA ATT GAC CAG CTT TTA GCG TAC TTA AAC CAC CGT ATC CAC CCTGTT ATC CCC CAA CAA GGT TCG CTG GGG GCC TCC GGC GAT TTG GCC CCT CTT AGC CAC CTT GCG TTG GCA CTG ATC GGA CA A GGG GAA GTG TTC TAC GAAGGA GCA CGT ATG CCC ACT GCT CAT GCC CT T GAA CAA ACC AAT CTG CAG CCC GCA GTC CTG ACA TCG AAG GAA GGG C TG GCG TTG ATC AAT GGG ACT CAGGCT ATG ACC GCA ATG GGC TTA ATC G CA TAC CTT GAA GCC GAA AAG TTG GCA TAT CAG AGC GAG CGC ATC GCT TCA TTG ACT ATC GAA GGA TTG CAA GGTATT ATT GAC GCG TTT GAC GAA GAT ATT CAT GCC GCT CGT GGA TAC CAG GAA CAA ATG GAT GTC GCT GAG CGC ATT GCG TAT TAT CTT TCG GAT TCG AAGCTG ACA ACC GTA CAA GGC GAG CTG CGT GTG CAA GAT GCT TAC TCC ATT CGC TGC ATC CCT CAA GT C CAC GGA GCT TCT TGG CAG ACC CTG GCG TAT GTGAAG GAG AAG TTA GA A ATT GAG ATG AAC GCT GCT ACT GAT AAC CCT TTA ATT TTT GAA GAC G GG GCC AAA ATT ATC TCG GGG GGG AAC TTT CAC GGG CAACCG ATC GCG T TT GCA ATG GAC TTC TTG AAA GTA GCT GCT GCT GAG TTG GCT AAT ATC AGC GAG CGC CGT ATT GAG CGT CTT GTC AAT CCA CAG CTG AATGAC CTT CCT CCT TTT CTT TCG CCG CAA CCG GGT TTA CAG TCT GGT GCC ATG ATT ATG CAG TAC GCC GCT GCC TCC TTG GTC TCG GAA AAC AAA ACA CTTGCG CAT CCC GCC TCA GTC GAC TCA ATC CCC TCC TCG GCT AAC CAG GAG GA T CAC GTC TCC ATG GGG ACG ATC GCT TCA CGT CAT GCT TAC CAG ATT A TTGCA AAC ACT CGT CGC GTA TTA GCC GTC GGA CGT ATT TGC GCT TTA C AA GCT GTA GAG TAC CGT GGG GAA GAG CAC TGC GCT AGC TAC ACG AAA CAA CTTTAC CAT GAG ATG CGT AAC ATC GTG CCA TCG ATT CAG GAG GAC CGT GTT TTC TCG TAC GAC ATC GAG CAC TTA TCC GAC TGG CTT AAA AAG GAA TCC TTCTTA CCT AAT GAA CAC CAC CAA AAG TTA ATG ACT AAT GAG GGC GGG TTA ACT CGC |
| 94 | Histidine ABC transporter, histidine-binding periplasmic protein precursor HisJ (Escherichia coli O145: H28 str. RM12581]) GenBank: AHY71563.1 | ATG AAG AAA CTT GTC CTT TCA TTG TCT CTG GTA TTA GCG TTC AGT TCA GCA ACT GCA GCA TTC GCT GCT ATT CCG CAA AAT ATC CGC ATC GGG AC G GATCCC ACG TAT GCG CCA TTC GAG TCA AAG AAT TCA CAA GGT GAA TT G GTC GGG TTC GAT ATT GAC CTG GCG AAA GAA TTG TGT AAA CGT ATC A AT ACC CAATGC ACG TTC GTG GAA AAT CCC TTG GAT GCA TTA ATT CCG T CT TTG AAA GCG AAA AAA ATC GAT GCC ATC ATG ACC TCC CTT TCT ATC ACA GAA AAG CGCCAG CAG GAG ATT GCC TTC ACA GAC AAG TTG TAC GCT GCA GAC AGC CGC CTG GTC GTT GCA AAG AAT TCT GAC ATT CAA CCT ACC GTG GAA TCG CTG AAGGGC AAG CGC GTA GGG GTC TTG CAG GGC ACT ACT CAG GAA ACA TTT GGG AAC GAA CAT TGG GCG CCT AAG GGA ATT GAG AT C GTG TCT TAT CAG GGT CAGGAT AAC ATC TAC AGT GAT CTG ACA GCC GG A CGT ATT GAC GCC GCT TTT CAG GAC GAG GTG GCG GCA TCT GAA GGG T TC TTA AAG CAG CCA GTC GGC AAAGAC TAC AAA TTT GGT GGG CCG AGC G TG AAG GAC GAG AAA TTG TTT GGG GTA GGA ACA GGG ATG GGC TTG CGT AAG GAG GAC AAT GAA TTA CGT GAA GCTCTT AAT AAA GCC TTT GCT GAG ATG CGT GCG GAC GGG ACT TAC GAA AAA CTT GCA AAA AAG TAT TTC GAC TTT GAC GTC TAC GGC GGT |
| 95 | Histidine ABC transporter, permease protein HisQ | ATG CTG TAT GGA TTC AGT GGC GTT ATC TTG CAG GGG GCT CTT GTC ACT TTA GAG TTA GCT ATC TCG TCC GTT GTG TTA GCT GTC ATT ATT GGA CT T ATCGGG GCT GGT GGC AAA TTG AGT CAG AAC CGT TTG AGC GGC CTT AT T TTT GAA GGG TAC ACA ACC TTA ATT CGC GGA GTC CCA GAC TTA GTG C TG ATG TTGCTT ATT TTC TAT GGT TTA CAG ATC GCT TTG AAT ACG GTT A |

-continued

Sequence Listing

| SEQ ID NO: | Gene or Operon | Sequence |
|---|---|---|
| | (*Escherichia coli* O145: H28 str. RM12581) GenBank: AHY71562.1 | CC GAG GCA ATG GGG GTC GGC CAA ATC GAT ATC GAT CCT ATG GTG GCT<br>GGA ATC ATT ACTTTG GGC TTC ATT TAC GGG GCA TAT TTC ACG GAG ACG<br>TTC CGC GGA GCT TTC ATG GCC GTC CCG AAG GGC CAC ATT GAA GCG GCA<br>ACA GCT TTT GGA TTCACT CGT GGG CAA GTT TTC CGT CGC ATC ATG TTT<br>CCA GCG ATG ATG CGC TAT GCG CTT CCT GGG ATC GGG AAT AAC TGG CA<br>G GTA ATC TTA AAA TCG ACGGCT TTA GTC AGT TTA TTG GGG TTG GAA GA<br>T GTC GTA AAA GCG ACC CAG TTG GCT GGG AAA TCG ACT TGG GAG CCC T<br>TT TAC TTC GCT ATT GTG TGT GGCGTT ATT TAC TTA GTT TTC ACT ACA G<br>TA TCA AAC GGT GTG TTA TTG TTT TTG GAA CGT CGC TAC AGC GTG GGT<br>GTA AAG CGT GCT GAT TTG |
| 96 | hisP (*Escherichia coli* EPEC C342-62) GenBank: EIQ70323.1 | ATG TCC GAG AAC AAA TTA AAT GTT ATC GAT TTG CAT AAG CGT TAT GGA<br>GAG CAT GAA GTG TTG AAA GGA GTG TCT CTT CAA GCA AAC GCG GGG GA<br>C GTAATT TCT ATC ATC GGA TCG TCT GGT TCT GGT AAG TCA ACC TTC CT<br>G CGT TGT ATT AAC TTC TTA GAG AAG CCG TCT GAG GGT TCT ATT GTA G<br>TT AAT GGGCAG ACC ATC AAT CTT GTG CGC GAT AAG GAC GGC CAG TTG A<br>AA GTG GCA GAC AAA AAC CAA CTT CGT TTG CTT CGC ACC CGT CTT ACC<br>ATG GTA TTC CAACAC TTC AAC CTG TGG TCG CAC ATG ACG GTA CTT GAG<br>AAC GTG ATG GAA GCG CCA ATT CAG GTA CTT GGA TTG AGC AAA CAA GAA<br>GCC CGC GAA CGT GCGGTG AAA TAT TTG GCC AAG GTG GGT ATC GAC GAG<br>CGT GCG CAG GGC AAA TAC CCC GTT CAC TTG TCC GGG GGT CAA CAA CA<br>G CGT GTC AGT ATT GCC CGCGCT CTG GCT ATG GAA CCA GAG GTG CTT CT<br>G TTT GAC GAG CCG ACG TCA GCT TTG GAC CCG GAA TTA GTG GGC GAA G<br>TA TTG CGC ATC ATG CAG CAG TTAGCA GAA GAA GGC AAG ACC ATG GTT G<br>TT GTC ACA CAC GAA ATG GGG TTT GCG CGT CAT GTC TCG ACT CAT GTA<br>ATC TTC TTG CAT CAA GGT AAA ATC GAGGAA GAA GGA GCG CCG GAA CAG<br>TTA TTC GGG AAT CCT CAA TCC CCC CGT CTG CAG CAG TTT CTT AAA GGG<br>TCC TTA AAG |
| 97 | proline reductase (*Clostridium botulinum*) NCBI Reference Sequence: WP_024933653.1 | ATG TCA ATG TCC GCT GAG CAC GCT GAG GAA TTA AAA AAT GAA CCT GCG<br>GTC GTT TGT TGT CGC ACT GAG GAG GGG ACC ATC TTG TCA GCC GAT AA<br>T TTGGAA GAC CCA AAC ATT TTT CCA GAT ATG GTG GAT AGC GGT TTA CT<br>G AAC ATT CCT GGG GAC TGC TTA AAA GTT GGG GAA GTA ATC GGG GCC A<br>AA CTG CTTAAG ACG ATT GAC TCT TTG ACC CCT CTT GCC AAG GAC ATC A<br>TT GAG GGG GCC AAA TCC TTA GAC GGA GAC GTA CGC AGT AAA TCA GAG<br>ATT CAG ATC GAATCA CCA GAG GAG AAG GCG ATC CTT AAA AAC AAT TTG<br>AAG GCG GGA GAT ATT ATC AAG GTT GAG GAC CTG GAG AAC CCT ATG CAC<br>TTC GCC AAG TTA CAAGAT TCG CTT CTT ATC AAG CTG GAT GAG AAA GTG<br>CTT ACG CGC CGC GAA GTT GTA GAC GCG AAA CTT ACG GAA GAT GCA CC<br>G GCG ATT TCA GGG GTC ACTGCA TCA ATG TTG GAA GGC TTC GAG GAA AA<br>G GCC CTG GAG ATT ACC CAA GAT AGC AAG GAT GTG GAC TTC AAT TCA G<br>TA ATT CCA CTG AAC GGC AAT CGTGAA TTC CTT CGT TTG AAA ATC GAG G<br>AA GGC ACA GGC ATT TAT ATC GAA ATT CCC TTT ACC CAA GTC |
| 98 | Proline porter II (*Escherichia coli* PMV-1) GenBank: CDH67546.1 | ATG TCA GAA AAA CTT CCG GCA CCT CGC GAG GGT TTA TCC GGT AAA GCT<br>ATG CGT CGT GTT GTC ATG GGT AGC TTT GCC GGT GCA TTA ATG GAA TG<br>G TATGAT TTC TTC ATC TTT GGG ACG GCG GCG GGT CTT GTT TTT GCA CC<br>G CTG TTT TAT CCT GAC AGT GAT CCG TTT ATT GGG TTG ATC GCG TCG T<br>TC GCT ACATTT GGA GTT GGT TTT TTG ACC CGC CCG TTA GGA GGT ATC G<br>TG TTC GGT CAT TTT GGT GAC AAG ATC GGG CGT AAG ATT ACC TTA ATC<br>TGG ACA TTG GCGATT GTG GGG TGT TCT ACA TTC TTA ATC GGT TTC ATT<br>CCA ACG TAC CAA GAA ATC GGC ATT TGG GCC CCT TTG GTC CTT ATG GTT<br>TTG CGC CTG ATT CAGGGT TTT GGC TTG GGA GGA GAA TAC GGA GGG GCG<br>GCG TTA ATG ACC ATC GAA AGT GCC CCC GAA AGC CGC CGT GGT TTT CT<br>T GGG TCA TTG CCA CAG ACGGCC GCC AGC GTC GGC ATC ATG CTT GCA AC<br>G GGT ATT TTC GCG CTT TGT AAT CAT TTC CTT ACT TCT GAA CAG TTC T<br>TA TCA TGG GGC TGG CGT ATT CCCTTC TGG TTG TCC GCG GTT ATG TTA A<br>TC GTC GGA CTT TTT ATC CGT CTG CAT ACT GAA GAG ACG CTT GAC TTT<br>CAG AAG CAA AAA ACG ACT AAC AAT AAAGAA AAG TCG GTT CCC CCC CTT<br>ATC GAG CTT TTT AAG AAA CAT CCA CGC AAT ATT TTG TTG GCC TTG GGG<br>GCC CGC CTT GCG GAG TCA GTA AGC AGC AACATC ATT AAT GCA TTC GGC<br>ATC GTC TAT ATC AGC AGT CAA CTT GCA CTG AGC CGT GAC ATC CCC TT<br>G ACT GGG ATG CTG ATT GCA AGC GCC ATC GGA ATTTTT AGT TGC CCA TT<br>G GTA GGC TGG CTT TCG GAC CGT ATC GGA CAG AAA TCA TTA TAT TTG T<br>CA GGC GCT GGA TTT TGT GTC CTG TTT GCC TTC CCG TTTTTT CTG CTG T<br>TG GAC TCG AAG AGT ACA CTG ATT ATC TGG TGC TCA ATG ATT TTG GGC<br>TAT AAC TTG GGT CCA ACT ATG ATG TTT GCT GTA CAA CCA ACATTG TTT<br>ACT CGT ATG TTC GGC ACC AAG GTC CGC TAC ACA GGC TTA TCA TTT GCT<br>TAC CAG TTC TCG GCT ATC TTA GGC GGC CTG TCC CCA CTG ATT GCATCC<br>TCA CTT CTT GCG TTG GGG GGC GGC AAA CCC TGG TAT GTC GCC TTG TT<br>C CTT TTC GCT GTG TCC GTG TTA TCT TTC GTC TGT GTA TGG TTA ATC G<br>AGCCC ACA GAC GAA CAA GAG ACG GCT TCA TAC CGC TAC ATC CGC GAA C<br>AA AGT CAT GAG AAC |

| SEQ ID NO: | Gene or Operon | Sequence |
|---|---|---|
| 99 | *Escherichia coli* PheP | ATGAAAAACGCGTCAACCGTATCGGAAGATACTGCGTCGAATCAAGAGCCGACGCTTCATCGC<br>GGATTACATAACCGTCATATTCAACTGATTGCGTTGGGTGGCGCAATTGGTACTGGTCTGTTT<br>CTTGGCATTGGCCCGGCGATTCAGATGGCGGGTCCGGCTGTATTGCTGGGCTACGGCGTCGCC<br>GGGATCATCGCTTTCCTGATTATGCGCCAGCTTGGCGAAATGGTGGTTGAGGAGCCGGTATCC<br>GGTTCATTTGCCCACTTTGCCTATAAATACTGGGGACCGTTTGCGGGCTTCCTCTCTGGCTGG<br>AACTACTGGGTAATGTTCGTGCTGGTGGGAATGGCAGAGCTGACCGCTGCGGGCATCTATATG<br>CAGTACTGGTTCCCGGATGTTCCAACGTGGATTTGGGCTGCCGCCTTCTTTATTATCATCAAC<br>GCCGTTAACCTGGTGAACGTGCGCTTATATGGCGAAACCGAGTTCTGGTTTGCGTTGATTAAA<br>GTGCTGGCAATCATCGGTATGATCGGCTTTGGCCTGTGGCTGCTGTTTTCTGGTCACGGCGGC<br>GAGAAAGCCAGTATCGACAACCTCTGGCGCTACGGTGGTTTCTTCGCCACCGGCTGGAATGGG<br>CTGATTTTGTCGCTGGCGGTAATTATGTTCTCCTTCGGCGGTCTGGAGCTGATTGGGATTACT<br>GCCGCTGAAGCGCGCGATCCGGAAAAAGCATTCCAAAAGCGGTAAATCAGGTGGTGTATCGC<br>ATCCTGCTGTTTTACATCGGTTCACTGGTGGTTTTACTGGCGCTCTATCCGTGGGTGGAAGTG<br>AAATCCAACAGTAGCCCGTTTGTGATGATTTTCCATAATCTCGACAGCAACGTGGTAGCTTCT<br>GCGCTGAACTTCGTCATTCTGGTAGCATCGCTGCTGTCAGTGTATAACAGCGGGGTTTACTCTAAC<br>AGCCGCATGCTGTTTGGCCTTTCTGTGCAGGGTAATGCGCCGAAGTTTTTGACTCGCGTCAGC<br>CGTCGCGGTGTGCCGATTAACTCGCTGATGCTTTCCGGAGCGATCACTTCGCTGGTGGTGTTA<br>ATCAACTATCTGCTGCCGCAAAAAGCGTTTGGTCTGCTGATGGCGCTGGTGGTAGCAACGCTG<br>CTGTTGAACTGGATTATGATCTGTCTGGCGCATCTGCGTTTCGTGCAGCGATGCGACGTCAG<br>GGGCGTGAAACACAGTTTAAGGCGCTGCTCTATCCGTTCGGCAACTATCTCTGCATTGCCTTC<br>CTCGGCATGATTTTGCTGCTGATGTGCACGATGGATGATATGCGCTTGTCAGCGATCCTGCTG<br>CCGGTGTGGATTGTATTCCTGTTTATGGCATTTAAAACGCTGCGTCGGAAATAA |
| 100 | *Anabaena variabilis* PAL1 | ATGAAAACACTATCACAGGCCCAATCTAAAACTTCTTCACAGCAATTCAGCTTTACCGGGAAC<br>TCGTCTGCGAATGTAATTATCGGCAATCAAAAGCTGACCATTAATGATGTAGCTCGCGTTGCC<br>CGGAATGGCACTTTGGTGTCACTGACGAACAATACCGACATTCTGCAAGGTATTCAAGCTAGC<br>TGCGATTATATCAATAACGCCGTTGAATCTGGCGAGCCAATCTACGGGGTAACAAGCGGTTTT<br>GGTGGGATGGCGAACGTTGCCATTAGCCGTGAACAGGCGAGCGAACTTCAGACCAACCTCGTT<br>TGGTTCCTAAAGACAGGAGCTGGTAATAAGTTACCTCTGGCTGACGTAAGAGCCGCGATGCTG<br>CTTCGCGCTAATAGTCACATGCGCGGCGCCAGTGGTATCCGTCTTGAGCTTATCAAGAGGATG<br>GAAATCTTCCTCAACGCGGGTGTCACACCATATGTTTATGAGTTTGGTAGTATCGGAGCCAGT<br>GGTGATCTTGTTCCCCTGAGTTATATTACGGGTTCATTGATTGGTTTAGACCCGTCCTTTAAA<br>GTGGATTTTAACGGGAAAGAAATGGACGCCCCGACCGCTTTACGACAGCTTAATCTGAGCCCA<br>CTTACTTTGCTCCCTAAAGAAGGTCTTGCCATGATGAATGGCACCTCTGTGATGACTGGAATT<br>GCCGCGAATTGTGTGTATGACACGCAGATCCTAACGGCCATTGCCATGGGTGTTCACGCGTTG<br>GACATTCAAGCCCTGAATGGTACAAACCAGTCGTTTCATCCGTTTATCCATAATTCAAAACCC<br>CATCCGGGACAGCTTTGGGCTGCTGATCAGATGATCTCACTCCTGGCCAATAGTCAACTGGTT<br>CGGGACGAGCTCGACGGCAAACATGATTATCGCGATCATGAGCTCATCCAGGACCGGTATTCA<br>CTTCGTTGTCTCCCACAATACCTGGGGCCTATCGTTGATGGTATATCTCAAATTGCGAAGCAA<br>ATTGAAATTGAGATCAATAGCGTAACCGACAACCCGCTTATCGATGTTGATAATCAGGCCTCT<br>TATCACGGTGGCAATTTTCTGGGCCAGTATGTTGGTATGGGGATGGATCACCTGCGGTACTAT<br>ATTGGGCTTCTGGCTAAACATCTTGATGTGCAGATTGCCTTATTAGCTTCACCAGAATTTTCA<br>AATGGACTGCCGCCATCATTGCTCGGTAACAGAGAAAGGAAAGTAAATATGGGCCTTAAGGGC<br>CTTCAGATATGTGGTAACTCAATCATGCCCCTCCTGACCTTTTATGGGAACTCAATTGCTGAT<br>CGTTTTCCGACACATGCTGAACAGTTTAACCAAAACATTAACTCACAGGGCTATACATCCGCG<br>ACGTTAGCGCGTCGGTCCGTGGATATCTTCCAGAATTATGTTGCTATCGCTCTGATGTTCGGC<br>GTACAGGCCGTTGATTTGCGCACTTATAAAAAAACCGGTCACTACGATGCTCGGGCTTGCCTG<br>TCGCCTGCCACCGAGCGGCTTTTATAGCGCCGTACGTCATGTTGTGGGTCAGAAACCGACGTCG<br>GACCGCCCCTATATTTGGAATGATAATGAACAAGGGCTGGATGAACACATCGCCCGGATATCT<br>GCCGATATTGCCGCCGGAGGTGTCATCGTCCAGGCGGTACAAGACATACTTCCTTGCCTGCAT<br>TAA |
| 101 | *Photorhabdus luminescens* PAL3 | ATGAAAGCTAAAGATGTTCAGCCAACCATTATTATTAATAAAAATGGCCTTATCTCTTTGGAA<br>GATATCTATGACATTGCGATAAAACAAAAAAAAGTAGAAATATCAACGGAGATCACTGAACTT<br>TTGACGCATGGTCGTGAAAAATTAGAGGAAAAATTAAATTCAGGAGAGGTTATATATGGAATC<br>AATACAGGATTTGGAGGGAATGCCAATTTAGTTGTGCCATTTGAGAAAATCGCAGAGCATCAG<br>CAAAATCTGTTAACTTTTCTTTCTGCTGGTACTGGGACTATATGTCCAAACCTTGTATTAAA<br>GCGTCACAATTTACTATGTTACTTTCTGTTTGCAAAGGTTGGTCTGCAACCAGACCAATTGTC<br>GCTCAAGCAATTGTTGATCATATTAATCATGACATTGTTCCTCTGGTTCCTCGCTATGGCTCA<br>GTGGGTGCAAGCGGTGATTTAATTCCTTTATCTTATATTGCACGAGCATTATGTGGTATCGGC<br>AAAGTTTATTATATGGGCGCAGAAATTGACGCTGCTGAAGCAATTAAACGTGCAGGGTTGACA<br>CCATTATCGTTAAAAGCCAAAGAAGGTCTTGCTCTGATTAACGGCACCCGGGTAATGTCAGGA<br>ATCAGTGCAATCACCGTCATTAAACTGGAAAAACTATTTAAAGCCTCAATTTCTGCGATTGCC<br>CTTGCTGTTGAAGCATTACTTGCATCTCATGAACATTATGATGCCCGGATTCAACAAGTAAAA<br>AATCATCCTGGTCAAAACGCGGTGGCAAGTCATTGCGTAATTTATTGGCAGGTTCAACGCAG<br>GTTAATCTATTATCTGGGGTTAAAGAACAAGCCAATAAAGCTTGTCGTCATCAAGAAATTACC<br>CAACTAAATGATACCTTACAGGAAGTTTATTCAATTCGCTGTGCACCACAAGTATTAGGTATA<br>GTGCCAGAATCTTTAGCTACCGCTCGGAAAATATTGGAACGGGAAGTTATCTCAGCTAATGAT<br>AATCCATTGATAGATCCAGAAAATGGCGATGTTCTACACGGTGGAAATTTTATGGGGCAATAT<br>GTCGCCCGAACAATGGATGCATTAAAACTGGATATTGCTTTAATTGCCAATCATCTTCACGCC<br>ATTGTGGCTCTTATGATGGATAACCGTTTCTCTCGTGGATTACCTAATTCACTGAGTCCGACA<br>CCCGGCATGTATCAAGGTTTTAAAGGCGTCCAACTTTCTCAAACCGCTTTAGTTGCTGCAATT |

| SEQ ID NO: | Gene or Operon | Sequence |
|---|---|---|
| | | CGCCATGATTGTGCTGCATCAGGTATTCATACCCTCGCCACAGAACAATACAATCAAGATATT<br>GTCAGTTTAGGTCTGCATGCCGCTCAAGATGTTTTAGAGATGGAGCAGAAATTACGCAATATT<br>GTTTCAATGACAATTCTGGTAGTTTGTCAGGCCATTCATCTTCGCGGCAATATTAGTGAAATT<br>GCGCCTGAAACTGCTAAATTTTACCATGCAGTACGCGAAATCAGTTCTCCTTTGATCACTGAT<br>CGTGCGTTGGATGAAGATATAATCCGCATTGCGGATGCAATTATTAATGATCAACTTCCTCTG<br>CCAGAAATCATGCTGGAAGAATAA |
| 102 | Legionella pneumophila phhA | ATGGAGTTTAGTAGCCGGTATGTCGCACATGTCCCTGATGCTCAGGGTTTAGTCGATTATTCG<br>GCACAAGAAAATAGAATTTGGAATATTTTATTTGAGAGGCAACTCAAGTTATTGCCAGGAAGA<br>GCTTGTGATGAATTTCTGTCTGGATTACAGACTTTAGGACTTAACTCCTCGACTATTCCACAA<br>CTTCCAGAAGTAAGTGAGCGATTAAAGGCCAAAACGGGATGGCAAGTAGCGCCAGTTGCTGCT<br>TTAATTTCAGCCAGGGAATTTTTTGAATTATTAGCAGAAAAATATTTTCCTGCGGCGACTTTT<br>ATTCGAAGTGAAGAAGAATTGGATTATGTTCAAGAACCTGATATTTTTCATGAGCTTTTTGGT<br>CATTGTCCTATGTTAACCGATAGAGTCTATGCTGAATTTGTCCATGATTACGCATGTAAGGTA<br>TTAACTTTTCCTGAACAGGATTGGCCTTTATTGCAAAGAATGTTTTGGTTTACTGTAGAGTTT<br>GGATTGATTAAAACGCCTAAAGGGCTTAGAGCATACGGCGGGGGAATTTTATCTTCTATCAGT<br>GAAACGGTATATTGTGTGGAAAGTGATATTCCTGTGCGAATTTTATTTGATCCAGTGGTGGCT<br>TTTCGAATGCCTTATCGGATTGACCAGCTACAACCTGTTTATTTCGTTATTGACAGCTATCAA<br>AATTTATATGATTTCGTGCTTTCTGACATGGGTAAATTCATGGATCGTGCGCGAGAGTTAGGT<br>GAATTTCCACCGTATTTTGATGTGGATCCGGATAATCCAAATATTCATATAAGGGCTTGTTAA |
| 103 | Escherichia coli hisM | GTGATCGAAATCTTACATGAATACTGGAAACCGCTGCTGTGGACCGACGGTTATCGCTTTACT<br>GGTGTGGCGATCACTCTGTGGCTGCTTATTTTGTCGGTAGTGATAGGCGGAGTCCTGGCGCTG<br>TTTCTGGCGATTGGTCGTGTCTCCAGTAATAAATACATCCAGTTTCTCCAATCTGGTTATTTACC<br>TATATTTTTCGCGGTACGCCGCTGTATGTTCAGTTGCTGGTGTTCTATTCCGGCATGTACACG<br>CTTGAGATTGTTAAGGGAACCGAATTCCTTAACGCTTTCTTCCGCAGTGGCCTGAACTGTACC<br>GTGCTGGCGCTGACGCTTAACACCTGCGCTTACACTACCGAGATTTTTGCTGGGGCAATCCGT<br>TCGGTTCCGCATGGGGAAATTGAAGCCGCCAGAGCCTATGCTTCTCGACTTTTAAAATGTAT<br>CGCTGCATTATTTTGCCTTCTGCGCTGCGTATTGCGTTACCGGCATACAGCAACGAAGTGATC<br>CTGATGCTGCACTCTACTGCGTTGGCATTTACTGCCACGGTGCCGGATCTGCTGAAAATAGCC<br>CGCGATATTAACGCCGCCACGTATCAACCTTTTACCGCCTTCGGCATTGCCGCGGTGCTCTAT<br>TTAATCATCTCTTATGTCCTGATCAGCCTCTTTCGCAGAGCGGAAAAACGCTGGTTGCAGCAT<br>GTGAAACCTTCTTCAACGCACTGA |
| 104 | clbA (wild-type) | caaatatcacataatcttaacatatcaataaacacagtaaagtttcatgtgaaaaacatcaaa<br>cataaaatacaagctcggaatacgaatcacgctatacacattgctaacaggaatgagattatc<br>taaatgaggattgatatattaattggacatactagttttttttcatcaaaccagtagagataac<br>ttccttcactatctcaatgaggaagaaataaaacgctatgatcagtttcattttgtgagtgat<br>aaagaactctatattttaagccgtatcctgctcaaaacagcactaaaaagatatcaacctgat<br>gtctcattacaatcatggcaatttagtacgtgcaaatatggcaaaccatttatagttttttcct<br>cagttggcaaaaaagatttttttttaacctttcccatactatagatacagtagcgttgctatt<br>agttctcactgcgagcttggtgtcgatattgaacaaataagagatttagacaactcttatctg<br>aatatcagtcagcatttttttactccacaggaagctactaacatagtttcacttcctcgttat<br>gaaggtcaattactttttttggaaaatgtggacgctcaaagaagcttacatcaaatatcgaggt<br>aaaggcctatctttaggactggattgtattgaatttcatttaacaaataaaaaaactaacttca<br>aaatatagaggttcacctgtttatttctctcaatggaaaatatgtaactcatttctcgcatta<br>gcctctccactcatcacccctaaaataactattgagctatttcctatgcagtcccaactttat<br>caccacgactatcagctaattcattcgtcaaatgggcagaattgaatcgccacggataatcta<br>gacacttctgagccgtcgataatattgattttcatattccgtcggtggtgtaagtatcccgca<br>taatcgtgccattcacatttag |
| 105 | clbA knock-out | ggatgggggggaaacatggataagttcaaagaaaaaaacccgttatctctgcgtgaaagacaag<br>tattgcgcatgctggcacaaggtgatgagtactctcaaatatcacataatcttaacatatcaa<br>taaacacagtaaagtttcatgtgaaaaacatcaaacataaaatacaagctcggaatacgaatc<br>acgctatacacattgctaacaggaatgagattatctaaatgaggattgaTGTGTAGGCTGGAG<br>CTGCTTCGAAGTTCCTATACTTTCTAGAGAATAGGAACTTCGGAATAGGAACTTCGGAATAGG<br>AACTAAGGAGGATATTCATATGtcgtcaaatgggcagaattgaatcgccacggataatctaga<br>cacttctgagccgtcgataatattgattttcatattccgtcggtgg |
| 106 | Prp promoter (prpR sequence - underlined; Ribosome binding site - lower case; start codon of gene of interest (italicized atg) | <u>TTACCCGTCTGGATTTTCAGTACGCGCTTTTAAACGACGCCACAGCGTGGTACGGCTGATCCC</u><br><u>CAAATAACGTGCGGCGGCGCGCTTATCGCCATTAAAGCGTGCGAGCACCTCCTGCAATGGAAG</u><br><u>CGCTTCTGCTGACGAGGGCGTGATTTGCTGTGGTCCCCACCAGTTCAGGTAATAATTGCCG</u><br><u>CATAAATTGTCTGTCCAGTGTTGGTTGCGGGATCGACGCTTAAAAAAAGCGCCAGGCGTTCCAT</u><br><u>CATATTCCGCAGTTCGCGAATATTACCGGGCCAATGATAGTTCAGTAGAAGCGGCTGACACTG</u><br><u>CGTCAGCCCATGACGCACCGATTCGGTAAAAGGGATCTCCATCGCGGCCAGCGATTGTTTTAA</u><br><u>AAAGTTTTCCGCCAGAGGCAGAATATCAGGCTGTCGCTCGCGCAAGGGGGAAGCGGCAGACG</u><br><u>CAGAATGCTCAAACGGTAAAACAGATCGGTACGAAAACGTCCTTGCGTTATCTCCCGATCCAG</u><br><u>ATCGCAATGCGTGGCGCTGATCACCCGGACATCTACCGGGATCGGCTGATGCCCGCCAACGCG</u><br><u>GGTGACGGCTTTTCCTCCAGTACGCGTAGAAGGCGGGTTTGTAACGGCAGCGGCATTTCGCC</u><br><u>AATTTCGTCAAGAAACAGCGTGCCGCCGTGGGCGACCTCAAACAGCCCCGCACGTCCACCTCG</u><br><u>TCTTGAGCCGGTAAACGCTCCCTCCTCATAGCCAAACAGTTCAGCCTCCAGCAACGACTCGGT</u><br><u>AATCGCGCCGCAATTAACGGCGACAAAGGGCGGAGAAGGCTTGTTCTGACGGTGGGGCTGACG</u><br><u>GTTAAACAACGCCTGATGAATCGCTTGCGCCGCCAGCTCTTTCCCGGTCCCTGTTTCCCCCTG</u> |

| SEQ ID NO: | Gene or Operon | Sequence |
|---|---|---|
| | | AATCAGCACTGCCGCGCGGGAACGGGCATAGAGTGTAATCGTATGGCGAACCTGCTCCATTTG TGGTGAATCGCCGAGGATATCGCTCAGCGCATAACGGGTCTGTAATCCCTTGCTGGAGGTATG CTGGCTATACTGACGCCGTGTCAGGCGGGTCATATCCAGCGCATCATGGAAAGCCTGACGTAC GGTGGCCGCTGAATAAATAAAGATGGCGGTCATTCCTGCCTCTTCCGCCAGGTCGGTAATTAG TCCTGCCCCAATTACAGCCTCAATGCCGTTAGCTTTGAGCTCGTTAATTTGCCCGCGAGCATC CTCTTCAGTGATATAGCTTCGCTGTTCAAGACGGAGGTGAAACGTTTTCTGAAAGGCGACCAG AGCCGGAATGGTCTCCTGATAGGTCACGATTCCCATTGAGGAAGTCAGCTTTCCCGCTTTTGC CAGAGCCTGTAATACATCGAATCCGCTGGGTTTGATGAGGATGACAGGTACCGACAGTCGGCT TTTTAAATAAGCGCCGTTGGAACCTGCCGCGATAATCGCGTCGCAGCGTTCGGTTGCCAGTTT TTTGCGAATGTAGGCTACTGCCTTTTCAAAACCGAGCTGAATAGGCGTGATCGTCGCCAGATG ATCAAACTCCAGGCTGATATCCCGAAATAGTTCGAACAGGCGCGTTACCGAGACCGTCCAGAT CACCGGTTTATCGCTATTATCGCGCGAAGCGCTATGCACAGTAACCATCGTCGTAGATTCATG TTTAAGGAACGAATTCTTGTTTTATAGATGTTTCGTTAATGTTGCAATGAAACACAGGCCTCC GTTTCATGAAACGTTAGCTGACTCGTTTTTCTTGTGACTCGTCTGTCAGTATTAAAAAGATT TTTCATTTAACTGATTGTTTTTAAATTGAATTTTATTTAATGGTTTCTCGGTTTTTGGGTCTG GCATATCCCTTGCTTTAATGAGTGCATCTTAATTAACAATTCAATAACAAGAGGGCTGAATag taatttcaacaaaataacgagcattcgaatg |
| 107 | Tsx -<br>Salmonella<br>enterica<br>subsp.<br>enterica<br>serovar<br>Typhimurium<br>LT2<br>(STM0413) | Atgaaaaaacttactcgcagtcagcgcagcgctggcgctcacctcatctttactgctaac gcagcagaaaatgatcagccgcagtattttgtccgactggtggcaccagagcgtaaacgtggta ggcagctaccatacccgtttctcgccgaaattgaacaacgacgtctatctggaatatgaagca tttgccaaaaaagactggtttgatttctacggctatatcgatattcccaaaacctttgattgg ggtaacggcaacgataaaggtatctggtccgacggttctccgctgttcatggaaatcgaaccg cgtttctcaattgataagctgaccggcgcagacctgagcttcggcccgttaaagagtggtat ttcgccaacaactacatctacgatgggcgataacaaagccagccgccagagcacgtggtat atgggtctggggaccgatatcgacaccgcctgccgatgggctgtcgctgaacgtgtatgcg aaatatcagtggcaaaactacggcgcgtccaatgaaaacgaatgggacggctaccgtttcaaa gtgaaatacttcgtcccatcaccgatctgtgggcggtaaactgagctatatcggctttacc aactttgactgggatctgatttaggcgacgatccgaaccgtaccagcaactccatcgcttcc agccatatcctggcgctgaactacgatcactggcactactcggtcgttgcgcgttacttccat aacggcggacagtggcagaatggcgcaaaactgaactggggcgacggcgatttcagcgcgaaa tctaccggctggggcggctacctggtcgtgggttacaacttctaa |
| 136 | Tsx -<br>Salmonella<br>enterica<br>subsp.<br>enterica<br>serovar<br>Typhimurium<br>LT2<br>(STM0413) | MKKTLLAVSAALALTSSFTANAAENDQPQYLSDWWHQSVNVVGSYHTRFSPKLNNDVYLEYEA FAKKDWFDFYGYIDIPKTFDWGNGNDKGIWSDGSPLFMEIEPRFSIDKLTGADLSFGPFKEWY FANNYIYDMGDNKASRQSTWYMGLGTDIDTGLPMGLSLNVYAKYQWQNYGASNENEWDGYRFK VKYFVPITDLWGGKLSYIGFTNFDWGSDLGDDPNRTSNSIASSHILALNYDHWHYSVVARYFH NGGQWQNGAKLNWGDGDFSAKSTGWGGYLVVGYNF |
| 108 | Tsx -<br>Escherichia<br>coli K-12<br>MG1655<br>(b0411) | atgaaaaaacattactggcagccggtgcggtactggcgctctcttcgtcttttactgtc aacgcagctgaaaacgacaaaccgcagtatcttccgactggtggcaccagagcgcgttaac gttgtcggaagctatcacacccgtttcggaccgcagatccgcaacgatacctaccttgag tacgaagcattcgctaaaaaagactggttcgacttctatggttatgcggatgcgccggta ttcttcggcggtaactccgatgctaaaggtatctggaaccacggttctccgctgtttatg gaaatcgaaccacgtttctccatcgacaagctgaccaatactgaccttagcttcggtccg ttcaaagagtggtacttcgcgaacaactacatttacgacatgggtcgtaataaagatggt cgccagagcacctggtacatgggtctgggtaccgatatcgacactggcctgccgatgagc ctgtccatgaacgtctatgcgaaataccagtggcagaactatggcgcagcgaacgaaaac gagtgggacggttaccgtttcaaaattaaatacttttgtgccgattaccgatctgtggggc ggtcagctgagctacatcggcttcaccaacttcgactgggggttccgattaggggatgac agcggtaacgcaatcaacggtattaagacccgtactaataactctatcgcttccagccat attctggctctgaactacgatcactggcactactctgtcgtagctcgttactggcacgac ggtggtcagtggaacgacgatgcagaactgaacttcggcaacggcaacttcaacgttcgc tctaccggctggggtggtacctggtagtaggttacaacttctga |
| 109 | BH1446 -<br>Bacillus<br>halodurans<br>(BAB05165) | atgaatattttgtggggtttattaggaatcgtcgttgtttttctaatcgcttttgcatttcc acaaatcgtcgtgcaattaaaccacgaacgatattaggtggtctcgcgattcagctattattt gcgattattgtattaaaaattccagctggacaagcgttacttgagagcttaaccaatgtagtt ttgaacattattagttatgcgaatgaaggatcgacttcgtattggtggatttttcgaagaa ggttcaggcgctaggcttcgttttttgcaattaacgttttgtctgtcgtcattttcttctcagca ctaatctcgatccttttattatttagggatcatgcaatttgtcattaaaattatcggtggtgcg ctgtcctggctactcggaacatcaaaggcagaatcaatgtcagcagcagctaacattttcgtt gggcaaacggaagcgccactcgttgttaagccatacttaccaaaaatgacgcaatccgagctc tttgcggttatgaccggggagcttgcttctgttgctggtttctgttttaatcggttattctctt ttaggagtaccgctacaatatttattagcggcaagcttttatggctgctcctgcgggcttgatt atggcgaaaatgatcatgcctgaaacggagaaaacaaccgatgcagaagatgactttaagctc gcaaaggatgaagagtccacgaacttgattgacgcgccgccaatgggcgagcactggggtta atgctcgttctaaatattgcggcgatgttactagcgttcgttgcattgattgcattaattaat ggaattcttggatggatcggaggattgttgggcgtcgcaattgtcttagagttaatcctc |

-continued

| SEQ ID NO: | Gene or Operon | Sequence |
|---|---|---|
| | | ggatacgtgtttgctccgcttgcgtttgtcatcggaattccttgggctgaagcgcttcaagcg<br>ggaagctacatcggacagaaactcgtagtgaacgaatttgttgcctacttaagctttgcacca<br>gaaattgaaaacctttcagataaagcggtgatggtgattagttttgcccttttgcggatttgct<br>aacttctcatccctcggaatcctttaggaggattgggtaagcttgctccgagccgtcgccct<br>gatattgcccgtctcggattacgcgcgatccttgcaggtacgctagcttctttactcagcgcc<br>tccattgcgggaatgttattctaa |
| 137 | BH1446 - Bacillus halodurans (BAB05165) | MNILWGLLGIVVVFLIAFAFSTNRRAIKPRTILGGLAIQLLFAIIVLKIPAGQALLESLTNVV<br>LNIISYANEGIDFVFGGFFEEGSGVGFVFAINVLSVVIFFSALISILYYLGIMQFVIKIIGGA<br>LSWLLGTSKAESMSAAANIFVGQTEAPLVVKPYLPKMIQSELFAVMTGGLASVAGSVLIGYSL<br>LGVPLQYLLAASFMAAPAGLIMAKMIMPETEKTTDAEDDFKLAKDEESTNLIDAAANGASTGL<br>MLVLNIAAMLLAFVALIALINGILGWIGGLFGASQLSLELILGYVFAPLAFVIGIPWAEALQA<br>GSYIGQKLVVNEFVAYLSFAPEIENLSDKAVMVISFALCGFANFSSLGILLGGLGKLAPSRRP<br>DIARLGLRAILAGTLASLLSASIAGMLF |
| 110 | nupC - Bacillus Subtilis subsp. subtilis 168 (BSU39410; CAA57663 ) | atgaagtatttgattgggattatcggtttaatcgtgttttaggcctcgcgtggatcgcgagc<br>agcggcaaaaaaagaattaagatccgccaattgttgttatgctcatttttgcaatttattctt<br>ggctacattctcctcaataccggaatagggaattcctcgtgggagggatttgcaaaaggattc<br>ggttacctgcttgaatacgcggcagagggaattaactttgtgtttggcggcttggtgaatgcg<br>gaccaaaacgacactctttatgaatgtctcttgccaatcgtgttttatttccgctctgatcggg<br>attctgcaaaagtggaaagtcctcccgtttatcattagatatatcggccttgccctcagcaag<br>gtaaacggtatgggaagattggaatcgtataacgcagtggcttctgcgatttttagggcagtca<br>gaagtatttatctccttgaagaaagaactcggtctttttaaatcagcagcgcttgtacacgctt<br>tgcgcatctgcgatgtcaactgtacaatgtcgattgtcggtgcgtatatgacaatgctgaaa<br>ccggaatatgttgtaacagcgcttgttttgaacttatttggcggtttcattatcgcttctatt<br>atcaatccgtacgaggttgcaaaagaagaggatatgcttcgtgttgaggaagaagaaaaacaa<br>tccttcttcgaagtgctcggagaatacattcttgacggtttcaaagtagcggttgtcgtcgct<br>gcgatgctgattggatttgtcgcgattattgcattgatcaatggcattttaatgcagtattc<br>ggtatttcgttccaaggcattcttggatatgtgtttgccattcgcttttcttgtcggtatc<br>ccatggaatgaagctgttaatgcgggaagcattatggcaacaaaaatggtatcgaatgaattt<br>gtcgccatgacgtcgcttacgcaaaacggtttccatttcagcggccgtacaacagcgatcgta<br>tcggtattccttgtgtcatttgcgaacttctcctcaatcggaatcattgccggtgccgtaaaa<br>ggactgaatgaaaagcaaggaaatgtcgtcgctcgtttcggcttgaaattattatacggtgct<br>acgcttgtcagcttttctatcagcagcaattgtgggcttgatttactga |
| 138 | | MKYLIGIIGLIVFLGLAWIASSGKKRIKIRPIVVMLILQFILGYILLNTGIGNFLVGGFAKGF<br>GYLLEYAAEGINFVFGGLVNADQTTFFMNVLLPIVFISALIGILQKWKVLPFIIRYIGLALSK<br>VNGMGRLESYNAVASAILGQSEVFISLKKELGLLNQQRLYTLCASAMSTVSMSIVGAYMTMLK<br>PEYVVTALVLNLFGGFIIASIINPYEVAKEEDMLRVEEEEKQSFFEVLGEYILDGFKVAVVVA<br>AMLIGFVAIIALINGIFNAVFGISFQGILGYVFAPFAFLVGIPWNEAVNAGSIMATKMVSNEF<br>VAMTSLIQNGFHFSGRTTAIVSVFLVSFANFSSIGIIAGAVKGLNEKQGNVVARFGLKLLYGA<br>TLVSFLSAAIVGLIY |
| 111 | yutK - Bacillus Subtilis subsp. subtilis 168: BSU32180 | atgaatgttctgtgggggctgctgggcgcagttgcgatcattgctatcgcgttttttatttca<br>gaaaagaaaagcaatattaagataagaaccgtcatcgttggtttatgcacacaggtggcgttt<br>ggatacatcgtgttgaaatgggaagcgggacgcgctgttttttatggttttcaagccgtgta<br>cagcttctgattgactatgcgaatgaagcatcagttttattttggaccgcttctaaaggtc<br>ggagacagtccggcatttgcattaagtgtactgcccgttatcatttttcttctcagcactgatt<br>gcagttttatatcatttgaaaatcatgcagctcgttttccgtgtcattggcggcggattgtcg<br>aagctccttggaacaagcaaaacggaatctctcgtagctgctgccaatattttgtaggacaa<br>tcagaatctccgttagtgatcaaaccctgattgccgggctgacgcgctctgagttgtttacg<br>attatgacgagcggtctatcggcagttgcgggatctaccttgtttgggtacgcgcttctcggt<br>attccgattgagtacttgctggcggcagctttatggctgctccagctggactagtcttggt<br>aaattgattatacccgaaacggaaaaacgcaaaccgtaaaagcgatttcaaatggatgaa<br>ggcgaaggcgcagccaatgtcattgacgcagctgcaaagggagcgtcaacaggactgcaaatt<br>gcgttaaatgttggggcgatgctgcttgcgtttgttgcgttaatcgctgtagtaaacggtatt<br>ctcggcggggctttcggcttgttcggttaaaaggcgtaacattagaatccattctcggctat<br>gtgttttctcctatcgcctttttgattggcgtgccttggcatgaagcattgcaggcgggaagc<br>tatatcggccagaaattggtgctgaatgagtttgtcgcttattctaacttcggttcgcacatc<br>ggcgagttttctaagaaaactgctaccattatcagtttcgcgttatgcggattcgccaattt<br>tcatcaattgcgattatgcttggtacgcttggcggtttagcgcccagccgccgttcagatatc<br>gcacgtctcggcctgaaggctgttcttgcaggaacattagccaatctgctcagcgcagccatt<br>gccggcatgttttatataa |
| 139 | | MNVLWGLLGAVAIIAIAFLFSEKKSNIKIRTVIVGLCTQVAFGYIVLKWEAGRAVFLWFSSRV<br>QLLIDYANEGISFIFGPLLKVGDSPAFALSVLPVIIFFSALIAVLYHLKIMQLVFRVIGGGLS<br>KLLGTSKTESLAAAANIFVGQSESPLVIKPLIAGLTRSELFTIMTSGLSAVAGSTLFGYALLG<br>IPIEYLLAASFMAAPAGLVFGKLIIPETEKTQTVKSDFKMDEGEGAANVIDAAAKGASTGLQI<br>ALNVGAMLLAFVALIAVVNGILGGAFGLFGLKGVTLESILGYVFSPIAFLIGVPWHEALQAGS<br>YIGQKLVLNEFVAYSNFGSHIGEFSKKTATIISFALCGFANFSSIAIMLGTLGGLAPSRRSDI<br>ARLGLKAVLAGTLANLLSAAIAGMFI |

| SEQ ID NO: | Gene or Operon | Sequence |
|---|---|---|
| 112 | yxjA - Bacillus Subtilis subsp. spizizenii W23 (BSUW23_19355) | atgtacttttattaaaccttgtcggtctcattgtgattatggcagttgtgttcctatgctcc ccgcagaaaaagaaaatccagtggcgtccgatcattacgttaattgttctggaattgctgatt acttggtttatgctgggaacaaaggtcgggagctgggccatcggtaaaattggtgatttcttc acttggctgattgcttgcgccagtgacggtatcgcgtttgccttcccgtcagtcatggcgaat gaaacagtagacttttcttagtgcacttcttccaattatctttatcgtcacattctttgat attttaacatatttcggcatttttgccttggctgattgataaaatcggatgggtgatttcaaag gcttcccgcttgccgaaattagaaagcttttttctctattcaaatgatgttcttgggaaatact gaagcacttgcggtcatccgccagcagcttacggtattaaataacaaccgcttgcttacattt ggcttaatgagcatgagcagcatcagcggctccattattggatcttacctgtcaatggtgccg gcgacatacgtgtttacagcgattccattgaactgcttaaacgcgctgattattgcaaacctg ctgaaccctgttcatgtgccggaggatgaagatatcatctataccacgccctaaagaagagaag aaagacttttttctctacgatttctaacagtatgcttgtcggcatgaacatggttatcgttatt ttggcaatggtgatcggatatgtagcattaacgtctgcagtcaatggcattcttggtgttttc gtacacggcctgaccatccagacaatttttgcttatctcttcagtccgttcgcattcctgctt ggtctgccagtacatgatgcaatgtatgtcgctcaagcaatgggaatgaaattggcaactgaac gagtttgttgcgatgcttgacttgaaaaacaatcttacaacacttccgcctcacacagttgcg gtggcgacgacattcctgacgtcatttgccaacttcagtactgtcggcatgatttacggaacg tacaactcgatccttgacggcgaaaagtcaacggtcatcgggaaaaacgtgtggaaattgctc gtcagcggcattgcggtatctttactaagtgctgcgattgtcggcctgtttgtgtggtag |
| 140 | yxjA - Bacillus subtilis sus. spizizenii W23 (BSUW23_19355) | MYFLLNLVGLIVIMAVVFLCSPQKKKIQWRPIITLIVLELLITWFMLGTKVGSWAIGKIGDFF TWLIACASDGIAFAFPSVMANETVDFFFSALLPIIFIVTFFDILTYFGILPWLIDKIGWVISK ASRLPKLESFFSIQMMFLGNTEALAVIRQQLTVLNNNRLLTFGLMSMSSISGSIIGSYLSMVP ATYVFTAIPLNCLNALIIANLLNPVHVPEDEDIIYTPPKEEKKDFFSTISNSMLVGMNMVIVI LAMVIGYVALTSAVNGILGVFVHGLTIQTIFAYLFSPFAFLLGLPVHDAMYVAQLMGMKLATN EFVAMLDLKNNLTTLPPHTVAVATTFLTSFANFSTVGMIYGTYNSILDGEKSTVIGKNVWKLL VSGIAVSLLSAAIVGLFVW |
| 113 | ccCNT (CC2089) - Caulobacter crescentus CB15 (AAK24060 ) | atgttccgtcccgagaacgttcaggccctcgcgggtctggcgctcaccctgggcctgtgctgg ctcgtttccgagaatcgcaagcggtt ccc ctggggcctggccatcggcgcggtcgtcattcag gtcctgctggtcctggtcctgttcggcctgccgcaagcccagcagatgctgcgcggcgtcaac ggccggtggagggccttgccgcctcgacccaggccggcaccgccttcgtgttcggcttt ctg gccggcggcgaccagcccatccggtcagcaatccgggcgcgggcttcatcttcgccttccgc gtgctgccggtgatcctggtggtctgcgccctgtcggcgctgctgtggcactggaagattctc aagtggctggctcagggcttcggctttgtgttccagaagacgctgggcctgcgcggcccgccg gccctggccaccgccgcgaccatcttcatgggtcaggtcgaggggccgattcttcatccgcgc tatctcgacaagctgagccgctcggaactcttcatgctgatcgcggtcggcatggcctgcgtg tcgggctcgaccatggtcgcctacgccaccatcctggccgacgtcctgcccaacgccgccgcc cacgtgctgaccgcctcgatcatctcggctccggccggcgtgctgctggcccggatcattgtg ccgtccgatccgatggagaagagcgccgatcttgatctgtcgaccgaggacaagacctatggc agctcgatcgacgccgtgatgaagggcaccaccgacggcctgcagatcgcgctgaacgtcggc gccacccctgatcgtcttcgtggccctggccaccatggtcgacaaggtcctgggcgccttcccg ccggtgggcggcgagccgctgagcatcgcgcgcggcctgggcgtggtcttcgcgccgctggcc tggtcgatgggcatcccgtggaaagaagcgggcacggccggcggtctgctgggcgtgaagctg atcctgaccgagttcaccgccttcatccagctgtccaaggtgggcgaagccctgctggacgaa cgcaccccgatgatcatgacctacgctctgtgcggtttcgccaatatcggctcggtcggcatg aacgtcgccggcttctcggtgctggtgccccagcgccggcaggaagtgctgggcctggtctgg aaggcgatgatggccggcttcctggccacctgcctgaccgcctcgctggtcggcctgatgccg cgaagcctgtttgggctgtaa |
| 141 | ccCNT (CC2089) - Caulobacter crescentus CB15 (AAK24060) | MFRPENVQALAGLALTLGLCWLVSENRKRFPWGLAIGAVVIQVLLVLVLFGLPQAQQMLRGVN GAVEGLAASTQAGTAFVFGFLAGGDQPYPVSNPGAGFIFAFRVLPVILVVCALSALLWHWKIL KWLAQGFGFVFQKTLGLRGPPALATAATIFMGQVEGPIFIRAYLDKLSRSELFMLIAVGMACV SGSTMVAYATILADVLPNAAAHVLTASIISAPAGVLLARIIVPSDPMEKSADLDLSTEDKTYG SSIDAVMKGTTDGLQIALNVGATLIVFVALATMVDKVLGAFPPVGGEPLSIARGLGVVFAPLA WSMGIPWKEAGTAGGLLGVKLILTEFTAFIQLSKVGEALLDERTRMIMTYALCGFANIGSVGM NVAGFSVLVPQRRQEVLGLVWKAMMAGFLATCLTASLVGLMPRSLFGL |
| 114 | yeiJ - Escherichia coli K-12 W3110 (AAC75222; JW2148) | atgatgtcatgagaagtgttctgggaatggtggtattgctgacgattgcgttttactgtca gtaaacaagaagaagatcagcctgcgtaccgttggcgcggcgttagtgttacaggtcgtgatt ggcggcattatgctttggttaccgccagggcgttgggtcgctgaaaaagtcgcttttggcgtg cataaagtgatggcgtacagcgacgtgggtagcgcatttatcttcggttctctgtcggcaccg aaaatggataccttatttgatggtgcaggattatctttgtttcagggtgttaccggcaatt atcttcgtcaccgcgctggtgagtattctctactacatcggtgtgatggggattttaattcga attctcggcggtatcttccagaaagcattaaatatcagcaagatcgagtcattcgtcgcgtc accaccatttttcctcgggcaaaacgaaattccgcaatcgtcaaaccctttatcgatcgtctg aatcgcaatgaattatttacagcgatttgtagtgcatgcggtgtttgttgcgacaatg attggttacgccgcactgggcgtgcctggaatatctgctggcggcatcattaatgcgatc cctggcgggatcttgtttgccgcctgttaagcccggcaacggaatcttcgcaggtttccttt aataacctctcttcaccgaaacaccgccaaaaagcattattgaagccgctgcgacaggggca atgaccgggctgaaatcgccgcaggtgtggcaacagtggtgatggcatttgttgcaataatt gcgttgattaacggtattatcggcggcgttggtggctggttggttttgaacatgcctcgctg |

-continued

| SEQ ID NO: | Gene or Operon | Sequence |
|---|---|---|
| | | gagtccatttaggttacctgctggctccactggcgtgggtgatgggtgtggactggagtgat<br>gcgaatcttgccgggagtttgattggacagaaactggcaataaatgaatttgtcgcttatctc<br>aatttctcaccctatctgcaaacggctggcactctcgatgctaaaactgtggcgattatttcc<br>ttcgcgttgtgcggtttcgctaactttggttctatcggggtggtggtggggcgttttctgcg<br>gttgcgccacaccgtgcgccggaaatcgcccagcttggtttacgggcgctggcggcggacg<br>ctttccaacttgatgagtgcgaccattgccgggttctttattggtttagcttga |
| 142 | yeiJ -<br>Escherichia<br>coli K-12<br>W3110<br>(AAC75222;<br>JW2148) | MDVMRSVLGMVVLLTIAFLLSVNKKKISLRTVGAALVLQVVIGGIMLWLPPGRWVAEKVAFGV<br>HKVMAYSDAGSAFIFGSLVGPKMDTLFDGAGFIFGFRVLPAIIFVTALVSILYYIGVMGILIR<br>ILGGIFQKALNISKIESFVAVTTIFLGQNEIPAIVKPFIDRLNRNELFTAICSGMASIAGSTM<br>IGYAALGVPVEYLLAASLMAIPGGILFARLLSPATESSQVSFNNLSFTETPPKSIIEAAATGA<br>MTGLKIAAGVATVVMAFVAIIALINGIIGGVGGWFGFEHASLESILGYLLAPLAWVMGVDWSD<br>ANLAGSLIGQKLAINEFVAYLNFSPYLQTAGILDAKTVAIISFALCGFANFGSIGVVVGAFSA<br>VAPHRAPEIAQLGLRALAAATLSNLMSATIAGFFIGLA |
| 115 | yeiM -<br>Escherichia<br>coli K-12<br>W3110<br>(AAC75225;<br>JW2151 ) | atggatataatgagaagtgttgtggggatggtggtgttactggcaatagcatttctgttgtca<br>gtgaataaaaagagcatcagtttgcgcacggttggagccgcactgctgctgcaaatcgctatt<br>ggtggcatcatgctctacttcccaccgggaaatgggcagtagaacaggcggcattaggcgtt<br>cataaagtgatgtcttacagtgatgccgtagcgccttcatttttggttcgctggttgggccg<br>aaaatggatgtcctgtttgacggtgcggttttatcttcgccttcgcgtacttccggcgatt<br>attttcgttactgcgctcatcagtctgctgtactacattggcgtgatgggcgtgctgattcgc<br>atccttggcagcattttccagaaagccctcaacatcagcaaaatcgaatctttgttgcggtt<br>actactattttcctcgggcaaaatgagatcccggcgatcgttaaaccgtttatcgatcgcatg<br>aatcgcaacgagttgtttaccgcaatttgtagcgggatggcgtccattgctggtcgatgatg<br>attggttatgccggaatgggcgtaccaattgactacctgttagcggcatcgctgatgcgatc<br>cctggcgggattttgtttgcacgtattcttagcccggcaaccgagccttcgcaggtcacatt<br>gaaaatctgtcgttcagcgaaacgccgccaaaaagctttatcgaagcggcggcgagcggtgcg<br>atgaccgggctaaaaatcgccgctggtgtggcgacggtggtaatggcgtttgtcgcaattat<br>gcgctgatcaacgcgcattatcggcgaattggcggctggtttggtttcgccaatgcctctctg<br>gaaagtattttttggctatgtgctggcaccgctggcgtggatcatgggtgtggactggagtgat<br>gccaatcttgcgggtagcctgattgggcagaaactggcgattaacgaattcgtcgcttacctg<br>agtttctccccatacctgcaaacgggcggcacgctggaagtgaaaaccattgcgattatctcc<br>tttgcgctttgtggttttgctaactttggttctatcggtgttgtcgttggcgcattttcggct<br>atttcgccaaaacgcgcgccggaaatcgcccagcttggtttacgggcgctggcagcagcaacg<br>ctttccaacctgatgagtgcgactattgccgggttctttattggtctggcgtaa |
| 143 | yeiM -<br>Escherichia<br>coli K-12<br>W3110<br>(AAC75225;<br>JW2151) | MDIMRSVVGMVVLLAIAFLLSVNKKSISLRTVGAALLLQIAIGGIMLYFPPGKWAVEQAALGV<br>HKVMSYSDAGSAFIFGSLVGPKMDVLFDGAGFIFAFRVLPAIIFVTALISLLYYIGVMGLLIR<br>ILGSIFQKALNISKIESFVAVTTIFLGQNEIPAIVKPFIDRMNRNELFTAICSGMASIAGSMM<br>IGYAGMGVPIDYLLAASLMAIPGGILFARILSPATEPSQVTFENLSFSETPPKSFIEAAASGA<br>MTGLKIAAGVATVVMAFVAIIALINGIIGGIGGWFGFANASLESIFGYVLAPLAWIMGVDWSD<br>ANLAGSLIGQKLAINEFVAYLSFSPYLQTGGTLEVKTIAIISFALCGFANFGSIGVVVGAFSA<br>ISPKRAPEIAQLGLRALAAATLSNLMSATIAGFFIGLA |
| 116 | HI0519 -<br>Haemophilus<br>influenzae<br>Rd KW20<br>serotype<br>d(AAC22177 | atgagtgtgttaagcagcatttttgggaatggtcgtattaatcgctattgccgtgttactttct<br>aataatcgtaaagcgattagtattcgaaccgtaggtagggggcgttagcaatccaagtaggattt<br>gccgcccttattttatatgtgccagcaggtaaacaagcgttgggtgccgctgcggatatggta<br>tccaatgttattgcctatggtaatgacgggattaatttcgttttcggcggattggcagatcca<br>agtaaaccatccggtttcatttttgcagtgaaagtattaccgattatcgtgttcttctctggc<br>ttaatttctgtgctttactatctcggcattatgcaagtcgtgattaaagtattaggtggcgca<br>ttacaaaaagcattgggtacgtcaaaagcggaatcaatgtcagcggcggcgaatatcttcgtc<br>ggtcaaactgaagcaccattagttgttcgcccttacattaaaaatatgacccaatctgaatta<br>tttgccattatggtggtggtacagcgtctatcgcgggttcagtaatggcaggttatgctgga<br>atgggcgtgccattgacatactttaatcgctgcgtcatttatggcggcaccagcaggtttatta<br>tttgcgaaattaatgttcccacaaaccgaacaattcacagataaacaaccagaagacaatgat<br>tcagaaaaaccaactaacgtacttgaagcaatggcgggcggtgcgagtgcaggtatgcaactt<br>gcgttaaacgtaggtgcaatgttaatcgcattcgttggtttaattgcattaattaatggtatt<br>ttaagtggcgtaggcggatggttcggctatggcgacttaaccttacaatgctatctttggttta<br>atttttaaaccattagcatacttaatcggtgtaactgatggtgctgaagcaggtattgcagga<br>caaatgatcgggatgaaattagcggttaatgaatttgtgggttatcttgaatttgcaaaatat<br>ttacaaccagattctgcaattgtattaactgaaaaaaccaaagcgattattactttcgcactt<br>tgtggttttgctaacttcagctcaattgcaatcttaattggtggtttaggtggtatggcacca<br>agccgtcgtagtgatgttgctcgtttaggtatcaaagcccgttatcgctggtactctcgctaac<br>ttaatgagtgcaactattgctggtttatttatcggcttaggtgctgcagcactttaa |
| 144 | HI0519 -<br>Haemophilus<br>influenzae<br>Rd KW 20<br>serotype<br>d(AAC22177 | MSVLSSILGMVVLIAIAVLLSNNRKAISIRTVVGALAIQVGFAALILYVPAGKQALGAAADMV<br>SNVIAYGNDINFVFGGLADPSKPSGFIFAVKVLPIIVFFSGLISVLYYLGIMQVVIKVLGGA<br>LQKALGTSKAESMSAAANIFVGQTEAPLVVRPYIKNMTQSELFAIMVGGIASIAGSVMAGYAG<br>MGVPLTYLIAASFMAAPAGLLFAKLMFPQTEQFTDKQPEDNDSEKPTNVLEAMAGGASAGMQL<br>ALNVGAMLIAFVGLIALINGILSGVGGWFGYGDLTLQSIFGLIFKPLAYLIGVTDGAEAGIAG<br>QMIGMKLAVNEFVGYLEFAKYLQPDSAIVLTEKTKAIITFALCGFANFSSIAILIGGLGGMAP<br>SRRSDVARLGIKAVIAGTLANLMSATIAGLFIGLGAAAL |

-continued

Sequence Listing

| SEQ ID NO: | Gene or Operon | Sequence |
|---|---|---|
| 117 | nupC (HP1180) - Helicobacter pylori 26695 (AAD08224) | atgatttttagctctcttttttagtgttgtagggatggcggtgcttttttcttattgcttgg gtgttttctagcaataaaagggctattaattatcgcacgattgtcagtgcctttgtgatt caagtggcttlaggggcgttggctttatatgtgcctttgggtagggaaatgctgcaaggc ttagccagcggcatacaaagcgtgattcttacggctatgaggggtgcgttttttattt ggcaatctcgctccaaacgctaagggcgatcaagggataggggggtttgtctttgcgatc aatgtttagcgatcattatctttttgctagcttgatttcacttctatatattaaaa atcatgccttatttatcaatctcatcggtggggcgttgcaaaaatgcttaggcacttct agagcagaaagcatgagtgcagcggctaatattttgtagcgcacaccgaagcgcccta gtcattaaaccttattgaaaagcatgagcgattcagagattttgcggtcatgtgcgtg ggcatggctagcgttgcgggcctgtgttagccgggtatgcgagcatgggcattcctttg ccttattgatcgccgcttcgtttatgtccgctcctgggggtttgttgttcgctaaaatc atttacccacaaaacgaaaccatttctagccatgcagatgtttctatagaaaagcatgtc aatgccatagaagctatcgctaatggggcaagcacagggctaaatttagccttgcatgtg ggagcgatgcttagcctttgtggggatgctcgcgctcattaacgggcttttaggggtt gtaggggttttttaggcatggacatttgtctttaggttattttaggcacgctctta aaaccctagcctttatgttaggcatccttggagccaggccgggattgccggagaaatc ataggcattaaaatcgcgctcaatgaatttgtgggctatatgcagttattgccttatttg ggcgataaccctccttaatcttgagcgagaaaactaaagcgatcatcacttttgcgttg tgcgggtttgctaatttaagctcagtcgctatgctcagttggagggcttggcagtttagtg cctaaaaagaaggatctcattgtaaggcttgctttaaaagcggtgcttgtaggcacgctt tctaatttcatgagcgcgactatcgccgggttattcataggctaaacgctcattaa |
| 145 | nup C (HP1180) - Helicobacter pylori 26695 (AAD08224) | MIFSSLFSVVGMAVLFLIAWVFSSNKRAINYRTIVSAFVIQVALGALALYVPLGREMLQG LASGIQSVISYGYEGVRFLFGNLAPNAKGDQGIGGFVFAINVLAIIIFFASLISLLYYLK IMPLFINLIGGALQKCLGTSRAESMSAAANIFVAHTEAPLVIKPYLKSMSDSEIFAVMCV GMASVAGPVLAGYASMGIPLPYLIAASFMSAPGGLLFAKIIYPQNETISSHADVSIEKHV NAIEAIANGASTGLNLALHVGAMLLAFVGMLALINGLLGVVGGFLGMEHLSLGLILGTLL KPLAFMLGIPWSQAGIAGEIIGIKIALNEFVGYMQLLPYLGDNPPLILSEKTKAIITFAL CGFANLSSVAMLIGGLGSLVPKKKDLIVRLALKAVLVGTLSNFMSATIAGLFIGLNAH |
| 118 | nupC (SA0600) - Staphylococcus aureus subsp. aureus N315 (BAB41833) | ATGTTTTTATTAATCAACATTATTGGTCTAATTGTATTTCTTGGTATTGCGGTATTATTTCA AGAGATCGCAAAAATATCCAATGGCAATCAATTGGGATCTTAGTTGTTTTAAACCTGTTTTTA GCATGGTTCTTTATTTATTTTGATTGGGGTCAAAAAGCAGTAAGAGGAGCAGCCAATGGTATC GCTTGGGTAGTTCAGTCAGCGCATGCTGGTACAGGTTTTGCATTTGCAAGTTTGACAAATGTT AAAATGATGGATATGGCTGTTGCAGCCTTATTCCCAATATTATTAATAGTGCCATTATTTGAT ATCTTAATGTACTTTAATATTTTACCGAAAATTATTGGAGGTATTGGTTTGGTTACTAGCTAAA GTAACAAGACAACCTAAATTCGAGTCATTCTTTGGGATAGAAATGATGTTCTTAGGGAAATACT GAAGCATTAGCCGTATCAAGTGAGCAACTAAAACGTATGAATGAAATGCGTGTATTAACAATC GCAATGATGTCAATGAGCTCTGTATCCGGAGCTATTGTAGGTGCGTATGTACAAATGGTACCA GGAGAACTGGTACTAACGGCAATTCCACTAAATATCGTTAACGCCGTATTATTGTGTCATTGCTTG TTGAATCCAGTAAGTGTTGAAGAGAAAGAAGATATTATTTACAGTCTTAAAAACAATGAAGTT GAACGTCAACCATTCTTCTCATTCCTTGGAGATTCTGTATTAGCAGCAGGTAAATTAGTATTA ATCATCATCGCATTTGTTATTAGTTTTGTAGCGTTAGCTGATCTATTTGATCGTTTTATCAAT TTGATTACAGGATTGATAGCAGGATGGATAGGCATAAAAGGTAGTTTCGGTTTAAACCAAATT TTAGGTGTGTTTATGTATCCATTTGCGCTATTACTCGGTTTACCTTATGATGAAGCGTGGTTG GTAGCACAACAAATGGCTAAGAAAATTGTTACAAATGAATTTGTTGTTATGGGTGAAATTTCT AAAGATATTGCATCTTATACACCACACCATCGTGCGGTTATTACAACATTCTTAATTTCATTT GCAAACTTCTCAACGATTGGTATGATTATCGGTACATTGAAAGGCATTGTTGATAAAAAGACA TCAGACTTTGTATCTAAATATGTACCTATGATGCTATTATCAGGTATCCTAGTTTCATTATTA ACAGCAGCTTTCGTTGGTTTATTTGCATGGTAA |
| 146 | nupC (SA0600) - Staphylococcus aureus subsp. aureus N315 (BAB41833) | MFLLINIIGLIVFLGIAVLFSRDRKNIQWQSIGILVVLNLFLAWFFIYFDWGQKAVRGAANGI AWVVQSAHAGTGFAFASLTNVKMMDMAVAALFPILLIVPLFDILMYFNILPKIIGGIGWLLAK VTRQPKFESFFGIEMMFLGNTEALAVSSEQLKRMNEMRVLTIAMMSMSSVSGAIVGAYVQMVP GELVLTAIPLNIVNAIIVSCLLNPVSVEEKEDIIYSLKNNEVERQPFFSFLGDSVLAAGKLVL IIIAFVISFVALADLFDRFINLITGLIAGWIGIKGSFGLNQILGVFMYPFALLLGLPYDEAWL VAQQMAKKIVTNEFVVMGEISKDIASYTPHHRAVITTFLISFANFSTIGMIIGTLKGIVDKKT SDFVSKYVPMMLLSGILVSLLTAAFVGLFAW |
| 119 | nup C (SAV0645) - Staphylococcus aureus subsp. aureus Mu50 (BAB56807) | atgttttattaatcaacattattggtctaattgtatttcttggtattgcggtattattt tcaagagatcgcaaaaatatccaatggcaatcaattgggatcttagttgttttaaacctg ttttagcatggttctttatttattttgattggggtcaaaaagcagtaagaggagcagcc aatggtatcgcttgggtagttcagtcagcgcatgctggtacaggttttgcatttgcaagt ttgacaaatgttaaaatgatggatatggctgttgcagccttattcccaatattattaata gtgccattatttgatatcttaatgtactttaatattttaccgaaaattattggaggtatt ggttggttactagctaaagtaacaagacaacctaaattcgagtcattctttgggatagaa atgatgttcttaggaaatactgaagcattagccgtatcaagtgagcaactaaaacgtatg aatgaaatgcgtgtattaacaatcgcaatgatgtcaatgagctctgtatccggagctatt gtaggtgcgtatgtacaaatggtaccaggagaactggtactaacggcaattccactaaat atcgttaacgcgattattgtgtcattgcttgttgaatccagtaagtgttgaagagaaagaa gatattatttacagtcttaaaaacaatgaagttgaacgtcaaccattcttctcattcctt ggagattctgtattagcagcaggtaaattagtattaatcatcatcgcatttgttattagt |

| SEQ ID NO: | Gene or Operon | Sequence |
|---|---|---|
| | | tttgtagcgttagctgatctatttgatcgttttatcaatttgattacaggattgatagca ggatggataggcataaaaggtagtttcggtttaaaccaaattttaggtgtgtttatgtat ccatttgcgctattactcggtttacctttatgatgaagcgtggttggtagcacaacaaatg gctaagaaaattgttacaaatgaatttgttgttatgggtgaaatttctaaagatattgca tcttatacaccacaccatcgtgcggttattacaacattcttaatttcatttgcaaacttc tcaacgattggtatgattatcggtacattgaaaggcattgttgataaaaagacatcagac tttgtatctaaatatgtacctatgatgctattatcaggtatcctagtttcattattaaca gcagctttcgttggtttatttgcatggtaa |
| 147 | nupC (SAV0645) - Staphylococcus aureus subsp. aureus Mu50 (BAB56807) | MFLLINIIGLIVFLGIAVLFSRDRKNIQWQSIGILVVLNLFLAWFFIYFDWGQKAVRGAA NGIAWVVQSAHAGIGFAFASLINVKMMDMAVAALFPILLIVPLFDILMYFNILPKIIGGI GWLLAKVIRQPKFESFFGIEMMFLGNTEALAVSSEQLKRMNEMRVLTIAMMSMSSVSGAI VGAYVQMVPGELVLTAIPLNIVNAIIVSCLLNPVSVEEKEDIIYSLKNNEVERQPFFSFL GDSVLAAGKLVLIIIAFVISFVALADLFDRFINLITGLIAGWIGIKGSFGLNQILGVFMY PFALLLGLPYDEAWLVAQQMAKKIVINEFVVMGEISKDIASYTPHHRAVITTFLISFANF STIGMIIGILKGIVDKKTSDFVSKYVPMMLLSGILVSLLTAAFVGLFAW |
| 120 | nupC (SNupC) - Streptococcus pyogenes SF370 serotype M1 (AAK34582) | atgcaatttattatatagtattattggtattttattggtattaggaattgtgtatgcaatt tctttcaatcgtaagagtgtttctctaagtttaattggaaaagctcttatcgttcaattc attattgcgctaatcttagtacgtatcccactaggccaacaaattgttagtgttgtttca actggagttactagcgtaatcaactgtcaagctggtttaaattttgtgtttgggtca ttagcagatagtggcgcaaaaactggttttattttcgctattcaaacgcttggtaatatt gttttcttatctgccctagtagtctacttattatgtaggaatccttggatttgtagta aaatggataggtaagggcgttggtaaaattatgaaatcctcagaggttgagagttttgtt gctgtagctaatatgtttcttggtcaaacagacagtccaatcttggttagcaaatacccta ggtcgtatgactgatagtgagataatggttgtgttggtatcaggtatgggaagtatgtca gttctattcttggtggctatattgcattaggcattccaatggaatatctcttgattgct tcaacaatggttcctattggcagtattctcattgctaaaatcttattgcctcaaacagaa cctgttcaaaaaattgatgaattggataataaaggtaataacgccaatgtgatt gatgcaatcgctgagggtgcaagcacaggtgcacaaatggcttctcaattggtgctagt ttgattgccttttgttggtttagtttctttgattaatatgatgttaagtggattgggaatc cgcttagaacaaatcttttcatatgtttttgctccatttggttttcttatgggatttgac cacaaaaacattcttctagaaggaaaaccttcttggaagtaagttgattttaaatgagttt gtttcgttccaacaattgggtcacctaatcaaatcttagattatcgtacagcattagta gcaactatttcactctgtggttttgctaatttatcaagtttaggtatttgtgtttcaggt attgctgttctttgcccgagagaaacgtagcaccctagctcgacttgttttccgtgcaatg attggtggtattgctgtaagtatgcttagcgccttatcgtcggtattgtaactctattc taa |
| 148 | nupC (SpNupC) - Streptococcus pyogenes SF370 serotype M1 (AAK34582) | MQFIYSIIGILLVLGIVYAISFNRKSVSLSLIGKALIVQFIIALILVRIPLGQQIVSVVS TGVTSVINCGQAGLNFVFGSLADSGAKTGFIFAIQTLGNIVFLSALVSLLYYVGILGFVV KWIGKGVGKIMKSSEVESFVAVANMFLGQTDSPILVSKYLGRMTDSEIMVVLVSGMGSMS VSILGGYIALGIPMEYLLIASTMVPIGSILIAKILLPQTEPVQKIDDIKMDNKGNNANVI DAIAEGASTGAQMAFSIGASLIAFVGLVSLINMMLSGLGIRLEQIFSYVFAPFGFLMGFD HKNILLEGNLLGSKLILNEFVSFQQLGHLIKSLDYRTALVATISLCGFANLSSLGICVSG IAVLCPEKRSTLARLVFRAMIGGIAVSMLSAFIVGIVTLF |
| 121 | nupC (VC2352) - Vibrio cholerae O1 biovar El Tor N16961 (AAF95495) | atgagcctgtttatgagcctcatcggcatggcagttctgctaggaatcgcagttctactg tcaagtaaccgtaaagctatcaatctaagaactgtgggtggcgcttttgctatccaattt tcactgggtgcatttattctgtatgtgccttggggccaagagctacttcgtggctttcg gatgccgtatcgaatgttattaactacggtaacgatggtacttcattcctcttcggtgga ctggtatcaggcaaatgtttgaagtgtttggcggcggcggtttcattttcgcattccgc tactaccaacactgatcttcttctcagcactgatttctgtactgtactacttgggtgtt atgcaatgggttatccgcattcttggcggtggtctgcaaaaagcactgggtacatcacgc gcggaatctatgtctgcggctgcaaacattttcgtgggtcaaactgaagcaccattagtt gttcgtccattcgttccaaaaatgactcaatctgagctgtttcgggtaatgtgtggtggc ttggcttctatcgcaggtggtgtacttgcgggttacgcttcaatgggcgttaagatcgaa tacttggtagcggcgtcattcatggcggcaccgggtggtctgctgttcgcaaaactgatg atgcctgaaactgaaaaaccacaagacaatgaagacattacttcttgatggtggtgacgac aaaccggctaacgttatcgatgcggctgctggcggtgctctgctggtctgcaacttgct ctgaacgttggtgcaatgttgattgcctttatcggtttgattgctctgatcaacggtatg ttgggtggcatcggtggttggttcggtatgcctgaactgaaactggaaatgctactgggc tggttgtttgcgcctctggctttcctgatcggtgttccttggaacgaagcaactgttgcg ggtgagttcatcgctctaaaaaccgttgctaacgaattcgttgcttactctcagtttgcg ccttacctgactgaagcggcaccagtggttctgtctgagaaaaccaaagcgatcatctct ttcgctctgtgtggttttgcgaacctttcttctatcgcaattctgcttggtggtttgggt agcttggcacctaagcgtcgtggcacatcgctcgtatgggggtcaaagcggttatcgca ggtactctatctaacctgatggcagcgaccatcgctggcttcttcctctctttctaa |
| 149 | nupC (VC2352) - Vibrio cholerae O1 biovar El | MSLFMSLIGMAVLLGIAVLLSSNRKAINLRTVGGAFAIQFSLGAFILYVPWGQELLRGFS DAVSNVINYGNDGTSFLFGGLVSGKMFEVFGGGGFIFAFRVLPTLIFFSALISVLYYLGV MQWVIRILGGGLQKALGTSRAESMSAAANIFVGQTEAPLVVRPFVPKMTQSELFAVMCGG LASIAGGVLAGYASMGVKIEYLVAASFMAAPGGLLFAKLMMPETEKPQDNEDITLDGGDD KPANVIDAAAGGASAGLQLALNVGAMLIAFIGLIALINGMLGGIGGWFGMPELKLEMLLG |

Sequence Listing

| SEQ ID NO: | Gene or Operon | Sequence |
|---|---|---|
| | Tor N16961 (AAF95495) | WLFAPLAFLIGVPWNEATVAGEFIGLKTVANEFVAYSQFAPYLTEAAPVVLSEKTKAIIS FALCGFANLSSIAILLGGLGSLAPKRRGDIARMGVKAVIAGTLSNLMAATIAGFFLSF |
| 122 | nupC (VC1953) - *Vibrio Cholerae* O1 biovar El Tor N16961 (AAF95101) | ttgggcggcgttatgtcatcactcctcggtatgggcgcaattttgctggttgcgtggcta ttttctaccaatagaaaaaatatcaacttgcgtacagttcttagcgttactgctgcaa atcttcttcgccttactggtgctgtatgtacctgcgggtaaagaggcactcaatcgtgtg acgggcgcggtgtcacaactgatcaactatgggcaagatggtatcggttttgtgtttggt ggcctcgccaatggcagcgtaggttttgtgtttgcgattaatgtccttggcatcatcatt tcttctctgcactgatttctggcctttaccatttaggcatcatgccgaaagtgattaac ctcatcggtggtgttacagaaattgcttggcacaggccgtgcagaatccctttctgct accgcaaacattttcgtgggtatgattgaagcgccgctggtggtgaaacctatcttcat aaaatgaccgattcgcaattctttgcagtgatgacgggcgggcttagcgtcggttgctggc ggtactttggttggttatgcctcttaggtgtggaattgaactatctgatcgcggcggct tcatgtctgcccctgcgggtctttgatggcaaaaatcatgttgccagaaaccgaacac gtcgatgccgcgattgcgcaagatgagttggatctgccgaaatccactaacgtcgtcgaa gcgattgcggatggcgcgatgtcgggtgtgaaaattgctgttgcggtaggggcgacttg ctcgctttcgtgagtgtgattgctctgttaaacggcttgctcggttggtttggtggctgg tttggcatcgagctaagctttgaactgatcatggggtatgttttcgctccggtagcttgg ctgattggtattccatggcatgaggcgatcacggcaggctcgctgattggtaacaaagtg gtggtgaacgatttgtcgctttcattcaactgattgaagtgaaagagcaattgagtgcg cattcacaagcgatcgtgactttcgcgctgtgcggttttgcgaatatttctaccatggcg attttgattggtggtttgggtagccttgtacctgaacgtcgctcttttatctcccaatac ggcttccgtgcgattggcgcaggcgtattagctaacctaatgagtgcatcgatcgctgga gtgattttgtctttgtga |
| 150 | nupC (VC1953) - *Vibrio cholerae* O1 biovar El Tor N16961 (AAF 95101) | MGGVMSSLLGMGAILLVAWLFSTNRKNINLRTVSLALLLQIFFALLVLYVPAGKEALNRV TGAVSQLINYGQDGIGFVFGGLANGSVGFVFAINVLGIIIFFSALISGLYHLGIMPKVIN LIGGGLQKLLGTGRAESLSATANIFVGMIEAPLVVKPYLHKMTDSQFFAVMTGGLASVAG GTLVGYASLGVELNYLIAAAFMSAPAGLLMAKIMLPETEHVDAAIAQDELDLPKSTNVVE AIADGAMSGVKIAVAVGATLLAFVSVIALLNGLLGWFGGWFGIELSFELIMGYVFAPVAW LIGIPWHEAITAGSLIGNKVVVNEFVAFIQLIEVKEQLSAHSQAIVTFALCGFANISTMA ILIGGLGSLVPERRSFISQYGFRAIGAGVLANLMSASIAGVILSL |
| 123 | nupC (VCA0179) - *Vibrio cholerae* O1 biovar El Tor N16961 (AAF96092) | atggcgattttgtttggaatcatcggtgttacggtactgatcttatgcgcgtatctgctc tctgaaagccgcagtgcgattaattggaaaaccatttcccgagccttgttgttgcaaatt ggttttgcggctcttgtgcttatttcccattggggcaaaccgcgctaagcagcttgagt aatggggtttctggtttgcttggtttgccgatgtcggcattcgcttctgtgtttggtgat cttgccgatacggctttattttgctgttcgtgtattacctatcatcatcttcttcagt gcgctgatttctgcccttattaccttggtgtgatgcaaaaagtgatcgccctgatcggc ggtggcattcaacgcttcttaggcaccagtaaggcggaatcactggtcgcgacaggcaat attttcctatcacaaggcgaatcgccacttttggtgcgccccttccttgccaatatgaca cgctctgaactgtttgcggtcatggcgggcggtatggcatcggtagcaggctctgtgctg ggtggttacgcaggtttagggggttgagctgaaataccgattgcagcgagtttcatggcg gcgccgggcagtttaatgatggcgaaaatcatcgttcctgagcgtggtgtgccaatcgat caaagccaagtcgagttagataaagcgcaagacagccaacttgattgatgctctcgctag ggtgcgatgaatggtatgaaagtcgccgttgcagtgggcactatgttgattgcgttcgtc agcgtgatcgctatggtcaacactggccttgaaaatctgggcgatctggttgggtttagc ggcattaccttacaagccatgttcggttatctgtttgctcctctggcatgggtggattggc attccaagtcacgaagtgctggcggcaggttcctacatcggtcagaaagtggtgatgaac gaatttgtggctttcattgacttgttgagcataaagcgctgctttctgagcatagccaa gtcatcatcacgtttgcattgtgtggctttgccaacattggctctatcgcgatccaatta ggctccattggcgtgatagcccctgagcgccgctcggaagtggcgaacctaggcataaaa gcggtcattgctgcactttagccaacctaatgagcgcttgcttagcggggattttcatc tcgctataa |
| 124 | yegT - *Eschericia coli* K-12 W3110 (P76417; JW2085) | atgaaaacaacagcaaagctgtcgttcatgatgtttgttgaatggtttatctggggcgcg tggtttgtgccattgtggttgtggttaagtaaaagcggttttagtgccggagaaattggc tggtcgtatgcctgtaccgccattgcggcgatcctgcaatttctggttggctccatc actgaccgcttttctcggcgcaaaaagtgctggcggtattgatgttcgcaggcgcgctg ctgatgtatttcgctgcgcaacgaccacttttgccgggttcttccccgttactgctggcc tactcgctaacctatatgccgaccattgcgctgactaacagcatcgcttttgccaacgtg ccggatgttgagcgtgatttcccgcgcattcgtgtgatgggcactatcggctggattgcc tccggtctggcatggttcttgccgcaaatactggggtatgccgatatctcaccgact aacatcccgctgctgattaccgccggaagttctgctctgctcggtgtgtttgcgttttc ctgcccgacacgccaccaaaaagcaccggcaaaatggatattaaagtcatgctcggcctg gatgcgctgatcctgctgcgcgataaaaacttcctcgtctttttcttctgttcattcctg tttgcgatgccactagcgttctattacatctttgccaacggttatctgaccgaagttggc atgaaaaacgcaccggctggatgacgctcggccagttctctgaaatcttctttatgctg gcattgccgttttcactaaacgcttggtatcaaaaaggtattattgcttggtctggtc accgctgcgatccgctatggcttcttatttacggtagtgcggatgaatatttcacctac gcgttactgttcctcggtattttgcttcacggcgtaagttacgattttactacgttacc gcttacatctatgtcgataaaaaagccccgtgcatatgcgtaccgctgcgcagggctg atcacgctctgctgccagggcttcggcagtttgctcggctatcgtcttggcggtgtgatg |

| SEQ ID NO: | Gene or Operon | Sequence |
|---|---|---|
| | | atggaaaagatgttcgcttatcaggaaccggtaaacggactgactttcaactggtccggg<br>atgtggactttcggcgcggtgatgattgccattatcgccgtgctgttcatgattttttc<br>cgcgaatccgacaacgaaattacggctatcaaggtcgatgatcgcgatattgcgttgaca<br>caaggggaagttaaatga |
| 151 | yegT -<br>Escherichia<br>coli K-12<br>W3110<br>(P76417;<br>JW2085) | MKTTAKLSFMMFVEWFIWGAWFVPLWLWLSKSGFSAGEIGWSYACTAIAAILSPILVGSI<br>TDRFFSAQKVLAVLMFAGALLMYFAAQQTTFAGFFPLLLAYSLTYMPTIALTNSIAFANV<br>PDVERDFPRIRVMGTIGWIASGLACGFLPQILGYADISPTNIPLLITAGSSALLGVFAFF<br>LPDTPPKSTGKMDIKVMLGLDALILLRDKNFLVFFFCSFLFAMPLAFYYIFANGYLTEVG<br>MKNATGWMTLGQFSEIFFMLALPFFTKRFGIKKVLLLGLVTAAIRYGFFIYGSADEYFTY<br>ALLFLGILLHGVSYDFYYVTAYIYVDKKAPVHMRTAAQGLITLCCQGFGSLLGYRLGGVM<br>MEKMFAYQEPVNGLTFNWSGMWTFGAVMIAIIAVLFMIFFRESDNEITAIKVDDRDIALT<br>QGEVK |
| 125 | nupG -<br>Escherichia<br>coli K-12<br>W3110<br>JW2932;<br>(P09452 | atgaatcttaagctgcagctgaaaatcctctcttttctgcagttctgtctgtggggaagt<br>tggctgacgaccctcggctcctatatgtttgttaaccctgaagtttgacggtgcttctatt<br>ggcgcagtttatagctcactgggatcgcagcggtctttatgcctgcgctgctggggatt<br>gtggccgacaaatggttaagtgcgaaatgggtatatgccatttgccacaccattggcgct<br>atcacgctgttcatggcggcacaggtcacgacaccggaagcgatgttccttgtgatattg<br>attaactcgtttgcttatatgccacgcttgggttaatcaacaccatctcttactatcgc<br>ctgcaaaatgccgggatggatatcgttactgactgtcccgccaatccgtatctggggcacc<br>atcggctttatcatggcaatgtgggtggtgagcctgtctggcttcgaattaagccacatg<br>cagctgtatattggcgcagcacttttccgccattctggttctgtttaccctgactctgccg<br>catattccggttgctaaacagcaagcgaatcagagctggacaaccctgctgggcctcgat<br>gcattcgcgctgtttaaaaacaagcgtatggcaatcttctttatcttctcaatgctgctg<br>ggcgcggaactgcagattaccaacatgttcggtaataccttcctgcacagcttcgacaaa<br>gatccgatgtttgccagcagctttattgtgcagcatgcgtcaatcatcatgtcgatttcg<br>cagatctctgaaaccctgttcattctgaccatcccgttcttcttaagccgctacggtatt<br>aagaacgtaatgatgatcagtattgtggcgtggatcctgcgttttgcgctgtttgcttac<br>ggcgacccgactccgttcggtactgtactggtactgtcgatgatcgttacggttgc<br>gcattcgacttcttcaacatctctggttcggtgtttgtcgaaaaagaagttagcccggca<br>attcgcgccagtgcacaagggatgttcctgatgatgactaacggcttcggctgtatcctc<br>ggcggcatcgtgagcggtaaagttgttgagatgtacacccaaaacgcattaccgactgg<br>cagaccgtatggttgattttcgctggttactccgtggttctggcctcgcgttcatggcg<br>atgttcaaatataaacacgttcgtgtcccgacaggcacacagacggttagccactaa |
| 152 | nupG -<br>Escherichia<br>coli K-12<br>W3110<br>(P09452;<br>JW2932 | MNLKLQLKILSFLQFCLWGSWLTTLGSYMFVTLKFDGASIGAVYSSLGIAAVFMPALLGI<br>VADKWLSAKWVYAICHTIGAITLFMAAQVTTPEAMFLVILINSFAYMPTLGLINTISYYR<br>LQNAGMDIVTDFPPIRIWGTIGFIMAMWVVSLSGFELSHMQLYIGAALSAILVLFTLTLP<br>HIPVAKQQANQSWTTLLGLDAFALFKNKRMAIFFIFSMLLGAELQITNMFGNTFLHSFDK<br>DPMFASSFIVQHASIIMSISQISETLFILTIPFFLSRYGIKNVMMISIVAWILRFALFAY<br>GDPTPFGTVLLVLSMIVYGCAFDFFNISGSVFVEKEVSPAIRASAQGMFLMMTNGFGCIL<br>GGIVSGKVVEMYTQNGITDWQTVWLIFAGYSVVLAFAFMAMFKYKHVRVPTGTQTVSH |
| 126 | xapB -<br>Escherichia<br>coli K-12<br>W3110<br>(P45562;<br>JW2397) | atgagcatcgcgatgcgcttaaaggtaatgtcctttttgcaatattttatctgggggagc<br>tggctggttaccctcggctcttacatgattaatactcttcatttcaccggcgctaatgtt<br>ggcatggtttacagttccaaagggatcgccgcgattattatgcctggtataatgggatc<br>atcgcagacaaatggctgcgcgcagaacgtcatacatgctgtgtcacctggtgtgtgcg<br>ggcgtacttttttatgcggcatccgtaactgatccggatatgatgtttggtgatgtta<br>gtcaatgcgatggcgtttatgccgactattgcgttatcgaacagcgtctcttattcctgt<br>cttgcccaggcagggcttgacccgtgaccgcttccccgcccattcgcgttttggtacg<br>gtgggggttcattgtcgcgatgtgggcagtaagcctgctgcatctggaattgagtagtctg<br>cagctgtatatcgcgtccggtgcgtcattgctgctgtcggcttatgcgctgactttgccg<br>aagattccggttgcggagaaaaaagcgaccacatcgcttgccagcaagctgggtctggat<br>gccttcgtgctgtttaaaaatccacgcatggcatcttttttcctctttgccatgatgctg<br>ggtgcggtactgcaaattaccaacgttttggtaatccgttcctacatgatttcgcccgt<br>aacccggagtttgctgacagttttgtggtgaaatatccctccattttactgtcagtttca<br>cagatggcagaagtgggctttataactgattatcccattcttttttaaagcgatttggcatt<br>aaaaccgtcatgctgatgagtatggtggcctggacgctgcgctttggcttcttcgcctat<br>ggcgatccgtcaacaaccggatttattttgctgctgctgtcgatgattgtttatggctgt<br>gcattcgatttcttcaatatttctggttcggtatttgtcgaacaggaagttgattccagc<br>attcgtgccagcgcgcaggggctctttatgaccatggtaaatggtgtcggcgcatgggtt<br>ggctcgattctgagtggcatggcagtagattacttttcggtggatggcgtaaaagactgg<br>caaactatctggctggtgtttgcaggatatgctcttttttctcgcagtgatattttctttt<br>gggtttaaatataatcatgaccctgaaaagataaagcatcgagcggtgactcattaa |
| 153 | xapB -<br>Escherichia<br>coli K-12<br>W3110<br>(P45562;<br>JW2397) | MSIAMRLKVMSFLQYFIWGSWLVTLGSYMINTLHFTGANVGMVYSSKGIAAIIMPGIMGI<br>IADKWLRAERAYMLCHLVCAGVLFYAASVTDPDMMFWVMLVNAMAFMPTIALSNSVSYSC<br>LAQAGLDPVTAFPPIRVFGTVGFIVAMWAVSLLHLELSSLQLYIASGASLLLSAYALTLP<br>KIPVAEKKATTSLASKLGLDAFVLFKNPRMAIFFLFAMMLGAVLQITNVFGNPFLHDFAR<br>NPEFADSFVVKYPSILLSVSQMAEVGFILTIPFFLKRFGIKTVMLMSMVAWTLRFGFFAY<br>GDPSTTGFILLLLSMIVYGCAFDFFNISGSVFVEQEVDSSIRASAQGLFMTMVNGVGAWV<br>GSILSGMAVDYFSVDGVKDWQTIWLVFAGYALFLAVIFFFGFKYNHDPEKIKHRAVTH |

| SEQ ID NO: | Gene or Operon | Sequence |
|---|---|---|
| 127 | CC1628 – Caulobacter crescentus CB15 (AAK23606) | ATGGGGACGAGTTTCCGTCTGTTCGTGATGATGGTGCTGCAGCTGGCGATCTGGGGCGCCTGG<br>GCGCCCAAGATCTTCCCCTACATGGGCATGCTGGGCTTCGCGCCCTGGCAGCAGTCGCTGGTC<br>GGCAGCGCCTGGGGCGTGGCGGCGCTGGTGGGCATCTTCTTCTCGAATCAGTTCGCCGACCGG<br>AACTTCTCGGCCGAGCGGTTCCTGGCGGTCAGCCACCTGATCGGCGGCGTGGCGCTGCTGGGC<br>ACGGCCTTCTCGACGGAGTTCTGGCCGTTCTTTGCCTGTTACCTCGTTTTCAGCCTGGTCTAT<br>GTGCCGACGCTGTCGGTCACCAACTCGATCGCCTTCGCCAATCTGCGCGATCCGGCGGCCGGC<br>TTCGGCGGGGTGCGGATGGGCGGAACCGTCGGCTGGGTGCTGGTCAGCTGGCCCTTCGTGTTC<br>CTGCTGGGCGCCCAAGCGACGGTGGAGCAGGTCCGCTGGATCTTCCTGGTGGCGGCGATCGTC<br>TCCTTCGTTTTCGCCGGTTACGCTCTGACCCTGCCGCACACGCCGCCGCGCAAGGCCGATGAC<br>GCTGTCGACAAGCTGGCCTGGCGACGGGCGTTCAAGCTACTGGGGCGCGCCCTTCGTGTTTGTC<br>CTCTTTTGTCGTGACCTTCATCGATTCCGTGATCCACAACGGCTACTTCGTGATGGCCGACGCC<br>TTCCTGACCAACCGGGTCGGGATCGCGGGCAATCTCAGCATGGTCGTGCTGAGCCTGGGCCAG<br>GTGGCCGAAATCATCACCATGCTGCTGTTGGGCCGCGTGCTGGCCAAGCTGGGCTGGAAGGTC<br>ACCATGATCGTCGGCGTGCTGGGCCACGCCGCGCGCTTTGCGGTCTTCGCCTACTTCGCCGAC<br>AGCGTGCCGGTCATCGTGGCGGTGCAGCTGCTGCACGGCGTCTGCTACGCCTTCTTCTTCGCC<br>ACGGTTTACATCTTCGTCGACGCCGTCTTCCCCGAAAGATGTCCGCTCCAGCGCGCAGGGTCTG<br>TTCAACTTGCTGATCCTGGGCGTCGGCAATGTGGCCGCCAGCTTCATCTTCCCCGCGCTGATC<br>GGTCGCCTGACCACCGATGGGTCCGTCGACTACACGACGCTGTTCCTCGTGCCGACCGCCATG<br>GCTTTGGCGGCGGTCTGCCTGCTGGCGCTGTTCTTCCGGCCGCCCACGCGGGGACCTGTTTCG<br>GAGGCGGATTCCGCTTCATCCGCCGCCAGTTCGGCCCCAAGCCTAG |
| 154 | CC1628 – Caulobacter crescentus CB15 (AAK23606) | MGTSFRLFVMMVLQLAIWGAWAPKIFPYMGMLGFAPWQQSLVGSAWGVAALVGIFFSNQFADR<br>NFSAERFLAVSHLIGGVALLGTAFSTEFWPFFACYLVFSLVYVPTLSVTNSIAFANLRDPAAG<br>FGGVRMGGTVGWVLVSWPFVFLLGAQATVEQVRWIFLVAAIVSFVFAGYALTLPHTPPRKADD<br>AVDKLAWRRAFKLLGAPFVFVLFVVTFIDSVIHNGYFVMADAFLTNRVGIAGNLSMVVLSLGQ<br>VAEIITMLLLGRVLAKLGWKVTMIVGVLGHAARFAVFAYFADSVPVIVAVQLLHGVCYAFFFA<br>TVYIFVDAVFPKDVRSSAQGLFNLLILGVGNVAASFIFPALIGRLTTDGSVDYTTLFLVPTAM<br>ALAAVCLLALFFRPPTRGPVSEADSASSAASSAQA |
| 128 | codB – Escherichia coli K-12 W3110 (P25525; JW0327) | gtgtcgcaagataacaactttagccaggggccagtcccgcagtcggcgcggaaaggggta<br>ttggcattgacgttcgtcatgctgggattaaccttcttttccgccagtatgtggaccggc<br>ggcactctcggaaccggtcttagctatcatgatttcttcctcgcagttctcatcggtaat<br>cttctcctcggtatttacacttcatttctcggttacattggcgcaaaaaccggcctgacc<br>actcatcttcttgctcgcttctcgtttggtgttaaaggctcatggctgccttcactgcta<br>ctgggcggaactcaggttggctggtttggcgtcggtgtggcgatgtttgccattccggtg<br>ggtaaggcaaccgggctgcgatattaatttgctgattgccgtttccggtttactgatgac<br>gtcaccgtcttttttggcatttcggcgctgacggttctttcggtgattgcggttccggct<br>atcgcctgcctgggcggttattccgtgtggctggctgttaacggcatgggcggcctggac<br>gcattaaaagcggtcgttcccgcacaaccgttagatttcaatgtcgcgctggcgctggtt<br>gtggggtcatttatcagtgcgggtacgctcaccgctgacttttgtccggtttggtcgcaat<br>gccaaactggcggtgctggtggcgatggtggcctttttcctcggcaactcgttgatgttt<br>attttcggtgcagcgggcgctgcggcactgggcatggcggatatctctgatgtgatgatt<br>gctcagggcctgctgctgcctgcgattgtggtgctggggctgaatatctggaccaccaac<br>gataacgcactctatgcgtcgggtttaggtttcgccaacattaccggagtctgcgagcaaa<br>acccttttcggtaatcaacggtattatcggtacggctcgcgcattatggctgtataacaat<br>tttgtcggctggttgaccttcctttcggcagctattcctccagtgggtggcgtgatcatc<br>gccgactatctgatgaaccgtcgccgctatgagcactttgcgaccacgcgtatgatgagt<br>gtcaattgggtggcgattctggcggtcgccttggggattgctgcaggccactggttaccg<br>ggaattgttccggtcaacgcggtattaggtggcgcgctgagctatctgatccttaacccg<br>attttgaatcgtaaaacgacagcagcaatgacgcatgtggaggctaacagtgtcgaataa |
| 155 | codB – Escherichia coli K-12 W3110 (P25525; JW0327) | MSQDNNFSQGPVPQSARKGVLALTFVMLGLTFFSASMWTGGTLGTGLSYHDFFLAVLIGN<br>LLLGIYTSFLGYIGAKTGLTTHLLARFSFGVKGSWLPSLLLGGTQVGWFGVGVAMFAIPV<br>GKATGLDINLLIAVSGLLMTVTVFFGISALTVLSVIAVPAIACLGGYSVWLAVNGMGGLD<br>ALKAVVPAQPLDFNVALALVVGSFISAGTLTADFVRFGRNAKLAVLVAMVAFFLGNSLMF<br>IFGAAGAAALGMADISDVMIAQGLLLPAIVVLGLNIWTTNDNALYASGLGFANITGMSSK<br>TLSVINGIIGTVCALWLYNNFVGWLTFLSAAIPPVGGVIIADYLMNRRRYEHFATTRMMS<br>VNWVAILAVALGIAAGHWLPGIVPVNAVLGGALSYLILNPILNRKTTAAMTHVEANSVE |
| 129 | mctC – Corynebacterium | ATGAATTCCACTATTCTCCTTGCACAAGACGCTGTTTCTGAGGGCGTCGGTAATCCGATTCTT<br>AACATCAGTGTCTTCGTCGTCTTCATTATTGTGACGATGACCGTGGTGCTTCGCGTGGGCAAG<br>AGCACCAGCGAATCTCACCGACTTCTACACCGGTGGTGCTTCCTTCTCCGGAACCCAGAACGGT<br>CTGGCTATCGCAGGTGACTACCTGTCTGCAGCGTCCTTCCTCGGAATCGTTGGTGCAATTTCA<br>CTCAACGGTTACGACGGATTCCTTTACTCCATCGGCTTCTTCGTCGCATGGCTTGTTGCACTG<br>CTGCTCGTGGCAGAGCCACTTCGTAACGTGGGCCGCTTCACCATGGCTGACGTGCTGTCCTTC<br>CGACTGCGTCAGAAACCAGTCCGCGTCGCTGCGGCCTGCGGTACCCTCGCGGTTACCCTCTTT<br>TACTTGATCGCTCAGATGGCTGGTCAGGTTCGCTTGTGTCCGTTCTGCTGGACATCCACGAG<br>TTCAAGTGGCAGGCAGTTGTTGTCGGTATCGTTGGCATTGTCATGATCGCCTACGTTCTTCTT<br>GGCGGTATGAAGGGCACCACATACGTTCAGATGATTAAGGCAGTTCTGCTGGTCGGTGGCGTT<br>GCCATTATGACCGTTCTGACCTTCGTCAAGGTGTCTGGTGGCCTGACCACCCTTTTAAATGAC<br>GCTGTTGAGAAGCACGCCGCTTCAGATTACGCTGCCACCAAGGGGTACGATCCAACCCAGATC<br>CTGGAGCCTGGTCTGCAGTACGGTGCAACTCTGACCACTCAGCTGGACTTCATTTCCTTGGCT |

| SEQ ID NO: | Gene or Operon | Sequence |
|---|---|---|
| | | CTCGCTCTGTGTCTTGGAACCGCTGGTCTGCCACACGTTCTGATGCGCTTCTACACCGTTCCT<br>ACCGCCAAGGAAGCACGTAAGTCTGTGACCTGGGCTATCGTCCTCATTGGTGCGTTCTACCTG<br>ATGACCCTGGTCCTTGGTTACGGCGCTGCGGCACTGGTCGGTCCAGACCGCGTCATTGCCGCA<br>CCAGGTGCTGCTAATGCTGCTGCTCCTCTGCTGGCCTTCGAGCTTGGTGGTTCCATCTTCATG<br>GCGCTGATTTCCGCAGTTGCGTTCGCTACCGTTCTCGCCGTGGTCGCAGGTCTTGCAATTACC<br>GCATCCGCTGCTGTTGGTCACGACATCTACAACGCTGTTATCCGCAACGGTCAGTCCACCGAA<br>GCGGAGCAGGTCCGAGTATCCCGCATCACCGTTGTCGTCATTGGCCTGATTTCCATTGTCCTG<br>GGAATTCTTGCAATGACCCAGAACGTTGCGTTCCTCGTGGCCCTGGCCTTCGCAGTTGCAGCA<br>TCCGCTAACCTGCCAACCATCCTGTACTCCCTGTACTGGAAGAAGTTCAACACCACCGGCGCT<br>GTGGCCGCTATCTACACCGGTCTCATCTCCGCGCTGCTGCTGATCTTCCTGTCCCCAGCAGTC<br>TCCGGTAATGACAGCGCAATGGTTCCAGGTGCAGACTGGGCAATCTTCCCACTGAAGAACCCA<br>GGCCTCGTCTCCATCCCACTGGCATTCATCGCTGGTTGGATCGGCACTTTGGTTGGCAAGCCA<br>GACAACATGGATGATCTTGCTGCCGAAATGGAAGTTCGTTCCCTCACCGGTGTCGGTGTTGAA<br>AAGGCTGTTGATCACTAA |
| 130 | putP_6 - Virgibacillus sp. | atggatcttacgacattaataactttatagtatatctactagggatgttggcgattggcctc<br>atcatgtattatcgaaccaataatttatcagattatgttcttggtggacgtgatcttggtcca<br>ggcgtagctgcattgagtgctggtgcatcggatatgagtggttggctgttattaggtttgcct<br>ggagcgatttatgcatctggtatgtctgaagcttggatggggatcgggttagctgtaggtgct<br>tatttaaattggcaatttgtagctaagcgattacgcgtttataccgaggtatcaaataattcc<br>attacgatcccagattattttgaaaatcggtttaaagataactcacatattcttcgtgttata<br>tctgctatcgtaattttgttattcttcacttttatacatcttcaggaatggttgcaggagca<br>aaattatttgaggcttcattcggtctccaatacgaaactgctctgtggattggtgcggttgta<br>gttgtatcttatacgttacttggaggattttctagcggttgcatggacagactttattcaaggt<br>attcttatgttccttgcactaattgttgttccaatcgtcgcattagatcaaatgggtggctgg<br>aatcaagcggtacaagctgttggtgaaattaatccttccacctcaatatggttgaaggtgtt<br>ggaataatggcaattatttcatcacttgcttggggcttaggtttattttggacagccacatatt<br>attgttcgttttatggcattacgttcggcgaaagatgttccgaaagcgaaatttattggaaca<br>gcttggatgattttaggacttttatggagcaatctttactggttttgtaggactagcatttatc<br>agtacacaagaagtaccgattctgtctgaattcgggattcaagtagttaatgagaatggttta<br>caaatgttagccgatcctgaaaagatatttattgcttctcccaaatactattccatccagta<br>gttgccggtatcttactagcggcaatcttgtctgcaattatgagtaccgttgattcacagtta<br>cttgtatcatcttcagcggttgcagaagatttctataaagctattttccgtaaaaaagctact<br>ggtaaagagcttgtttgggttggacgtattgctacagtgataattgcgattgttgctttaatt<br>attgcaatgaaaccagatagctctgtattggatctagttagttatgcatgggctggatttggt<br>gcagcatttggaccaattatcatcttgtcattattctggaagagaatcacaagaaatggtgca<br>ctagcgggtatcattgtaggtgccattacggtaattgtatggggagacttttctatctggaggt<br>atctttgacctctacgaaattgttccaggctttatcttaaatatgattgtcaccgttattgtg<br>agtcttatcgataaaccgaatccagatttagaagctgactttgatgaaaccgtagaaaaatg<br>aaagaataa |
| 131 | cbsT1 - Lactobacillus johnsonii | ATGTCGACCACACCGACACAGCCATCATCACGAAAACAGGCTGTTTACCCGTACTTGATCGTG<br>CTGTCGGGCATCGTCTTCACGGCCATCCCGGTATCGCTGGTCTGCAGTTGCGCAGGTATCTTC<br>TTCACGCCTGTCAGCAGCTACTTCCATGTTCCCAAGGCCGCATTCACCGGATATTTCAGCATA<br>TTCAGCATCACCATGGTCGCCTTCCTGCCGGTGGCCGGATGGCTGATGCACCGCTACGATCTG<br>CGCATCGTACTGACCGCAAGCACCGTCCTGGCTGGATGGGCTGCCTGGGTATGTCCCGATCA<br>TCCGCCATGTGGCAGTTCTATCTATGCGGAGTGGTTCTGGGAATCGGCATGCCGGCCGTCCTC<br>TATCTGTCAGTGCCAACACTCATCAACGCCTGGTTCCGCAAGCGGGTCGGGTTCTTCATCGGC<br>CTGTGCATGGCCTTCACCGGCATAGGCCACCATGATCATCAACCAGATAGGCACCATGATCATC<br>AGATCCGCCCCTGATGGATGGAGGCGGGGATATCTGGTTTTCGCTATTCTCATCCTGGTGATC<br>ACCCTGCCCTTCACCATTTTCGTCATTCGCAGCACACCCGAACAGATGGGTCTGCATCCCTAC<br>GGCGCCGACCAGGAGCCTGATGCAGCTGAGACGGCCACCAATAGTGCAGGCACCGGGAGCAAA<br>GACCAAAAGAGTCCTGAGCCTGCAGCGTCAACCGTAGGCATGACTGCCTCCCAGGCCTTGCGC<br>TCCCCTGCCTTCTGGGCGCTGGCGCTCTTCGCGGTCTGATCACCATGAATCAGACCATTTAC<br>CAGTTCCTGCCCTCCTACGCGGCATCCCTGCCATCCATGGCAGCCTACACGGGACTGATCGCC<br>TCCTCCTGCATGGCCGGCCAGGCCATCGGCAAGATCATCCTGGGCATGGTCAACGACGGCAGC<br>ATCGTAGGCGGTCTCTGTCTGGGCATCGGCGGCGGCATTCTCGGCGTCTGCCTCATGGTCGCC<br>TTCCCCGGATTGCCCGTGCTCCTCCTGCTGGGAGCCTTTGCCTTCGGCCTTGTCTACGCCTGC<br>ACTACTGTGCAGACACCAATCCTGGTTACAGCGGTCTTCGGCTCGCGCTGACTACACCAACATC<br>TATGCACGTATCCAGATGGTTGGGTCCCTAGCCTCGGCCTTCGCAGCTCTCTTCTGGGGCGCC<br>ATCGCTGACCAGCCCCACGGCTACATCATCATGTTCGGTCTGAGCATCCTGATCATGGTTGTG<br>GCCTTGTTCCTAGGCATTATCCCTCTGAAAGGTACGCGCAAGTTGACCGATCAGATCGCCTGA |
| 132 | cbsT2 - Lactobacillus johnsonii | atgtctactgatgccgctactaaagataaagtagtaagcaagggctataaatacttcatggtt<br>ttcctttgtatgttaacccaagctattccttatggaattgctcaaaacattcagcctttgttt<br>atccacccttagttaatactttccactttaccttagcatcgtacacattaatttttacgttt<br>ggtgcggttttgcttcagttgcttctccattttattggtaaggcattagaaaaagttaacttc<br>cgactaatgtatttaattggtattggtcttctgctattgctcacgtaattttttggaattagt<br>acaaaactaccggtttctatattgccgctatcatttgtatggttggttcaacctttactcc<br>ggccaaggtgttccctgggtattaaccactggttcccagcaaagggacgtggggctgccta<br>ggaattgccttctgcggtggttctattggtaatatcttttacaaccagcaacccaagctatt<br>ttaaaacactacatgacaggtaatactaagaccggtcatttaacctctatggcaccattctt<br>atctttgccgtagctttattagtaatcggtgtaattatcgcctgcttcattagaaccccctaag |

| SEQ ID NO: | Gene or Operon | Sequence |
|---|---|---|
| | | aaagacgaaattgttgtttctgatgcagaactagctgaaagcaagaaagctgaagccgcagcc aaagctaaagagtttaaaggctggactagtaaacaagtgttacaaatgaaatggttctggatt ttcagccttggttcttaatcattggtttaggcttagcttcttttaaatgaagactatgccgcc ttccttgatactaagcttctctttaaccgatgttggtttagttgggtcaatgtacggtgttggt tgtttaatcggaaatatttctggtggtttcttatttgataaatttggtacagcaaaatcaatg acctatgctggttgtatgtatattttatctattctgatgatgatctttattagcttccagcca tatggttcatctattagtaaggctgctggcattggctatgctatcttttgcggcttagctgta tttagttacatgtcaggcccagccttcatggcaaaagacctctttggttcaagagatcaaggt gtcatgcttggatacgttggtttagcttatgcaattggctatgccattggtgctccactattt gggattattaagggagcggcaagcttacagttgcttggtacttttatgattgcctttgttgca attggttttatcattttagtatttgccgttatccaaattaagagataccaaaagaaatacatt gcagagcaagcagcaaaagctaatgctaaataa |
| 133 | amtB - *Escherichia coli* K-12 MG1655 (B0451; 945084) | atgaagatagcgacgataaaaactgggcttgcttcactggcgatgcttccgggactggta atggctgcacctgcggtggccgataaagccgacaatgcgtttatgatgatttgtactgcg ctggtgctgtttatgactattccggggattccctgttttacggtgggttgattcgccggc aaaaacgtgctgtcgatgctgacgcaggtgacggtgacatttgcactggtctgtattctc tgggtggttacggttactcgctggcgtttggtgagggcaacaacttcttcggcaacatt aactggttgatgctgaaaaacatcgaactgacggcggtgatgggcagcatttatcagtat atccacgtggcgtttcagggatcgtttgcctgcattaccgtcggcttgatagttgggcg ctggcggaacgaatccgcttctcagctgtgttgattttcgtggtggtatggctgacgctc tcttacattccgattgcgcatatggtgtggggcggtggtttgctggcttctcacggtgcg ctggatttcgcgggtggcaccgtggtgcacattaacgccgcaatcgccggtctggtgggc gcgtatctgataggaaaacgcgtgggcttcggtaaagaggcgtttaaaccgcacaacctg ccgatggtcttcaccgggactgccattctctatatcggttggtttggctttaacgccggg tcagcgggcacggcgaatgaaatcgcggcactggcatttgtgaatactgtggtcgcaacg gcggcggcaattcttggctggatcttcggtaatgggcgctgcgtggtaagccttcactg ctggggcgtgttctggcgcgattgccggtctggtcggcgtgacgccagcctgcggctac attggggttggcggcgcgttgattatctggtggtagctggtcttggcgggcttgtgggagc gttaccatgctcaaacgcttgctgcgggtggatgatccctgcgatgtcttcggtgtgcac ggcgtttgtggcattgtcggctgtatcatgaccgggattttgccgccagctcgctgggc ggcgtgggcttcgctgaaggtgtgacgatgggccatcagttgctggtacagctggaaagc atcgccattacgatctcgtggtccggtgttgtggcatttatcggctacaaattggcggat ctgacggttggtctgcgtgtaccggaagagcaggagcgagaagggctggatgtcaacagc cacggcgagaatgcctataacgcgtaa |
| 156 | amtB - *Escherichia coli* K-12 MG1655 (B0451; 945084) | MKIATIKTGLASLAMLPGLVMAAPAVADKADNAFMMICTALVLFMTIPGIALFYGGLIRG KNVLSMLTQVTVTFALVCILWVVYGYSLAFGEGNNFFGNINWLMLKNIELTAVMGSIYQY IHVAFQGSFACITVGLIVGALAERIRFSAVLIVVVWLTLSYIPIAHMVWGGGLLASHGA LDFAGGTVVHINAAIAGLVGAYLIGKRVGFGKEAFKPHNLPMVFTGTAILYIGWFGFNAG SAGTANEIAALAFVNTVVATAAAILGWIFGEWALRGKPSLLGACSGAIAGLVGVTPACGY IGVGGALIIGVVAGLAGLWGVTMLKRLLRVDDPCDVFGVHGVCGIVGCIMTGIFAASSLG GVGFAEGVTMGHQLLVQLESIAITIVWSGVVAFIGYKLADLTVGLRVPEEQEREGLDVNS HGENAYNA |
| 134 | GABA permease GabP - *Escherichia coli* | atggggcaatcatcgcaaccacatgagttaggcggcgggctgaagtcacgccacgtcaccatg ttgtctattgccggtgttatcggcgcaagtctgtttgtcggttccagcgtcgccatcgccgaa gcgggcccggcggtattactggcctatctgttcgccggattactggtggttatgattatgcgg atgttggcggaaatggcagttgccacgcccgataccggttcgttttccacctatgccgataaa gccattggccgctgggcgggttataccatcggctggctgtactggttggttttcgggtactggtt atcccgctggaagccaacatcgccgctatgatcctgcactcgtgggttccaggcattcccatc tggttattttccctcgtcattaccctcgcctaactggcagtaatttattaagcgttaaaaac tacggcgaatttgagttctggctggcgctgtgcaaagtcatcgctatcctggcctttatttc cttggtcagtcgcaattagcggttttaccccttatgccgaagtgagcgggatctcaagattg tgggatagcggcggctttatgcccaacggtttcggtgcggtattaagcgcgatgttgatcacc atgttctcgtttatgggcgcagaaattgtcaccattgccgccgggaatccgacacgccgaa aaacatattgtccgcgccactaactcggttatctggcgtatttctatcttctatttgtgctct atttttgtcgtagtggcgttaataccgtggaatatgccggggctgaaagccgttggttcttat cgctccggttctggaattgctcaatattcccatgcgaaattaatcatggactgcgtgatatta ctttccgtaaccagctgtctgaactcggcgctgtataccgtcaaggatgctctactcctta agccgtcgcggtgatgcgcccgcggtaatgggcaaatcaaccgcagtaaaaccccgtatgtg gcggtgttactctccaccggagcggcattttaacggtggtggtgaactattacgcacctgcg aaagtgtttaaattcctgatagacagctccggtgctatcgccctgctggtttattagtcatc gccgtttcacagttgcggatgcgtaaaatctgcgagcagaaggaagcgaaattcgcttgcgc atgtggcttatccggtggctcacctggctggtaataggctttattacctttgtgttggtagtg atgctattccgcccggcgcaacagttagaagtgatctctaccgcgcttattagcgatagggatt atctgtaccgtgccgattatggcgcgctggaaaaagctggtattgtggcaaaaaacacccgtt cataatacgcgctga |
| 157 | GABA permease GabP - *Escherichia coli* | MGQSSQPHELGGGLKSRHVTMLSIAGVIGASLFVGSSVAIAEAGPAVLLAYLFAGLLVVMIMR MLAEMAVATPDTGSFSTYADKAIGRWAGYTIGWLYWWFWVLVIPLEANIAAMILHSWVPGIPI WLFSLVITLALTGSNLLSVKNYGEFEFWLALCKVIAILAFIFLGAVAISGFYPYAEVSGISRL WDSGGFMPNGFGAVLSAMLITMFSFMGAEIVTIAAAESDTPEKHIVRATNSVIWRISIFYLCS |

| SEQ ID NO: | Gene or Operon | Sequence |
|---|---|---|
| | | IFVVVALIPWNMPGLKAVGSYRSVLELLNIPHAKLIMDCVILLSVTSCLNSALYTASRMLYSL SRRGDAPAVMGKINRSKTPYVAVLLSTGAAFLTVVVNYYAPAKVFKFLIDSSGAIALLVYLVI AVSQLRMRKILRAEGSEIRLRMWLYPWLTWLVIGFITFVLVVMLFRPAQQLEVISTGLLAIGI ICTVPIMARWKKLVLWQKTPVHNTR |
| 135 | mtnH - *Escherichia coli* | atgacgaactatcgcgttgagagtagcagcggacgggcggcgcgcaagatgaggctcgcatta atgggacctgcgttcattgcggcgattggttatatcgatcccggtaactttgcgaccaatatt caggcgggtgccagcttcggctatcagctgtgggttgtcgtttgggccaacctgatggcg atgctgattcagatcctctctgccaaactagggattgccaccggtaaaaatctggcggagcag attcgcgatcactatccgcgtcccgtagtgtggttctattgggttcaggcagaaattattgcg atggcaaccgacctggcggaatttattggtgcggcgatcggttttaaactcattcttggtgtc tcgttgttgcagggcgcggtgctgacggggatcgcgacttttcctgattttaatgctgcaacgt cgcgggcaaaaaccgctggagaaagtgattggcgggttactgttgtttgttgccgcggcttac attgtcgagttgatttttctcccagcctaacctggcgcagctgggtaaaggaatggtgatcccg agtttacctacttcggaggcggtcttcctggcagcaggcgtgttaggggcgacgattatgccg catgtgatttatttgcactcctcgctcactcagcatttacatggcgggtcgcgtcaacaacgt tattccgccaccaaatgggatgtggctatcgccatgacgattgccggttttgtcaatctggcg atgatggctacagctgcggcggcgttccactttctggtcatactggtgttgccgatcttgat gaggcttatctgacgctgcaaccgctgttaagccatgctgcggcaacggtctttgggttaagt ctggttgctgccggactgtcctcaacggtggtggggacactggcggggcaggtggtgatgcag ggattcattcgcttccatatcccgctgtgggtgcgtcgtacagtcaccatgttgccgtcattt attgtcattctgatgggattagatccgacacggattctggttatgagtcaggtgctgttaagt tttggtatcgccctggcgctggttccactgctgattttcaccagtgacagcaagttgatgggc gatctggtgaacagcaaacgcgtaaaacagacaggctgggtgattgtagtgctggtcgtggcg ctgaatatctggttgttggtggggacggcgctgggattgtag |
| 158 | mtnH - *Escherichia coli* | MTNYRVESSSGRAARKMRLALMGPAFIAAIGYIDPGNFATNIQAGASFGYQLLWVVVWANLMA MLIQILSAKLGIATGKNLAEQIRDHYPRPVVWFYWVQAEIIAMATDLAEFIGAAIGFKLILGV SLLQGAVLTGIATFLILMLQRRGQKPLEKVIGGLLLFVAAAYIVELIFSQPNLAQLGKGMVIP SLPTSEAVFLAAGVLGATIMPHVIYLHSSLTQHLHGGSRQQRYSATKWDVAIAMTIAGFVNLA MMATAAAAFHFSGHTGVADLDEAYLTLQPLLSHAAATVFGLSLVAAGLSSTVVGTLAGQVVMQ GFIRFHIPLWVRRTVTMLPSFIVILMGLDPTRILVMSQVLLSFGIALALVPLLIFTSDSKLMG DLVNSKRVKQTGWVIVVLVVALNIWLLVGTALGL |

The invention claimed is:

1. A recombinant non-pathogenic bacterium capable of metabolizing phenylalanine, wherein the bacterium comprises at least one heterologous gene encoding a phenylalanine transporter for importing phenylalanine into the bacterium, wherein the gene encoding the transporter is operably linked to a directly or indirectly inducible promoter that is not associated with the transporter in nature;
   wherein the bacterium further comprises at least one heterologous gene encoding a polypeptide for metabolizing phenylalanine, and wherein the gene encoding the polypeptide is operably linked to a directly or indirectly inducible promoter that is not associated with the polypeptide in nature.

2. The recombinant bacterium of claim 1, wherein the promoter operably linked to the gene encoding the transporter and the promoter operably linked to the gene encoding the polypeptide are separate copies of the same promoter.

3. The recombinant bacterium of claim 1, wherein the gene encoding the transporter and the gene encoding the polypeptide are operably linked to the same copy of the same promoter.

4. The recombinant bacterium of claim 1, wherein the promoter operably linked to the gene encoding the transporter and the promoter operably linked to the gene encoding the polypeptide are directly or indirectly induced by exogenous environmental conditions.

5. The recombinant bacterium of claim 4, wherein the promoter operably linked to the gene encoding the transporter and the promoter operably linked to the polypeptide are directly or indirectly induced by exogenous environmental conditions found in the gut of a mammal.

6. The recombinant bacterium of claim 4, wherein the promoter operably linked to the gene encoding the transporter and the promoter operably linked to the gene encoding the polypeptide are directly or indirectly induced by exogenous environmental conditions found in the microenvironment of a tumor.

7. The recombinant bacterium of claim 4, wherein the promoter operably linked to the gene encoding the transporter and the promoter operably linked to the gene encoding the polypeptide are directly or indirectly induced under low-oxygen or anaerobic conditions.

8. The recombinant bacterium of claim 7, wherein the promoter operably linked to the gene encoding the transporter and the promoter operably linked to the gene encoding the polypeptide are selected from the group consisting of an FNR-responsive promoter, an ANR-responsive promoter, and a DNR-responsive promoter.

9. The recombinant bacterium of claim 1, wherein the gene encoding the transporter is located on a chromosome in the bacterium.

10. The recombinant bacterium of claim 1, wherein the gene encoding the transporter is located on a plasmid in the bacterium.

11. The recombinant bacterium of claim 1, wherein the gene encoding the polypeptide is located on a plasmid in the bacterium.

12. The recombinant bacterium of claim 1, wherein the gene encoding the polypeptide is located on a chromosome in the bacterium.

13. The recombinant bacterium of claim 1, wherein the bacterium is a probiotic bacterium.

14. The recombinant bacterium of claim 13, wherein the bacterium is selected from the group consisting of *Bacteroides*, *Bifidobacterium*, *Clostridium*, *Escherichia*, *Lactobacillus*, and *Lactococcus*.

15. The recombinant bacterium of claim 14, wherein the bacterium is *Escherichia coli* strain Nissle.

16. The recombinant bacterium of claim 1, wherein the bacterium is an auxotroph in a gene that is complemented when the bacterium is present in a mammalian gut.

17. The recombinant bacterium of claim 16, wherein mammalian gut is a human gut.

18. The recombinant bacterium of claim 16, wherein the bacterium is an auxotroph in diaminopimelic acid or an enzyme in the thymidine biosynthetic pathway.

19. The recombinant bacterium of claim 1, wherein the bacterium is further engineered to harbor a gene encoding a substance toxic to the bacterium, wherein the gene is under the control of a promoter that is directly or indirectly induced by an environmental factor not naturally present in a mammalian gut.

20. A pharmaceutically acceptable composition comprising the bacterium of claim 1; and a pharmaceutically acceptable carrier.

21. The composition of claim 20 formulated for oral administration.

22. A recombinant bacterium capable of metabolizing phenylalanine,
   wherein the bacterium comprises at least one heterologous gene encoding a phenylalanine transporter for importing the phenylalanine into the bacterium, wherein the gene encoding the transporter is operably linked to a directly or indirectly inducible promoter that is not associated with the transporter in nature;
   wherein the bacterium further comprises at least one heterologous gene encoding a polypeptide for metabolizing the phenylalanine, and wherein the gene encoding the polypeptide is operably linked to a directly or indirectly inducible promoter that is not associated with the polypeptide in nature; and
   wherein the bacterium is capable of reducing the level of the phenylalanine in an in vitro culture by about 50% as compared to a bacterium that does not comprise a heterologous gene encoding a polypeptide for metabolizing phenylalanine.

* * * * *